(12) United States Patent
Zuccola et al.

(10) Patent No.: US 8,192,972 B2
(45) Date of Patent: Jun. 5, 2012

(54) CRYSTAL STRUCTURE OF HUMAN JAK3 KINASE DOMAIN COMPLEX AND BINDING POCKETS THEREOF

(75) Inventors: Harmon Zuccola, Westwood, MA (US); Marc Jacobs, Boston, MA (US); Lovorka Swenson, Belmont, MA (US); Kumkum Saxena, Framingham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 265 days.

(21) Appl. No.: 12/471,896

(22) Filed: May 26, 2009

(65) Prior Publication Data
US 2011/0014680 A1 Jan. 20, 2011

Related U.S. Application Data

(62) Division of application No. 11/114,979, filed on Apr. 26, 2005, now Pat. No. 7,558,717.

(60) Provisional application No. 60/669,771, filed on Apr. 8, 2005, provisional application No. 60/566,393, filed on Apr. 28, 2004.

(51) Int. Cl.
*C12N 9/00* (2006.01)
*C12N 9/10* (2006.01)
(52) U.S. Cl. .................................. 435/183; 435/194
(58) Field of Classification Search .................. None
See application file for complete search history.

(56) References Cited

U.S. PATENT DOCUMENTS

| | | | |
|---|---|---|---|
| 4,886,646 A | 12/1989 | Carter et al. | |
| 5,096,676 A | 3/1992 | McPherson et al. | |
| 5,130,105 A | 7/1992 | Carter et al. | |
| 5,221,410 A | 6/1993 | Kushner et al. | |
| 5,400,741 A | 3/1995 | DeTitta et al. | |
| 5,884,230 A | 3/1999 | Srinivasan et al. | |
| 2004/0137518 A1 | 7/2004 | Lambert et al. | |

FOREIGN PATENT DOCUMENTS

WO   WO 02/060927 A1   8/2002

OTHER PUBLICATIONS

Kierzek et al. (Biophys Chem 91:1-20, 2001).*
Branden et al. ("Introduction to Protein Structure Second Edition", Garland Publishing Inc., New York, 1999).*
Drenth ("Principles of X-ray Crystallography," Springer, New York, 1995).*
Balbes et al., "A Perspective of Modern Methods in Computer-Aided Drug Design", *Reviews in Computational Chemistry*, 5:337-379 (1994).
Bartlett et al., "CAVEAT: A Program to Facilitate the Structure-Derived Design of Biologically Active Molecules", *Molecular Recognition*, 78:182-196 (1989).
Becker et al., "Three-Dimensional Structure of the Stat3β Homodimer Bound to DNA", *Nature*, 394:145-151 (1998).
Blundell et al., "Knowledge-Based Prediction of Protein Structures and the Design of Novel Molecules", *Nature*, 326:347-352 (1987).
Böhm, "The Computer Program LUDI: A New Method for the De Novo Design of Enzyme Inhibitors", *Journal of Computer-Aided Molecular Design*, 6:61-78 (1992).
Boggon et al., "Crystal Structure of the Jak3 Kinase Domain in Complex with a Staurosporine Analog", *Blood*, 106:996-1002 (2005).
Branden et al., "Introduction to Protein Structure," Second Edition, Garland Publishing Inc., New York (1999).
Brünger et al., "*Crystallography & NMR System*: A New Software Suite for Macromolecular Structure Determination", *Acta Crystallographica*, D54:905-921 (1998).
Carson, "RIBBONS 2.0", *Journal of Applied Crystallography*, 24:958-961 (1991).
Cetkovic-Cvrlje et al., "Prevention of Islet Allograft Rejection in Diabetic Mice by Targeting Janus Kinase 3 with 4-(4'-Hydroxyphenyl)-amino-6,7-dimethoxyquinazoline (JANEX-1)", *Arzneim-Forsch Drug Research*, 53:648-654 (2003).
Cetkovic-Cvrlje et al., "Targeting JAK3 with JANEX-1 for Prevention of Autoimmune Type 1 Diabetes in NOD Mice", *Clinical Immunology*, 106:213-225 (2003).
Cetkovic-Cvrlje et al., "Targeting Janus Kinase 3 in the Treatment of Leukemia and Inflammatory Diseases", *Arch. Immunol. Ther. Exp.*, 52:69-82 (2004).
Changelian et al., "Prevention of Organ Allograft Rejection by a Specific Janus Kinase 3 Inhibitor", *Science*, 302:875-878 (2003).
Chayen, "A Novel Technique to Control the Rate of Vapour Diffusion, Giving Larger Protein Crystals", *Journal of Applied Crystallography*, 30:198-202 (1997).
Chen et al., "Crystal Structure of a Tyrosine Phosorylated STAT-1 Dimer Bound to DNA", *Cell*, 93:827-839 (1998).
Chen et al., "Complex Effects of Naturally Occurring Mutations in the JAK3 Pseudokinase Domain: Evidence for Interations Between the Kinase and Pseudokinase Domains", *Molecular and Cellular Biology*, 20:947-956 (2000).

(Continued)

*Primary Examiner* — Suzanne M Noakes
*Assistant Examiner* — Jae W Lee
(74) *Attorney, Agent, or Firm* — Ropes & Gray LLP; James F. Haley, Jr.; Raymond M. Doss

(57) ABSTRACT

The present invention relates to human Janus Kinase 3 (JAK3) and JAK3-like binding pockets. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to JAK3 protein or JAK3 protein homologues, or complexes thereof. The invention also relates to crystallizable compositions and crystals comprising JAK3 kinase domain and JAK3 kinase domain complexed with AMP-PNP.

7 Claims, 9 Drawing Sheets

OTHER PUBLICATIONS

Cohen et al., "Molecular Modeling Software and Methods for Medicinal Chemistry", *Journal of Medicinal Chemistry*, 33:883-894 (1990).

Cory et al., "MATCHMOL, An Interactive Computer Graphics Procedure for Superposition of Molecular Models", *Journal of Molecular Graphics*, 2(2):39-42 (1984).

D'Arcy et al., "A Novel Approach to Crystallising Proteins under Oil", *Journal of Crystal Growth*, 168:175-180 (1996).

Darnell et al., "Jak-STAT Pathways and Transcriptional Activation in Response to IFNs and Other Extracellular Signaling Proteins", *Science*, 264:1415-1421 (1994).

Drenth, "Principles of Protein X-Ray Crystallography," Springer-Verlag, 16-17 (1995).

Eisen et al., "HOOK: A Program for Finding Novel Molecular Architectures That Satisfy the Chemical and Steric Requirements of a Macromolecule Binding Site", *Proteins Structure Function and Genetics*, 19:199-221 (1994).

Feng et al., "Activation of Jak2 Catalytic Activity Requires Phosphorylation of $Y^{1007}$ in the Kinase Activation Loop", *Molecular and Cellular Biology.*, 17:2497-2501 (1997).

Fetrow et al., "New Programs for Protein Tertiary Structure Prediction", *Biotechnology*, 11:479-484 (1993).

Flower et al., "Drug Design: Cutting Edge Approaches," *The Royal Society of Chemistry*, 21-27 (2002).

Gauzzi et al., "Interferon-α-Dependent Activation of Tyk2 Requires Phosphorylation of Positive Regulatory Tyrosines by Another Kinase", *Journal of Biological Chemistry*, 271:20494-20500 (1996).

Gillet et al., "SPROUT: A Program for Structure Generation", *Journal of Computer-Aided Molecular Design*, 7:127-153 (1993).

Girault et al., "The N-Termini of FAK and JAKs Contain Divergent Band 4.1 Domains", *Trends in Biochemical Sciences*, 24:54-57 (1999).

Goodford, "A Computational Procedure for Determining Energetically Favorable Binding Sites on Biologically Important Macromolecules", *Journal of Medicinal Chemistry*, 28:849-857 (1985).

Goodsell et al., "Automated Docking of Substrates to Proteins by Simulated Annealing", *Proteins Structure Function and Genetics*, 8:195-202 (1990).

Greer, "Comparative Modeling of Homologous Proteins", *Methods in Enzymology*, 202:239-252 (1991).

Gschwend et al., "Molecular Docking Towards Drug Discovery", *Journal of Molecular Recognition*, 9:75-186 (1996).

Guex et al., "Swiss-Model and the Swiss-PdbViewer: An Environment for Comparative Protein Modeling", *Electrophoresis*, 18:2714-2723 (1997).

Guida, "Software for Structure-Based Drug Design", *Current Opinion in Structural Biology*, 4:777-781 (1994).

Hanks, et al., "The Protein Kinase Family: Conserved Features and Deduced Phylogeny of the Catalytic Domains", *Science*, 241:42-52 (1988).

Hanks et al., "Protein Kinase Catalytic Domain Sequence Database: Identification of Conserved Features of Primary Structure and Classification of Family Members", *Methods in Enzymology*, 200:38-62 (1991).

Hamada et al., "Structural Basis of the Membrane-Targeting and Unmasking Mechanisms of the Radixin FERM Domain", *EMBO Journal*, 19:4449-4462 (2000).

Hamada et al., "Structural Basis of Adhesion-Molecule Recognition by ERM Proteins Revealed by the Crystal Structure of the Radixin-ICAM-2 Complex", *EMBO Journal*, 22:502-514 (2003).

Haystead et al., "γ-Phosphate-Linked ATP-Sepharose for the Affinity Purification of Protein Kinases. Rapid Purification to Homogeneity of Skeletal Muscle Mitogen-Activated Protein Kinase Kinase", *European Journal of Biochemistry,*, 214:459-467 (1993).

Hegyi et al., "The relationship between protein structure and function: a comprehensive survey with application to the yeast genome," *Journal of Molecular Biology*, 288:147-164 (1999).

Higgins et al., "Using CLUSTAL for Multiple Sequence Alignments", *Methods in Enzymology*, 266:383-402 (1996).

Hubbard, "Crystal Structure of the Activated Insulin Receptor Tyrosine Kinase in Complex with Peptide Substrate and ATP Analog", *EMBO Journal*, 16:572-5581 (1997).

Huse et al., "The Conformational Plasticity of Protein Kinases", *Cell*, 109:275-282 (2002).

Ihle, " The *Janus* Protein Kinase Family and Its Role in Cytokine Signaling", *Advances in Immunology*, 60:1-35 (1995).

Johnson et al, "Knowledge-Based Protein Modeling", *Critical Reviews in Biochemistry and Molecular Biology*, 29:1-68 (1994).

Jones et al., "Improved Methods for Building Protein Models in Electron Density Maps and the Location of Errors in these Models", *Acta Crystallographica*, A47:110-119 (1991).

Kierzek et al., "Models of protein crystal growth," *Biophysical Chemistry*, 91:1-20 (2001).

Kirken, "Targeting JAK3 for Immune Suppression and Allograft Acceptance", *Transplantation Proceedings*, 33:3268-3270 (2001).

Kisseleva et al., "Signaling Through the JAK/STAT Pathway, Recent Advances and Future Challenges", *Gene*, 285:1-24 (2002).

Kuntz et al., "A Geometric Approach to Macromolecule-Ligand Interactions", *Journal of Molecular Biology*, 161:269-288 (1982).

Lattman, "Use of the Rotation and Translation Functions", *Methods in Enzymology*, 115:55-77 (1985).

Lauri et al., "CAVEAT: A Program to Facilitate the Design of Organic Molecules", *Journal of Computer-Aided Molecular Design,*, 8:51-66 (1994).

Lindauer et al., "Prediction of the Structure of Human Janus Kinase 2 (JAK2) Comprising the Two Carboxy-Terminal Domains Reveals a Mechanism for Autoregulation", *Protein Engineering*, 14:27-37 (2001).

Martin, "3D Database Searching in Drug Design", *Journal of Medicinal Chemistry*, 35:2145-2154 (1992).

McPherson, "Current approaches to macromolecular crystallization," 189:1-23 (1990).

Miranker et al., "Functionality Maps of Binding Sites: A Multiple Copy Simultaneous Search Method." *Proteins Structure Function and Genetics*, 11:29-34 (1991).

Meng et al., "Automated Docking with Grid-Based Energy Evaluation," *Journal of Computational Chemistry*, 13:505-524 (1992).

Mohammadi et al., "Structure of the FGF Receptor Tyrosine Kinase Domain Reveals a Novel Autoinhibitory Mechanism", *Cell*, 86:577-587 (1996).

Navia et al., "Use of Structural Information in Drug Design", *Current Opinion in Structural Biology*, 2:202-210 (1992).

Nishibata et al., "Automatic Creation of Drug Candidate Structures Based on Receptor Structure. Starting Point for Artificial Lead Generation", *Tetrahedron*, 47:8985-8990 (1991).

Notarangelo et al., "Mutations in Severe Combined Immune Deficiency (SCID) Due to JAK3 Deficiency", *Human Mutation*, 18:255-263 (2001).

Ohren et al., "Structures of Human MAP Kinase 1 (MEK1) and MEK2 Describe Novel Noncompetitive Kinase Inhibition", *Nature Structural and Molecular Biology*, 11:1192-1197 (2004).

O'Shea et al., "Cytokine Signaling in 2002: New Surprises in the Jak/Stat Pathway", *Cell*, 109:S121-S131 (2002).

Pav et al., "Microtube Batch Protein Crystallization: Applications to Human Immunodeficiency Virus Type 2 (HIV-2) Protease and Human Renin", *Proteins Structure Function and Genetics*, 20:98-102 (1994).

Pearson et al., "Structure of the ERM Protein Moesin Reveals the FERM Domain Fold Masked by an Extended Actin Binding Tail Domain", *Cell*, 101:259-270 (2000).

Rane et al., "JAK 3: A Novel JAK Kinase Associated with Terminal Differentiation of Hematopoietic Cells", *Oncogene*, 9:2415-2423 (1994).

Rane et al., "JAKs, STATs and Src Kinases in Hematopoiesis", *Oncogene*, 21:3334-3358 (2002).

Rane et al., "Janus Kinases: Components of Multiple Signaling Pathways", *Oncogene*, 19:5662-5679 (2000).

Read, "Pushing the Boundaries of Molecular Replacement with Maximum Likelihood", *Acta Crystallographica*, D57:1373-1382 (2001).

Redington, "MOLFIT: A Computer Program for Molecular Superposition", *Comput. Chem.*, 16:217-222 (1992).

Roberts et al., "Janus Kinase 3 (JAK3) Deficiency: Clinical, Immunologic, and Molecular Analyses of 10 Patients and Outcomes of Stem Cell Transplantation", *Blood*, 103:2009-2018 (2004).

Säemann et al., "Suppression of Early T-Cell-Receptor-Triggered Cellular Activation by the Janus Kinase 3 Inhibitor WHI-P-154", *Transplantation*, 75:1864-1872 (2003).

Saharinen et al., "Regulation of the Jak2 Tyrosine Kinase by Its Pseudokinase Domain", *Molecular and Cellular Biology*, 20:3387-3395 (2000).

Saharinen et al., "The Pseudokinase Domain is Required for Suppression of Basal Activity of Jak2 and Jak3 Tyrosine Kinases and for Cytokine-Inducible Activation of Signal Transduction", *Journal of Biological Chemistry*, 277:47954-47963 (2002).

Saharinen et al., "Autoinhibition of Jak2 Tyrosine Kinase is Dependent on Specific Regions in its Pseudokinase Domain", *Molecular Biology of the Cell*, 14:1448-1459 (2003).

Schnare et al., "Comprehensive Comparison of Structural Characteristics in Eukaryotic Cytoplasmic Large Subunit (23 S-like) Ribosomal RNA", *Journal of Molecular Biology*, 256:701-719 (1996).

Schulze-Gahmen et al., "Multiple Modes of Ligand Recognition: Crystal Structures of Cyclin-Dependent Protein Kinase 2 in Complex with ATP and Two Inhibitors, Olomoucine and Isopentenyladenine", *Proteins Structure Function and Genetics*, 22:378-391 (1995).

Schulze-Gahmen et al., "High-Resolution Crystal Structures of Human Cyclin-Dependent Kinase 2 with and without ATP: Bound Waters and Natural Ligand as Guides for Inhibitor Design", *Journal of Medicinal Chemistry*, 39:4540-4546 (1996).

Smith et al., "Comparison of Biosequences", *Advances in Applied Mathematics*, 2:482-489 (1981).

Stamos et al., "Structure of the Epidermal Growth Factor Receptor Kinase Domain Alone and in Complex with a 4-Anilinoquinazoline Inhibitor", *Journal of Biological Chemistry*, 277:46265-46272 (2002).

Stepkowski et al., "Selective Inhibitor of Janus Tyrosine Kinase 3, PNU156804, Prolongs Allograft Survival and Acts Synergistically with Cyclosporine but Additively with Rapamycin", *Blood*, 15:680-689 (2002).

Sudbeck et al., "Structure-Based Design of Specific Inhibitors of Janus Kinase 3 as Apoptosis-Inducing Antileukemic Agents", *Clinical Cancer Research*, 5:1569-1582 (1999).

Szklarz et al., "Use of Homology Modeling in Conjunction with Site-Directed Mutagenesis for Analysis of Structure-Function Relationships of Mammalian Cytochromes P450", *Life Sciences*, 61:2507-2520 (1997).

Terawaki et al., "Crystallographic Characterization of the Radixin FERM Domain Bound to C-terminal Region of the Human $Na^+/H^+$-Exchanger Regulatory Factor (NHERF)", *Acta Crystallographica*, D59:177-179 (2003).

Thomis et al., "Defects in B Lymphocyte Maturation and T Lymphocyte Activation in Mice Lacking Jak3", *Science*, 270:794-797 (1995).

Vihinen et al., "Molecular Modeling of the JAK3 Kinase Domains and Structural Basis for Severe Combined Immunodeficiency", *Clinical Immunology*, 96:108-118 (2000).

Wishart et al., "Constrained Multiple Sequence Alignment Using XALIGN", *Computer Applications in the Biosciences*, 10:687-688 (1994).

Xie et al., "Crystal Structure of JNK3: A Kinase Implicated in Neuronal Apoptosis", *Structure*, 6:983-991 (1998).

Xu et al., "Three-Dimensional Structure of the Tyrosine Kinase c-Src", *Nature*, 385:595-602 (1997).

Zhou et al., "Distinct Tyrosine Phosphorylation Sites in Jak3 Kinase Domain Positively and Negatively Regulate Its Enzymatic Activity", *PNAS*, 94:13850-13855 (1997).

Zhou et al., "Unexpected Effects of FERM Domain Mutations on Catalytic Activity of Jak3: Structural Implication for Janus Kinases", *Molecular Cell*, 8:959-969 (2001).

"The *CCP4* Suite: Programs for Protein Crystallography", Collaborative Computational Project, No. 4, *Acta Crystallographica*, D50:760-763 (1994).

\* cited by examiner

CRYSTAL STRUCTURE OF HUMAN JAK3 KINASE DOMAIN COMPLEX AND BINDING POCKETS THEREOF

This application is a divisional of U.S. application Ser. No. 11/114,979, filed Apr. 26, 2005, now U.S. Pat. No. 7,558,717, which claims priority from Provisional Application No. 60/669,771, filed Apr. 8, 2005 and Provisional Application No. 60/566,393, filed Apr. 28, 2004. Each of these prior applications is incorporated herein by reference.

TECHNICAL FIELD OF INVENTION

The present invention relates to human Janus Kinase 3 (JAK3) and JAK3-like binding pockets. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to JAK3 protein or JAK3 protein homologues, or complexes thereof. The invention also relates to crystallizable compositions and crystals comprising JAK3 kinase domain and JAK3 kinase domain complexed with AMP-PNP.

BACKGROUND OF THE INVENTION

Janus kinases (JAKs) are non-receptor tyrosine kinases that play an essential role in cytokine signaling (Darnell et al., *Science* 264: 1415-1421 (1994); Ihle, *Adv. Immunol.* 60:1-35 (1995)). The JAK family consists of four evolutionary-conserved mammalian JAK proteins, JAK1, JAK2, JAK3 and TYK2, which are each approximately 120 kDa in molecular mass, and homologues in other vertebrates such as chicken, and zebrafish and *drosophila*. These kinases appear to be responsible for the transmission of signal by most cytokines and neurokines (Rane and Reddy, *Oncogene* 19: 5662-5679 (2000)). Accumulated evidence suggests that binding of cytokines to their receptors induces receptor oligomerization, which results in an increased affinity of the cytoplasmic domain of the receptor for the JAK kinases. As a consequence of this increased affinity, the JAK kinases are recruited to the receptors resulting in their phosphorylation and subsequent activation. The activated JAKs then phosphorylate the cytoplasmic tails of the receptors on target tyrosines residues, which in turn serve as the docking sites for the Src-homology-2 (SH2) domains of signal transducer and activation of transcription (STAT) proteins. The recruited STATs are phosphorylated by JAKs on specific tyrosine residues, which causes their release from the receptor and finally dimerization through a reciprocal phosphotyrosine-SH2 domain interaction (Chen et al., *Cell* 93:827-839 (1998); Becker et al., *Nature* 394: 145-151 (1998)). The dimerized STAT proteins then translocate to the nucleus where they act as transcription factors.

A unique feature of the domain-structure of JAKs that distinguishes them from other tyrosine kinases is the presence of two tandem domains with extensive homology to tyrosine kinases, a C-terminal catalytic domain and an immediately preceded pseudokinase domain (Ihle, supra). The pseudokinase domain lacks canonical residues that are essential for catalytic function. Several lines of evidence suggest that this domain regulates catalytic activity and autophosphorylation (Saharinen et al., *Mol. Biol. Cell* 14: 1448-1459 (2003); Saharinen et al., *Mol. Cell. Biol.* 20: 3387-3395 (2000); Saharinen et al., *J. Biol. Chem.* 277: 47954-47963 (2002); Chen et al., *Mol. Cell. Biol.* 20: 947-956 (2000)).

In addition to the two kinase domains, JAKs contain an N-terminal band four-point-one, erzin, radixin, moesin (FERM) homology domain and an SH2-like domain (Girault et al., *Trends Biochem. Sci.* 24: 54-57 (1999)). The FERM domain is a 300-amino acid protein-protein interaction module that mediates receptor interactions and is important for the preservation of proper catalytic function (Terawaki et al., *Acta Crystallog.* D59: 177-179 (2003); Smith et al., *J. Biol. Chem.* 278: 4949-4956 (2003); Hamada et al., *EMBO J.* 19: 4449-4462 (2000); Hamada et al., *EMBO J.* 22: 502-514 (2003); Pearson et al., *Cell* 101: 259-270 (2000); Zhou et al., *Mol. Cell.* 8: 959-969 (2001)).

The activity of JAKs is also regulated by the two tyrosines in the activation loop of the catalytic domain (Gauzzi et al., *J. Biol. Chem.* 271: 20494-20500 (1996); Feng et al., *Mol. Cell. Biol.* 17: 2497-2501 (1997); Zhou et al., *Proc. Natl. Acad. Sci. USA* 94: 13850-13855 (1997)). In JAK3, phosphorylation of Tyr980 and Tyr981 results in positive and negative regulation of its enzymatic activity, respectively (Zhou, supra).

JAK3 is predominantly expressed in lymphoid and myeloid cell lines and in hematopoietic tissues such as the thymus, bone marrow, spleen, and fetal liver (Rane and Reddy, *Oncogene* 21:3334-3358 (2002)). In contrast, other JAKs are ubiquitously expressed. JAK3 specifically associates with the common γ chain (γc) of the cytokine receptors for interleukin-2 (IL-2), IL-4, IL-7, IL-9, IL-15 and IL-21 (Kisseleva et al., *Gene* 285:1-24 (2002); O'Shea et al., *Cell* 109 Suppl: S121-131 (2002)). In humans, mutations in JAK3 or γc result in severe combined immunodeficiency (SCID), which is characterized by the absence of circulating mature T cells and natural killer cells, but not B cells (T$^-$B$^+$SCID) (Notarangelo et al., *Hum. Mutat.* 18: 255-263 (2001); Roberts et al., *Blood* 103:2009-2018 (2004); Epub in November 2003). JAK3−− mice also exhibit severe immunodeficiency (Thomis et al., *Science* 270: 794-797 (1995)).

Therapeutic targeting of JAK3 kinase has received particular attention, because the effects owing to the complete absence of JAK3 are limited to the immune system. Several JAK3 inhibitors, such as JANEX-1, AG-490, WHI-P154 and PNU156804 have been reported (Sudbeck et al., *Clin. Cancer Res.* 5: 1569-1582 (1999); Cetkovic-Cvrlje et al., *Arzneimittelforschung* 53: 648-654 (2003); Cetkovic-Cvrlje et al., *Clin. Immunol.* 106: 213-225 (2003); Saemann et al., *Transplantation* 75: 1864-1874 (2003); Stepkowski et al., *Blood* 99: 680-689 (2002)). More recently, Pfizer reported an orally active JAK3 selective inhibitor, CP-690,550 as an immunosuppressive agent in mouse and monkey transplant models (Changelian et al., *Science* 302: 875-878 (2003)). Collectively these data suggest that JAK3 is an attractive pharmacologic target for the treatment of immune-mediated transplant rejection (Kirken, *Transplant Proc.* 33: 3268-3270 (2001)).

Despite its importance in SCID and as a clinical target for immunosuppression, very little is known about the three-dimensional structure of JAK3. Drug design for human therapy has been hampered because the structure of JAK3 was not previously known. Without structural information of JAK3, the detailed knowledge of the mechanism is limited and progress of designing drugs as specific inhibitors is impeded. Structural information on the unique features of the active site of human JAK3 would facilitate drug discovery.

SUMMARY OF THE INVENTION

The present invention solves the problems identified above by providing for the first time the crystal structure of JAK3-

AMP-PNP complex. This crystal structure of human JAK3 kinase domain in complex with AMP-PNP bound to its ATP-binding site provides important structural information for the development of novel JAK3 selective inhibitors.

The present invention also provides molecules comprising JAK3 binding pockets, or JAK3-like binding pockets that have similar three-dimensional shapes. In one embodiment, the molecules are JAK3 kinase domain complexes. In another embodiment, the molecules are JAK3 kinase domain homologues, or complexes thereof. In another embodiment, the molecules are in crystalline form.

The invention provides crystallizable compositions and crystals comprising JAK3 kinase domain, complexes thereof, or homologues thereof.

The invention provides a computer comprising a machine-readable storage medium, comprising a data storage material encoded with machine-readable data, wherein the data defines the JAK3 or JAK3-like binding pocket or domain according to the structure coordinates of Table 2. Such storage medium when read and utilized by a computer programmed with appropriate software can display, on a computer screen or similar viewing device, a three-dimensional graphical representation of such binding pockets. In one embodiment, the structure coordinates of said binding pocket or domain are produced by homology modeling of at least portion of the coordinates of Table 2.

The invention also provides methods for designing, selecting, evaluating and identifying and/or optimizing compounds which bind to the molecules or molecular complexes or their binding pockets. Such compounds are potential inhibitors of JAK3, JAK3-like proteins or its homologues.

The invention also provides a method for determining at least a portion of the three-dimensional structure of molecules or molecular complexes which contain at least some structurally similar features to JAK3, particularly JAK3 homologues. This is achieved by using at least some of the structure coordinates obtained from the JAK3 kinase domain.

The present invention provides a crystal comprising a human Janus Kinase 3 kinase domain.

The present invention provides a crystal comprising a Janus Kinase 3 kinase domain homologue.

The present invention provides a crystal comprising a human Janus Kinase 3 kinase domain complex.

The present invention provides a crystal comprising a Janus Kinase 3 kinase domain homologue complex.

The present invention also provides a crystal, wherein said human Janus Kinase 3 kinase domain complex comprises human Janus Kinase 3 kinase domain and a chemical entity selected from the group consisting of adenosine, ATP, an ATP analogue, AMP-PNP, a nucleotide triphosphate, a nucleotide diphosphate, phosphate and active site inhibitor.

The present invention also provides a crystal, wherein said human Janus Kinase 3 kinase domain complex comprises human Janus Kinase 3 kinase domain and AMP-PNP.

The present invention also provides a crystal, wherein said human Janus Kinase 3 kinase domain is selected from the group consisting of amino acid residues 810-1100 of SEQ ID NO:1, amino acid residues 810-1104 of SEQ ID NO:1, amino acid residues 810-1115 of SEQ ID NO:1, amino acid residues 810-1124 of SEQ ID NO:1, and amino acid residues 813-1100 of SEQ ID NO:1.

The present invention also provides a crystal, wherein said human Janus Kinase 3 kinase domain is amino acid residues 810-1115 of SEQ ID NO:1.

The present invention provides a crystallizable composition comprising a human Janus Kinase 3 kinase domain.

The present invention provides a crystallizable composition comprising a Janus Kinase 3 kinase domain homologue.

The present invention provides a crystallizable composition comprising a human Janus Kinase 3 kinase domain complex.

The present invention provides a crystallizable composition comprising a Janus Kinase 3 kinase domain homologue complex.

The present invention also provides the crystallizable composition according to paragraph [0026], wherein said human Janus Kinase 3 kinase domain complex comprises human Janus Kinase 3 kinase domain and a chemical entity selected from the group consisting of adenosine, ATP, an ATP analogue, AMP-PNP, a nucleotide triphosphate, a nucleotide diphosphate, phosphate and active site inhibitor.

The present invention also provides the crystallizable composition according to paragraph [0026], wherein said human Janus Kinase 3 kinase domain complex comprises human Janus Kinase 3 kinase domain and AMP-PNP.

The present invention also provides the crystallizable composition according to any one of paragraphs [0024], [0026], [0028] and [0029], wherein said human Janus Kinase 3 kinase domain is selected from the group consisting of amino acid residues 810-1100 of SEQ ID NO:1, amino acid residues 813-1104 of SEQ ID NO:1, amino acid residues 810-1115 of SEQ ID NO:1, amino acid residues 810-1124 of SEQ ID NO:1, and amino acid residues 813-1100 of SEQ ID NO:1.

The present invention also provides the crystallizable composition according to any one of paragraphs [0024], [0026], [0028] and [0029], wherein said human Janus Kinase 3 kinase domain is amino acid residues 810-1115 of SEQ ID NO:1.

The present invention provides a computer comprising:
(a) a machine-readable data storage medium, comprising a data storage material encoded with machine-readable data, wherein said data defines a binding pocket or domain selected from the group consisting of:
  (i) a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the root mean square deviation of the backbone atoms between said set of amino acid residues and said human Janus Kinase 3 amino acid residues is not greater than about 2.5 Å; and
  (ii) a set of amino acid residues that are identical to human Janus Kinase 3 amino acid residues according to Table 2, wherein the root mean square deviation between said set of amino acid residues and said human Janus Kinase 3 amino acid residues is not more than about 3.0 Å;
(b) a working memory for storing instructions for processing said machine-readable data;
(c) a central processing unit coupled to said working memory and to said machine-readable data storage medium for processing said machine-readable data and a means for generating three-dimensional structural information of said binding pocket or domain; and
(d) output hardware coupled to said central processing unit for outputting three-dimensional structural information of said binding pocket or domain, or information produced using said three-dimensional structural information of said binding pocket or domain.

The present invention also provides a computer, wherein the binding pocket is produced by homology modeling of the structure coordinates of said Janus Kinase 3 amino acid residues according to Table 2.

The present invention also provides a computer, wherein said means for generating three-dimensional structural information is provided by means for generating a three-dimensional graphical representation of said binding pocket or domain.

The present invention also provides a computer, wherein said output hardware is a display terminal, a printer, CD or DVD recorder, ZIP™ or JAZ™ drive, a disk drive, or other machine-readable data storage device.

The present invention provides a method of using a computer for selecting an orientation of a chemical entity that interacts favorably with a binding pocket or domain selected from the group consisting of:
  (i) a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the root mean square deviation of the backbone atoms between said set of amino acid residues and said human Janus Kinase 3 amino acid residues is not greater than about 2.5 Å; and
  (ii) a set of amino acid residues that are identical to human Janus Kinase 3 amino acid residues according to Table 2, wherein the root mean square deviation between said set of amino acid residues and said human Janus Kinase 3 amino acid residues is not more than about 3.0 Å;
said method comprising the steps of:
  (a) providing the structure coordinates of said binding pocket or domain thereof on a computer comprising the means for generating three-dimensional structural information from said structure coordinates;
  (b) employing computational means to dock a first chemical entity in the binding pocket or domain;
  (c) quantifying the association between said chemical entity and all or part of the binding pocket or domain for different orientations of the chemical entity; and
  (d) selecting the orientation of the chemical entity with the most favorable interaction based on said quantified association.

The present invention also provides a method, further comprising generating a three-dimensional graphical representation of the binding pocket or domain prior to step (b).

The present invention also provides a method, wherein energy minimization, molecular dynamics simulations, or rigid-body minimizations are performed simultaneously with or following step (b).

The present invention also provides a method, further comprising the steps of:
  (e) repeating steps (b) through (d) with a second chemical entity; and
  (f) selecting at least one of said first or second chemical entity that interacts more favorably with said binding pocket or domain based on said quantified association of said first or second chemical entity.

The present invention provides a method of using a computer for selecting an orientation of a chemical entity with a favorable shape complementarity in a binding pocket consisting of a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the root mean square deviation of the backbone atoms between said set of amino acid residues and said human Janus Kinase 3 amino acid residues is not greater than about 2.5 Å;
said method comprising the steps of:
  (a) providing the structure coordinates of said binding pocket and all or part of the ligand bound therein on a computer comprising the means for generating three-dimensional structural information from said structure coordinates;
  (b) employing computational means to dock a first chemical entity in the binding pocket;
  (c) quantitating the contact score of said chemical entity in different orientations; and
  (d) selecting an orientation with the highest contact score.

The present invention also provides a method, further comprising generating a three-dimensional graphical representation of the binding pocket and all or part of the ligand bound therein prior to step (b).

The present invention also provides a method, further comprising the steps of:
  (e) repeating steps (b) through (d) with a second chemical entity; and
  (f) selecting at least one of said first or second chemical entity that has a higher contact score based on said quantitated contact score of said first or second chemical entity.

The present invention provides a method for identifying a candidate inhibitor of a molecule or molecular complex comprising a binding pocket or domain selected from the group consisting of:
  (i) a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the root mean square deviation of the backbone atoms between said set of amino acid residues and said human Janus Kinase 3 amino acid residues is not greater than about 2.5 Å; and
  (ii) a set of amino acid residues that are identical to human Janus Kinase 3 amino acid residues according to Table 2, wherein the root mean square deviation between said set of amino acid residues and said human Janus Kinase 3 amino acid residues is not more than about 3.0 Å;
comprising the steps of:
  (a) using a three-dimensional structure of the binding pocket or domain to design, select or optimize a plurality of chemical entities;

(b) contacting each chemical entity with the molecule or the molecular complex;
(c) monitoring the inhibition to the catalytic activity of the molecule or molecular complex by each chemical entity; and
(d) selecting a chemical entity based on the inhibitory effect of the chemical entity on the catalytic activity of the molecule or molecular complex.

The present invention provides a method of designing a compound or complex that interacts with a binding pocket or domain selected from the group consisting of:
(i) a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the root mean square deviation of the backbone atoms between said set of amino acid residues and said human Janus Kinase 3 amino acid residues is not greater than about 2.5 Å; and
(ii) a set of amino acid residues that are identical to human Janus Kinase 3 amino acid residues according to Table 2, wherein the root mean square deviation between said set of amino acid residues and said human Janus Kinase 3 amino acid residues is not more than about 3.0 Å;
comprising the steps of:
(a) providing the structure coordinates of said binding pocket or domain on a computer comprising the means for generating three-dimensional structural information from said structure coordinates;
(b) using the computer to dock a first chemical entity in part of the binding pocket or domain;
(c) docking at least a second chemical entity in another part of the binding pocket or domain;
(d) quantifying the association between the first or second chemical entity and part of the binding pocket or domain;
(e) repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket or domain on a computer screen using the three-dimensional graphical representation of the binding pocket or domain and said first and second chemical entity; and
(g) assembling the first and second chemical entity into a compound or complex that interacts with said binding pocket or domain by model building.

The present invention provides a method of utilizing molecular replacement to obtain structural information about a molecule or a molecular complex of unknown structure, wherein the molecule is sufficiently homologous to human Janus Kinase 3 kinase domain, comprising the steps of:
(a) crystallizing said molecule or molecular complex;
(b) generating an X-ray diffraction pattern from said crystallized molecule or molecular complex; and
(c) applying at least a portion of the structure coordinates set forth in Table 2 or homology model thereof to the X-ray diffraction pattern to generate a three-dimensional electron density map of at least a portion of the molecule or molecular complex whose structure is unknown; and
(d) generating a structural model of the molecule or molecular complex from the three-dimensional electron density map.

The present invention also provides a method, wherein the molecule is selected from the group consisting of a Janus Kinase 3 protein and a protein comprising a Janus Kinase 3 kinase domain Homologue.

The present invention also provides a method, wherein the molecular complex is selected from the group consistiong of a Janus Kinase 3 protein complex, a Janus Kinase 3 kinase domain complex, and a Janus Kinase 3 kinase domain homologue complex.

The present invention also provides a method for identifying a candidate inhibitor that interacts with a binding site of a human Janus Kinase 3 kinase protein or a homologue thereof, comprising the steps of:
(a) obtaining a crystal comprising said human Janus Kinase 3kinase protein or said homologue thereof, wherein the crystal is characterized with space group $P2_1$ and has unit cell parameters of a=59.98 Å, b=90.19 Å, c=69,00 Å; β=111.5°;
(b) obtaining the structure coordinates of amino acids of the crystal of step (a), wherein the structure coordinates are set forth in Table 2;
(c) generating a three-dimensional model of said human Janus Kinase 3 kinase protein or said homologue thereof using the structure coordinates of the amino acids obtained in step (b), a root mean square deviation from backbone atoms of said amino acids of not more than ±2.0 Å;
(d) determining a binding site of said human Janus Kinase 3 kinase protein or said homologue thereof from said three-dimensional model; and
(e) performing computer fitting analysis to identify the candidate inhibitor which interacts with said binding site.

The present invention also provides a method, further comprising the step of:
(f) contacting the identified candidate inhibitor with said human Janus Kinase 3 kinase protein or said homologue thereof in order to determine the effect of the inhibitor on human Janus Kinase 3 kinase protein activity.

The present invention also provides a method, wherein the binding site said human Janus Kinase 3 kinase protein or said homologue thereof determined in step (d) comprises the structure coordinates according to Table 2 of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957Ala966, Asp967Leu970, Glu985, Gln988, Ser989, Pro990 and Trp 993, wherein the root mean square deviation from the backbone atoms of said amino acids is not more than ±2.0 Å.

The present invention also provides a method for identifying a candidate inhibitor that interacts with a binding site of a human Janus Kinase 3 kinase protein or a homologue thereof, comprising the steps of:
(a) obtaining a crystal comprising said human Janus Kinase 3 kinase protein or said homologue thereof, wherein the crystal is characterized with space group P2₁ and has unit cell parameters of a=59.98 Å, b=90.19 Å, c=69.00 Å; β=111.5°;

(b) obtaining the structure coordinates of amino acids of the crystal of step (a);

(c) generating a three-dimensional model of said human Janus Kinase 3 kinase protein or said homologue thereof using the structure coordinates of the amino acids generated in step (b), a root mean square deviation from backbone atoms of said amino acids of not more than ±2.0 Å;

(d) determining a binding site of said human Janus Kinase 3 kinase protein or said homologue thereof from said three-dimensional model; and (e) performing computer fitting analysis to identify the candidate inhibitor which interacts with said binding site.

The present invention also provides a method, further comprising the step of:

(f) contacting the identified candidate inhibitor with said human Janus Kinase 3 kinase protein or said homologue thereof in order to determine the effect of the inhibitor on human Janus Kinase 3 kinase protein activity.

The present invention also provides a method, wherein the binding site of said human Janus Kinase 3 kinase protein or said homologue thereof determined in step (d) comprises the structure coordinates according to Table 2 of a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993, wherein the root mean square deviation from the backbone atoms of said amino acids is not more than ±2.0 Å.

The present invention also provides the method for identifying a candidate inhibitor that interacts with a binding site of a human Janus Kinase 3 kinase protein or a homologue thereof, comprising the step of determining a binding site of said human Janus Kinase 3 kinase protein or the homologue thereof from a three-dimensional model to design or identify the candidate inhibitor which interacts with said binding site.

The present invention also provides a method, wherein the binding site of said human Janus Kinase 3 kinase protein or said homologue thereof determined comprises the structure coordinates according to Table 2 of a set of amino acid residues that are identical to human Janus Kinase 3amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993, wherein the root mean square deviation from the backbone atoms of said amino acids is not more than ±2.0 Å.

The present invention also provides a method for identifying a candidate inhibitor of a molecule or molecular complex comprising a binding pocket or domain selected from the group consisting of:

(i) a set of amino acid residues which are identical to human Janus Kinase 3 kinase a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993 according to Table 2, wherein the root mean square deviation of the backbone atoms between said set of amino acid residues and said human Janus Kinase 3 kinase amino acid residues is not greater than about 2.0 Å; and (ii) a set of amino acid residues that are identical to human Janus Kinase 3kinase amino acid residues according to Table 2, wherein the root mean square deviation between said set of amino acid residues and said human Janus Kinase 3 kinase amino acid residues is not more than about 3.0 Å;

comprising the steps of:

(a) using a three-dimensional structure of the binding pocket or domain to design, select or optimize a plurality of chemical entities; and (b) selecting said candidate inhibitor based on the inhibitory effect of said chemical entities a human Janus Kinase 3 kinase protein or a human Janus Kinase 3kinase protein homologue on the catalytic activity of the molecule or molecular complex.

The present invention also provides a method of using the crystal in an inhibitor screening assay comprising:

(a) selecting a potential inhibitor by performing rational drug design with a three-dimensional structure determined for the crystal, wherein said selecting is performed in conjunction with computer modeling;

(b) contacting the potential inhibitor with a kinase; and (c) detecting the ability of the potential inhibitor for inhibiting the kinase.

DESCRIPTION OF THE INVENTION

Figure 1:
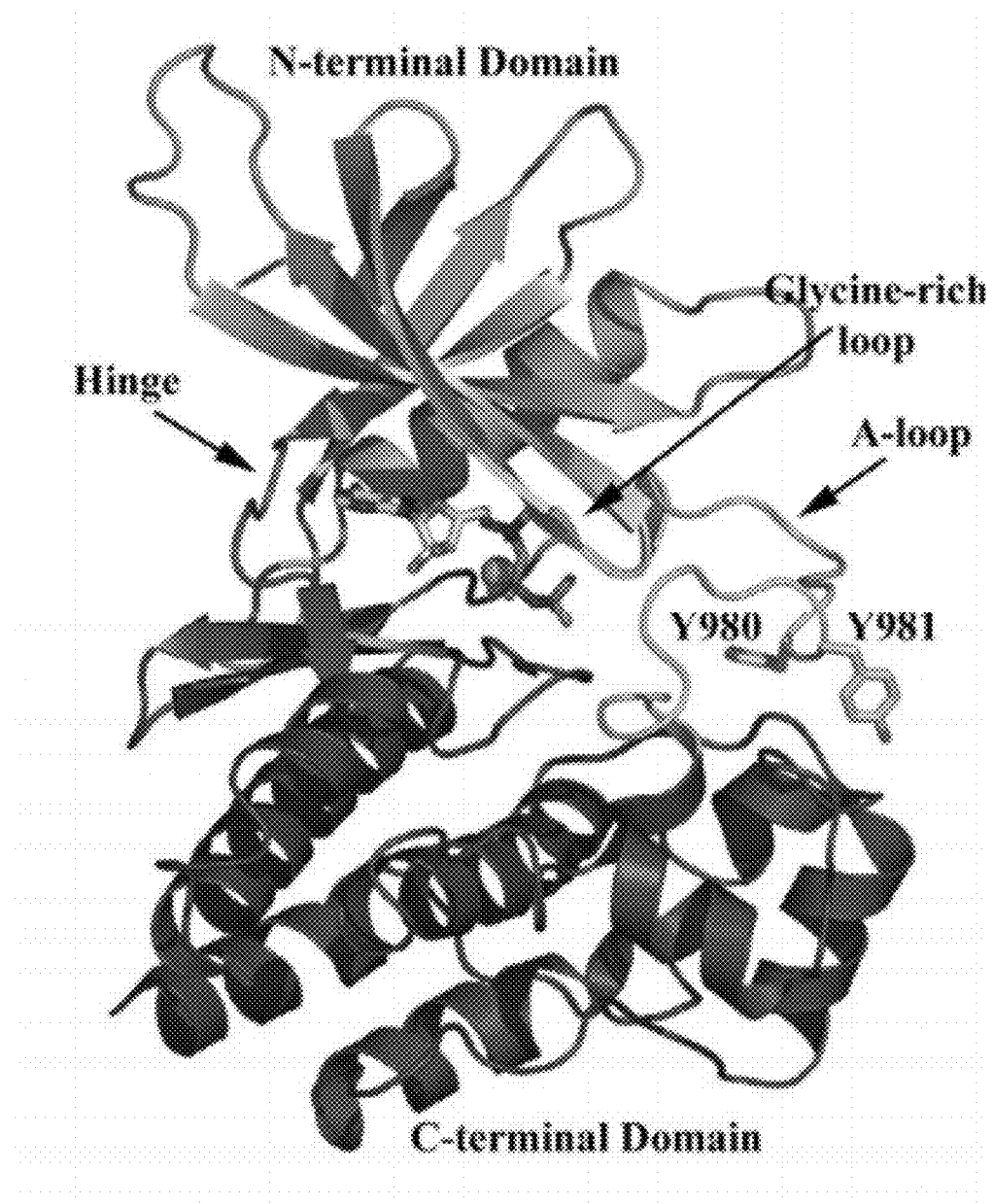
FIG. 1 depicts a ribbon diagram of the overall fold of the JAK3-AMP-PNP complex. The N-terminal and the C-terminal domains are colored light gray and dark gray, respectively. The N-terminal domain, the C-terminal domain, the glycine-rich loop or P-loop which contains the G-X-G-X-X-G motif (SEQ ID NO: 7) in the N-terminal lobe, the hinge region between the N- and C-terminal domains, and the activation loop or A-loop in the C-terminal domain are labeled. The AMP-PNP is shown in a stick representation, and the magnesium ion is represented by a sphere. The two tyrosines which have been shown to be phosphorylated (Y980 and Y981) are on the A-loop and are shown in sticks representation and labeled.
Figure 2:
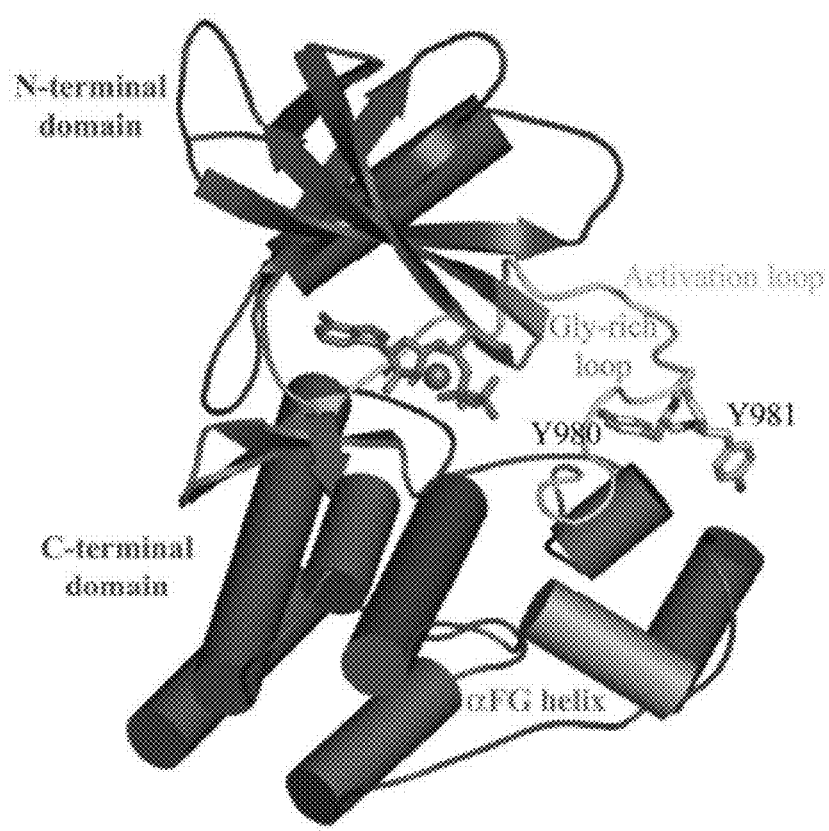
FIG. 2 depicts the overall structure of the Jak3-AMP-PNP complex. The structure is shown with β-sheets as arrows and the α-helices as cylinders. The N-terminal lobe is shown with the glycine rich loop. The C-terminal lobe is shown with the activation loop. The α-FG helix is labeled. The non-hydrolyzable ATP analogue, AMP-PNP, is shown as ball-and-stick format, in the active site. The sites of phosphorylation located in the activation loop, Tyr980 and Tyr981, are shown. All structural figures were prepared with Pymol (DeLano, W. L. (2002), DeLano Scientific, San Carlos, Calif., USA).
Figure 3:
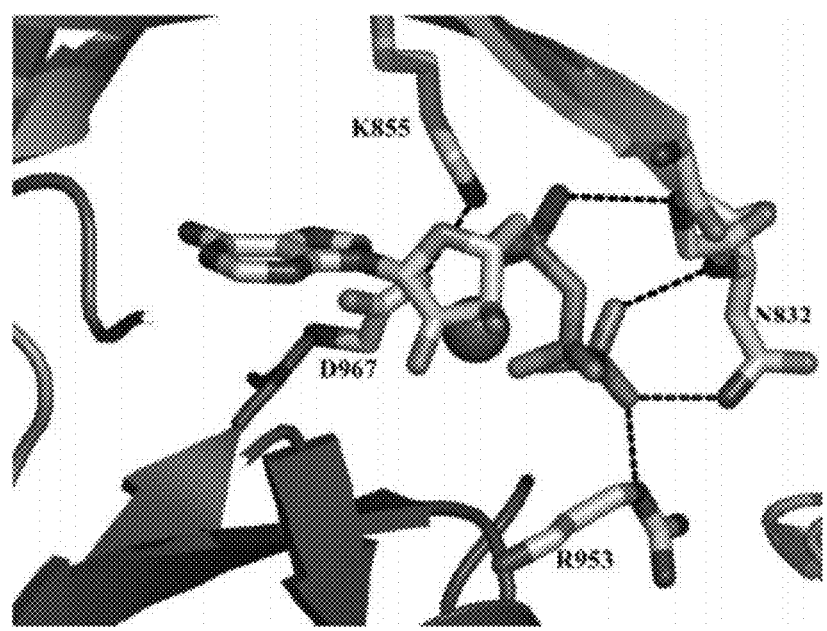
FIG. 3 shows a detailed representation of the active site of JAK3 with AMP-PNP depicting some of the hydrogen bonds formed between the AMP-PNP and amino acid sidechains of JAK3 as dashed-lines. The bond between the catalytic amino acid residue K855 and D967 is also shown as a dashed-line.
Figure 4:
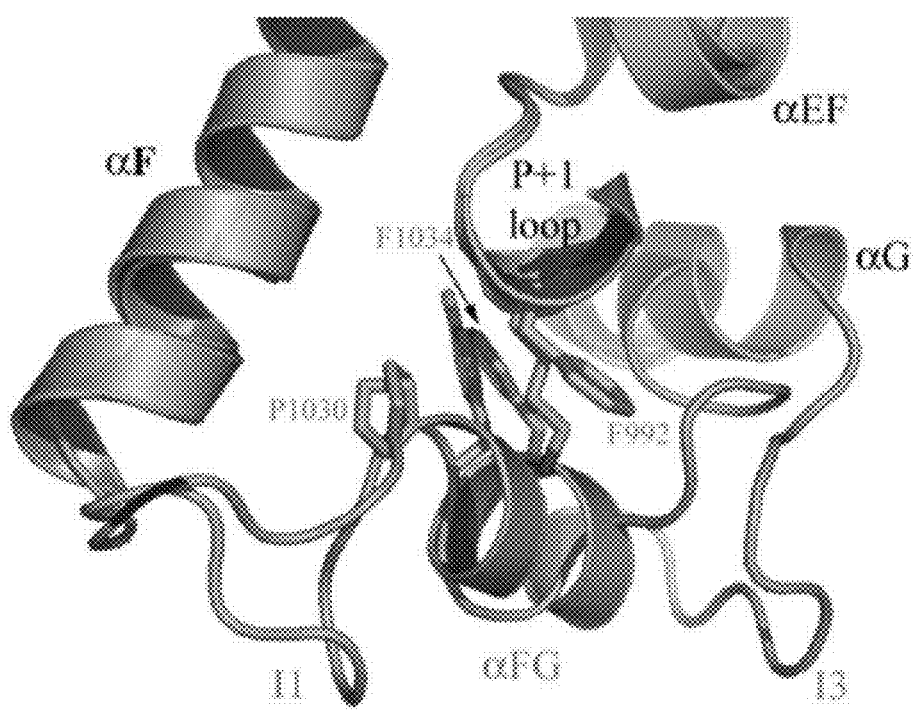
FIG. 4 shows αF and αG of Jak3 were superimposed on c-Src. The I1 and I3 regions jut out from this area. This is perhaps an area for either intra or inter protein-protein interactions. The proximity of the αFG region to the activation loop suggests that it may play a role in the activation of Jak3.
Figure 5:
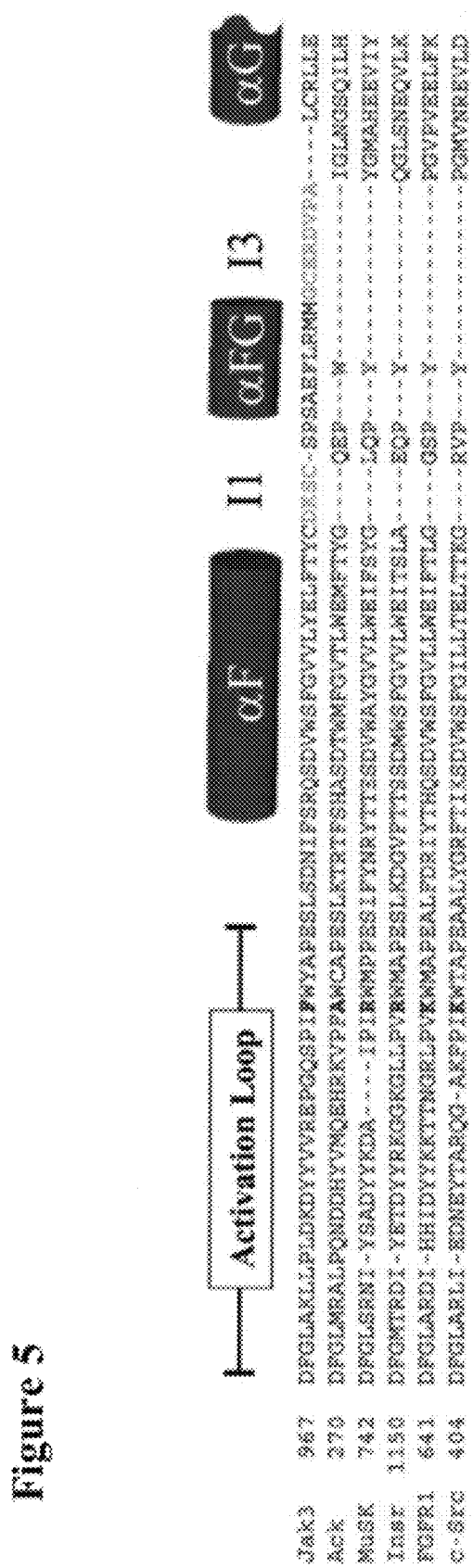
FIG. 5 shows the α-FG region is unique to Janus kinases. The sequence between αF and αG is conserved in the janus kinases and unique among the other tyrosine kinases. The aligned sequences of Jak3 (amino acid residues 967-1052 of SEQ ID NO: 1) with a variety of other tyrosine kinases, including Ack (SEQ ID NO: 2); MuSK (SEQ ID NO: 3); Insr (SEQ ID NO: 4); FGFR1 (SEQ ID NO: 5); c-Src (SEQ ID NO: 6). The sequences were aligned using the "Align and Superpose" option in Quanta, and then manually aligned based on the resultant structural superposition. The bold black residue corresponds to the residue in the P+1 loop that is typical an arginine or lysine in all tyrosine kinases except the four mammalian Jaks and the closely related 2 Ack kinases, Ack1 and Tnk1.

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | | |
|---|---|---|
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |

-continued

| | | |
|---|---|---|
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |

Other abbreviations that are used throughout the application include: ANP (for AMP-PNP).

As used herein, the following definitions shall apply unless otherwise indicated.

The term "about" when used in the context of root mean square deviation (RMSD) values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding, hydrophobic, van der Waals or electrostatic interactions—or it may be covalent.

The term "ATP analogue" refers to a compound derived from adenosine-5'-triphosphate (ATP). The compound can be adenosine, AMP, ADP, or a non-hydrolyzable analogue, such as, but not limited to AMP-PNP. The analogue may be in complex with magnesium or manganese ions.

The term "binding pocket" refers to a region of a molecule or molecular complex, that, as a result of its shape, favorably associates with another chemical entity. The term "pocket" includes, but is not limited to, a cleft, channel or site. JAK3, JAK3-like molecules or homologues thereof may have binding pockets which include, but are not limited to, peptide or substrate binding sites, and ATP-binding sites. The shape of a binding pocket may be largely pre-formed before binding of a chemical entity, may be formed simultaneously with binding of a chemical entity, or may be formed by the binding of another chemical entity to a different binding pocket of the molecule, which in turn induces a change in shape of the binding pocket.

The term "catalytic active site" or "active site" refers to the portion of the protein kinase to which nucleotide substrates bind. For example, the catalytic active site of JAK3 is at the interface between the N-terminal and C-terminal domains.

The term "chemical entity" refers to chemical compounds, complexes of at least two chemical compounds, and fragments of such compounds or complexes. The chemical entity can be, for example, a ligand, substrate, nucleotide triphosphate, nucleotide diphosphate, phosphate, nucleotide, agonist, antagonist, inhibitor, antibody, peptide, protein or drug. In one embodiment, the chemical entity is an inhibitor or substrate for the active site.

The term "conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure*, 5: 345-352 (1978 & Supp.), which is incorporated herein by reference. Examples of conservative substitutions are substitutions including but not limited to the following groups: (a) valine, glycine; (b) glycine, alanine; (c)

valine, isoleucine, leucine; (d) aspartic acid, glutamic acid; (e) asparagine, glutamine; (f) serine, threonine; (g) lysine, arginine, methionine; and (h) phenylalanine, tyrosine.

The term "contact score" refers to a measure of shape complementarity between the chemical entity and binding pocket, which is correlated with an RMSD value obtained from a least square superimposition between all or part of the atoms of the chemical entity and all or part of the atoms of the ligand bound (for example, AMP-PNP) in the binding pocket according to Table 2. The docking process may be facilitated by the contact score or RMSD values. For example, if the chemical entity moves to an orientation with high RMSD, the system will resist the motion. A set of orientations of a chemical entity can be ranked by contact score. A lower RMSD value will give a higher contact score. See Meng et al. *J. Comp. Chem.* 4: 505-524 (1992).

The term "correspond to" or "corresponding amino acid" when used in the context of amino acid residues that correspond to JAK3 amino acid residues refers to particular amino acid residues or analogues thereof in a JAK3 kinase domain homologue that corresponds to amino acid residues in the human JAK3 kinase domain. The corresponding amino acid may be an identical, mutated, chemically modified, conserved, conservatively substituted, functionally equivalent or homologous amino acid residue when compared to the JAK3 amino acid residue to which it corresponds.

Methods for identifying a corresponding amino acid are known in the art and are based upon sequence, structural alignment, its functional position, or a combination thereof as compared to the JAK3 kinase. For example, corresponding amino acids may be identified by superimposing the backbone atoms of the amino acids in JAK3 and the protein using well known software applications, such as QUANTA (Accelrys, San Diego, Calif. ©2001, 2002). The corresponding amino acids may also be identified using sequence alignment programs such as the "bestfit" program or CLUSTAL W Alignment Tool (Higgins et al., *Methods Enzymol.* 266: 383-402 (1996)).

The term "crystallization solution" refers to a solution that promotes crystallization comprising at least one agent, including a buffer, one or more salts, a precipitating agent, one or more detergents, sugars or organic compounds, lanthanide ions, a poly-ionic compound and/or a stabilizer.

The term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et al. *J. Comp. Chem.* 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., *J. Mol. Recognition* 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., *J. Med. Chem.* 33:889-894 (1990)). Docking can also be performed by combining a Monte Carlo search technique with rapid energy evaluation using molecular affinity potentials. See Goodsell and Olson, *Proteins: Structure, Function and Genetics* 8:195-202 (1990). Software programs that carry out docking functions include but are not limited to MATCH-MOL (Cory et al., *J. Mol. Graphics* 2: 39 (1984); MOLFIT (Redington, *Comput. Chem.* 16 217 (1992)) and DOCK (Meng et al., supra).

The term "full-length JAK3" refers to the complete human JAK3 protein (amino acid residues 1 to 1124; SEQ ID NO:1).

The term "generating a three-dimensional structure" or "generating a three-dimensional representation" refers to converting the lists of structure coordinates into structural models or graphical representation in three-dimensional space. This can be achieved through commercially or publicly available software. A model of a three-dimensional structure of a molecule or molecular complex can thus be constructed on a computer screen by a computer that is given the structure coordinates and that comprises the correct software. The three-dimensional structure may be displayed or used to perform computer modeling or fitting operations. In addition, the structure coordinates themselves, without the displayed model, may be used to perform computer-based modeling and fitting operations.

The term "homologue of JAK3 kinase domain" or "JAK3 kinase domain homologue" refers to a domain that retains JAK3 kinase activity and that has mutations, conservative substitutions, or both, as compared to the human JAK3 kinase domain. In one embodiment, the homologue is at least 95%, 96%, 97%, 98% or 99% identical in sequence to amino acid residues 810-1124 of SEQ ID NO:1, and has conservative substitutions as compared to the JAK3 kinase domain. In another embodiment, the homologue is at least 95%, 96%, 97%, 98% or 99% identical in sequence to amino acid residues 813-1100 of SEQ ID NO:1, and has conservative substitutions as compared to the JAK3 kinase domain. Examples of homologues include but are not limited to the following: the kinase domains of JAK3 from another species or the foregoing, with mutations, conservative substitutions, or both. Such animal species include, but are not limited to, mouse, rat, a primate such as monkey or other primates.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "interaction energy" refers to the energy determined for the interaction of a chemical entity and a binding pocket, domain, molecule or molecular complex or portion thereof. Interactions include but are not limited to one or more of covalent interactions, non-covalent interactions such as hydrogen bond, electrostatic, hydrophobic, aromatic, van der Waals interactions, and non-complementary electrostatic interactions such as repulsive charge-charge, dipole-dipole and charge-dipole interactions. As interaction energies are measured in negative values, the lower the value the more favorable the interaction.

The term "JAK" refers to the kinases from the JAK kinase family. Examples of this family of kinases include but are not limited to JAK3, JAK2, JAK1 and TYK2.

The term "JAK3 ATP-binding pocket" refers to a binding pocket of a molecule or molecular complex defined by the structure coordinates of a certain set of amino acid residues present in the JAK3 structure, as described below. In general, the ligand for the ATP-binding pocket is a nucleotide such as ATP. This binding pocket is in the catalytic active site of the catalytic domain. In the protein kinase family, the ATP-binding pocket is generally located at the interface of the N-terminal and C-terminal domains, and is bordered by the glycine rich loop and the hinge (See, Xie et al., *Structure* 6: 983-991 (1998), incorporated herein by reference).

The term "JAK3 catalytic domain", "JAK3 kinase catalytic domain", "JAK3 protein kinase catalytic domain", "JAK3 catalytic kinase domain" or "JAK3 kinase domain" refers to human JAK3 amino acid residues 810-1115 of SEQ ID NO:1, or the foregoing with additions and deletions of up to 9 amino acid residues at the C-terminal and/or 20 amino acids at the N-terminal of these amino acid residues. The kinase domain includes the catalytic active site.

The term "JAK3 inhibitor-binding pocket" refers to that portion of the JAK3 enzyme active site to which the inhibitor binds. The inhibitor-binding pocket is defined by the structure coordinates of a certain set of amino acid residues present in the JAK3-inhibitor structure.

The term "JAK3-like" refers to all or a portion of a molecule or molecular complex that has a commonality of shape to all or a portion of the JAK3 protein. For example, in the JAK3-like ATP-binding pocket, the commonality of shape is defined by a root mean square deviation of the structure coordinates of the backbone atoms between the amino acids in the JAK3-like ATP-binding pocket and the JAK3 amino acids in the JAK3 ATP-binding pocket as set forth in Table 2. Compared to the amino acids of the JAK3 ATP-binding pocket, the corresponding amino acid residues in the JAK3-like binding pocket may or may not be identical. Depending on the set of JAK3 amino acid residues that define the JAK3 ATP-binding pocket, one skilled in the art would be able to locate the corresponding amino acid residues that define a JAK3-like binding pocket in a protein based on sequence or structural homology.

The term "JAK3 protein complex" or "JAK3 homologue complex" refers to a molecular complex formed by associating the JAK3 protein or JAK3 homologue with a chemical entity, for example, a ligand, a substrate, nucleotide triphosphate, nucleotide diphosphate, phosphate, an agonist or antagonist, inhibitor, antibody, drug or compound.

The term "motif" refers to a group of amino acid residues in the JAK3 kinase or homologue that defines a structural compartment or carries out a function in the protein, for example, catalysis, structural stabilization or phosphorylation. The motif may be conserved in sequence, structure and function. The motif can be contiguous in primary sequence or three-dimensional space. Examples of a motif include, but are not limited to, a binding pocket, activation loop, the glycine-rich loop, and the DFG loop (See, Xie et al., *Structure* 6: 983-991 (1998).

The term "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. For example, the portion of amino acid residues may be key residues that play a role in ligand binding, or may be residues that are spatially related and define a three-dimensional compartment of the binding pocket. The amino acid residues may be contiguous or non-contiguous in primary sequence. In one embodiment, part of the binding pocket has at least two amino acid residues, preferably at least three, six, eight, ten, fourteen or fifteen amino acid residues.

The term "part of a JAK3 kinase domain" or "part of a JAK3 kinase domain homologue" refers to less than all of the amino acid residues of a JAK3 kinase domain or kinase domain homologue. In one embodiment, part of the JAK3 kinase domain or kinase domain homologue defines the binding pockets, sub-domains, and motifs. The structure coordinates of amino acid residues that constitute part of a JAK3 kinase domain or JAK3 kinase domain homologue may be specific for defining the chemical environment of the protein, or useful in designing fragments of an inhibitor that interact with those residues. The portion of amino acid residues may also be residues that are spatially related and define a three-dimensional compartment of the binding pocket or motif. The amino acid residues may be contiguous or non-contiguous in primary sequence. For example, the portion of amino acid residues may be key residues that play a role in ligand or substrate binding, peptide binding, antibody binding, catalysis, structural stabilization or degradation.

The term "quantified association" refers to calculations of distance geometry and energy. Energy can include but is not limited to interaction energy, free energy and deformation energy. See Cohen, supra.

The term "root mean square deviation" or "RMSD" means the square root of the arithmetic mean of the squares of the deviations from the mean. It is a way to express the deviation or variation from a trend or object. For purposes of the invention, the "root mean square deviation" defines the variation in the backbone atoms of JAK3, a binding pocket, a motif, a domain, or portion thereof, as defined by the structure coordinates of JAK3 described herein. It would be apparent to the skilled worker that the calculation of RMSD involves a standard error of ±0.1 Å.

The term "soaked" refers to a process in which the crystal is transferred to a solution containing the compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain.

The term "substantially all of a JAK3 binding pocket" or "substantially all of a JAK3 kinase domain" refers to all or almost all of the amino acids in the JAK3 binding pocket or kinase domain. For example, substantially all of a JAK3 binding pocket can be 100%, 95%, 90%, 80%, or 70% of the residues defining the JAK3 binding pocket.

The term "substrate binding pocket" refers to the binding pocket for a substrate of JAK3 or homologue thereof. A substrate is generally defined as the molecule upon which an enzyme performs catalysis. Natural substrates, synthetic substrates or peptides, or mimics of a natural substrate of JAK3 or homologue thereof may associate with the substrate binding pocket.

The term "sufficiently homologous to JAK3" kinase domain refers to a protein that has a sequence identity of at least 25% compared to JAK3 kinase domain. In other embodiments, the sequence identity is at least 40%. In other embodiments, the sequence identity is at least 50%, 60%, 70%, 80%, 90%, 95%, 96%, 97%, 98% or 99%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for a JAK3 molecule or molecular complex or homologues thereof, calculating or minimizing energies for an association of a JAK3 molecule or molecular complex or homologues thereof to a chemical entity.

Crystallizable Compositions and Crystals of JAK3 Kinase Domain and Complexes Thereof According to one embodiment, the invention provides a crystal or crystallizable composition comprising a JAK3 kinase domain, a JAK3 kinase domain homologue, a JAK3 kinase domain complex, or a JAK3 kinase domain homologue complex. In one embodiment, the chemical entity is an ATP analogue, nucleotide triphosphate, nucleotide diphosphate, phosphate, adenosine or AMP-PNP. In a certain embodiment, the chemical entity is AMP-PNP.

The JAK3 kinase domain in the crystal or crystallizable composition may be amino acid residues 810-1124 of SEQ ID NO:1, amino acid residues 810-1115 of SEQ ID NO:1, amino acid residues 810-1104 of SEQ ID NO:1, amino acid residues 810-1100 of SEQ ID NO:1 or amino acid residues 813-1100 of SEQ ID NO:1; the JAK3 kinase domain homologue may be the foregoing with conservative substitutions.

```
                                                    SEQ ID NO: 1
         10         20         30         40         50
MAPPSEETPL IPQRSCSLLS TEAGALHVLL PARGPGPPQR LSFSFGDHLA 60         70         80         90        100
EDLCVQAAKA SGILPVYHSL FALATEDLSC WFPPSHIFSV EDASTQVLLY 110        120        130        140        150
RIRFYFPNWF GLEKCHRFGL RKDLASAILD LPVLEHLFAQ HRSDLVSGRL 160        170        180        190        200
PVGLSLKEQG ECLSLAVLDL ARMAREQAQR PGELLKTVSY KACLPPSLRD 210        220        230        240        250
LIQGLSFVTR RRIRRTVRRA LRRVAACQAD RHSLMAKYIM DLERLDPAGA 260        270        280        290        300
AETFHVGLPG ALGGHDGLGL LRVAGDGGIA WTQGEQEVLQ PFCDFPEIVD 310        320        330        340        350
ISIKQAPRVG PAGEHRLVTV TRTDNQILEA EFPGLPEALS FVALVDGYFR 360        370        380        390        400
LTTDSQHFFC KEVAPPRLLE EVAEQCHGPI TLDFAINKLK TGGSRPGSYV 410        420        430        440        450
LRRSPQDFDS FLLTVCVQNP LGPDYKGCLI RRSPTGTFLL VGLSRPHSSL 460        470        480        490        500
RELLATCWDG GLHVDGVAVT LTSCCIPRPK EKSNLIVVQR GHSPPTSSLV 510        520        530        540        550
QPQSQYQLSQ MTFHKIPADS LEWHENLGHG SFTKIYRGCR HEVVDGEARK 560        570        580        590        600
TEVLLKVMDA KHKNCMESFL EAASLMSQVS YRHLVLLHGV CMAGDSTMVQ 610        620        630        640        650
EFVHLGAIDM YLRKRGHLVP ASWKLQVVKQ LAYALNYLED KGLPHGNVSA 660        670        680        690        700
RKVLLAREGA DGSPPFIKLS DPGVSPAVLS LEMLTDRIPW VAPECLREAQ 710        720        730        740        750
TLSLEADKWG FGATVWEVFS GVTMPISALD PAKKLQFYED RQQLPAPKWT 760        770        780        790        800
ELALLIQQCM AYEPVQRPSF RAVIRDLNSL ISSDYELLSD PTPGALAPRD 810        820        830        840        850
GLWNGAQLYA CQDPTIFEER HLKYISQLGK GNFGSVELCR YDPLGDNTGA 860        870        880        890        900
LVAVKQLQHS GPDQQRDFQR EIQILKALHS DFIVKYRGVS YGPGRQSLRL 910        920        930        940        950
VMEYLPSGCL RDFLQRHRAR LDASRLLLYS SQICKGMEYL GSRRCVHRDL 960        970        980        990       1000
AARNILVESE AHVKIADFGL AKLLPLDKDY YVVREPGQSP IFWYAPESLS 1010       1020       1030       1040       1050
DNIFSRQSDV WSFGVVLYEL FTYCDKSCSP SAEFLRMMGC ERDVPALCRL
```

```
        1060       1070       1080       1090       1100
LELLEEGQRL PAPPACPAEV HELMKLCWAP SPQDRPSFSA LGPQLDMLWS 1110       1120
GSRGCETHAF TAHPEGKHHS LSFS
```

In one embodiment, the a crystallizable composition comprises a crystallization solution of equal volumes of JAK3 protein (7.5-30 mg/ml), a salt, a buffer between pH 5.0 and 7.0, 0-10 mM DTT and a polyethylene glycol. The salt includes, but is not limited to, KCl, NaCl and $(NH_4)_2SO_4$. The polyethylene glycol includes, but is not limited to, PEGMME 550, PEGMME2000, PEG4000, PEG6000. If the crystals are derived from seeding techniques, the concentrations of the polyethylene glycol may be less than 20%. In another embodiment, the crystallizable composition comprises a crystallization solution of equal volumes of JAK3 protein (10-15 mgmL in 50 mM Hepes at pH 8.0, 500 mM NaCl, 20% (vv) glycerol, 5 mM DTT, and 0.05% (wv) β-octylglucopyranoside and a solution of 20-26% PEG 3350, 200-260 mM KCl, 20 mM spermine, 10 mM DTT and 100 mM bis-Tris pH 6.0. In one embodiment, the volume of protein used is 0.5 µL. In another embodiment, the volume of protein used in 1.0 µL. In another embodiment, the volume of protein used is 2.0 µL.

Crystals can be grown using sitting drop or hanging drop vapour diffusion techniques, such as, but not limited to techniques described in Example 3. Crystals can be grown in the Corning® 384 Well plate (available from Fisher Scientific), Greiner crystallization low profile plates (available from Hampton Research (Aliso Viejo, CA)), both the 96-well CrystalQuick™ standard profile round and flat bottom plates (available from Hampton Research (Aliso Viejo, Calif.)), and the 24 well VDX plates (available from Hampton Research (Aliso Viejo, Calif.)). The volume of the reservoir for the 384-well plate can be 50 µL. The volume of the reservoir for the 96-well low profile plate can be 100 µL, and for the CrystalQuick™ plates it can be varied between 70-100 µL. Crystals can also be grown in 72-well terasaki plates using the microbatch method. They also can be grown in 96-well Corning® (available from Hampton Research (Aliso Viejo, Calif.)) with a reservoir of 50 µL.

According to one embodiment, the invention provides for a crystal with unit cell dimensions of a=59.98 Å b=90.19 Å, c=69.00 Å, $\alpha=\gamma=90$, $\beta=111.5°$ and space group $P2_1$ with 2 molecules in the asymmetric unit. Preferably, the crystal comprises the JAK3-AMP-PNP complex.

According to another embodiment, the invention provides for a crystal with unit cell dimensions of a=72.36 Å b=90.04 Å, c=105.60 Å, $\alpha=\beta=\gamma=90°$ and a space group $P2_12_12_1$ with 2 molecules in the asymmetric unit. Preferably, the crystal comprises the JAK3-AMP-PNP complex.

It will be readily apparent to those skilled in the art that the unit cells of the crystal compositions may deviate up to ±1-4 Å in cell length (and 7-8° in β angle in the $P2_1$ space group) from the above cell dimensions depending on the deviation in the unit cell calculations or conformational change in the protein.

The JAK3 kinase domain or homologue thereof may be produced by any well-known method, including synthetic methods, such as solid phase, liquid phase and combination solid phase liquid phase syntheses; recombinant DNA methods, including cDNA cloning, optionally combined with site directed mutagenesis; and/or purification of the natural products. In one embodiment, the protein is overexpressed in a baculovirus system.

Methods of Obtaining Crystals of JAK3 Kinase Domain, Complexes Thereof or Homologues Thereof The invention also relates to a method of obtaining a crystal of JAK3 kinase domain or JAK3 homologue thereof, comprising the steps of:
a) producing and purifying a JAK3 kinase domain or homologue thereof;
b) combining a crystallizable solution with said JAK3 kinase domain or homologue thereof to produce a crystallizable composition; and
c) subjecting said crystallizable composition to conditions which promote crystallization and obtaining said crystals.

The invention also relates to a method of obtaining a crystal of a JAK3 kinase domain complex or JAK3 kinase domain homologue complex, further comprising the step of:
d) soaking said crystal in a buffer solution comprising a chemical entity.

The invention also relates to a method of obtaining a crystal of JAK3 kinase domain complex or JAK3 kinase domain homologue complex, comprising the steps of:
a) producing and purifying a JAK3 kinase domain or homologue thereof;
b) combining a crystallizable solution with said JAK3 kinase domain or homologue thereof in the presence of a chemical entity to produce a crystallizable composition; and
c) subjecting said crystallizable composition to conditions which promote crystallization and obtaining said crystals.

In one embodiment, the chemical entity is selected from the group consisting of an ATP analogue, nucleotide triphosphate, nucleotide diphosphate, phosphate, adenosine, AMP-PNP, substrate inhibitor, or active site inhibitor. In another embodiment, the crystallization solution is as described previously. In another embodiment, the composition is treated with micro-crystals of JAK3 kinase domain or JAK3 kinase domain homologues, or complexes thereof.

In certain embodiments, the method of making crystals of JAK3 kinase domain, JAK3 kinase domain homologues, or complexes thereof, includes the use of a device for promoting crystallizations. Devices for promoting crystallization can include but are not limited to the hanging-drop, sitting-drop, dialysis or microtube batch devices. (U.S. Pat. Nos. 4,886, 646, 5,096,676, 5,130,105, 5,221,410 and 5,400,741; Pay et al., *Proteins: Structure, Function, and Genetics* 20: 98-102 (1994), incorporated herein by reference). The hanging-drop, sitting-drop, and some adaptations of the microbatch methods (D'Arcy et al., *J. Cryst. Growth* 168: 175-180 (1996) and Chayen, *J. Appl. Cryst.* 30: 198-202 (1997)) produce crystals by vapor diffusion. The hanging drop and sitting drop containing the crystallizable composition is equilibrated in a reservoir containing a higher or lower concentration of the precipitant. As the drop approaches equilibrium with the reservoir, the saturation of protein in the solution leads to the formation of crystals.

Microseeding or seeding may be used to increase the size and quality of crystals. In this instance, micro-crystals are crushed to yield a stock seed solution. The stock seed solution is diluted in series. Using a needle, glass rod, micro-pipet, micro-loop or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of a JAK3 kinase domain homologue, a JAK3 kinase domain homologue complex, a JAK3 kinase domain or another JAK3 kinase domain complex. Such variations include, but are not limited to, adjusting pH, protein concentration and/or crystallization temperature, changing the identity or concentration of salt and/or precipitant used, using a different method of crystallization, or introducing additives such as detergents (e.g., TWEEN 20 (monolaurate), LDAO, Brij 30 (4 lauryl ether)), sugars (e.g., glucose, maltose), organic compounds (e.g., dioxane, dimethylformamide), lanthanide ions or poly-ionic compounds that aid in crystallization. High throughput crystallization assays may also be used to assist in finding or optimizing the crystallization condition.

Binding Pockets of JAK3 Kinase Domain or Homologue Thereof

As disclosed herein, applicants have provided the three-dimensional X-ray structure of JAK3-AMP-PNP complex. The atomic coordinates for the structures of JAK3-AMP-PNP complex are presented in Table 2.

To use the structure coordinates generated for the JAK3 complex or one of its binding pockets or homologues thereof, it may be necessary to convert the structure coordinates, or portions thereof, into a three-dimensional shape (i.e., a three-dimensional representation of these complexes or binding pockets). This is achieved through the use of a computer and commercially available software that is capable of generating the three-dimensional representations or structures of molecules or molecular complexes, or portions thereof, from a set of structural coordinates. These three-dimensional representations may be displayed on a computer screen.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The binding pockets of this invention will be important for drug design.

The conformations of JAK3 and other proteins at a particular amino acid site, along the polypeptide backbone, can be compared using well-known procedures for performing sequence alignments of the amino acids. Such sequence alignments allow for the equivalent sites on these proteins to be compared. Such methods for performing sequence alignment include, but are not limited to, the "bestfit" program and CLUSTAL W Alignment Tool, Higgins et al., supra.

In one embodiment, the ATP-binding pocket comprises amino acid residues Leu828, Gly829, Lys830, Gly831, Asn 832, Phe833, Gly834, Ser835, Val836, Ala853, Lys855, Val884, Met902, Glu903, Tyr904, Leu905, Pro906, Cys909, Arg911, Asp949, Arg953, Asn954, Leu956, Asp967, and Gln988 according to the structure of the JAK3-AMP-PNP complex in Table 2. These amino acid residues are within 5 Å ("5 Å sphere of amino acids") of AMP-PNP bound in the ATP-binding pocket as identified using the program QUANTA (Accelrys, San Diego, Calif. ©2001, 2002).

In another embodiment, the ATP-binding pocket comprises amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to the structure of the JAK3-AMP-PNP complex in Table 2. These amino acid residues are within 8 Å ("8 Å sphere of amino acids") of AMP-PNP bound in the ATP-binding pockets as identified using the program QUANTA (Accelrys, San Diego, Calif. ©2001, 2002).

It will be readily apparent to those of skill in the art that the numbering of amino acid residues in homologues of human JAK3 may be different than that set forth for human JAK3. Corresponding amino acids in JAK3 homologues are easily identified by visual inspection of the amino acid sequences or by using commercially available homology software programs. Homologues of JAK3 include, for example, JAK3 from other species, such as non-humans primates, mouse, rat, etc.

Those of skill in the art understand that a set of structure coordinates for an enzyme or an enzyme-complex, or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated because of mathematical manipulations of the JAK3-AMP-PNP structure coordinates. For example, the structure coordinates set forth in Table 2 may undergo crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal may also account for variations in structure coordinates. If such variations are within a certain root mean square deviation as compared to the original coordinates, the resulting three-dimensional shape is considered encompassed by this invention. Thus, for example, a ligand that bound to the ATP-binding pocket of JAK3 would also be expected to bind to another binding pocket whose structure coordinates defined a shape that fell within the RMSD value.

Various computational analyses may be necessary to determine whether a molecule or binding pocket, or portion thereof, is sufficiently similar to the binding pockets above-described. Such analyses may be carried out in well known software applications, such as ProFit (ProFit version 1.8, available from A.C.R. Martin, University College London); Swiss-Pdb Viewer (Guex and Peitsch, *Electrophoresis* 18: 2714-2723 (1997)); the Molecular Similarity application of QUANTA (Accelrys, San Diego, Calif. ©2001, 2002) and as described in the accompanying User's Guide, which are incorporated herein by reference.

The above programs permit comparisons between different structures, different conformations of the same structure, and different parts of the same structure. The procedure used in QUANTA (Accelrys, San Diego, Calif. ©2001, 2002) and Swiss-Pdb Viewer (Guex and Peitsch, *Electrophoresis* 18: 2714-2723 (1997) to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within QUANTA (Accelrys, San Diego, Calif. ©2001, 2002) is defined by user input, for the purposes of this invention, we will define equivalent atoms as protein backbone atoms N, O, C and Cα for all corresponding amino acid residues between two structures being compared.

The corresponding amino acids may be identified by sequence alignment programs such as the "bestfit" program available from the Genetics Computer Group which uses the local homology algorithm described by Smith and Waterman in *Advances in Applied Mathematics* 2: 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids (Hanks et al., *Science* 241: 42 (1988); Hanks and Quinn, *Methods in Enzymology* 200: 38 (1991)). The identification of equivalent residues can also be assisted by secondary structure alignment, for example, aligning the α-helices, β-sheets in the structure. The program Swiss-Pdb viewer (Guex and Peitsch, *Electrophoresis* 18: 2714-2723 (1997) utilizes a best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program (Guex and Peitsch, *Electrophoresis* 18: 2714-2723 (1997) sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in Table 2 are encompassed by this invention.

One embodiment of this invention provides a crystalline molecule comprising a protein defined by structure coordinates of a set of amino acid residues that are identical to JAK3 amino acid residues according to Table 2, wherein the RMSD between backbone atoms of said set of amino acid residues and said JAK3 amino acid residues is not more than about 3.0 Å. In other embodiments, the RMSD between backbone atoms of said set of amino acid residues and said JAK3 amino acid residues is not greater than about 2.0 Å, not greater than about 1.5 Å, not greater than about 1.1 Å, not greater than about 1.0 Å, not greater than about 0.9 Å, not greater than about 0.8 Å, not greater than about 0.7 Å, not greater than about 0.6 Å, or not greater than about 0.5 Å. Calculations of RMSD values were done with Swiss Pdb Viewer (Guex and Peitsch, *Electrophoresis* 18: 2714-2723 (1997)).

In one embodiment, the present invention provides a crystalline molecule comprising all or part of a binding pocket defined by a set of amino acid residues comprising amino acid residues which are identical to human JAK3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Lys978, Glu985, Gln988, Ser989, Pro990 and Trp 993 according to Table 2, wherein the RMSD of the backbone atoms between said JAK3 amino acid residues and said amino acid residues which are identical is not greater than about 2.5 Å. In other embodiments, the RMSD is not greater than about 2.4 Å, 2.2 Å, 2.0 Å, 1.8 Å, 1.6 Å, 1.4 Å, 1.2 Å, 1.0 Å, 0.8 Å, 0.5 Å, 0.3 Å, or 0.2 Å. In other embodiments, the binding pocket is defined by a set of amino acid residues comprising at least four, six, eight, ten, twelve, fifteen, twenty, twenty-five, thirty, thirty-five, forty, forty-five or fifty amino acid residues which are identical to said JAK3 amino acid residues.

Computer Systems

According to another embodiment, this invention provides a machine-readable data storage medium, comprising a data storage material encoded with machine-readable data, wherein said data defines the above-mentioned molecules or molecular complexes. In one embodiment, the data defines the above-mentioned binding pockets by comprising the structure coordinates of said amino acid residues according to Table 2. To use the structure coordinates generated for JAK3, homologues thereof, or one of its binding pockets, it is at times necessary to convert them into a three-dimensional shape or to extract three-dimensional structural information from them. This is achieved through the use of commercially or publicly available software that is capable of generating a three-dimensional structure or a three-dimensional representation of molecules or portions thereof from a set of structure coordinates. In one embodiment, three-dimensional structure or representation may be displayed graphically.

Therefore, according to another embodiment, this invention provides a machine-readable data storage medium comprising a data storage material encoded with machine readable data. In one embodiment, a machine programmed with instructions for using said data is capable of generating a three-dimensional structure or three-dimensional representation of any of the molecules, or molecular complexes or binding pockets thereof, that are described herein.

This invention also provides a computer comprising:
(a) a machine-readable data storage medium, comprising a data storage material encoded with machine-readable data, wherein said data defines any one of the above molecules or molecular complexes;
(b) a working memory for storing instructions for processing said machine-readable data;

(c) a central processing unit (CPU) coupled to said working memory and to said machine-readable data storage medium for processing said machine readable data and means for generating three-dimensional structural information of said molecule or molecular complex; and (d) output hardware coupled to said central processing unit for outputting three-dimensional structural information of said molecule or molecular complex, or information produced by using said three-dimensional structural information of said molecule or molecular complex.

In one embodiment, the data defines the binding pocket of the molecule or molecular complex.

Three-dimensional data generation may be provided by an instruction or set of instructions such as a computer program or commands for generating a three-dimensional structure or graphical representation from structure coordinates, or by subtracting distances between atoms, calculating chemical energies for a JAK3 molecule or molecular complex or homologues thereof, or calculating or minimizing energies for an association of a JAK3 molecule or molecular complex or homologues thereof to a chemical entity. The graphical representation can be generated or displayed by commercially available software programs. Examples of software programs include but are not limited to QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

Information of said binding pocket or information produced by using said binding pocket can be outputted through display terminals, touchscreens, facsimile machines, modems, CD-ROMs, printers, a CD or DVD recorder, ZIP™ or JAZ™ drives or disk drives. The information can be in graphical or alphanumeric form.

In one embodiment, the computer is executing an instruction such as a computer program for generating three-dimensional structure or docking. In another embodiment, the computer further comprises a commercially available software program to display the information as a graphical representation. Examples of software programs include but as not limited to, QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), all of which are incorporated herein by reference.

Figure 8:
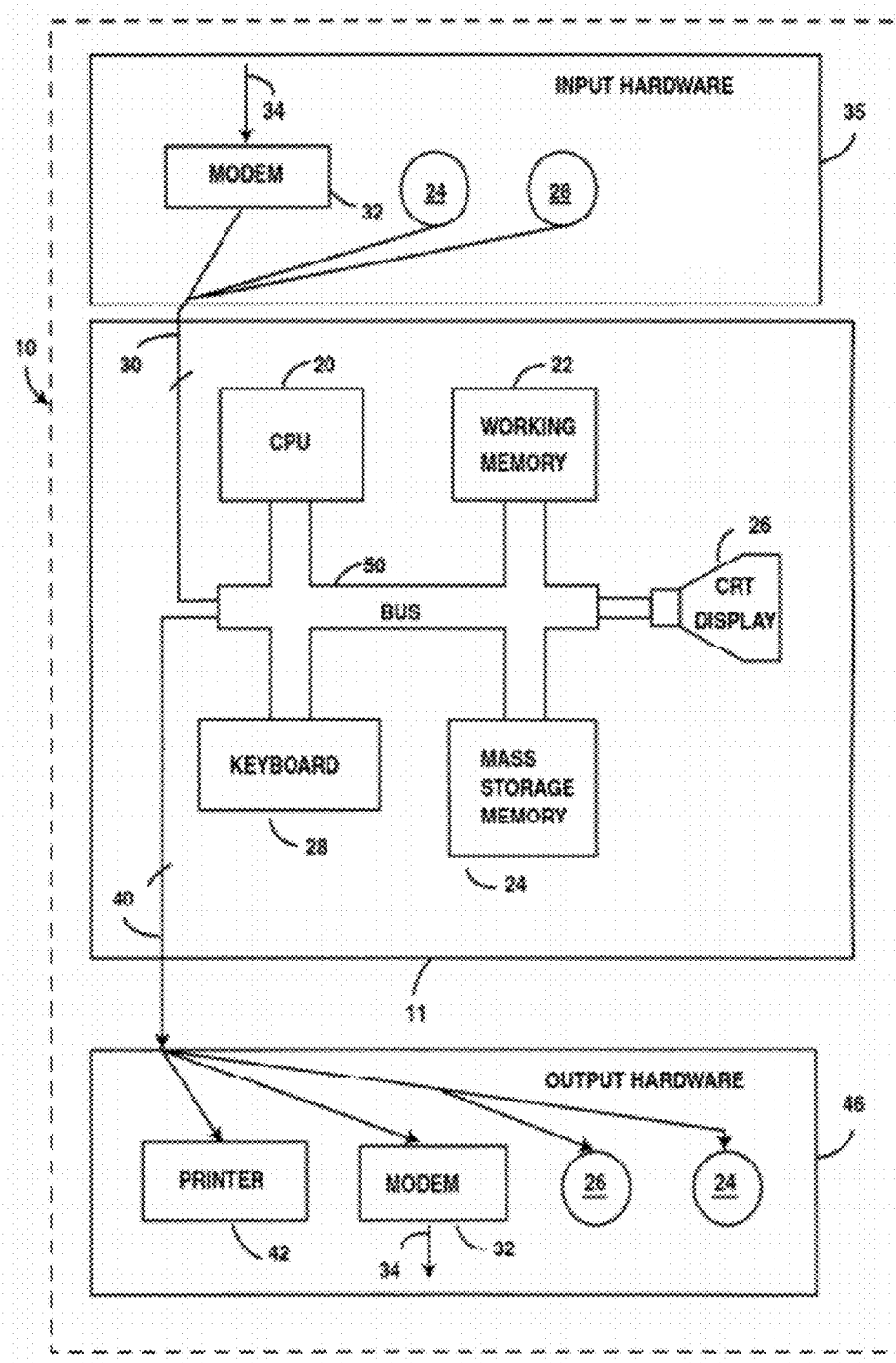
FIG. 8 shows a diagram of a system used to carry out the instructions encoded by the storage medium of FIGS. 9 and 10.

FIG. 8 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives, CD-ROM drives or DVD-ROM drives), one or more cathode-ray tube ("CRT") display terminals (26), one or more keyboards (28), one or more input lines (30), and one or more output lines (40), all of which are interconnected by a conventional bi-directional system bus (50).

Input hardware (35), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (35) may comprise CD-ROM or DVD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA (Accelrys, San Diego, Calif. ©2001, 2002) as described herein. Output hardware may also include a printer (42), so that hard copy output may be produced, or a disk drive (24), to store system output for later use. Output hardware may also include a display terminal, touch-screens, facsimile machines, modems, a CD or DVD recorder, ZIP™ or JAZ™ drives, disk drives, or other machine-readable data storage device.

In operation, CPU (20) coordinates the use of the various input and output devices (35), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

Figure 9:
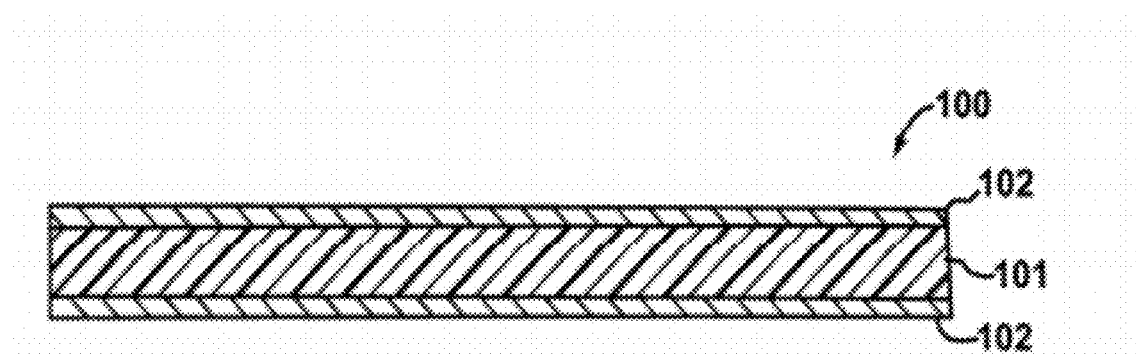
FIG. 9 shows a cross section of a magnetic storage medium.

FIG. 9 shows a cross section of a magnetic data storage medium (100) which can be encoded with a machine-readable data that can be carried out by a system such as system (10) of FIG. 8. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 8.

Figure 10:
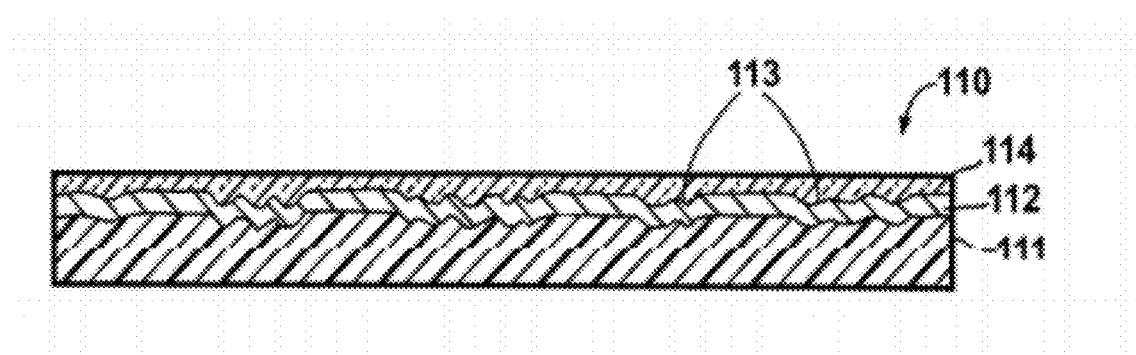
FIG. 10 shows a cross section of a optically-readable data storage medium.

FIG. 10 shows a cross section of an optically-readable data storage medium (110) which also can be encoded with such a machine-readable data, or set of instructions, which can be carried out by a system such as system (10) of FIG. 8. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of Table 2. Homology modeling can be used to generate structural models of JAK3 homologues or other homologous proteins based on the known structure of JAK3. This can be achieved by performing one or more of the following steps: performing sequence alignment between the amino acid sequence of a molecule (possibly an unknown molecule) against the amino acid sequence of JAK3; identifying conserved and variable regions by sequence or structure; generating structure coordinates for structurally conserved residues of the unknown structure from those of JAK3; generating conformations for the structurally variable residues in the unknown structure; replacing the non-conserved residues of JAK3 with residues in the unknown structure; building side chain conformations; and refining and/or evaluating the unknown structure.

Software programs that are useful in homology modeling include XALIGN (Wishart et al., *Comput. Appl. Biosci.* 10: 687-688 (1994)) and CLUSTAL W Alignment Tool, Higgins et al., supra. See also, U.S. Pat. No. 5,884,230. These references are incorporated herein by reference.

To perform the sequence alignment, programs such as the "bestfit" program available from the Genetics Computer Group (Waterman in *Advances in Applied Mathematics* 2: 482 (1981), which is incorporated herein by reference) and CLUSTAL W Alignment Tool (Higgins et al., supra, which is incorporated by reference) can be used. To model the amino acid side chains of homologous molecules, the amino acid residues in JAK3 can be replaced, using a computer graphics program such as "O" (Jones et al., *Acta Cryst. Sect. A* 47: 110-119 (1997)), by those of the homologous protein, where they differ. The same orientation or a different orientation of the amino acid can be used. Insertions and deletions of amino acid residues may be necessary where gaps occur in the sequence alignment. However, certain portions of the active site of JAK3 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol.* 256: 701-719 (1996); Blundell et al., *Nature* 326: 347-352 (1987); Fetrow and Bryant, *BioTechnology* 11:479-484 (1993); Greer, *Methods in Enzymology* 202: 239-252 (1991); and Johnson et al., *Crit. Rev. Biochem. Mol Biol.* 29: 1-68 (1994). An example of homology modeling can be found, for example, in Szklarz, *Life Sci.* 61: 2507-2520 (1997). These references are incorporated herein by reference.

Thus, in accordance with the present invention, data capable of generating the three-dimensional structure or three-dimensional representation of the above molecules or molecular complexes, or binding pockets thereof, can be stored in a machine-readable storage medium, which is capable of displaying structural information or a graphical three-dimensional representation of the structure. In one embodiment, the means of generating three-dimensional information is provided by the means for generating a three-dimensional structural representation of the binding pocket or protein of a molecule or molecular complex.

Rational Drug Design

The JAK3 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with JAK3 may inhibit or activate JAK3 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

In one embodiment, the invention provides for a method of using a computer for selecting an orientation of a chemical entity that interacts favorably with a binding pocket or domain comprising the steps of:

(a) providing the structure coordinates of said binding pocket or domain on a computer comprising the means for generating three-dimensional structural information from said structure coordinates;

(b) employing computational means to dock a first chemical entity in the binding pocket or domain;

(c) quantifying the association between said chemical entity and all or part of the binding pocket or domain for different orientations of the chemical entity; and (d) selecting the orientation of the chemical entity with the most favorable interaction based on said quantified association.

In one embodiment, the docking is facilitated by said quantified association.

In one embodiment, the above method further comprises the following steps before step (a):

(e) producing a crystal of a molecule or molecular complex comprising JAK3 kinase domain or homologue thereof;

(f) determining the three-dimensional structure coordinates of the molecule or molecular complex by X-ray diffraction of the crystal; and (g) identifying all or part of a binding pocket that corresponds to said binding pocket.

Three-dimensional structural information in step (a) may be generated by instructions such as a computer program or commands that can generate a three-dimensional representation; subtract distances between atoms; calculate chemical energies for a JAK3 molecule, molecular complex or homologues thereof; or calculate or minimize the chemical energies of an association of JAK3 molecule, molecular complex or homologues thereof to a chemical entity. These types of computer programs are known in the art. The graphical representation can be generated or displayed by commercially available software programs. Examples of software programs include but are not limited to QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

The above method may further comprise the following step after step (d): outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both, of the molecule or molecular complex prior to step (b).

One embodiment of this invention provides for the above method, wherein energy minimization, molecular dynamics simulations, or rigid body minimizations are performed simultaneously with or following step (b).

The above method may further comprise the steps of:
(e) repeating steps (b) through (d) with a second chemical entity; and
(f) selecting at least one of said first or second chemical entity that interacts more favorably with said binding pocket or domain based on said quantified association of said first or second chemical entity.

In another embodiment, the invention provides for the method of using a computer for selecting an orientation of a chemical entity with a favorable shape complementarity in a binding pocket comprising the steps of:
(a) providing the structure coordinates of said binding pocket and all or part of the ligand bound therein on a computer comprising the means for generating three-dimensional structural information from said structure coordinates;
(b) employing computational means to dock a first chemical entity in the binding pocket;
(c) quantitating the contact score of said chemical entity in different orientations; and
(d) selecting an orientation with the highest contact score.

In one embodiment, the docking is facilitated by the contact score.

The method above may further comprise the step of generating a three-dimensional graphical representation of the binding pocket and all or part of the ligand bound therein prior to step (b).

The method above may further comprise the steps of:
(e) repeating steps (b) through (d) with a second chemical entity; and
(f) selecting at least one of said first or second chemical entity that has a higher contact score based on said quantitated contact score of said first or second chemical entity.

In another embodiment, the invention provides a method for screening a plurality of chemical entities to associate at a deformation energy of binding of less than −7 kcal/mol with said binding pocket:
(a) employing computational means, which utilize said structure coordinates to dock one of said plurality of chemical entities in said binding pocket;
(b) quantifying the deformation energy of binding between the chemical entity and the binding pocket;
(c) repeating steps (a) and (b) for each remaining chemical entity; and
(d) outputting a set of chemical entities that associate with the binding pocket at a deformation energy of binding of less than −7 kcal/mol to a suitable output hardware.

In another embodiment, the method comprises the steps of:
(a) constructing a computer model of the binding pocket of said molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a JAK3 kinase domain, or homologue thereof;
(c) employing computational means to dock said chemical entity to be evaluated in said binding pocket in order to provide an energy-minimized configuration of said chemical entity in the binding pocket; and
(d) evaluating the results of said docking to quantify the association between said chemical entity and the binding pocket.

Alternatively, the structure coordinates of the JAK3 binding pockets may be utilized in a method for identifying a candidate inhibitor of a molecule or molecular complex comprising a binding pocket of JAK3. This method comprises the steps of:
(a) using a three-dimensional structure of the binding pocket or domain to design, select or optimize a plurality of chemical entities;
(b) contacting each chemical entity with the molecule and molecular complex;
(c) monitoring the inhibition to the catalytic activity of the molecule or molecular complex by the chemical entity; and
(d) selecting a chemical entity based on the effect of the chemical entity on the activity of the molecule or molecular complex.

In one embodiment, the three-dimensional structure is displayed as a graphical representation.

In another embodiment, the method comprises the steps of:
(a) constructing a computer model of a binding pocket of the molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a JAK3 kinase domain or homologue thereof;
(c) employing computational means to dock said chemical entity to be evaluated and said binding pocket in order to provide an energy-minimized configuration of said chemical entity in the binding pocket; and
(d) evaluating the results of said docking to quantify the association between said chemical entity and the binding pocket;
(e) synthesizing said chemical entity; and
(f) contacting said chemical entity with said molecule or molecular complex to determine the ability of said chemical entity to activate or inhibit said molecule.

In one embodiment, the invention provides a method of designing a compound or complex that associates with all or part of the binding pocket comprising the steps of:
(a) providing the structure coordinates of said binding pocket or domain on a computer comprising the means for generating three-dimensional structural information from said structure coordinates;
(b) using the computer to dock a first chemical entity in part of the binding pocket or domain;
(c) docking a second chemical entity in another part of the binding pocket or domain;
(d) quantifying the association between the first and second chemical entity and part of the binding pocket or domain;
(e) repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket or domain on a computer screen using the three-dimensional graphical representation of the binding pocket or domain and said first and second chemical entity; and (g) assembling the first and second chemical entity into a compound or complex that interacts with said binding pocket by model building.

For the first time, the present invention permits the use of molecular design techniques to identify, select and design chemical entities, including inhibitory compounds, capable of binding to JAK3 or JAK3-like binding pockets, motifs and domains.

Applicants' elucidation of binding pockets on JAK3 provides the necessary information for designing new chemical entities and compounds that may interact with JAK3 substrate, active site, in whole or in part.

Throughout this section, discussions about the ability of a chemical entity to bind to, interact with or inhibit JAK3 binding pockets refer to features of the entity alone.

The design of compounds that bind to or inhibit JAK3 binding pockets according to this invention generally involves consideration of two factors. First, the chemical entity must be capable of physically and structurally associating with parts or all of the JAK3 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the JAK3 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the JAK3 or JAK3-like binding pockets.

The potential inhibitory or binding effect of a chemical entity on JAK3 binding pockets may be analyzed prior to its actual synthesis and testing by the use of computer modeling techniques. If the theoretical structure of the given entity suggests insufficient interaction and association between it and the JAK3 binding pockets, testing of the entity is obviated. However, if computer modeling indicates a strong interaction, the molecule may then be synthesized and tested for its ability to bind to a JAK3 binding pocket. This may be achieved by testing the ability of the molecule to inhibit JAK3 using the assay described in Example 9.

A potential inhibitor of a JAK3 binding pocket may be computationally evaluated by means of a series of steps in which chemical entities or fragments are screened and selected for their ability to associate with the JAK3 binding pockets.

One skilled in the art may use one of several methods to screen chemical entities or fragments or moieties thereof for their ability to associate with the binding pockets described herein. This process may begin by visual inspection of, for example, any of the binding pockets on the computer screen based on the JAK3 structure coordinates Table 2 or other coordinates which define a similar shape generated from the machine-readable storage medium. Selected chemical entities, or fragments or moieties thereof may then be positioned in a variety of orientations, or docked, within that binding pocket as defined supra. Docking may be accomplished using software such as QUANTA (Accelrys, San Diego, Calif. ©2001, 2002) and Sybyl (Tripos Associates, St. Louis, Mo.), followed by, or performed simultaneously with, energy minimization, rigid-body minimization (Gshwend, supra) and molecular dynamics with standard molecular mechanics force fields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", *J. Med. Chem.* 28: 849-857 (1985)). GRID is available from Oxford University, Oxford, UK.
2. MCSS (Miranker et al., "Functionality Maps of Binding Sites: A Multiple Copy Simultaneous Search Method." *Proteins Struct. Funct. Genet.* 11: 29-34 (1991)). MCSS is available from Molecular Simulations, San Diego, Calif.
3. AUTODOCK (Goodsell et al., "Automated Docking of Substrates to Proteins by Simulated Annealing", *Proteins Struct. Funct. and Genet.* 8: 195-202 (1990)). AUTODOCK is available from Scripps Research Institute, La Jolla, Calif.
4. DOCK (Kuntz et al., "A Geometric Approach to Macromolecule-Ligand Interactions", *J. Mol. Biol.* 161: 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of JAK3. This would be followed by manual model building using software such as QUANTA (Accelrys, San Diego, Calif. ©2001, 2002) or Sybyl (Tripos Associates, St. Louis, Mo.).

Useful programs to aid one of skill in the art in connecting the individual chemical entities or fragments include:

1. CAVEAT (Bartlett et al., "CAVEAT: A Program to Facilitate the Structure-Derived Design of Biologically Active Molecules", in *Molecular Recognition in Chemical and Biological Problems*, S. M. Roberts, Ed., Royal Society of Chemistry, Special Publication No. 78: 182-196 (1989); Lauri, G. and Bartlett, P. A., "CAVEAT: A Program to Facilitate the Design of Organic Molecules", *J. Comp. Aid. Molec. Design* 8: 51-66 (1994)). CAVEAT is available from the University of California, Berkeley, Calif.
2. 3D Database systems such as ISIS (MDL Information Systems, San Leandro, Calif.). This area is reviewed in Martin, Y. C., "3D Database Searching in Drug Design", *J. Med. Chem.* 35: 2145-2154 (1992).
3. HOOK (Eisen et al., "HOOK: A Program for Finding Novel Molecular Architectures that Satisfy the Chemical and Steric Requirements of a Macromolecule Binding Site", *Proteins Struct. Funct. Genet.* 19: 199-221 (1994)). HOOK is available from Molecular Simulations, San Diego, Calif.

Instead of proceeding to build an inhibitor of a JAK3 binding pocket in a step-wise fashion one fragment or chemical entity at a time as described above, inhibitory or other JAK3 binding compounds may be designed as a whole or "de novo" using either an empty binding pocket or optionally including some portion(s) of a known inhibitor(s). There are many de novo ligand design methods including:

1. LUDI (Bohm, H.-J., "The Computer Program LUDI: A New Method for the De Novo Design of Enzyme Inhibitors", *J. Comp. Aid, Molec. Design* 6: 61-78 (1992)). LUDI is available from Molecular Simulations Incorporated, San Diego, Calif.

2. LEGEND (Nishibata et al., *Tetrahedron* 47: 8985-8990 (1991)). LEGEND is available from Molecular Simulations Incorporated, San Diego, Calif.
3. LeapFrog™(available from Tripos Associates, St. Louis, Mo.).
4. SPROUT (Gillet et al., "SPROUT: A Program for Structure Generation)", *J. Comp. Aid. Molec. Design* 7: 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry", *J. Med. Chem.* 33: 883-894 (1990); see also, Navia, M. A. and Murcko, M. A., "The Use of Structural Information in Drug Design", Current Opinions in Structural Biology 2: 202-210 (1992); Balbes et al., "A Perspective of Modern Methods in Computer-Aided Drug Design", in *Reviews in Computational Chemistry*, K. B. Lipkowitz and D. B. Boyd, Eds., VCH Publishers, New York, 5: 337-379 (1994); see also, Guida, W. C., "Software For Structure-Based Drug Design", *Curr. Opin. Struct. Biology* 4: 777-781 (1994)).

Once a chemical entity has been designed or selected by the above methods, the efficiency with which that entity may bind to any of the above binding pockets may be tested and optimized by computational evaluation. For example, an effective binding pocket inhibitor must preferably demonstrate a relatively small difference in energy between its bound and free states (i.e., a small deformation energy of binding). Thus, the most efficient binding pocket inhibitors should preferably be designed with a deformation energy of binding of not greater than about 10 kcal/mole, more preferably, not greater than 7 kcal/mole. Binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

A chemical entity designed or selected as binding to any one of the above binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburg Pa. ©1995); AMBER, version 4.1 (P. A, Kollman, University of California at San Francisco, ©1995); QUANTA/CHARMM (Accelrys, San Diego, Calif. ©2001, 2002); Insight II/Discover™(Molecular Simulations, Inc., San Diego, Calif. © 1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2with "IMPACT" graphics. Other hardware systems and software packages will be known to those skilled in the art.

Another approach enabled by this invention is the computational screening of small molecule databases for chemical entities or compounds that can bind in whole, or in part, to any of the above binding pocket. In this screening, the quality of fit of such entities to the binding pocket may be judged either by shape complementarity or by estimated interaction energy (Meng et al., *J. Comp. Chem.* 13: 505-524 (1992)).

Another particularly useful drug design technique enabled by this invention is iterative drug design. Iterative drug design is a method for optimizing associations between a protein and a chemical entity by determining and evaluating the three-dimensional structures of successive sets of proteinchemical entity complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new proteincompound complex, solving the three-dimensional structure of the complex, and comparing the associations between the new proteincompound complex and previously solved proteincompound complexes. By observing how changes in the compound affected the proteincompound associations, these associations may be optimized.

In some cases, iterative drug design is carried out by forming successive protein-compound complexes and then crystallizing each new complex. High throughput crystallization assays may be used to find a new crystallization condition or to optimize the original protein crystallization condition for the new complex. Alternatively, a pre-formed protein crystal may be soaked in the presence of an inhibitor, thereby forming a proteincompound complex and obviating the need to crystallize each individual proteincompound complex.

In one embodiment, this invention provides a method for identifying a candidate inhibitor that interacts with a binding site of a Janus Kinase 3 kinase protein or a homologue thereof, comprising the steps of:
  (a) obtaining a crystal comprising said human Janus Kinase 3kinase protein or said homologue thereof, wherein the crystal is characterized with space group $P2_1$ and has unit cell parameters of a=59.98 Å, b=90.19 Å, c=69.00 Å; $\beta=111.5°$;
  (b) obtaining the structure coordinates of amino acids of the crystal of step (a), wherein the structure coordinates are set forth in Table 2;
  (c) generating a three-dimensional model of said human Janus Kinase 3kinase protein or said homologue thereof using the structure coordinates of the amino acids obtained in step (b), a root mean square deviation from backbone atoms of said amino acids of not more than ±2.0 Å;
  (d) determining a binding site of said human Janus Kinase 3 kinase protein or said homologue thereof from said three-dimensional model; and
  (e) performing computer fitting analysis to identify the candidate inhibitor which interacts with said binding site.

In one embodiment, this method further comprising the step of:
  (f) contacting the identified candidate inhibitor with said human Janus Kinase 3 kinase protein or said homologue thereof in order to determine the effect of the inhibitor on human Janus Kinase 3 kinase protein activity.

In another embodiment, the binding site of said human Janus Kinase 3 kinase protein or said homologue thereof determined in step (d) comprises the structure coordinates according to Table 2 of amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993, wherein the root mean square deviation from the backbone atoms of said amino acids is not more than ±2.0 Å.

In one embodiment, this invention provides for a method of for identifying a candidate inhibitor that interacts with a binding site of a human Janus Kinase 3 kinase protein or a homologue thereof, comprising the steps of:
(a) obtaining a crystal comprising said human Janus Kinase 3 kinase protein or said homologue thereof, wherein the crystal is characterized with space group P2$_1$ and has unit cell parameters of a=59.98 Å, b=90.19 Å, c=69.00 Å; β=111.5°;
(b) obtaining the structure coordinates of amino acids of the crystal of step (a);
(c) generating a three-dimensional model of said human Janus Kinase 3 kinase protein or said homologue thereof using the structure coordinates of the amino acids generated in step (b), a root mean square deviation from backbone atoms of said amino acids of not more than ±2.0 Å;
(d) determining a binding site of said human Janus Kinase 3 kinase protein or said homologue thereof from said three-dimensional model; and
(e) performing computer fitting analysis to identify the candidate inhibitor which interacts with said binding site.

In one embodiment, this method further comprising the step of:
(f) contacting the identified candidate inhibitor with said human Janus Kinase 3 kinase protein or said homologue thereof in order to determine the effect of the inhibitor on human Janus Kinase 3 kinase protein activity.

In another embodiment, the binding site of said human Janus Kinase 3 kinase protein or said homologue thereof determined in step (d) comprises the structure coordinates according to Table 2 of a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990and Trp 993, wherein the root mean square deviation from the backbone atoms of said amino acids is not more than ±2.0 Å.

In another embodiment, this invention provides a method for identifying a candidate inhibitor that interacts with a binding site of a human Janus Kinase 3 kinase protein or a homologue thereof, comprising the step of determining a binding site said human Janus Kinase 3 kinase protein or the homologue thereof from a three-dimensional model to design or identify the candidate inhibitor which interacts with said binding site.

In one embodiment, the binding site of said human Janus Kinase 3 kinase protein or said homologue thereof determined comprises the structure coordinates according to Table 2 of a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993, wherein the root mean square deviation from the backbone atoms of said amino acids is not more than ±2.0 Å.

In one embodiment, this invention provides a method for identifying a candidate inhibitor of a molecule or molecular complex comprising a binding pocket or domain selected from the group consisting of:
(i) a set of amino acid residues which are identical to human Janus Kinase 3 kinase a set of amino acid residues that are identical to human Janus Kinase 3 amino acid residues Gln827, Leu828, Gly829, Lys830, Gly831, Asn 832, Phe833, Gly834, Ser835, Val836, Glu837, Leu838, Val852, Ala853, Val854, Lys855, Gln856, Leu857, Val884, Lys885, Tyr886, Leu900, Val901, Met902, Glu903, Tyr904, Leu905, Pro906, Ser907, Gly908, Cys909, Leu910, Arg911, Asp912, His947, Asp949, Leu950, Ala951, Ala952, Arg953, Asn954, Ile955, Leu956, Val957, Ala966, Asp967, Leu970, Glu985, Gln988, Ser989, Pro990 and Trp 993 according to Table 2, wherein the root mean square deviation of the backbone atoms between said set of amino acid residues and said human Janus Kinase 3 kinase amino acid residues is not greater than about 2.0 Å; and
(ii) a set of amino acid residues that are identical to Janus Kinase 3 kinase amino acid residues according to Table 2, wherein the root mean square deviation between said set of amino acid residues and said human Janus Kinase 3kinase amino acid residues is not more than about 3.0 Å;
comprising the steps of:
(a) using a three-dimensional structure of the binding pocket or domain to design, select or optimize a plurality of chemical entities; and
(b) selecting said candidate inhibitor based on the inhibitory effect of said chemical entities on a human Janus Kinase 3 kinase protein or a human Janus Kinase 3kinase protein homologue on the catalytic activity of the molecule or molecular complex.

In another embodiment, this invention provides a method of using a crystal of this invention in an inhibitor screening assay comprising:
(a) selecting a potential inhibitor by performing rational drug design with a three-dimensional structure determined for the crystal, wherein said selecting is performed in conjunction with computer modeling;
(b) contacting the potential inhibitor with a kinase; and
(c) detecting the ability of the potential inhibitor for inhibiting the kinase.

Any of the above methods may be used to design peptide or small molecule mimics of the a ligand which may have inhibitory effects on full-length JAK3 protein or fragments thereof, or on full-length JAK3 protein which is mutated in or fragments of the mutated protein thereof.

Structure Determination of Other Molecules

The structure coordinates set forth in Table 2 can also be used in obtaining structural information about other crystallized molecules or molecular complexes. This may be achieved by any of a number of well-known techniques, including molecular replacement.

According to one embodiment, the machine-readable data storage medium comprises a data storage material encoded with a first set of machine readable data which comprises the Fourier transform of at least a portion of the structure coordinates set forth in Table 2 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex having an unknown structure, wherein said computer comprises:

(a) a machine-readable data storage medium comprising a data storage material encoded with machine-readable data, wherein said data comprises at least a portion of the structure coordinates of JAK3 according to Table 2 or homology model thereof;

(b) a machine-readable data storage medium comprising a data storage material encoded with machine-readable data, wherein said data comprises X-ray diffraction data obtained from said molecule or molecular complex having an unknown structure; and (c) instructions for performing a Fourier transform of the machine-readable data of (a) and for processing said machine-readable data of (b) into structure coordinates.

For example, the Fourier transform of at least a portion of the structure coordinates set forth in Table 2 or homology model thereof may be used to determine at least a portion of the structure coordinates of the molecule or molecular complex.

Therefore, in another embodiment this invention provides a method of utilizing molecular replacement to obtain structural information about a molecule or a molecular complex of unknown structure wherein the molecule or molecular complex is sufficiently homologous to JAK3 kinase domain, comprising the steps of:

(a) crystallizing said molecule or molecular complex of unknown structure;

(b) generating X-ray diffraction data from said crystallized molecule or molecular complex;

(c) applying at least a portion of the JAK3 structure coordinates set forth in one of Table 2 or a homology model thereof to the X-ray diffraction data to generate a three-dimensional electron density map of at least a portion of the molecule or molecular complex whose structure is unknown; and (d) generating a structural model of the molecule or molecular complex from the three-dimensional electron density map.

In one embodiment, the method is performed using a computer. In another embodiment, the molecule is selected from the group consisting of JAK3 kinase domain and a JAK3 kinase domain homologue. In another embodiment, the molecular complex is a JAK3 kinase domain complex or a JAK3 kinase domain homologue complex.

By using molecular replacement, all or part of the structure coordinates of JAK3 as provided by this invention (and set forth in Table 2) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of JAK3 kinase domain according to Table 2 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.* 115: 55-77 (1985); M. G. Rossmann, ed., "The Molecular Replacement Method", Int. Sci. Rev. Ser. No. 13, Gordon & Breach, N.Y. (1972)).

The structure of any portion of any crystallized molecule or molecular complex that is sufficiently homologous to any portion of the structure of human JAK3 kinase domain can be resolved by this method.

In one embodiment, the method of molecular replacement is utilized to obtain structural information about a JAK3 homologue. The structure coordinates of JAK3 as provided by this invention are particularly useful in solving the structure of JAK3 complexes that are bound by ligands, substrates and inhibitors.

Furthermore, the structure coordinates of JAK3 kinase domain as provided by this invention are useful in solving the structure of JAK3 kinase domains that have amino acid substitutions, additions and/or deletions (referred to collectively as "JAK3 mutants", as compared to naturally occurring JAK3). These JAK3 mutants may optionally be crystallized in co-complex with a chemical entity. The crystal structures of a series of such complexes may then be solved by molecular replacement and compared with that of wild-type JAK3. Potential sites for modification within the various binding pockets of the enzyme may thus be identified. This information provides an additional tool for determining the most efficient binding interactions, for example, increased hydrophobic interactions, between JAK3 and a chemical entity or compound.

The structure coordinates are also particularly useful in solving the structure of crystals of the kinase domain of JAK3 or homologues co-complexed with a variety of chemical entities. This approach enables the determination of the optimal sites for interaction between chemical entities, including candidate JAK3 inhibitors. For example, high resolution X-ray diffraction data collected from crystals exposed to different types of solvent allows the determination of where each type of solvent molecule resides. Small molecules that bind tightly to those sites can then be designed and synthesized and tested for their JAK3 inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzy-*

In order that this invention be more fully understood, the following examples are set forth. These examples are for the purpose of illustration only and are not to be construed as limiting the scope of the invention in any way.

EXAMPLE 1

Cloning and Expression of JAK3

The full-length JAK3 cDNA (GenBank accession number AAD22741) was obtained by RT-PCR from human bone marrow mRNA (Clontech). A kinase domain of human JAK3 (A810-E1115) was cloned by PCR from the previously isolated full-length JAK3 cDNA. The PCR product of the kinase domain was cloned into the baculoviral transfer vector pBEV10 for insect cell expression. The recombinant virus was plaque purified and amplified to obtain a high-titer clonal viral stock. For production, High-5 insect cells were grown to $2\times10^6$ cellml in Excell-405 medium (JRH Bioscience, KS, US) and infected with virus at a multiplicity of infection of 2.5 and incubated for 72-96 hours at 27° C.

Using the same procedure above, the following kinase domains of human JAK3 were also cloned and expressed: amino acid residues 810-1124, amino acid residues 810-1104, and amino acid residues 810-1100.

EXAMPLE 2

Purification of JAK3

Frozen cell paste was thawed in 5 volumes of Buffer A (50 mM Hepes at pH 8.0, 500 mM NaCl, 20% (vv) glycerol, 0.2% (vv) Tween 20, 0.05% (vv) mM β-mercaptoethanol, 5 mM imidazole, 1 mM PMSF, 5 μg/ml leupeptin, 3 mM benzamidine, and 25 μl/L in Benzonase (Novagen, Madison, Wis.) and mechanically lysed in a microfluidizer (Microfluidics, Newton, Mass.). The lysate was centrifuged at 54,000×g for 1 hour, and the supernatant incubated with Talon metal affinity resin (Clonetech, Palo Alto, Calif.) overnight at 4° C. After extensive washing with 20 column volumes of Buffer A, the kinase domain was eluted with Buffer A containing 100 mM imidazole with the pH readjusted to 8.0.

The elution pool was concentrated by ultrafiltration (30 KDa MWCO) in an Amicon stirred cell concentrator (Millipore, Billerica, Mass.) and loaded onto a HR 1660 Superdex-200 size-exclusion column (Amersham Biosciences, Uppsala, Sweden) equilibrated in Buffer B (50 mM Hepes at pH 8.0, 500 mM NaCl, 20% (vv) glycerol, 5 mM DTT, and 0.05% (wv) β-octylglucopyranoside). The JAK3 kinase domain was pooled based on SDS-PAGE analysis and $MgCl_2$ was added to give a final concentration of 20 mM $MgCl_2$.

The JAK3 kinase domain was loaded onto a γ-phenyl ATP-Sepharose column (Haystead et al., *Eur. J. Biochem.* 214: 459-467 (1993)) pre-equilibrated with Buffer C (50 mM Hepes at pH 8.0, 20% (vv) glycerol, 0.5 M NaCl, 20 mM $MgCl_2$, 0.05% β-octylglucopyranoside, and 5 mM DTT). After washing with two column volumes of Buffer C, JAK3 kinase domain was eluted from the column with 10 mM ADP in Buffer C and the fractions containing JAK3 kinase domain were pooled based on SDS-PAGE analysis.

The hexahistidine tag was cleaved by incubating the protein with 4 Units/ml thrombin (Calbiochem, La Jolla, Calif.) at room temperature for two hours. The completion of the cleavage was confirmed by SDS-PAGE and thrombin was removed by treating the protein with benzamidine Sepharose™ 6B (Amersham Biosciences, Uppsala, Sweden) for 30 minutes at room temperature.

The buffer was exchanged to Buffer B using a HR 1660 Superdex-200 size exclusion column (Amersham Biosciences, Uppsala, Sweden). The kinase domain containing fractions were pooled and concentrated to 15 mgml using a 10 KDa MWCO Vivaspin concentrator (Vivascience, Hanover, Germany) in the presence of 2 mM AMP-PNP (ANP) and 4 mM $MgCl_2$. Samples were subjected to ultracentrifugation at 90,000×g for 10 minutes prior to freezing for storage at −80° C.

EXAMPLE 3

Crystallization of JAK3-Adenosine Complex

The concentrated protein stored at −80° C. from Example 2 above was thawed on ice and centrifuged in a microcentrifuge for 5 minutes prior to crystallization. The protein (10-15 mgmL in 50 mM Hepes at pH 8.0, 500 mM NaCl, 20% (vv) glycerol, 5 mM DTT, and 0.05% (wv) β-octylglucopyranoside) was crystallized by the vapor diffusion method in sitting drop or hanging drop plates using 20-26% PEG 3350 as the precipitant, 200-260 mM KCl, 20 mM spermine, 10 mM DTT and 100 mM bis-tris pH 6.0. Equal volumes of protein and reservoir solution (0.5 μL) were used to form drops. Bigger drops would also grow from 1.0 μL of protein and 1.0 μL of reservoir solution. Crystals usually grew overnight as extremely thin (150×50 X<10 μm) highly malleable plates.

Crystals were grown in the Corning® 384 Well plate (available from Fisher Scientific), Greiner crystallization low profile plates (available from Hampton Research (Aliso Viejo, Calif.)), both the 96-well CrystalQuick™ standard profile round and flat bottom plates (available from Hampton Research (Aliso Viejo, Calif.)), and the 24 well VDX plates (available from Hampton Research (Aliso Viejo, Calif.)). The volume of the reservoir for the 384-well plate was 50 μL. The volume of the reservoir for the 96-well low profile plate was 100 μL, and for the CrystalQuick™ plates, it was varied between 70-100 μL.

Crystals were obtained for JAK3 protein constructs comprising amino acid residues 810-1100, amino acid residues 810-1104, amino acid residues 810-1115 and amino acid residues 810-1124.

EXAMPLE 4

X-Ray Data Collection and Structure Determination

Data was collected from crystals of the protein constructs comprising amino acid residues 810-1115 and 810-1124. The details described below, which generated the final data sets used to solve the structure of human JAK3 kinase domain, are for the protein construct comprising amino acid residues 810-1115.

Cryosolvent (reservoir solution containing 25% glycerol) was slowly mixed with the protein drop until no further mixing was observed. The crystals were mounted in nylon loops and flash frozen directly in the nitrogen stream and then stored in liquid nitrogen until the time of data collection. Flash freezing in the nitrogen stream caused less damage to the crystals than freezing directly into liquid nitrogen. The crystals diffracted to greater than 2.1 Å resolution, but the spot shape was distorted at higher than 2.5 Å resolution, and the data suffered from severe anisotropy. Therefore, although the crystals diffracted to greater than 2.1 Å, data were only useable to 2.5 Å.

The data were collected at the beamline 5.0.2 at the Advanced Light Source (ALS) Berkeley, Calif. using 1.0 Å X-rays and an ADSC CCD detector. The data from the crystal were integrated and scaled using d*TREK (Pflugrath, *Acta Crystallogr*. D55: 1718-1725 (1999)). Structure factors were calculated using TRUNCATE (Bailey, *Acta Crystallogr*. D50: 760-763). Table 1 summarizes the data collection.

The crystal belonged to spacegroup P2$_1$ with unit cell dimensions a=59.98 Å, b=90.19 Å, c=69.00 Å, $\alpha$=90°, $\beta$=111.5°, $\gamma$=90° with 2 molecules in the asymmetric unit. A second crystal form that belonged to spacegroup P2$_1$2$_1$2$_1$ with unit cell dimensions a=72.36 Å, b=90.04 Å, c=105.60 Å, $\alpha$=$\beta$=$\gamma$=90° also formed. The discussions below will be limited to the crystals belonging to the P2$_1$ spacegroup.

The orientation and position of JAK3 within the asymmetric unit was achieved by molecular replacement using BEAST (Read, *Acta Crystallogr*. D57: 1373-1382 (2001)). BEAST uses maximum likelihood targets for the rotation and translation functions, and allows the use of multiple models, allowing the creation of a statistically-weighted set of averaged structure factors. The use of BEAST was essential in solving the structure. Protein kinases are very flexible molecules in their inactive state (Huse and Kuriyan, *Cell* 109: pp. 275-282 (2002)). While conventional molecular replacement methods failed, BEAST, which uses maximum likelihood targets for the rotation and translation functions, allowed the use of multiple models, and created from these models a statistically-weighted set of averaged structure factors.

Multiple superimposed kinase domains with the activation loop removed were used as the search model (Protein Data Bank (PDB) accession codes 1M17, 1LUF, 1FVR, 1IEP, 1JPA, 1AGW, 1IR3, 1QPC, and 1GJO). The superposition of the structures was done using the program DeepView (Guex and Peitsch, *Electrophoresis* 18: 2714-2723). The initial set of structures chosen represented molecules with high sequence homology to JAK3, and were in a variety of conformations. The BEAST rotation function yielded two distinct peaks, which were related by the observed non-crystallographic symmetry. Of the kinase domains used, epidermal growth factor receptor (1M17), had the highest sequence homology to JAK3, therefore, EGFR was used as the initial model for rigid body refinement in CNX (Accelrys, San Diego, Calif.).

Initial calculated electron density maps revealed that the C-terminal domain was positioned correctly, but the N-terminal domain was not. In order to find the proper orientation of the N-terminal domain, several hybrid molecules were created. The C-terminal domain of another tyrosine kinase was superimposed onto the C-terminal domain of EGFR. The new molecule used for rigid body refinement consisted of the C-terminal domain of EGFR and the newly positioned N-terminal domain of the other kinase. Of the hybrid kinases created, the molecule with the N-terminal domain of src kinase (PDB accession code 2SRC) and the C-terminal domain of EGFR yielded an easily interpretable electron density map in both domains.

The position of the ANP ligand could be clearly seen in the initial electron density maps. The structure was refined using CNX (Accelrys, San Diego, Calif.). Initial rigid-body refinement of the hybrid Src-EGFR kinase domain was followed by mutation of the necessary side chains in order to reflect the human JAK3 sequence, and proper placement of those side chains into the initial electron density maps. Subsequent refinement consisted of rounds of energy minimization, simulated annealing, and B factor refinement using NCS restraints, which were alternated with manual rebuilding of the structure in QUANTA (Accelrys, San Diego, Calif. ©2001, 2002).

Table 1 summarizes refinement statistics. Poor electron density was observed for the extreme N-terminus of the molecule (residues 810-812) and no electron density was observed for the extreme C-terminus (residues 1102-1115). A glycerol molecule was modeled into unaccounted electron density near the surface of the molecule. The final refined structure model includes human JAK3 kinase amino acid residues 813-1100 of SEQ ID NO:1.

The asymmetric unit contains two molecules of human JAK3 (labeled as mol A and B in FIG. 1). The overall RMSD for 288 C$\alpha$ atoms between the two structures is 0.20 Å, and the overall RMSD for 1152 backbone atoms is 0.23 Å. Throughout the refinement non-crystallographic restraints were used. The largest area of difference between the two molecules is the activation loop. If Molecule B is the fixed molecule and Molecule A is the moving molecule, then the relationship between A and B is the following:

ROTATION MATRIX:

| −0.54749 | −0.00940 | 0.83676 |
|---|---|---|
| 0.00861 | −0.99995 | −0.00560 |
| 0.83677 | 0.00414 | 0.54754 |

TRANSLATION VECTOR IN AS 4.32576 73.98868 6.79225

The overall R-factor and R$_{free}$ of the final model were 24.5% and 31.1%, respectively. The test set was composed of 7.9% of the total reflections.

Table 2 lists the atomic structure coordinates in Protein Data Bank (PDB)-like format and header for human JAK3 in complex with AMP-PNP (JAK3-AMP-PNP complex), as derived by X-ray diffraction from a crystal of the complex. The structure model includes human JAK3 kinase amino acid residues 813-1100 of SEQ ID NO:1).

The following abbreviations are used in Table 2:

"Atom type" refers to the element whose coordinates are measured. The first letter in the column defines the element.

"Resid" refers to the amino acid residue in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to a molecule in the asymmetric unit. Mol A and Mol B are JAK3 protein molecules. Mol Y and Mol Z are AMP-PNP. Mol Y and Mol Z binds to Mol A and Mol B of JAK3 protein, respectively. Mol W is water.

Residue "AMP" represents AMP-PNP.

EXAMPLE 8

Overview of Crystal Structure of JAK3-AMP-PNP Complex

FIG. 1 shows the overall fold of the JAK3 kinase domain. The overall structure of the unactivated JAK3 kinase domain is similar to the typical kinase-fold found in both serinethreonine and tyrosine kinases. The protein structure is composed of two domains connected by a flexible linker or hinge (residues 898-905). The smaller N-terminal domain is mostly β-sheet structure (β1-β5), with the exception of a predominant helix, called the αC helix. The C-terminal domain is composed of two β-strands (β7 and β8) and seven conserved helices (αD, αE, αEF, and αF-αI), which are found in all protein kinases. However, the JAK3 C-terminal domain also contains structural insertions including an extra helix between αF and αG, referred to herein as αFG.

The JAK3 C-terminal domain region between αF and αG contains a total of three structural insertions when compared to other tyrosine kinases. The first insertion (I1) is between amino acid residues 1024 and 1029. Here the chain juts out away from the C-terminal domain as compared to that of other tyrosine kinases. The structure briefly returns to register with other tyrosine kinases at P1030. The second structural insertion is the short αFG helix (1030-1038). In the αFG helix the side chain of amino acid residue F1034 is in the approximate position of the phenyl ring of a conserved tyrosine found in other tyrosine kinases. The final insertion (I3), amino acid residues 1039-1046, like I1, extends away from the C-terminal domain.

Comparisons of Structures of JAK3-Inhibitor Complexes to Structures of Other Kinases Comparison of the JAK3 with other protein kinases reveals that the overall orientation of the N- and C-terminal domains is related to that of the Src-2 structure (Xu et al., *Mol. Cell* 3: pp. 629-638 (1999)). The root mean square deviation between Src-2 and JAK3 using 260 equivalent Cα positions is 3.4 Å. Both structures are in an inactive conformation. Like Src-2 and the unactivated CDK2ATP structure (Schulze-Gahmen et al., *J. Med. Chem.* 39: pp. 4540-4546 (1996)), the position of the C-helix results in a nonproductive alignment of the AMP-PNP phosphate groups. The major difference in the overall architecture of the JAK3 structure and the structures of the inactive forms of Src-2 and CDK2ATP is the αFG helix region and the conformation of the activation loop. In addition, CDK2 is a SerineThreonine kinase, not a Tyrosine kinase as are Src-2 and JAK3, and as such, it has a large insertion region between the G and H helices.

While the N-terminus of the activation loop of JAK3 is similar to that of Src-2 structure, the C-terminus of the activation loop is kinked similar to the activation loops of the FGF-1 receptorACP and CDK2ATP complex structures. This kink effectively blocks the peptide substrate site. In the FGF-1 receptor, although the C-terminus of the activation loop is kinked, the overall structure is in a more open conformation and the activation loop does not reach the glycine-rich loop. However, in the unactivated CDK2ATP structure, the activation loop does interact with the glycine-rich loop (Schulze-Gahmen et al., *J. Med. Chem.* 39: pp. 4540-4546 (1996)). In JAK3, N832 of the glycine-rich loop makes two hydrogen bonds to the activation loop. The main chain carbonyl group is hydrogen bonded to the Nζ group of K978 and the Nδ of the side chain is hydrogen bonded to the main chain carbonyl group of E988. The interaction network also includes the γ-phosphate of the ATP analogue.

Figure 6:
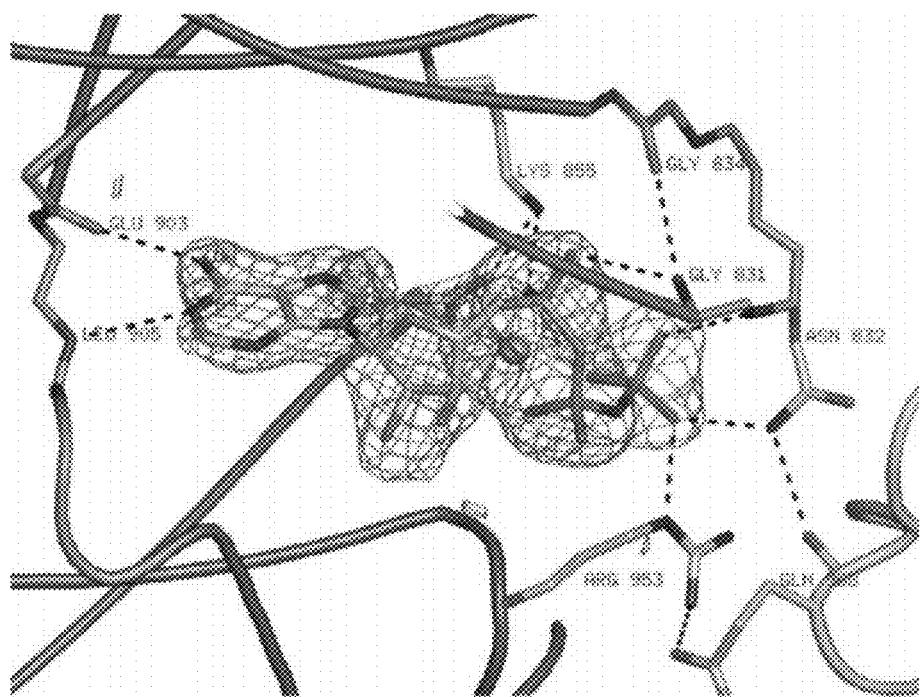
FIG. 6 shows interactions between unactivated Jak3 and AMP-PNP in the ATP-binding site. Interactions between Jak3 and AMP-PNP in the ATP-binding site. The protein backbone is depicted as a thin coil. Fo-Fc experimental electron density for the inhibitor is shown in as wire lines, contoured at 2.0σ at 2.5 Å resolution.
Figure 7:
FIG. 7 shows the location of SCID mutation L910S. Leucine 910 is located at the beginning of the αD helix and is surrounded by a number of other hydrophobic residues from adjoining parts of the C-lobe. Burying a polar sidechain, serine 910, in this hydrophobic pocket would probably lead to disruption of this region of the protein. The results could be the disruption of ATP, substrate binding, or both, resulting in a nonfunctioning kinase. The sidechains of L910 and the surrounding residues are shown.

The active site, which contains the non-hydrolyzable ATP analogue, AMP-PNP, is formed by a groove at the interface between the N and C-terminal lobes. The hinge region, the glycine rich loop (residues 829-834), and the activation loop (residues 967-990) enclose the ligand. The NH2 of the purine ring is hydrogen bonded to the backbone oxygen of Glu 903 (FIG. 6). The phosphates of the AMP-PNP participate in an extensive hydrogen bonding network that includes both the activation and glycine-rich loops (FIG. 6).

The orientation of the N and C-terminal lobes of Jak3 KD1 structure is most similar to that of the unactivated Src kinase (Xu, W., Doshi, A., Lei, M., Eck, M. J., and Harrison, S. C. (1999) *Mol Cell* 3, 629-638), Cdk-2 (Schulze-Gahmen, U., Brandsen, J., Jones, H. D., Morgan, D. O., Meijer, L., Vesely, J., and Kim, S. H. (1995) *Proteins* 22, 378-391), and the recently solved structures of Mek1 and Mek2 (Ohren, J. F., Chen, H., Pavlovsky, A., Whitehead, C., Zhang, E., Kuffa, P., Yan, C., McConnell, P., Spessard, C., Banotai, C., Mueller, W. T., Delaney, A., Omer, C., Sebolt-Leopold, J., Dudley, D. T., Leung, I. K., Flamme, C., Warmus, J., Kaufman, M., Barrett, S., Tecle, H., and Hasemann, C. A. (2004) *Nat Struct Mol Biol* 11, 1192-1197). The root mean square deviation (r.m.s.d.) between Jak3 and the Src-2, Cdk-2, Mek-1, and Mek-2 structures is 1.15 Å (using 215 equivalent Cα positions), 1.36 Å (using 186 equivalent Cα positions), 1.56 Å (using 190 equivalent Cα positions), and 1.63 Å (using 191 equivalent Cα positions) respectively. As in the previously mentioned structures, the αC-helix which contains the conserved glutamic acid, Glu 871, is swung out, away from the active site preventing the formation of the salt bridge between Glu 871 and the conserved catalytic lysine, Lys 855, which in activated kinases coordinates the α and β phosphates of the ATP. Instead Lys 855 is hydrogen bonded to the α-phosphate of the AMP-PNP, and the aspartic acid, Asp 967, at the beginning of the activation loop. The conformation of the AMP-PNP, the coordination of the Mg$^{2+}$ ion, and the interaction with the catalytic lysine, Lys 855, are all very similar to that seen in the inactive Cdk-2ATP (Schulze-Gahmen, U., De Bondt, H. L., and Kim, S. H. (1996) *J Med Chem* 39, 4540-4546) and Src-2 structures (Xu, W., Doshi, A., Lei, M., Eck, M. J., and Harrison, S. C. (1999) *Mol Cell* 3, 629-638).

The beginning of the activation loop, containing the conserved DFG sequence (residues 967-968), is almost identical in conformation to that in the Src-2 and unactivated Cdk-2 structures. However, the Jak3 KD1 activation loop notably diverges from the previously mentioned structures, Src-2 and Cdk-2, as it kinks towards the glycine-rich loop. Superposition of Jak3 on insulin receptor kinase with a bound peptide substrate (PDB #1IR3) clearly showed the kink in the activation loop (residues 978-989) blocks the protein substrate binding site, similar to that seen in unactivated Cdk-2 (PDB #1HCK) (Schulze-Gahmen, U., De Bondt, H. L., and Kim, S. H. (1996) *J Med Chem* 39, 4540-4546) and fibroblast growth factor receptor kinase (PDB #1FGK) (Mohammadi, M., Schlessinger, J., and Hubbard, S. R. (1996) *Cell* 86, 577-587). This region of the activation loop includes the potential autophosphorylation tyrosines, Tyr 980 and Tyr 981.

Regulation of the Catalytic Domain of JAK3

Regulation of the catalytic domain of Janus kinases takes place through interactions with domains N-terminal to the kinase domain. Both the pseudokinase domain and the FERM domain play pivotal roles in controlling activity of the catalytic domain. Furthermore, it has been shown that both of these domains can interact with the kinase domain. Previous studies in JAK3 have focused on naturally occurring mutations in the FERM domain and pseudokinase domain that have been found in SCID patients. Unique region around αFG is a possible site for interaction with the other JAK3 domains.

Some known SCID mutations affect the kinase domain. There are two known SCID mutations that prematurely terminate the kinase domain. These premature stops remove the αFG-αI helices. These prematurely terminated kinases probably result in an unstable kinase domain, which may be rapidly degraded in cells. This would explain the undetectable levels of protein expressed in cells containing these mutations. The only naturally occurring point mutation in the catalytic domain resulting in SCID known is the mutation of a leucine at position 910 (L910) to serine. L910 occurs at the beginning of the αD helix. The side chain of L910 contributes to the hydrophobic core of the C-terminal domain. This residue is only five residues away from L905, which is involved in positioning the purine ring of the ATP substrate, and one residue away from R911, which along with other equivalent residues in insulin receptor kinase, Q915 and R918, have been implicated in binding the peptide substrate at the P-1, P-2 and P-3 positions. The replacement of a highly conserved hydrophobic residue, leucine, with a polar residue, serine, may result in the disruption or distortion of the αD helix, which may affect the binding of either the ATP substrate and/or the peptide substrate.

The insertion between αF and αG appears to be a unique feature of the JAK family when compared to the same region in other receptor and non-receptor tyrosine kinases. This insertion structurally encompasses a rather large region on the surface of the kinase domain as compared to other kinases, such as c-src. The αFG insertion region creates a large potential binding surface for recognition by another domain of the JAK kinases, specifically, the N-terminal FERM domain or the pseudokinase domain or perhaps another protein. In fact, it has been suggested that messages in other domains affect the function of the kinase domain. This region may be a docking site for either another domain within the JAK kinase or for an exogenous protein substrate.

EXAMPLE 9

Activity Assay

To each well of a 96-well polycarbonate plate is added 1.5 µL of a candidate JAK3 inhibitor along with 50 µL of kinase buffer (100 mM Hepes at pH 7.4, 1 mM DTT, 10 mM $MgCl_2$, 25 mM NaCl and 0.01% BSA) containing 2 uM poly(Glu)$_4$Tyr and 10 µM ATP. This is then mixed and 50 µL of kinase buffer containing 2 nM JAK3 enzyme is added to start the reaction. After 20 minutes at room temperature (25° C.), the reaction is stopped with 50 µL of 20% trichloroacetic acid (TCA) that also contains 0.4 mM ATP. The entire contents of each well is then transferred to a 96-well glass fiber filter plate using a TomTek Cell Harvester. After washing, 60 µL of scintillation fluid is added and $^{33}P$ incorporation is detected on a Perkin Elmer® TopCount instrument.

JAK2 activity can be assayed as above, except that final poly(Glu)$_4$Tyr concentration is 15 µM and final ATP concentration is 12 µM.

While we have described a number of embodiments of this invention, it is apparent that our basic constructions may be altered to provide other embodiments which utilize the products, processes and methods of this invention.

TABLE 1

Data Collection and Refinement Statistics

| Data set | AMP-PNP |
|---|---|
| Data collection | |
| X-ray source | ALS 5.0.2 |
| Space group | $P2_1$ |
| Unit cell parameters (Å) | a = 59.98 Å b = 90.19 Å, c = 69.00 Å, β = 111.5° |
| Resolution (Å) | 45.54-2.50 (2.59-2.50) |
| Unique reflections | 23427 |
| Redundancy | 3.23 (3.12) |
| Completeness (%)* | 98.6 (94.2) |
| $R_{merge}$* | 0.124 (0.393) |
| <I/σ>* | 5.4 (2.2) |
| Refinement | |
| Reflections used | 22832 |
| Test reflections | 1806 |
| R-factor | 24.5% (28.5%) |
| Free R-factor (% data) | 31.1% (36.1%) |
| RMS deviation | |
| Bond lengths (Å) | 0.009 |
| Bond angles (°) | 1.4 |
| Dihedral angles (°) | 22.4 |
| Protein atoms | 4612 |
| Solvent atoms | 176 |

*Values for the highest resolution shell are shown in parentheses.

$R_{merge} = \Sigma_{hkl} \Sigma_i |I(hkl)_i - \langle I(hkl) \rangle|/\Sigma_{hkl} \Sigma_i \langle I(hkl)_i \rangle$ over i observations of reflection hkl.
R-factor = $\Sigma ||F_{obs}| - |F_{calc}||/\Sigma|F_{obs}|$ where $F_{obs}$ and $F_{calc}$ are the observed and calculated structure factors, respectively.
Free R-factor is calculated from a randomly chosen subset of reflections not used for refinement.

| REMARK | 3 | | |
|---|---|---|---|
| REMARK | 3 | REFINEMENT. | |
| REMARK | 3 | PROGRAM: | CNX 2002 |
| REMARK | 3 | AUTHORS: | Brunger, Adams, Clore, Delano, |
| REMARK | 3 | | Gros, Grosse-Kunstleve, Jiang, |
| REMARK | 3 | | Kuszewski, Nilges, Pannu, Read, |
| REMARK | 3 | | Rice, Simonson, Warren |
| REMARK | 3 | | And |
| REMARK | 3 | | Accelrys Inc., |
| REMARK | 3 | | (Badger, Berard, Kumar, Szalma, |
| REMARK | 3 | | Yip, Dzakula). |
| REMARK | 3 | | |
| REMARK | 3 | DATA USED IN REFINEMENT. | |
| REMARK | 3 | RESOLUTION RANGE HIGH (ANGSTROMS) | 2.50 |
| REMARK | 3 | RESOLUTION RANGE LOW (ANGSTROMS) | 19.83 |
| REMARK | 3 | DATA CUTOFF (SIGMA(F)) | 1.0 |
| REMARK | 3 | DATA CUTOFF HIGH (ABS(F)) | 1153422.38 |
| REMARK | 3 | DATA CUTOFF LOW (ABS(F)) | 0.000000 |
| REMARK | 3 | COMPLETENESS (WORKING + TEST) (%) | 96.2 |
| REMARK | 3 | NUMBER OF REFLECTIONS | 22832 |
| REMARK | 3 | | |
| REMARK | 3 | FIT TO DATA USED IN REFINEMENT. | |

| | | | | |
|---|---|---|---|---|
| REMARK | 3 | CROSS-VALIDATION METHOD | THROUGHOUT | |
| REMARK | 3 | FREE R VALUE TEST SET SELECTION | RANDOM | |
| REMARK | 3 | R VALUE (WORKING SET) | 0.245 | |
| REMARK | 3 | FREE R VALUE | 0.311 | |
| REMARK | 3 | FREE R VALUE TEST SET SIZE (%) | 7.9 | |
| REMARK | 3 | FREE R VALUE TEST SET COUNT | 1806 | |
| REMARK | 3 | ESTIMATED ERROR OF FREE R VALUE | 0.007 | |
| REMARK | 3 | | | |
| REMARK | 3 | FIT IN THE HIGHEST RESOLUTION BIN. | | |
| REMARK | 3 | TOTAL NUMBER OF BINS USED | 6 | |
| REMARK | 3 | BIN RESOLUTION RANGE HIGH (A) | 2.50 | |
| REMARK | 3 | BIN RESOLUTION RANGE LOW (A) | 2.66 | |
| REMARK | 3 | BIN COMPLETENESS (WORKING + TEST) (%) | 94.7 | |
| REMARK | 3 | REFLECTIONS IN BIN (WORKING SET) | 3423 | |
| REMARK | 3 | BIN R VALUE (WORKING SET) | 0.285 | |
| REMARK | 3 | BIN FREE R VALUE | 0.361 | |
| REMARK | 3 | BIN FREE R VALUE TEST SET SIZE (%) | 7.7 | |
| REMARK | 3 | BIN FREE R VALUE TEST SET COUNT | 286 | |
| REMARK | 3 | ESTIMATED ERROR OF BIN FREE R VALUE | 0.021 | |
| REMARK | 3 | | | |
| REMARK | 3 | NUMBER OF NON-HYDROGEN ATOMS USED IN REFINEMENT. | | |
| REMARK | 3 | PROTEIN ATOMS | 4612 | |
| REMARK | 3 | NUCLEIC ACID ATOMS | 0 | |
| REMARK | 3 | HETEROGEN ATOMS | 64 | |
| REMARK | 3 | SOLVENT ATOMS | 176 | |
| REMARK | 3 | | | |
| REMARK | 3 | B VALUES. | | |
| REMARK | 3 | FROM WILSON PLOT (A**2) | 24.1 | |
| REMARK | 3 | MEAN B VALUE (OVERALL, A**2) | 33.3 | |
| REMARK | 3 | OVERALL ANISOTROPIC B VALUE. | | |
| REMARK | 3 | B11 (A**2) | 5.72 | |
| REMARK | 3 | B22 (A**2) | 0.10 | |
| REMARK | 3 | B33 (A**2) | −5.81 | |
| REMARK | 3 | B12 (A**2) | 0.00 | |
| REMARK | 3 | B13 (A**2) | −4.61 | |
| REMARK | 3 | B23 (A**2) | 0.00 | |
| REMARK | 3 | | | |
| REMARK | 3 | BULK SOLVENT MODELING. | | |
| REMARK | 3 | METHOD USED | FLAT MODEL | |
| REMARK | 3 | KSOL | 0.398536 | |
| REMARK | 3 | BSOL | 68.0347 (A**2) | |
| REMARK | 3 | | | |
| REMARK | 3 | ESTIMATED COORDINATE ERROR. | | |
| REMARK | 3 | ESD FROM LUZZATI PLOT (A) | 0.34 | |
| REMARK | 3 | ESD FROM SIGMAA (A) | 0.35 | |
| REMARK | 3 | LOW RESOLUTION CUTOFF (A) | 5.00 | |
| REMARK | 3 | | | |
| REMARK | 3 | CROSS-VALIDATED ESTIMATED COORDINATE ERROR. | | |
| REMARK | 3 | ESD FROM C-V LUZZATI PLOT (A) | 0.45 | |
| REMARK | 3 | ESD FROM C-V SIGMAA (A) | 0.42 | |
| REMARK | 3 | | | |
| REMARK | 3 | RMS DEVIATIONS FROM IDEAL VALUES. | | |
| REMARK | 3 | BOND LENGTHS (A) | 0.009 | |
| REMARK | 3 | BOND ANGLES (DEGREES) | 1.4 | |
| REMARK | 3 | DIHEDRAL ANGLES (DEGREES) | 22.4 | |
| REMARK | 3 | IMPROPER ANGLES (DEGREES) | 0.82 | |
| REMARK | 3 | | | |
| REMARK | 3 | ISOTROPIC THERMAL MODEL | RESTRAINED | |
| REMARK | 3 | | | |
| REMARK | 3 | ISOTROPIC THERMAL FACTOR RESTRAINTS. | RMS | SIGMA |
| REMARK | 3 | MAIN-CHAIN BOND (A**2) | 1.38; | 1.50 |
| REMARK | 3 | MAIN-CHAIN ANGLE (A**2) | 2.29; | 2.00 |
| REMARK | 3 | SIDE-CHAIN BOND (A**2) | 2.01; | 2.00 |
| REMARK | 3 | SIDE-CHAIN ANGLE (A**2) | 2.92; | 2.50 |
| REMARK | 3 | | | |
| REMARK | 3 | NCD MODEL | CONSTR | |
| REMARK | 3 | | | |
| REMARK | 3 | NCS RESTRAINTS. | RMS | SIGMA/WEIGHT |
| REMARK | 3 | GROUP 1 POSITIONAL (A) | NULL; | NULL |
| REMARK | 3 | GROUP 1 B-FACTOR (A**2) | NULL; | NULL |
| REMARK | 3 | | | |
| REMARK | 3 | PARAMETER FILE 1 | ACCELRYS_CNX:libraries/toppar/protein_rep.param | |
| REMARK | 3 | PARAMETER FILE 2 | ACCELRYS_CNX:libraries/toppar/water_rep.param | |
| REMARK | 3 | PARAMETER FILE 3 | parm/missing.dat | |
| REMARK | 3 | PARAMETER FILE 4 | parm/parmxray.xpl | |
| REMARK | 3 | PARAMETER FILE 5 | ACCELRYS_CNX:libraries/toppar/ion.param | |
| REMARK | 3 | TOPOLOGY FILE 1 | ACCELRYS_CNX:libraries/toppar/protein.param | |
| REMARK | 3 | TOPOLOGY FILE 2 | parm/mass1.dat | |
| REMARK | 3 | TOPOLOGY FILE 3 | ACCELRYS_CNX:libraries/toppar/water.top | |
| REMARK | 3 | TOPOLOGY FILE 4 | inhib.gol.rtf | |

-continued

| | | | | | | | | | | | | | | | |
|---|---|---|---|---|---|---|---|---|---|---|---|---|---|---|---|
| REMARK | 3 | TOPOLOGY FILE 5 | | | ACCELRYS_CNX:libraries/toppar/ion.top | | | | | | | | | | |
| REMARK | 3 | | | | | | | | | | | | | | |
| REMARK | 3 | OTHER REFINEMENT REMARKS | | | | NULL | | | | | | | | | |
| SEQRES | 1 | A | 288 | ASP | PRO | THR | ILE | PHE | GLU | GLU | ARG | HIS | LEU | LYS | TYR | ILE |
| SEQRES | 2 | A | 283 | SER | GLN | LEU | GLY | LYS | GLY | ASN | PHE | GLY | SER | VAL | GLU | LEU |
| SEQRES | 3 | A | 283 | CYS | ARG | TYR | ASP | PRO | LEU | GLY | ASP | ASN | THR | GLY | ALA | LEU |
| SEQRES | 4 | A | 288 | VAL | ALA | VAL | LYS | GLN | LEU | GLN | HIS | SER | GLY | PRO | ASP | GLN |
| SEQRES | 5 | A | 288 | GLN | ARG | ASP | PHE | GLN | ARG | GLU | ILE | GLN | ILE | LEU | LYS | ALA |
| SEQRES | 6 | A | 288 | LEU | HIS | SER | ASP | PHE | ILE | VAL | LYS | TYR | ARG | GLY | VAL | SER |
| SEQRES | 7 | A | 288 | TYR | GLY | PRO | GLY | ARG | GLN | SER | LEU | ARG | LEU | VAL | MET | GLU |
| SEQRES | 8 | A | 288 | TYR | LEU | PRO | SER | GLY | CYS | LEU | ARG | ASP | PHE | LEU | GLN | ARG |
| SEQRES | 9 | A | 288 | HIS | ARG | ALA | ARG | LEU | ASP | ALA | SER | ARG | LEU | LEU | LEU | TYR |
| SEQRES | 10 | A | 288 | SER | SER | GLN | ILE | CYS | LYS | GLY | MET | GLU | TYR | LEU | GLY | SER |
| SEQRES | 11 | A | 288 | ARG | ARG | CYS | VAL | HIS | ARG | ASP | LEU | ALA | ALA | ARG | ASN | ILE |
| SEQRES | 12 | A | 288 | LEU | VAL | GLU | SER | GLU | ALA | HIS | VAL | LYS | ILE | ALA | ASP | PHE |
| SEQRES | 13 | A | 288 | GLY | LEU | ALA | LYS | LEU | LEU | PRO | LEU | ASP | LYS | ASP | TYR | TYR |
| SEQRES | 14 | A | 288 | VAL | VAL | ARG | GLU | PRO | GLY | GLN | SER | PRO | ILE | PHE | TRP | TYR |
| SEQRES | 15 | A | 288 | ALA | PRO | GLU | SER | LEU | SER | ASP | ASN | ILE | PHE | SER | ARG | GLN |
| SEQRES | 16 | A | 288 | SER | ASP | VAL | TRP | SER | PHE | GLY | VAL | VAL | LEU | TYR | GLU | LEU |
| SEQRES | 17 | A | 288 | PHE | THR | TYR | CYS | ASP | LYS | SER | CYS | SER | PRO | SER | ALA | GLU |
| SEQRES | 18 | A | 288 | PHE | LEU | ARG | MET | MET | GLY | CYS | GLU | ARG | ASP | VAL | PRO | ALA |
| SEQRES | 19 | A | 288 | LEU | CYS | ARG | LEU | LEU | GLU | LEU | LEU | GLU | GLU | GLY | GLN | ARG |
| SEQRES | 20 | A | 288 | LEU | PRO | ALA | PRO | PRO | ALA | CYS | PRO | ALA | GLU | VAL | HIS | GLU |
| SEQRES | 21 | A | 288 | LEU | MET | LYS | LEU | CYS | TRP | ALA | PRO | SER | PRO | GLN | ASP | ARG |
| SEQRES | 22 | A | 288 | PRO | SER | PHE | SER | ALA | LEU | GLY | PRO | GLN | LEU | ASP | MET | LEU |
| SEQRES | 23 | A | 288 | TRP | SER | | | (amino acid residues 813-1100 of SEQ ID NO: 1) | | | | | | | | | | |
| SEQRES | 1 | B | 288 | ASP | PRO | THR | ILE | PHE | GLU | GLU | ARG | HIS | LEU | LYS | TYR | ILE |
| SEQRES | 2 | B | 283 | SER | GLN | LEU | GLY | LYS | GLY | ASN | PHE | GLY | SER | VAL | GLU | LEU |
| SEQRES | 3 | B | 283 | CYS | ARG | TYR | ASP | PRO | LEU | GLY | ASP | ASN | THR | GLY | ALA | LEU |
| SEQRES | 4 | B | 288 | VAL | ALA | VAL | LYS | GLN | LEU | GLN | HIS | SER | GLY | PRO | ASP | GLN |
| SEQRES | 5 | B | 288 | GLN | ARG | ASP | PHE | GLN | ARG | GLU | ILE | GLN | ILE | LEU | LYS | ALA |
| SEQRES | 6 | B | 288 | LEU | HIS | SER | ASP | PHE | ILE | VAL | LYS | TYR | ARG | GLY | VAL | SER |
| SEQRES | 7 | B | 288 | TYR | GLY | PRO | GLY | ARG | GLN | SER | LEU | ARG | LEU | VAL | MET | GLU |
| SEQRES | 8 | B | 288 | TYR | LEU | PRO | SER | GLY | CYS | LEU | ARG | ASP | PHE | LEU | GLN | ARG |
| SEQRES | 9 | B | 288 | HIS | ARG | ALA | ARG | LEU | ASP | ALA | SER | ARG | LEU | LEU | LEU | TYR |
| SEQRES | 10 | B | 288 | SER | SER | GLN | ILE | CYS | LYS | GLY | MET | GLU | TYR | LEU | GLY | SER |
| SEQRES | 11 | B | 288 | ARG | ARG | CYS | VAL | HIS | ARG | ASP | LEU | ALA | ALA | ARG | ASN | ILE |
| SEQRES | 12 | B | 288 | LEU | VAL | GLU | SER | GLU | ALA | HIS | VAL | LYS | ILE | ALA | ASP | PHE |
| SEQRES | 13 | B | 288 | GLY | LEU | ALA | LYS | LEU | LEU | PRO | LEU | ASP | LYS | ASP | TYR | TYR |
| SEQRES | 14 | B | 288 | VAL | VAL | ARG | GLU | PRO | GLY | GLN | SER | PRO | ILE | PHE | TRP | TYR |
| SEQRES | 15 | B | 288 | ALA | PRO | GLU | SER | LEU | SER | ASP | ASN | ILE | PHE | SER | ARG | GLN |
| SEQRES | 16 | B | 288 | SER | ASP | VAL | TRP | SER | PHE | GLY | VAL | VAL | LEU | TYR | GLU | LEU |
| SEQRES | 17 | B | 288 | PHE | THR | TYR | CYS | ASP | LYS | SER | CYS | SER | PRO | SER | ALA | GLU |
| SEQRES | 18 | B | 288 | PHE | LEU | ARG | MET | MET | GLY | CYS | GLU | ARG | ASP | VAL | PRO | ALA |
| SEQRES | 19 | B | 288 | LEU | CYS | ARG | LEU | LEU | GLU | LEU | LEU | GLU | GLU | GLY | GLN | ARG |
| SEQRES | 20 | B | 288 | LEU | PRO | ALA | PRO | PRO | ALA | CYS | PRO | ALA | GLU | VAL | HIS | GLU |
| SEQRES | 21 | B | 288 | LEU | MET | LYS | LEU | CYS | TRP | ALA | PRO | SER | PRO | GLN | ASP | ARG |
| SEQRES | 22 | B | 288 | PRO | SER | PHE | SER | ALA | LEU | GLY | PRO | GLN | LEU | ASP | MET | LEU |
| SEQRES | 23 | B | 288 | TRP | SER | | | (amino acid residues 813-1100 of SEQ ID NO: 1) | | | | | | | | | | |
| CRYST1 | | 59.979 | | 90.191 | | 68.998 | 90.00 | | 111.49 | 90.00 | | P | 21 | 4 | |
| ORIGX1 | | 1.000000 | | 0.000000 | | 0.000000 | 0.000000 | | | | | | | | |
| ORIGX2 | | 0.000000 | | 1.000000 | | 0.000000 | 0.000000 | | | | | | | | |
| ORIGX3 | | 0.000000 | | 0.000000 | | 1.000000 | 0.000000 | | | | | | | | |
| SCALE1 | | 0.016672 | | 0.000000 | | 0.006563 | 0.000000 | | | | | | | | |
| SCALE2 | | 0.000000 | | 0.011088 | | 0.000000 | 0.000000 | | | | | | | | |
| SCALE3 | | 0.000000 | | 0.000000 | | 0.015576 | 0.000000 | | | | | | | | |
| ATOM | 1 | CB | ASP | A | 813 | 0.580 | 50.367 | −0.785 | 1.00 | 41.79 | A | C | | | |
| ATOM | 2 | CG | ASP | A | 813 | 1.998 | 49.832 | −0.801 | 1.00 | 43.65 | A | C | | | |
| ATOM | 3 | OD1 | ASP | A | 813 | 2.838 | 50.329 | −0.016 | 1.00 | 46.37 | A | O | | | |
| ATOM | 4 | OD2 | ASP | A | 813 | 2.273 | 48.916 | −1.599 | 1.00 | 42.84 | A | O | | | |
| ATOM | 5 | C | ASP | A | 813 | 1.327 | 52.295 | −2.160 | 1.00 | 40.95 | A | C | | | |
| ATOM | 6 | O | ASP | A | 813 | 1.392 | 51.562 | −3.146 | 1.00 | 42.84 | A | O | | | |
| ATOM | 7 | N | ASP | A | 813 | −0.881 | 52.355 | −1.021 | 1.00 | 40.53 | A | N | | | |
| ATOM | 8 | CA | ASP | A | 813 | 0.529 | 51.886 | −0.931 | 1.00 | 41.34 | A | C | | | |
| ATOM | 9 | N | PRO | A | 814 | 1.959 | 53.476 | −2.104 | 1.00 | 39.43 | A | N | | | |
| ATOM | 10 | CD | PRO | A | 814 | 1.808 | 54.433 | −0.997 | 1.00 | 38.58 | A | C | | | |
| ATOM | 11 | CA | PRO | A | 814 | 2.775 | 54.055 | −3.176 | 1.00 | 37.23 | A | C | | | |
| ATOM | 12 | CB | PRO | A | 814 | 3.106 | 55.453 | −2.654 | 1.00 | 37.73 | A | C | | | |
| ATOM | 13 | CG | PRO | A | 814 | 1.992 | 55.748 | −1.708 | 1.00 | 39.50 | A | C | | | |
| ATOM | 14 | C | PRO | A | 814 | 4.044 | 53.287 | −3.480 | 1.00 | 35.24 | A | C | | | |
| ATOM | 15 | O | PRO | A | 814 | 4.660 | 52.693 | −2.598 | 1.00 | 34.89 | A | O | | | |
| ATOM | 16 | N | THR | A | 815 | 4.424 | 53.332 | −4.748 | 1.00 | 34.06 | A | N | | | |
| ATOM | 17 | CA | THR | A | 815 | 5.634 | 52.702 | −5.241 | 1.00 | 31.98 | A | C | | | |
| ATOM | 18 | CB | THR | A | 815 | 5.350 | 51.911 | −6.492 | 1.00 | 30.59 | A | C | | | |
| ATOM | 19 | OG1 | THR | A | 815 | 4.429 | 50.863 | −6.172 | 1.00 | 30.79 | A | O | | | |
| ATOM | 20 | CG2 | THR | A | 815 | 6.637 | 51.342 | −7.065 | 1.00 | 26.89 | A | C | | | |
| ATOM | 21 | C | THR | A | 815 | 6.534 | 53.867 | −5.604 | 1.00 | 32.10 | A | C | | | |
| ATOM | 22 | O | THR | A | 815 | 7.705 | 53.702 | −5.925 | 1.00 | 30.98 | A | O | | | |
| ATOM | 23 | N | ILE | A | 816 | 5.945 | 55.054 | −5.552 | 1.00 | 32.69 | A | N | | | |
| ATOM | 24 | CA | ILE | A | 816 | 6.628 | 56.297 | −5.858 | 1.00 | 33.81 | A | C | | | |

-continued

| ATOM | 25 | CB | ILE | A | 816 | 6.003 | 56.976 | −7.097 | 1.00 | 35.98 | A | C |
| ATOM | 26 | CG2 | ILE | A | 816 | 6.212 | 58.473 | −7.038 | 1.00 | 36.08 | A | C |
| ATOM | 27 | CG1 | ILE | A | 816 | 6.586 | 56.359 | −8.378 | 1.00 | 38.71 | A | C |
| ATOM | 28 | CD1 | ILE | A | 816 | 6.128 | 54.918 | −8.667 | 1.00 | 37.14 | A | C |
| ATOM | 29 | C | ILE | A | 816 | 6.482 | 57.205 | −4.645 | 1.00 | 32.03 | A | C |
| ATOM | 30 | O | ILE | A | 816 | 5.380 | 57.406 | −4.146 | 1.00 | 33.36 | A | O |
| ATOM | 31 | N | PHE | A | 817 | 7.603 | 57.736 | −4.174 | 1.00 | 29.99 | A | N |
| ATOM | 32 | CA | PHE | A | 817 | 7.628 | 58.601 | −3.011 | 1.00 | 28.59 | A | C |
| ATOM | 33 | CB | PHE | A | 817 | 8.362 | 57.897 | −1.863 | 1.00 | 28.20 | A | C |
| ATOM | 34 | CG | PHE | A | 817 | 7.528 | 56.863 | −1.149 | 1.00 | 25.21 | A | C |
| ATOM | 35 | CD1 | PHE | A | 817 | 6.790 | 57.203 | −0.033 | 1.00 | 25.13 | A | C |
| ATOM | 36 | CD2 | PHE | A | 817 | 7.481 | 55.556 | −1.593 | 1.00 | 23.71 | A | C |
| ATOM | 37 | CE1 | PHE | A | 817 | 6.022 | 56.258 | 0.630 | 1.00 | 22.04 | A | C |
| ATOM | 38 | CE2 | PHE | A | 817 | 6.712 | 54.609 | −0.928 | 1.00 | 21.29 | A | C |
| ATOM | 39 | CZ | PHE | A | 817 | 5.987 | 54.965 | 0.181 | 1.00 | 19.64 | A | C |
| ATOM | 40 | C | PHE | A | 817 | 8.303 | 59.927 | −3.324 | 1.00 | 28.82 | A | C |
| ATOM | 41 | O | PHE | A | 817 | 9.451 | 59.981 | −3.778 | 1.00 | 27.53 | A | O |
| ATOM | 42 | N | GLU | A | 818 | 7.575 | 61.001 | −3.064 | 1.00 | 29.51 | A | N |
| ATOM | 43 | CA | GLU | A | 818 | 8.067 | 62.344 | −3.311 | 1.00 | 31.25 | A | C |
| ATOM | 44 | CB | GLU | A | 818 | 6.872 | 63.273 | −3.540 | 1.00 | 31.85 | A | C |
| ATOM | 45 | CG | GLU | A | 818 | 7.228 | 64.650 | −4.033 | 1.00 | 35.45 | A | C |
| ATOM | 46 | CD | GLU | A | 818 | 6.011 | 65.460 | −4.446 | 1.00 | 36.12 | A | C |
| ATOM | 47 | OE1 | GLU | A | 818 | 6.193 | 66.667 | −4.710 | 1.00 | 36.77 | A | O |
| ATOM | 48 | OE2 | GLU | A | 818 | 4.889 | 64.894 | −4.510 | 1.00 | 34.70 | A | O |
| ATOM | 49 | C | GLU | A | 818 | 8.884 | 62.774 | −2.097 | 1.00 | 30.93 | A | C |
| ATOM | 50 | O | GLU | A | 818 | 8.411 | 62.680 | −0.958 | 1.00 | 30.09 | A | O |
| ATOM | 51 | N | GLU | A | 819 | 10.120 | 63.213 | −2.342 | 1.00 | 30.52 | A | N |
| ATOM | 52 | CA | GLU | A | 819 | 11.017 | 63.635 | −1.265 | 1.00 | 31.39 | A | C |
| ATOM | 53 | CB | GLU | A | 819 | 12.291 | 64.276 | −1.836 | 1.00 | 29.12 | A | C |
| ATOM | 54 | CG | GLU | A | 819 | 13.384 | 63.303 | −2.288 | 1.00 | 28.07 | A | C |
| ATOM | 55 | CD | GLU | A | 819 | 13.967 | 62.480 | −1.138 | 1.00 | 26.19 | A | C |
| ATOM | 56 | OE1 | GLU | A | 819 | 13.771 | 62.869 | 0.031 | 1.00 | 27.05 | A | O |
| ATOM | 57 | OE2 | GLU | A | 819 | 14.632 | 61.455 | −1.402 | 1.00 | 23.85 | A | O |
| ATOM | 58 | C | GLU | A | 819 | 10.349 | 64.607 | −0.297 | 1.00 | 33.23 | A | C |
| ATOM | 59 | O | GLU | A | 819 | 10.489 | 64.477 | 0.923 | 1.00 | 34.49 | A | O |
| ATOM | 60 | N | ARG | A | 820 | 9.616 | 65.571 | −0.843 | 1.00 | 34.22 | A | N |
| ATOM | 61 | CA | ARG | A | 820 | 8.917 | 66.574 | −0.042 | 1.00 | 35.27 | A | C |
| ATOM | 62 | CB | ARG | A | 820 | 8.063 | 67.444 | −0.973 | 1.00 | 36.97 | A | C |
| ATOM | 63 | CG | ARG | A | 820 | 7.375 | 68.619 | −0.321 | 1.00 | 41.68 | A | C |
| ATOM | 64 | CD | ARG | A | 820 | 5.891 | 68.350 | −0.106 | 1.00 | 46.06 | A | C |
| ATOM | 65 | NE | ARG | A | 820 | 5.539 | 68.200 | 1.306 | 1.00 | 49.53 | A | N |
| ATOM | 66 | CZ | ARG | A | 820 | 5.588 | 69.176 | 2.213 | 1.00 | 51.16 | A | C |
| ATOM | 67 | NH1 | ARG | A | 820 | 5.978 | 70.398 | 1.867 | 1.00 | 50.30 | A | N |
| ATOM | 68 | NH2 | ARG | A | 820 | 5.242 | 68.926 | 3.471 | 1.00 | 51.02 | A | N |
| ATOM | 69 | C | ARG | A | 820 | 8.046 | 65.991 | 1.087 | 1.00 | 34.18 | A | C |
| ATOM | 70 | O | ARG | A | 820 | 7.749 | 66.681 | 2.060 | 1.00 | 35.87 | A | O |
| ATOM | 71 | N | HIS | A | 821 | 7.638 | 64.730 | 0.964 | 1.00 | 32.13 | A | N |
| ATOM | 72 | CA | HIS | A | 821 | 6.809 | 64.097 | 1.980 | 1.00 | 29.99 | A | C |
| ATOM | 73 | CB | HIS | A | 821 | 5.700 | 63.251 | 1.327 | 1.00 | 31.61 | A | C |
| ATOM | 74 | CG | HIS | A | 821 | 4.699 | 64.054 | 0.547 | 1.00 | 35.95 | A | C |
| ATOM | 75 | CD2 | HIS | A | 821 | 4.203 | 63.889 | −0.703 | 1.00 | 35.71 | A | C |
| ATOM | 76 | ND1 | HIS | A | 821 | 4.121 | 65.205 | 1.038 | 1.00 | 35.92 | A | N |
| ATOM | 77 | CE1 | HIS | A | 821 | 3.319 | 65.719 | 0.122 | 1.00 | 35.31 | A | C |
| ATOM | 78 | NE2 | HIS | A | 821 | 3.351 | 64.940 | −0.943 | 1.00 | 34.98 | A | N |
| ATOM | 79 | C | HIS | A | 821 | 7.630 | 63.228 | 2.937 | 1.00 | 30.47 | A | C |
| ATOM | 80 | O | HIS | A | 821 | 7.084 | 62.609 | 3.845 | 1.00 | 31.60 | A | O |
| ATOM | 81 | N | LEU | A | 822 | 8.938 | 63.155 | 2.746 | 1.00 | 29.14 | A | N |
| ATOM | 82 | CA | LEU | A | 822 | 9.734 | 62.357 | 3.669 | 1.00 | 30.38 | A | C |
| ATOM | 83 | CB | LEU | A | 822 | 10.779 | 61.516 | 2.911 | 1.00 | 28.09 | A | C |
| ATOM | 84 | CG | LEU | A | 822 | 10.229 | 60.403 | 1.992 | 1.00 | 27.43 | A | C |
| ATOM | 85 | CD1 | LEU | A | 822 | 11.359 | 59.787 | 1.205 | 1.00 | 25.73 | A | C |
| ATOM | 86 | CD2 | LEU | A | 822 | 9.504 | 59.322 | 2.811 | 1.00 | 24.78 | A | C |
| ATOM | 87 | C | LEU | A | 822 | 10.402 | 63.296 | 4.678 | 1.00 | 30.74 | A | C |
| ATOM | 88 | O | LEU | A | 822 | 11.342 | 64.017 | 4.353 | 1.00 | 31.28 | A | O |
| ATOM | 89 | N | LYS | A | 823 | 9.893 | 63.305 | 5.903 | 1.00 | 31.44 | A | N |
| ATOM | 90 | CA | LYS | A | 823 | 10.455 | 64.169 | 6.934 | 1.00 | 31.93 | A | C |
| ATOM | 91 | CB | LYS | A | 823 | 9.367 | 64.596 | 7.917 | 1.00 | 32.76 | A | C |
| ATOM | 92 | CG | LYS | A | 823 | 8.439 | 65.660 | 7.385 | 1.00 | 35.51 | A | C |
| ATOM | 93 | CD | LYS | A | 823 | 7.557 | 65.135 | 6.284 | 1.00 | 37.19 | A | C |
| ATOM | 94 | CE | LYS | A | 823 | 6.627 | 66.226 | 5.808 | 1.00 | 36.96 | A | C |
| ATOM | 95 | NZ | LYS | A | 823 | 7.411 | 67.355 | 5.255 | 1.00 | 39.29 | A | N |
| ATOM | 96 | C | LYS | A | 823 | 11.601 | 63.513 | 7.700 | 1.00 | 30.88 | A | C |
| ATOM | 97 | O | LYS | A | 823 | 11.407 | 62.522 | 8.405 | 1.00 | 29.92 | A | O |
| ATOM | 98 | N | TYR | A | 824 | 12.793 | 64.080 | 7.549 | 1.00 | 30.36 | A | N |
| ATOM | 99 | CA | TYR | A | 824 | 13.986 | 63.584 | 8.225 | 1.00 | 31.67 | A | C |
| ATOM | 100 | CB | TYR | A | 824 | 15.169 | 64.521 | 7.956 | 1.00 | 31.69 | A | C |
| ATOM | 101 | CG | TYR | A | 824 | 16.378 | 64.226 | 8.821 | 1.00 | 33.19 | A | C |
| ATOM | 102 | CD1 | TYR | A | 824 | 17.277 | 63.221 | 8.476 | 1.00 | 34.10 | A | C |
| ATOM | 103 | CE1 | TYR | A | 824 | 18.358 | 62.910 | 9.281 | 1.00 | 34.40 | A | C |
| ATOM | 104 | CD2 | TYR | A | 824 | 16.598 | 64.921 | 10.006 | 1.00 | 34.17 | A | C |

-continued

| | | | | | | | | | | | |
|---|---|---|---|---|---|---|---|---|---|---|---|
| ATOM | 105 | CE2 | TYR | A | 824 | 17.681 | 64.613 | 10.822 | 1.00 | 36.17 | A | C |
| ATOM | 106 | CZ | TYR | A | 824 | 18.555 | 63.603 | 10.452 | 1.00 | 36.25 | A | C |
| ATOM | 107 | OH | TYR | A | 824 | 19.612 | 63.258 | 11.263 | 1.00 | 37.45 | A | O |
| ATOM | 108 | C | TYR | A | 824 | 13.788 | 63.481 | 9.738 | 1.00 | 32.15 | A | C |
| ATOM | 109 | O | TYR | A | 824 | 13.279 | 64.406 | 10.369 | 1.00 | 29.97 | A | O |
| ATOM | 110 | N | ILE | A | 825 | 14.190 | 62.356 | 10.321 | 1.00 | 33.67 | A | N |
| ATOM | 111 | CA | ILE | A | 825 | 14.065 | 62.188 | 11.762 | 1.00 | 34.78 | A | C |
| ATOM | 112 | CB | ILE | A | 825 | 13.177 | 60.959 | 12.123 | 1.00 | 34.51 | A | C |
| ATOM | 113 | CG2 | ILE | A | 825 | 13.321 | 60.619 | 13.600 | 1.00 | 32.74 | A | C |
| ATOM | 114 | CG1 | ILE | A | 825 | 11.703 | 61.262 | 11.801 | 1.00 | 33.78 | A | C |
| ATOM | 115 | CD1 | ILE | A | 825 | 10.735 | 60.128 | 12.156 | 1.00 | 31.83 | A | C |
| ATOM | 116 | C | ILE | A | 825 | 15.458 | 62.040 | 12.380 | 1.00 | 36.16 | A | C |
| ATOM | 117 | O | ILE | A | 825 | 15.781 | 62.696 | 13.377 | 1.00 | 36.26 | A | O |
| ATOM | 118 | N | SER | A | 826 | 16.284 | 61.194 | 11.770 | 1.00 | 36.00 | A | N |
| ATOM | 119 | CA | SER | A | 826 | 17.645 | 60.963 | 12.247 | 1.00 | 37.27 | A | C |
| ATOM | 120 | CB | SER | A | 826 | 17.637 | 60.362 | 13.653 | 1.00 | 37.84 | A | C |
| ATOM | 121 | OG | SER | A | 826 | 17.216 | 59.011 | 13.615 | 1.00 | 41.26 | A | O |
| ATOM | 122 | C | SER | A | 826 | 18.383 | 60.017 | 11.312 | 1.00 | 36.08 | A | C |
| ATOM | 123 | O | SER | A | 826 | 17.785 | 59.401 | 10.433 | 1.00 | 36.11 | A | O |
| ATOM | 124 | N | GLN | A | 827 | 19.693 | 59.914 | 11.499 | 1.00 | 35.73 | A | N |
| ATOM | 125 | CA | GLN | A | 827 | 20.495 | 59.034 | 10.672 | 1.00 | 35.07 | A | C |
| ATOM | 126 | CB | GLN | A | 827 | 21.853 | 59.660 | 10.372 | 1.00 | 36.39 | A | C |
| ATOM | 127 | CG | GLN | A | 827 | 21.839 | 60.555 | 9.144 | 1.00 | 41.54 | A | C |
| ATOM | 128 | CD | GLN | A | 827 | 23.123 | 61.333 | 8.970 | 1.00 | 44.27 | A | C |
| ATOM | 129 | OE1 | GLN | A | 827 | 23.527 | 62.094 | 9.852 | 1.00 | 46.01 | A | O |
| ATOM | 130 | NE2 | GLN | A | 827 | 23.773 | 61.147 | 7.830 | 1.00 | 46.06 | A | N |
| ATOM | 131 | C | GLN | A | 827 | 20.685 | 57.706 | 11.362 | 1.00 | 34.12 | A | C |
| ATOM | 132 | O | GLN | A | 827 | 20.851 | 57.646 | 12.579 | 1.00 | 32.64 | A | O |
| ATOM | 133 | N | LEU | A | 828 | 20.644 | 56.639 | 10.568 | 1.00 | 32.89 | A | N |
| ATOM | 134 | CA | LEU | A | 828 | 20.818 | 55.294 | 11.084 | 1.00 | 30.70 | A | C |
| ATOM | 135 | CB | LEU | A | 828 | 19.852 | 54.338 | 10.380 | 1.00 | 29.69 | A | C |
| ATOM | 136 | CG | LEU | A | 828 | 18.371 | 54.593 | 10.675 | 1.00 | 30.57 | A | C |
| ATOM | 137 | CD1 | LEU | A | 828 | 17.500 | 53.653 | 9.851 | 1.00 | 28.22 | A | C |
| ATOM | 138 | CD2 | LEU | A | 828 | 18.107 | 54.400 | 12.174 | 1.00 | 27.72 | A | C |
| ATOM | 139 | C | LEU | A | 828 | 22.253 | 54.793 | 10.937 | 1.00 | 28.35 | A | C |
| ATOM | 140 | O | LEU | A | 828 | 22.695 | 53.966 | 11.716 | 1.00 | 27.97 | A | O |
| ATOM | 141 | N | GLY | A | 829 | 22.981 | 55.293 | 9.945 | 1.00 | 29.46 | A | N |
| ATOM | 142 | CA | GLY | A | 829 | 24.354 | 54.853 | 9.756 | 1.00 | 28.42 | A | C |
| ATOM | 143 | C | GLY | A | 829 | 24.780 | 54.760 | 8.302 | 1.00 | 27.74 | A | C |
| ATOM | 144 | O | GLY | A | 829 | 23.968 | 54.944 | 7.394 | 1.00 | 25.98 | A | O |
| ATOM | 145 | N | LYS | A | 830 | 26.064 | 54.472 | 8.092 | 1.00 | 27.82 | A | N |
| ATOM | 146 | CA | LYS | A | 830 | 26.658 | 54.339 | 6.765 | 1.00 | 28.70 | A | C |
| ATOM | 147 | CB | LYS | A | 830 | 27.716 | 55.418 | 6.542 | 1.00 | 31.68 | A | C |
| ATOM | 148 | CG | LYS | A | 830 | 28.729 | 55.005 | 5.483 | 1.00 | 38.00 | A | C |
| ATOM | 149 | CD | LYS | A | 830 | 30.008 | 55.815 | 5.517 | 1.00 | 42.10 | A | C |
| ATOM | 150 | CE | LYS | A | 830 | 31.047 | 55.190 | 4.587 | 1.00 | 44.14 | A | C |
| ATOM | 151 | NZ | LYS | A | 830 | 32.187 | 56.113 | 4.301 | 1.00 | 46.55 | A | N |
| ATOM | 152 | C | LYS | A | 830 | 27.327 | 52.968 | 6.636 | 1.00 | 27.26 | A | C |
| ATOM | 153 | O | LYS | A | 830 | 28.028 | 52.535 | 7.546 | 1.00 | 27.49 | A | O |
| ATOM | 154 | N | GLY | A | 831 | 27.131 | 52.300 | 5.501 | 1.00 | 25.76 | A | N |
| ATOM | 155 | CA | GLY | A | 831 | 27.716 | 50.985 | 5.302 | 1.00 | 24.03 | A | C |
| ATOM | 156 | C | GLY | A | 831 | 28.751 | 50.940 | 4.196 | 1.00 | 23.33 | A | C |
| ATOM | 157 | O | GLY | A | 831 | 29.557 | 51.861 | 4.063 | 1.00 | 23.56 | A | O |
| ATOM | 158 | N | ASN | A | 832 | 28.704 | 49.869 | 3.401 | 1.00 | 23.05 | A | N |
| ATOM | 159 | CA | ASN | A | 832 | 29.613 | 49.614 | 2.278 | 1.00 | 21.30 | A | C |
| ATOM | 160 | CB | ASN | A | 832 | 29.756 | 48.104 | 2.063 | 1.00 | 19.33 | A | C |
| ATOM | 161 | CG | ASN | A | 832 | 30.556 | 47.424 | 3.150 | 1.00 | 18.24 | A | C |
| ATOM | 162 | OD1 | ASN | A | 832 | 31.731 | 47.712 | 3.315 | 1.00 | 18.72 | A | O |
| ATOM | 163 | ND2 | ASN | A | 832 | 29.927 | 46.511 | 3.890 | 1.00 | 13.29 | A | N |
| ATOM | 164 | C | ASN | A | 832 | 29.182 | 50.222 | 0.946 | 1.00 | 22.90 | A | C |
| ATOM | 165 | O | ASN | A | 832 | 29.986 | 50.315 | 0.018 | 1.00 | 22.04 | A | O |
| ATOM | 166 | N | PHE | A | 833 | 27.913 | 50.604 | 0.829 | 1.00 | 24.50 | A | N |
| ATOM | 167 | CA | PHE | A | 833 | 27.439 | 51.157 | −0.434 | 1.00 | 25.47 | A | C |
| ATOM | 168 | CB | PHE | A | 833 | 26.633 | 50.109 | −1.197 | 1.00 | 24.25 | A | C |
| ATOM | 169 | CG | PHE | A | 833 | 27.366 | 48.819 | −1.401 | 1.00 | 24.66 | A | C |
| ATOM | 170 | CD1 | PHE | A | 833 | 27.226 | 47.778 | −0.497 | 1.00 | 24.28 | A | C |
| ATOM | 171 | CD2 | PHE | A | 833 | 28.215 | 48.650 | −2.485 | 1.00 | 23.57 | A | C |
| ATOM | 172 | CE1 | PHE | A | 833 | 27.919 | 46.591 | −0.672 | 1.00 | 23.07 | A | C |
| ATOM | 173 | CE2 | PHE | A | 833 | 28.910 | 47.464 | −2.662 | 1.00 | 23.02 | A | C |
| ATOM | 174 | CZ | PHE | A | 833 | 28.761 | 46.437 | −1.755 | 1.00 | 21.21 | A | C |
| ATOM | 175 | C | PHE | A | 833 | 26.618 | 52.426 | −0.333 | 1.00 | 26.66 | A | C |
| ATOM | 176 | O | PHE | A | 833 | 26.543 | 53.175 | −1.299 | 1.00 | 29.44 | A | O |
| ATOM | 177 | N | GLY | A | 834 | 26.002 | 52.667 | 0.822 | 1.00 | 26.24 | A | N |
| ATOM | 178 | CA | GLY | A | 834 | 25.199 | 53.859 | 0.986 | 1.00 | 26.25 | A | C |
| ATOM | 179 | C | GLY | A | 834 | 24.949 | 54.274 | 2.428 | 1.00 | 29.49 | A | C |
| ATOM | 180 | O | GLY | A | 834 | 25.604 | 53.809 | 3.370 | 1.00 | 30.21 | A | O |
| ATOM | 181 | N | SER | A | 835 | 23.990 | 55.171 | 2.610 | 1.00 | 29.04 | A | N |
| ATOM | 182 | CA | SER | A | 835 | 23.665 | 55.644 | 3.938 | 1.00 | 30.18 | A | C |
| ATOM | 183 | CB | SER | A | 835 | 24.092 | 57.104 | 4.099 | 1.00 | 29.43 | A | C |
| ATOM | 184 | OG | SER | A | 835 | 24.164 | 57.744 | 2.840 | 1.00 | 32.95 | A | O |

| | | | | | -continued | | | | | | |
|---|---|---|---|---|---|---|---|---|---|---|---|
| ATOM | 185 | C | SER | A | 835 | 22.178 | 55.480 | 4.138 | 1.00 | 29.88 | A | C |
| ATOM | 186 | O | SER | A | 835 | 21.420 | 55.418 | 3.166 | 1.00 | 31.77 | A | O |
| ATOM | 187 | N | VAL | A | 836 | 21.770 | 55.404 | 5.400 | 1.00 | 28.84 | A | N |
| ATOM | 188 | CA | VAL | A | 836 | 20.373 | 55.201 | 5.752 | 1.00 | 27.14 | A | C |
| ATOM | 189 | CB | VAL | A | 836 | 20.167 | 53.788 | 6.323 | 1.00 | 26.52 | A | C |
| ATOM | 190 | CG1 | VAL | A | 836 | 18.684 | 53.558 | 6.635 | 1.00 | 26.80 | A | C |
| ATOM | 191 | CG2 | VAL | A | 836 | 20.697 | 52.747 | 5.336 | 1.00 | 26.73 | A | C |
| ATOM | 192 | C | VAL | A | 836 | 19.874 | 56.195 | 6.783 | 1.00 | 28.59 | A | C |
| ATOM | 193 | O | VAL | A | 836 | 20.559 | 56.489 | 7.771 | 1.00 | 27.84 | A | O |
| ATOM | 194 | N | GLU | A | 837 | 18.666 | 56.698 | 6.550 | 1.00 | 28.68 | A | N |
| ATOM | 195 | CA | GLU | A | 837 | 18.032 | 57.646 | 7.460 | 1.00 | 29.30 | A | C |
| ATOM | 196 | CB | GLU | A | 837 | 17.847 | 58.998 | 6.780 | 1.00 | 29.51 | A | C |
| ATOM | 197 | CG | GLU | A | 837 | 19.100 | 59.647 | 6.279 | 1.00 | 29.26 | A | C |
| ATOM | 198 | CD | GLU | A | 837 | 18.836 | 61.075 | 5.896 | 1.00 | 28.21 | A | C |
| ATOM | 199 | OE1 | GLU | A | 837 | 17.661 | 61.375 | 5.602 | 1.00 | 29.43 | A | O |
| ATOM | 200 | OE2 | GLU | A | 837 | 19.781 | 61.890 | 5.880 | 1.00 | 29.52 | A | O |
| ATOM | 201 | C | GLU | A | 837 | 16.656 | 57.143 | 7.902 | 1.00 | 30.42 | A | C |
| ATOM | 202 | O | GLU | A | 837 | 16.020 | 56.341 | 7.206 | 1.00 | 30.43 | A | O |
| ATOM | 203 | N | LEU | A | 838 | 16.201 | 57.618 | 9.061 | 1.00 | 30.98 | A | N |
| ATOM | 204 | CA | LEU | A | 838 | 14.886 | 57.253 | 9.584 | 1.00 | 30.21 | A | C |
| ATOM | 205 | CB | LEU | A | 838 | 14.921 | 57.034 | 11.100 | 1.00 | 30.08 | A | C |
| ATOM | 206 | CG | LEU | A | 838 | 13.571 | 56.846 | 11.822 | 1.00 | 30.36 | A | C |
| ATOM | 207 | CD1 | LEU | A | 838 | 12.825 | 55.640 | 11.294 | 1.00 | 29.07 | A | C |
| ATOM | 208 | CD2 | LEU | A | 838 | 13.812 | 56.679 | 13.297 | 1.00 | 29.13 | A | C |
| ATOM | 209 | C | LEU | A | 838 | 14.002 | 58.437 | 9.271 | 1.00 | 31.11 | A | C |
| ATOM | 210 | O | LEU | A | 838 | 14.210 | 59.528 | 9.804 | 1.00 | 33.21 | A | O |
| ATOM | 211 | N | CYS | A | 839 | 13.030 | 58.225 | 8.392 | 1.00 | 30.58 | A | N |
| ATOM | 212 | CA | CYS | A | 839 | 12.113 | 59.282 | 7.996 | 1.00 | 31.03 | A | C |
| ATOM | 213 | CB | CYS | A | 839 | 12.262 | 59.581 | 6.503 | 1.00 | 29.27 | A | C |
| ATOM | 214 | SG | CYS | A | 839 | 13.914 | 59.993 | 5.930 | 1.00 | 27.80 | A | S |
| ATOM | 215 | C | CYS | A | 839 | 10.654 | 58.916 | 8.261 | 1.00 | 32.73 | A | C |
| ATOM | 216 | O | CYS | A | 839 | 10.316 | 57.768 | 8.563 | 1.00 | 33.99 | A | O |
| ATOM | 217 | N | ARG | A | 840 | 9.780 | 59.900 | 8.134 | 1.00 | 32.93 | A | N |
| ATOM | 218 | CA | ARG | A | 840 | 8.372 | 59.642 | 8.312 | 1.00 | 34.97 | A | C |
| ATOM | 219 | CB | ARG | A | 840 | 7.820 | 60.439 | 9.499 | 1.00 | 37.08 | A | C |
| ATOM | 220 | CG | ARG | A | 840 | 6.325 | 60.238 | 9.734 | 1.00 | 39.75 | A | C |
| ATOM | 221 | CD | ARG | A | 840 | 5.744 | 61.214 | 10.764 | 1.00 | 42.91 | A | C |
| ATOM | 222 | NE | ARG | A | 840 | 6.009 | 60.817 | 12.145 | 1.00 | 45.02 | A | N |
| ATOM | 223 | CZ | ARG | A | 840 | 6.779 | 61.492 | 12.995 | 1.00 | 46.42 | A | C |
| ATOM | 224 | NH1 | ARG | A | 840 | 7.378 | 62.617 | 12.616 | 1.00 | 45.99 | A | N |
| ATOM | 225 | NH2 | ARG | A | 840 | 6.950 | 61.036 | 14.231 | 1.00 | 46.11 | A | N |
| ATOM | 226 | C | ARG | A | 840 | 7.685 | 60.072 | 7.029 | 1.00 | 34.39 | A | C |
| ATOM | 227 | O | ARG | A | 840 | 7.911 | 61.177 | 6.544 | 1.00 | 33.96 | A | O |
| ATOM | 228 | N | TYR | A | 841 | 6.885 | 59.184 | 6.452 | 1.00 | 36.23 | A | N |
| ATOM | 229 | CA | TYR | A | 841 | 6.145 | 59.516 | 5.241 | 1.00 | 38.35 | A | C |
| ATOM | 230 | CB | TYR | A | 841 | 5.696 | 58.246 | 4.511 | 1.00 | 38.71 | A | C |
| ATOM | 231 | CG | TYR | A | 841 | 4.982 | 58.516 | 3.206 | 1.00 | 38.68 | A | C |
| ATOM | 232 | CD1 | TYR | A | 841 | 5.490 | 59.430 | 2.294 | 1.00 | 37.37 | A | C |
| ATOM | 233 | CE1 | TYR | A | 841 | 4.859 | 59.673 | 1.101 | 1.00 | 36.58 | A | C |
| ATOM | 234 | CD2 | TYR | A | 841 | 3.811 | 57.848 | 2.878 | 1.00 | 39.63 | A | C |
| ATOM | 235 | CE2 | TYR | A | 841 | 3.172 | 58.085 | 1.680 | 1.00 | 39.84 | A | C |
| ATOM | 236 | CZ | TYR | A | 841 | 3.703 | 58.998 | 0.798 | 1.00 | 38.61 | A | C |
| ATOM | 237 | OH | TYR | A | 841 | 3.066 | 59.234 | −0.397 | 1.00 | 41.90 | A | O |
| ATOM | 238 | C | TYR | A | 841 | 4.947 | 60.259 | 5.801 | 1.00 | 40.68 | A | C |
| ATOM | 239 | O | TYR | A | 841 | 4.146 | 59.679 | 6.531 | 1.00 | 40.74 | A | O |
| ATOM | 240 | N | ASP | A | 842 | 4.832 | 61.543 | 5.474 | 1.00 | 43.88 | A | N |
| ATOM | 241 | CA | ASP | A | 842 | 3.755 | 62.370 | 6.009 | 1.00 | 46.15 | A | C |
| ATOM | 242 | CB | ASP | A | 842 | 4.326 | 63.219 | 7.152 | 1.00 | 46.02 | A | C |
| ATOM | 243 | CG | ASP | A | 842 | 3.358 | 63.397 | 8.303 | 1.00 | 46.16 | A | C |
| ATOM | 244 | OD1 | ASP | A | 842 | 2.749 | 62.395 | 8.730 | 1.00 | 46.36 | A | O |
| ATOM | 245 | OD2 | ASP | A | 842 | 3.225 | 64.538 | 8.797 | 1.00 | 44.93 | A | O |
| ATOM | 246 | C | ASP | A | 842 | 3.135 | 63.277 | 4.950 | 1.00 | 48.03 | A | C |
| ATOM | 247 | O | ASP | A | 842 | 3.262 | 64.500 | 5.029 | 1.00 | 47.67 | A | O |
| ATOM | 248 | N | PRO | A | 843 | 2.453 | 62.688 | 3.948 | 1.00 | 50.40 | A | N |
| ATOM | 249 | CD | PRO | A | 843 | 2.212 | 61.242 | 3.809 | 1.00 | 50.93 | A | C |
| ATOM | 250 | CA | PRO | A | 843 | 1.801 | 63.427 | 2.858 | 1.00 | 51.87 | A | C |
| ATOM | 251 | CB | PRO | A | 843 | 0.980 | 62.348 | 2.154 | 1.00 | 51.29 | A | C |
| ATOM | 252 | CG | PRO | A | 843 | 1.792 | 61.125 | 2.359 | 1.00 | 50.63 | A | C |
| ATOM | 253 | C | PRO | A | 843 | 0.923 | 64.556 | 3.389 | 1.00 | 53.34 | A | C |
| ATOM | 254 | O | PRO | A | 843 | 0.848 | 65.633 | 2.798 | 1.00 | 54.36 | A | O |
| ATOM | 255 | N | LEU | A | 844 | 0.263 | 64.295 | 4.511 | 1.00 | 54.96 | A | N |
| ATOM | 256 | CA | LEU | A | 844 | −0.612 | 65.273 | 5.144 | 1.00 | 56.98 | A | C |
| ATOM | 257 | CB | LEU | A | 844 | −1.832 | 64.569 | 5.745 | 1.00 | 57.16 | A | C |
| ATOM | 258 | CG | LEU | A | 844 | −2.540 | 63.518 | 4.878 | 1.00 | 57.83 | A | C |
| ATOM | 259 | CD1 | LEU | A | 844 | −2.826 | 64.080 | 3.490 | 1.00 | 57.39 | A | C |
| ATOM | 260 | CD2 | LEU | A | 844 | −1.667 | 62.287 | 4.770 | 1.00 | 58.93 | A | C |
| ATOM | 261 | C | LEU | A | 844 | 0.158 | 66.004 | 6.245 | 1.00 | 58.02 | A | C |
| ATOM | 262 | O | LEU | A | 844 | 1.173 | 65.510 | 6.736 | 1.00 | 58.53 | A | O |
| ATOM | 263 | N | GLY | A | 845 | −0.320 | 67.178 | 6.636 | 1.00 | 59.34 | A | N |
| ATOM | 264 | CA | GLY | A | 845 | 0.366 | 67.926 | 7.676 | 1.00 | 60.48 | A | C |

-continued

| | | | | | | | | | | | |
|---|---|---|---|---|---|---|---|---|---|---|---|
| ATOM | 265 | C | GLY | A | 845 | 0.607 | 67.135 | 8.956 | 1.00 | 61.50 | A | C |
| ATOM | 266 | O | GLY | A | 845 | 1.748 | 66.986 | 9.400 | 1.00 | 61.55 | A | O |
| ATOM | 267 | N | ASP | A | 846 | −0.471 | 66.631 | 9.551 | 1.00 | 61.30 | A | N |
| ATOM | 268 | CA | ASP | A | 846 | −0.383 | 65.862 | 10.785 | 1.00 | 61.54 | A | C |
| ATOM | 269 | CB | ASP | A | 846 | −1.731 | 65.199 | 11.100 | 1.00 | 63.49 | A | C |
| ATOM | 270 | CG | ASP | A | 846 | −2.244 | 64.334 | 9.960 | 1.00 | 64.35 | A | C |
| ATOM | 271 | OD1 | ASP | A | 846 | −3.385 | 63.835 | 10.056 | 1.00 | 66.21 | A | O |
| ATOM | 272 | OD2 | ASP | A | 846 | −1.510 | 64.148 | 8.968 | 1.00 | 65.16 | A | O |
| ATOM | 273 | C | ASP | A | 846 | 0.700 | 64.806 | 10.684 | 1.00 | 61.10 | A | C |
| ATOM | 274 | O | ASP | A | 846 | 0.805 | 64.108 | 9.677 | 1.00 | 61.50 | A | O |
| ATOM | 275 | N | ASN | A | 847 | 1.501 | 64.690 | 11.735 | 1.00 | 59.87 | A | N |
| ATOM | 276 | CA | ASN | A | 847 | 2.589 | 63.723 | 11.763 | 1.00 | 57.70 | A | C |
| ATOM | 277 | CB | ASN | A | 847 | 3.512 | 64.038 | 12.924 | 1.00 | 58.23 | A | C |
| ATOM | 278 | CG | ASN | A | 847 | 4.087 | 65.416 | 12.826 | 1.00 | 58.62 | A | C |
| ATOM | 279 | OD1 | ASN | A | 847 | 4.999 | 65.663 | 12.039 | 1.00 | 59.48 | A | O |
| ATOM | 280 | ND2 | ASN | A | 847 | 3.543 | 66.337 | 13.607 | 1.00 | 59.51 | A | N |
| ATOM | 281 | C | ASN | A | 847 | 2.083 | 62.304 | 11.895 | 1.00 | 55.91 | A | C |
| ATOM | 282 | O | ASN | A | 847 | 2.803 | 61.426 | 12.374 | 1.00 | 56.51 | A | O |
| ATOM | 283 | N | THR | A | 848 | 0.845 | 62.085 | 11.465 | 1.00 | 53.41 | A | N |
| ATOM | 284 | CA | THR | A | 848 | 0.222 | 60.771 | 11.541 | 1.00 | 51.20 | A | C |
| ATOM | 285 | CB | THR | A | 848 | −1.273 | 60.836 | 11.136 | 1.00 | 50.55 | A | C |
| ATOM | 286 | OG1 | THR | A | 848 | −1.390 | 61.250 | 9.768 | 1.00 | 49.25 | A | O |
| ATOM | 287 | CG2 | THR | A | 848 | −2.023 | 61.818 | 12.023 | 1.00 | 49.29 | A | C |
| ATOM | 288 | C | THR | A | 848 | 0.920 | 59.735 | 10.663 | 1.00 | 50.05 | A | C |
| ATOM | 289 | O | THR | A | 848 | 0.606 | 58.547 | 10.732 | 1.00 | 51.27 | A | O |
| ATOM | 290 | N | GLY | A | 849 | 1.866 | 60.184 | 9.845 | 1.00 | 47.22 | A | N |
| ATOM | 291 | CA | GLY | A | 849 | 2.582 | 59.274 | 8.965 | 1.00 | 44.27 | A | C |
| ATOM | 292 | C | GLY | A | 849 | 3.322 | 58.124 | 9.632 | 1.00 | 41.86 | A | C |
| ATOM | 293 | O | GLY | A | 849 | 3.518 | 58.109 | 10.848 | 1.00 | 42.65 | A | O |
| ATOM | 294 | N | ALA | A | 850 | 3.750 | 57.159 | 8.822 | 1.00 | 40.05 | A | N |
| ATOM | 295 | CA | ALA | A | 850 | 4.467 | 55.984 | 9.315 | 1.00 | 37.02 | A | C |
| ATOM | 296 | CB | ALA | A | 850 | 3.994 | 54.730 | 8.571 | 1.00 | 36.14 | A | C |
| ATOM | 297 | C | ALA | A | 850 | 5.979 | 56.103 | 9.188 | 1.00 | 36.11 | A | C |
| ATOM | 298 | O | ALA | A | 850 | 6.501 | 56.891 | 8.397 | 1.00 | 35.06 | A | O |
| ATOM | 299 | N | LEU | A | 851 | 6.682 | 55.309 | 9.982 | 1.00 | 34.16 | A | N |
| ATOM | 300 | CA | LEU | A | 851 | 8.130 | 55.307 | 9.930 | 1.00 | 33.37 | A | C |
| ATOM | 301 | CB | LEU | A | 851 | 8.704 | 54.832 | 11.264 | 1.00 | 35.31 | A | C |
| ATOM | 302 | CG | LEU | A | 851 | 9.165 | 55.901 | 12.257 | 1.00 | 36.20 | A | C |
| ATOM | 303 | CD1 | LEU | A | 851 | 8.253 | 57.120 | 12.182 | 1.00 | 36.82 | A | C |
| ATOM | 304 | CD2 | LEU | A | 851 | 9.181 | 55.297 | 13.664 | 1.00 | 34.32 | A | C |
| ATOM | 305 | C | LEU | A | 851 | 8.611 | 54.394 | 8.806 | 1.00 | 31.96 | A | C |
| ATOM | 306 | O | LEU | A | 851 | 8.015 | 53.354 | 8.540 | 1.00 | 31.31 | A | O |
| ATOM | 307 | N | VAL | A | 852 | 9.682 | 54.802 | 8.134 | 1.00 | 31.01 | A | N |
| ATOM | 308 | CA | VAL | A | 852 | 10.258 | 54.012 | 7.055 | 1.00 | 27.90 | A | C |
| ATOM | 309 | CB | VAL | A | 852 | 9.715 | 54.441 | 5.672 | 1.00 | 26.77 | A | C |
| ATOM | 310 | CG1 | VAL | A | 852 | 8.205 | 54.243 | 5.603 | 1.00 | 28.29 | A | C |
| ATOM | 311 | CG2 | VAL | A | 852 | 10.065 | 55.876 | 5.416 | 1.00 | 24.56 | A | C |
| ATOM | 312 | C | VAL | A | 852 | 11.773 | 54.200 | 7.047 | 1.00 | 29.02 | A | C |
| ATOM | 313 | O | VAL | A | 852 | 12.286 | 55.216 | 7.528 | 1.00 | 28.76 | A | O |
| ATOM | 314 | N | ALA | A | 853 | 12.486 | 53.212 | 6.513 | 1.00 | 28.28 | A | N |
| ATOM | 315 | CA | ALA | A | 853 | 13.937 | 53.293 | 6.404 | 1.00 | 27.51 | A | C |
| ATOM | 316 | CB | ALA | A | 853 | 14.564 | 51.949 | 6.642 | 1.00 | 27.05 | A | C |
| ATOM | 317 | C | ALA | A | 853 | 14.218 | 53.749 | 4.985 | 1.00 | 28.18 | A | C |
| ATOM | 318 | O | ALA | A | 853 | 13.746 | 53.132 | 4.016 | 1.00 | 28.55 | A | O |
| ATOM | 319 | N | VAL | A | 854 | 14.983 | 54.828 | 4.857 | 1.00 | 26.18 | A | N |
| ATOM | 320 | CA | VAL | A | 854 | 15.297 | 55.366 | 3.546 | 1.00 | 25.26 | A | C |
| ATOM | 321 | CB | VAL | A | 854 | 14.806 | 56.815 | 3.404 | 1.00 | 24.58 | A | C |
| ATOM | 322 | CG1 | VAL | A | 854 | 15.175 | 57.355 | 2.020 | 1.00 | 25.67 | A | C |
| ATOM | 323 | CG2 | VAL | A | 854 | 13.306 | 56.868 | 3.640 | 1.00 | 20.74 | A | C |
| ATOM | 324 | C | VAL | A | 854 | 16.779 | 55.343 | 3.275 | 1.00 | 25.34 | A | C |
| ATOM | 325 | O | VAL | A | 854 | 17.523 | 56.142 | 3.827 | 1.00 | 27.35 | A | O |
| ATOM | 326 | N | LYS | A | 855 | 17.211 | 54.430 | 2.418 | 1.00 | 24.66 | A | N |
| ATOM | 327 | CA | LYS | A | 855 | 18.622 | 54.339 | 2.091 | 1.00 | 25.16 | A | C |
| ATOM | 328 | CB | LYS | A | 855 | 19.087 | 52.877 | 2.050 | 1.00 | 22.54 | A | C |
| ATOM | 329 | CG | LYS | A | 855 | 20.264 | 52.682 | 1.088 | 1.00 | 20.44 | A | C |
| ATOM | 330 | CD | LYS | A | 855 | 20.761 | 51.253 | 0.972 | 1.00 | 18.74 | A | C |
| ATOM | 331 | CE | LYS | A | 855 | 21.444 | 50.753 | 2.237 | 1.00 | 18.04 | A | C |
| ATOM | 332 | NZ | LYS | A | 855 | 22.347 | 49.633 | 1.878 | 1.00 | 16.00 | A | N |
| ATOM | 333 | C | LYS | A | 855 | 18.944 | 54.987 | 0.746 | 1.00 | 26.42 | A | C |
| ATOM | 334 | O | LYS | A | 855 | 18.185 | 54.861 | −0.214 | 1.00 | 23.35 | A | O |
| ATOM | 335 | N | GLN | A | 856 | 20.071 | 55.693 | 0.702 | 1.00 | 27.46 | A | N |
| ATOM | 336 | CA | GLN | A | 856 | 20.557 | 56.315 | −0.522 | 1.00 | 29.59 | A | C |
| ATOM | 337 | CB | GLN | A | 856 | 20.792 | 57.818 | −0.325 | 1.00 | 29.19 | A | C |
| ATOM | 338 | CG | GLN | A | 856 | 21.044 | 58.568 | −1.637 | 1.00 | 32.25 | A | C |
| ATOM | 339 | CD | GLN | A | 856 | 21.048 | 60.101 | −1.489 | 1.00 | 33.60 | A | C |
| ATOM | 340 | OE1 | GLN | A | 856 | 21.849 | 60.654 | −0.742 | 1.00 | 38.48 | A | O |
| ATOM | 341 | NE2 | GLN | A | 856 | 20.157 | 60.782 | −2.213 | 1.00 | 28.07 | A | N |
| ATOM | 342 | C | GLN | A | 856 | 21.882 | 55.624 | −0.875 | 1.00 | 30.88 | A | C |
| ATOM | 343 | O | GLN | A | 856 | 22.804 | 55.563 | −0.054 | 1.00 | 31.97 | A | O |
| ATOM | 344 | N | LEU | A | 857 | 21.967 | 55.088 | −2.085 | 1.00 | 32.50 | A | N |

-continued

| | | | | | | | | | | | |
|---|---|---|---|---|---|---|---|---|---|---|---|
| ATOM | 345 | CA | LEU | A | 857 | 23.178 | 54.412 | −2.542 | 1.00 | 35.93 | A | C |
| ATOM | 346 | CB | LEU | A | 857 | 22.837 | 53.379 | −3.620 | 1.00 | 33.15 | A | C |
| ATOM | 347 | CG | LEU | A | 857 | 21.875 | 52.268 | −3.202 | 1.00 | 31.85 | A | C |
| ATOM | 348 | CD1 | LEU | A | 857 | 21.562 | 51.361 | −4.379 | 1.00 | 31.75 | A | C |
| ATOM | 349 | CD2 | LEU | A | 857 | 22.494 | 51.484 | −2.072 | 1.00 | 31.93 | A | C |
| ATOM | 350 | C | LEU | A | 857 | 24.202 | 55.386 | −3.114 | 1.00 | 38.69 | A | C |
| ATOM | 351 | O | LEU | A | 857 | 23.845 | 56.347 | −3.796 | 1.00 | 37.21 | A | O |
| ATOM | 352 | N | GLN | A | 858 | 25.473 | 55.146 | −2.814 | 1.00 | 43.02 | A | N |
| ATOM | 353 | CA | GLN | A | 858 | 26.540 | 55.979 | −3.347 | 1.00 | 48.51 | A | C |
| ATOM | 354 | CB | GLN | A | 858 | 27.899 | 55.516 | −2.808 | 1.00 | 49.56 | A | C |
| ATOM | 355 | CG | GLN | A | 858 | 29.091 | 56.039 | −3.601 | 1.00 | 52.69 | A | C |
| ATOM | 356 | CD | GLN | A | 858 | 30.384 | 55.277 | −3.320 | 1.00 | 55.55 | A | C |
| ATOM | 357 | OE1 | GLN | A | 858 | 30.403 | 54.044 | −3.301 | 1.00 | 56.97 | A | O |
| ATOM | 358 | NE2 | GLN | A | 858 | 31.474 | 56.013 | −3.113 | 1.00 | 56.46 | A | N |
| ATOM | 359 | C | GLN | A | 858 | 26.465 | 55.749 | −4.854 | 1.00 | 51.62 | A | C |
| ATOM | 360 | O | GLN | A | 858 | 26.836 | 54.687 | −5.354 | 1.00 | 52.30 | A | O |
| ATOM | 361 | N | HIS | A | 859 | 25.968 | 56.737 | −5.579 | 1.00 | 56.16 | A | N |
| ATOM | 362 | CA | HIS | A | 859 | 25.827 | 56.591 | −7.019 | 1.00 | 59.85 | A | C |
| ATOM | 363 | CB | HIS | A | 859 | 24.361 | 56.781 | −7.414 | 1.00 | 60.11 | A | C |
| ATOM | 364 | CG | HIS | A | 859 | 24.025 | 56.251 | −8.772 | 1.00 | 61.57 | A | C |
| ATOM | 365 | CD2 | HIS | A | 859 | 23.561 | 56.872 | −9.882 | 1.00 | 62.54 | A | C |
| ATOM | 366 | ND1 | HIS | A | 859 | 24.157 | 54.921 | −9.103 | 1.00 | 62.61 | A | N |
| ATOM | 367 | CE1 | HIS | A | 859 | 23.789 | 54.743 | −10.360 | 1.00 | 63.08 | A | C |
| ATOM | 368 | NE2 | HIS | A | 859 | 23.423 | 55.911 | −10.855 | 1.00 | 63.34 | A | N |
| ATOM | 369 | C | HIS | A | 859 | 26.699 | 57.605 | −7.744 | 1.00 | 61.51 | A | C |
| ATOM | 370 | O | HIS | A | 859 | 26.380 | 58.794 | −7.795 | 1.00 | 62.00 | A | O |
| ATOM | 371 | N | SER | A | 860 | 27.811 | 57.129 | −8.291 | 1.00 | 63.34 | A | N |
| ATOM | 372 | CA | SER | A | 860 | 28.726 | 57.996 | −9.018 | 1.00 | 64.52 | A | C |
| ATOM | 373 | CB | SER | A | 860 | 30.132 | 57.916 | −8.416 | 1.00 | 65.20 | A | C |
| ATOM | 374 | OG | SER | A | 860 | 30.108 | 58.201 | −7.025 | 1.00 | 65.35 | A | O |
| ATOM | 375 | C | SER | A | 860 | 28.746 | 57.574 | −10.480 | 1.00 | 65.06 | A | C |
| ATOM | 376 | O | SER | A | 860 | 29.523 | 56.708 | −10.886 | 1.00 | 64.96 | A | O |
| ATOM | 377 | N | GLY | A | 861 | 27.862 | 58.198 | −11.252 | 1.00 | 65.21 | A | N |
| ATOM | 378 | CA | GLY | A | 861 | 27.738 | 57.924 | −12.670 | 1.00 | 65.25 | A | C |
| ATOM | 379 | C | GLY | A | 861 | 26.374 | 58.427 | −13.094 | 1.00 | 65.25 | A | C |
| ATOM | 380 | O | GLY | A | 861 | 25.606 | 58.885 | −12.245 | 1.00 | 65.70 | A | O |
| ATOM | 381 | N | PRO | A | 862 | 26.032 | 58.368 | −14.389 | 1.00 | 64.70 | A | N |
| ATOM | 382 | CD | PRO | A | 862 | 26.713 | 57.725 | −15.526 | 1.00 | 65.03 | A | C |
| ATOM | 383 | CA | PRO | A | 862 | 24.707 | 58.854 | −14.783 | 1.00 | 63.21 | A | C |
| ATOM | 384 | CB | PRO | A | 862 | 24.678 | 58.591 | −16.287 | 1.00 | 63.52 | A | C |
| ATOM | 385 | CG | PRO | A | 862 | 25.548 | 57.375 | −16.425 | 1.00 | 64.47 | A | C |
| ATOM | 386 | C | PRO | A | 862 | 23.598 | 58.107 | −14.046 | 1.00 | 61.61 | A | C |
| ATOM | 387 | O | PRO | A | 862 | 23.425 | 56.904 | −14.232 | 1.00 | 61.26 | A | O |
| ATOM | 388 | N | ASP | A | 863 | 22.865 | 58.823 | −13.197 | 1.00 | 59.69 | A | N |
| ATOM | 389 | CA | ASP | A | 863 | 21.763 | 58.228 | −12.444 | 1.00 | 56.82 | A | C |
| ATOM | 390 | CB | ASP | A | 863 | 20.950 | 59.303 | −11.721 | 1.00 | 58.54 | A | C |
| ATOM | 391 | CG | ASP | A | 863 | 20.091 | 60.133 | −12.680 | 1.00 | 59.27 | A | C |
| ATOM | 392 | OD1 | ASP | A | 863 | 20.662 | 60.803 | −13.574 | 1.00 | 60.57 | A | O |
| ATOM | 393 | OD2 | ASP | A | 863 | 18.849 | 60.115 | −12.541 | 1.00 | 58.02 | A | O |
| ATOM | 394 | C | ASP | A | 863 | 20.859 | 57.574 | −13.461 | 1.00 | 54.16 | A | C |
| ATOM | 395 | O | ASP | A | 863 | 20.821 | 58.004 | −14.612 | 1.00 | 54.94 | A | O |
| ATOM | 396 | N | GLN | A | 864 | 20.126 | 56.548 | −13.044 | 1.00 | 49.49 | A | N |
| ATOM | 397 | CA | GLN | A | 864 | 19.212 | 55.875 | −13.953 | 1.00 | 44.06 | A | C |
| ATOM | 398 | CB | GLN | A | 864 | 19.861 | 54.620 | −14.509 | 1.00 | 46.96 | A | C |
| ATOM | 399 | CG | GLN | A | 864 | 21.098 | 54.950 | −15.309 | 1.00 | 49.97 | A | C |
| ATOM | 400 | CD | GLN | A | 864 | 20.834 | 56.024 | −16.348 | 1.00 | 51.95 | A | C |
| ATOM | 401 | OE1 | GLN | A | 864 | 21.748 | 56.732 | −16.769 | 1.00 | 54.75 | A | O |
| ATOM | 402 | NE2 | GLN | A | 864 | 19.580 | 56.149 | −16.769 | 1.00 | 53.04 | A | N |
| ATOM | 403 | C | GLN | A | 864 | 17.883 | 55.553 | −13.297 | 1.00 | 39.54 | A | C |
| ATOM | 404 | O | GLN | A | 864 | 17.674 | 54.464 | −12.767 | 1.00 | 37.98 | A | O |
| ATOM | 405 | N | GLN | A | 865 | 16.995 | 56.540 | −13.343 | 1.00 | 34.60 | A | N |
| ATOM | 406 | CA | GLN | A | 865 | 15.671 | 56.455 | −12.766 | 1.00 | 30.90 | A | C |
| ATOM | 407 | CB | GLN | A | 865 | 14.875 | 57.702 | −13.173 | 1.00 | 29.99 | A | C |
| ATOM | 408 | CG | GLN | A | 865 | 13.395 | 57.657 | −12.845 | 1.00 | 27.24 | A | C |
| ATOM | 409 | CD | GLN | A | 865 | 12.635 | 56.758 | −13.792 | 1.00 | 25.91 | A | C |
| ATOM | 410 | OE1 | GLN | A | 865 | 12.783 | 56.867 | −15.013 | 1.00 | 26.96 | A | O |
| ATOM | 411 | NE2 | GLN | A | 865 | 11.815 | 55.866 | −13.241 | 1.00 | 26.05 | A | N |
| ATOM | 412 | C | GLN | A | 865 | 14.937 | 55.178 | −13.164 | 1.00 | 30.14 | A | C |
| ATOM | 413 | O | GLN | A | 865 | 14.330 | 54.514 | −12.317 | 1.00 | 29.46 | A | O |
| ATOM | 414 | N | ARG | A | 866 | 14.992 | 54.835 | −14.446 | 1.00 | 28.26 | A | N |
| ATOM | 415 | CA | ARG | A | 866 | 14.339 | 53.630 | −14.939 | 1.00 | 27.87 | A | C |
| ATOM | 416 | CB | ARG | A | 866 | 14.556 | 53.480 | −16.442 | 1.00 | 30.08 | A | C |
| ATOM | 417 | CG | ARG | A | 866 | 13.762 | 54.460 | −17.277 | 1.00 | 31.40 | A | C |
| ATOM | 418 | CD | ARG | A | 866 | 14.135 | 54.349 | −18.744 | 1.00 | 30.86 | A | C |
| ATOM | 419 | NE | ARG | A | 866 | 13.327 | 55.237 | −19.577 | 1.00 | 31.25 | A | N |
| ATOM | 420 | CZ | ARG | A | 866 | 13.453 | 56.561 | −19.620 | 1.00 | 31.81 | A | C |
| ATOM | 421 | NH1 | ARG | A | 866 | 12.661 | 57.268 | −20.410 | 1.00 | 30.66 | A | N |
| ATOM | 422 | NH2 | ARG | A | 866 | 14.370 | 57.181 | −18.883 | 1.00 | 30.91 | A | N |
| ATOM | 423 | C | ARG | A | 866 | 14.843 | 52.386 | −14.225 | 1.00 | 27.32 | A | C |
| ATOM | 424 | O | ARG | A | 866 | 14.039 | 51.559 | −13.790 | 1.00 | 24.87 | A | O |

-continued

| | | | | | | | | | | | |
|---|---|---|---|---|---|---|---|---|---|---|---|
| ATOM | 425 | N | ASP | A | 867 | 16.165 | 52.247 | −14.111 | 1.00 | 29.27 | A | N |
| ATOM | 426 | CA | ASP | A | 867 | 16.762 | 51.096 | −13.420 | 1.00 | 30.55 | A | C |
| ATOM | 427 | CB | ASP | A | 867 | 18.287 | 51.202 | −13.357 | 1.00 | 31.56 | A | C |
| ATOM | 428 | CG | ASP | A | 867 | 18.961 | 50.950 | −14.701 | 1.00 | 34.40 | A | C |
| ATOM | 429 | OD1 | ASP | A | 867 | 18.384 | 50.263 | −15.578 | 1.00 | 35.17 | A | O |
| ATOM | 430 | OD2 | ASP | A | 867 | 20.094 | 51.439 | −14.869 | 1.00 | 36.88 | A | O |
| ATOM | 431 | C | ASP | A | 867 | 16.228 | 50.944 | −12.001 | 1.00 | 31.08 | A | C |
| ATOM | 432 | O | ASP | A | 867 | 15.568 | 49.948 | −11.694 | 1.00 | 31.13 | A | O |
| ATOM | 433 | N | PHE | A | 868 | 16.508 | 51.919 | −11.134 | 1.00 | 31.00 | A | N |
| ATOM | 434 | CA | PHE | A | 868 | 16.018 | 51.844 | −9.755 | 1.00 | 31.24 | A | C |
| ATOM | 435 | CB | PHE | A | 868 | 16.192 | 53.180 | −9.024 | 1.00 | 30.81 | A | C |
| ATOM | 436 | CG | PHE | A | 868 | 17.597 | 53.467 | −8.598 | 1.00 | 28.20 | A | C |
| ATOM | 437 | CD1 | PHE | A | 868 | 18.591 | 53.669 | −9.536 | 1.00 | 27.55 | A | C |
| ATOM | 438 | CD2 | PHE | A | 868 | 17.921 | 53.533 | −7.254 | 1.00 | 28.80 | A | C |
| ATOM | 439 | CE1 | PHE | A | 868 | 19.884 | 53.931 | −9.143 | 1.00 | 28.47 | A | C |
| ATOM | 440 | CE2 | PHE | A | 868 | 19.207 | 53.793 | −6.848 | 1.00 | 27.69 | A | C |
| ATOM | 441 | CZ | PHE | A | 868 | 20.194 | 53.993 | −7.792 | 1.00 | 29.38 | A | C |
| ATOM | 442 | C | PHE | A | 868 | 14.536 | 51.487 | −9.758 | 1.00 | 31.43 | A | C |
| ATOM | 443 | O | PHE | A | 868 | 14.076 | 50.687 | −8.950 | 1.00 | 32.47 | A | O |
| ATOM | 444 | N | GLN | A | 869 | 13.800 | 52.095 | −10.676 | 1.00 | 31.87 | A | N |
| ATOM | 445 | CA | GLN | A | 869 | 12.364 | 51.871 | −10.814 | 1.00 | 33.84 | A | C |
| ATOM | 446 | CB | GLN | A | 869 | 11.827 | 52.814 | −11.901 | 1.00 | 34.67 | A | C |
| ATOM | 447 | CG | GLN | A | 869 | 10.323 | 52.847 | −12.055 | 1.00 | 39.76 | A | C |
| ATOM | 448 | CD | GLN | A | 869 | 9.621 | 53.521 | −10.902 | 1.00 | 42.28 | A | C |
| ATOM | 449 | OE1 | GLN | A | 869 | 8.422 | 53.775 | −10.960 | 1.00 | 43.86 | A | O |
| ATOM | 450 | NE2 | GLN | A | 869 | 10.366 | 53.815 | −9.842 | 1.00 | 45.51 | A | N |
| ATOM | 451 | C | GLN | A | 869 | 12.053 | 50.405 | −11.169 | 1.00 | 32.83 | A | C |
| ATOM | 452 | O | GLN | A | 869 | 11.157 | 49.777 | −10.593 | 1.00 | 30.45 | A | O |
| ATOM | 453 | N | ARG | A | 870 | 12.807 | 49.868 | −12.121 | 1.00 | 31.56 | A | N |
| ATOM | 454 | CA | ARG | A | 870 | 12.619 | 48.490 | −12.567 | 1.00 | 29.61 | A | C |
| ATOM | 455 | CB | ARG | A | 870 | 13.578 | 48.192 | −13.720 | 1.00 | 29.76 | A | C |
| ATOM | 456 | CG | ARG | A | 870 | 13.476 | 46.795 | −14.306 | 1.00 | 30.49 | A | C |
| ATOM | 457 | CD | ARG | A | 870 | 14.608 | 46.577 | −15.294 | 1.00 | 27.79 | A | C |
| ATOM | 458 | NE | ARG | A | 870 | 15.918 | 46.749 | −14.671 | 1.00 | 26.84 | A | N |
| ATOM | 459 | CZ | ARG | A | 870 | 16.841 | 47.605 | −15.098 | 1.00 | 27.83 | A | C |
| ATOM | 460 | NH1 | ARG | A | 870 | 16.588 | 48.373 | −16.152 | 1.00 | 24.51 | A | N |
| ATOM | 461 | NH2 | ARG | A | 870 | 18.023 | 47.679 | −14.485 | 1.00 | 25.65 | A | N |
| ATOM | 462 | C | ARG | A | 870 | 12.849 | 47.495 | −11.438 | 1.00 | 29.71 | A | C |
| ATOM | 463 | O | ARG | A | 870 | 12.092 | 46.535 | −11.266 | 1.00 | 30.22 | A | O |
| ATOM | 464 | N | GLU | A | 871 | 13.893 | 47.736 | −10.658 | 1.00 | 30.06 | A | N |
| ATOM | 465 | CA | GLU | A | 871 | 14.244 | 46.851 | −9.564 | 1.00 | 29.79 | A | C |
| ATOM | 466 | CB | GLU | A | 871 | 15.625 | 47.219 | −9.054 | 1.00 | 29.83 | A | C |
| ATOM | 467 | CG | GLU | A | 871 | 16.677 | 47.061 | −10.127 | 1.00 | 30.10 | A | C |
| ATOM | 468 | CD | GLU | A | 871 | 16.663 | 45.668 | −10.734 | 1.00 | 32.26 | A | C |
| ATOM | 469 | OE1 | GLU | A | 871 | 16.906 | 45.543 | −11.956 | 1.00 | 33.53 | A | O |
| ATOM | 470 | OE2 | GLU | A | 871 | 16.417 | 44.699 | −9.985 | 1.00 | 32.71 | A | O |
| ATOM | 471 | C | GLU | A | 871 | 13.230 | 46.858 | −8.435 | 1.00 | 32.02 | A | C |
| ATOM | 472 | O | GLU | A | 871 | 12.617 | 45.829 | −8.127 | 1.00 | 31.99 | A | O |
| ATOM | 473 | N | ILE | A | 872 | 13.035 | 48.016 | −7.822 | 1.00 | 33.05 | A | N |
| ATOM | 474 | CA | ILE | A | 872 | 12.081 | 48.115 | −6.727 | 1.00 | 33.73 | A | C |
| ATOM | 475 | CB | ILE | A | 872 | 11.839 | 49.581 | −6.320 | 1.00 | 34.18 | A | C |
| ATOM | 476 | CG2 | ILE | A | 872 | 10.647 | 49.683 | −5.409 | 1.00 | 34.71 | A | C |
| ATOM | 477 | CG1 | ILE | A | 872 | 13.055 | 50.096 | −5.563 | 1.00 | 35.67 | A | C |
| ATOM | 478 | CD1 | ILE | A | 872 | 13.377 | 49.261 | −4.352 | 1.00 | 33.28 | A | C |
| ATOM | 479 | C | ILE | A | 872 | 10.753 | 47.453 | −7.061 | 1.00 | 32.84 | A | C |
| ATOM | 480 | O | ILE | A | 872 | 10.156 | 46.805 | −6.200 | 1.00 | 33.81 | A | O |
| ATOM | 481 | N | GLN | A | 873 | 10.286 | 47.594 | −8.301 | 1.00 | 31.38 | A | N |
| ATOM | 482 | CA | GLN | A | 873 | 9.014 | 46.972 | −8.669 | 1.00 | 31.13 | A | C |
| ATOM | 483 | CB | GLN | A | 873 | 8.554 | 47.407 | −10.060 | 1.00 | 31.19 | A | C |
| ATOM | 484 | CG | GLN | A | 873 | 8.194 | 48.867 | −10.119 | 1.00 | 33.73 | A | C |
| ATOM | 485 | CD | GLN | A | 873 | 7.213 | 49.198 | −11.218 | 1.00 | 36.91 | A | C |
| ATOM | 486 | OE1 | GLN | A | 873 | 6.858 | 50.366 | −11.396 | 1.00 | 41.17 | A | O |
| ATOM | 487 | NE2 | GLN | A | 873 | 6.761 | 48.181 | −11.960 | 1.00 | 35.88 | A | N |
| ATOM | 488 | C | GLN | A | 873 | 9.128 | 45.462 | −8.614 | 1.00 | 30.57 | A | C |
| ATOM | 489 | O | GLN | A | 873 | 8.187 | 44.773 | −8.209 | 1.00 | 30.27 | A | O |
| ATOM | 490 | N | ILE | A | 874 | 10.291 | 44.961 | −9.022 | 1.00 | 28.38 | A | N |
| ATOM | 491 | CA | ILE | A | 874 | 10.571 | 43.538 | −9.000 | 1.00 | 26.50 | A | C |
| ATOM | 492 | CB | ILE | A | 874 | 11.906 | 43.224 | −9.738 | 1.00 | 25.96 | A | C |
| ATOM | 493 | CG2 | ILE | A | 874 | 12.444 | 41.878 | −9.304 | 1.00 | 25.39 | A | C |
| ATOM | 494 | CG1 | ILE | A | 874 | 11.693 | 43.227 | −11.252 | 1.00 | 23.07 | A | C |
| ATOM | 495 | CD1 | ILE | A | 874 | 12.985 | 43.153 | −12.033 | 1.00 | 24.11 | A | C |
| ATOM | 496 | C | ILE | A | 874 | 10.693 | 43.093 | −7.542 | 1.00 | 27.93 | A | C |
| ATOM | 497 | O | ILE | A | 874 | 10.192 | 42.031 | −7.157 | 1.00 | 27.66 | A | O |
| ATOM | 498 | N | LEU | A | 875 | 11.361 | 43.922 | −6.737 | 1.00 | 27.30 | A | N |
| ATOM | 499 | CA | LEU | A | 875 | 11.576 | 43.629 | −5.323 | 1.00 | 26.34 | A | C |
| ATOM | 500 | CB | LEU | A | 875 | 12.698 | 44.514 | −4.769 | 1.00 | 25.39 | A | C |
| ATOM | 501 | CG | LEU | A | 875 | 14.108 | 44.249 | −5.324 | 1.00 | 23.64 | A | C |
| ATOM | 502 | CD1 | LEU | A | 875 | 15.052 | 45.341 | −4.844 | 1.00 | 23.64 | A | C |
| ATOM | 503 | CD2 | LEU | A | 875 | 14.610 | 42.897 | −4.876 | 1.00 | 22.26 | A | C |
| ATOM | 504 | C | LEU | A | 875 | 10.308 | 43.802 | −4.491 | 1.00 | 26.93 | A | C |

-continued

| | | | | | | | | | | | | |
|---|---|---|---|---|---|---|---|---|---|---|---|---|
| ATOM | 505 | O | LEU | A | 875 | 10.068 | 43.056 | −3.541 | 1.00 | 27.40 | A | O |
| ATOM | 506 | N | LYS | A | 876 | 9.486 | 44.774 | −4.862 | 1.00 | 26.36 | A | N |
| ATOM | 507 | CA | LYS | A | 876 | 8.256 | 45.025 | −4.134 | 1.00 | 27.17 | A | C |
| ATOM | 508 | CB | LYS | A | 876 | 7.669 | 46.380 | −4.540 | 1.00 | 24.25 | A | C |
| ATOM | 509 | CG | LYS | A | 876 | 6.551 | 46.819 | −3.634 | 1.00 | 24.74 | A | C |
| ATOM | 510 | CD | LYS | A | 876 | 5.952 | 48.150 | −4.014 | 1.00 | 25.31 | A | C |
| ATOM | 511 | CE | LYS | A | 876 | 4.882 | 48.496 | −3.008 | 1.00 | 24.35 | A | C |
| ATOM | 512 | NZ | LYS | A | 876 | 4.120 | 49.691 | −3.413 | 1.00 | 28.04 | A | N |
| ATOM | 513 | C | LYS | A | 876 | 7.227 | 43.917 | −4.369 | 1.00 | 29.28 | A | C |
| ATOM | 514 | O | LYS | A | 876 | 6.211 | 43.830 | −3.666 | 1.00 | 32.41 | A | O |
| ATOM | 515 | N | ALA | A | 877 | 7.475 | 43.067 | −5.358 | 1.00 | 28.69 | A | N |
| ATOM | 516 | CA | ALA | A | 877 | 6.533 | 41.990 | −5.629 | 1.00 | 29.42 | A | C |
| ATOM | 517 | CB | ALA | A | 877 | 6.501 | 41.678 | −7.130 | 1.00 | 27.23 | A | C |
| ATOM | 518 | C | ALA | A | 877 | 6.883 | 40.736 | −4.814 | 1.00 | 29.56 | A | C |
| ATOM | 519 | O | ALA | A | 877 | 6.053 | 39.841 | −4.653 | 1.00 | 28.54 | A | O |
| ATOM | 520 | N | LEU | A | 878 | 8.107 | 40.694 | −4.288 | 1.00 | 29.51 | A | N |
| ATOM | 521 | CA | LEU | A | 878 | 8.585 | 39.573 | −3.473 | 1.00 | 27.97 | A | C |
| ATOM | 522 | CB | LEU | A | 878 | 10.094 | 39.691 | −3.250 | 1.00 | 26.08 | A | C |
| ATOM | 523 | CG | LEU | A | 878 | 10.959 | 39.783 | −4.503 | 1.00 | 27.63 | A | C |
| ATOM | 524 | CD1 | LEU | A | 878 | 12.350 | 40.250 | −4.135 | 1.00 | 27.67 | A | C |
| ATOM | 525 | CD2 | LEU | A | 878 | 10.991 | 38.444 | −5.209 | 1.00 | 26.13 | A | C |
| ATOM | 526 | C | LEU | A | 878 | 7.896 | 39.556 | −2.117 | 1.00 | 27.99 | A | C |
| ATOM | 527 | O | LEU | A | 878 | 7.899 | 40.560 | −1.414 | 1.00 | 29.76 | A | O |
| ATOM | 528 | N | HIS | A | 879 | 7.308 | 38.425 | −1.745 | 1.00 | 29.32 | A | N |
| ATOM | 529 | CA | HIS | A | 879 | 6.643 | 38.314 | −0.451 | 1.00 | 31.36 | A | C |
| ATOM | 530 | CB | HIS | A | 879 | 5.130 | 38.240 | −0.630 | 1.00 | 32.39 | A | C |
| ATOM | 531 | CG | HIS | A | 879 | 4.550 | 39.450 | −1.285 | 1.00 | 39.51 | A | C |
| ATOM | 532 | CD2 | HIS | A | 879 | 3.661 | 39.582 | −2.296 | 1.00 | 40.92 | A | C |
| ATOM | 533 | ND1 | HIS | A | 879 | 4.907 | 40.732 | −0.918 | 1.00 | 42.50 | A | N |
| ATOM | 534 | CE1 | HIS | A | 879 | 4.266 | 41.599 | −1.679 | 1.00 | 43.10 | A | C |
| ATOM | 535 | NE2 | HIS | A | 879 | 3.504 | 40.929 | −2.525 | 1.00 | 44.26 | A | N |
| ATOM | 536 | C | HIS | A | 879 | 7.103 | 37.131 | 0.408 | 1.00 | 31.51 | A | C |
| ATOM | 537 | O | HIS | A | 879 | 6.948 | 35.968 | 0.022 | 1.00 | 31.05 | A | O |
| ATOM | 538 | N | SER | A | 880 | 7.666 | 37.454 | 1.575 | 1.00 | 30.02 | A | N |
| ATOM | 539 | CA | SER | A | 880 | 8.132 | 36.464 | 2.541 | 1.00 | 28.69 | A | C |
| ATOM | 540 | CB | SER | A | 880 | 9.564 | 36.052 | 2.251 | 1.00 | 27.94 | A | C |
| ATOM | 541 | OG | SER | A | 880 | 10.046 | 35.269 | 3.324 | 1.00 | 25.72 | A | O |
| ATOM | 542 | C | SER | A | 880 | 8.062 | 37.010 | 3.959 | 1.00 | 30.58 | A | C |
| ATOM | 543 | O | SER | A | 880 | 8.201 | 38.211 | 4.170 | 1.00 | 31.38 | A | O |
| ATOM | 544 | N | ASP | A | 881 | 7.848 | 36.132 | 4.933 | 1.00 | 31.77 | A | N |
| ATOM | 545 | CA | ASP | A | 881 | 7.762 | 36.568 | 6.322 | 1.00 | 32.73 | A | C |
| ATOM | 546 | CB | ASP | A | 881 | 7.001 | 35.543 | 7.169 | 1.00 | 36.42 | A | C |
| ATOM | 547 | CG | ASP | A | 881 | 5.539 | 35.439 | 6.786 | 1.00 | 41.67 | A | C |
| ATOM | 548 | OD1 | ASP | A | 881 | 4.841 | 36.479 | 6.830 | 1.00 | 43.68 | A | O |
| ATOM | 549 | OD2 | ASP | A | 881 | 5.090 | 34.318 | 6.446 | 1.00 | 43.38 | A | O |
| ATOM | 550 | C | ASP | A | 881 | 9.144 | 36.783 | 6.917 | 1.00 | 32.05 | A | C |
| ATOM | 551 | O | ASP | A | 881 | 9.284 | 37.257 | 8.046 | 1.00 | 31.81 | A | O |
| ATOM | 552 | N | PHE | A | 882 | 10.167 | 36.429 | 6.152 | 1.00 | 29.45 | A | N |
| ATOM | 553 | CA | PHE | A | 882 | 11.538 | 36.573 | 6.611 | 1.00 | 27.95 | A | C |
| ATOM | 554 | CB | PHE | A | 882 | 12.195 | 35.194 | 6.685 | 1.00 | 27.05 | A | C |
| ATOM | 555 | CG | PHE | A | 882 | 11.355 | 34.172 | 7.401 | 1.00 | 25.73 | A | C |
| ATOM | 556 | CD1 | PHE | A | 882 | 11.060 | 34.318 | 8.741 | 1.00 | 24.96 | A | C |
| ATOM | 557 | CD2 | PHE | A | 882 | 10.794 | 33.111 | 6.712 | 1.00 | 27.21 | A | C |
| ATOM | 558 | CE1 | PHE | A | 882 | 10.209 | 33.427 | 9.388 | 1.00 | 26.21 | A | C |
| ATOM | 559 | CE2 | PHE | A | 882 | 9.943 | 32.217 | 7.353 | 1.00 | 27.67 | A | C |
| ATOM | 560 | CZ | PHE | A | 882 | 9.650 | 32.378 | 8.691 | 1.00 | 24.82 | A | C |
| ATOM | 561 | C | PHE | A | 882 | 12.281 | 37.472 | 5.639 | 1.00 | 28.22 | A | C |
| ATOM | 562 | O | PHE | A | 882 | 13.422 | 37.210 | 5.282 | 1.00 | 27.42 | A | O |
| ATOM | 563 | N | ILE | A | 883 | 11.608 | 38.533 | 5.203 | 1.00 | 28.53 | A | N |
| ATOM | 564 | CA | ILE | A | 883 | 12.185 | 39.492 | 4.267 | 1.00 | 27.18 | A | C |
| ATOM | 565 | CB | ILE | A | 883 | 11.707 | 39.203 | 2.825 | 1.00 | 27.90 | A | C |
| ATOM | 566 | CG2 | ILE | A | 883 | 11.013 | 40.427 | 2.239 | 1.00 | 27.92 | A | C |
| ATOM | 567 | CG1 | ILE | A | 883 | 12.892 | 38.779 | 1.966 | 1.00 | 26.54 | A | C |
| ATOM | 568 | CD1 | ILE | A | 883 | 13.414 | 37.448 | 2.314 | 1.00 | 23.32 | A | C |
| ATOM | 569 | C | ILE | A | 883 | 11.749 | 40.898 | 4.661 | 1.00 | 26.07 | A | C |
| ATOM | 570 | O | ILE | A | 883 | 10.608 | 41.101 | 5.070 | 1.00 | 26.87 | A | O |
| ATOM | 571 | N | VAL | A | 884 | 12.652 | 41.865 | 4.551 | 1.00 | 25.78 | A | N |
| ATOM | 572 | CA | VAL | A | 884 | 12.327 | 43.245 | 4.900 | 1.00 | 25.41 | A | C |
| ATOM | 573 | CB | VAL | A | 884 | 13.579 | 44.019 | 5.310 | 1.00 | 25.86 | A | C |
| ATOM | 574 | CG1 | VAL | A | 884 | 13.209 | 45.438 | 5.667 | 1.00 | 25.61 | A | C |
| ATOM | 575 | CG2 | VAL | A | 884 | 14.244 | 43.327 | 6.479 | 1.00 | 27.98 | A | C |
| ATOM | 576 | C | VAL | A | 884 | 11.677 | 43.928 | 3.701 | 1.00 | 25.52 | A | C |
| ATOM | 577 | O | VAL | A | 884 | 12.314 | 44.168 | 2.680 | 1.00 | 24.56 | A | O |
| ATOM | 578 | N | LYS | A | 885 | 10.398 | 44.246 | 3.851 | 1.00 | 26.64 | A | N |
| ATOM | 579 | CA | LYS | A | 885 | 9.605 | 44.855 | 2.798 | 1.00 | 26.33 | A | C |
| ATOM | 580 | CB | LYS | A | 885 | 8.174 | 45.059 | 3.301 | 1.00 | 27.25 | A | C |
| ATOM | 581 | CG | LYS | A | 885 | 7.258 | 43.868 | 3.055 | 1.00 | 29.12 | A | C |
| ATOM | 582 | CD | LYS | A | 885 | 5.912 | 44.038 | 3.735 | 1.00 | 31.39 | A | C |
| ATOM | 583 | CE | LYS | A | 885 | 6.068 | 44.055 | 5.241 | 1.00 | 31.87 | A | C |
| ATOM | 584 | NZ | LYS | A | 885 | 4.750 | 43.980 | 5.915 | 1.00 | 34.16 | A | N |

-continued

| | | | | | | | | | | | |
|---|---|---|---|---|---|---|---|---|---|---|---|
| ATOM | 585 | C | LYS | A | 885 | 10.100 | 46.150 | 2.162 | 1.00 | 26.24 | A | C |
| ATOM | 586 | O | LYS | A | 885 | 10.219 | 47.179 | 2.825 | 1.00 | 25.99 | A | O |
| ATOM | 587 | N | TYR | A | 886 | 10.409 | 46.081 | 0.870 | 1.00 | 25.58 | A | N |
| ATOM | 588 | CA | TYR | A | 886 | 10.808 | 47.264 | 0.125 | 1.00 | 24.39 | A | C |
| ATOM | 589 | CB | TYR | A | 886 | 11.464 | 46.875 | −1.209 | 1.00 | 22.20 | A | C |
| ATOM | 590 | CG | TYR | A | 886 | 12.945 | 46.541 | −1.126 | 1.00 | 21.86 | A | C |
| ATOM | 591 | CD1 | TYR | A | 886 | 13.885 | 47.509 | −0.768 | 1.00 | 20.74 | A | C |
| ATOM | 592 | CE1 | TYR | A | 886 | 15.236 | 47.200 | −0.681 | 1.00 | 19.63 | A | C |
| ATOM | 593 | CD2 | TYR | A | 886 | 13.399 | 45.264 | −1.397 | 1.00 | 20.05 | A | C |
| ATOM | 594 | CE2 | TYR | A | 886 | 14.742 | 44.949 | −1.313 | 1.00 | 19.69 | A | C |
| ATOM | 595 | CZ | TYR | A | 886 | 15.655 | 45.917 | −0.953 | 1.00 | 20.05 | A | C |
| ATOM | 596 | OH | TYR | A | 886 | 16.992 | 45.596 | −0.860 | 1.00 | 17.58 | A | O |
| ATOM | 597 | C | TYR | A | 886 | 9.461 | 47.948 | −0.130 | 1.00 | 24.24 | A | C |
| ATOM | 598 | O | TYR | A | 886 | 8.430 | 47.273 | −0.267 | 1.00 | 24.22 | A | O |
| ATOM | 599 | N | ARG | A | 887 | 9.452 | 49.272 | −0.189 | 1.00 | 22.95 | A | N |
| ATOM | 600 | CA | ARG | A | 887 | 8.201 | 49.982 | −0.406 | 1.00 | 23.16 | A | C |
| ATOM | 601 | CB | ARG | A | 887 | 7.854 | 50.811 | 0.828 | 1.00 | 23.19 | A | C |
| ATOM | 602 | CG | ARG | A | 887 | 7.348 | 49.964 | 1.972 | 1.00 | 27.32 | A | C |
| ATOM | 603 | CD | ARG | A | 887 | 6.714 | 50.824 | 3.034 | 1.00 | 31.16 | A | C |
| ATOM | 604 | NE | ARG | A | 887 | 5.672 | 51.681 | 2.476 | 1.00 | 32.24 | A | N |
| ATOM | 605 | CZ | ARG | A | 887 | 4.932 | 52.523 | 3.192 | 1.00 | 33.92 | A | C |
| ATOM | 606 | NH1 | ARG | A | 887 | 5.124 | 52.618 | 4.502 | 1.00 | 33.39 | A | N |
| ATOM | 607 | NH2 | ARG | A | 887 | 3.998 | 53.263 | 2.597 | 1.00 | 33.24 | A | N |
| ATOM | 608 | C | ARG | A | 887 | 8.138 | 50.861 | −1.644 | 1.00 | 23.65 | A | C |
| ATOM | 609 | O | ARG | A | 887 | 7.051 | 51.144 | −2.140 | 1.00 | 24.45 | A | O |
| ATOM | 610 | N | GLY | A | 888 | 9.291 | 51.285 | −2.150 | 1.00 | 24.72 | A | N |
| ATOM | 611 | CA | GLY | A | 888 | 9.299 | 52.139 | −3.323 | 1.00 | 24.04 | A | C |
| ATOM | 612 | C | GLY | A | 888 | 10.585 | 52.927 | −3.492 | 1.00 | 23.39 | A | C |
| ATOM | 613 | O | GLY | A | 888 | 11.577 | 52.673 | −2.805 | 1.00 | 23.48 | A | O |
| ATOM | 614 | N | VAL | A | 889 | 10.562 | 53.877 | −4.420 | 1.00 | 20.54 | A | N |
| ATOM | 615 | CA | VAL | A | 889 | 11.709 | 54.719 | −4.722 | 1.00 | 20.10 | A | C |
| ATOM | 616 | CB | VAL | A | 889 | 12.123 | 54.570 | −6.200 | 1.00 | 21.03 | A | C |
| ATOM | 617 | CG1 | VAL | A | 889 | 13.115 | 55.656 | −6.584 | 1.00 | 21.45 | A | C |
| ATOM | 618 | CG2 | VAL | A | 889 | 12.719 | 53.200 | −6.435 | 1.00 | 19.77 | A | C |
| ATOM | 619 | C | VAL | A | 889 | 11.317 | 56.167 | −4.485 | 1.00 | 21.40 | A | C |
| ATOM | 620 | O | VAL | A | 889 | 10.159 | 56.527 | −4.684 | 1.00 | 22.69 | A | O |
| ATOM | 621 | N | SER | A | 890 | 12.262 | 57.001 | −4.057 | 1.00 | 20.80 | A | N |
| ATOM | 622 | CA | SER | A | 890 | 11.952 | 58.406 | −3.830 | 1.00 | 22.34 | A | C |
| ATOM | 623 | CB | SER | A | 890 | 12.629 | 58.920 | −2.556 | 1.00 | 21.30 | A | C |
| ATOM | 624 | OG | SER | A | 890 | 13.977 | 59.280 | −2.804 | 1.00 | 24.15 | A | O |
| ATOM | 625 | C | SER | A | 890 | 12.410 | 59.250 | −5.012 | 1.00 | 24.18 | A | C |
| ATOM | 626 | O | SER | A | 890 | 13.359 | 58.896 | −5.717 | 1.00 | 24.15 | A | O |
| ATOM | 627 | N | TYR | A | 891 | 11.718 | 60.365 | −5.229 | 1.00 | 25.30 | A | N |
| ATOM | 628 | CA | TYR | A | 891 | 12.060 | 61.284 | −6.309 | 1.00 | 27.29 | A | C |
| ATOM | 629 | CB | TYR | A | 891 | 11.002 | 61.224 | −7.411 | 1.00 | 27.04 | A | C |
| ATOM | 630 | CG | TYR | A | 891 | 11.081 | 59.936 | −8.178 | 1.00 | 28.70 | A | C |
| ATOM | 631 | CD1 | TYR | A | 891 | 12.162 | 59.667 | −9.000 | 1.00 | 29.90 | A | C |
| ATOM | 632 | CE1 | TYR | A | 891 | 12.291 | 58.455 | −9.626 | 1.00 | 28.35 | A | C |
| ATOM | 633 | CD2 | TYR | A | 891 | 10.128 | 58.955 | −8.014 | 1.00 | 26.81 | A | C |
| ATOM | 634 | CE2 | TYR | A | 891 | 10.248 | 57.743 | −8.632 | 1.00 | 27.95 | A | C |
| ATOM | 635 | CZ | TYR | A | 891 | 11.333 | 57.491 | −9.437 | 1.00 | 27.15 | A | C |
| ATOM | 636 | OH | TYR | A | 891 | 11.482 | 56.253 | −10.028 | 1.00 | 25.99 | A | O |
| ATOM | 637 | C | TYR | A | 891 | 12.236 | 62.715 | −5.803 | 1.00 | 27.89 | A | C |
| ATOM | 638 | O | TYR | A | 891 | 11.358 | 63.256 | −5.136 | 1.00 | 28.25 | A | O |
| ATOM | 639 | N | GLY | A | 892 | 13.384 | 63.295 | −6.149 | 1.00 | 29.35 | A | N |
| ATOM | 640 | CA | GLY | A | 892 | 13.791 | 64.640 | −5.767 | 1.00 | 34.56 | A | C |
| ATOM | 641 | C | GLY | A | 892 | 12.859 | 65.827 | −5.824 | 1.00 | 37.08 | A | C |
| ATOM | 642 | O | GLY | A | 892 | 11.709 | 65.745 | −5.397 | 1.00 | 41.32 | A | O |
| ATOM | 643 | N | PRO | A | 893 | 13.343 | 66.975 | −6.314 | 1.00 | 37.48 | A | N |
| ATOM | 644 | CD | PRO | A | 893 | 12.587 | 68.245 | −6.303 | 1.00 | 37.32 | A | C |
| ATOM | 645 | CA | PRO | A | 893 | 14.706 | 67.183 | −6.804 | 1.00 | 37.32 | A | C |
| ATOM | 646 | CB | PRO | A | 893 | 14.587 | 68.489 | −7.576 | 1.00 | 36.43 | A | C |
| ATOM | 647 | CG | PRO | A | 893 | 13.638 | 69.267 | −6.701 | 1.00 | 37.84 | A | C |
| ATOM | 648 | C | PRO | A | 893 | 15.710 | 67.298 | −5.663 | 1.00 | 37.83 | A | C |
| ATOM | 649 | O | PRO | A | 893 | 15.576 | 66.660 | −4.606 | 1.00 | 38.11 | A | O |
| ATOM | 650 | N | GLY | A | 894 | 16.714 | 68.134 | −5.884 | 1.00 | 35.65 | A | N |
| ATOM | 651 | CA | GLY | A | 894 | 17.725 | 68.332 | −4.865 | 1.00 | 33.37 | A | C |
| ATOM | 652 | C | GLY | A | 894 | 18.628 | 67.132 | −4.686 | 1.00 | 30.83 | A | C |
| ATOM | 653 | O | GLY | A | 894 | 18.401 | 66.080 | −5.272 | 1.00 | 29.44 | A | O |
| ATOM | 654 | N | ARG | A | 895 | 19.654 | 67.308 | −3.861 | 1.00 | 31.54 | A | N |
| ATOM | 655 | CA | ARG | A | 895 | 20.645 | 66.280 | −3.566 | 1.00 | 29.64 | A | C |
| ATOM | 656 | CB | ARG | A | 895 | 21.477 | 66.703 | −2.359 | 1.00 | 30.82 | A | C |
| ATOM | 657 | CG | ARG | A | 895 | 21.949 | 68.136 | −2.436 | 1.00 | 36.81 | A | C |
| ATOM | 658 | CD | ARG | A | 895 | 22.739 | 68.556 | −1.201 | 1.00 | 37.21 | A | C |
| ATOM | 659 | NE | ARG | A | 895 | 23.919 | 67.725 | −1.002 | 1.00 | 39.51 | A | N |
| ATOM | 660 | CZ | ARG | A | 895 | 23.966 | 66.658 | −0.215 | 1.00 | 42.26 | A | C |
| ATOM | 661 | NH1 | ARG | A | 895 | 22.885 | 66.279 | 0.471 | 1.00 | 41.34 | A | N |
| ATOM | 662 | NH2 | ARG | A | 895 | 25.100 | 65.971 | −0.125 | 1.00 | 41.86 | A | N |
| ATOM | 663 | C | ARG | A | 895 | 20.044 | 64.919 | −3.283 | 1.00 | 27.07 | A | C |
| ATOM | 664 | O | ARG | A | 895 | 20.516 | 63.913 | −3.784 | 1.00 | 26.22 | A | O |

| | | | | | -continued | | | | | | |
|---|---|---|---|---|---|---|---|---|---|---|---|
| ATOM | 665 | N | GLN | A | 896 | 19.000 | 64.881 | −2.474 | 1.00 | 25.66 | A | N |
| ATOM | 666 | CA | GLN | A | 896 | 18.418 | 63.605 | −2.141 | 1.00 | 26.88 | A | C |
| ATOM | 667 | CB | GLN | A | 896 | 17.974 | 63.605 | −0.674 | 1.00 | 27.75 | A | C |
| ATOM | 668 | CG | GLN | A | 896 | 19.095 | 63.703 | 0.367 | 1.00 | 23.25 | A | C |
| ATOM | 669 | CD | GLN | A | 896 | 18.560 | 63.532 | 1.786 | 1.00 | 25.71 | A | C |
| ATOM | 670 | OE1 | GLN | A | 896 | 17.686 | 64.279 | 2.219 | 1.00 | 25.96 | A | O |
| ATOM | 671 | NE2 | GLN | A | 896 | 19.077 | 62.538 | 2.511 | 1.00 | 24.24 | A | N |
| ATOM | 672 | C | GLN | A | 896 | 17.253 | 63.187 | −3.041 | 1.00 | 28.96 | A | C |
| ATOM | 673 | O | GLN | A | 896 | 16.220 | 63.870 | −3.113 | 1.00 | 32.60 | A | O |
| ATOM | 674 | N | SER | A | 897 | 17.436 | 62.056 | −3.717 | 1.00 | 26.09 | A | N |
| ATOM | 675 | CA | SER | A | 897 | 16.436 | 61.488 | −4.605 | 1.00 | 25.53 | A | C |
| ATOM | 676 | CB | SER | A | 897 | 16.200 | 62.418 | −5.790 | 1.00 | 26.04 | A | C |
| ATOM | 677 | OG | SER | A | 897 | 15.213 | 61.887 | −6.648 | 1.00 | 23.93 | A | O |
| ATOM | 678 | C | SER | A | 897 | 16.828 | 60.086 | −5.101 | 1.00 | 25.24 | A | C |
| ATOM | 679 | O | SER | A | 897 | 17.987 | 59.674 | −4.993 | 1.00 | 22.93 | A | O |
| ATOM | 680 | N | LEU | A | 898 | 15.856 | 59.365 | −5.656 | 1.00 | 24.91 | A | N |
| ATOM | 681 | CA | LEU | A | 898 | 16.097 | 58.010 | −6.125 | 1.00 | 24.03 | A | C |
| ATOM | 682 | CB | LEU | A | 898 | 17.112 | 57.998 | −7.268 | 1.00 | 24.88 | A | C |
| ATOM | 683 | CG | LEU | A | 898 | 16.549 | 58.464 | −8.609 | 1.00 | 23.32 | A | C |
| ATOM | 684 | CD1 | LEU | A | 898 | 17.616 | 58.439 | −9.659 | 1.00 | 24.28 | A | C |
| ATOM | 685 | CD2 | LEU | A | 898 | 15.419 | 57.550 | −9.015 | 1.00 | 26.25 | A | C |
| ATOM | 686 | C | LEU | A | 898 | 16.630 | 57.180 | −4.962 | 1.00 | 24.34 | A | C |
| ATOM | 687 | O | LEU | A | 898 | 17.584 | 56.433 | −5.117 | 1.00 | 24.06 | A | O |
| ATOM | 688 | N | ARG | A | 899 | 16.021 | 57.336 | −3.791 | 1.00 | 24.15 | A | N |
| ATOM | 689 | CA | ARG | A | 899 | 16.433 | 56.589 | −2.614 | 1.00 | 23.36 | A | C |
| ATOM | 690 | CB | ARG | A | 899 | 16.396 | 57.491 | −1.376 | 1.00 | 22.23 | A | C |
| ATOM | 691 | CG | ARG | A | 899 | 17.290 | 58.737 | −1.484 | 1.00 | 22.55 | A | C |
| ATOM | 692 | CD | ARG | A | 899 | 17.531 | 59.430 | −0.121 | 1.00 | 23.29 | A | C |
| ATOM | 693 | NE | ARG | A | 899 | 16.342 | 60.077 | 0.435 | 1.00 | 22.79 | A | N |
| ATOM | 694 | CZ | ARG | A | 899 | 16.231 | 60.489 | 1.698 | 1.00 | 23.20 | A | C |
| ATOM | 695 | NH1 | ARG | A | 899 | 15.115 | 61.066 | 2.109 | 1.00 | 21.75 | A | N |
| ATOM | 696 | NH2 | ARG | A | 899 | 17.226 | 60.320 | 2.557 | 1.00 | 21.19 | A | N |
| ATOM | 697 | C | ARG | A | 899 | 15.522 | 55.370 | −2.427 | 1.00 | 24.79 | A | C |
| ATOM | 698 | O | ARG | A | 899 | 14.410 | 55.313 | −2.972 | 1.00 | 23.87 | A | O |
| ATOM | 699 | N | LEU | A | 900 | 16.005 | 54.395 | −1.664 | 1.00 | 23.94 | A | N |
| ATOM | 700 | CA | LEU | A | 900 | 15.258 | 53.175 | −1.425 | 1.00 | 23.43 | A | C |
| ATOM | 701 | CB | LEU | A | 900 | 16.234 | 51.992 | −1.334 | 1.00 | 25.73 | A | C |
| ATOM | 702 | CG | LEU | A | 900 | 17.254 | 51.879 | −2.479 | 1.00 | 22.68 | A | C |
| ATOM | 703 | CD1 | LEU | A | 900 | 18.236 | 50.767 | −2.198 | 1.00 | 21.83 | A | C |
| ATOM | 704 | CD2 | LEU | A | 900 | 16.513 | 51.625 | −3.782 | 1.00 | 23.99 | A | C |
| ATOM | 705 | C | LEU | A | 900 | 14.467 | 53.306 | −0.134 | 1.00 | 23.36 | A | C |
| ATOM | 706 | O | LEU | A | 900 | 15.055 | 53.495 | 0.924 | 1.00 | 25.79 | A | O |
| ATOM | 707 | N | VAL | A | 901 | 13.140 | 53.215 | −0.224 | 1.00 | 23.16 | A | N |
| ATOM | 708 | CA | VAL | A | 901 | 12.247 | 53.327 | 0.943 | 1.00 | 21.00 | A | C |
| ATOM | 709 | CB | VAL | A | 901 | 10.967 | 54.161 | 0.598 | 1.00 | 19.18 | A | C |
| ATOM | 710 | CG1 | VAL | A | 901 | 10.220 | 54.541 | 1.872 | 1.00 | 16.79 | A | C |
| ATOM | 711 | CG2 | VAL | A | 901 | 11.346 | 55.412 | −0.179 | 1.00 | 16.04 | A | C |
| ATOM | 712 | C | VAL | A | 901 | 11.816 | 51.921 | 1.367 | 1.00 | 21.72 | A | C |
| ATOM | 713 | O | VAL | A | 901 | 11.301 | 51.163 | 0.550 | 1.00 | 20.89 | A | O |
| ATOM | 714 | N | MET | A | 902 | 12.018 | 51.573 | 2.635 | 1.00 | 22.44 | A | N |
| ATOM | 715 | CA | MET | A | 902 | 11.654 | 50.244 | 3.133 | 1.00 | 22.31 | A | C |
| ATOM | 716 | CB | MET | A | 902 | 12.914 | 49.415 | 3.418 | 1.00 | 23.41 | A | C |
| ATOM | 717 | CG | MET | A | 902 | 14.029 | 49.527 | 2.402 | 1.00 | 24.33 | A | C |
| ATOM | 718 | SD | MET | A | 902 | 15.610 | 48.975 | 3.107 | 1.00 | 28.16 | A | S |
| ATOM | 719 | CE | MET | A | 902 | 16.470 | 50.599 | 3.415 | 1.00 | 18.42 | A | C |
| ATOM | 720 | C | MET | A | 902 | 10.879 | 50.342 | 4.445 | 1.00 | 22.84 | A | C |
| ATOM | 721 | O | MET | A | 902 | 10.780 | 51.417 | 5.036 | 1.00 | 22.65 | A | O |
| ATOM | 722 | N | GLU | A | 903 | 10.341 | 49.212 | 4.901 | 1.00 | 23.07 | A | N |
| ATOM | 723 | CA | GLU | A | 903 | 9.637 | 49.174 | 6.175 | 1.00 | 24.06 | A | C |
| ATOM | 724 | CB | GLU | A | 903 | 8.908 | 47.835 | 6.369 | 1.00 | 21.47 | A | C |
| ATOM | 725 | CG | GLU | A | 903 | 9.829 | 46.644 | 6.571 | 1.00 | 25.28 | A | C |
| ATOM | 726 | CD | GLU | A | 903 | 9.094 | 45.325 | 6.793 | 1.00 | 25.14 | A | C |
| ATOM | 727 | OE1 | GLU | A | 903 | 8.169 | 45.267 | 7.634 | 1.00 | 23.48 | A | O |
| ATOM | 728 | OE2 | GLU | A | 903 | 9.458 | 44.333 | 6.129 | 1.00 | 27.12 | A | O |
| ATOM | 729 | C | GLU | A | 903 | 10.769 | 49.342 | 7.204 | 1.00 | 26.12 | A | C |
| ATOM | 730 | O | GLU | A | 903 | 11.907 | 48.919 | 6.962 | 1.00 | 25.33 | A | O |
| ATOM | 731 | N | TYR | A | 904 | 10.465 | 49.956 | 8.342 | 1.00 | 25.19 | A | N |
| ATOM | 732 | CA | TYR | A | 904 | 11.480 | 50.213 | 9.350 | 1.00 | 25.53 | A | C |
| ATOM | 733 | CB | TYR | A | 904 | 11.375 | 51.682 | 9.774 | 1.00 | 26.19 | A | C |
| ATOM | 734 | CG | TYR | A | 904 | 12.144 | 52.041 | 11.014 | 1.00 | 24.20 | A | C |
| ATOM | 735 | CD1 | TYR | A | 904 | 13.520 | 51.938 | 11.052 | 1.00 | 23.09 | A | C |
| ATOM | 736 | CE1 | TYR | A | 904 | 14.216 | 52.277 | 12.180 | 1.00 | 23.97 | A | C |
| ATOM | 737 | CD2 | TYR | A | 904 | 11.489 | 52.491 | 12.143 | 1.00 | 23.37 | A | C |
| ATOM | 738 | CE2 | TYR | A | 904 | 12.179 | 52.832 | 13.273 | 1.00 | 23.70 | A | C |
| ATOM | 739 | CZ | TYR | A | 904 | 13.541 | 52.728 | 13.287 | 1.00 | 22.96 | A | C |
| ATOM | 740 | OH | TYR | A | 904 | 14.225 | 53.123 | 14.408 | 1.00 | 26.04 | A | O |
| ATOM | 741 | C | TYR | A | 904 | 11.437 | 49.303 | 10.576 | 1.00 | 25.47 | A | C |
| ATOM | 742 | O | TYR | A | 904 | 10.451 | 49.286 | 11.309 | 1.00 | 25.58 | A | O |
| ATOM | 743 | N | LEU | A | 905 | 12.516 | 48.553 | 10.795 | 1.00 | 24.91 | A | N |
| ATOM | 744 | CA | LEU | A | 905 | 12.610 | 47.649 | 11.942 | 1.00 | 24.94 | A | C |

-continued

| ATOM | 745 | CB | LEU | A | 905 | 13.104 | 46.273 | 11.492 | 1.00 | 25.49 | A | C |
|------|-----|-----|-----|---|-----|--------|--------|--------|------|-------|---|---|
| ATOM | 746 | CG | LEU | A | 905 | 12.069 | 45.313 | 10.883 | 1.00 | 26.77 | A | C |
| ATOM | 747 | CD1 | LEU | A | 905 | 11.533 | 45.849 | 9.540 | 1.00 | 22.44 | A | C |
| ATOM | 748 | CD2 | LEU | A | 905 | 12.739 | 43.934 | 10.703 | 1.00 | 24.93 | A | C |
| ATOM | 749 | C | LEU | A | 905 | 13.567 | 48.243 | 12.977 | 1.00 | 24.77 | A | C |
| ATOM | 750 | O | LEU | A | 905 | 14.774 | 48.153 | 12.835 | 1.00 | 23.75 | A | O |
| ATOM | 751 | N | PRO | A | 906 | 13.021 | 48.844 | 14.043 | 1.00 | 25.08 | A | N |
| ATOM | 752 | CD | PRO | A | 906 | 11.573 | 48.801 | 14.296 | 1.00 | 25.48 | A | C |
| ATOM | 753 | CA | PRO | A | 906 | 13.717 | 49.499 | 15.157 | 1.00 | 26.75 | A | C |
| ATOM | 754 | CB | PRO | A | 906 | 12.564 | 50.077 | 15.981 | 1.00 | 24.51 | A | C |
| ATOM | 755 | CG | PRO | A | 906 | 11.499 | 49.097 | 15.781 | 1.00 | 25.37 | A | C |
| ATOM | 756 | C | PRO | A | 906 | 14.725 | 48.710 | 16.010 | 1.00 | 27.00 | A | C |
| ATOM | 757 | O | PRO | A | 906 | 15.696 | 49.291 | 16.514 | 1.00 | 27.95 | A | O |
| ATOM | 758 | N | SER | A | 907 | 14.511 | 47.408 | 16.171 | 1.00 | 26.18 | A | N |
| ATOM | 759 | CA | SER | A | 907 | 15.424 | 46.585 | 16.963 | 1.00 | 24.34 | A | C |
| ATOM | 760 | CB | SER | A | 907 | 14.858 | 45.187 | 17.145 | 1.00 | 22.15 | A | C |
| ATOM | 761 | OG | SER | A | 907 | 13.651 | 45.257 | 17.880 | 1.00 | 24.29 | A | O |
| ATOM | 762 | C | SER | A | 907 | 16.830 | 46.503 | 16.379 | 1.00 | 24.51 | A | C |
| ATOM | 763 | O | SER | A | 907 | 17.781 | 46.200 | 17.093 | 1.00 | 24.00 | A | O |
| ATOM | 764 | N | GLY | A | 908 | 16.963 | 46.765 | 15.085 | 1.00 | 23.26 | A | N |
| ATOM | 765 | CA | GLY | A | 908 | 18.277 | 46.751 | 14.485 | 1.00 | 22.85 | A | C |
| ATOM | 766 | C | GLY | A | 908 | 18.759 | 45.418 | 13.965 | 1.00 | 23.80 | A | C |
| ATOM | 767 | O | GLY | A | 908 | 18.047 | 44.407 | 14.014 | 1.00 | 23.46 | A | O |
| ATOM | 768 | N | CYS | A | 909 | 19.994 | 45.425 | 13.465 | 1.00 | 23.36 | A | N |
| ATOM | 769 | CA | CYS | A | 909 | 20.605 | 44.232 | 12.899 | 1.00 | 23.89 | A | C |
| ATOM | 770 | CB | CYS | A | 909 | 21.937 | 44.568 | 12.253 | 1.00 | 21.36 | A | C |
| ATOM | 771 | CG | CYS | A | 909 | 23.205 | 45.003 | 13.439 | 1.00 | 23.09 | A | S |
| ATOM | 772 | C | CYS | A | 909 | 20.822 | 43.143 | 13.931 | 1.00 | 24.75 | A | C |
| ATOM | 773 | O | CYS | A | 909 | 20.742 | 43.383 | 15.133 | 1.00 | 24.37 | A | O |
| ATOM | 774 | N | LEU | A | 910 | 21.113 | 41.943 | 13.438 | 1.00 | 24.76 | A | N |
| ATOM | 775 | CA | LEU | A | 910 | 21.331 | 40.788 | 14.285 | 1.00 | 25.40 | A | C |
| ATOM | 776 | CB | LEU | A | 910 | 21.058 | 39.497 | 13.501 | 1.00 | 23.11 | A | C |
| ATOM | 777 | CG | LEU | A | 910 | 21.209 | 38.168 | 14.251 | 1.00 | 19.95 | A | C |
| ATOM | 778 | CD1 | LEU | A | 910 | 20.317 | 38.176 | 15.486 | 1.00 | 19.52 | A | C |
| ATOM | 779 | CD2 | LEU | A | 910 | 20.833 | 37.002 | 13.331 | 1.00 | 17.68 | A | C |
| ATOM | 780 | C | LEU | A | 910 | 22.761 | 40.796 | 14.793 | 1.00 | 27.11 | A | C |
| ATOM | 781 | O | LEU | A | 910 | 23.032 | 40.324 | 15.892 | 1.00 | 27.00 | A | O |
| ATOM | 782 | N | ARG | A | 911 | 23.669 | 41.331 | 13.983 | 1.00 | 28.24 | A | N |
| ATOM | 783 | CA | ARG | A | 911 | 25.075 | 41.415 | 14.352 | 1.00 | 28.19 | A | C |
| ATOM | 784 | CB | ARG | A | 911 | 25.839 | 42.249 | 13.316 | 1.00 | 28.23 | A | C |
| ATOM | 785 | CG | ARG | A | 911 | 27.309 | 42.450 | 13.625 | 1.00 | 30.58 | A | C |
| ATOM | 786 | CD | ARG | A | 911 | 27.646 | 43.926 | 13.789 | 1.00 | 33.24 | A | C |
| ATOM | 787 | NE | ARG | A | 911 | 27.952 | 44.595 | 12.524 | 1.00 | 36.27 | A | N |
| ATOM | 788 | CZ | ARG | A | 911 | 27.695 | 45.878 | 12.268 | 1.00 | 37.56 | A | C |
| ATOM | 789 | NH1 | ARG | A | 911 | 27.115 | 46.636 | 13.194 | 1.00 | 34.55 | A | N |
| ATOM | 790 | NH2 | ARG | A | 911 | 28.029 | 46.408 | 11.090 | 1.00 | 36.66 | A | N |
| ATOM | 791 | C | ARG | A | 911 | 25.205 | 42.050 | 15.735 | 1.00 | 29.66 | A | C |
| ATOM | 792 | O | ARG | A | 911 | 25.791 | 41.461 | 16.633 | 1.00 | 28.96 | A | O |
| ATOM | 793 | N | ASP | A | 912 | 24.645 | 43.245 | 15.911 | 1.00 | 30.49 | A | N |
| ATOM | 794 | CA | ASP | A | 912 | 24.726 | 43.937 | 17.19B | 1.00 | 31.99 | A | C |
| ATOM | 795 | CB | ASP | A | 912 | 24.300 | 45.396 | 17.041 | 1.00 | 31.19 | A | C |
| ATOM | 796 | CG | ASP | A | 912 | 25.211 | 46.166 | 16.109 | 1.00 | 35.19 | A | C |
| ATOM | 797 | OD1 | ASP | A | 912 | 24.896 | 47.327 | 15.778 | 1.00 | 37.95 | A | O |
| ATOM | 798 | OD2 | ASP | A | 912 | 26.251 | 45.609 | 15.705 | 1.00 | 39.20 | A | O |
| ATOM | 799 | C | ASP | A | 912 | 23.885 | 43.274 | 18.283 | 1.00 | 32.12 | A | C |
| ATOM | 800 | O | ASP | A | 912 | 24.265 | 43.257 | 19.454 | 1.00 | 33.14 | A | O |
| ATOM | 801 | N | PHE | A | 913 | 22.744 | 42.729 | 17.877 | 1.00 | 31.11 | A | N |
| ATOM | 802 | CA | PHE | A | 913 | 21.818 | 42.053 | 18.780 | 1.00 | 29.01 | A | C |
| ATOM | 803 | CB | PHE | A | 913 | 20.610 | 41.561 | 17.984 | 1.00 | 27.73 | A | C |
| ATOM | 804 | CG | PHE | A | 913 | 19.543 | 40.927 | 18.820 | 1.00 | 25.27 | A | C |
| ATOM | 805 | CD1 | PHE | A | 913 | 18.543 | 41.699 | 19.380 | 1.00 | 25.20 | A | C |
| ATOM | 806 | CD2 | PHE | A | 913 | 19.529 | 39.559 | 19.028 | 1.00 | 25.36 | A | C |
| ATOM | 807 | CE1 | PHE | A | 913 | 17.544 | 41.121 | 20.132 | 1.00 | 26.53 | A | C |
| ATOM | 808 | CE2 | PHE | A | 913 | 18.533 | 38.966 | 19.783 | 1.00 | 27.33 | A | C |
| ATOM | 809 | CZ | PHE | A | 913 | 17.537 | 39.749 | 20.335 | 1.00 | 25.91 | A | C |
| ATOM | 810 | C | PHE | A | 913 | 22.476 | 40.857 | 19.472 | 1.00 | 29.07 | A | C |
| ATOM | 811 | O | PHE | A | 913 | 22.295 | 40.636 | 20.664 | 1.00 | 29.72 | A | O |
| ATOM | 812 | N | LEU | A | 914 | 23.219 | 40.074 | 18.707 | 1.00 | 28.66 | A | N |
| ATOM | 813 | CA | LEU | A | 914 | 23.883 | 38.910 | 19.242 | 1.00 | 28.77 | A | C |
| ATOM | 814 | CB | LEU | A | 914 | 24.586 | 38.145 | 18.119 | 1.00 | 28.26 | A | C |
| ATOM | 815 | CG | LEU | A | 914 | 23.745 | 37.401 | 17.074 | 1.00 | 29.50 | A | C |
| ATOM | 816 | CD1 | LEU | A | 914 | 24.598 | 37.156 | 15.834 | 1.00 | 28.14 | A | C |
| ATOM | 817 | CD2 | LEU | A | 914 | 23.220 | 36.097 | 17.634 | 1.00 | 25.43 | A | C |
| ATOM | 818 | C | LEU | A | 914 | 24.910 | 39.294 | 20.294 | 1.00 | 30.60 | A | C |
| ATOM | 819 | O | LEU | A | 914 | 25.041 | 38.616 | 21.305 | 1.00 | 30.77 | A | O |
| ATOM | 820 | N | GLN | A | 915 | 25.639 | 40.380 | 20.057 | 1.00 | 31.78 | A | N |
| ATOM | 821 | CA | GLN | A | 915 | 26.682 | 40.812 | 20.986 | 1.00 | 32.32 | A | C |
| ATOM | 822 | CB | GLN | A | 915 | 27.550 | 41.897 | 20.346 | 1.00 | 29.51 | A | C |
| ATOM | 823 | CG | GLN | A | 915 | 28.275 | 41.430 | 19.105 | 1.00 | 27.89 | A | C |
| ATOM | 824 | CD | GLN | A | 915 | 28.986 | 42.558 | 18.381 | 1.00 | 30.62 | A | C |

-continued

| | | | | | | | | | | | |
|---|---|---|---|---|---|---|---|---|---|---|---|
| ATOM | 825 | OE1 | GLN | A | 915 | 29.960 | 43.110 | 18.879 | 1.00 | 34.44 | A | O |
| ATOM | 826 | NE2 | GLN | A | 915 | 28.493 | 42.911 | 17.201 | 1.00 | 32.70 | A | N |
| ATOM | 827 | C | GLN | A | 915 | 26.147 | 41.309 | 22.314 | 1.00 | 32.56 | A | C |
| ATOM | 828 | O | GLN | A | 915 | 26.696 | 40.998 | 23.367 | 1.00 | 33.01 | A | O |
| ATOM | 829 | N | ARG | A | 916 | 25.072 | 42.080 | 22.259 | 1.00 | 35.64 | A | N |
| ATOM | 830 | CA | ARG | A | 916 | 24.470 | 42.618 | 23.466 | 1.00 | 38.93 | A | C |
| ATOM | 831 | CB | ARG | A | 916 | 23.378 | 43.623 | 23.111 | 1.00 | 40.92 | A | C |
| ATOM | 832 | CG | ARG | A | 916 | 22.567 | 44.085 | 24.316 | 1.00 | 46.49 | A | C |
| ATOM | 833 | CD | ARG | A | 916 | 23.376 | 45.002 | 25.246 | 1.00 | 51.88 | A | C |
| ATOM | 834 | NE | ARG | A | 916 | 23.508 | 46.365 | 24.717 | 1.00 | 55.94 | A | N |
| ATOM | 835 | CZ | ARG | A | 916 | 22.523 | 47.263 | 24.672 | 1.00 | 56.13 | A | C |
| ATOM | 836 | NH1 | ARG | A | 916 | 21.311 | 46.961 | 25.125 | 1.00 | 56.04 | A | N |
| ATOM | 837 | NH2 | ARG | A | 916 | 22.755 | 48.470 | 24.171 | 1.00 | 56.78 | A | N |
| ATOM | 838 | C | ARG | A | 916 | 23.880 | 41.530 | 24.350 | 1.00 | 39.54 | A | C |
| ATOM | 839 | O | ARG | A | 916 | 24.391 | 41.269 | 25.432 | 1.00 | 41.77 | A | O |
| ATOM | 840 | N | HIS | A | 917 | 22.814 | 40.890 | 23.881 | 1.00 | 40.60 | A | N |
| ATOM | 841 | CA | HIS | A | 917 | 22.128 | 39.861 | 24.657 | 1.00 | 40.90 | A | C |
| ATOM | 842 | CB | HIS | A | 917 | 20.702 | 39.682 | 24.144 | 1.00 | 41.88 | A | C |
| ATOM | 843 | CG | HIS | A | 917 | 20.000 | 40.970 | 23.863 | 1.00 | 43.18 | A | C |
| ATOM | 844 | CD2 | HIS | A | 917 | 19.191 | 41.736 | 24.632 | 1.00 | 43.95 | A | C |
| ATOM | 845 | ND1 | HIS | A | 917 | 20.124 | 41.635 | 22.660 | 1.00 | 43.84 | A | N |
| ATOM | 846 | CE1 | HIS | A | 917 | 19.421 | 42.750 | 22.702 | 1.00 | 45.33 | A | C |
| ATOM | 847 | NE2 | HIS | A | 917 | 18.844 | 42.838 | 23.889 | 1.00 | 45.00 | A | N |
| ATOM | 848 | C | HIS | A | 917 | 22.801 | 38.506 | 24.677 | 1.00 | 40.71 | A | C |
| ATOM | 849 | O | HIS | A | 917 | 22.189 | 37.520 | 25.080 | 1.00 | 40.37 | A | O |
| ATOM | 850 | N | ARG | A | 918 | 24.054 | 38.451 | 24.249 | 1.00 | 41.70 | A | N |
| ATOM | 851 | CA | ARG | A | 918 | 24.784 | 37.193 | 24.222 | 1.00 | 43.37 | A | C |
| ATOM | 852 | CB | ARG | A | 918 | 26.288 | 37.459 | 24.141 | 1.00 | 44.88 | A | C |
| ATOM | 853 | CG | ARG | A | 918 | 27.124 | 36.231 | 23.793 | 1.00 | 46.33 | A | C |
| ATOM | 854 | CD | ARG | A | 918 | 28.607 | 36.535 | 23.906 | 1.00 | 48.49 | A | C |
| ATOM | 855 | NE | ARG | A | 918 | 29.442 | 35.414 | 23.485 | 1.00 | 51.68 | A | N |
| ATOM | 856 | CZ | ARG | A | 918 | 29.319 | 34.174 | 23.942 | 1.00 | 53.95 | A | C |
| ATOM | 857 | NH1 | ARG | A | 918 | 28.386 | 33.879 | 24.840 | 1.00 | 55.47 | A | N |
| ATOM | 858 | NH2 | ARG | A | 918 | 30.137 | 33.228 | 23.502 | 1.00 | 55.10 | A | N |
| ATOM | 859 | C | ARG | A | 918 | 24.471 | 36.386 | 25.476 | 1.00 | 44.88 | A | C |
| ATOM | 860 | O | ARG | A | 918 | 24.252 | 35.176 | 25.416 | 1.00 | 45.56 | A | O |
| ATOM | 861 | N | ALA | A | 919 | 24.436 | 37.078 | 26.610 | 1.00 | 46.35 | A | N |
| ATOM | 862 | CA | ALA | A | 919 | 24.164 | 36.459 | 27.900 | 1.00 | 46.62 | A | C |
| ATOM | 863 | CB | ALA | A | 919 | 23.801 | 37.532 | 28.904 | 1.00 | 46.80 | A | C |
| ATOM | 864 | C | ALA | A | 919 | 23.082 | 35.375 | 27.886 | 1.00 | 46.74 | A | C |
| ATOM | 865 | O | ALA | A | 919 | 23.342 | 34.226 | 28.242 | 1.00 | 45.80 | A | O |
| ATOM | 866 | N | ARG | A | 920 | 21.871 | 35.737 | 27.477 | 1.00 | 46.25 | A | N |
| ATOM | 867 | CA | ARG | A | 920 | 20.774 | 34.780 | 27.457 | 1.00 | 46.08 | A | C |
| ATOM | 868 | CB | ARG | A | 920 | 19.622 | 35.308 | 28.316 | 1.00 | 47.54 | A | C |
| ATOM | 869 | CG | ARG | A | 920 | 19.363 | 36.807 | 28.203 | 1.00 | 47.40 | A | C |
| ATOM | 870 | CD | ARG | A | 920 | 18.610 | 37.168 | 26.940 | 1.00 | 49.45 | A | C |
| ATOM | 871 | NE | ARG | A | 920 | 18.194 | 38.569 | 26.925 | 1.00 | 49.65 | A | N |
| ATOM | 872 | CZ | ARG | A | 920 | 17.400 | 39.098 | 26.001 | 1.00 | 49.78 | A | C |
| ATOM | 873 | NH1 | ARG | A | 920 | 16.933 | 38.342 | 25.013 | 1.00 | 49.39 | A | N |
| ATOM | 874 | NH2 | ARG | A | 920 | 17.069 | 40.379 | 26.067 | 1.00 | 49.52 | A | N |
| ATOM | 875 | C | ARG | A | 920 | 20.261 | 34.405 | 26.074 | 1.00 | 46.13 | A | C |
| ATOM | 876 | O | ARG | A | 920 | 19.134 | 34.750 | 25.705 | 1.00 | 44.96 | A | O |
| ATOM | 877 | N | LEU | A | 921 | 21.085 | 33.678 | 25.322 | 1.00 | 45.06 | A | N |
| ATOM | 878 | CA | LEU | A | 921 | 20.727 | 33.241 | 23.973 | 1.00 | 44.84 | A | C |
| ATOM | 879 | CB | LEU | A | 921 | 21.149 | 34.290 | 22.942 | 1.00 | 44.96 | A | C |
| ATOM | 880 | CG | LEU | A | 921 | 20.422 | 35.635 | 22.925 | 1.00 | 45.84 | A | C |
| ATOM | 881 | CD1 | LEU | A | 921 | 21.093 | 36.550 | 21.892 | 1.00 | 45.14 | A | C |
| ATOM | 882 | CD2 | LEU | A | 921 | 18.940 | 35.427 | 22.594 | 1.00 | 45.08 | A | C |
| ATOM | 883 | C | LEU | A | 921 | 21.401 | 31.922 | 23.639 | 1.00 | 44.13 | A | C |
| ATOM | 884 | O | LEU | A | 921 | 22.491 | 31.906 | 23.071 | 1.00 | 44.16 | A | O |
| ATOM | 885 | N | ASP | A | 922 | 20.749 | 30.816 | 23.980 | 1.00 | 43.31 | A | N |
| ATOM | 886 | CA | ASP | A | 922 | 21.317 | 29.496 | 23.720 | 1.00 | 42.52 | A | C |
| ATOM | 887 | CB | ASP | A | 922 | 20.505 | 28.420 | 24.443 | 1.00 | 42.97 | A | C |
| ATOM | 888 | CG | ASP | A | 922 | 19.069 | 28.384 | 23.995 | 1.00 | 42.64 | A | C |
| ATOM | 889 | OD1 | ASP | A | 922 | 18.842 | 28.390 | 22.772 | 1.00 | 43.81 | A | O |
| ATOM | 890 | OD2 | ASP | A | 922 | 18.169 | 28.341 | 24.857 | 1.00 | 43.17 | A | O |
| ATOM | 891 | C | ASP | A | 922 | 21.418 | 29.150 | 22.235 | 1.00 | 40.48 | A | C |
| ATOM | 892 | O | ASP | A | 922 | 21.060 | 29.945 | 21.377 | 1.00 | 41.42 | A | O |
| ATOM | 893 | N | ALA | A | 923 | 21.896 | 27.947 | 21.942 | 1.00 | 38.52 | A | N |
| ATOM | 894 | CA | ALA | A | 923 | 22.068 | 27.495 | 20.565 | 1.00 | 36.73 | A | C |
| ATOM | 895 | CB | ALA | A | 923 | 22.890 | 26.215 | 20.546 | 1.00 | 36.05 | A | C |
| ATOM | 896 | C | ALA | A | 923 | 20.743 | 27.273 | 19.839 | 1.00 | 36.44 | A | C |
| ATOM | 897 | O | ALA | A | 923 | 20.691 | 27.246 | 18.610 | 1.00 | 35.30 | A | O |
| ATOM | 898 | N | SER | A | 924 | 19.675 | 27.103 | 20.604 | 1.00 | 35.48 | A | N |
| ATOM | 899 | CA | SER | A | 924 | 18.371 | 26.892 | 20.010 | 1.00 | 35.00 | A | C |
| ATOM | 900 | CB | SER | A | 924 | 17.343 | 26.562 | 21.095 | 1.00 | 34.87 | A | C |
| ATOM | 901 | OG | SER | A | 924 | 17.551 | 25.248 | 21.574 | 1.00 | 36.69 | A | O |
| ATOM | 902 | C | SER | A | 924 | 17.954 | 28.144 | 19.256 | 1.00 | 33.85 | A | C |
| ATOM | 903 | O | SER | A | 924 | 17.547 | 28.087 | 18.095 | 1.00 | 33.17 | A | O |
| ATOM | 904 | N | ARG | A | 925 | 18.067 | 29.276 | 19.931 | 1.00 | 32.59 | A | N |

-continued

| | | | | | | | | | | | |
|---|---|---|---|---|---|---|---|---|---|---|---|
| ATOM | 905 | CA | ARG | A | 925 | 17.707 | 30.548 | 19.348 | 1.00 | 32.54 | A | C |
| ATOM | 906 | CB | ARG | A | 925 | 17.974 | 31.663 | 20.364 | 1.00 | 33.17 | A | C |
| ATOM | 907 | CG | ARG | A | 925 | 17.325 | 32.978 | 20.013 | 1.00 | 36.60 | A | C |
| ATOM | 908 | CD | ARG | A | 925 | 16.015 | 33.157 | 20.747 | 1.00 | 39.24 | A | C |
| ATOM | 909 | NE | ARG | A | 925 | 15.178 | 31.964 | 20.685 | 1.00 | 42.43 | A | N |
| ATOM | 910 | CZ | ARG | A | 925 | 13.937 | 31.905 | 21.157 | 1.00 | 42.81 | A | C |
| ATOM | 911 | NH1 | ARG | A | 925 | 13.237 | 30.779 | 21.073 | 1.00 | 43.91 | A | N |
| ATOM | 912 | NH2 | ARG | A | 925 | 13.391 | 32.983 | 21.699 | 1.00 | 41.57 | A | N |
| ATOM | 913 | C | ARG | A | 925 | 18.522 | 30.776 | 18.066 | 1.00 | 31.35 | A | C |
| ATOM | 914 | O | ARG | A | 925 | 17.989 | 31.220 | 17.045 | 1.00 | 30.98 | A | O |
| ATOM | 915 | N | LEU | A | 926 | 19.812 | 30.461 | 18.123 | 1.00 | 29.39 | A | N |
| ATOM | 916 | CA | LEU | A | 926 | 20.684 | 30.645 | 16.968 | 1.00 | 26.98 | A | C |
| ATOM | 917 | CB | LEU | A | 926 | 22.137 | 30.278 | 17.321 | 1.00 | 25.24 | A | C |
| ATOM | 918 | CG | LEU | A | 926 | 22.729 | 30.922 | 18.586 | 1.00 | 26.47 | A | C |
| ATOM | 919 | CD1 | LEU | A | 926 | 24.164 | 30.453 | 18.762 | 1.00 | 22.76 | A | C |
| ATOM | 920 | CD2 | LEU | A | 926 | 22.660 | 32.470 | 18.498 | 1.00 | 23.66 | A | C |
| ATOM | 921 | C | LEU | A | 926 | 20.177 | 29.759 | 15.835 | 1.00 | 25.57 | A | C |
| ATOM | 922 | O | LEU | A | 926 | 20.222 | 30.144 | 14.674 | 1.00 | 25.52 | A | O |
| ATOM | 923 | N | LEU | A | 927 | 19.695 | 28.573 | 16.185 | 1.00 | 24.45 | A | N |
| ATOM | 924 | CA | LEU | A | 927 | 19.166 | 27.636 | 15.203 | 1.00 | 25.10 | A | C |
| ATOM | 925 | CB | LEU | A | 927 | 18.913 | 26.276 | 15.860 | 1.00 | 23.29 | A | C |
| ATOM | 926 | CG | LEU | A | 927 | 20.192 | 25.452 | 16.079 | 1.00 | 23.60 | A | C |
| ATOM | 927 | CD1 | LEU | A | 927 | 19.914 | 24.230 | 16.951 | 1.00 | 21.29 | A | C |
| ATOM | 928 | CD2 | LEU | A | 927 | 20.741 | 25.045 | 14.713 | 1.00 | 21.28 | A | C |
| ATOM | 929 | C | LEU | A | 927 | 17.881 | 28.176 | 14.579 | 1.00 | 25.54 | A | C |
| ATOM | 930 | O | LEU | A | 927 | 17.653 | 28.021 | 13.387 | 1.00 | 27.60 | A | O |
| ATOM | 931 | N | LEU | A | 928 | 17.043 | 28.813 | 15.382 | 1.00 | 26.21 | A | N |
| ATOM | 932 | CA | LEU | A | 928 | 15.817 | 29.377 | 14.860 | 1.00 | 28.46 | A | C |
| ATOM | 933 | CB | LEU | A | 928 | 14.986 | 29.994 | 15.990 | 1.00 | 29.01 | A | C |
| ATOM | 934 | CG | LEU | A | 928 | 13.640 | 30.609 | 15.580 | 1.00 | 30.63 | A | C |
| ATOM | 935 | CD1 | LEU | A | 928 | 12.726 | 29.543 | 14.983 | 1.00 | 28.56 | A | C |
| ATOM | 936 | CD2 | LEU | A | 928 | 12.984 | 31.247 | 16.798 | 1.00 | 30.31 | A | C |
| ATOM | 937 | C | LEU | A | 928 | 16.172 | 30.452 | 13.829 | 1.00 | 28.78 | A | C |
| ATOM | 938 | O | LEU | A | 928 | 15.627 | 30.467 | 12.727 | 1.00 | 31.05 | A | O |
| ATOM | 939 | N | TYR | A | 929 | 17.092 | 31.345 | 14.188 | 1.00 | 28.81 | A | N |
| ATOM | 940 | CA | TYR | A | 929 | 17.499 | 32.404 | 13.278 | 1.00 | 26.06 | A | C |
| ATOM | 941 | CB | TYR | A | 929 | 18.554 | 33.313 | 13.917 | 1.00 | 24.85 | A | C |
| ATOM | 942 | CG | TYR | A | 929 | 18.091 | 34.038 | 15.171 | 1.00 | 24.20 | A | C |
| ATOM | 943 | CD1 | TYR | A | 929 | 16.739 | 34.249 | 15.420 | 1.00 | 22.44 | A | C |
| ATOM | 944 | CE1 | TYR | A | 929 | 16.319 | 34.898 | 16.562 | 1.00 | 23.86 | A | C |
| ATOM | 945 | CD2 | TYR | A | 929 | 19.014 | 34.512 | 16.108 | 1.00 | 24.65 | A | C |
| ATOM | 946 | CE2 | TYR | A | 929 | 18.600 | 35.165 | 17.251 | 1.00 | 23.64 | A | C |
| ATOM | 947 | CZ | TYR | A | 929 | 17.255 | 35.352 | 17.476 | 1.00 | 23.72 | A | C |
| ATOM | 948 | OH | TYR | A | 929 | 16.836 | 35.970 | 18.627 | 1.00 | 26.16 | A | O |
| ATOM | 949 | C | TYR | A | 929 | 18.068 | 31.765 | 12.032 | 1.00 | 25.81 | A | C |
| ATOM | 950 | O | TYR | A | 929 | 17.813 | 32.217 | 10.924 | 1.00 | 26.45 | A | O |
| ATOM | 951 | N | SER | A | 930 | 18.843 | 30.707 | 12.208 | 1.00 | 25.98 | A | N |
| ATOM | 952 | CA | SER | A | 930 | 19.426 | 30.035 | 11.059 | 1.00 | 27.82 | A | C |
| ATOM | 953 | CB | SER | A | 930 | 20.325 | 28.885 | 11.513 | 1.00 | 28.75 | A | C |
| ATOM | 954 | OG | SER | A | 930 | 21.528 | 29.393 | 12.064 | 1.00 | 30.14 | A | O |
| ATOM | 955 | C | SER | A | 930 | 18.360 | 29.507 | 10.111 | 1.00 | 28.13 | A | C |
| ATOM | 956 | O | SER | A | 930 | 18.482 | 29.628 | 8.886 | 1.00 | 27.24 | A | O |
| ATOM | 957 | N | SER | A | 931 | 17.313 | 28.932 | 10.694 | 1.00 | 27.11 | A | N |
| ATOM | 958 | CA | SER | A | 931 | 16.211 | 28.360 | 9.934 | 1.00 | 25.57 | A | C |
| ATOM | 959 | CB | SER | A | 931 | 15.262 | 27.618 | 10.887 | 1.00 | 25.40 | A | C |
| ATOM | 960 | OG | SER | A | 931 | 14.196 | 26.996 | 10.183 | 1.00 | 26.62 | A | O |
| ATOM | 961 | C | SER | A | 931 | 15.446 | 29.432 | 9.148 | 1.00 | 23.59 | A | C |
| ATOM | 962 | O | SER | A | 931 | 15.193 | 29.284 | 7.957 | 1.00 | 21.65 | A | O |
| ATOM | 963 | N | GLN | A | 932 | 15.089 | 30.515 | 9.821 | 1.00 | 21.56 | A | N |
| ATOM | 964 | CA | GLN | A | 932 | 14.340 | 31.576 | 9.173 | 1.00 | 20.32 | A | C |
| ATOM | 965 | CB | GLN | A | 932 | 13.915 | 32.619 | 10.197 | 1.00 | 19.20 | A | C |
| ATOM | 966 | CG | GLN | A | 932 | 13.032 | 32.067 | 11.272 | 1.00 | 13.20 | A | C |
| ATOM | 967 | CD | GLN | A | 932 | 12.775 | 33.085 | 12.345 | 1.00 | 17.11 | A | C |
| ATOM | 968 | OE1 | GLN | A | 932 | 13.518 | 34.061 | 12.478 | 1.00 | 19.07 | A | O |
| ATOM | 969 | NE2 | GLN | A | 932 | 11.730 | 32.864 | 13.136 | 1.00 | 18.46 | A | N |
| ATOM | 970 | C | GLN | A | 932 | 15.146 | 32.228 | 8.066 | 1.00 | 19.98 | A | C |
| ATOM | 971 | O | GLN | A | 932 | 14.611 | 32.482 | 7.004 | 1.00 | 20.76 | A | O |
| ATOM | 972 | N | ILE | A | 933 | 16.430 | 32.487 | 8.304 | 1.00 | 19.95 | A | N |
| ATOM | 973 | CA | ILE | A | 933 | 17.294 | 33.088 | 7.287 | 1.00 | 19.59 | A | C |
| ATOM | 974 | CB | ILE | A | 933 | 18.744 | 33.298 | 7.834 | 1.00 | 16.81 | A | C |
| ATOM | 975 | CG2 | ILE | A | 933 | 19.716 | 33.611 | 6.700 | 1.00 | 13.19 | A | C |
| ATOM | 976 | CG1 | ILE | A | 933 | 18.747 | 34.420 | 8.876 | 1.00 | 14.44 | A | C |
| ATOM | 977 | CD1 | ILE | A | 933 | 19.937 | 34.392 | 9.822 | 1.00 | 10.84 | A | C |
| ATOM | 978 | C | ILE | A | 933 | 17.336 | 32.167 | 6.067 | 1.00 | 21.91 | A | C |
| ATOM | 979 | O | ILE | A | 933 | 17.282 | 32.635 | 4.931 | 1.00 | 24.84 | A | O |
| ATOM | 980 | N | CYS | A | 934 | 17.422 | 30.858 | 6.302 | 1.00 | 22.23 | A | N |
| ATOM | 981 | CA | CYS | A | 934 | 17.471 | 29.894 | 5.201 | 1.00 | 23.32 | A | C |
| ATOM | 982 | CB | CYS | A | 934 | 17.708 | 28.471 | 5.715 | 1.00 | 21.69 | A | C |
| ATOM | 983 | SG | CYS | A | 934 | 18.292 | 27.313 | 4.412 | 1.00 | 30.12 | A | S |
| ATOM | 984 | C | CYS | A | 934 | 16.174 | 29.912 | 4.401 | 1.00 | 23.55 | A | C |

-continued

| | | | | | | | | | | | |
|---|---|---|---|---|---|---|---|---|---|---|---|
| ATOM | 985 | O | CYS | A | 934 | 16.186 | 29.820 | 3.181 | 1.00 | 22.75 | A | O |
| ATOM | 986 | N | LYS | A | 935 | 15.053 | 30.005 | 5.101 | 1.00 | 25.04 | A | N |
| ATOM | 987 | CA | LYS | A | 935 | 13.758 | 30.047 | 4.447 | 1.00 | 26.11 | A | C |
| ATOM | 988 | CB | LYS | A | 935 | 12.641 | 30.114 | 5.487 | 1.00 | 28.76 | A | C |
| ATOM | 989 | CG | LYS | A | 935 | 12.201 | 28.770 | 5.994 | 1.00 | 30.78 | A | C |
| ATOM | 990 | CD | LYS | A | 935 | 11.682 | 27.924 | 4.849 | 1.00 | 37.03 | A | C |
| ATOM | 991 | CE | LYS | A | 935 | 10.571 | 28.633 | 4.079 | 1.00 | 38.59 | A | C |
| ATOM | 992 | NZ | LYS | A | 935 | 9.503 | 29.151 | 4.978 | 1.00 | 39.74 | A | N |
| ATOM | 993 | C | LYS | A | 935 | 13.684 | 31.280 | 3.558 | 1.00 | 25.61 | A | C |
| ATOM | 994 | O | LYS | A | 935 | 13.192 | 31.218 | 2.432 | 1.00 | 25.18 | A | O |
| ATOM | 995 | N | GLY | A | 936 | 14.184 | 32.401 | 4.063 | 1.00 | 23.46 | A | N |
| ATOM | 996 | CA | GLY | A | 936 | 14.139 | 33.625 | 3.288 | 1.00 | 25.18 | A | C |
| ATOM | 997 | C | GLY | A | 936 | 14.925 | 33.529 | 1.997 | 1.00 | 25.97 | A | C |
| ATOM | 998 | O | GLY | A | 936 | 14.438 | 33.854 | 0.910 | 1.00 | 25.47 | A | O |
| ATOM | 999 | N | MET | A | 937 | 16.160 | 33.068 | 2.122 | 1.00 | 25.86 | A | N |
| ATOM | 1000 | CA | MET | A | 937 | 17.025 | 32.935 | 0.968 | 1.00 | 25.43 | A | C |
| ATOM | 1001 | CB | MET | A | 937 | 18.398 | 32.465 | 1.415 | 1.00 | 21.83 | A | C |
| ATOM | 1002 | CG | MET | A | 937 | 19.145 | 33.521 | 2.195 | 1.00 | 22.95 | A | C |
| ATOM | 1003 | SD | MET | A | 937 | 19.251 | 35.048 | 1.253 | 1.00 | 19.04 | A | S |
| ATOM | 1004 | CE | MET | A | 937 | 20.391 | 34.539 | 0.040 | 1.00 | 19.63 | A | C |
| ATOM | 1005 | C | MET | A | 937 | 16.452 | 31.990 | −0.070 | 1.00 | 25.93 | A | C |
| ATOM | 1006 | O | MET | A | 937 | 16.563 | 32.247 | −1.269 | 1.00 | 25.39 | A | O |
| ATOM | 1007 | N | GLU | A | 938 | 15.844 | 30.898 | 0.396 | 1.00 | 25.81 | A | N |
| ATOM | 1008 | CA | GLU | A | 938 | 15.249 | 29.907 | −0.492 | 1.00 | 28.06 | A | C |
| ATOM | 1009 | CB | GLU | A | 938 | 14.692 | 28.711 | 0.305 | 1.00 | 29.00 | A | C |
| ATOM | 1010 | CG | GLU | A | 938 | 13.949 | 27.709 | −0.573 | 1.00 | 34.20 | A | C |
| ATOM | 1011 | CD | GLU | A | 938 | 12.966 | 26.819 | 0.187 | 1.00 | 37.81 | A | C |
| ATOM | 1012 | OE1 | GLU | A | 938 | 12.368 | 27.286 | 1.189 | 1.00 | 41.55 | A | O |
| ATOM | 1013 | OE2 | GLU | A | 938 | 12.781 | 25.653 | −0.234 | 1.00 | 37.20 | A | O |
| ATOM | 1014 | C | GLU | A | 938 | 14.129 | 30.559 | −1.309 | 1.00 | 28.74 | A | C |
| ATOM | 1015 | O | GLU | A | 938 | 14.013 | 30.344 | −2.513 | 1.00 | 27.91 | A | O |
| ATOM | 1016 | N | TYR | A | 939 | 13.304 | 31.358 | −0.647 | 1.00 | 28.43 | A | N |
| ATOM | 1017 | CA | TYR | A | 939 | 12.232 | 32.039 | −1.341 | 1.00 | 27.01 | A | C |
| ATOM | 1018 | CB | TYR | A | 939 | 11.367 | 32.814 | −0.346 | 1.00 | 27.10 | A | C |
| ATOM | 1019 | CG | TYR | A | 939 | 10.389 | 33.739 | −1.025 | 1.00 | 26.91 | A | C |
| ATOM | 1020 | CD1 | TYR | A | 939 | 9.233 | 33.245 | −1.631 | 1.00 | 25.87 | A | C |
| ATOM | 1021 | CE1 | TYR | A | 939 | 8.373 | 34.090 | −2.330 | 1.00 | 25.22 | A | C |
| ATOM | 1022 | CD2 | TYR | A | 939 | 10.654 | 35.101 | −1.130 | 1.00 | 26.73 | A | C |
| ATOM | 1023 | CE2 | TYR | A | 939 | 9.803 | 35.946 | −1.825 | 1.00 | 26.34 | A | C |
| ATOM | 1024 | CZ | TYR | A | 939 | 8.671 | 35.436 | −2.424 | 1.00 | 25.07 | A | C |
| ATOM | 1025 | OH | TYR | A | 939 | 7.873 | 36.269 | −3.156 | 1.00 | 24.42 | A | O |
| ATOM | 1026 | C | TYR | A | 939 | 12.823 | 33.007 | −2.377 | 1.00 | 27.57 | A | C |
| ATOM | 1027 | O | TYR | A | 939 | 12.354 | 33.085 | −3.515 | 1.00 | 27.74 | A | O |
| ATOM | 1028 | N | LEU | A | 940 | 13.865 | 33.739 | −1.986 | 1.00 | 27.06 | A | N |
| ATOM | 1029 | CA | LEU | A | 940 | 14.483 | 34.697 | −2.892 | 1.00 | 25.89 | A | C |
| ATOM | 1030 | CB | LEU | A | 940 | 15.561 | 35.505 | −2.160 | 1.00 | 25.81 | A | C |
| ATOM | 1031 | CG | LEU | A | 940 | 15.134 | 36.223 | −0.866 | 1.00 | 27.33 | A | C |
| ATOM | 1032 | CD1 | LEU | A | 940 | 16.214 | 37.236 | −0.463 | 1.00 | 25.01 | A | C |
| ATOM | 1033 | CD2 | LEU | A | 940 | 13.807 | 36.937 | −1.051 | 1.00 | 25.43 | A | C |
| ATOM | 1034 | C | LEU | A | 940 | 15.057 | 34.002 | −4.126 | 1.00 | 26.08 | A | C |
| ATOM | 1035 | O | LEU | A | 940 | 14.907 | 34.479 | −5.252 | 1.00 | 26.56 | A | O |
| ATOM | 1036 | N | GLY | A | 941 | 15.707 | 32.865 | −3.924 | 1.00 | 26.30 | A | N |
| ATOM | 1037 | CA | GLY | A | 941 | 16.246 | 32.138 | −5.062 | 1.00 | 25.14 | A | C |
| ATOM | 1038 | C | GLY | A | 941 | 15.156 | 31.632 | −6.004 | 1.00 | 23.69 | A | C |
| ATOM | 1039 | O | GLY | A | 941 | 15.274 | 31.741 | −7.223 | 1.00 | 21.15 | A | O |
| ATOM | 1040 | N | SER | A | 942 | 14.079 | 31.089 | −5.452 | 1.00 | 22.19 | A | N |
| ATOM | 1041 | CA | SER | A | 942 | 13.019 | 30.577 | −6.306 | 1.00 | 24.17 | A | C |
| ATOM | 1042 | CB | SER | A | 942 | 11.900 | 29.952 | −5.468 | 1.00 | 21.56 | A | C |
| ATOM | 1043 | OG | SER | A | 942 | 11.195 | 30.924 | −4.706 | 1.00 | 21.92 | A | O |
| ATOM | 1044 | C | SER | A | 942 | 12.452 | 31.681 | −7.199 | 1.00 | 26.30 | A | C |
| ATOM | 1045 | O | SER | A | 942 | 11.878 | 31.406 | −8.257 | 1.00 | 27.98 | A | O |
| ATOM | 1046 | N | ARG | A | 943 | 12.623 | 32.928 | −6.776 | 1.00 | 24.94 | A | N |
| ATOM | 1047 | CA | ARG | A | 943 | 12.117 | 34.059 | −7.535 | 1.00 | 25.38 | A | C |
| ATOM | 1048 | CB | ARG | A | 943 | 11.431 | 35.055 | −6.597 | 1.00 | 26.85 | A | C |
| ATOM | 1049 | CG | ARG | A | 943 | 10.155 | 34.526 | −5.972 | 1.00 | 28.29 | A | C |
| ATOM | 1050 | CD | ARG | A | 943 | 9.079 | 34.335 | −7.038 | 1.00 | 34.65 | A | C |
| ATOM | 1051 | NE | ARG | A | 943 | 7.827 | 33.831 | −6.480 | 1.00 | 35.43 | A | N |
| ATOM | 1052 | CZ | ARG | A | 943 | 7.681 | 32.630 | −5.926 | 1.00 | 37.49 | A | C |
| ATOM | 1053 | NH1 | ARG | A | 943 | 6.501 | 32.258 | −5.435 | 1.00 | 36.56 | A | N |
| ATOM | 1054 | NH2 | ARG | A | 943 | 8.710 | 31.794 | −5.871 | 1.00 | 36.84 | A | N |
| ATOM | 1055 | C | ARG | A | 943 | 13.247 | 34.734 | −8.300 | 1.00 | 25.91 | A | C |
| ATOM | 1056 | O | ARG | A | 943 | 13.121 | 35.867 | −8.767 | 1.00 | 25.66 | A | O |
| ATOM | 1057 | N | ARG | A | 944 | 14.356 | 34.015 | −8.425 | 1.00 | 27.92 | A | N |
| ATOM | 1058 | CA | ARG | A | 944 | 15.539 | 34.497 | −9.140 | 1.00 | 28.02 | A | C |
| ATOM | 1059 | CB | ARG | A | 944 | 15.225 | 34.609 | −10.633 | 1.00 | 29.49 | A | C |
| ATOM | 1060 | CG | ARG | A | 944 | 14.771 | 33.282 | −11.235 | 1.00 | 33.87 | A | C |
| ATOM | 1061 | CD | ARG | A | 944 | 14.640 | 33.361 | −12.738 | 1.00 | 38.79 | A | C |
| ATOM | 1062 | NE | ARG | A | 944 | 13.924 | 32.213 | −13.289 | 1.00 | 41.68 | A | N |
| ATOM | 1063 | CZ | ARG | A | 944 | 14.406 | 30.977 | −13.353 | 1.00 | 42.92 | A | C |
| ATOM | 1064 | NH1 | ARG | A | 944 | 15.622 | 30.700 | −12.903 | 1.00 | 44.38 | A | N |

-continued

| | | | | | | | | | | | |
|---|---|---|---|---|---|---|---|---|---|---|---|
| ATOM | 1065 | NH2 | ARG | A | 944 | 13.660 | 30.010 | −13.865 | 1.00 | 43.95 | A | N |
| ATOM | 1066 | C | ARG | A | 944 | 16.134 | 35.806 | −8.616 | 1.00 | 26.36 | A | C |
| ATOM | 1067 | O | ARG | A | 944 | 16.580 | 36.652 | −9.380 | 1.00 | 27.18 | A | O |
| ATOM | 1068 | N | CYS | A | 945 | 16.158 | 35.957 | −7.300 | 1.00 | 25.76 | A | N |
| ATOM | 1069 | CA | CYS | A | 945 | 16.715 | 37.152 | −6.691 | 1.00 | 25.68 | A | C |
| ATOM | 1070 | CB | CYS | A | 945 | 15.708 | 37.756 | −5.711 | 1.00 | 26.82 | A | O |
| ATOM | 1071 | SG | CYS | A | 945 | 16.350 | 39.138 | −4.735 | 1.00 | 32.67 | A | S |
| ATOM | 1072 | C | CYS | A | 945 | 18.009 | 36.812 | −5.951 | 1.00 | 23.68 | A | C |
| ATOM | 1073 | O | CYS | A | 945 | 18.003 | 36.003 | −5.029 | 1.00 | 21.55 | A | O |
| ATOM | 1074 | N | VAL | A | 946 | 19.107 | 37.434 | −6.369 | 1.00 | 22.39 | A | N |
| ATOM | 1075 | CA | VAL | A | 946 | 20.421 | 37.242 | −5.748 | 1.00 | 22.12 | A | C |
| ATOM | 1076 | CB | VAL | A | 946 | 21.531 | 37.211 | −6.820 | 1.00 | 20.56 | A | C |
| ATOM | 1077 | CG1 | VAL | A | 946 | 22.898 | 37.089 | −6.167 | 1.00 | 19.82 | A | C |
| ATOM | 1078 | CG2 | VAL | A | 946 | 21.296 | 36.053 | −7.757 | 1.00 | 18.31 | A | C |
| ATOM | 1079 | C | VAL | A | 946 | 20.699 | 38.396 | −4.777 | 1.00 | 22.09 | A | C |
| ATOM | 1080 | O | VAL | A | 946 | 20.579 | 39.568 | −5.152 | 1.00 | 25.08 | A | O |
| ATOM | 1081 | N | HIS | A | 947 | 21.070 | 38.058 | −3.544 | 1.00 | 21.72 | A | N |
| ATOM | 1082 | CA | HIS | A | 947 | 21.360 | 39.037 | −2.485 | 1.00 | 23.37 | A | C |
| ATOM | 1083 | CB | HIS | A | 947 | 21.438 | 38.345 | −1.118 | 1.00 | 21.69 | A | C |
| ATOM | 1084 | CG | HIS | A | 947 | 21.439 | 39.299 | 0.036 | 1.00 | 20.53 | A | C |
| ATOM | 1085 | CD2 | HIS | A | 947 | 22.147 | 40.432 | 0.263 | 1.00 | 17.46 | A | C |
| ATOM | 1086 | ND1 | HIS | A | 947 | 20.554 | 39.183 | 1.088 | 1.00 | 16.91 | A | N |
| ATOM | 1087 | CE1 | HIS | A | 947 | 20.710 | 40.208 | 1.903 | 1.00 | 15.92 | A | C |
| ATOM | 1088 | NE2 | HIS | A | 947 | 21.669 | 40.982 | 1.427 | 1.00 | 17.07 | A | N |
| ATOM | 1089 | C | HIS | A | 947 | 22.657 | 39.792 | −2.706 | 1.00 | 24.97 | A | C |
| ATOM | 1090 | O | HIS | A | 947 | 22.679 | 41.018 | −2.693 | 1.00 | 27.85 | A | O |
| ATOM | 1091 | N | ARG | A | 948 | 23.741 | 39.051 | −2.887 | 1.00 | 28.00 | A | N |
| ATOM | 1092 | CA | ARG | A | 948 | 25.065 | 39.629 | −3.127 | 1.00 | 31.02 | A | C |
| ATOM | 1093 | CB | ARG | A | 948 | 25.015 | 40.688 | −4.243 | 1.00 | 32.92 | A | C |
| ATOM | 1094 | CG | ARG | A | 948 | 26.344 | 41.444 | −4.373 | 1.00 | 38.57 | A | C |
| ATOM | 1095 | CD | ARG | A | 948 | 26.349 | 42.551 | −5.425 | 1.00 | 41.31 | A | C |
| ATOM | 1096 | NE | ARG | A | 948 | 27.434 | 43.507 | −5.196 | 1.00 | 42.45 | A | N |
| ATOM | 1097 | CZ | ARG | A | 948 | 27.956 | 44.285 | −6.138 | 1.00 | 47.28 | A | C |
| ATOM | 1098 | NH1 | ARG | A | 948 | 28.936 | 45.129 | −5.838 | 1.00 | 48.64 | A | N |
| ATOM | 1099 | NH2 | ARG | A | 948 | 27.505 | 44.210 | −7.384 | 1.00 | 48.13 | A | N |
| ATOM | 1100 | C | ARG | A | 948 | 25.797 | 40.218 | −1.912 | 1.00 | 30.74 | A | C |
| ATOM | 1101 | O | ARG | A | 948 | 27.021 | 40.378 | −1.951 | 1.00 | 32.58 | A | O |
| ATOM | 1102 | N | ASP | A | 949 | 25.080 | 40.531 | −0.836 | 1.00 | 28.19 | A | N |
| ATOM | 1103 | CA | ASP | A | 949 | 25.741 | 41.085 | 0.347 | 1.00 | 25.95 | A | C |
| ATOM | 1104 | CB | ASP | A | 949 | 25.628 | 42.611 | 0.325 | 1.00 | 28.52 | A | C |
| ATOM | 1105 | CG | ASP | A | 949 | 26.488 | 43.282 | 1.373 | 1.00 | 29.95 | A | C |
| ATOM | 1106 | OD1 | ASP | A | 949 | 27.589 | 42.767 | 1.656 | 1.00 | 29.48 | A | O |
| ATOM | 1107 | OD2 | ASP | A | 949 | 26.069 | 44.339 | 1.899 | 1.00 | 29.30 | A | O |
| ATOM | 1108 | C | ASP | A | 949 | 25.110 | 40.515 | 1.613 | 1.00 | 24.72 | A | C |
| ATOM | 1109 | O | ASP | A | 949 | 24.730 | 41.245 | 2.522 | 1.00 | 21.62 | A | O |
| ATOM | 1110 | N | LEU | A | 950 | 25.006 | 39.194 | 1.672 | 1.00 | 23.77 | A | N |
| ATOM | 1111 | CA | LEU | A | 950 | 24.383 | 38.558 | 2.822 | 1.00 | 22.86 | A | C |
| ATOM | 1112 | CB | LEU | A | 950 | 23.932 | 37.141 | 2.451 | 1.00 | 19.95 | A | C |
| ATOM | 1113 | CG | LEU | A | 950 | 23.108 | 36.364 | 3.482 | 1.00 | 20.83 | A | C |
| ATOM | 1114 | CD1 | LEU | A | 950 | 21.733 | 37.032 | 3.667 | 1.00 | 15.52 | A | C |
| ATOM | 1115 | CD2 | LEU | A | 950 | 22.938 | 34.917 | 3.005 | 1.00 | 17.15 | A | C |
| ATOM | 1116 | C | LEU | A | 950 | 25.370 | 38.529 | 3.979 | 1.00 | 21.92 | A | C |
| ATOM | 1117 | O | LEU | A | 950 | 26.556 | 38.301 | 3.781 | 1.00 | 19.70 | A | O |
| ATOM | 1118 | N | ALA | A | 951 | 24.876 | 38.762 | 5.189 | 1.00 | 21.14 | A | N |
| ATOM | 1119 | CA | ALA | A | 951 | 25.740 | 38.768 | 6.358 | 1.00 | 19.64 | A | C |
| ATOM | 1120 | CB | ALA | A | 951 | 26.860 | 39.772 | 6.165 | 1.00 | 16.06 | A | C |
| ATOM | 1121 | C | ALA | A | 951 | 24.917 | 39.115 | 7.585 | 1.00 | 21.41 | A | C |
| ATOM | 1122 | O | ALA | A | 951 | 23.812 | 39.664 | 7.475 | 1.00 | 23.99 | A | O |
| ATOM | 1123 | N | ALA | A | 952 | 25.447 | 38.796 | 8.760 | 1.00 | 21.05 | A | N |
| ATOM | 1124 | CA | ALA | A | 952 | 24.729 | 39.063 | 10.002 | 1.00 | 19.39 | A | C |
| ATOM | 1125 | CB | ALA | A | 952 | 25.569 | 38.616 | 11.205 | 1.00 | 18.53 | A | C |
| ATOM | 1126 | C | ALA | A | 952 | 24.325 | 40.532 | 10.137 | 1.00 | 18.69 | A | C |
| ATOM | 1127 | O | ALA | A | 952 | 23.322 | 40.844 | 10.772 | 1.00 | 21.48 | A | O |
| ATOM | 1128 | N | ARG | A | 953 | 25.114 | 41.440 | 9.570 | 1.00 | 17.77 | A | N |
| ATOM | 1129 | CA | ARG | A | 953 | 24.757 | 42.854 | 9.618 | 1.00 | 19.31 | A | C |
| ATOM | 1130 | CB | ARG | A | 953 | 25.922 | 43.735 | 9.171 | 1.00 | 17.94 | A | C |
| ATOM | 1131 | CG | ARG | A | 953 | 26.277 | 43.580 | 7.723 | 1.00 | 16.54 | A | C |
| ATOM | 1132 | CD | ARG | A | 953 | 27.394 | 44.538 | 7.370 | 1.00 | 18.36 | A | C |
| ATOM | 1133 | NE | ARG | A | 953 | 28.034 | 44.230 | 6.088 | 1.00 | 20.26 | A | N |
| ATOM | 1134 | CZ | ARG | A | 953 | 28.894 | 43.232 | 5.895 | 1.00 | 18.10 | A | C |
| ATOM | 1135 | NH1 | ARG | A | 953 | 29.222 | 42.432 | 6.902 | 1.00 | 22.15 | A | N |
| ATOM | 1136 | NH2 | ARG | A | 953 | 29.437 | 43.039 | 4.703 | 1.00 | 14.98 | A | N |
| ATOM | 1137 | C | ARG | A | 953 | 23.551 | 43.142 | 8.704 | 1.00 | 20.52 | A | C |
| ATOM | 1138 | O | ARG | A | 953 | 22.786 | 44.069 | 8.955 | 1.00 | 19.49 | A | O |
| ATOM | 1139 | N | ASN | A | 954 | 23.384 | 42.376 | 7.629 | 1.00 | 20.55 | A | N |
| ATOM | 1140 | CA | ASN | A | 954 | 22.235 | 42.638 | 6.768 | 1.00 | 22.29 | A | C |
| ATOM | 1141 | CB | ASN | A | 954 | 22.614 | 42.519 | 5.274 | 1.00 | 18.54 | A | C |
| ATOM | 1142 | CG | ASN | A | 954 | 23.351 | 43.761 | 4.753 | 1.00 | 17.79 | A | C |
| ATOM | 1143 | OD1 | ASN | A | 954 | 23.022 | 44.875 | 5.122 | 1.00 | 19.98 | A | O |
| ATOM | 1144 | ND2 | ASN | A | 954 | 24.335 | 43.566 | 3.889 | 1.00 | 17.35 | A | N |

-continued

| | | | | | | | | | | | |
|---|---|---|---|---|---|---|---|---|---|---|---|
| ATOM | 1145 | C | ASN | A | 954 | 21.022 | 41.759 | 7.124 | 1.00 | 22.75 | A | C |
| ATOM | 1146 | O | ASN | A | 954 | 20.183 | 41.472 | 6.279 | 1.00 | 23.62 | A | O |
| ATOM | 1147 | N | ILE | A | 955 | 20.952 | 41.339 | 8.389 | 1.00 | 24.09 | A | N |
| ATOM | 1148 | CA | ILE | A | 955 | 19.837 | 40.533 | 8.902 | 1.00 | 23.45 | A | C |
| ATOM | 1149 | CB | ILE | A | 955 | 20.306 | 39.205 | 9.575 | 1.00 | 23.56 | A | C |
| ATOM | 1150 | CG2 | ILE | A | 955 | 19.135 | 38.562 | 10.335 | 1.00 | 22.40 | A | C |
| ATOM | 1151 | CG1 | ILE | A | 955 | 20.812 | 38.215 | 8.527 | 1.00 | 22.88 | A | C |
| ATOM | 1152 | CD1 | ILE | A | 955 | 19.716 | 37.621 | 7.691 | 1.00 | 21.73 | A | C |
| ATOM | 1153 | C | ILE | A | 955 | 19.211 | 41.390 | 9.988 | 1.00 | 24.33 | A | C |
| ATOM | 1154 | O | ILE | A | 955 | 19.818 | 41.580 | 11.038 | 1.00 | 25.58 | A | O |
| ATOM | 1155 | N | LEU | A | 956 | 18.014 | 41.917 | 9.737 | 1.00 | 25.10 | A | N |
| ATOM | 1156 | CA | LEU | A | 956 | 17.326 | 42.762 | 10.712 | 1.00 | 23.60 | A | C |
| ATOM | 1157 | CB | LEU | A | 956 | 16.487 | 43.821 | 9.990 | 1.00 | 20.79 | A | C |
| ATOM | 1158 | CG | LEU | A | 956 | 17.271 | 44.953 | 9.322 | 1.00 | 19.09 | A | C |
| ATOM | 1159 | CD1 | LEU | A | 956 | 16.344 | 45.759 | 8.426 | 1.00 | 15.72 | A | C |
| ATOM | 1160 | CD2 | LEU | A | 956 | 17.901 | 45.843 | 10.386 | 1.00 | 16.65 | A | C |
| ATOM | 1161 | C | LEU | A | 956 | 16.446 | 41.944 | 11.655 | 1.00 | 25.28 | A | C |
| ATOM | 1162 | O | LEU | A | 956 | 15.913 | 40.893 | 11.282 | 1.00 | 27.16 | A | O |
| ATOM | 1163 | N | VAL | A | 957 | 16.301 | 42.441 | 12.880 | 1.00 | 24.88 | A | N |
| ATOM | 1164 | CA | VAL | A | 957 | 15.505 | 41.773 | 13.902 | 1.00 | 24.09 | A | C |
| ATOM | 1165 | CB | VAL | A | 957 | 16.188 | 41.866 | 15.313 | 1.00 | 23.67 | A | C |
| ATOM | 1166 | CG1 | VAL | A | 957 | 15.218 | 41.439 | 16.419 | 1.00 | 18.34 | A | C |
| ATOM | 1167 | CG2 | VAL | A | 957 | 17.431 | 40.979 | 15.346 | 1.00 | 22.54 | A | C |
| ATOM | 1168 | C | VAL | A | 957 | 14.093 | 42.329 | 14.006 | 1.00 | 24.66 | A | C |
| ATOM | 1169 | O | VAL | A | 957 | 13.885 | 43.510 | 14.288 | 1.00 | 23.71 | A | O |
| ATOM | 1170 | N | GLU | A | 958 | 13.125 | 41.456 | 13.761 | 1.00 | 25.24 | A | N |
| ATOM | 1171 | CA | GLU | A | 958 | 11.729 | 41.821 | 13.842 | 1.00 | 27.40 | A | C |
| ATOM | 1172 | CB | GLU | A | 958 | 10.877 | 40.821 | 13.061 | 1.00 | 27.40 | A | C |
| ATOM | 1173 | CG | GLU | A | 958 | 9.407 | 40.926 | 13.373 | 1.00 | 29.36 | A | C |
| ATOM | 1174 | CD | GLU | A | 956 | 8.805 | 42.206 | 12.865 | 1.00 | 30.52 | A | C |
| ATOM | 1175 | OE1 | GLU | A | 958 | 7.699 | 42.558 | 13.321 | 1.00 | 33.77 | A | O |
| ATOM | 1176 | OE2 | GLU | A | 958 | 9.432 | 42.856 | 12.001 | 1.00 | 34.54 | A | O |
| ATOM | 1177 | C | GLU | A | 958 | 11.380 | 41.769 | 15.324 | 1.00 | 27.35 | A | C |
| ATOM | 1178 | O | GLU | A | 958 | 10.733 | 42.669 | 15.855 | 1.00 | 29.14 | A | O |
| ATOM | 1179 | N | SER | A | 959 | 11.822 | 40.704 | 15.982 | 1.00 | 28.13 | A | N |
| ATOM | 1180 | CA | SER | A | 959 | 11.598 | 40.519 | 17.409 | 1.00 | 29.62 | A | C |
| ATOM | 1181 | CB | SER | A | 959 | 10.139 | 40.162 | 17.700 | 1.00 | 27.47 | A | C |
| ATOM | 1182 | OG | SER | A | 959 | 9.899 | 38.786 | 17.467 | 1.00 | 27.72 | A | O |
| ATOM | 1183 | C | SER | A | 959 | 12.514 | 39.388 | 17.873 | 1.00 | 32.26 | A | C |
| ATOM | 1184 | O | SER | A | 959 | 13.239 | 38.808 | 17.071 | 1.00 | 31.08 | A | O |
| ATOM | 1185 | N | GLU | A | 960 | 12.474 | 39.083 | 19.168 | 1.00 | 34.51 | A | N |
| ATOM | 1186 | CA | GLU | A | 960 | 13.304 | 38.041 | 19.755 | 1.00 | 35.90 | A | C |
| ATOM | 1187 | CB | GLU | A | 960 | 12.896 | 37.807 | 21.208 | 1.00 | 39.24 | A | C |
| ATOM | 1188 | CG | GLU | A | 960 | 13.184 | 38.980 | 22.141 | 1.00 | 46.55 | A | C |
| ATOM | 1189 | CD | GLU | A | 960 | 12.187 | 40.140 | 22.010 | 1.00 | 48.81 | A | C |
| ATOM | 1190 | OE1 | GLU | A | 960 | 12.358 | 41.143 | 22.752 | 1.00 | 49.24 | A | O |
| ATOM | 1191 | OE2 | GLU | A | 960 | 11.244 | 40.048 | 21.183 | 1.00 | 46.66 | A | O |
| ATOM | 1192 | C | GLU | A | 960 | 13.252 | 36.721 | 19.002 | 1.00 | 35.00 | A | C |
| ATOM | 1193 | O | GLU | A | 960 | 14.272 | 36.044 | 18.834 | 1.00 | 34.68 | A | O |
| ATOM | 1194 | N | ALA | A | 961 | 12.060 | 36.361 | 18.547 | 1.00 | 32.61 | A | N |
| ATOM | 1195 | CA | ALA | A | 961 | 11.884 | 35.114 | 17.825 | 1.00 | 31.46 | A | C |
| ATOM | 1196 | CB | ALA | A | 961 | 10.787 | 34.309 | 18.475 | 1.00 | 33.09 | A | C |
| ATOM | 1197 | C | ALA | A | 961 | 11.568 | 35.285 | 16.349 | 1.00 | 29.88 | A | C |
| ATOM | 1198 | O | ALA | A | 961 | 10.867 | 34.457 | 15.787 | 1.00 | 30.47 | A | O |
| ATOM | 1199 | N | HIS | A | 962 | 12.079 | 36.332 | 15.709 | 1.00 | 27.98 | A | N |
| ATOM | 1200 | CA | HIS | A | 962 | 11.781 | 36.552 | 14.293 | 1.00 | 26.94 | A | C |
| ATOM | 1201 | CB | HIS | A | 962 | 10.367 | 37.137 | 14.150 | 1.00 | 26.76 | A | C |
| ATOM | 1202 | CG | HIS | A | 962 | 9.845 | 37.164 | 12.746 | 1.00 | 29.25 | A | C |
| ATOM | 1203 | CD2 | HIS | A | 962 | 10.482 | 37.125 | 11.548 | 1.00 | 30.41 | A | C |
| ATOM | 1204 | ND1 | HIS | A | 962 | 8.499 | 37.259 | 12.461 | 1.00 | 29.15 | A | N |
| ATOM | 1205 | CE1 | HIS | A | 962 | 8.328 | 37.277 | 11.149 | 1.00 | 29.36 | A | C |
| ATOM | 1206 | NE2 | HIS | A | 962 | 9.515 | 37.197 | 10.573 | 1.00 | 29.28 | A | N |
| ATOM | 1207 | C | HIS | A | 962 | 12.785 | 37.483 | 13.635 | 1.00 | 25.52 | A | C |
| ATOM | 1208 | O | HIS | A | 962 | 12.830 | 38.671 | 13.934 | 1.00 | 24.49 | A | O |
| ATOM | 1209 | N | VAL | A | 963 | 13.583 | 36.942 | 12.723 | 1.00 | 24.67 | A | N |
| ATOM | 1210 | CA | VAL | A | 963 | 14.579 | 37.739 | 12.020 | 1.00 | 22.77 | A | C |
| ATOM | 1211 | CB | VAL | A | 963 | 15.997 | 37.135 | 12.211 | 1.00 | 21.51 | A | C |
| ATOM | 1212 | CG1 | VAL | A | 963 | 16.385 | 37.214 | 13.677 | 1.00 | 18.57 | A | C |
| ATOM | 1213 | CG2 | VAL | A | 963 | 16.043 | 35.690 | 11.716 | 1.00 | 15.30 | A | C |
| ATOM | 1214 | C | VAL | A | 963 | 14.253 | 37.831 | 10.532 | 1.00 | 24.24 | A | C |
| ATOM | 1215 | O | VAL | A | 963 | 13.710 | 36.888 | 9.950 | 1.00 | 24.35 | A | O |
| ATOM | 1216 | N | LYS | A | 964 | 14.577 | 38.968 | 9.920 | 1.00 | 24.66 | A | N |
| ATOM | 1217 | CA | LYS | A | 964 | 14.306 | 39.159 | 8.493 | 1.00 | 26.34 | A | C |
| ATOM | 1218 | CB | LYS | A | 964 | 13.298 | 40.291 | 8.284 | 1.00 | 29.10 | A | C |
| ATOM | 1219 | CG | LYS | A | 964 | 11.887 | 40.014 | 8.784 | 1.00 | 27.26 | A | C |
| ATOM | 1220 | CD | LYS | A | 964 | 10.995 | 41.233 | 8.537 | 1.00 | 26.26 | A | C |
| ATOM | 1221 | CE | LYS | A | 964 | 9.534 | 40.902 | 8.778 | 1.00 | 26.90 | A | C |
| ATOM | 1222 | NZ | LYS | A | 964 | 8.647 | 42.060 | 8.526 | 1.00 | 30.62 | A | N |
| ATOM | 1223 | C | LYS | A | 964 | 15.546 | 39.468 | 7.665 | 1.00 | 25.93 | A | C |
| ATOM | 1224 | O | LYS | A | 964 | 16.495 | 40.076 | 8.155 | 1.00 | 28.44 | A | O |

-continued

| | | | | | | | | | | | |
|---|---|---|---|---|---|---|---|---|---|---|---|
| ATOM | 1225 | N | ILE | A | 965 | 15.535 | 39.040 | 6.408 | 1.00 | 24.00 | A | N |
| ATOM | 1226 | CA | ILE | A | 965 | 16.654 | 39.305 | 5.510 | 1.00 | 23.02 | A | C |
| ATOM | 1227 | CB | ILE | A | 965 | 16.684 | 38.296 | 4.332 | 1.00 | 23.20 | A | C |
| ATOM | 1228 | CG2 | ILE | A | 965 | 17.821 | 38.625 | 3.385 | 1.00 | 21.71 | A | C |
| ATOM | 1229 | CG1 | ILE | A | 965 | 16.894 | 36.871 | 4.857 | 1.00 | 22.96 | A | C |
| ATOM | 1230 | CD1 | ILE | A | 965 | 16.961 | 35.812 | 3.758 | 1.00 | 21.77 | A | C |
| ATOM | 1231 | C | ILE | A | 965 | 16.506 | 40.735 | 4.972 | 1.00 | 23.73 | A | C |
| ATOM | 1232 | O | ILE | A | 965 | 15.398 | 41.173 | 4.614 | 1.00 | 22.06 | A | O |
| ATOM | 1233 | N | ALA | A | 966 | 17.625 | 41.460 | 4.919 | 1.00 | 23.15 | A | N |
| ATOM | 1234 | CA | ALA | A | 966 | 17.627 | 42.852 | 4.470 | 1.00 | 21.44 | A | C |
| ATOM | 1235 | CB | ALA | A | 966 | 17.822 | 43.780 | 5.676 | 1.00 | 19.27 | A | C |
| ATOM | 1236 | C | ALA | A | 966 | 18.669 | 43.176 | 3.410 | 1.00 | 21.34 | A | C |
| ATOM | 1237 | O | ALA | A | 966 | 19.700 | 42.518 | 3.319 | 1.00 | 19.18 | A | O |
| ATOM | 1238 | N | ASP | A | 967 | 18.373 | 44.197 | 2.605 | 1.00 | 20.95 | A | N |
| ATOM | 1239 | CA | ASP | A | 967 | 19.280 | 44.669 | 1.565 | 1.00 | 21.84 | A | C |
| ATOM | 1240 | CB | ASP | A | 967 | 20.620 | 45.061 | 2.203 | 1.00 | 25.14 | A | C |
| ATOM | 1241 | CG | ASP | A | 967 | 20.589 | 46.450 | 2.832 | 1.00 | 28.31 | A | C |
| ATOM | 1242 | OD1 | ASP | A | 967 | 19.687 | 46.736 | 3.661 | 1.00 | 33.06 | A | O |
| ATOM | 1243 | OD2 | ASP | A | 967 | 21.474 | 47.260 | 2.491 | 1.00 | 28.34 | A | O |
| ATOM | 1244 | C | ASP | A | 967 | 19.508 | 43.681 | 0.431 | 1.00 | 20.89 | A | C |
| ATOM | 1245 | O | ASP | A | 967 | 20.583 | 43.615 | −0.144 | 1.00 | 19.01 | A | O |
| ATOM | 1246 | N | PHE | A | 968 | 18.472 | 42.936 | 0.087 | 1.00 | 23.31 | A | N |
| ATOM | 1247 | CA | PHE | A | 968 | 18.578 | 41.948 | −0.973 | 1.00 | 23.74 | A | C |
| ATOM | 1248 | CB | PHE | A | 968 | 17.660 | 40.776 | −0.643 | 1.00 | 22.73 | A | C |
| ATOM | 1249 | CG | PHE | A | 968 | 16.220 | 41.174 | −0.452 | 1.00 | 21.43 | A | C |
| ATOM | 1250 | CD1 | PHE | A | 968 | 15.337 | 41.180 | −1.518 | 1.00 | 21.04 | A | C |
| ATOM | 1251 | CD2 | PHE | A | 968 | 15.752 | 41.535 | 0.795 | 1.00 | 21.28 | A | C |
| ATOM | 1252 | CE1 | PHE | A | 968 | 14.014 | 41.535 | −1.340 | 1.00 | 21.80 | A | C |
| ATOM | 1253 | CE2 | PHE | A | 968 | 14.427 | 41.893 | 0.977 | 1.00 | 21.96 | A | C |
| ATOM | 1254 | CZ | PHE | A | 968 | 13.558 | 41.890 | −0.094 | 1.00 | 21.99 | A | C |
| ATOM | 1255 | C | PHE | A | 968 | 18.246 | 42.484 | −2.364 | 1.00 | 25.69 | A | C |
| ATOM | 1256 | O | PHE | A | 966 | 17.488 | 43.454 | −2.513 | 1.00 | 24.40 | A | O |
| ATOM | 1257 | N | GLY | A | 969 | 18.841 | 41.835 | −3.368 | 1.00 | 27.11 | A | N |
| ATOM | 1258 | CA | GLY | A | 969 | 18.623 | 42.164 | −4.770 | 1.00 | 28.84 | A | C |
| ATOM | 1259 | C | GLY | A | 969 | 18.930 | 43.573 | −5.239 | 1.00 | 28.12 | A | C |
| ATOM | 1260 | O | GLY | A | 969 | 18.100 | 44.195 | −5.887 | 1.00 | 29.45 | A | O |
| ATOM | 1261 | N | LEU | A | 970 | 20.128 | 44.066 | −4.945 | 1.00 | 27.97 | A | N |
| ATOM | 1262 | CA | LEU | A | 970 | 20.522 | 45.415 | −5.345 | 1.00 | 27.04 | A | C |
| ATOM | 1263 | CB | LEU | A | 970 | 20.882 | 46.223 | −4.098 | 1.00 | 27.31 | A | C |
| ATOM | 1264 | CG | LEU | A | 970 | 19.885 | 47.280 | −3.650 | 1.00 | 29.99 | A | C |
| ATOM | 1265 | CD1 | LEU | A | 970 | 18.47b | 46.876 | −4.035 | 1.00 | 29.45 | A | C |
| ATOM | 1266 | CD2 | LEU | A | 970 | 20.017 | 47.474 | −2.149 | 1.00 | 31.52 | A | C |
| ATOM | 1267 | C | LEU | A | 970 | 21.705 | 45.418 | −6.313 | 1.00 | 25.60 | A | C |
| ATOM | 1268 | O | LEU | A | 970 | 22.214 | 46.480 | −6.671 | 1.00 | 24.22 | A | O |
| ATOM | 1269 | N | ALA | A | 971 | 22.134 | 44.234 | −6.736 | 1.00 | 24.75 | A | N |
| ATOM | 1270 | CA | ALA | A | 971 | 23.278 | 44.103 | −7.638 | 1.00 | 27.57 | A | C |
| ATOM | 1271 | CB | ALA | A | 971 | 23.325 | 42.695 | −8.231 | 1.00 | 26.59 | A | C |
| ATOM | 1272 | C | ALA | A | 971 | 23.271 | 45.135 | −8.753 | 1.00 | 29.20 | A | C |
| ATOM | 1273 | O | ALA | A | 971 | 24.162 | 45.980 | −8.820 | 1.00 | 31.64 | A | O |
| ATOM | 1274 | N | LYS | A | 972 | 22.259 | 45.065 | −9.615 | 1.00 | 29.46 | A | N |
| ATOM | 1275 | CA | LYS | A | 972 | 22.112 | 45.979 | −10.744 | 1.00 | 30.77 | A | C |
| ATOM | 1276 | CB | LYS | A | 972 | 20.697 | 45.850 | −11.322 | 1.00 | 32.32 | A | C |
| ATOM | 1277 | CG | LYS | A | 972 | 20.347 | 44.427 | −11.749 | 1.00 | 34.37 | A | C |
| ATOM | 1278 | CD | LYS | A | 972 | 21.454 | 43.844 | −12.607 | 1.00 | 36.13 | A | C |
| ATOM | 1279 | CE | LYS | A | 972 | 21.197 | 42.389 | −12.946 | 1.00 | 39.38 | A | C |
| ATOM | 1280 | NZ | LYS | A | 972 | 22.346 | 41.812 | −13.722 | 1.00 | 41.41 | A | N |
| ATOM | 1281 | C | LYS | A | 972 | 22.406 | 47.446 | −10.414 | 1.00 | 30.81 | A | C |
| ATOM | 1282 | O | LYS | A | 972 | 23.055 | 48.155 | −11.182 | 1.00 | 30.44 | A | O |
| ATOM | 1283 | N | LEU | A | 973 | 21.930 | 47.899 | −9.265 | 1.00 | 30.52 | A | N |
| ATOM | 1284 | CA | LEU | A | 973 | 22.141 | 49.276 | −8.858 | 1.00 | 29.45 | A | C |
| ATOM | 1285 | CB | LEU | A | 973 | 21.110 | 49.654 | −7.792 | 1.00 | 27.35 | A | C |
| ATOM | 1286 | CG | LEU | A | 973 | 19.690 | 50.011 | −8.250 | 1.00 | 26.99 | A | C |
| ATOM | 1287 | CD1 | LEU | A | 973 | 19.474 | 49.507 | −9.674 | 1.00 | 27.84 | A | C |
| ATOM | 1288 | CD2 | LEU | A | 973 | 18.645 | 49.444 | −7.269 | 1.00 | 23.63 | A | C |
| ATOM | 1289 | C | LEU | A | 973 | 23.548 | 49.544 | −8.322 | 1.00 | 30.66 | A | C |
| ATOM | 1290 | O | LEU | A | 973 | 23.988 | 50.685 | −8.308 | 1.00 | 30.62 | A | O |
| ATOM | 1291 | N | LEU | A | 974 | 24.258 | 48.504 | −7.888 | 1.00 | 32.78 | A | N |
| ATOM | 1292 | CA | LEU | A | 974 | 25.589 | 48.690 | −7.314 | 1.00 | 35.10 | A | C |
| ATOM | 1293 | CB | LEU | A | 974 | 26.035 | 47.429 | −6.560 | 1.00 | 34.09 | A | C |
| ATOM | 1294 | CG | LEU | A | 974 | 25.141 | 47.021 | −5.372 | 1.00 | 31.33 | A | C |
| ATOM | 1295 | CD1 | LEU | A | 974 | 25.844 | 46.011 | −4.476 | 1.00 | 31.22 | A | C |
| ATOM | 1296 | CD2 | LEU | A | 974 | 24.786 | 48.258 | −4.582 | 1.00 | 29.58 | A | C |
| ATOM | 1297 | C | LEU | A | 974 | 26.644 | 49.095 | −8.327 | 1.00 | 39.13 | A | C |
| ATOM | 1298 | O | LEU | A | 974 | 26.683 | 48.588 | −9.444 | 1.00 | 39.72 | A | O |
| ATOM | 1299 | N | PRO | A | 975 | 27.533 | 50.013 | −7.931 | 1.00 | 42.43 | A | N |
| ATOM | 1300 | CD | PRO | A | 975 | 27.809 | 50.379 | −6.532 | 1.00 | 41.80 | A | C |
| ATOM | 1301 | CA | PRO | A | 975 | 28.594 | 50.500 | −8.811 | 1.00 | 43.55 | A | C |
| ATOM | 1302 | CB | PRO | A | 975 | 29.427 | 51.381 | −7.883 | 1.00 | 43.38 | A | C |
| ATOM | 1303 | CG | PRO | A | 975 | 29.288 | 50.685 | −6.574 | 1.00 | 42.77 | A | C |
| ATOM | 1304 | C | PRO | A | 975 | 29.407 | 49.380 | −9.438 | 1.00 | 44.80 | A | C |

-continued

| | | | | | | | | | | | |
|---|---|---|---|---|---|---|---|---|---|---|---|
| ATOM | 1305 | O | PRO | A | 975 | 29.676 | 48.370 | −8.799 | 1.00 | 45.65 | A | O |
| ATOM | 1306 | N | LEU | A | 976 | 29.778 | 49.563 | −10.700 | 1.00 | 46.34 | A | N |
| ATOM | 1307 | CA | LEU | A | 976 | 30.580 | 48.578 | −11.403 | 1.00 | 47.22 | A | C |
| ATOM | 1308 | CB | LEU | A | 976 | 30.980 | 49.108 | −12.787 | 1.00 | 47.95 | A | C |
| ATOM | 1309 | CG | LEU | A | 976 | 29.859 | 49.044 | −13.840 | 1.00 | 48.59 | A | C |
| ATOM | 1310 | CD1 | LEU | A | 976 | 29.441 | 47.571 | −14.033 | 1.00 | 48.06 | A | C |
| ATOM | 1311 | CD2 | LEU | A | 976 | 28.666 | 49.890 | −13.389 | 1.00 | 47.77 | A | C |
| ATOM | 1312 | C | LEU | A | 976 | 31.815 | 48.314 | −10.558 | 1.00 | 48.24 | A | C |
| ATOM | 1313 | O | LEU | A | 976 | 31.776 | 47.482 | −9.643 | 1.00 | 49.05 | A | O |
| ATOM | 1314 | N | ASP | A | 977 | 32.898 | 49.039 | −10.854 | 1.00 | 48.80 | A | N |
| ATOM | 1315 | CA | ASP | A | 977 | 34.163 | 48.909 | −10.119 | 1.00 | 48.49 | A | C |
| ATOM | 1316 | CB | ASP | A | 977 | 35.294 | 49.712 | −10.785 | 1.00 | 50.18 | A | C |
| ATOM | 1317 | CG | ASP | A | 977 | 36.480 | 49.982 | −9.818 | 1.00 | 52.34 | A | C |
| ATOM | 1318 | OD1 | ASP | A | 977 | 37.652 | 49.670 | −10.196 | 1.00 | 52.04 | A | O |
| ATOM | 1319 | OD2 | ASP | A | 977 | 36.233 | 50.509 | −8.690 | 1.00 | 51.47 | A | O |
| ATOM | 1320 | C | ASP | A | 977 | 34.033 | 49.427 | −8.706 | 1.00 | 47.71 | A | C |
| ATOM | 1321 | O | ASP | A | 977 | 33.806 | 50.620 | −8.506 | 1.00 | 47.53 | A | O |
| ATOM | 1322 | N | LYS | A | 978 | 34.207 | 48.547 | −7.726 | 1.00 | 46.64 | A | N |
| ATOM | 1323 | CA | LYS | A | 978 | 34.139 | 48.946 | −6.315 | 1.00 | 46.31 | A | C |
| ATOM | 1324 | CB | LYS | A | 978 | 33.282 | 47.950 | −5.522 | 1.00 | 44.80 | A | C |
| ATOM | 1325 | CG | LYS | A | 978 | 33.214 | 48.272 | −4.029 | 1.00 | 43.21 | A | C |
| ATOM | 1326 | CD | LYS | A | 978 | 32.755 | 49.717 | −3.804 | 1.00 | 41.49 | A | C |
| ATOM | 1327 | CE | LYS | A | 978 | 32.597 | 50.038 | −2.322 | 1.00 | 40.48 | A | C |
| ATOM | 1328 | NZ | LYS | A | 978 | 31.726 | 49.077 | −1.599 | 1.00 | 37.88 | A | N |
| ATOM | 1329 | C | LYS | A | 978 | 35.552 | 49.007 | −5.714 | 1.00 | 46.70 | A | C |
| ATOM | 1330 | O | LYS | A | 978 | 36.359 | 48.077 | −5.894 | 1.00 | 46.71 | A | O |
| ATOM | 1331 | N | ASP | A | 979 | 35.861 | 50.097 | −5.016 | 1.00 | 47.20 | A | N |
| ATOM | 1332 | CA | ASP | A | 979 | 37.182 | 50.241 | −4.396 | 1.00 | 47.47 | A | C |
| ATOM | 1333 | CB | ASP | A | 979 | 37.659 | 51.698 | −4.492 | 1.00 | 49.44 | A | C |
| ATOM | 1334 | CG | ASP | A | 979 | 39.165 | 51.840 | −4.312 | 1.00 | 49.88 | A | C |
| ATOM | 1335 | OD1 | ASP | A | 979 | 39.708 | 52.886 | −4.737 | 1.00 | 50.87 | A | O |
| ATOM | 1336 | OD2 | ASP | A | 979 | 39.798 | 50.921 | −3.742 | 1.00 | 49.55 | A | O |
| ATOM | 1337 | C | ASP | A | 979 | 37.052 | 49.805 | −2.942 | 1.00 | 45.95 | A | C |
| ATOM | 1338 | O | ASP | A | 979 | 36.785 | 50.618 | −2.052 | 1.00 | 44.33 | A | O |
| ATOM | 1339 | N | TYR | A | 980 | 37.233 | 48.505 | −2.727 | 1.00 | 45.35 | A | N |
| ATOM | 1340 | CA | TYR | A | 980 | 37.107 | 47.891 | −1.407 | 1.00 | 45.75 | A | C |
| ATOM | 1341 | CB | TYR | A | 980 | 37.086 | 46.367 | −1.557 | 1.00 | 42.56 | A | C |
| ATOM | 1342 | CG | TYR | A | 980 | 35.856 | 45.844 | −2.267 | 1.00 | 40.45 | A | C |
| ATOM | 1343 | CD1 | TYR | A | 980 | 34.639 | 45.743 | −1.613 | 1.00 | 37.80 | A | C |
| ATOM | 1344 | CE1 | TYR | A | 980 | 33.512 | 45.271 | −2.267 | 1.00 | 36.59 | A | C |
| ATOM | 1345 | CD2 | TYR | A | 980 | 35.912 | 45.461 | −3.597 | 1.00 | 39.77 | A | C |
| ATOM | 1346 | CE2 | TYR | A | 980 | 34.793 | 44.993 | −4.256 | 1.00 | 37.65 | A | C |
| ATOM | 1347 | CZ | TYR | A | 980 | 33.597 | 44.898 | −3.591 | 1.00 | 36.99 | A | C |
| ATOM | 1348 | OH | TYR | A | 980 | 32.489 | 44.433 | −4.267 | 1.00 | 36.66 | A | O |
| ATOM | 1349 | C | TYR | A | 980 | 38.153 | 48.296 | −0.367 | 1.00 | 47.00 | A | C |
| ATOM | 1350 | O | TYR | A | 980 | 38.011 | 47.982 | 0.814 | 1.00 | 47.86 | A | O |
| ATOM | 1351 | N | TYR | A | 981 | 39.196 | 48.994 | −0.800 | 1.00 | 48.44 | A | N |
| ATOM | 1352 | CA | TYR | A | 981 | 40.239 | 49.433 | 0.117 | 1.00 | 49.65 | A | C |
| ATOM | 1353 | CB | TYR | A | 981 | 41.552 | 49.597 | −0.641 | 1.00 | 51.45 | A | C |
| ATOM | 1354 | CG | TYR | A | 981 | 42.026 | 48.307 | −1.261 | 1.00 | 54.63 | A | C |
| ATOM | 1355 | CD1 | TYR | A | 981 | 42.798 | 48.311 | −2.416 | 1.00 | 55.85 | A | C |
| ATOM | 1356 | CE1 | TYR | A | 981 | 43.214 | 47.127 | −3.002 | 1.00 | 57.90 | A | C |
| ATOM | 1357 | CD2 | TYR | A | 981 | 41.680 | 47.080 | −0.703 | 1.00 | 56.41 | A | C |
| ATOM | 1358 | CE2 | TYR | A | 981 | 42.089 | 45.888 | −1.281 | 1.00 | 57.59 | A | C |
| ATOM | 1359 | CZ | TYR | A | 981 | 42.854 | 45.919 | −2.431 | 1.00 | 58.54 | A | C |
| ATOM | 1360 | OH | TYR | A | 981 | 43.256 | 44.741 | −3.016 | 1.00 | 60.20 | A | O |
| ATOM | 1361 | C | TYR | A | 981 | 39.824 | 50.743 | 0.781 | 1.00 | 48.81 | A | C |
| ATOM | 1362 | O | TYR | A | 981 | 40.504 | 51.260 | 1.673 | 1.00 | 48.86 | A | O |
| ATOM | 1363 | N | VAL | A | 982 | 38.688 | 51.266 | 0.339 | 1.00 | 48.42 | A | N |
| ATOM | 1364 | CA | VAL | A | 982 | 38.140 | 52.501 | 0.880 | 1.00 | 46.99 | A | C |
| ATOM | 1365 | CB | VAL | A | 982 | 37.831 | 53.528 | −0.243 | 1.00 | 46.43 | A | C |
| ATOM | 1366 | CG1 | VAL | A | 982 | 37.265 | 54.802 | 0.359 | 1.00 | 45.87 | A | C |
| ATOM | 1367 | CG2 | VAL | A | 982 | 39.090 | 53.827 | −1.045 | 1.00 | 44.80 | A | C |
| ATOM | 1368 | C | VAL | A | 982 | 36.845 | 52.148 | 1.605 | 1.00 | 46.90 | A | C |
| ATOM | 1369 | O | VAL | A | 982 | 35.773 | 52.122 | 1.004 | 1.00 | 45.78 | A | O |
| ATOM | 1370 | N | VAL | A | 983 | 36.965 | 51.866 | 2.898 | 1.00 | 47.59 | A | N |
| ATOM | 1371 | CA | VAL | A | 983 | 35.824 | 51.510 | 3.729 | 1.00 | 48.25 | A | C |
| ATOM | 1372 | CB | VAL | A | 983 | 35.733 | 49.970 | 3.898 | 1.00 | 48.58 | A | C |
| ATOM | 1373 | CG1 | VAL | A | 983 | 37.076 | 49.417 | 4.360 | 1.00 | 49.17 | A | C |
| ATOM | 1374 | CG2 | VAL | A | 983 | 34.631 | 49.608 | 4.884 | 1.00 | 47.78 | A | C |
| ATOM | 1375 | C | VAL | A | 983 | 35.928 | 52.175 | 5.100 | 1.00 | 49.02 | A | C |
| ATOM | 1376 | O | VAL | A | 983 | 37.005 | 52.243 | 5.691 | 1.00 | 49.70 | A | O |
| ATOM | 1377 | N | ARG | A | 984 | 34.803 | 52.671 | 5.601 | 1.00 | 49.82 | A | N |
| ATOM | 1378 | CA | ARG | A | 984 | 34.778 | 53.333 | 6.895 | 1.00 | 49.53 | A | C |
| ATOM | 1379 | CB | ARG | A | 984 | 33.426 | 54.011 | 7.127 | 1.00 | 52.18 | A | C |
| ATOM | 1380 | CG | ARG | A | 984 | 33.463 | 55.085 | 8.205 | 1.00 | 55.52 | A | C |
| ATOM | 1381 | CD | ARG | A | 984 | 32.063 | 55.466 | 8.673 | 1.00 | 59.59 | A | C |
| ATOM | 1382 | NE | ARG | A | 984 | 32.062 | 56.701 | 9.457 | 1.00 | 62.13 | A | N |
| ATOM | 1383 | CZ | ARG | A | 984 | 32.749 | 56.885 | 10.581 | 1.00 | 63.45 | A | C |
| ATOM | 1384 | NH1 | ARG | A | 984 | 32.678 | 58.052 | 11.210 | 1.00 | 64.01 | A | N |

-continued

| ATOM | 1385 | NH2 | ARG | A | 984 | 33.499 | 55.908 | 11.079 | 1.00 | 61.84 | A | N |
|------|------|-----|-----|---|-----|--------|--------|--------|------|-------|---|---|
| ATOM | 1386 | C | ARG | A | 984 | 35.036 | 52.324 | 8.001 | 1.00 | 48.55 | A | C |
| ATOM | 1387 | O | ARG | A | 984 | 35.748 | 52.619 | 8.962 | 1.00 | 49.22 | A | O |
| ATOM | 1388 | N | GLU | A | 985 | 34.449 | 51.137 | 7.871 | 1.00 | 46.54 | A | N |
| ATOM | 1389 | CA | GLU | A | 985 | 34.631 | 50.081 | 8.864 | 1.00 | 44.17 | A | C |
| ATOM | 1390 | CB | GLU | A | 985 | 33.338 | 49.854 | 9.653 | 1.00 | 45.48 | A | C |
| ATOM | 1391 | CG | GLU | A | 985 | 33.574 | 49.373 | 11.092 | 1.00 | 50.99 | A | C |
| ATOM | 1392 | CD | GLU | A | 985 | 33.937 | 50.504 | 12.068 | 1.00 | 53.46 | A | C |
| ATOM | 1393 | OE1 | GLU | A | 985 | 34.598 | 50.216 | 13.094 | 1.00 | 54.69 | A | O |
| ATOM | 1394 | OE2 | GLU | A | 985 | 33.549 | 51.672 | 11.820 | 1.00 | 54.79 | A | O |
| ATOM | 1395 | C | GLU | A | 985 | 35.050 | 48.793 | 8.159 | 1.00 | 41.59 | A | C |
| ATOM | 1396 | O | GLU | A | 985 | 34.220 | 47.947 | 7.842 | 1.00 | 41.99 | A | O |
| ATOM | 1397 | N | PRO | A | 986 | 36.363 | 48.626 | 7.928 | 1.00 | 39.68 | A | N |
| ATOM | 1398 | CD | PRO | A | 986 | 37.384 | 49.483 | 8.550 | 1.00 | 37.11 | A | C |
| ATOM | 1399 | CA | PRO | A | 986 | 36.988 | 47.476 | 7.261 | 1.00 | 37.84 | A | C |
| ATOM | 1400 | CB | PRO | A | 986 | 38.479 | 47.779 | 7.389 | 1.00 | 37.70 | A | C |
| ATOM | 1401 | CG | PRO | A | 986 | 38.550 | 48.546 | 8.663 | 1.00 | 37.19 | A | C |
| ATOM | 1402 | C | PRO | A | 986 | 36.613 | 46.090 | 7.788 | 1.00 | 36.77 | A | C |
| ATOM | 1403 | O | PRO | A | 986 | 36.536 | 45.131 | 7.026 | 1.00 | 37.02 | A | O |
| ATOM | 1404 | N | GLY | A | 987 | 36.380 | 45.970 | 9.085 | 1.00 | 35.59 | A | N |
| ATOM | 1405 | CA | GLY | A | 987 | 36.010 | 44.671 | 9.607 | 1.00 | 33.97 | A | C |
| ATOM | 1406 | C | GLY | A | 987 | 34.746 | 44.114 | 8.963 | 1.00 | 32.82 | A | C |
| ATOM | 1407 | O | GLY | A | 987 | 34.510 | 42.912 | 9.012 | 1.00 | 32.56 | A | O |
| ATOM | 1408 | N | GLN | A | 988 | 33.927 | 44.974 | 8.366 | 1.00 | 30.14 | A | N |
| ATOM | 1409 | CA | GLN | A | 988 | 32.700 | 44.512 | 7.737 | 1.00 | 29.16 | A | C |
| ATOM | 1410 | CB | GLN | A | 988 | 31.493 | 45.292 | 8.268 | 1.00 | 30.41 | A | C |
| ATOM | 1411 | CG | GLN | A | 988 | 31.206 | 45.078 | 9.756 | 1.00 | 29.44 | A | C |
| ATOM | 1412 | CD | GLN | A | 988 | 30.776 | 43.654 | 10.082 | 1.00 | 31.42 | A | C |
| ATOM | 1413 | OE1 | GLN | A | 988 | 29.653 | 43.244 | 9.684 | 1.00 | 26.26 | A | O |
| ATOM | 1414 | NE2 | GLN | A | 988 | 31.576 | 42.947 | 10.735 | 1.00 | 32.03 | A | N |
| ATOM | 1415 | C | GLN | A | 988 | 32.765 | 44.645 | 6.226 | 1.00 | 29.17 | A | C |
| ATOM | 1416 | O | GLN | A | 988 | 31.740 | 44.806 | 5.570 | 1.00 | 27.90 | A | O |
| ATOM | 1417 | N | SER | A | 989 | 33.978 | 44.584 | 5.678 | 1.00 | 29.64 | A | N |
| ATOM | 1418 | CA | SER | A | 989 | 34.172 | 44.687 | 4.236 | 1.00 | 27.96 | A | C |
| ATOM | 1419 | CB | SER | A | 989 | 35.656 | 44.774 | 3.888 | 1.00 | 29.01 | A | C |
| ATOM | 1420 | OG | SER | A | 989 | 35.843 | 44.762 | 2.483 | 1.00 | 28.27 | A | O |
| ATOM | 1421 | C | SER | A | 989 | 33.587 | 43.442 | 3.604 | 1.00 | 28.16 | A | C |
| ATOM | 1422 | O | SER | A | 989 | 33.928 | 42.327 | 3.982 | 1.00 | 26.58 | A | O |
| ATOM | 1423 | N | PRO | A | 990 | 32.714 | 43.624 | 2.608 | 1.00 | 28.39 | A | N |
| ATOM | 1424 | CD | PRO | A | 990 | 32.449 | 44.935 | 1.982 | 1.00 | 29.19 | A | C |
| ATOM | 1425 | CA | PRO | A | 990 | 32.035 | 42.551 | 1.879 | 1.00 | 28.46 | A | C |
| ATOM | 1426 | CB | PRO | A | 990 | 31.472 | 43.272 | 0.653 | 1.00 | 29.64 | A | C |
| ATOM | 1427 | CG | PRO | A | 990 | 31.205 | 44.662 | 1.169 | 1.00 | 28.86 | A | C |
| ATOM | 1428 | C | PRO | A | 990 | 32.893 | 41.355 | 1.489 | 1.00 | 26.71 | A | C |
| ATOM | 1429 | O | PRO | A | 990 | 32.386 | 40.242 | 1.408 | 1.00 | 27.68 | A | O |
| ATOM | 1430 | N | ILE | A | 991 | 34.181 | 41.590 | 1.247 | 1.00 | 25.64 | A | N |
| ATOM | 1431 | CA | ILE | A | 991 | 35.109 | 40.542 | 0.829 | 1.00 | 23.27 | A | C |
| ATOM | 1432 | CB | ILE | A | 991 | 36.508 | 41.121 | 0.543 | 1.00 | 22.53 | A | C |
| ATOM | 1433 | CG2 | ILE | A | 991 | 36.390 | 42.242 | −0.472 | 1.00 | 21.72 | A | C |
| ATOM | 1434 | CG1 | ILE | A | 991 | 37.162 | 41.592 | 1.851 | 1.00 | 21.38 | A | C |
| ATOM | 1435 | CD1 | ILE | A | 991 | 38.659 | 41.885 | 1.740 | 1.00 | 17.35 | A | C |
| ATOM | 1436 | C | ILE | A | 991 | 35.282 | 39.340 | 1.759 | 1.00 | 22.89 | A | C |
| ATOM | 1437 | O | ILE | A | 991 | 35.628 | 38.267 | 1.292 | 1.00 | 22.75 | A | O |
| ATOM | 1438 | N | PHE | A | 992 | 35.061 | 39.504 | 3.060 | 1.00 | 22.83 | A | N |
| ATOM | 1439 | CA | PHE | A | 992 | 35.218 | 38.367 | 3.972 | 1.00 | 24.27 | A | C |
| ATOM | 1440 | CB | PHE | A | 992 | 35.468 | 38.832 | 5.423 | 1.00 | 21.98 | A | C |
| ATOM | 1441 | CG | PHE | A | 992 | 36.692 | 39.675 | 5.575 | 1.00 | 18.63 | A | C |
| ATOM | 1442 | CD1 | PHE | A | 992 | 37.905 | 39.225 | 5.092 | 1.00 | 19.36 | A | C |
| ATOM | 1443 | CD2 | PHE | A | 992 | 36.621 | 40.944 | 6.129 | 1.00 | 18.42 | A | C |
| ATOM | 1444 | CE1 | PHE | A | 992 | 39.042 | 40.021 | 5.144 | 1.00 | 18.38 | A | C |
| ATOM | 1445 | CE2 | PHE | A | 992 | 37.747 | 41.751 | 6.188 | 1.00 | 20.39 | A | C |
| ATOM | 1446 | CZ | PHE | A | 992 | 38.965 | 41.286 | 5.689 | 1.00 | 19.03 | A | C |
| ATOM | 1447 | C | PHE | A | 992 | 34.010 | 37.434 | 3.945 | 1.00 | 24.41 | A | C |
| ATOM | 1448 | O | PHE | A | 992 | 33.986 | 36.436 | 4.669 | 1.00 | 23.48 | A | O |
| ATOM | 1449 | N | TRP | A | 993 | 33.014 | 37.767 | 3.122 | 1.00 | 24.17 | A | N |
| ATOM | 1450 | CA | TRP | A | 993 | 31.801 | 36.952 | 2.977 | 1.00 | 24.08 | A | C |
| ATOM | 1451 | CB | TRP | A | 993 | 30.549 | 37.762 | 3.318 | 1.00 | 20.25 | A | C |
| ATOM | 1452 | CG | TRP | A | 993 | 30.322 | 37.968 | 4.776 | 1.00 | 18.22 | A | C |
| ATOM | 1453 | CD2 | TRP | A | 993 | 30.934 | 38.962 | 5.609 | 1.00 | 17.81 | A | C |
| ATOM | 1454 | CE2 | TRP | A | 993 | 30.465 | 38.750 | 6.923 | 1.00 | 16.65 | A | C |
| ATOM | 1455 | CE3 | TRP | A | 993 | 31.836 | 40.012 | 5.371 | 1.00 | 17.27 | A | C |
| ATOM | 1456 | CD1 | TRP | A | 993 | 29.524 | 37.222 | 5.593 | 1.00 | 18.48 | A | C |
| ATOM | 1457 | NE1 | TRP | A | 993 | 29.608 | 37.683 | 6.885 | 1.00 | 18.25 | A | N |
| ATOM | 1458 | CZ2 | TRP | A | 993 | 30.867 | 39.544 | 7.998 | 1.00 | 16.84 | A | C |
| ATOM | 1459 | CZ3 | TRP | A | 993 | 32.235 | 40.800 | 6.439 | 1.00 | 13.99 | A | C |
| ATOM | 1460 | CH2 | TRP | A | 993 | 31.752 | 40.562 | 7.738 | 1.00 | 15.16 | A | C |
| ATOM | 1461 | C | TRP | A | 993 | 31.674 | 36.458 | 1.547 | 1.00 | 25.04 | A | C |
| ATOM | 1462 | O | TRP | A | 993 | 30.772 | 35.691 | 1.224 | 1.00 | 27.65 | A | O |
| ATOM | 1463 | N | TYR | A | 994 | 32.590 | 36.891 | 0.691 | 1.00 | 26.08 | A | N |
| ATOM | 1464 | CA | TYR | A | 994 | 32.539 | 36.516 | −0.713 | 1.00 | 26.22 | A | C |

| | | | | | -continued | | | | | | |
|---|---|---|---|---|---|---|---|---|---|---|---|
| ATOM | 1465 | CB | TYR | A | 994 | 33.385 | 37.473 | −1.556 | 1.00 | 26.01 | A | C |
| ATOM | 1466 | CG | TYR | A | 994 | 32.752 | 38.812 | −1.830 | 1.00 | 25.79 | A | C |
| ATOM | 1467 | CD1 | TYR | A | 994 | 31.565 | 39.180 | −1.224 | 1.00 | 25.47 | A | C |
| ATOM | 1468 | CE1 | TYR | A | 994 | 30.997 | 40.421 | −1.472 | 1.00 | 29.26 | A | C |
| ATOM | 1469 | CD2 | TYR | A | 994 | 33.358 | 39.719 | −2.695 | 1.00 | 27.78 | A | C |
| ATOM | 1470 | CE2 | TYR | A | 994 | 32.798 | 40.958 | −2.949 | 1.00 | 27.26 | A | C |
| ATOM | 1471 | CZ | TYR | A | 994 | 31.620 | 41.304 | −2.337 | 1.00 | 28.61 | A | C |
| ATOM | 1472 | OH | TYR | A | 994 | 31.056 | 42.529 | −2.598 | 1.00 | 31.86 | A | O |
| ATOM | 1473 | C | TYR | A | 994 | 33.018 | 35.111 | −0.989 | 1.00 | 26.70 | A | C |
| ATOM | 1474 | O | TYR | A | 994 | 33.871 | 34.587 | −0.281 | 1.00 | 26.37 | A | O |
| ATOM | 1475 | N | ALA | A | 995 | 32.462 | 34.516 | −2.040 | 1.00 | 27.56 | A | N |
| ATOM | 1476 | CA | ALA | A | 995 | 32.846 | 33.180 | −2.479 | 1.00 | 27.85 | A | C |
| ATOM | 1477 | CB | ALA | A | 995 | 31.653 | 32.478 | −3.148 | 1.00 | 26.19 | A | C |
| ATOM | 1478 | C | ALA | A | 995 | 33.980 | 33.383 | −3.488 | 1.00 | 28.75 | A | C |
| ATOM | 1479 | O | ALA | A | 995 | 34.156 | 34.486 | −4.027 | 1.00 | 29.61 | A | O |
| ATOM | 1480 | N | PRO | A | 996 | 34.762 | 32.329 | −3.760 | 1.00 | 27.48 | A | N |
| ATOM | 1481 | CD | PRO | A | 996 | 34.696 | 30.981 | −3.181 | 1.00 | 26.63 | A | C |
| ATOM | 1482 | CA | PRO | A | 996 | 35.872 | 32.429 | −4.711 | 1.00 | 28.77 | A | C |
| ATOM | 1483 | CB | PRO | A | 996 | 36.309 | 30.978 | −4.880 | 1.00 | 26.97 | A | C |
| ATOM | 1484 | CG | PRO | A | 996 | 36.050 | 30.418 | −3.535 | 1.00 | 25.72 | A | C |
| ATOM | 1485 | C | PRO | A | 996 | 35.494 | 33.082 | −6.041 | 1.00 | 29.95 | A | C |
| ATOM | 1486 | O | PRO | A | 996 | 36.092 | 34.089 | −6.423 | 1.00 | 32.04 | A | O |
| ATOM | 1487 | N | GLU | A | 997 | 34.507 | 32.517 | −6.736 | 1.00 | 30.01 | A | N |
| ATOM | 1488 | CA | GLU | A | 997 | 34.080 | 33.050 | −8.026 | 1.00 | 30.26 | A | C |
| ATOM | 1489 | CB | GLU | A | 997 | 32.822 | 32.323 | −8.549 | 1.00 | 30.28 | A | C |
| ATOM | 1490 | CG | GLU | A | 997 | 31.606 | 32.373 | −7.648 | 1.00 | 30.56 | A | C |
| ATOM | 1491 | CD | GLU | A | 997 | 31.601 | 31.268 | −6.606 | 1.00 | 32.94 | A | C |
| ATOM | 1492 | OE1 | GLU | A | 997 | 32.683 | 30.961 | −6.052 | 1.00 | 31.09 | A | O |
| ATOM | 1493 | OE2 | GLU | A | 997 | 30.506 | 30.717 | −6.338 | 1.00 | 33.32 | A | O |
| ATOM | 1494 | C | GLU | A | 997 | 33.829 | 34.550 | −7.948 | 1.00 | 30.85 | A | C |
| ATOM | 1495 | O | GLU | A | 997 | 34.057 | 35.281 | −8.909 | 1.00 | 31.80 | A | O |
| ATOM | 1496 | N | SER | A | 998 | 33.368 | 35.017 | −6.797 | 1.00 | 32.03 | A | N |
| ATOM | 1497 | CA | SER | A | 998 | 33.132 | 36.440 | −6.626 | 1.00 | 32.09 | A | C |
| ATOM | 1498 | CB | SER | A | 998 | 32.300 | 36.688 | −5.379 | 1.00 | 31.27 | A | C |
| ATOM | 1499 | OG | SER | A | 996 | 30.955 | 36.327 | −5.607 | 1.00 | 32.96 | A | O |
| ATOM | 1500 | C | SER | A | 998 | 34.442 | 37.214 | −6.522 | 1.00 | 32.18 | A | C |
| ATOM | 1501 | O | SER | A | 998 | 34.644 | 38.198 | −7.224 | 1.00 | 34.53 | A | O |
| ATOM | 1502 | N | LEU | A | 999 | 35.329 | 36.770 | −5.642 | 1.00 | 32.83 | A | N |
| ATOM | 1503 | CA | LEU | A | 999 | 36.606 | 37.447 | −5.448 | 1.00 | 33.92 | A | C |
| ATOM | 1504 | CB | LEU | A | 999 | 37.435 | 36.730 | −4.374 | 1.00 | 31.31 | A | C |
| ATOM | 1505 | CG | LEU | A | 999 | 37.076 | 36.949 | −2.897 | 1.00 | 29.60 | A | C |
| ATOM | 1506 | CD1 | LEU | A | 999 | 37.992 | 36.101 | −2.035 | 1.00 | 28.05 | A | C |
| ATOM | 1507 | CD2 | LEU | A | 999 | 37.226 | 38.417 | −2.515 | 1.00 | 28.42 | A | C |
| ATOM | 1508 | C | LEU | A | 999 | 37.432 | 37.568 | −6.724 | 1.00 | 35.90 | A | C |
| ATOM | 1509 | O | LEU | A | 999 | 38.101 | 38.574 | −6.936 | 1.00 | 36.64 | A | O |
| ATOM | 1510 | N | SER | A | 1000 | 37.374 | 36.556 | −7.581 | 1.00 | 36.91 | A | N |
| ATOM | 1511 | CA | SER | A | 1000 | 38.152 | 36.566 | −8.608 | 1.00 | 37.30 | A | C |
| ATOM | 1512 | CB | SER | A | 1000 | 38.755 | 35.192 | −9.032 | 1.00 | 36.47 | A | C |
| ATOM | 1513 | OG | SER | A | 1000 | 37.724 | 34.247 | −9.246 | 1.00 | 34.60 | A | O |
| ATOM | 1514 | C | SER | A | 1000 | 37.425 | 36.977 | −10.084 | 1.00 | 39.08 | A | C |
| ATOM | 1515 | O | SER | A | 1000 | 38.062 | 37.421 | −11.033 | 1.00 | 40.17 | A | O |
| ATOM | 1516 | N | ASP | A | 1001 | 36.109 | 36.831 | −10.132 | 1.00 | 40.32 | A | N |
| ATOM | 1517 | CA | ASP | A | 1001 | 35.396 | 37.191 | −11.351 | 1.00 | 42.54 | A | C |
| ATOM | 1518 | CB | ASP | A | 1001 | 35.041 | 35.925 | −12.126 | 1.00 | 43.98 | A | C |
| ATOM | 1519 | CG | ASP | A | 1001 | 36.266 | 35.162 | −12.574 | 1.00 | 45.00 | A | C |
| ATOM | 1520 | OD1 | ASP | A | 1001 | 37.062 | 35.734 | −13.349 | 1.00 | 44.52 | A | O |
| ATOM | 1521 | OD2 | ASP | A | 1001 | 36.433 | 33.998 | −12.147 | 1.00 | 45.98 | A | O |
| ATOM | 1522 | C | ASP | A | 1001 | 34.142 | 38.031 | −11.171 | 1.00 | 42.36 | A | C |
| ATOM | 1523 | O | ASP | A | 1001 | 33.359 | 38.178 | −12.104 | 1.00 | 42.53 | A | O |
| ATOM | 1524 | N | ASN | A | 1002 | 33.957 | 38.589 | −9.983 | 1.00 | 42.42 | A | N |
| ATOM | 1525 | CA | ASN | A | 1002 | 32.781 | 39.390 | −9.703 | 1.00 | 42.92 | A | C |
| ATOM | 1526 | CB | ASN | A | 1002 | 32.703 | 40.590 | −10.641 | 1.00 | 44.00 | A | C |
| ATOM | 1527 | CG | ASN | A | 1002 | 33.246 | 41.847 | −10.015 | 1.00 | 45.61 | A | C |
| ATOM | 1528 | OD1 | ASN | A | 1002 | 34.455 | 42.005 | −9.646 | 1.00 | 49.08 | A | O |
| ATOM | 1529 | ND2 | ASN | A | 1002 | 32.349 | 42.753 | −9.653 | 1.00 | 45.40 | A | N |
| ATOM | 1530 | C | ASN | A | 1002 | 31.514 | 38.570 | −9.841 | 1.00 | 42.00 | A | C |
| ATOM | 1531 | O | ASN | A | 1002 | 30.421 | 39.095 | −9.676 | 1.00 | 43.55 | A | O |
| ATOM | 1532 | N | ILE | A | 1003 | 31.667 | 37.285 | −10.143 | 1.00 | 40.07 | A | N |
| ATOM | 1533 | CA | ILE | A | 1003 | 30.535 | 36.376 | −10.303 | 1.00 | 37.80 | A | C |
| ATOM | 1534 | CB | ILE | A | 1003 | 30.994 | 34.944 | −10.651 | 1.00 | 38.03 | A | C |
| ATOM | 1535 | CG2 | ILE | A | 1003 | 29.822 | 33.987 | −10.536 | 1.00 | 35.71 | A | C |
| ATOM | 1536 | CG1 | ILE | A | 1003 | 31.629 | 34.902 | −12.037 | 1.00 | 35.29 | A | C |
| ATOM | 1537 | CD1 | ILE | A | 1003 | 31.993 | 33.514 | −12.454 | 1.00 | 33.06 | A | C |
| ATOM | 1538 | C | ILE | A | 1003 | 29.704 | 36.255 | −9.037 | 1.00 | 37.43 | A | C |
| ATOM | 1539 | O | ILE | A | 1003 | 30.230 | 35.936 | −7.969 | 1.00 | 38.59 | A | O |
| ATOM | 1540 | N | PHE | A | 1004 | 28.404 | 36.488 | −9.170 | 1.00 | 36.18 | A | N |
| ATOM | 1541 | CA | PHE | A | 1004 | 27.474 | 36.390 | −8.055 | 1.00 | 34.51 | A | C |
| ATOM | 1542 | CB | PHE | A | 1004 | 27.055 | 37.787 | −7.598 | 1.00 | 32.45 | A | C |
| ATOM | 1543 | CG | PHE | A | 1004 | 28.126 | 38.525 | −6.828 | 1.00 | 34.32 | A | C |
| ATOM | 1544 | CD1 | PHE | A | 1004 | 28.492 | 38.110 | −5.549 | 1.00 | 32.69 | A | C |

-continued

| | | | | | | | | | | | |
|---|---|---|---|---|---|---|---|---|---|---|---|
| ATOM | 1545 | CD2 | PHE | A | 1004 | 28.757 | 39.637 | −7.371 | 1.00 | 31.98 | A C |
| ATOM | 1546 | CE1 | PHE | A | 1004 | 29.462 | 38.789 | −4.824 | 1.00 | 31.46 | A C |
| ATOM | 1547 | CE2 | PHE | A | 1004 | 29.730 | 40.322 | −6.651 | 1.00 | 33.05 | A C |
| ATOM | 1548 | CZ | PHE | A | 1004 | 30.081 | 39.895 | −5.373 | 1.00 | 32.10 | A C |
| ATOM | 1549 | C | PHE | A | 1004 | 26.256 | 35.591 | −8.511 | 1.00 | 35.47 | A C |
| ATOM | 1550 | O | PHE | A | 1004 | 25.696 | 35.854 | −9.575 | 1.00 | 37.28 | A O |
| ATOM | 1551 | N | SER | A | 1005 | 25.853 | 34.610 | −7.709 | 1.00 | 34.92 | A N |
| ATOM | 1552 | CA | SER | A | 1005 | 24.713 | 33.774 | −8.045 | 1.00 | 32.73 | A C |
| ATOM | 1553 | CB | SER | A | 1005 | 25.158 | 32.584 | −8.888 | 1.00 | 33.36 | A C |
| ATOM | 1554 | OG | SER | A | 1005 | 25.959 | 31.704 | −8.114 | 1.00 | 36.71 | A O |
| ATOM | 1555 | C | SER | A | 1005 | 24.051 | 33.245 | −6.794 | 1.00 | 31.68 | A C |
| ATOM | 1556 | O | SER | A | 1005 | 24.536 | 33.449 | −5.681 | 1.00 | 31.32 | A O |
| ATOM | 1557 | N | ARG | A | 1006 | 22.937 | 32.553 | −6.996 | 1.00 | 29.32 | A N |
| ATOM | 1558 | CA | ARG | A | 1006 | 22.197 | 31.961 | −5.900 | 1.00 | 28.94 | A C |
| ATOM | 1559 | CB | ARG | A | 1006 | 21.040 | 31.130 | −6.452 | 1.00 | 29.85 | A C |
| ATOM | 1560 | CG | ARG | A | 1006 | 20.005 | 31.949 | −7.202 | 1.00 | 35.55 | A C |
| ATOM | 1561 | CD | ARG | A | 1006 | 18.924 | 31.062 | −7.843 | 1.00 | 38.40 | A C |
| ATOM | 1562 | NE | ARG | A | 1006 | 18.345 | 30.128 | −6.876 | 1.00 | 43.57 | A N |
| ATOM | 1563 | CZ | ARG | A | 1006 | 17.471 | 29.168 | −7.174 | 1.00 | 44.56 | A C |
| ATOM | 1564 | NH1 | ARG | A | 1006 | 17.009 | 28.367 | −6.220 | 1.00 | 41.70 | A N |
| ATOM | 1565 | NH2 | ARG | A | 1006 | 17.053 | 29.012 | −8.420 | 1.00 | 44.91 | A N |
| ATOM | 1566 | C | ARG | A | 1006 | 23.125 | 31.068 | −5.081 | 1.00 | 27.76 | A C |
| ATOM | 1567 | O | ARG | A | 1006 | 22.995 | 30.967 | −3.661 | 1.00 | 25.65 | A O |
| ATOM | 1568 | N | GLN | A | 1007 | 24.077 | 30.433 | −5.755 | 1.00 | 27.21 | A N |
| ATOM | 1569 | CA | GLN | A | 1007 | 24.979 | 29.524 | −5.067 | 1.00 | 27.69 | A C |
| ATOM | 1570 | CB | GLN | A | 1007 | 25.552 | 28.492 | −6.041 | 1.00 | 27.27 | A C |
| ATOM | 1571 | CG | GLN | A | 1007 | 24.566 | 27.386 | −6.456 | 1.00 | 30.11 | A C |
| ATOM | 1572 | CD | GLN | A | 1007 | 24.008 | 26.541 | −5.273 | 1.00 | 32.03 | A C |
| ATOM | 1573 | OE1 | GLN | A | 1007 | 22.897 | 26.788 | −4.771 | 1.00 | 28.18 | A O |
| ATOM | 1574 | NE2 | GLN | A | 1007 | 24.785 | 25.542 | −4.836 | 1.00 | 29.04 | A N |
| ATOM | 1575 | C | GLN | A | 1007 | 26.093 | 30.236 | −4.313 | 1.00 | 27.70 | A C |
| ATOM | 1576 | O | GLN | A | 1007 | 26.567 | 29.750 | −3.276 | 1.00 | 26.19 | A O |
| ATOM | 1577 | N | SER | A | 1008 | 26.506 | 31.390 | −4.822 | 1.00 | 26.86 | A N |
| ATOM | 1578 | CA | SER | A | 1008 | 27.542 | 32.155 | −4.150 | 1.00 | 26.66 | A C |
| ATOM | 1579 | CB | SER | A | 1008 | 27.997 | 33.331 | −5.018 | 1.00 | 29.18 | A C |
| ATOM | 1580 | OG | SER | A | 1008 | 26.903 | 34.144 | −5.400 | 1.00 | 31.80 | A O |
| ATOM | 1581 | C | SER | A | 1008 | 26.950 | 32.654 | −2.830 | 1.00 | 26.32 | A C |
| ATOM | 1582 | O | SER | A | 1008 | 27.659 | 32.816 | −1.828 | 1.00 | 26.69 | A O |
| ATOM | 1583 | N | ASP | A | 1009 | 25.641 | 32.892 | −2.830 | 1.00 | 25.13 | A N |
| ATOM | 1584 | CA | ASP | A | 1009 | 24.974 | 33.341 | −1.620 | 1.00 | 24.62 | A C |
| ATOM | 1585 | CB | ASP | A | 1009 | 23.493 | 33.663 | −1.882 | 1.00 | 26.26 | A C |
| ATOM | 1586 | CG | ASP | A | 1009 | 23.275 | 35.087 | −2.421 | 1.00 | 29.77 | A C |
| ATOM | 1587 | OD1 | ASP | A | 1009 | 22.195 | 35.364 | −2.993 | 1.00 | 31.03 | A O |
| ATOM | 1588 | OD2 | ASP | A | 1009 | 24.175 | 35.937 | −2.268 | 1.00 | 30.20 | A O |
| ATOM | 1589 | C | ASP | A | 1009 | 25.097 | 32.221 | −0.602 | 1.00 | 23.09 | A C |
| ATOM | 1590 | O | ASP | A | 1009 | 25.382 | 32.469 | 0.566 | 1.00 | 24.34 | A O |
| ATOM | 1591 | N | VAL | A | 1010 | 24.904 | 30.987 | −1.051 | 1.00 | 21.87 | A N |
| ATOM | 1592 | CA | VAL | A | 1010 | 24.986 | 29.833 | −0.155 | 1.00 | 21.43 | A C |
| ATOM | 1593 | CB | VAL | A | 1010 | 24.906 | 28.497 | −0.933 | 1.00 | 18.75 | A C |
| ATOM | 1594 | CG1 | VAL | A | 1010 | 25.308 | 27.344 | −0.033 | 1.00 | 18.01 | A C |
| ATOM | 1595 | CG2 | VAL | A | 1010 | 23.499 | 28.277 | −1.432 | 1.00 | 17.23 | A C |
| ATOM | 1596 | C | VAL | A | 1010 | 26.279 | 29.868 | 0.649 | 1.00 | 21.21 | A C |
| ATOM | 1597 | O | VAL | A | 1010 | 26.285 | 29.538 | 1.827 | 1.00 | 18.67 | A O |
| ATOM | 1598 | N | TRP | A | 1011 | 27.355 | 30.289 | −0.012 | 1.00 | 22.19 | A N |
| ATOM | 1599 | CA | TRP | A | 1011 | 28.671 | 30.408 | 0.582 | 1.00 | 21.30 | A C |
| ATOM | 1600 | CB | TRP | A | 1011 | 29.676 | 30.823 | −0.494 | 1.00 | 21.09 | A C |
| ATOM | 1601 | CG | TRP | A | 1011 | 31.004 | 31.272 | 0.051 | 1.00 | 22.20 | A C |
| ATOM | 1602 | CD2 | TRP | A | 1011 | 32.242 | 30.555 | −0.013 | 1.00 | 23.32 | A C |
| ATOM | 1603 | CE2 | TRP | A | 1011 | 33.216 | 31.343 | 0.643 | 1.00 | 23.77 | A C |
| ATOM | 1604 | CE3 | TRP | A | 1011 | 32.622 | 29.326 | −0.558 | 1.00 | 23.63 | A C |
| ATOM | 1605 | CD1 | TRP | A | 1011 | 31.271 | 32.436 | 0.726 | 1.00 | 22.11 | A C |
| ATOM | 1606 | NE1 | TRP | A | 1011 | 32.596 | 32.484 | 1.084 | 1.00 | 22.41 | A N |
| ATOM | 1607 | CZ2 | TRP | A | 1011 | 34.546 | 30.940 | 0.769 | 1.00 | 23.00 | A C |
| ATOM | 1608 | CZ3 | TRP | A | 1011 | 33.949 | 28.926 | −0.433 | 1.00 | 25.04 | A C |
| ATOM | 1609 | CH2 | TRP | A | 1011 | 34.893 | 29.734 | 0.226 | 1.00 | 24.41 | A C |
| ATOM | 1610 | C | TRP | A | 1011 | 28.642 | 31.456 | 1.690 | 1.00 | 21.41 | A C |
| ATOM | 1611 | O | TRP | A | 1011 | 29.159 | 31.231 | 2.780 | 1.00 | 20.92 | A O |
| ATOM | 1612 | N | SER | A | 1012 | 28.035 | 32.602 | 1.401 | 1.00 | 22.30 | A N |
| ATOM | 1613 | CA | SER | A | 1012 | 27.940 | 33.684 | 2.373 | 1.00 | 21.76 | A C |
| ATOM | 1614 | CB | SER | A | 1012 | 27.286 | 34.926 | 1.742 | 1.00 | 24.85 | A C |
| ATOM | 1615 | OG | SER | A | 1012 | 27.933 | 35.297 | 0.534 | 1.00 | 28.52 | A O |
| ATOM | 1616 | C | SER | A | 1012 | 27.107 | 33.232 | 3.565 | 1.00 | 19.93 | A C |
| ATOM | 1617 | O | SER | A | 1012 | 27.303 | 33.713 | 4.677 | 1.00 | 20.35 | A O |
| ATOM | 1618 | N | PHE | A | 1013 | 26.167 | 32.322 | 3.332 | 1.00 | 18.72 | A N |
| ATOM | 1619 | CA | PHE | A | 1013 | 25.324 | 31.823 | 4.409 | 1.00 | 19.74 | A C |
| ATOM | 1620 | CB | PHE | A | 1013 | 24.197 | 30.958 | 3.850 | 1.00 | 21.64 | A C |
| ATOM | 1621 | CG | PHE | A | 1013 | 23.267 | 30.431 | 4.902 | 1.00 | 21.29 | A C |
| ATOM | 1622 | CD1 | PHE | A | 1013 | 22.582 | 31.307 | 5.738 | 1.00 | 21.35 | A C |
| ATOM | 1623 | CD2 | PHE | A | 1013 | 23.048 | 29.069 | 5.033 | 1.00 | 20.51 | A C |
| ATOM | 1624 | CE1 | PHE | A | 1013 | 21.689 | 30.832 | 6.684 | 1.00 | 20.93 | A C |

| | | | | | -continued | | | | | | |
|---|---|---|---|---|---|---|---|---|---|---|---|
| ATOM | 1625 | CE2 | PHE | A | 1013 | 22.156 | 28.579 | 5.973 | 1.00 | 21.44 | A | C |
| ATOM | 1626 | CZ | PHE | A | 1013 | 21.470 | 29.462 | 6.804 | 1.00 | 21.79 | A | C |
| ATOM | 1627 | C | PHE | A | 1013 | 26.191 | 31.002 | 5.355 | 1.00 | 18.87 | A | C |
| ATOM | 1628 | O | PHE | A | 1013 | 25.924 | 30.912 | 6.549 | 1.00 | 18.16 | A | O |
| ATOM | 1629 | N | GLY | A | 1014 | 27.236 | 30.399 | 4.806 | 1.00 | 19.32 | A | N |
| ATOM | 1630 | CA | GLY | A | 1014 | 28.143 | 29.634 | 5.639 | 1.00 | 23.18 | A | C |
| ATOM | 1631 | C | GLY | A | 1014 | 28.825 | 30.545 | 6.654 | 1.00 | 24.21 | A | C |
| ATOM | 1632 | O | GLY | A | 1014 | 28.994 | 30.177 | 7.815 | 1.00 | 23.51 | A | O |
| ATOM | 1633 | N | VAL | A | 1015 | 29.206 | 31.745 | 6.216 | 1.00 | 25.95 | A | N |
| ATOM | 1634 | CA | VAL | A | 1015 | 29.874 | 32.705 | 7.093 | 1.00 | 26.43 | A | C |
| ATOM | 1635 | CB | VAL | A | 1015 | 30.547 | 33.841 | 6.282 | 1.00 | 25.36 | A | C |
| ATOM | 1636 | CG1 | VAL | A | 1015 | 31.399 | 34.710 | 7.195 | 1.00 | 26.40 | A | C |
| ATOM | 1637 | CG2 | VAL | A | 1015 | 31.404 | 33.253 | 5.185 | 1.00 | 24.13 | A | C |
| ATOM | 1638 | C | VAL | A | 1015 | 28.873 | 33.305 | 8.070 | 1.00 | 27.70 | A | C |
| ATOM | 1639 | O | VAL | A | 1015 | 29.229 | 33.721 | 9.174 | 1.00 | 29.33 | A | O |
| ATOM | 1640 | N | VAL | A | 1016 | 27.610 | 33.345 | 7.674 | 1.00 | 26.63 | A | N |
| ATOM | 1641 | CA | VAL | A | 1016 | 26.600 | 33.897 | 8.559 | 1.00 | 26.58 | A | C |
| ATOM | 1642 | CB | VAL | A | 1016 | 25.275 | 34.134 | 7.813 | 1.00 | 27.70 | A | C |
| ATOM | 1643 | CG1 | VAL | A | 1016 | 24.194 | 34.545 | 8.804 | 1.00 | 25.02 | A | C |
| ATOM | 1644 | CG2 | VAL | A | 1016 | 25.469 | 35.196 | 6.738 | 1.00 | 24.95 | A | C |
| ATOM | 1645 | C | VAL | A | 1016 | 26.363 | 32.924 | 9.709 | 1.00 | 26.56 | A | C |
| ATOM | 1646 | O | VAL | A | 1016 | 26.105 | 33.334 | 10.843 | 1.00 | 25.68 | A | O |
| ATOM | 1647 | N | LEU | A | 1017 | 26.445 | 31.630 | 9.406 | 1.00 | 25.79 | A | N |
| ATOM | 1648 | CA | LEU | A | 1017 | 26.259 | 30.595 | 10.420 | 1.00 | 25.37 | A | C |
| ATOM | 1649 | CB | LEU | A | 1017 | 26.231 | 29.204 | 9.768 | 1.00 | 24.57 | A | C |
| ATOM | 1650 | CG | LEU | A | 1017 | 24.935 | 28.765 | 9.069 | 1.00 | 23.17 | A | C |
| ATOM | 1651 | CD1 | LEU | A | 1017 | 25.212 | 27.540 | 8.190 | 1.00 | 22.94 | A | C |
| ATOM | 1652 | CD2 | LEU | A | 1017 | 23.856 | 28.468 | 10.107 | 1.00 | 19.40 | A | C |
| ATOM | 1653 | C | LEU | A | 1017 | 27.417 | 30.702 | 11.404 | 1.00 | 25.14 | A | C |
| ATOM | 1654 | O | LEU | A | 1017 | 27.242 | 30.556 | 12.609 | 1.00 | 24.28 | A | O |
| ATOM | 1655 | N | TYR | A | 1018 | 28.603 | 30.964 | 10.871 | 1.00 | 26.09 | A | N |
| ATOM | 1656 | CA | TYR | A | 1018 | 29.788 | 31.130 | 11.687 | 1.00 | 27.05 | A | C |
| ATOM | 1657 | CB | TYR | A | 1018 | 31.003 | 31.388 | 10.601 | 1.00 | 28.96 | A | C |
| ATOM | 1658 | CG | TYR | A | 1018 | 32.276 | 31.654 | 11.584 | 1.00 | 32.69 | A | C |
| ATOM | 1659 | CD1 | TYR | A | 1018 | 32.924 | 30.627 | 12.263 | 1.00 | 31.98 | A | C |
| ATOM | 1660 | CE1 | TYR | A | 1018 | 34.082 | 30.865 | 12.978 | 1.00 | 31.92 | A | C |
| ATOM | 1661 | CD2 | TYR | A | 1018 | 32.830 | 32.936 | 11.647 | 1.00 | 31.48 | A | C |
| ATOM | 1662 | CE2 | TYR | A | 1018 | 33.993 | 33.180 | 12.364 | 1.00 | 31.23 | A | C |
| ATOM | 1663 | CZ | TYR | A | 1018 | 34.610 | 32.139 | 13.023 | 1.00 | 32.76 | A | C |
| ATOM | 1664 | OH | TYR | A | 1018 | 35.763 | 32.357 | 13.732 | 1.00 | 34.73 | A | O |
| ATOM | 1665 | C | TYR | A | 1018 | 29.590 | 32.316 | 12.636 | 1.00 | 28.41 | A | C |
| ATOM | 1666 | O | TYR | A | 1018 | 29.937 | 32.228 | 13.807 | 1.00 | 29.27 | A | O |
| ATOM | 1667 | N | GLU | A | 1019 | 29.024 | 33.416 | 12.130 | 1.00 | 28.77 | A | N |
| ATOM | 1668 | CA | GLU | A | 1019 | 28.786 | 34.623 | 12.931 | 1.00 | 28.13 | A | C |
| ATOM | 1669 | CB | GLU | A | 1019 | 28.258 | 35.773 | 12.046 | 1.00 | 29.97 | A | C |
| ATOM | 1670 | CG | GLU | A | 1019 | 29.188 | 36.251 | 10.919 | 1.00 | 29.60 | A | C |
| ATOM | 1671 | CD | GLU | A | 1019 | 28.738 | 37.577 | 10.299 | 1.00 | 29.59 | A | C |
| ATOM | 1672 | OE1 | GLU | A | 1019 | 28.910 | 38.638 | 10.937 | 1.00 | 31.77 | A | O |
| ATOM | 1673 | OE2 | GLU | A | 1019 | 28.208 | 37.564 | 9.171 | 1.00 | 28.17 | A | O |
| ATOM | 1674 | C | GLU | A | 1019 | 27.796 | 34.396 | 14.086 | 1.00 | 27.33 | A | C |
| ATOM | 1675 | O | GLU | A | 1019 | 27.988 | 34.897 | 15.195 | 1.00 | 25.68 | A | O |
| ATOM | 1676 | N | LEU | A | 1020 | 26.730 | 33.650 | 13.825 | 1.00 | 27.14 | A | N |
| ATOM | 1677 | CA | LEU | A | 1020 | 25.735 | 33.394 | 14.855 | 1.00 | 26.16 | A | C |
| ATOM | 1678 | CB | LEU | A | 1020 | 24.513 | 32.683 | 14.255 | 1.00 | 25.72 | A | C |
| ATOM | 1679 | CG | LEU | A | 1020 | 23.673 | 33.449 | 13.223 | 1.00 | 27.06 | A | C |
| ATOM | 1680 | CD1 | LEU | A | 1020 | 22.199 | 33.148 | 13.464 | 1.00 | 26.70 | A | C |
| ATOM | 1681 | CD2 | LEU | A | 1020 | 23.917 | 34.949 | 13.329 | 1.00 | 26.86 | A | C |
| ATOM | 1682 | C | LEU | A | 1020 | 26.318 | 32.560 | 15.988 | 1.00 | 25.00 | A | C |
| ATOM | 1683 | O | LEU | A | 1020 | 26.214 | 32.929 | 17.153 | 1.00 | 23.85 | A | O |
| ATOM | 1684 | N | PHE | A | 1021 | 26.935 | 31.438 | 15.637 | 1.00 | 25.96 | A | N |
| ATOM | 1685 | CA | PHE | A | 1021 | 27.540 | 30.551 | 16.622 | 1.00 | 28.26 | A | C |
| ATOM | 1686 | CB | PHE | A | 1021 | 27.756 | 29.173 | 15.998 | 1.00 | 28.65 | A | C |
| ATOM | 1687 | CG | PHE | A | 1021 | 26.514 | 28.328 | 15.974 | 1.00 | 30.48 | A | C |
| ATOM | 1688 | CD1 | PHE | A | 1021 | 26.105 | 27.648 | 17.107 | 1.00 | 30.22 | A | C |
| ATOM | 1689 | CD2 | PHE | A | 1021 | 25.721 | 28.270 | 14.846 | 1.00 | 31.61 | A | C |
| ATOM | 1690 | CE1 | PHE | A | 1021 | 24.932 | 26.932 | 17.119 | 1.00 | 32.06 | A | C |
| ATOM | 1691 | CE2 | PHE | A | 1021 | 24.537 | 27.552 | 14.853 | 1.00 | 33.64 | A | C |
| ATOM | 1692 | CZ | PHE | A | 1021 | 24.145 | 26.882 | 15.994 | 1.00 | 33.78 | A | C |
| ATOM | 1693 | C | PHE | A | 1021 | 28.848 | 31.115 | 17.184 | 1.00 | 29.12 | A | C |
| ATOM | 1694 | O | PHE | A | 1021 | 29.517 | 30.477 | 17.992 | 1.00 | 30.42 | A | O |
| ATOM | 1695 | N | THR | A | 1022 | 29.190 | 32.325 | 16.751 | 1.00 | 29.23 | A | N |
| ATOM | 1696 | CA | THR | A | 1022 | 30.386 | 33.014 | 17.201 | 1.00 | 28.15 | A | C |
| ATOM | 1697 | CB | THR | A | 1022 | 31.291 | 33.380 | 15.994 | 1.00 | 28.82 | A | C |
| ATOM | 1698 | OG1 | THR | A | 1022 | 32.643 | 32.998 | 16.273 | 1.00 | 30.39 | A | O |
| ATOM | 1699 | CG2 | THR | A | 1022 | 31.237 | 34.859 | 15.693 | 1.00 | 28.63 | A | C |
| ATOM | 1700 | C | THR | A | 1022 | 29.899 | 34.276 | 17.905 | 1.00 | 28.32 | A | C |
| ATOM | 1701 | O | THR | A | 1022 | 30.692 | 35.071 | 18.422 | 1.00 | 27.51 | A | O |
| ATOM | 1702 | N | TYR | A | 1023 | 28.573 | 34.427 | 17.931 | 1.00 | 28.68 | A | N |
| ATOM | 1703 | CA | TYR | A | 1023 | 27.897 | 35.573 | 18.545 | 1.00 | 27.59 | A | C |
| ATOM | 1704 | CB | TYR | A | 1023 | 28.003 | 35.531 | 20.067 | 1.00 | 27.08 | A | O |

| | | | | | -continued | | | | | | |
|---|---|---|---|---|---|---|---|---|---|---|---|
| ATOM | 1705 | CG | TYR | A | 1023 | 27.151 | 34.471 | 20.710 | 1.00 | 27.19 | A | C |
| ATOM | 1706 | CD1 | TYR | A | 1023 | 27.691 | 33.252 | 21.089 | 1.00 | 27.11 | A | C |
| ATOM | 1707 | CE1 | TYR | A | 1023 | 26.900 | 32.281 | 21.682 | 1.00 | 26.29 | A | C |
| ATOM | 1708 | CD2 | TYR | A | 1023 | 25.799 | 34.690 | 20.937 | 1.00 | 26.09 | A | C |
| ATOM | 1709 | CE2 | TYR | A | 1023 | 25.006 | 33.730 | 21.524 | 1.00 | 25.32 | A | C |
| ATOM | 1710 | CZ | TYR | A | 1023 | 25.559 | 32.528 | 21.896 | 1.00 | 26.71 | A | C |
| ATOM | 1711 | OH | TYR | A | 1023 | 24.766 | 31.569 | 22.484 | 1.00 | 27.13 | A | O |
| ATOM | 1712 | C | TYR | A | 1023 | 28.471 | 36.886 | 18.062 | 1.00 | 26.01 | A | C |
| ATOM | 1713 | O | TYR | A | 1023 | 28.307 | 37.913 | 18.712 | 1.00 | 26.91 | A | O |
| ATOM | 1714 | N | CYS | A | 1024 | 29.150 | 36.849 | 16.924 | 1.00 | 24.48 | A | N |
| ATOM | 1715 | CA | CYS | A | 1024 | 29.760 | 38.042 | 16.359 | 1.00 | 27.84 | A | C |
| ATOM | 1716 | CB | CYS | A | 1024 | 28.698 | 39.077 | 15.971 | 1.00 | 27.22 | A | C |
| ATOM | 1717 | SG | CYS | A | 1024 | 27.882 | 38.643 | 14.441 | 1.00 | 31.28 | A | S |
| ATOM | 1718 | C | CYS | A | 1024 | 30.787 | 38.681 | 17.266 | 1.00 | 28.38 | A | C |
| ATOM | 1719 | O | CYS | A | 1024 | 30.903 | 39.905 | 17.346 | 1.00 | 28.99 | A | O |
| ATOM | 1720 | N | ASP | A | 1025 | 31.543 | 37.845 | 17.950 | 1.00 | 28.57 | A | N |
| ATOM | 1721 | CA | ASP | A | 1025 | 32.582 | 38.353 | 18.807 | 1.00 | 30.59 | A | C |
| ATOM | 1722 | CB | ASP | A | 1025 | 33.163 | 37.211 | 19.630 | 1.00 | 35.06 | A | C |
| ATOM | 1723 | CG | ASP | A | 1025 | 34.099 | 37.697 | 20.698 | 1.00 | 39.47 | A | C |
| ATOM | 1724 | OD1 | ASP | A | 1025 | 33.658 | 38.530 | 21.525 | 1.00 | 42.23 | A | O |
| ATOM | 1725 | OD2 | ASP | A | 1025 | 35.269 | 37.249 | 20.704 | 1.00 | 42.12 | A | O |
| ATOM | 1726 | C | ASP | A | 1025 | 33.647 | 38.945 | 17.874 | 1.00 | 30.39 | A | C |
| ATOM | 1727 | O | ASP | A | 1025 | 34.007 | 38.326 | 16.870 | 1.00 | 29.56 | A | O |
| ATOM | 1728 | N | LYS | A | 1026 | 34.139 | 40.136 | 18.201 | 1.00 | 31.27 | A | N |
| ATOM | 1729 | CA | LYS | A | 1026 | 35.143 | 40.817 | 17.381 | 1.00 | 33.10 | A | C |
| ATOM | 1730 | CB | LYS | A | 1026 | 35.401 | 42.228 | 17.914 | 1.00 | 35.51 | A | C |
| ATOM | 1731 | CG | LYS | A | 1026 | 34.153 | 43.016 | 18.261 | 1.00 | 39.16 | A | C |
| ATOM | 1732 | CD | LYS | A | 1026 | 33.229 | 43.169 | 17.082 | 1.00 | 42.21 | A | C |
| ATOM | 1733 | CE | LYS | A | 1026 | 33.853 | 43.995 | 15.984 | 1.00 | 43.30 | A | C |
| ATOM | 1734 | NZ | LYS | A | 1026 | 32.833 | 44.288 | 14.939 | 1.00 | 46.56 | A | N |
| ATOM | 1735 | C | LYS | A | 1026 | 36.468 | 40.065 | 17.327 | 1.00 | 33.00 | A | C |
| ATOM | 1736 | O | LYS | A | 1026 | 37.176 | 40.116 | 16.323 | 1.00 | 32.10 | A | O |
| ATOM | 1737 | N | SER | A | 1027 | 36.797 | 39.368 | 18.410 | 1.00 | 34.41 | A | N |
| ATOM | 1738 | CA | SER | A | 1027 | 38.042 | 38.605 | 18.491 | 1.00 | 34.79 | A | C |
| ATOM | 1739 | CB | SER | A | 1027 | 38.153 | 37.909 | 19.856 | 1.00 | 33.89 | A | C |
| ATOM | 1740 | OG | SER | A | 1027 | 37.889 | 38.809 | 20.914 | 1.00 | 38.74 | A | O |
| ATOM | 1741 | C | SER | A | 1027 | 38.156 | 37.545 | 17.391 | 1.00 | 34.36 | A | C |
| ATOM | 1742 | O | SER | A | 1027 | 39.198 | 37.413 | 16.750 | 1.00 | 33.83 | A | O |
| ATOM | 1743 | N | CYS | A | 1028 | 37.080 | 36.790 | 17.178 | 1.00 | 33.80 | A | N |
| ATOM | 1744 | CA | CYS | A | 1028 | 37.075 | 35.716 | 16.182 | 1.00 | 32.68 | A | C |
| ATOM | 1745 | CB | CYS | A | 1028 | 36.650 | 34.408 | 16.850 | 1.00 | 32.82 | A | C |
| ATOM | 1746 | SG | CYS | A | 1028 | 35.060 | 34.533 | 17.704 | 1.00 | 33.09 | A | S |
| ATOM | 1747 | C | CYS | A | 1028 | 36.164 | 35.973 | 14.982 | 1.00 | 30.73 | A | C |
| ATOM | 1748 | O | CYS | A | 1028 | 35.772 | 35.043 | 14.282 | 1.00 | 30.74 | A | O |
| ATOM | 1749 | N | SER | A | 1029 | 35.627 | 37.230 | 14.741 | 1.00 | 29.90 | A | N |
| ATOM | 1750 | CA | SER | A | 1029 | 34.959 | 37.558 | 13.626 | 1.00 | 29.19 | A | C |
| ATOM | 1751 | CB | SER | A | 1029 | 34.726 | 39.067 | 13.567 | 1.00 | 28.66 | A | C |
| ATOM | 1752 | OG | SER | A | 1029 | 35.884 | 39.732 | 13.096 | 1.00 | 31.25 | A | O |
| ATOM | 1753 | C | SER | A | 1029 | 35.598 | 37.086 | 12.327 | 1.00 | 28.26 | A | C |
| ATOM | 1754 | O | SER | A | 1029 | 36.762 | 36.669 | 12.303 | 1.00 | 30.05 | A | O |
| ATOM | 1755 | N | PRO | A | 1030 | 34.834 | 37.121 | 11.229 | 1.00 | 25.74 | A | N |
| ATOM | 1756 | CD | PRO | A | 1030 | 33.369 | 37.260 | 11.198 | 1.00 | 22.85 | A | C |
| ATOM | 1757 | CA | PRO | A | 1030 | 35.350 | 36.694 | 9.928 | 1.00 | 24.51 | A | C |
| ATOM | 1758 | CB | PRO | A | 1030 | 34.149 | 36.904 | 9.017 | 1.00 | 23.05 | A | C |
| ATOM | 1759 | CG | PRO | A | 1030 | 33.010 | 36.539 | 9.929 | 1.00 | 24.45 | A | C |
| ATOM | 1760 | C | PRO | A | 1030 | 36.605 | 37.469 | 9.475 | 1.00 | 24.86 | A | C |
| ATOM | 1761 | O | PRO | A | 1030 | 37.535 | 36.898 | 8.872 | 1.00 | 23.18 | A | O |
| ATOM | 1762 | N | SER | A | 1031 | 36.632 | 38.766 | 9.768 | 1.00 | 24.48 | A | N |
| ATOM | 1763 | CA | SER | A | 1031 | 37.772 | 39.609 | 9.406 | 1.00 | 24.82 | A | C |
| ATOM | 1764 | CB | SER | A | 1031 | 37.422 | 41.084 | 9.609 | 1.00 | 21.99 | A | C |
| ATOM | 1765 | OG | SER | A | 1031 | 36.210 | 41.207 | 10.327 | 1.00 | 27.23 | A | O |
| ATOM | 1766 | C | SER | A | 1031 | 39.013 | 39.245 | 10.231 | 1.00 | 25.14 | A | C |
| ATOM | 1767 | O | SER | A | 1031 | 40.072 | 38.938 | 9.685 | 1.00 | 25.36 | A | O |
| ATOM | 1768 | N | ALA | A | 1032 | 38.875 | 39.279 | 11.548 | 1.00 | 27.52 | A | N |
| ATOM | 1769 | CA | ALA | A | 1032 | 39.979 | 38.950 | 12.435 | 1.00 | 28.18 | A | C |
| ATOM | 1770 | CB | ALA | A | 1032 | 39.474 | 38.857 | 13.876 | 1.00 | 27.52 | A | C |
| ATOM | 1771 | C | ALA | A | 1032 | 40.668 | 37.648 | 12.031 | 1.00 | 29.01 | A | C |
| ATOM | 1772 | O | ALA | A | 1032 | 41.877 | 37.637 | 11.783 | 1.00 | 30.30 | A | O |
| ATOM | 1773 | N | GLU | A | 1033 | 39.905 | 36.556 | 11.966 | 1.00 | 29.03 | A | N |
| ATOM | 1774 | CA | GLU | A | 1033 | 40.458 | 35.247 | 11.593 | 1.00 | 28.45 | A | C |
| ATOM | 1775 | CB | GLU | A | 1033 | 39.354 | 34.183 | 11.531 | 1.00 | 31.07 | A | C |
| ATOM | 1776 | CG | GLU | A | 1033 | 38.745 | 33.851 | 12.870 | 1.00 | 33.50 | A | C |
| ATOM | 1777 | CD | GLU | A | 1033 | 39.798 | 33.685 | 13.925 | 1.00 | 35.91 | A | C |
| ATOM | 1778 | OE1 | GLU | A | 1033 | 40.810 | 33.015 | 13.637 | 1.00 | 37.80 | A | O |
| ATOM | 1779 | OE2 | GLU | A | 1033 | 39.615 | 34.220 | 15.036 | 1.00 | 36.97 | A | O |
| ATOM | 1780 | C | GLU | A | 1033 | 41.190 | 35.262 | 10.260 | 1.00 | 26.35 | A | C |
| ATOM | 1781 | O | GLU | A | 1033 | 42.372 | 34.948 | 10.186 | 1.00 | 25.54 | A | O |
| ATOM | 1782 | N | PHE | A | 1034 | 40.479 | 35.610 | 9.199 | 1.00 | 27.44 | A | N |
| ATOM | 1783 | CA | PHE | A | 1034 | 41.083 | 35.649 | 7.879 | 1.00 | 27.26 | A | C |
| ATOM | 1784 | CB | PHE | A | 1034 | 40.080 | 36.198 | 6.872 | 1.00 | 26.93 | A | C |

-continued

| | | | | | | | | | | | | |
|---|---|---|---|---|---|---|---|---|---|---|---|---|
| ATOM | 1785 | CG | PHE | A | 1034 | 39.129 | 35.165 | 6.337 | 1.00 | 29.70 | A | C |
| ATOM | 1786 | CD1 | PHE | A | 1034 | 37.809 | 35.493 | 6.063 | 1.00 | 29.12 | A | C |
| ATOM | 1787 | CD2 | PHE | A | 1034 | 39.566 | 33.882 | 6.055 | 1.00 | 28.02 | A | C |
| ATOM | 1788 | CE1 | PHE | A | 1034 | 36.947 | 34.559 | 5.517 | 1.00 | 29.46 | A | C |
| ATOM | 1789 | CE2 | PHE | A | 1034 | 38.707 | 32.950 | 5.508 | 1.00 | 29.09 | A | C |
| ATOM | 1790 | CZ | PHE | A | 1034 | 37.396 | 33.289 | 5.238 | 1.00 | 29.30 | A | C |
| ATOM | 1791 | C | PHE | A | 1034 | 42.323 | 36.512 | 7.699 | 1.00 | 27.70 | A | C |
| ATOM | 1792 | O | PHE | A | 1034 | 43.342 | 36.168 | 7.298 | 1.00 | 28.43 | A | O |
| ATOM | 1793 | N | LEU | A | 1035 | 42.242 | 37.635 | 8.600 | 1.00 | 28.83 | A | N |
| ATOM | 1794 | CA | LEU | A | 1035 | 43.371 | 38.550 | 8.668 | 1.00 | 31.32 | A | C |
| ATOM | 1795 | CB | LEU | A | 1035 | 42.936 | 39.863 | 9.326 | 1.00 | 30.92 | A | C |
| ATOM | 1796 | CG | LEU | A | 1035 | 43.110 | 41.158 | 8.527 | 1.00 | 29.53 | A | C |
| ATOM | 1797 | CD1 | LEU | A | 1035 | 42.484 | 41.056 | 7.144 | 1.00 | 27.99 | A | C |
| ATOM | 1798 | CD2 | LEU | A | 1035 | 42.468 | 42.274 | 9.318 | 1.00 | 29.65 | A | C |
| ATOM | 1799 | C | LEU | A | 1035 | 44.560 | 37.936 | 9.408 | 1.00 | 33.17 | A | C |
| ATOM | 1800 | O | LEU | A | 1035 | 45.703 | 38.007 | 8.938 | 1.00 | 31.72 | A | O |
| ATOM | 1801 | N | ARG | A | 1036 | 44.300 | 37.321 | 10.560 | 1.00 | 31.84 | A | N |
| ATOM | 1802 | CA | ARG | A | 1036 | 45.395 | 36.717 | 11.292 | 1.00 | 34.63 | A | C |
| ATOM | 1803 | CB | ARG | A | 1036 | 45.012 | 36.432 | 12.746 | 1.00 | 34.04 | A | C |
| ATOM | 1804 | CG | ARG | A | 1036 | 43.831 | 35.531 | 12.933 | 1.00 | 36.91 | A | C |
| ATOM | 1805 | CD | ARG | A | 1036 | 43.730 | 35.091 | 14.385 | 1.00 | 36.17 | A | C |
| ATOM | 1806 | NE | ARG | A | 1036 | 44.811 | 34.176 | 14.715 | 1.00 | 34.71 | A | N |
| ATOM | 1807 | CZ | ARG | A | 1036 | 44.721 | 32.855 | 14.611 | 1.00 | 33.73 | A | C |
| ATOM | 1808 | NH1 | ARG | A | 1036 | 43.590 | 32.298 | 14.203 | 1.00 | 32.21 | A | N |
| ATOM | 1809 | NH2 | ARG | A | 1036 | 45.775 | 32.093 | 14.879 | 1.00 | 33.32 | A | N |
| ATOM | 1810 | C | ARG | A | 1036 | 45.890 | 35.441 | 10.621 | 1.00 | 36.65 | A | C |
| ATOM | 1811 | O | ARG | A | 1036 | 47.060 | 35.084 | 10.752 | 1.00 | 38.90 | A | O |
| ATOM | 1812 | N | MET | A | 1037 | 45.014 | 34.764 | 9.886 | 1.00 | 38.66 | A | N |
| ATOM | 1813 | CA | MET | A | 1037 | 45.404 | 33.539 | 9.207 | 1.00 | 40.19 | A | C |
| ATOM | 1814 | CB | MET | A | 1037 | 44.189 | 32.894 | 8.525 | 1.00 | 41.26 | A | C |
| ATOM | 1815 | CG | MET | A | 1037 | 43.389 | 31.971 | 9.443 | 1.00 | 41.69 | A | C |
| ATOM | 1816 | SD | MET | A | 1037 | 41.858 | 31.301 | 8.730 | 1.00 | 42.48 | A | S |
| ATOM | 1817 | CE | MET | A | 1037 | 42.498 | 30.138 | 7.523 | 1.00 | 42.39 | A | C |
| ATOM | 1818 | C | MET | A | 1037 | 46.516 | 33.791 | 8.192 | 1.00 | 41.59 | A | C |
| ATOM | 1819 | O | MET | A | 1037 | 47.477 | 33.023 | 8.108 | 1.00 | 42.63 | A | O |
| ATOM | 1820 | N | MET | A | 1038 | 46.398 | 34.871 | 7.428 | 1.00 | 43.48 | A | N |
| ATOM | 1821 | CA | MET | A | 1038 | 47.418 | 35.187 | 6.433 | 1.00 | 43.88 | A | C |
| ATOM | 1822 | CB | MET | A | 1038 | 46.753 | 35.624 | 5.120 | 1.00 | 44.08 | A | C |
| ATOM | 1823 | CG | MET | A | 1038 | 45.450 | 36.379 | 5.283 | 1.00 | 44.10 | A | C |
| ATOM | 1824 | SD | MET | A | 1038 | 44.666 | 36.794 | 3.686 | 1.00 | 42.80 | A | S |
| ATOM | 1825 | CE | MET | A | 1038 | 43.115 | 37.477 | 4.272 | 1.00 | 43.10 | A | C |
| ATOM | 1826 | C | MET | A | 1038 | 48.457 | 36.218 | 6.897 | 1.00 | 44.50 | A | C |
| ATOM | 1827 | O | MET | A | 1038 | 49.252 | 36.722 | 6.096 | 1.00 | 44.74 | A | O |
| ATOM | 1828 | N | GLY | A | 1039 | 48.443 | 36.508 | 8.196 | 1.00 | 44.49 | A | N |
| ATOM | 1829 | CA | GLY | A | 1039 | 49.394 | 37.434 | 8.791 | 1.00 | 45.60 | A | C |
| ATOM | 1830 | C | GLY | A | 1039 | 49.386 | 38.877 | 8.331 | 1.00 | 46.45 | A | C |
| ATOM | 1831 | O | GLY | A | 1039 | 50.383 | 39.579 | 8.503 | 1.00 | 46.86 | A | O |
| ATOM | 1832 | N | CYS | A | 1040 | 48.265 | 39.324 | 7.768 | 1.00 | 47.04 | A | N |
| ATOM | 1833 | CA | CYS | A | 1040 | 48.124 | 40.690 | 7.270 | 1.00 | 45.91 | A | C |
| ATOM | 1834 | CB | CYS | A | 1040 | 46.874 | 40.805 | 6.406 | 1.00 | 44.80 | A | C |
| ATOM | 1835 | SG | CYS | A | 1040 | 46.619 | 42.464 | 5.760 | 1.00 | 44.01 | A | S |
| ATOM | 1836 | C | CYS | A | 1040 | 48.033 | 41.715 | 8.392 | 1.00 | 46.80 | A | C |
| ATOM | 1837 | O | CYS | A | 1040 | 47.246 | 41.552 | 9.321 | 1.00 | 45.47 | A | O |
| ATOM | 1838 | N | GLU | A | 1041 | 48.834 | 42.774 | 8.299 | 1.00 | 47.51 | A | N |
| ATOM | 1839 | CA | GLU | A | 1041 | 48.823 | 43.823 | 9.314 | 1.00 | 49.46 | A | C |
| ATOM | 1840 | CB | GLU | A | 1041 | 50.229 | 44.395 | 9.504 | 1.00 | 49.04 | A | C |
| ATOM | 1841 | CG | GLU | A | 1041 | 51.136 | 44.225 | 8.317 | 1.00 | 49.42 | A | C |
| ATOM | 1842 | CD | GLU | A | 1041 | 52.547 | 44.678 | 8.612 | 1.00 | 50.81 | A | C |
| ATOM | 1843 | OE1 | GLU | A | 1041 | 53.438 | 44.401 | 7.784 | 1.00 | 50.66 | A | O |
| ATOM | 1844 | OE2 | GLU | A | 1041 | 52.765 | 45.315 | 9.670 | 1.00 | 50.52 | A | O |
| ATOM | 1845 | C | GLU | A | 1041 | 47.834 | 44.929 | 8.957 | 1.00 | 50.58 | A | C |
| ATOM | 1846 | O | GLU | A | 1041 | 47.369 | 45.680 | 9.822 | 1.00 | 50.40 | A | O |
| ATOM | 1847 | N | ARG | A | 1042 | 47.522 | 45.017 | 7.668 | 1.00 | 50.93 | A | N |
| ATOM | 1848 | CA | ARG | A | 1042 | 46.558 | 45.985 | 7.164 | 1.00 | 51.11 | A | C |
| ATOM | 1849 | CB | ARG | A | 1042 | 46.623 | 46.047 | 5.638 | 1.00 | 52.02 | A | C |
| ATOM | 1850 | CG | ARG | A | 1042 | 47.953 | 46.510 | 5.094 | 1.00 | 54.33 | A | C |
| ATOM | 1851 | CD | ARG | A | 1042 | 47.964 | 46.457 | 3.580 | 1.00 | 56.72 | A | C |
| ATOM | 1852 | NE | ARG | A | 1042 | 48.896 | 47.432 | 3.029 | 1.00 | 58.81 | A | N |
| ATOM | 1853 | CZ | ARG | A | 1042 | 48.728 | 48.746 | 3.124 | 1.00 | 59.85 | A | C |
| ATOM | 1854 | NH1 | ARG | A | 1042 | 47.661 | 49.232 | 3.746 | 1.00 | 59.79 | A | N |
| ATOM | 1855 | NH2 | ARG | A | 1042 | 49.629 | 49.572 | 2.609 | 1.00 | 60.58 | A | N |
| ATOM | 1856 | C | ARG | A | 1042 | 45.177 | 45.499 | 7.583 | 1.00 | 50.01 | A | C |
| ATOM | 1857 | O | ARG | A | 1042 | 44.984 | 44.308 | 7.843 | 1.00 | 49.66 | A | O |
| ATOM | 1858 | N | ASP | A | 1043 | 44.210 | 46.406 | 7.644 | 1.00 | 48.38 | A | N |
| ATOM | 1859 | CA | ASP | A | 1043 | 42.866 | 46.002 | 8.031 | 1.00 | 46.88 | A | C |
| ATOM | 1860 | CB | ASP | A | 1043 | 42.072 | 47.208 | 8.536 | 1.00 | 48.76 | A | C |
| ATOM | 1861 | CG | ASP | A | 1043 | 42.676 | 47.815 | 9.780 | 1.00 | 50.44 | A | C |
| ATOM | 1862 | OD1 | ASP | A | 1043 | 43.032 | 47.040 | 10.692 | 1.00 | 49.73 | A | O |
| ATOM | 1863 | OD2 | ASP | A | 1043 | 42.793 | 49.061 | 9.848 | 1.00 | 53.87 | A | O |
| ATOM | 1864 | C | ASP | A | 1043 | 42.131 | 45.344 | 6.869 | 1.00 | 44.75 | A | C |

| | | | | | -continued | | | | | | |
|---|---|---|---|---|---|---|---|---|---|---|---|
| ATOM | 1865 | O | ASP | A | 1043 | 41.085 | 44.720 | 7.058 | 1.00 | 44.07 | A | O |
| ATOM | 1866 | N | VAL | A | 1044 | 42.686 | 45.487 | 5.669 | 1.00 | 43.28 | A | N |
| ATOM | 1867 | CA | VAL | A | 1044 | 42.088 | 44.918 | 4.461 | 1.00 | 42.27 | A | C |
| ATOM | 1868 | CB | VAL | A | 1044 | 41.217 | 45.960 | 3.700 | 1.00 | 39.69 | A | C |
| ATOM | 1869 | CG1 | VAL | A | 1044 | 40.503 | 45.297 | 2.552 | 1.00 | 38.77 | A | C |
| ATOM | 1870 | CG2 | VAL | A | 1044 | 40.219 | 46.602 | 4.631 | 1.00 | 39.30 | A | C |
| ATOM | 1871 | C | VAL | A | 1044 | 43.219 | 44.479 | 3.543 | 1.00 | 41.86 | A | C |
| ATOM | 1872 | O | VAL | A | 1044 | 43.960 | 45.303 | 3.018 | 1.00 | 42.88 | A | O |
| ATOM | 1873 | N | PRO | A | 1045 | 43.353 | 43.170 | 3.328 | 1.00 | 41.70 | A | N |
| ATOM | 1874 | CD | PRO | A | 1045 | 42.500 | 42.111 | 3.901 | 1.00 | 42.62 | A | C |
| ATOM | 1875 | CA | PRO | A | 1045 | 44.394 | 42.596 | 2.477 | 1.00 | 41.48 | A | C |
| ATOM | 1876 | CB | PRO | A | 1045 | 44.510 | 41.181 | 3.013 | 1.00 | 42.55 | A | C |
| ATOM | 1877 | CG | PRO | A | 1045 | 43.055 | 40.839 | 3.243 | 1.00 | 42.55 | A | C |
| ATOM | 1878 | C | PRO | A | 1045 | 44.017 | 42.597 | 1.007 | 1.00 | 41.10 | A | C |
| ATOM | 1879 | O | PRO | A | 1045 | 42.840 | 42.654 | 0.672 | 1.00 | 41.90 | A | O |
| ATOM | 1880 | N | ALA | A | 1046 | 45.018 | 42.532 | 0.133 | 1.00 | 40.68 | A | N |
| ATOM | 1881 | CA | ALA | A | 1046 | 44.763 | 42.478 | -1.300 | 1.00 | 40.27 | A | C |
| ATOM | 1882 | CB | ALA | A | 1046 | 46.063 | 42.224 | -2.060 | 1.00 | 38.59 | A | C |
| ATOM | 1883 | C | ALA | A | 1046 | 43.797 | 41.313 | -1.500 | 1.00 | 40.14 | A | C |
| ATOM | 1884 | O | ALA | A | 1046 | 43.802 | 40.359 | -0.71B | 1.00 | 39.01 | A | O |
| ATOM | 1885 | N | LEU | A | 1047 | 42.973 | 41.387 | -2.540 | 1.00 | 39.96 | A | N |
| ATOM | 1886 | CA | LEU | A | 1047 | 42.002 | 40.330 | -2.801 | 1.00 | 39.57 | A | C |
| ATOM | 1887 | CB | LEU | A | 1047 | 40.917 | 40.840 | -3.754 | 1.00 | 40.40 | A | C |
| ATOM | 1888 | CG | LEU | A | 1047 | 39.964 | 41.889 | -3.172 | 1.00 | 41.57 | A | C |
| ATOM | 1889 | CD1 | LEU | A | 1047 | 40.729 | 42.949 | -2.374 | 1.00 | 41.75 | A | C |
| ATOM | 1890 | CD2 | LEU | A | 1047 | 39.193 | 42.524 | -4.306 | 1.00 | 41.77 | A | C |
| ATOM | 1891 | C | LEU | A | 1047 | 42.651 | 39.070 | -3.364 | 1.00 | 39.02 | A | C |
| ATOM | 1892 | O | LEU | A | 1047 | 42.210 | 37.954 | -3.084 | 1.00 | 37.37 | A | O |
| ATOM | 1893 | N | CYS | A | 1048 | 43.700 | 39.247 | -4.156 | 1.00 | 37.99 | A | N |
| ATOM | 1894 | CA | CYS | A | 1048 | 44.390 | 38.105 | -4.735 | 1.00 | 39.05 | A | C |
| ATOM | 1895 | CB | CYS | A | 1048 | 45.504 | 38.576 | -5.687 | 1.00 | 40.67 | A | C |
| ATOM | 1896 | SG | CYS | A | 1048 | 46.817 | 39.620 | -4.933 | 1.00 | 44.56 | A | S |
| ATOM | 1897 | C | CYS | A | 1048 | 44.974 | 37.254 | -3.609 | 1.00 | 38.04 | A | C |
| ATOM | 1898 | O | CYS | A | 1048 | 45.072 | 36.038 | -3.726 | 1.00 | 37.74 | A | O |
| ATOM | 1899 | N | ARG | A | 1049 | 45.337 | 37.912 | -2.512 | 1.00 | 37.48 | A | N |
| ATOM | 1900 | CA | ARG | A | 1049 | 45.903 | 37.260 | -1.334 | 1.00 | 38.07 | A | C |
| ATOM | 1901 | CB | ARG | A | 1049 | 46.426 | 38.334 | -0.385 | 1.00 | 41.00 | A | C |
| ATOM | 1902 | CG | ARG | A | 1049 | 47.138 | 37.822 | 0.848 | 1.00 | 44.03 | A | C |
| ATOM | 1903 | CD | ARG | A | 1049 | 47.472 | 38.995 | 1.746 | 1.00 | 49.13 | A | C |
| ATOM | 1904 | NE | ARG | A | 1049 | 48.367 | 38.655 | 2.849 | 1.00 | 52.70 | A | N |
| ATOM | 1905 | CZ | ARG | A | 1049 | 48.742 | 39.529 | 3.777 | 1.00 | 54.00 | A | C |
| ATOM | 1906 | NH1 | ARG | A | 1049 | 49.559 | 39.168 | 4.756 | 1.00 | 54.29 | A | N |
| ATOM | 1907 | NH2 | ARG | A | 1049 | 48.288 | 40.775 | 3.722 | 1.00 | 55.55 | A | N |
| ATOM | 1908 | C | ARG | A | 1049 | 44.845 | 36.408 | -0.616 | 1.00 | 36.85 | A | C |
| ATOM | 1909 | O | ARG | A | 1049 | 45.070 | 35.237 | -0.297 | 1.00 | 35.82 | A | O |
| ATOM | 1910 | N | LEU | A | 1050 | 43.695 | 37.022 | -0.359 | 1.00 | 33.99 | A | N |
| ATOM | 1911 | CA | LEU | A | 1050 | 42.583 | 36.357 | 0.296 | 1.00 | 33.03 | A | C |
| ATOM | 1912 | CB | LEU | A | 1050 | 41.436 | 37.352 | 0.511 | 1.00 | 31.26 | A | C |
| ATOM | 1913 | CG | LEU | A | 1050 | 40.191 | 36.791 | 1.203 | 1.00 | 31.23 | A | C |
| ATOM | 1914 | CD1 | LEU | A | 1050 | 40.584 | 36.118 | 2.516 | 1.00 | 31.70 | A | C |
| ATOM | 1915 | CD2 | LEU | A | 1050 | 39.196 | 37.891 | 1.447 | 1.00 | 27.72 | A | C |
| ATOM | 1916 | C | LEU | A | 1050 | 42.110 | 35.184 | -0.564 | 1.00 | 32.10 | A | C |
| ATOM | 1917 | O | LEU | A | 1050 | 41.851 | 34.098 | -0.050 | 1.00 | 29.58 | A | O |
| ATOM | 1918 | N | LEU | A | 1051 | 42.001 | 35.413 | -1.870 | 1.00 | 32.63 | A | N |
| ATOM | 1919 | CA | LEU | A | 1051 | 41.587 | 34.376 | -2.813 | 1.00 | 34.32 | A | C |
| ATOM | 1920 | CB | LEU | A | 1051 | 41.476 | 34.957 | -4.226 | 1.00 | 33.80 | A | C |
| ATOM | 1921 | CG | LEU | A | 1051 | 41.255 | 33.929 | -5.342 | 1.00 | 34.32 | A | C |
| ATOM | 1922 | CD1 | LEU | A | 1051 | 39.849 | 33.357 | -5.237 | 1.00 | 31.96 | A | C |
| ATOM | 1923 | CD2 | LEU | A | 1051 | 41.469 | 34.582 | -6.716 | 1.00 | 33.65 | A | C |
| ATOM | 1924 | C | LEU | A | 1051 | 42.603 | 33.233 | -2.817 | 1.00 | 34.75 | A | C |
| ATOM | 1925 | O | LEU | A | 1051 | 42.243 | 32.065 | -2.967 | 1.00 | 34.98 | A | O |
| ATOM | 1926 | N | GLU | A | 1052 | 43.875 | 33.586 | -2.663 | 1.00 | 35.72 | A | N |
| ATOM | 1927 | CA | GLU | A | 1052 | 44.958 | 32.609 | -2.631 | 1.00 | 36.23 | A | C |
| ATOM | 1928 | CB | GLU | A | 1052 | 46.304 | 33.326 | -2.548 | 1.00 | 39.64 | A | C |
| ATOM | 1929 | CG | GLU | A | 1052 | 47.475 | 32.427 | -2.167 | 1.00 | 43.74 | A | C |
| ATOM | 1930 | CD | GLU | A | 1052 | 48.809 | 33.137 | -2.295 | 1.00 | 46.95 | A | C |
| ATOM | 1931 | OE1 | GLU | A | 1052 | 49.015 | 34.155 | -1.591 | 1.00 | 48.67 | A | O |
| ATOM | 1932 | OE2 | GLU | A | 1052 | 49.644 | 32.678 | -3.106 | 1.00 | 47.66 | A | O |
| ATOM | 1933 | C | GLU | A | 1052 | 44.811 | 31.692 | -1.429 | 1.00 | 35.08 | A | C |
| ATOM | 1934 | O | GLU | A | 1052 | 45.019 | 30.487 | -1.522 | 1.00 | 33.30 | A | O |
| ATOM | 1935 | N | LEU | A | 1053 | 44.469 | 32.281 | -0.292 | 1.00 | 35.01 | A | N |
| ATOM | 1936 | CA | LEU | A | 1053 | 44.285 | 31.518 | 0.930 | 1.00 | 32.96 | A | C |
| ATOM | 1937 | CB | LEU | A | 1053 | 43.964 | 32.459 | 2.096 | 1.00 | 30.50 | A | C |
| ATOM | 1938 | CG | LEU | A | 1053 | 43.745 | 31.774 | 3.443 | 1.00 | 30.65 | A | C |
| ATOM | 1939 | CD1 | LEU | A | 1053 | 45.030 | 31.079 | 3.864 | 1.00 | 32.92 | A | C |
| ATOM | 1940 | CD2 | LEU | A | 1053 | 43.321 | 32.784 | 4.487 | 1.00 | 32.45 | A | C |
| ATOM | 1941 | C | LEU | A | 1053 | 43.144 | 30.521 | 0.743 | 1.00 | 32.04 | A | C |
| ATOM | 1942 | O | LEU | A | 1053 | 43.240 | 29.378 | 1.182 | 1.00 | 32.79 | A | O |
| ATOM | 1943 | N | LEU | A | 1054 | 42.072 | 30.958 | 0.085 | 1.00 | 31.62 | A | N |
| ATOM | 1944 | CA | LEU | A | 1054 | 40.907 | 30.105 | -0.145 | 1.00 | 31.95 | A | C |

-continued

| | | | | | | | | | | | |
|---|---|---|---|---|---|---|---|---|---|---|---|
| ATOM | 1945 | CB | LEU | A | 1054 | 39.682 | 30.957 | −0.527 | 1.00 | 30.46 | A | C |
| ATOM | 1946 | CG | LEU | A | 1054 | 39.007 | 31.743 | 0.619 | 1.00 | 28.90 | A | C |
| ATOM | 1947 | CD1 | LEU | A | 1054 | 37.990 | 32.716 | 0.083 | 1.00 | 27.05 | A | C |
| ATOM | 1948 | CD2 | LEU | A | 1054 | 38.336 | 30.776 | 1.571 | 1.00 | 28.35 | A | C |
| ATOM | 1949 | C | LEU | A | 1054 | 41.176 | 29.056 | −1.212 | 1.00 | 32.04 | A | C |
| ATOM | 1950 | O | LEU | A | 1054 | 40.636 | 27.951 | −1.152 | 1.00 | 30.77 | A | O |
| ATOM | 1951 | N | GLU | A | 1055 | 42.022 | 29.406 | −2.178 | 1.00 | 34.23 | A | N |
| ATOM | 1952 | CA | GLU | A | 1055 | 42.391 | 28.499 | −3.261 | 1.00 | 35.51 | A | C |
| ATOM | 1953 | CB | GLU | A | 1055 | 43.157 | 29.265 | −4.344 | 1.00 | 35.87 | A | C |
| ATOM | 1954 | CG | GLU | A | 1055 | 42.246 | 30.077 | −5.257 | 1.00 | 39.71 | A | C |
| ATOM | 1955 | CD | GLU | A | 1055 | 42.980 | 30.842 | −6.353 | 1.00 | 39.88 | A | C |
| ATOM | 1956 | OE1 | GLU | A | 1055 | 42.318 | 31.202 | −7.349 | 1.00 | 39.86 | A | O |
| ATOM | 1957 | OE2 | GLU | A | 1055 | 44.199 | 31.095 | −6.223 | 1.00 | 40.73 | A | O |
| ATOM | 1958 | C | GLU | A | 1055 | 43.228 | 27.321 | −2.764 | 1.00 | 36.34 | A | C |
| ATOM | 1959 | O | GLU | A | 1055 | 43.353 | 26.306 | −3.445 | 1.00 | 35.49 | A | O |
| ATOM | 1960 | N | GLU | A | 1056 | 43.799 | 27.456 | −1.575 | 1.00 | 37.58 | A | N |
| ATOM | 1961 | CA | GLU | A | 1056 | 44.615 | 26.396 | −1.014 | 1.00 | 38.62 | A | C |
| ATOM | 1962 | CB | GLU | A | 1056 | 45.799 | 26.980 | −0.239 | 1.00 | 40.75 | A | C |
| ATOM | 1963 | CG | GLU | A | 1056 | 46.638 | 27.967 | −1.050 | 1.00 | 46.03 | A | C |
| ATOM | 1964 | CD | GLU | A | 1056 | 47.817 | 28.551 | −0.266 | 1.00 | 49.39 | A | C |
| ATOM | 1965 | OE1 | GLU | A | 1056 | 47.625 | 29.026 | 0.879 | 1.00 | 50.27 | A | O |
| ATOM | 1966 | OE2 | GLU | A | 1056 | 48.944 | 28.544 | −0.812 | 1.00 | 51.90 | A | O |
| ATOM | 1967 | C | GLU | A | 1056 | 43.776 | 25.541 | −0.090 | 1.00 | 38.57 | A | C |
| ATOM | 1968 | O | GLU | A | 1056 | 44.303 | 24.669 | 0.596 | 1.00 | 39.87 | A | O |
| ATOM | 1969 | N | GLY | A | 1057 | 42.473 | 25.803 | −0.061 | 1.00 | 37.04 | A | N |
| ATOM | 1970 | CA | GLY | A | 1057 | 41.579 | 25.030 | 0.784 | 1.00 | 36.00 | A | C |
| ATOM | 1971 | C | GLY | A | 1057 | 41.388 | 25.534 | 2.203 | 1.00 | 36.34 | A | C |
| ATOM | 1972 | O | GLY | A | 1057 | 40.717 | 24.884 | 3.007 | 1.00 | 37.96 | A | O |
| ATOM | 1973 | N | GLN | A | 1058 | 41.959 | 26.691 | 2.520 | 1.00 | 34.56 | A | N |
| ATOM | 1974 | CA | GLN | A | 1058 | 41.837 | 27.261 | 3.855 | 1.00 | 33.27 | A | C |
| ATOM | 1975 | CB | GLN | A | 1058 | 42.883 | 28.358 | 4.032 | 1.00 | 34.13 | A | C |
| ATOM | 1976 | CG | GLN | A | 1058 | 44.307 | 27.852 | 3.907 | 1.00 | 35.03 | A | C |
| ATOM | 1977 | CD | GLN | A | 1058 | 44.927 | 27.530 | 5.250 | 1.00 | 36.09 | A | C |
| ATOM | 1978 | OE1 | GLN | A | 1058 | 44.310 | 26.873 | 6.087 | 1.00 | 37.42 | A | O |
| ATOM | 1979 | NE2 | GLN | A | 1058 | 46.159 | 27.989 | 5.461 | 1.00 | 35.08 | A | N |
| ATOM | 1980 | C | GLN | A | 1058 | 40.435 | 27.820 | 4.122 | 1.00 | 33.23 | A | C |
| ATOM | 1981 | O | GLN | A | 1058 | 39.807 | 28.399 | 3.236 | 1.00 | 33.08 | A | O |
| ATOM | 1982 | N | ARG | A | 1059 | 39.951 | 27.646 | 5.349 | 1.00 | 31.87 | A | N |
| ATOM | 1983 | CA | ARG | A | 1059 | 38.626 | 28.123 | 5.724 | 1.00 | 31.24 | A | C |
| ATOM | 1984 | CB | ARG | A | 1059 | 37.595 | 26.995 | 5.609 | 1.00 | 28.73 | A | C |
| ATOM | 1985 | CG | ARG | A | 1059 | 37.471 | 26.382 | 4.211 | 1.00 | 30.52 | A | C |
| ATOM | 1986 | CD | ARG | A | 1059 | 36.676 | 27.284 | 3.264 | 1.00 | 31.00 | A | C |
| ATOM | 1987 | NE | ARG | A | 1059 | 36.415 | 26.677 | 1.960 | 1.00 | 27.97 | A | N |
| ATOM | 1988 | CZ | ARG | A | 1059 | 37.266 | 26.682 | 0.936 | 1.00 | 27.94 | A | C |
| ATOM | 1989 | NH1 | ARG | A | 1059 | 38.448 | 27.265 | 1.046 | 1.00 | 24.82 | A | N |
| ATOM | 1990 | NH2 | ARG | A | 1059 | 36.934 | 26.100 | −0.210 | 1.00 | 28.85 | A | N |
| ATOM | 1991 | C | ARG | A | 1059 | 38.664 | 28.618 | 7.158 | 1.00 | 31.11 | A | C |
| ATOM | 1992 | O | ARG | A | 1059 | 39.686 | 28.523 | 7.817 | 1.00 | 31.41 | A | O |
| ATOM | 1993 | N | LEU | A | 1060 | 37.548 | 29.162 | 7.627 | 1.00 | 33.19 | A | N |
| ATOM | 1994 | CA | LEU | A | 1060 | 37.441 | 29.660 | 8.987 | 1.00 | 34.25 | A | C |
| ATOM | 1995 | CB | LEU | A | 1060 | 36.165 | 30.477 | 9.142 | 1.00 | 32.03 | A | C |
| ATOM | 1996 | CG | LEU | A | 1060 | 36.057 | 31.822 | 8.416 | 1.00 | 34.02 | A | C |
| ATOM | 1997 | CD1 | LEU | A | 1060 | 34.688 | 32.454 | 8.726 | 1.00 | 32.53 | A | C |
| ATOM | 1998 | CD2 | LEU | A | 1060 | 37.182 | 32.749 | 8.854 | 1.00 | 30.27 | A | C |
| ATOM | 1999 | C | LEU | A | 1060 | 37.413 | 28.517 | 9.998 | 1.00 | 36.03 | A | C |
| ATOM | 2000 | O | LEU | A | 1060 | 36.772 | 27.495 | 9.769 | 1.00 | 36.83 | A | O |
| ATOM | 2001 | N | PRO | A | 1061 | 38.112 | 28.678 | 11.132 | 1.00 | 37.96 | A | N |
| ATOM | 2002 | CD | PRO | A | 1061 | 38.966 | 29.821 | 11.495 | 1.00 | 37.87 | A | C |
| ATOM | 2003 | CA | PRO | A | 1061 | 38.153 | 27.652 | 12.180 | 1.00 | 39.04 | A | C |
| ATOM | 2004 | CB | PRO | A | 1061 | 39.247 | 28.154 | 13.110 | 1.00 | 38.27 | A | C |
| ATOM | 2005 | CG | PRO | A | 1061 | 39.108 | 29.640 | 12.998 | 1.00 | 38.72 | A | C |
| ATOM | 2006 | C | PRO | A | 1061 | 36.821 | 27.544 | 12.907 | 1.00 | 41.03 | A | C |
| ATOM | 2007 | O | PRO | A | 1061 | 36.318 | 28.537 | 13.428 | 1.00 | 44.44 | A | O |
| ATOM | 2008 | N | ALA | A | 1062 | 36.264 | 26.337 | 12.943 | 1.00 | 41.14 | A | N |
| ATOM | 2009 | CA | ALA | A | 1062 | 34.997 | 26.075 | 13.615 | 1.00 | 41.14 | A | C |
| ATOM | 2010 | CB | ALA | A | 1062 | 34.888 | 24.596 | 13.941 | 1.00 | 40.50 | A | C |
| ATOM | 2011 | C | ALA | A | 1062 | 34.867 | 26.890 | 14.894 | 1.00 | 41.04 | A | C |
| ATOM | 2012 | O | ALA | A | 1062 | 35.752 | 26.870 | 15.744 | 1.00 | 42.44 | A | O |
| ATOM | 2013 | N | PRO | A | 1063 | 33.759 | 27.627 | 15.044 | 1.00 | 40.13 | A | N |
| ATOM | 2014 | CD | PRO | A | 1063 | 32.615 | 27.790 | 14.130 | 1.00 | 37.87 | A | C |
| ATOM | 2015 | CA | PRO | A | 1063 | 33.586 | 28.426 | 16.257 | 1.00 | 41.05 | A | C |
| ATOM | 2016 | CB | PRO | A | 1063 | 32.262 | 29.153 | 16.003 | 1.00 | 38.84 | A | C |
| ATOM | 2017 | CG | PRO | A | 1063 | 31.540 | 28.242 | 15.057 | 1.00 | 38.22 | A | C |
| ATOM | 2018 | C | PRO | A | 1063 | 33.584 | 27.547 | 17.518 | 1.00 | 42.11 | A | C |
| ATOM | 2019 | O | PRO | A | 1063 | 33.066 | 26.431 | 17.513 | 1.00 | 41.67 | A | O |
| ATOM | 2020 | N | PRO | A | 1064 | 34.190 | 28.045 | 18.607 | 1.00 | 43.41 | A | N |
| ATOM | 2021 | CD | PRO | A | 1064 | 34.900 | 29.335 | 18.645 | 1.00 | 42.90 | A | C |
| ATOM | 2022 | CA | PRO | A | 1064 | 34.301 | 27.363 | 19.902 | 1.00 | 43.90 | A | C |
| ATOM | 2023 | CB | PRO | A | 1064 | 34.942 | 28.425 | 20.794 | 1.00 | 42.85 | A | C |
| ATOM | 2024 | CG | PRO | A | 1064 | 35.826 | 29.152 | 19.838 | 1.00 | 42.18 | A | C |

| | | | | | -continued | | | | | | |
|---|---|---|---|---|---|---|---|---|---|---|---|
| ATOM | 2025 | C | PRO | A | 1064 | 32.986 | 26.853 | 20.475 | 1.00 | 44.26 | A | C |
| ATOM | 2026 | O | PRO | A | 1064 | 32.100 | 27.641 | 20.809 | 1.00 | 45.70 | A | O |
| ATOM | 2027 | N | ALA | A | 1065 | 32.879 | 25.530 | 20.589 | 1.00 | 43.97 | A | N |
| ATOM | 2028 | CA | ALA | A | 1065 | 31.699 | 24.866 | 21.141 | 1.00 | 44.07 | A | C |
| ATOM | 2029 | CB | ALA | A | 1065 | 31.305 | 25.523 | 22.459 | 1.00 | 42.97 | A | C |
| ATOM | 2030 | C | ALA | A | 1065 | 30.508 | 24.854 | 20.187 | 1.00 | 44.37 | A | C |
| ATOM | 2031 | O | ALA | A | 1065 | 29.356 | 24.964 | 20.611 | 1.00 | 45.07 | A | O |
| ATOM | 2032 | N | CYS | A | 1066 | 30.784 | 24.706 | 18.900 | 1.00 | 43.46 | A | N |
| ATOM | 2033 | CA | CYS | A | 1066 | 29.723 | 24.696 | 17.909 | 1.00 | 43.03 | A | C |
| ATOM | 2034 | CB | CYS | A | 1066 | 30.255 | 25.251 | 16.582 | 1.00 | 43.32 | A | C |
| ATOM | 2035 | SG | CYS | A | 1066 | 28.994 | 25.547 | 15.320 | 1.00 | 45.07 | A | S |
| ATOM | 2036 | C | CYS | A | 1066 | 29.188 | 23.284 | 17.714 | 1.00 | 42.43 | A | C |
| ATOM | 2037 | O | CYS | A | 1066 | 29.952 | 22.318 | 17.665 | 1.00 | 42.66 | A | O |
| ATOM | 2038 | N | PRO | A | 1067 | 27.860 | 23.144 | 17.616 | 1.00 | 40.86 | A | N |
| ATOM | 2039 | CD | PRO | A | 1067 | 26.841 | 24.185 | 17.802 | 1.00 | 40.79 | A | C |
| ATOM | 2040 | CA | PRO | A | 1067 | 27.236 | 21.834 | 17.423 | 1.00 | 40.84 | A | C |
| ATOM | 2041 | CB | PRO | A | 1067 | 25.766 | 22.185 | 17.246 | 1.00 | 41.20 | A | C |
| ATOM | 2042 | CG | PRO | A | 1067 | 25.617 | 23.370 | 18.152 | 1.00 | 40.13 | A | C |
| ATOM | 2043 | C | PRO | A | 1067 | 27.831 | 21.147 | 16.200 | 1.00 | 40.94 | A | C |
| ATOM | 2044 | O | PRO | A | 1067 | 27.826 | 21.700 | 15.096 | 1.00 | 42.30 | A | O |
| ATOM | 2045 | N | ALA | A | 1068 | 28.351 | 19.943 | 16.409 | 1.00 | 39.79 | A | N |
| ATOM | 2046 | CA | ALA | A | 1068 | 28.977 | 19.168 | 15.344 | 1.00 | 39.39 | A | C |
| ATOM | 2047 | CB | ALA | A | 1068 | 29.105 | 17.706 | 15.779 | 1.00 | 37.82 | A | C |
| ATOM | 2048 | C | ALA | A | 1068 | 28.261 | 19.254 | 13.993 | 1.00 | 38.42 | A | C |
| ATOM | 2049 | O | ALA | A | 1068 | 28.881 | 19.558 | 12.970 | 1.00 | 36.38 | A | O |
| ATOM | 2050 | N | GLU | A | 1069 | 26.959 | 18.985 | 13.992 | 1.00 | 38.56 | A | N |
| ATOM | 2051 | CA | GLU | A | 1069 | 26.185 | 19.013 | 12.761 | 1.00 | 40.94 | A | C |
| ATOM | 2052 | CB | GLU | A | 1069 | 24.825 | 18.344 | 12.980 | 1.00 | 43.16 | A | C |
| ATOM | 2053 | CG | GLU | A | 1069 | 24.115 | 18.787 | 14.246 | 1.00 | 48.31 | A | C |
| ATOM | 2054 | CD | GLU | A | 1069 | 24.606 | 18.064 | 15.490 | 1.00 | 48.90 | A | C |
| ATOM | 2055 | OE1 | GLU | A | 1069 | 24.303 | 16.860 | 15.636 | 1.00 | 48.25 | A | O |
| ATOM | 2056 | OE2 | GLU | A | 1069 | 25.291 | 18.704 | 16.318 | 1.00 | 50.20 | A | O |
| ATOM | 2057 | C | GLU | A | 1069 | 26.004 | 20.416 | 12.170 | 1.00 | 40.52 | A | C |
| ATOM | 2058 | O | GLU | A | 1069 | 25.711 | 20.561 | 10.984 | 1.00 | 40.07 | A | O |
| ATOM | 2059 | N | VAL | A | 1070 | 26.182 | 21.447 | 12.990 | 1.00 | 39.74 | A | N |
| ATOM | 2060 | CA | VAL | A | 1070 | 26.056 | 22.822 | 12.511 | 1.00 | 39.24 | A | C |
| ATOM | 2061 | CB | VAL | A | 1070 | 25.897 | 23.811 | 13.679 | 1.00 | 39.84 | A | C |
| ATOM | 2062 | CG1 | VAL | A | 1070 | 26.045 | 25.229 | 13.167 | 1.00 | 41.40 | A | C |
| ATOM | 2063 | CG2 | VAL | A | 1070 | 24.542 | 23.633 | 14.337 | 1.00 | 40.18 | A | C |
| ATOM | 2064 | C | VAL | A | 1070 | 27.307 | 23.207 | 11.715 | 1.00 | 38.46 | A | C |
| ATOM | 2065 | O | VAL | A | 1070 | 27.232 | 23.876 | 10.683 | 1.00 | 35.39 | A | O |
| ATOM | 2066 | N | HIS | A | 1071 | 28.461 | 22.774 | 12.211 | 1.00 | 39.05 | A | N |
| ATOM | 2067 | CA | HIS | A | 1071 | 29.731 | 23.049 | 11.561 | 1.00 | 38.75 | A | C |
| ATOM | 2068 | CB | HIS | A | 1071 | 30.880 | 22.686 | 12.506 | 1.00 | 39.65 | A | C |
| ATOM | 2069 | CG | HIS | A | 1071 | 32.235 | 22.962 | 11.939 | 1.00 | 40.75 | A | C |
| ATOM | 2070 | CD2 | HIS | A | 1071 | 33.282 | 22.138 | 11.693 | 1.00 | 41.51 | A | C |
| ATOM | 2071 | ND1 | HIS | A | 1071 | 32.618 | 24.212 | 11.508 | 1.00 | 42.40 | A | N |
| ATOM | 2072 | CE1 | HIS | A | 1071 | 33.843 | 24.147 | 11.014 | 1.00 | 42.63 | A | C |
| ATOM | 2073 | NE2 | HIS | A | 1071 | 34.267 | 22.900 | 11.115 | 1.00 | 43.15 | A | N |
| ATOM | 2074 | C | HIS | A | 1071 | 29.847 | 22.265 | 10.248 | 1.00 | 38.96 | A | C |
| ATOM | 2075 | O | HIS | A | 1071 | 30.521 | 22.696 | 9.308 | 1.00 | 38.24 | A | O |
| ATOM | 2076 | N | GLU | A | 1072 | 29.176 | 21.119 | 10.172 | 1.00 | 38.32 | A | N |
| ATOM | 2077 | CA | GLU | A | 1072 | 29.233 | 20.318 | 8.955 | 1.00 | 39.59 | A | C |
| ATOM | 2078 | CB | GLU | A | 1072 | 28.687 | 18.914 | 9.213 | 1.00 | 44.08 | A | C |
| ATOM | 2079 | CG | GLU | A | 1072 | 29.130 | 17.901 | 8.180 | 1.00 | 49.99 | A | C |
| ATOM | 2080 | CD | GLU | A | 1072 | 29.125 | 16.493 | 8.735 | 1.00 | 55.49 | A | C |
| ATOM | 2081 | OE1 | GLU | A | 1072 | 28.020 | 15.960 | 8.998 | 1.00 | 57.05 | A | O |
| ATOM | 2082 | OE2 | GLU | A | 1072 | 30.231 | 15.930 | 8.919 | 1.00 | 57.75 | A | O |
| ATOM | 2083 | C | GLU | A | 1072 | 28.458 | 20.9V5 | 7.814 | 1.00 | 37.22 | A | C |
| ATOM | 2084 | O | GLU | A | 1072 | 28.882 | 20.927 | 6.657 | 1.00 | 36.12 | A | O |
| ATOM | 2085 | N | LEU | A | 1073 | 27.324 | 21.586 | 8.146 | 1.00 | 34.76 | A | N |
| ATOM | 2086 | CA | LEU | A | 1073 | 26.502 | 22.270 | 7.156 | 1.00 | 34.30 | A | C |
| ATOM | 2087 | CB | LEU | A | 1073 | 25.197 | 22.783 | 7.793 | 1.00 | 33.32 | A | C |
| ATOM | 2088 | CG | LEU | A | 1073 | 24.188 | 21.723 | 8.263 | 1.00 | 32.92 | A | C |
| ATOM | 2089 | CD1 | LEU | A | 1073 | 22.954 | 22.376 | 8.870 | 1.00 | 32.52 | A | C |
| ATOM | 2090 | CD2 | LEU | A | 1073 | 23.802 | 20.851 | 7.070 | 1.00 | 32.45 | A | C |
| ATOM | 2091 | C | LEU | A | 1073 | 27.281 | 23.444 | 6.557 | 1.00 | 34.69 | A | C |
| ATOM | 2092 | O | LEU | A | 1073 | 27.421 | 23.569 | 5.347 | 1.00 | 34.74 | A | O |
| ATOM | 2093 | N | MET | A | 1074 | 27.806 | 24.298 | 7.437 | 1.00 | 34.59 | A | N |
| ATOM | 2094 | CA | MET | A | 1074 | 28.549 | 25.441 | 6.961 | 1.00 | 33.88 | A | C |
| ATOM | 2095 | CB | MET | A | 1074 | 28.911 | 26.381 | 8.113 | 1.00 | 33.70 | A | C |
| ATOM | 2096 | CG | MET | A | 1074 | 30.006 | 25.915 | 9.028 | 1.00 | 32.46 | A | C |
| ATOM | 2097 | SD | MET | A | 1074 | 30.443 | 27.221 | 10.202 | 1.00 | 30.20 | A | S |
| ATOM | 2098 | CE | MET | A | 1074 | 28.953 | 27.318 | 11.178 | 1.00 | 24.80 | A | C |
| ATOM | 2099 | C | MET | A | 1074 | 29.790 | 24.960 | 6.245 | 1.00 | 34.28 | A | C |
| ATOM | 2100 | O | MET | A | 1074 | 30.260 | 25.598 | 5.309 | 1.00 | 36.55 | A | O |
| ATOM | 2101 | N | LYS | A | 1075 | 30.313 | 23.818 | 6.672 | 1.00 | 33.90 | A | N |
| ATOM | 2102 | CA | LYS | A | 1075 | 31.498 | 23.258 | 6.034 | 1.00 | 33.51 | A | C |
| ATOM | 2103 | CB | LYS | A | 1075 | 31.914 | 21.970 | 6.742 | 1.00 | 35.85 | A | C |
| ATOM | 2104 | CG | LYS | A | 1075 | 33.385 | 21.659 | 6.671 | 1.00 | 35.71 | A | C |

-continued

| | | | | | | | | | | | |
|---|---|---|---|---|---|---|---|---|---|---|---|
| ATOM | 2105 | CD | LYS | A | 1075 | 34.094 | 22.141 | 7.929 | 1.00 | 37.92 | A C |
| ATOM | 2106 | CE | LYS | A | 1075 | 35.611 | 22.142 | 7.732 | 1.00 | 39.92 | A C |
| ATOM | 2107 | NZ | LYS | A | 1075 | 36.041 | 23.064 | 6.618 | 1.00 | 37.97 | A N |
| ATOM | 2108 | C | LYS | A | 1075 | 31.150 | 22.954 | 4.572 | 1.00 | 32.67 | A C |
| ATOM | 2109 | O | LYS | A | 1075 | 31.969 | 23.147 | 3.688 | 1.00 | 34.17 | A O |
| ATOM | 2110 | N | LEU | A | 1076 | 29.926 | 22.476 | 4.340 | 1.00 | 30.61 | A N |
| ATOM | 2111 | CA | LEU | A | 1076 | 29.419 | 22.154 | 3.004 | 1.00 | 28.22 | A C |
| ATOM | 2112 | CB | LEU | A | 1076 | 28.101 | 21.389 | 3.127 | 1.00 | 27.15 | A C |
| ATOM | 2113 | CG | LEU | A | 1076 | 28.083 | 20.006 | 3.787 | 1.00 | 27.60 | A C |
| ATOM | 2114 | CD1 | LEU | A | 1076 | 26.637 | 19.545 | 3.999 | 1.00 | 25.25 | A C |
| ATOM | 2115 | CD2 | LEU | A | 1076 | 28.831 | 19.031 | 2.911 | 1.00 | 24.89 | A C |
| ATOM | 2116 | C | LEU | A | 1076 | 29.175 | 23.409 | 2.147 | 1.00 | 28.61 | A C |
| ATOM | 2117 | O | LEU | A | 1076 | 29.316 | 23.383 | 0.923 | 1.00 | 27.41 | A O |
| ATOM | 2118 | N | CYS | A | 1077 | 28.785 | 24.502 | 2.796 | 1.00 | 26.68 | A N |
| ATOM | 2119 | CA | CYS | A | 1077 | 28.529 | 25.746 | 2.088 | 1.00 | 24.29 | A C |
| ATOM | 2120 | CB | CYS | A | 1077 | 27.953 | 26.794 | 3.032 | 1.00 | 21.98 | A C |
| ATOM | 2121 | SG | CYS | A | 1077 | 26.297 | 26.455 | 3.616 | 1.00 | 19.81 | A S |
| ATOM | 2122 | C | CYS | A | 1077 | 29.798 | 26.301 | 1.476 | 1.00 | 24.04 | A C |
| ATOM | 2123 | O | CYS | A | 1077 | 29.738 | 27.048 | 0.500 | 1.00 | 23.84 | A O |
| ATOM | 2124 | N | TRP | A | 1078 | 30.951 | 25.940 | 2.042 | 1.00 | 24.55 | A N |
| ATOM | 2125 | CA | TRP | A | 1078 | 32.224 | 26.450 | 1.529 | 1.00 | 23.47 | A C |
| ATOM | 2126 | CB | TRP | A | 1078 | 33.164 | 26.849 | 2.670 | 1.00 | 24.02 | A C |
| ATOM | 2127 | CG | TRP | A | 1078 | 32.570 | 27.812 | 3.646 | 1.00 | 23.46 | A C |
| ATOM | 2128 | CD2 | TRP | A | 1078 | 32.859 | 27.895 | 5.042 | 1.00 | 23.76 | A C |
| ATOM | 2129 | CE2 | TRP | A | 1078 | 32.073 | 28.943 | 5.571 | 1.00 | 23.34 | A C |
| ATOM | 2130 | CE3 | TRP | A | 1078 | 33.705 | 27.183 | 5.901 | 1.00 | 21.71 | A C |
| ATOM | 2131 | CD1 | TRP | A | 1078 | 31.651 | 28.789 | 3.386 | 1.00 | 24.07 | A C |
| ATOM | 2132 | NE1 | TRP | A | 1078 | 31.344 | 29.472 | 4.537 | 1.00 | 24.54 | A N |
| ATOM | 2133 | CZ2 | TRP | A | 1078 | 32.107 | 29.300 | 6.916 | 1.00 | 21.87 | A C |
| ATOM | 2134 | CZ3 | TRP | A | 1078 | 33.73? | 27.538 | 7.235 | 1.00 | 22.31 | A C |
| ATOM | 2135 | CH2 | TRP | A | 1078 | 32.942 | 28.587 | 7.730 | 1.00 | 22.33 | A C |
| ATOM | 2136 | C | TRP | A | 1078 | 32.962 | 25.514 | 0.594 | 1.00 | 23.07 | A C |
| ATOM | 2137 | O | TRP | A | 1078 | 34.191 | 25.455 | 0.609 | 1.00 | 21.26 | A O |
| ATOM | 2138 | N | ALA | A | 1079 | 32.216 | 24.790 | −0.229 | 1.00 | 24.72 | A N |
| ATOM | 2139 | CA | ALA | A | 1079 | 32.837 | 23.889 | −1.190 | 1.00 | 26.31 | A C |
| ATOM | 2140 | CB | ALA | A | 1079 | 31.791 | 22.931 | −1.788 | 1.00 | 25.35 | A C |
| ATOM | 2141 | C | ALA | A | 1079 | 33.421 | 24.768 | −2.281 | 1.00 | 26.85 | A C |
| ATOM | 2142 | O | ALA | A | 1079 | 32.825 | 25.766 | −2.669 | 1.00 | 25.36 | A O |
| ATOM | 2143 | N | PRO | A | 1080 | 34.602 | 24.410 | −2.791 | 1.00 | 28.40 | A N |
| ATOM | 2144 | CD | PRO | A | 1080 | 35.464 | 23.286 | −2.388 | 1.00 | 27.17 | A C |
| ATOM | 2145 | CA | PRO | A | 1080 | 35.228 | 25.207 | −3.848 | 1.00 | 29.11 | A C |
| ATOM | 2146 | CB | PRO | A | 1080 | 36.371 | 24.318 | −4.318 | 1.00 | 27.39 | A C |
| ATOM | 2147 | CG | PRO | A | 1080 | 36.780 | 23.622 | −3.072 | 1.00 | 27.10 | A C |
| ATOM | 2148 | C | PRO | A | 1080 | 34.263 | 25.547 | −4.979 | 1.00 | 30.79 | A C |
| ATOM | 2149 | O | PRO | A | 1080 | 33.973 | 26.716 | −5.219 | 1.00 | 32.38 | A O |
| ATOM | 2150 | N | SER | A | 1081 | 33.767 | 24.521 | −5.667 | 1.00 | 31.66 | A N |
| ATOM | 2151 | CA | SER | A | 1081 | 32.851 | 24.716 | −6.791 | 1.00 | 31.24 | A C |
| ATOM | 2152 | CB | SER | A | 1081 | 32.873 | 23.504 | −7.724 | 1.00 | 35.04 | A C |
| ATOM | 2153 | OG | SER | A | 1081 | 32.003 | 23.698 | −8.829 | 1.00 | 39.04 | A O |
| ATOM | 2154 | C | SER | A | 1081 | 31.427 | 24.958 | −6.345 | 1.00 | 28.44 | A C |
| ATOM | 2155 | O | SER | A | 1081 | 30.903 | 24.244 | −5.494 | 1.00 | 28.65 | A O |
| ATOM | 2156 | N | PRO | A | 1082 | 30.775 | 25.968 | −6.939 | 1.00 | 26.44 | A N |
| ATOM | 2157 | CD | PRO | A | 1082 | 31.403 | 26.880 | −7.908 | 1.00 | 25.21 | A C |
| ATOM | 2158 | CA | PRO | A | 1082 | 29.397 | 26.383 | −6.667 | 1.00 | 26.31 | A C |
| ATOM | 2159 | CB | PRO | A | 1082 | 29.188 | 27.519 | −7.655 | 1.00 | 23.89 | A C |
| ATOM | 2160 | CG | PRO | A | 1082 | 30.552 | 28.100 | −7.783 | 1.00 | 24.30 | A C |
| ATOM | 2161 | C | PRO | A | 1082 | 28.376 | 25.264 | −6.852 | 1.00 | 28.12 | A C |
| ATOM | 2162 | O | PRO | A | 1082 | 27.398 | 25.176 | −6.113 | 1.00 | 28.72 | A O |
| ATOM | 2163 | N | GLN | A | 1083 | 28.604 | 24.409 | −7.839 | 1.00 | 28.62 | A N |
| ATOM | 2164 | CA | GLN | A | 1083 | 27.691 | 23.315 | −8.095 | 1.00 | 31.77 | A C |
| ATOM | 2165 | CB | GLN | A | 1083 | 27.953 | 22.722 | −9.477 | 1.00 | 36.51 | A C |
| ATOM | 2166 | CG | GLN | A | 1083 | 29.425 | 22.603 | −9.827 | 1.00 | 43.60 | A C |
| ATOM | 2167 | CD | GLN | A | 1083 | 29.670 | 21.625 | −10.960 | 1.00 | 48.06 | A C |
| ATOM | 2168 | OE1 | GLN | A | 1083 | 29.004 | 21.683 | −11.997 | 1.00 | 50.45 | A O |
| ATOM | 2169 | NE2 | GLN | A | 1083 | 30.633 | 20.721 | −10.771 | 1.00 | 50.35 | A N |
| ATOM | 2170 | C | GLN | A | 1083 | 27.805 | 22.227 | −7.040 | 1.00 | 31.92 | A C |
| ATOM | 2171 | O | GLN | A | 1083 | 27.016 | 21.289 | −7.031 | 1.00 | 30.95 | A O |
| ATOM | 2172 | N | ASP | A | 1084 | 28.775 | 22.350 | −6.141 | 1.00 | 33.65 | A N |
| ATOM | 2173 | CA | ASP | A | 1084 | 28.944 | 21.336 | −5.101 | 1.00 | 35.56 | A C |
| ATOM | 2174 | CB | ASP | A | 1084 | 30.420 | 20.927 | −4.989 | 1.00 | 37.26 | A C |
| ATOM | 2175 | CG | ASP | A | 1084 | 30.863 | 19.995 | −6.113 | 1.00 | 37.96 | A C |
| ATOM | 2176 | OD1 | ASP | A | 1084 | 32.049 | 20.052 | −6.502 | 1.00 | 39.77 | A O |
| ATOM | 2177 | OD2 | ASP | A | 1084 | 30.037 | 19.196 | −6.598 | 1.00 | 38.93 | A O |
| ATOM | 2178 | C | ASP | A | 1084 | 28.406 | 21.769 | −3.733 | 1.00 | 34.87 | A C |
| ATOM | 2179 | O | ASP | A | 1084 | 28.311 | 20.954 | −2.813 | 1.00 | 33.98 | A O |
| ATOM | 2180 | N | ARG | A | 1085 | 28.057 | 23.049 | −3.600 | 1.00 | 32.96 | A N |
| ATOM | 2181 | CA | ARG | A | 1085 | 27.509 | 23.557 | −2.343 | 1.00 | 29.33 | A C |
| ATOM | 2182 | CB | ARG | A | 1085 | 27.624 | 25.072 | −2.275 | 1.00 | 25.99 | A C |
| ATOM | 2183 | CG | ARG | A | 1085 | 29.028 | 25.556 | −2.474 | 1.00 | 25.88 | A C |
| ATOM | 2184 | CD | ARG | A | 1085 | 29.052 | 27.026 | −2.784 | 1.00 | 25.19 | A C |

-continued

| | | | | | | | | | | | |
|---|---|---|---|---|---|---|---|---|---|---|---|
| ATOM | 2185 | NE | ARG | A | 1085 | 30.372 | 27.424 | −3.241 | 1.00 | 22.90 | A | N |
| ATOM | 2186 | CZ | ARG | A | 1085 | 30.617 | 28.516 | −3.949 | 1.00 | 23.32 | A | C |
| ATOM | 2187 | NH1 | ARG | A | 1085 | 29.616 | 29.330 | −4.282 | 1.00 | 20.28 | A | N |
| ATOM | 2188 | NH2 | ARG | A | 1085 | 31.862 | 28.770 | −4.341 | 1.00 | 22.67 | A | N |
| ATOM | 2189 | C | ARG | A | 1085 | 26.051 | 23.183 | −2.325 | 1.00 | 29.39 | A | C |
| ATOM | 2190 | O | ARG | A | 1085 | 25.404 | 23.136 | −3.369 | 1.00 | 30.36 | A | O |
| ATOM | 2191 | N | PRO | A | 1086 | 25.508 | 22.908 | −1.139 | 1.00 | 29.52 | A | N |
| ATOM | 2192 | CD | PRO | A | 1086 | 26.123 | 22.945 | 0.198 | 1.00 | 27.74 | A | C |
| ATOM | 2193 | CA | PRO | A | 1086 | 24.097 | 22.541 | −1.064 | 1.00 | 29.00 | A | C |
| ATOM | 2194 | CB | PRO | A | 1086 | 23.946 | 22.070 | 0.375 | 1.00 | 29.16 | A | C |
| ATOM | 2195 | CG | PRO | A | 1086 | 24.918 | 22.947 | 1.101 | 1.00 | 29.76 | A | C |
| ATOM | 2196 | C | PRO | A | 1086 | 23.218 | 23.742 | −1.373 | 1.00 | 29.28 | A | C |
| ATOM | 2197 | O | PRO | A | 1086 | 23.659 | 24.884 | −1.287 | 1.00 | 30.82 | A | O |
| ATOM | 2198 | N | SER | A | 1087 | 21.976 | 23.475 | −1.744 | 1.00 | 28.64 | A | N |
| ATOM | 2199 | CA | SER | A | 1087 | 21.040 | 24.538 | −2.048 | 1.00 | 29.08 | A | C |
| ATOM | 2200 | CB | SER | A | 1087 | 19.990 | 24.048 | −3.055 | 1.00 | 26.07 | A | C |
| ATOM | 2201 | OG | SER | A | 1087 | 18.954 | 23.323 | −2.414 | 1.00 | 28.14 | A | O |
| ATOM | 2202 | C | SER | A | 1087 | 20.371 | 24.936 | −0.723 | 1.00 | 29.13 | A | C |
| ATOM | 2203 | O | SER | A | 1087 | 20.535 | 24.255 | 0.292 | 1.00 | 30.28 | A | O |
| ATOM | 2204 | N | PHE | A | 1088 | 19.631 | 26.039 | −0.727 | 1.00 | 27.78 | A | N |
| ATOM | 2205 | CA | PHE | A | 1088 | 18.958 | 26.480 | 0.476 | 1.00 | 27.90 | A | C |
| ATOM | 2206 | CB | PHE | A | 1088 | 18.426 | 27.906 | 0.289 | 1.00 | 27.36 | A | C |
| ATOM | 2207 | CG | PHE | A | 1088 | 19.481 | 28.974 | 0.431 | 1.00 | 28.07 | A | C |
| ATOM | 2208 | CD1 | PHE | A | 1088 | 19.957 | 29.337 | 1.690 | 1.00 | 25.93 | A | C |
| ATOM | 2209 | CD2 | PHE | A | 1088 | 20.032 | 29.586 | −0.696 | 1.00 | 25.71 | A | C |
| ATOM | 2210 | CE1 | PHE | A | 1088 | 20.960 | 30.285 | 1.816 | 1.00 | 25.98 | A | C |
| ATOM | 2211 | CE2 | PHE | A | 1088 | 21.035 | 30.532 | −0.580 | 1.00 | 24.01 | A | C |
| ATOM | 2212 | CZ | PHE | A | 1088 | 21.504 | 30.884 | 0.675 | 1.00 | 24.15 | A | C |
| ATOM | 2213 | C | PHE | A | 1088 | 17.813 | 25.527 | 0.B09 | 1.00 | 29.45 | A | C |
| ATOM | 2214 | O | PHE | A | 1088 | 17.482 | 25.321 | 1.976 | 1.00 | 30.46 | A | O |
| ATOM | 2215 | N | SER | A | 1089 | 17.217 | 24.930 | −0.216 | 1.00 | 29.59 | A | N |
| ATOM | 2216 | CA | SER | A | 1089 | 16.099 | 24.025 | 0.007 | 1.00 | 30.75 | A | C |
| ATOM | 2217 | CB | SER | A | 1089 | 15.436 | 23.665 | −1.315 | 1.00 | 30.39 | A | C |
| ATOM | 2218 | OG | SER | A | 1089 | 16.272 | 22.786 | −2.037 | 1.00 | 34.77 | A | O |
| ATOM | 2219 | C | SER | A | 1089 | 16.581 | 22.758 | 0.698 | 1.00 | 31.30 | A | C |
| ATOM | 2220 | O | SER | A | 1089 | 15.834 | 22.117 | 1.439 | 1.00 | 30.83 | A | O |
| ATOM | 2221 | N | ALA | A | 1090 | 17.837 | 22.405 | 0.445 | 1.00 | 31.74 | A | N |
| ATOM | 2222 | CA | ALA | A | 1090 | 18.444 | 21.227 | 1.056 | 1.00 | 33.23 | A | C |
| ATOM | 2223 | CB | ALA | A | 1090 | 19.648 | 20.771 | 0.228 | 1.00 | 32.69 | A | C |
| ATOM | 2224 | C | ALA | A | 1090 | 18.874 | 21.507 | 2.505 | 1.00 | 33.07 | A | C |
| ATOM | 2225 | O | ALA | A | 1090 | 18.610 | 20.710 | 3.399 | 1.00 | 33.17 | A | O |
| ATOM | 2226 | N | LEU | A | 1091 | 19.524 | 22.644 | 2.740 | 1.00 | 33.22 | A | N |
| ATOM | 2227 | CA | LEU | A | 1091 | 19.979 | 22.993 | 4.089 | 1.00 | 33.26 | A | C |
| ATOM | 2228 | CB | LEU | A | 1091 | 20.848 | 24.252 | 4.044 | 1.00 | 31.95 | A | C |
| ATOM | 2229 | CG | LEU | A | 1091 | 22.176 | 24.091 | 3.305 | 1.00 | 31.49 | A | C |
| ATOM | 2230 | CD1 | LEU | A | 1091 | 22.732 | 25.436 | 2.893 | 1.00 | 29.88 | A | C |
| ATOM | 2231 | CD2 | LEU | A | 1091 | 23.146 | 23.352 | 4.208 | 1.00 | 32.95 | A | C |
| ATOM | 2232 | C | LEU | A | 1091 | 18.819 | 23.219 | 5.047 | 1.00 | 33.65 | A | C |
| ATOM | 2233 | O | LEU | A | 1091 | 18.876 | 22.810 | 6.210 | 1.00 | 33.75 | A | O |
| ATOM | 2234 | N | GLY | A | 1092 | 17.771 | 23.869 | 4.545 | 1.00 | 33.60 | A | N |
| ATOM | 2235 | CA | GLY | A | 1092 | 16.597 | 24.172 | 5.350 | 1.00 | 33.92 | A | C |
| ATOM | 2236 | C | GLY | A | 1092 | 16.140 | 23.084 | 6.307 | 1.00 | 35.32 | A | C |
| ATOM | 2237 | O | GLY | A | 1092 | 16.383 | 23.174 | 7.514 | 1.00 | 33.70 | A | O |
| ATOM | 2238 | N | PRO | A | 1093 | 15.463 | 22.042 | 5.798 | 1.00 | 35.60 | A | N |
| ATOM | 2239 | CD | PRO | A | 1093 | 15.256 | 21.731 | 4.376 | 1.00 | 36.28 | A | C |
| ATOM | 2240 | CA | PRO | A | 1093 | 14.985 | 20.949 | 6.646 | 1.00 | 37.04 | A | C |
| ATOM | 2241 | CB | PRO | A | 1093 | 14.523 | 19.899 | 5.633 | 1.00 | 37.68 | A | C |
| ATOM | 2242 | CG | PRO | A | 1093 | 15.311 | 20.234 | 4.383 | 1.00 | 37.09 | A | C |
| ATOM | 2243 | C | PRO | A | 1093 | 16.056 | 20.441 | 7.610 | 1.00 | 38.12 | A | C |
| ATOM | 2244 | O | PRO | A | 1093 | 15.751 | 20.082 | 8.750 | 1.00 | 38.30 | A | O |
| ATOM | 2245 | N | GLN | A | 1094 | 17.309 | 20.417 | 7.155 | 1.00 | 38.45 | A | N |
| ATOM | 2246 | CA | GLN | A | 1094 | 18.422 | 19.992 | 8.004 | 1.00 | 38.71 | A | C |
| ATOM | 2247 | CB | GLN | A | 1094 | 19.751 | 20.139 | 7.264 | 1.00 | 39.86 | A | C |
| ATOM | 2248 | CG | GLN | A | 1094 | 20.135 | 18.928 | 6.425 | 1.00 | 43.63 | A | C |
| ATOM | 2249 | CD | GLN | A | 1094 | 20.575 | 17.740 | 7.275 | 1.00 | 46.77 | A | C |
| ATOM | 2250 | OE1 | GLN | A | 1094 | 19.800 | 17.213 | 8.083 | 1.00 | 45.34 | A | O |
| ATOM | 2251 | NE2 | GLN | A | 1094 | 21.831 | 17.317 | 7.100 | 1.00 | 46.94 | A | N |
| ATOM | 2252 | C | GLN | A | 1094 | 18.442 | 20.850 | 9.268 | 1.00 | 39.49 | A | C |
| ATOM | 2253 | O | GLN | A | 1094 | 18.443 | 20.331 | 10.385 | 1.00 | 39.14 | A | O |
| ATOM | 2254 | N | LEU | A | 1095 | 18.446 | 22.168 | 9.087 | 1.00 | 40.38 | A | N |
| ATOM | 2255 | CA | LEU | A | 1095 | 18.448 | 23.089 | 10.220 | 1.00 | 40.12 | A | C |
| ATOM | 2256 | CB | LEU | A | 1095 | 16.596 | 24.533 | 9.727 | 1.00 | 37.84 | A | C |
| ATOM | 2257 | CG | LEU | A | 1095 | 19.983 | 24.906 | 9.179 | 1.00 | 38.91 | A | C |
| ATOM | 2258 | CD1 | LEU | A | 1095 | 19.930 | 26.219 | 8.418 | 1.00 | 37.27 | A | C |
| ATOM | 2259 | CD2 | LEU | A | 1095 | 20.973 | 24.992 | 10.324 | 1.00 | 37.75 | A | C |
| ATOM | 2260 | C | LEU | A | 1095 | 17.180 | 22.946 | 11.066 | 1.00 | 40.39 | A | C |
| ATOM | 2261 | O | LEU | A | 1095 | 17.237 | 22.991 | 12.296 | 1.00 | 38.60 | A | O |
| ATOM | 2262 | N | ASP | A | 1096 | 16.036 | 22.773 | 10.414 | 1.00 | 41.84 | A | N |
| ATOM | 2263 | CA | ASP | A | 1096 | 14.789 | 22.622 | 11.153 | 1.00 | 44.60 | A | C |
| ATOM | 2264 | CB | ASP | A | 1096 | 13.633 | 22.347 | 10.200 | 1.00 | 46.66 | A | C |

-continued

| | | | | | | | | | | | |
|---|---|---|---|---|---|---|---|---|---|---|---|
| ATOM | 2265 | CG | ASP | A | 1096 | 12.893 | 23.603 | 9.813 | 1.00 | 49.73 | A | C |
| ATOM | 2266 | OD1 | ASP | A | 1096 | 12.144 | 23.554 | 8.812 | 1.00 | 51.70 | A | O |
| ATOM | 2267 | OD2 | ASP | A | 1096 | 13.058 | 24.635 | 10.507 | 1.00 | 50.84 | A | O |
| ATOM | 2268 | C | ASP | A | 1096 | 14.883 | 21.496 | 12.172 | 1.00 | 44.97 | A | C |
| ATOM | 2269 | O | ASP | A | 1096 | 14.418 | 21.637 | 13.302 | 1.00 | 43.90 | A | O |
| ATOM | 2270 | N | MET | A | 1097 | 15.484 | 20.381 | 11.761 | 1.00 | 46.10 | A | N |
| ATOM | 2271 | CA | MET | A | 1097 | 15.649 | 19.227 | 12.636 | 1.00 | 46.72 | A | C |
| ATOM | 2272 | CB | MET | A | 1097 | 16.219 | 18.041 | 11.863 | 1.00 | 49.78 | A | C |
| ATOM | 2273 | CG | MET | A | 1097 | 15.238 | 17.360 | 10.932 | 1.00 | 51.99 | A | C |
| ATOM | 2274 | SD | MET | A | 1097 | 16.001 | 15.928 | 10.169 | 1.00 | 55.68 | A | S |
| ATOM | 2275 | CE | MET | A | 1097 | 16.746 | 16.676 | 8.742 | 1.00 | 54.91 | A | C |
| ATOM | 2276 | C | MET | A | 1097 | 16.580 | 19.548 | 13.788 | 1.00 | 46.48 | A | C |
| ATOM | 2277 | O | MET | A | 1097 | 16.275 | 19.246 | 14.938 | 1.00 | 47.57 | A | O |
| ATOM | 2278 | N | LEU | A | 1098 | 17.722 | 20.149 | 13.478 | 1.00 | 45.27 | A | N |
| ATOM | 2279 | CA | LEU | A | 1098 | 18.686 | 20.504 | 14.508 | 1.00 | 45.26 | A | C |
| ATOM | 2280 | CB | LEU | A | 1098 | 19.872 | 21.240 | 13.890 | 1.00 | 44.97 | A | C |
| ATOM | 2281 | CG | LEU | A | 1098 | 20.593 | 20.490 | 12.767 | 1.00 | 44.21 | A | C |
| ATOM | 2282 | CD1 | LEU | A | 1098 | 21.756 | 21.322 | 12.245 | 1.00 | 45.02 | A | C |
| ATOM | 2283 | CD2 | LEU | A | 1098 | 21.084 | 19.150 | 13.294 | 1.00 | 44.66 | A | C |
| ATOM | 2284 | C | LEU | A | 1098 | 18.031 | 21.383 | 15.566 | 1.00 | 46.70 | A | C |
| ATOM | 2285 | O | LEU | A | 1098 | 18.218 | 21.170 | 16.768 | 1.00 | 46.72 | A | O |
| ATOM | 2286 | N | TRP | A | 1099 | 17.261 | 22.367 | 15.108 | 1.00 | 47.34 | A | N |
| ATOM | 2287 | CA | TRP | A | 1099 | 16.568 | 23.288 | 16.003 | 1.00 | 47.89 | A | C |
| ATOM | 2288 | CB | TRP | A | 1099 | 15.587 | 24.157 | 15.210 | 1.00 | 46.51 | A | C |
| ATOM | 2289 | CG | TRP | A | 1099 | 14.761 | 25.053 | 16.073 | 1.00 | 46.41 | A | C |
| ATOM | 2290 | CD2 | TRP | A | 1099 | 13.347 | 24.974 | 16.274 | 1.00 | 46.89 | A | C |
| ATOM | 2291 | CE2 | TRP | A | 1099 | 12.999 | 25.985 | 17.190 | 1.00 | 46.27 | A | C |
| ATOM | 2292 | CE3 | TRP | A | 1099 | 12.341 | 24.144 | 15.770 | 1.00 | 46.19 | A | C |
| ATOM | 2293 | CD1 | TRP | A | 1099 | 15.202 | 26.085 | 16.852 | 1.00 | 46.39 | A | C |
| ATOM | 2294 | NE1 | TRP | A | 1099 | 14.148 | 26.649 | 17.528 | 1.00 | 44.71 | A | N |
| ATOM | 2295 | CZ2 | TRP | A | 1099 | 11.691 | 26.189 | 17.610 | 1.00 | 46.50 | A | C |
| ATOM | 2296 | CZ3 | TRP | A | 1099 | 11.043 | 24.347 | 16.189 | 1.00 | 45.66 | A | C |
| ATOM | 2297 | CH2 | TRP | A | 1099 | 10.729 | 25.359 | 17.100 | 1.00 | 46.54 | A | C |
| ATOM | 2298 | C | TRP | A | 1099 | 15.824 | 22.527 | 17.098 | 1.00 | 48.58 | A | C |
| ATOM | 2299 | O | TRP | A | 1099 | 15.812 | 22.943 | 18.258 | 1.00 | 48.53 | A | O |
| ATOM | 2300 | N | SER | A | 1100 | 15.210 | 21.408 | 16.723 | 1.00 | 49.93 | A | N |
| ATOM | 2301 | CA | SER | A | 1100 | 14.475 | 20.578 | 17.673 | 1.00 | 51.25 | A | C |
| ATOM | 2302 | CB | SER | A | 1100 | 13.238 | 19.965 | 16.997 | 1.00 | 51.15 | A | C |
| ATOM | 2303 | OG | SER | A | 1100 | 13.586 | 19.037 | 15.982 | 1.00 | 49.25 | A | O |
| ATOM | 2304 | C | SER | A | 1100 | 5.000 | 19.471 | 18.240 | 1.00 | 52.03 | A | C |
| ATOM | 2305 | O | SER | A | 1100 | 15.541 | 19.416 | 19.478 | 1.00 | 53.12 | A | O |
| ATOM | 2306 | OXT | SER | A | 1100 | 15.915 | 18.674 | 17.445 | 1.00 | 51.89 | A | O |
| TER | 1 | | SER | A | 1100 | | | | | | A | |
| ATOM | 2307 | CB | ASP | B | 813 | 2.825 | 23.672 | 6.637 | 1.00 | 41.77 | B | C |
| ATOM | 2308 | CG | ASP | B | 813 | 1.930 | 24.126 | 7.778 | 1.00 | 43.25 | B | C |
| ATOM | 2309 | OD1 | ASP | B | 813 | 1.989 | 23.509 | 8.863 | 1.00 | 45.61 | B | O |
| ATOM | 2310 | OD2 | ASP | B | 813 | 1.169 | 25.103 | 7.587 | 1.00 | 43.25 | B | O |
| ATOM | 2311 | C | ASP | B | 813 | 1.324 | 21.690 | 6.566 | 1.00 | 39.86 | B | C |
| ATOM | 2312 | O | ASP | B | 813 | 0.396 | 22.265 | 5.997 | 1.00 | 40.64 | B | O |
| ATOM | 2313 | N | ASP | B | 813 | 3.241 | 21.818 | 5.032 | 1.00 | 40.52 | B | N |
| ATOM | 2314 | CA | ASP | B | 813 | 2.754 | 22.160 | 6.398 | 1.00 | 40.76 | B | C |
| ATOM | 2315 | N | PRO | B | 814 | 1.133 | 20.629 | 7.357 | 1.00 | 38.57 | B | N |
| ATOM | 2316 | CD | PRO | B | 814 | 2.240 | 19.827 | 7.910 | 1.00 | 37.96 | B | C |
| ATOM | 2317 | CA | PRO | B | 814 | −0.157 | 20.006 | 7.657 | 1.00 | 36.41 | B | C |
| ATOM | 2318 | CB | PRO | B | 814 | 0.233 | 18.772 | 8.474 | 1.00 | 37.07 | B | C |
| ATOM | 2319 | CG | PRO | B | 814 | 1.617 | 18.459 | 8.004 | 1.00 | 36.97 | B | C |
| ATOM | 2320 | C | PRO | B | 814 | −1.126 | 20.888 | 8.433 | 1.00 | 35.03 | B | C |
| ATOM | 2321 | O | PRO | B | 814 | −0.726 | 21.746 | 9.224 | 1.00 | 34.82 | B | O |
| ATOM | 2322 | N | THR | B | 815 | −2.408 | 20.645 | 8.194 | 1.00 | 33.52 | B | N |
| ATOM | 2323 | CA | THR | B | 815 | −3.495 | 21.344 | 8.859 | 1.00 | 32.14 | B | C |
| ATOM | 2324 | CB | THR | B | 815 | −4.327 | 22.15B | 7.862 | 1.00 | 31.18 | B | C |
| ATOM | 2325 | OG1 | THR | B | 815 | −3.534 | 23.238 | 7.352 | 1.00 | 30.84 | B | O |
| ATOM | 2326 | CG2 | THR | B | 815 | −5.563 | 22.711 | 8.533 | 1.00 | 28.45 | B | C |
| ATOM | 2327 | C | THR | B | 815 | −4.364 | 20.247 | 9.461 | 1.00 | 32.63 | B | C |
| ATOM | 2328 | O | THR | B | 815 | −5.159 | 20.484 | 10.372 | 1.00 | 31.96 | B | O |
| ATOM | 2329 | N | ILE | B | 816 | −4.178 | 19.040 | 8.932 | 1.00 | 33.41 | B | N |
| ATOM | 2330 | CA | ILE | B | 816 | −4.896 | 17.842 | 9.352 | 1.00 | 33.58 | B | C |
| ATOM | 2331 | CB | ILE | B | 816 | −5.660 | 17.235 | 8.164 | 1.00 | 35.25 | B | C |
| ATOM | 2332 | CG2 | ILE | B | 816 | −6.418 | 15.992 | 8.595 | 1.00 | 37.17 | B | C |
| ATOM | 2333 | CG1 | ILE | B | 816 | −6.647 | 18.268 | 7.622 | 1.00 | 37.48 | B | C |
| ATOM | 2334 | CD1 | ILE | B | 816 | −7.728 | 18.638 | 8.595 | 1.00 | 34.45 | B | C |
| ATOM | 2335 | C | ILE | B | 816 | −3.858 | 16.846 | 9.850 | 1.00 | 32.05 | B | C |
| ATOM | 2336 | O | ILE | B | 816 | −3.011 | 16.390 | 9.087 | 1.00 | 34.53 | B | O |
| ATOM | 2337 | N | PHE | B | 817 | −3.933 | 16.505 | 11.128 | 1.00 | 29.25 | B | N |
| ATOM | 2338 | CA | PHE | B | 817 | −2.967 | 15.600 | 11.729 | 1.00 | 28.03 | B | C |
| ATOM | 2339 | CB | PHE | B | 817 | −2.381 | 16.230 | 13.002 | 1.00 | 26.53 | B | C |
| ATOM | 2340 | CG | PHE | B | 817 | −1.354 | 17.315 | 12.743 | 1.00 | 22.84 | B | C |
| ATOM | 2341 | CD1 | PHE | B | 817 | 0.001 | 17.017 | 12.719 | 1.00 | 22.76 | B | C |
| ATOM | 2342 | CD2 | PHE | B | 817 | −1.744 | 18.627 | 12.537 | 1.00 | 20.42 | B | C |
| ATOM | 2343 | CE1 | PHE | B | 817 | 0.949 | 18.013 | 12.496 | 1.00 | 21.47 | B | C |

-continued

| | | | | | | | | | | |
|---|---|---|---|---|---|---|---|---|---|---|
| ATOM | 2344 | CE2 | PHE | B | 817 | −0.801 | 19.628 | 12.311 | 1.00 | 21.52 | B | C |
| ATOM | 2345 | CZ | PHE | B | 817 | 0.546 | 19.319 | 12.292 | 1.00 | 19.38 | B | C |
| ATOM | 2346 | C | PHE | B | 817 | −3.543 | 14.243 | 12.069 | 1.00 | 28.62 | B | C |
| ATOM | 2347 | O | PHE | B | 817 | −4.620 | 14.127 | 12.661 | 1.00 | 28.42 | B | O |
| ATOM | 2348 | N | GLU | B | 818 | −2.801 | 13.212 | 11.706 | 1.00 | 28.25 | B | N |
| ATOM | 2349 | CA | GLU | B | 818 | −3.231 | 11.859 | 11.976 | 1.00 | 30.35 | B | C |
| ATOM | 2350 | CB | GLU | B | 818 | −2.673 | 10.932 | 10.901 | 1.00 | 31.20 | B | C |
| ATOM | 2351 | CG | GLU | B | 818 | −3.408 | 9.624 | 10.807 | 1.00 | 33.27 | B | C |
| ATOM | 2352 | CD | GLU | B | 818 | −2.963 | 8.817 | 9.632 | 1.00 | 34.34 | B | C |
| ATOM | 2353 | OE1 | GLU | B | 818 | −3.443 | 7.671 | 9.498 | 1.00 | 35.01 | B | O |
| ATOM | 2354 | OE2 | GLU | B | 818 | −2.136 | 9.334 | 8.849 | 1.00 | 33.80 | B | O |
| ATOM | 2355 | C | GLU | B | 818 | −2.740 | 11.430 | 13.358 | 1.00 | 30.11 | B | C |
| ATOM | 2356 | O | GLU | B | 818 | −1.557 | 11.591 | 13.670 | 1.00 | 29.23 | B | O |
| ATOM | 2357 | N | GLU | B | 819 | −3.651 | 10.898 | 14.178 | 1.00 | 28.41 | B | N |
| ATOM | 2358 | CA | GLU | B | 819 | −3.326 | 10.444 | 15.536 | 1.00 | 29.21 | B | C |
| ATOM | 2359 | CB | GLU | B | 819 | −4.560 | 9.853 | 16.228 | 1.00 | 27.11 | B | C |
| ATOM | 2360 | CG | GLU | B | 819 | −5.454 | 10.856 | 16.963 | 1.00 | 26.82 | B | C |
| ATOM | 2361 | CD | GLU | B | 819 | −4.707 | 11.618 | 18.056 | 1.00 | 26.05 | B | C |
| ATOM | 2362 | OE1 | GLU | B | 819 | −3.821 | 11.016 | 18.694 | 1.00 | 25.30 | B | O |
| ATOM | 2363 | OE2 | GLU | B | 819 | −5.010 | 12.809 | 18.282 | 1.00 | 22.67 | B | O |
| ATOM | 2364 | C | GLU | B | 819 | −2.186 | 9.428 | 15.630 | 1.00 | 31.75 | B | C |
| ATOM | 2365 | O | GLU | B | 819 | −1.368 | 9.499 | 16.551 | 1.00 | 33.63 | B | O |
| ATOM | 2366 | N | ARG | B | 820 | −2.120 | 8.485 | 14.694 | 1.00 | 32.89 | B | N |
| ATOM | 2367 | CA | ARG | B | 820 | −1.057 | 7.488 | 14.741 | 1.00 | 34.85 | B | C |
| ATOM | 2368 | CB | ARG | B | 820 | −1.301 | 6.394 | 13.685 | 1.00 | 37.02 | B | C |
| ATOM | 2369 | CG | ARG | B | 820 | −0.780 | 6.690 | 12.289 | 1.00 | 41.86 | B | C |
| ATOM | 2370 | CD | ARG | B | 820 | 0.333 | 5.717 | 11.892 | 1.00 | 46.24 | B | C |
| ATOM | 2371 | NE | ARG | B | 820 | 1.482 | 5.810 | 12.795 | 1.00 | 50.85 | B | N |
| ATOM | 2372 | CZ | ARG | B | 820 | 2.666 | 5.237 | 12.587 | 1.00 | 51.37 | B | C |
| ATOM | 2373 | NH1 | ARG | B | 820 | 2.884 | 4.516 | 11.494 | 1.00 | 53.33 | B | N |
| ATOM | 2374 | NH2 | ARG | B | 820 | 3.637 | 5.387 | 13.478 | 1.00 | 51.30 | B | N |
| ATOM | 2375 | C | ARG | B | 820 | 0.349 | 8.107 | 14.571 | 1.00 | 35.30 | B | C |
| ATOM | 2376 | O | ARG | B | 820 | 1.371 | 7.455 | 14.819 | 1.00 | 35.40 | B | O |
| ATOM | 2377 | N | HIS | B | 821 | 0.411 | 9.368 | 14.165 | 1.00 | 32.42 | B | N |
| ATOM | 2378 | CA | HIS | B | 821 | 1.706 | 9.996 | 13.997 | 1.00 | 31.18 | B | C |
| ATOM | 2379 | CB | HIS | B | 821 | 1.756 | 10.803 | 12.695 | 1.00 | 32.60 | B | C |
| ATOM | 2380 | CG | HIS | B | 821 | 1.583 | 9.969 | 11.460 | 1.00 | 35.70 | B | C |
| ATOM | 2381 | CD2 | HIS | B | 821 | 1.094 | 10.282 | 10.235 | 1.00 | 35.90 | B | C |
| ATOM | 2382 | ND1 | HIS | B | 821 | 1.964 | 8.645 | 11.391 | 1.00 | 37.49 | B | N |
| ATOM | 2383 | CE1 | HIS | B | 821 | 1.715 | 8.177 | 10.180 | 1.00 | 36.47 | B | C |
| ATOM | 2384 | NE2 | HIS | B | 821 | 1.187 | 9.150 | 9.461 | 1.00 | 37.66 | B | N |
| ATOM | 2385 | C | HIS | B | 821 | 2.050 | 10.887 | 15.184 | 1.00 | 30.63 | B | C |
| ATOM | 2386 | O | HIS | B | 821 | 3.115 | 11.508 | 15.215 | 1.00 | 30.21 | B | O |
| ATOM | 2387 | N | LEU | B | 822 | 1.157 | 10.955 | 16.166 | 1.00 | 28.80 | B | N |
| ATOM | 2388 | CA | LEU | B | 822 | 1.428 | 11.776 | 17.339 | 1.00 | 29.94 | B | C |
| ATOM | 2389 | CB | LEU | B | 822 | 0.172 | 12.579 | 17.739 | 1.00 | 28.15 | B | C |
| ATOM | 2390 | CG | LEU | B | 822 | −0.372 | 13.555 | 16.676 | 1.00 | 28.24 | B | C |
| ATOM | 2391 | CD1 | LEU | B | 822 | −1.490 | 14.423 | 17.249 | 1.00 | 27.85 | B | C |
| ATOM | 2392 | CD2 | LEU | B | 822 | 0.753 | 14.449 | 16.184 | 1.00 | 27.24 | B | C |
| ATOM | 2393 | C | LEU | B | 822 | 1.935 | 10.911 | 18.508 | 1.00 | 30.54 | B | C |
| ATOM | 2394 | O | LEU | B | 822 | 1.157 | 10.351 | 19.269 | 1.00 | 29.84 | B | O |
| ATOM | 2395 | N | LYS | B | 823 | 3.252 | 10.794 | 18.638 | 1.00 | 31.98 | B | N |
| ATOM | 2396 | CA | LYS | B | 823 | 3.811 | 9.987 | 19.715 | 1.00 | 32.61 | B | C |
| ATOM | 2397 | CB | LYS | B | 823 | 5.234 | 9.546 | 19.368 | 1.00 | 33.58 | B | C |
| ATOM | 2398 | CG | LYS | B | 823 | 5.295 | 8.359 | 18.418 | 1.00 | 36.00 | B | C |
| ATOM | 2399 | CD | LYS | B | 823 | 4.736 | 8.690 | 17.048 | 1.00 | 37.37 | B | C |
| ATOM | 2400 | CE | LYS | B | 823 | 4.240 | 7.436 | 16.336 | 1.00 | 37.83 | B | C |
| ATOM | 2401 | NZ | LYS | B | 823 | 5.262 | 6.364 | 16.216 | 1.00 | 40.50 | B | N |
| ATOM | 2402 | C | LYS | B | 823 | 3.809 | 10.698 | 21.065 | 1.00 | 31.17 | B | C |
| ATOM | 2403 | O | LYS | B | 823 | 4.499 | 11.696 | 21.255 | 1.00 | 31.27 | B | O |
| ATOM | 2404 | N | TYR | B | 824 | 3.014 | 10.178 | 21.992 | 1.00 | 30.97 | B | N |
| ATOM | 2405 | CA | TYR | B | 824 | 2.922 | 10.726 | 23.335 | 1.00 | 33.67 | B | C |
| ATOM | 2406 | CB | TYR | B | 824 | 1.984 | 9.868 | 24.184 | 1.00 | 34.02 | B | C |
| ATOM | 2407 | CG | TYR | B | 824 | 2.066 | 10.155 | 25.670 | 1.00 | 34.31 | B | C |
| ATOM | 2408 | CD1 | TYR | B | 824 | 1.183 | 11.035 | 26.276 | 1.00 | 34.19 | B | C |
| ATOM | 2409 | CE1 | TYR | B | 824 | 1.253 | 11.302 | 27.626 | 1.00 | 34.94 | B | C |
| ATOM | 2410 | CD2 | TYR | B | 824 | 3.030 | 9.549 | 26.463 | 1.00 | 36.32 | B | C |
| ATOM | 2411 | CE2 | TYR | B | 824 | 3.110 | 9.814 | 27.821 | 1.00 | 37.02 | B | C |
| ATOM | 2412 | CZ | TYR | B | 824 | 2.216 | 10.692 | 28.394 | 1.00 | 37.15 | B | C |
| ATOM | 2413 | OH | TYR | B | 824 | 2.275 | 10.962 | 29.746 | 1.00 | 39.76 | B | O |
| ATOM | 2414 | C | TYR | B | 824 | 4.299 | 10.757 | 24.010 | 1.00 | 34.77 | B | C |
| ATOM | 2415 | O | TYR | B | 824 | 5.037 | 9.769 | 23.988 | 1.00 | 31.82 | B | O |
| ATOM | 2416 | U | ILE | B | 825 | 4.632 | 11.885 | 24.626 | 1.00 | 35.64 | B | N |
| ATOM | 2417 | CA | ILE | B | 825 | 5.910 | 12.004 | 25.305 | 1.00 | 36.01 | B | C |
| ATOM | 2418 | CB | ILE | B | 825 | 6.751 | 13.173 | 24.749 | 1.00 | 34.52 | B | C |
| ATOM | 2419 | CG2 | ILE | B | 825 | 8.031 | 13.325 | 25.571 | 1.00 | 34.43 | B | C |
| ATOM | 2420 | CG1 | ILE | B | 825 | 7.083 | 12.926 | 23.275 | 1.00 | 33.06 | B | C |
| ATOM | 2421 | CD1 | ILE | B | 825 | 8.072 | 13.922 | 22.688 | 1.00 | 31.39 | B | C |
| ATOM | 2422 | C | ILE | B | 825 | 5.711 | 12.208 | 26.799 | 1.00 | 35.95 | B | C |
| ATOM | 2423 | O | ILE | B | 825 | 6.537 | 11.783 | 27.605 | 1.00 | 35.84 | B | O |

-continued

| | | | | | | | | | | | |
|---|---|---|---|---|---|---|---|---|---|---|---|
| ATOM | 2424 | N | SER | B | 826 | 4.610 | 12.853 | 27.165 | 1.00 | 36.03 | B | N |
| ATOM | 2425 | CA | SER | B | 826 | 4.303 | 13.115 | 28.573 | 1.00 | 36.98 | B | C |
| ATOM | 2426 | CB | SER | B | 826 | 5.507 | 13.725 | 29.300 | 1.00 | 36.75 | B | C |
| ATOM | 2427 | OG | SER | B | 826 | 5.831 | 15.003 | 28.779 | 1.00 | 37.67 | B | O |
| ATOM | 2428 | C | SER | B | 826 | 3.144 | 14.082 | 28.668 | 1.00 | 35.86 | B | C |
| ATOM | 2429 | O | SER | B | 826 | 2.789 | 14.734 | 27.688 | 1.00 | 37.04 | B | O |
| ATOM | 2430 | N | GLN | B | 827 | 2.565 | 14.179 | 29.857 | 1.00 | 36.30 | B | N |
| ATOM | 2431 | CA | GLN | B | 827 | 1.439 | 15.073 | 30.087 | 1.00 | 36.00 | B | C |
| ATOM | 2432 | CB | GLN | B | 827 | 0.463 | 14.425 | 31.073 | 1.00 | 37.07 | B | C |
| ATOM | 2433 | CG | GLN | B | 827 | −0.743 | 13.784 | 30.402 | 1.00 | 42.24 | B | C |
| ATOM | 2434 | CD | GLN | B | 827 | −1.219 | 12.532 | 31.120 | 1.00 | 46.18 | B | C |
| ATOM | 2435 | OE1 | GLN | B | 827 | −0.546 | 11.491 | 31.104 | 1.00 | 47.45 | B | O |
| ATOM | 2436 | NE2 | GLN | B | 827 | −2.382 | 12.625 | 31.759 | 1.00 | 47.48 | B | N |
| ATOM | 2437 | C | GLN | B | 827 | 1.893 | 16.433 | 30.609 | 1.00 | 34.37 | B | C |
| ATOM | 2438 | O | GLN | B | 827 | 2.720 | 16.510 | 31.521 | 1.00 | 33.94 | B | O |
| ATOM | 2439 | N | LEU | B | 828 | 1.350 | 17.501 | 30.023 | 1.00 | 32.18 | B | N |
| ATOM | 2440 | CA | LEU | B | 828 | 1.694 | 18.862 | 30.435 | 1.00 | 30.39 | B | C |
| ATOM | 2441 | CB | LEU | B | 828 | 1.616 | 19.814 | 29.239 | 1.00 | 29.07 | B | C |
| ATOM | 2442 | CG | LEU | B | 828 | 2.633 | 19.544 | 28.133 | 1.00 | 27.77 | B | C |
| ATOM | 2443 | CD1 | LEU | B | 828 | 2.337 | 20.429 | 26.957 | 1.00 | 25.72 | B | C |
| ATOM | 2444 | CD2 | LEU | B | 828 | 4.051 | 19.780 | 28.654 | 1.00 | 25.98 | B | C |
| ATOM | 2445 | C | LEU | B | 828 | 0.829 | 19.401 | 31.574 | 1.00 | 29.13 | B | C |
| ATOM | 2446 | O | LEU | B | 828 | 1.286 | 20.229 | 32.356 | 1.00 | 30.42 | B | O |
| ATOM | 2447 | N | GLY | B | 829 | −0.412 | 18.930 | 31.675 | 1.00 | 29.64 | B | N |
| ATOM | 2448 | CA | GLY | B | 829 | −1.303 | 19.384 | 32.733 | 1.00 | 27.62 | B | C |
| ATOM | 2449 | C | GLY | B | 829 | −2.758 | 19.513 | 32.304 | 1.00 | 29.05 | B | C |
| ATOM | 2450 | O | GLY | B | 829 | −3.083 | 19.433 | 31.115 | 1.00 | 29.17 | B | O |
| ATOM | 2451 | N | LYS | B | 830 | −3.642 | 19.706 | 33.277 | 1.00 | 29.83 | B | N |
| ATOM | 2452 | CA | LYS | B | 830 | −5.072 | 19.859 | 33.018 | 1.00 | 29.11 | B | C |
| ATOM | 2453 | CB | LYS | B | 830 | −5.867 | 18.796 | 33.775 | 1.00 | 31.52 | B | C |
| ATOM | 2454 | CG | LYS | B | 830 | −7.294 | 19.234 | 34.070 | 1.00 | 38.23 | B | C |
| ATOM | 2455 | CD | LYS | B | 830 | −8.018 | 18.309 | 35.034 | 1.00 | 41.99 | B | C |
| ATOM | 2456 | CE | LYS | B | 830 | −9.305 | 18.962 | 35.542 | 1.00 | 43.97 | B | C |
| ATOM | 2457 | NZ | LYS | B | 830 | −10.060 | 18.082 | 36.480 | 1.00 | 45.94 | B | N |
| ATOM | 2458 | C | LYS | B | 830 | −5.516 | 21.246 | 33.489 | 1.00 | 27.73 | B | C |
| ATOM | 2459 | O | LYS | B | 830 | −5.007 | 21.744 | 34.487 | 1.00 | 26.97 | B | O |
| ATOM | 2460 | N | GLY | B | 831 | −6.457 | 21.865 | 32.774 | 1.00 | 25.89 | B | N |
| ATOM | 2461 | CA | GLY | B | 831 | −6.937 | 23.182 | 33.153 | 1.00 | 23.83 | B | C |
| ATOM | 2462 | C | GLY | B | 831 | −8.447 | 23.217 | 33.310 | 1.00 | 24.22 | B | C |
| ATOM | 2463 | O | GLY | B | 831 | −9.044 | 22.225 | 33.717 | 1.00 | 24.73 | B | O |
| ATOM | 2464 | N | ASN | B | 832 | −9.055 | 24.353 | 32.961 | 1.00 | 23.96 | B | N |
| ATOM | 2465 | CA | ASN | B | 832 | −10.502 | 24.580 | 33.046 | 1.00 | 21.93 | B | C |
| ATOM | 2466 | CB | ASN | B | 832 | −10.804 | 26.075 | 33.033 | 1.00 | 21.24 | B | C |
| ATOM | 2467 | CG | ASN | B | 832 | −10.376 | 26.770 | 34.290 | 1.00 | 19.88 | B | C |
| ATOM | 2468 | OD1 | ASN | B | 832 | −10.895 | 26.475 | 35.363 | 1.00 | 18.71 | B | O |
| ATOM | 2469 | ND2 | ASN | B | 832 | −9.429 | 27.710 | 34.171 | 1.00 | 15.25 | B | N |
| ATOM | 2470 | C | ASN | B | 832 | −11.351 | 23.970 | 31.940 | 1.00 | 23.37 | B | C |
| ATOM | 2471 | O | ASN | B | 832 | −12.535 | 23.717 | 32.151 | 1.00 | 22.56 | B | O |
| ATOM | 2472 | N | PHE | B | 833 | −10.779 | 23.772 | 30.753 | 1.00 | 23.17 | B | N |
| ATOM | 2473 | CA | PHE | B | 833 | −11.567 | 23.228 | 29.647 | 1.00 | 24.16 | B | C |
| ATOM | 2474 | CB | PHE | B | 833 | −11.790 | 24.303 | 28.573 | 1.00 | 23.51 | B | C |
| ATOM | 2475 | CG | PHE | B | 833 | −12.414 | 25.567 | 29.094 | 1.00 | 23.24 | B | C |
| ATOM | 2476 | CD1 | PHE | B | 833 | −11.627 | 26.641 | 29.455 | 1.00 | 23.38 | B | C |
| ATOM | 2477 | CD2 | PHE | B | 833 | −13.791 | 25.675 | 29.242 | 1.00 | 22.46 | B | C |
| ATOM | 2478 | CE1 | PHE | B | 833 | −12.198 | 27.808 | 29.958 | 1.00 | 23.81 | B | C |
| ATOM | 2479 | CE2 | PHE | B | 833 | −14.369 | 26.842 | 29.747 | 1.00 | 23.47 | B | C |
| ATOM | 2480 | CZ | PHE | B | 833 | −13.572 | 27.905 | 30.104 | 1.00 | 23.00 | B | C |
| ATOM | 2481 | C | PHE | B | 833 | −11.005 | 21.973 | 28.974 | 1.00 | 25.60 | B | C |
| ATOM | 2482 | O | PHE | B | 833 | −11.657 | 21.397 | 28.106 | 1.00 | 25.79 | B | O |
| ATOM | 2483 | N | GLY | B | 834 | −9.805 | 21.548 | 29.360 | 1.00 | 24.96 | B | N |
| ATOM | 2484 | CA | GLY | B | 834 | −9.242 | 20.369 | 28.746 | 1.00 | 24.52 | B | C |
| ATOM | 2485 | C | GLY | B | 834 | −7.951 | 19.924 | 29.390 | 1.00 | 27.71 | B | C |
| ATOM | 2486 | O | GLY | B | 834 | −7.689 | 20.223 | 30.557 | 1.00 | 29.31 | B | O |
| ATOM | 2487 | N | SER | B | 835 | −7.149 | 19.189 | 28.626 | 1.00 | 27.33 | B | N |
| ATOM | 2488 | CA | SER | B | 835 | −5.872 | 18.688 | 29.096 | 1.00 | 28.87 | B | C |
| ATOM | 2489 | CB | SER | B | 835 | −6.027 | 17.258 | 29.604 | 1.00 | 28.44 | B | C |
| ATOM | 2490 | OG | SER | B | 835 | −6.763 | 16.488 | 28.673 | 1.00 | 32.42 | B | O |
| ATOM | 2491 | C | SER | B | 835 | −4.888 | 18.746 | 27.939 | 1.00 | 29.32 | B | C |
| ATOM | 2492 | O | SER | B | 835 | −5.280 | 18.656 | 26.775 | 1.00 | 30.81 | B | O |
| ATOM | 2493 | N | VAL | B | 836 | −3.610 | 18.892 | 28.263 | 1.00 | 28.87 | B | N |
| ATOM | 2494 | CA | VAL | B | 836 | −2.573 | 19.005 | 27.250 | 1.00 | 27.94 | B | C |
| ATOM | 2495 | CB | VAL | B | 836 | −1.864 | 20.358 | 27.379 | 1.00 | 27.26 | B | C |
| ATOM | 2496 | CG1 | VAL | B | 836 | −0.904 | 20.560 | 26.221 | 1.00 | 27.80 | B | C |
| ATOM | 2497 | CG2 | VAL | B | 836 | −2.902 | 21.478 | 27.442 | 1.00 | 28.52 | B | C |
| ATOM | 2498 | C | VAL | B | 836 | −1.525 | 17.915 | 27.352 | 1.00 | 29.07 | B | C |
| ATOM | 2499 | O | VAL | B | 836 | −1.244 | 17.412 | 28.437 | 1.00 | 30.56 | B | O |
| ATOM | 2500 | N | GLU | B | 837 | −0.941 | 17.556 | 26.213 | 1.00 | 30.14 | B | N |
| ATOM | 2501 | CA | GLU | B | 837 | 0.101 | 16.540 | 26.172 | 1.00 | 29.01 | B | C |
| ATOM | 2502 | CB | GLU | B | 837 | −0.432 | 15.215 | 25.635 | 1.00 | 29.10 | B | C |
| ATOM | 2503 | CG | GLU | B | 837 | −1.601 | 14.646 | 26.378 | 1.00 | 28.69 | B | C |

-continued

| | | | | | | | | | | | |
|---|---|---|---|---|---|---|---|---|---|---|---|
| ATOM | 2504 | CD | GLU | B | 837 | −1.757 | 13.170 | 26.110 | 1.00 | 26.28 | B | C |
| ATOM | 2505 | OE1 | GLU | B | 837 | −1.559 | 12.759 | 24.949 | 1.00 | 26.70 | B | O |
| ATOM | 2506 | OE2 | GLU | B | 837 | −2.081 | 12.427 | 27.054 | 1.00 | 25.64 | B | O |
| ATOM | 2507 | C | GLU | B | 837 | 1.213 | 16.997 | 25.252 | 1.00 | 29.17 | B | C |
| ATOM | 2508 | O | GLU | B | 837 | 0.973 | 17.733 | 24.293 | 1.00 | 27.85 | B | O |
| ATOM | 2509 | N | LEU | B | 838 | 2.430 | 16.552 | 25.564 | 1.00 | 30.14 | B | N |
| ATOM | 2510 | CA | LEU | B | 838 | 3.620 | 16.858 | 24.769 | 1.00 | 30.84 | B | C |
| ATOM | 2511 | CB | LEU | B | 838 | 4.837 | 17.118 | 25.671 | 1.00 | 30.33 | B | C |
| ATOM | 2512 | CG | LEU | B | 838 | 6.222 | 17.126 | 24.999 | 1.00 | 31.49 | B | C |
| ATOM | 2513 | CD1 | LEU | B | 838 | 6.315 | 18.235 | 23.951 | 1.00 | 31.48 | B | C |
| ATOM | 2514 | CD2 | LEU | B | 838 | 7.303 | 17.315 | 26.059 | 1.00 | 30.64 | B | C |
| ATOM | 2515 | C | LEU | B | 838 | 3.876 | 15.628 | 23.917 | 1.00 | 30.49 | B | C |
| ATOM | 2516 | O | LEU | B | 838 | 4.277 | 14.587 | 24.433 | 1.00 | 32.32 | B | O |
| ATOM | 2517 | N | CYS | B | 839 | 3.624 | 15.742 | 22.619 | 1.00 | 29.82 | B | N |
| ATOM | 2518 | CA | CYS | B | 839 | 3.819 | 14.627 | 21.700 | 1.00 | 29.62 | B | C |
| ATOM | 2519 | CB | CYS | B | 839 | 2.521 | 14.304 | 20.960 | 1.00 | 26.21 | B | C |
| ATOM | 2520 | SG | CYS | B | 839 | 1.103 | 14.029 | 21.990 | 1.00 | 25.86 | B | S |
| ATOM | 2521 | C | CYS | B | 839 | 4.867 | 14.972 | 20.655 | 1.00 | 30.35 | B | C |
| ATOM | 2522 | O | CYS | B | 839 | 5.418 | 16.069 | 20.646 | 1.00 | 29.37 | B | O |
| ATOM | 2523 | N | ARG | B | 840 | 5.138 | 14.023 | 19.769 | 1.00 | 32.26 | B | N |
| ATOM | 2524 | CA | ARG | B | 840 | 6.083 | 14.272 | 18.692 | 1.00 | 35.32 | B | C |
| ATOM | 2525 | CB | ARG | B | 840 | 7.361 | 13.442 | 18.879 | 1.00 | 36.76 | B | C |
| ATOM | 2526 | CG | ARG | B | 840 | 8.401 | 13.640 | 17.780 | 1.00 | 39.60 | B | C |
| ATOM | 2527 | CD | ARG | B | 840 | 9.699 | 12.899 | 18.083 | 1.00 | 42.80 | B | C |
| ATOM | 2528 | NE | ARG | B | 840 | 10.542 | 13.641 | 19.019 | 1.00 | 44.90 | B | N |
| ATOM | 2529 | CZ | ARG | B | 840 | 11.121 | 13.129 | 20.104 | 1.00 | 45.26 | B | C |
| ATOM | 2530 | NH1 | ARG | B | 840 | 10.964 | 11.645 | 20.421 | 1.00 | 44.02 | B | N |
| ATOM | 2531 | NH2 | ARG | B | 840 | 11.847 | 13.921 | 20.883 | 1.00 | 44.63 | B | N |
| ATOM | 2532 | C | ARG | B | 840 | 5.393 | 13.908 | 17.384 | 1.00 | 34.75 | B | C |
| ATOM | 2533 | O | ARG | B | 840 | 4.787 | 12.841 | 17.273 | 1.00 | 33.34 | B | O |
| ATOM | 2534 | N | TYR | B | 841 | 5.446 | 14.817 | 16.413 | 1.00 | 36.29 | B | N |
| ATOM | 2535 | CA | TYR | B | 841 | 4.832 | 14.566 | 15.116 | 1.00 | 39.08 | B | C |
| ATOM | 2536 | CB | TYR | B | 841 | 4.463 | 15.877 | 14.407 | 1.00 | 38.47 | B | C |
| ATOM | 2537 | CG | TYR | B | 841 | 3.756 | 15.674 | 13.079 | 1.00 | 39.29 | B | C |
| ATOM | 2538 | CD1 | TYR | B | 841 | 2.737 | 14.736 | 12.950 | 1.00 | 38.25 | B | C |
| ATOM | 2539 | CE1 | TYR | B | 841 | 2.092 | 14.538 | 11.743 | 1.00 | 37.76 | B | C |
| ATOM | 2540 | CD2 | TYR | B | 841 | 4.109 | 16.416 | 11.956 | 1.00 | 39.45 | B | C |
| ATOM | 2541 | CE2 | TYR | B | 841 | 3.467 | 16.228 | 10.741 | 1.00 | 38.84 | B | C |
| ATOM | 2542 | CZ | TYR | B | 841 | 2.458 | 15.285 | 10.642 | 1.00 | 39.62 | B | C |
| ATOM | 2543 | OH | TYR | B | 841 | 1.809 | 15.084 | 9.441 | 1.00 | 40.43 | B | O |
| ATOM | 2544 | C | TYR | B | 841 | 5.890 | 13.820 | 14.345 | 1.00 | 41.24 | B | C |
| ATOM | 2545 | O | TYR | B | 841 | 6.773 | 14.420 | 13.753 | 1.00 | 42.10 | B | O |
| ATOM | 2546 | N | ASP | B | 842 | 5.793 | 12.497 | 14.362 | 1.00 | 44.63 | B | N |
| ATOM | 2547 | CA | ASP | B | 842 | 6.781 | 11.662 | 13.711 | 1.00 | 46.51 | B | C |
| ATOM | 2548 | CB | ASP | B | 842 | 7.449 | 10.796 | 14.779 | 1.00 | 45.68 | B | C |
| ATOM | 2549 | CG | ASP | B | 842 | 8.819 | 10.324 | 14.369 | 1.00 | 45.45 | B | C |
| ATOM | 2550 | OD1 | ASP | B | 842 | 9.593 | 11.153 | 13.849 | 1.00 | 44.25 | B | O |
| ATOM | 2551 | OD2 | ASP | B | 842 | 9.124 | 9.130 | 14.579 | 1.00 | 44.55 | B | O |
| ATOM | 2552 | C | ASP | B | 842 | 6.237 | 10.787 | 12.586 | 1.00 | 48.84 | B | C |
| ATOM | 2553 | O | ASP | B | 842 | 6.237 | 9.558 | 12.688 | 1.00 | 49.65 | B | O |
| ATOM | 2554 | N | PRO | B | 843 | 5.773 | 11.412 | 11.491 | 1.00 | 51.03 | B | N |
| ATOM | 2555 | CD | PRO | B | 843 | 5.703 | 12.871 | 11.295 | 1.00 | 51.92 | B | C |
| ATOM | 2556 | CA | PRO | B | 843 | 5.228 | 10.700 | 10.330 | 1.00 | 52.68 | B | C |
| ATOM | 2557 | CB | PRO | B | 843 | 5.019 | 11.814 | 9.310 | 1.00 | 52.46 | B | C |
| ATOM | 2558 | CG | PRO | B | 843 | 4.709 | 12.999 | 10.165 | 1.00 | 52.25 | B | C |
| ATOM | 2559 | C | PRO | B | 843 | 6.197 | 9.628 | 9.819 | 1.00 | 54.74 | B | C |
| ATOM | 2560 | O | PRO | B | 843 | 5.793 | 8.688 | 9.141 | 1.00 | 55.91 | B | O |
| ATOM | 2561 | N | LEU | B | 844 | 7.478 | 9.780 | 10.145 | 1.00 | 56.20 | B | N |
| ATOM | 2562 | CA | LEU | B | 844 | 8.497 | 8.820 | 9.730 | 1.00 | 58.07 | B | C |
| ATOM | 2563 | CB | LEU | B | 844 | 9.699 | 9.555 | 9.133 | 1.00 | 58.51 | B | C |
| ATOM | 2564 | CG | LEU | B | 844 | 9.416 | 10.518 | 7.974 | 1.00 | 59.43 | B | C |
| ATOM | 2565 | CD1 | LEU | B | 844 | 8.650 | 9.777 | 6.893 | 1.00 | 58.93 | B | C |
| ATOM | 2566 | CD2 | LEU | B | 844 | 8.610 | 11.715 | 8.455 | 1.00 | 59.39 | B | C |
| ATOM | 2567 | C | LEU | B | 844 | 8.941 | 8.003 | 10.945 | 1.00 | 59.20 | B | C |
| ATOM | 2568 | O | LEU | B | 844 | 8.979 | 8.516 | 12.060 | 1.00 | 60.38 | B | O |
| ATOM | 2569 | N | GLY | B | 845 | 9.274 | 6.735 | 10.728 | 1.00 | 60.38 | B | N |
| ATOM | 2570 | CA | GLY | B | 845 | 9.694 | 5.882 | 11.82* | 1.00 | 60.46 | B | C |
| ATOM | 2571 | C | GLY | B | 845 | 10.727 | 6.510 | 12.740 | 1.00 | 61.81 | B | C |
| ATOM | 2572 | O | GLY | B | 845 | 10.627 | 6.417 | 13.966 | 1.00 | 62.35 | B | O |
| ATOM | 2573 | N | ASP | B | 846 | 11.725 | 7.149 | 12.138 | 1.00 | 61.41 | B | N |
| ATOM | 2574 | CA | ASP | B | 846 | 12.796 | 7.801 | 12.680 | 1.00 | 61.12 | B | C |
| ATOM | 2575 | CB | ASP | B | 846 | 13.815 | 8.393 | 11.902 | 1.00 | 63.52 | B | C |
| ATOM | 2576 | CG | ASP | B | 846 | 13.163 | 9.224 | 10.804 | 1.00 | 64.79 | B | C |
| ATOM | 2577 | OD1 | ASP | B | 846 | 13.865 | 9.584 | 9.833 | 1.00 | 65.93 | B | O |
| ATOM | 2578 | OD2 | ASP | B | 846 | 11.953 | 9.520 | 10.910 | 1.00 | 66.12 | B | O |
| ATOM | 2579 | C | ASP | B | 846 | 12.252 | 8.893 | 13.788 | 1.00 | 60.47 | B | C |
| ATOM | 2580 | O | ASP | B | 846 | 11.215 | 9.476 | 13.501 | 1.00 | 61.57 | B | O |
| ATOM | 2581 | N | ASN | B | 847 | 12.958 | 9.174 | 14.877 | 1.00 | 59.01 | B | N |
| ATOM | 2582 | CA | ASN | B | 847 | 12.530 | 10.199 | 15.627 | 1.00 | 56.87 | B | C |
| ATOM | 2583 | CB | ASN | B | 847 | 13.062 | 9.863 | 17.214 | 1.00 | 58.01 | B | C |

-continued

| | | | | | | | | | | | | |
|---|---|---|---|---|---|---|---|---|---|---|---|---|
| ATOM | 2584 | CG | ASN | B | 847 | 12.536 | 8.551 | 17.722 | 1.00 | 58.36 | B | C |
| ATOM | 2585 | OD1 | ASN | B | 847 | 11.474 | 8.494 | 18.341 | 1.00 | 58.73 | B | O |
| ATOM | 2586 | ND2 | ASN | B | 847 | 13.265 | 7.475 | 17.441 | 1.00 | 58.76 | B | N |
| ATOM | 2587 | C | ASN | B | 847 | 13.005 | 11.588 | 15.442 | 1.00 | 54.91 | B | C |
| ATOM | 2588 | O | ASN | B | 847 | 13.483 | 12.343 | 16.289 | 1.00 | 54.35 | B | O |
| ATOM | 2589 | N | THR | B | 848 | 12.870 | 11.924 | 14.167 | 1.00 | 52.24 | B | N |
| ATOM | 2590 | CA | THR | B | 848 | 13.299 | 13.226 | 13.684 | 1.00 | 51.03 | B | C |
| ATOM | 2591 | CB | THR | B | 848 | 13.704 | 13.157 | 12.214 | 1.00 | 50.95 | B | C |
| ATOM | 2592 | OG1 | THR | B | 848 | 12.547 | 12.871 | 11.419 | 1.00 | 50.21 | B | O |
| ATOM | 2593 | CG2 | THR | B | 848 | 14.738 | 12.069 | 12.004 | 1.00 | 50.33 | B | C |
| ATOM | 2594 | C | THR | B | 848 | 12.199 | 14.272 | 13.817 | 1.00 | 49.92 | B | C |
| ATOM | 2595 | O | THR | B | 848 | 12.481 | 15.465 | 13.911 | 1.00 | 49.66 | B | O |
| ATOM | 2596 | N | GLY | B | 849 | 10.950 | 13.817 | 13.820 | 1.00 | 47.29 | B | N |
| ATOM | 2597 | CA | GLY | B | 849 | 9.817 | 14.722 | 13.923 | 1.00 | 44.59 | B | C |
| ATOM | 2598 | C | GLY | B | 849 | 9.944 | 15.813 | 14.969 | 1.00 | 41.66 | B | C |
| ATOM | 2599 | O | GLY | B | 849 | 10.759 | 15.708 | 15.881 | 1.00 | 41.89 | B | O |
| ATOM | 2600 | N | ALA | B | 850 | 9.125 | 16.855 | 14.835 | 1.00 | 40.04 | B | N |
| ATOM | 2601 | CA | ALA | B | 850 | 9.124 | 17.993 | 15.755 | 1.00 | 37.64 | B | C |
| ATOM | 2602 | CB | ALA | B | 850 | 8.782 | 19.269 | 14.993 | 1.00 | 37.63 | B | C |
| ATOM | 2603 | C | ALA | B | 850 | 8.163 | 17.831 | 16.931 | 1.00 | 36.65 | B | C |
| ATOM | 2604 | O | ALA | B | 850 | 7.197 | 17.067 | 16.869 | 1.00 | 35.41 | B | O |
| ATOM | 2605 | N | LEU | B | 851 | 8.432 | 18.566 | 18.005 | 1.00 | 35.80 | B | N |
| ATOM | 2606 | CA | LEU | B | 851 | 7.581 | 18.515 | 19.189 | 1.00 | 35.03 | B | C |
| ATOM | 2607 | CB | LEU | B | 851 | 8.384 | 18.865 | 20.440 | 1.00 | 36.07 | B | C |
| ATOM | 2608 | CG | LEU | B | 851 | 9.620 | 18.013 | 20.740 | 1.00 | 38.49 | B | C |
| ATOM | 2609 | CD1 | LEU | B | 851 | 10.456 | 18.721 | 21.792 | 1.00 | 38.97 | B | C |
| ATOM | 2610 | CD2 | LEU | B | 851 | 9.214 | 16.630 | 21.219 | 1.00 | 38.23 | B | C |
| ATOM | 2611 | C | LEU | B | 851 | 6.429 | 19.501 | 19.045 | 1.00 | 32.82 | B | C |
| ATOM | 2612 | O | LEU | B | 851 | 6.566 | 20.529 | 18.386 | 1.00 | 32.71 | B | O |
| ATOM | 2613 | N | VAL | B | 852 | 5.293 | 19.179 | 19.658 | 1.00 | 30.52 | B | N |
| ATOM | 2614 | CA | VAL | B | 852 | 4.124 | 20.054 | 19.619 | 1.00 | 28.26 | B | C |
| ATOM | 2615 | CB | VAL | B | 852 | 3.228 | 19.804 | 18.360 | 1.00 | 28.68 | B | C |
| ATOM | 2616 | CG1 | VAL | B | 852 | 3.906 | 20.344 | 17.105 | 1.00 | 28.83 | B | C |
| ATOM | 2617 | CG2 | VAL | B | 852 | 2.923 | 18.315 | 18.212 | 1.00 | 26.07 | B | C |
| ATOM | 2618 | C | VAL | B | 852 | 3.251 | 19.850 | 20.852 | 1.00 | 27.93 | B | C |
| ATOM | 2619 | O | VAL | B | 852 | 3.344 | 18.832 | 21.537 | 1.00 | 27.53 | B | O |
| ATOM | 2620 | N | ALA | B | 853 | 2.407 | 20.826 | 21.147 | 1.00 | 26.02 | B | N |
| ATOM | 2621 | CA | ALA | B | 853 | 1.504 | 20.680 | 22.269 | 1.00 | 25.71 | B | C |
| ATOM | 2622 | CB | ALA | B | 853 | 1.305 | 21.998 | 22.946 | 1.00 | 25.74 | B | C |
| ATOM | 2623 | C | ALA | B | 853 | 0.178 | 20.181 | 21.694 | 1.00 | 27.28 | B | C |
| ATOM | 2624 | O | ALA | B | 853 | −0.270 | 20.650 | 20.642 | 1.00 | 26.81 | B | O |
| ATOM | 2625 | N | VAL | B | 854 | −0.446 | 19.223 | 22.371 | 1.00 | 26.44 | B | N |
| ATOM | 2626 | CA | VAL | B | 854 | −1.719 | 18.704 | 21.897 | 1.00 | 26.10 | B | C |
| ATOM | 2627 | CB | VAL | B | 854 | −1.603 | 17.240 | 21.464 | 1.00 | 24.99 | B | C |
| ATOM | 2628 | CG1 | VAL | B | 854 | −2.890 | 16.797 | 20.801 | 1.00 | 26.57 | B | C |
| ATOM | 2629 | CG2 | VAL | B | 854 | −0.433 | 17.074 | 20.509 | 1.00 | 25.76 | B | C |
| ATOM | 2630 | C | VAL | B | 854 | −2.793 | 18.817 | 22.971 | 1.00 | 26.92 | B | C |
| ATOM | 2631 | O | VAL | B | 854 | −2.791 | 18.068 | 23.945 | 1.00 | 27.18 | B | O |
| ATOM | 2632 | N | LYS | B | 855 | −3.709 | 19.766 | 22.798 | 1.00 | 26.33 | B | N |
| ATOM | 2633 | CA | LYS | B | 855 | −4.775 | 19.934 | 23.768 | 1.00 | 25.94 | B | C |
| ATOM | 2634 | CB | LYS | B | 855 | −5.015 | 21.409 | 24.084 | 1.00 | 22.34 | B | C |
| ATOM | 2635 | CG | LYS | B | 855 | −6.335 | 21.613 | 24.811 | 1.00 | 23.65 | B | C |
| ATOM | 2636 | CD | LYS | B | 855 | −6.706 | 23.063 | 25.021 | 1.00 | 19.73 | B | C |
| ATOM | 2637 | CE | LYS | B | 855 | −5.997 | 23.682 | 26.177 | 1.00 | 17.77 | B | C |
| ATOM | 2638 | NZ | LYS | B | 855 | −6.896 | 24.693 | 26.805 | 1.00 | 15.49 | B | N |
| ATOM | 2639 | C | LYS | B | 855 | −6.089 | 19.321 | 23.300 | 1.00 | 26.94 | B | C |
| ATOM | 2640 | O | LYS | B | 855 | −6.501 | 19.506 | 22.159 | 1.00 | 26.18 | B | O |
| ATOM | 2641 | N | GLN | B | 856 | −6.732 | 18.577 | 24.196 | 1.00 | 29.24 | B | N |
| ATOM | 2642 | CA | GLN | B | 856 | −8.021 | 17.964 | 23.919 | 1.00 | 29.00 | B | C |
| ATOM | 2643 | CB | GLN | B | 856 | −7.965 | 16.456 | 24.152 | 1.00 | 29.02 | B | C |
| ATOM | 2644 | CG | GLN | B | 856 | −9.299 | 15.739 | 23.913 | 1.00 | 31.97 | B | C |
| ATOM | 2645 | CD | GLN | B | 856 | −9.154 | 14.220 | 23.867 | 1.00 | 33.49 | B | C |
| ATOM | 2646 | OE1 | GLN | B | 856 | −8.570 | 13.613 | 24.764 | 1.00 | 37.69 | B | O |
| ATOM | 2647 | NE2 | GLN | B | 856 | −9.682 | 13.603 | 22.818 | 1.00 | 31.47 | B | N |
| ATOM | 2648 | C | GLN | B | 856 | −9.026 | 18.598 | 24.875 | 1.00 | 30.25 | B | C |
| ATOM | 2649 | O | GLN | B | 856 | −8.826 | 18.596 | 26.089 | 1.00 | 30.29 | B | O |
| ATOM | 2650 | N | LEU | B | 857 | −10.096 | 19.152 | 24.320 | 1.00 | 32.05 | B | N |
| ATOM | 2651 | CA | LEU | B | 857 | −11.135 | 19.793 | 25.116 | 1.00 | 34.93 | B | C |
| ATOM | 2652 | CB | LEU | B | 857 | −11.879 | 20.828 | 24.259 | 1.00 | 32.54 | B | C |
| ATOM | 2653 | CG | LEU | B | 857 | −11.173 | 22.161 | 23.971 | 1.00 | 32.83 | B | C |
| ATOM | 2654 | CD1 | LEU | B | 857 | −9.699 | 21.937 | 23.781 | 1.00 | 34.65 | B | C |
| ATOM | 2655 | CD2 | LEU | B | 857 | −11.765 | 22.817 | 22.733 | 1.00 | 32.44 | B | C |
| ATOM | 2656 | C | LEU | B | 857 | −12.133 | 18.779 | 25.670 | 1.00 | 37.68 | B | C |
| ATOM | 2657 | O | LEU | B | 857 | −12.298 | 17.689 | 25.125 | 1.00 | 35.98 | B | O |
| ATOM | 2658 | N | GLN | B | 858 | −12.771 | 19.135 | 26.778 | 1.00 | 41.97 | B | N |
| ATOM | 2659 | CA | GLN | B | 858 | −13.785 | 18.285 | 27.377 | 1.00 | 48.02 | B | C |
| ATOM | 2660 | CB | GLN | B | 858 | −14.058 | 18.705 | 28.820 | 1.00 | 49.27 | B | C |
| ATOM | 2661 | CG | GLN | B | 858 | −15.107 | 17.856 | 29.506 | 1.00 | 53.78 | B | C |
| ATOM | 2662 | CD | GLN | B | 858 | −15.374 | 18.277 | 30.942 | 1.00 | 56.64 | B | C |
| ATOM | 2663 | OE1 | GLN | B | 858 | −14.453 | 18.366 | 31.764 | 1.00 | 57.31 | B | O |

-continued

| | | | | | | | | | | |
|---|---|---|---|---|---|---|---|---|---|---|
| ATOM | 2664 | NE2 | GLN | B | 858 | −16.643 | 18.533 | 31.254 | 1.00 | 56.69 | B | N |
| ATOM | 2665 | C | GLN | B | 858 | −15.009 | 18.565 | 26.518 | 1.00 | 51.34 | B | C |
| ATOM | 2666 | O | GLN | B | 858 | −15.540 | 19.678 | 26.516 | 1.00 | 51.97 | B | O |
| ATOM | 2667 | N | HIS | B | 859 | −15.451 | 17.564 | 25.774 | 1.00 | 55.49 | B | N |
| ATOM | 2668 | CA | HIS | B | 859 | −16.585 | 17.750 | 24.888 | 1.00 | 59.37 | B | C |
| ATOM | 2669 | CB | HIS | B | 859 | −16.117 | 17.622 | 23.434 | 1.00 | 60.01 | B | C |
| ATOM | 2670 | CG | HIS | B | 859 | −17.057 | 18.227 | 22.438 | 1.00 | 61.60 | B | C |
| ATOM | 2671 | CD2 | HIS | B | 859 | −16.825 | 19.001 | 21.352 | 1.00 | 61.93 | B | C |
| ATOM | 2672 | ND1 | HIS | B | 859 | −18.419 | 18.026 | 22.482 | 1.00 | 62.55 | B | N |
| ATOM | 2673 | CE1 | HIS | B | 859 | −18.987 | 18.650 | 21.465 | 1.00 | 62.95 | B | C |
| ATOM | 2674 | NE2 | HIS | B | 859 | −18.042 | 19.248 | 20.764 | 1.00 | 63.01 | B | N |
| ATOM | 2675 | C | HIS | B | 859 | −17.670 | 16.728 | 25.172 | 1.00 | 61.41 | B | C |
| ATOM | 2676 | O | HIS | B | 859 | −17.551 | 15.563 | 24.791 | 1.00 | 62.79 | B | O |
| ATOM | 2677 | N | SER | B | 860 | −18.725 | 17.160 | 25.850 | 1.00 | 63.19 | B | N |
| ATOM | 2678 | CA | SER | B | 860 | −19.830 | 16.262 | 26.158 | 1.00 | 64.59 | B | C |
| ATOM | 2679 | CB | SER | B | 860 | −20.137 | 16.266 | 27.658 | 1.00 | 65.49 | B | C |
| ATOM | 2680 | OG | SER | B | 860 | −19.100 | 15.632 | 28.388 | 1.00 | 65.65 | B | O |
| ATOM | 2681 | C | SER | B | 860 | −21.061 | 16.671 | 25.369 | 1.00 | 65.19 | B | C |
| ATOM | 2682 | O | SER | B | 860 | −21.907 | 17.428 | 25.847 | 1.00 | 65.42 | B | O |
| ATOM | 2683 | N | GLY | B | 861 | −21.133 | 16.161 | 24.145 | 1.00 | 65.17 | B | N |
| ATOM | 2684 | CA | GLY | B | 861 | −22.241 | 16.438 | 23.252 | 1.00 | 64.91 | B | C |
| ATOM | 2685 | C | GLY | B | 861 | −21.825 | 15.917 | 21.892 | 1.00 | 64.88 | B | C |
| ATOM | 2686 | O | GLY | B | 861 | −20.727 | 15.374 | 21.771 | 1.00 | 65.32 | B | O |
| ATOM | 2687 | N | PRO | B | 862 | −22.664 | 16.039 | 20.854 | 1.00 | 64.29 | B | N |
| ATOM | 2688 | CD | PRO | B | 862 | −23.978 | 16.696 | 20.759 | 1.00 | 64.63 | B | C |
| ATOM | 2689 | CA | PRO | B | 862 | −22.231 | 15.533 | 19.547 | 1.00 | 63.09 | B | C |
| ATOM | 2690 | CB | PRO | B | 862 | −23.435 | 15.824 | 18.649 | 1.00 | 63.47 | B | C |
| ATOM | 2691 | CG | PRO | B | 862 | −24.050 | 17.029 | 19.291 | 1.00 | 63.98 | B | C |
| ATOM | 2692 | C | PRO | B | 862 | −20.954 | 16.244 | 19.082 | 1.00 | 61.34 | B | C |
| ATOM | 2693 | O | PRO | B | 862 | −20.909 | 17.471 | 18.994 | 1.00 | 60.26 | B | O |
| ATOM | 2694 | N | ASP | B | 863 | −19.913 | 15.464 | 18.815 | 1.00 | 59.65 | B | N |
| ATOM | 2695 | CA | ASP | B | 863 | −18.641 | 16.013 | 18.361 | 1.00 | 57.84 | B | C |
| ATOM | 2696 | CB | ASP | B | 863 | −17.621 | 14.898 | 18.145 | 1.00 | 59.72 | B | C |
| ATOM | 2697 | CG | ASP | B | 863 | −17.906 | 14.092 | 16.885 | 1.00 | 59.59 | B | C |
| ATOM | 2698 | OD1 | ASP | B | 863 | −19.027 | 13.543 | 16.778 | 1.00 | 60.44 | B | O |
| ATOM | 2699 | OD2 | ASP | B | 863 | −17.017 | 14.015 | 16.007 | 1.00 | 58.51 | B | O |
| ATOM | 2700 | C | ASP | B | 863 | −18.911 | 16.660 | 17.023 | 1.00 | 55.52 | B | C |
| ATOM | 2701 | O | ASP | B | 863 | −19.630 | 16.097 | 16.202 | 1.00 | 56.67 | B | O |
| ATOM | 2702 | N | GLN | B | 864 | −18.340 | 17.833 | 16.790 | 1.00 | 50.93 | B | N |
| ATOM | 2703 | CA | GLN | B | 864 | −18.553 | 18.496 | 15.518 | 1.00 | 45.49 | B | C |
| ATOM | 2704 | CB | GLN | B | 864 | −19.307 | 19.798 | 15.720 | 1.00 | 48.68 | B | C |
| ATOM | 2705 | CG | GLN | B | 864 | −20.798 | 19.572 | 15.845 | 1.00 | 51.79 | B | C |
| ATOM | 2706 | CD | GLN | B | 864 | −21.292 | 18.598 | 14.792 | 1.00 | 53.83 | B | C |
| ATOM | 2707 | OE1 | GLN | B | 864 | −21.023 | 18.775 | 13.597 | 1.00 | 55.56 | B | O |
| ATOM | 2708 | NE2 | GLN | B | 864 | −22.013 | 17.561 | 15.224 | 1.00 | 52.86 | B | N |
| ATOM | 2709 | C | GLN | B | 864 | −17.254 | 18.738 | 14.782 | 1.00 | 40.84 | B | C |
| ATOM | 2710 | O | GLN | B | 864 | −16.640 | 19.798 | 14.890 | 1.00 | 40.71 | B | O |
| ATOM | 2711 | N | GLN | B | 865 | −16.852 | 17.725 | 14.029 | 1.00 | 34.97 | B | N |
| ATOM | 2712 | CA | GLN | B | 865 | −15.629 | 17.754 | 13.266 | 1.00 | 31.61 | B | C |
| ATOM | 2713 | CB | GLN | B | 865 | −15.589 | 16.516 | 12.378 | 1.00 | 28.65 | B | C |
| ATOM | 2714 | CG | GLN | B | 865 | −14.437 | 16.458 | 11.410 | 1.00 | 27.56 | B | C |
| ATOM | 2715 | CD | GLN | B | 865 | −14.698 | 17.265 | 10.155 | 1.00 | 26.59 | B | C |
| ATOM | 2716 | OE1 | GLN | B | 865 | −15.741 | 17.111 | 9.508 | 1.00 | 24.08 | B | O |
| ATOM | 2717 | NE2 | GLN | B | 865 | −13.747 | 18.126 | 9.797 | 1.00 | 25.55 | B | N |
| ATOM | 2718 | C | GLN | B | 865 | −15.479 | 19.035 | 12.445 | 1.00 | 30.61 | B | C |
| ATOM | 2719 | O | GLN | B | 865 | −14.467 | 19.735 | 12.552 | 1.00 | 28.62 | B | O |
| ATOM | 2720 | N | ARG | B | 866 | −16.490 | 19.339 | 11.638 | 1.00 | 29.87 | B | N |
| ATOM | 2721 | CA | ARG | B | 866 | −16.476 | 20.532 | 10.800 | 1.00 | 28.92 | B | C |
| ATOM | 2722 | CB | ARG | B | 866 | −17.797 | 20.668 | 10.040 | 1.00 | 29.98 | B | C |
| ATOM | 2723 | CG | ARG | B | 866 | −17.936 | 19.702 | 8.876 | 1.00 | 32.46 | B | C |
| ATOM | 2724 | CD | ARG | B | 866 | −19.170 | 20.020 | 8.056 | 1.00 | 31.87 | B | C |
| ATOM | 2725 | NE | ARG | B | 866 | −20.035 | 18.859 | 7.879 | 1.00 | 34.46 | B | N |
| ATOM | 2726 | CZ | ARG | B | 866 | −19.936 | 17.987 | 6.881 | 1.00 | 33.51 | B | C |
| ATOM | 2727 | NH1 | ARG | B | 866 | −19.005 | 18.129 | 5.948 | 1.00 | 33.94 | B | N |
| ATOM | 2728 | NH2 | ARG | B | 866 | −20.783 | 16.974 | 6.806 | 1.00 | 30.60 | B | N |
| ATOM | 2729 | C | ARG | B | 866 | −16.196 | 21.805 | 11.596 | 1.00 | 27.94 | B | C |
| ATOM | 2730 | O | ARG | B | 866 | −15.380 | 22.623 | 11.182 | 1.00 | 25.73 | B | O |
| ATOM | 2731 | N | ASP | B | 867 | −16.869 | 21.978 | 12.730 | 1.00 | 29.03 | B | N |
| ATOM | 2732 | CA | ASP | B | 867 | −16.635 | 23.151 | 13.566 | 1.00 | 30.85 | B | C |
| ATOM | 2733 | CB | ASP | B | 867 | −17.448 | 23.070 | 14.859 | 1.00 | 32.87 | B | C |
| ATOM | 2734 | CG | ASP | B | 867 | −18.942 | 23.283 | 14.630 | 1.00 | 36.23 | B | C |
| ATOM | 2735 | OD1 | ASP | B | 867 | −19.339 | 24.352 | 14.103 | 1.00 | 36.54 | B | O |
| ATOM | 2736 | OD2 | ASP | B | 867 | −19.726 | 22.376 | 14.985 | 1.00 | 38.32 | B | O |
| ATOM | 2737 | C | ASP | B | 867 | −15.157 | 23.296 | 13.904 | 1.00 | 30.96 | B | C |
| ATOM | 2738 | O | ASP | B | 867 | −14.558 | 24.329 | 13.599 | 1.00 | 31.28 | B | O |
| ATOM | 2739 | N | PHE | B | 868 | −14.571 | 22.267 | 14.526 | 1.00 | 32.13 | B | N |
| ATOM | 2740 | CA | PHE | B | 868 | −13.148 | 22.297 | 14.894 | 1.00 | 31.94 | B | C |
| ATOM | 2741 | CB | PHE | B | 868 | −12.675 | 20.940 | 15.446 | 1.00 | 29.88 | B | C |
| ATOM | 2742 | CG | PHE | B | 868 | −13.005 | 20.707 | 16.896 | 1.00 | 27.56 | B | C |
| ATOM | 2743 | CD1 | PHE | B | 868 | −14.312 | 20.517 | 17.306 | 1.00 | 26.67 | B | C |

-continued

| | | | | | | | | | | | |
|---|---|---|---|---|---|---|---|---|---|---|---|
| ATOM | 2744 | CD2 | PHE | B | 868 | −11.999 | 20.675 | 17.852 | 1.00 | 28.33 | B | C |
| ATOM | 2745 | CE1 | PHE | B | 868 | −14.612 | 20.301 | 18.648 | 1.00 | 27.39 | B | C |
| ATOM | 2746 | CE2 | PHE | B | 868 | −12.289 | 20.461 | 19.196 | 1.00 | 27.40 | B | C |
| ATOM | 2747 | CZ | PHE | B | 868 | −13.596 | 20.27b | 19.595 | 1.00 | 25.66 | B | C |
| ATOM | 2748 | C | PHE | B | 868 | −12.312 | 22.627 | 13.662 | 1.00 | 32.28 | B | C |
| ATOM | 2749 | O | PHE | B | 868 | −11.351 | 23.389 | 13.722 | 1.00 | 33.97 | B | O |
| ATOM | 2750 | N | GLN | B | 869 | −12.688 | 22.038 | 12.540 | 1.00 | 32.23 | B | N |
| ATOM | 2751 | CA | GLN | B | 869 | −11.974 | 22.249 | 11.291 | 1.00 | 32.63 | B | C |
| ATOM | 2752 | CB | GLN | B | 869 | −12.571 | 21.327 | 10.223 | 1.00 | 33.42 | B | C |
| ATOM | 2753 | CG | GLN | B | 869 | −11.852 | 21.318 | 8.896 | 1.00 | 38.59 | B | C |
| ATOM | 2754 | CD | GLN | B | 869 | −10.454 | 20.729 | 8.970 | 1.00 | 42.27 | B | C |
| ATOM | 2755 | OE1 | GLN | B | 869 | −9.720 | 20.742 | 7.982 | 1.00 | 45.09 | B | O |
| ATOM | 2756 | NE2 | GLN | B | 869 | −10.078 | 20.209 | 10.135 | 1.00 | 42.53 | B | N |
| ATOM | 2757 | C | GLN | B | 869 | −12.056 | 23.713 | 10.850 | 1.00 | 31.04 | B | C |
| ATOM | 2758 | O | GLN | B | 869 | −11.073 | 24.300 | 10.398 | 1.00 | 31.14 | B | O |
| ATOM | 2759 | N | ARG | B | 870 | −13.232 | 24.303 | 11.002 | 1.00 | 29.80 | B | N |
| ATOM | 2760 | CA | ARG | B | 870 | −13.453 | 25.684 | 10.600 | 1.00 | 28.79 | B | C |
| ATOM | 2761 | CB | ARG | B | 870 | −14.947 | 26.016 | 10.751 | 1.00 | 28.73 | B | C |
| ATOM | 2762 | CG | ARG | B | 870 | −15.346 | 27.449 | 10.417 | 1.00 | 29.41 | B | C |
| ATOM | 2763 | CD | ARG | B | 870 | −16.761 | 27.746 | 10.889 | 1.00 | 26.01 | B | C |
| ATOM | 2764 | NE | ARG | B | 870 | −16.875 | 27.628 | 12.338 | 1.00 | 24.89 | B | N |
| ATOM | 2765 | CZ | ARG | B | 870 | −17.761 | 26.859 | 12.960 | 1.00 | 26.54 | B | C |
| ATOM | 2766 | NH1 | ARG | B | 870 | −18.624 | 26.129 | 12.258 | 1.00 | 23.91 | B | N |
| ATOM | 2767 | NH2 | ARG | B | 870 | −17.780 | 26.815 | 14.288 | 1.00 | 23.42 | B | N |
| ATOM | 2768 | C | ARG | B | 870 | −12.602 | 26.657 | 11.415 | 1.00 | 28.20 | B | C |
| ATOM | 2769 | O | ARG | B | 870 | −11.893 | 27.492 | 10.857 | 1.00 | 27.89 | B | O |
| ATOM | 2770 | N | GLU | B | 871 | −12.670 | 26.535 | 12.735 | 1.00 | 28.44 | B | N |
| ATOM | 2771 | CA | GLU | B | 871 | −11.932 | 27.416 | 13.629 | 1.00 | 29.10 | B | C |
| ATOM | 2772 | CB | GLU | B | 871 | −12.327 | 27.110 | 15.073 | 1.00 | 28.98 | B | C |
| ATOM | 2773 | CG | GLU | B | 871 | −13.821 | 27.293 | 15.330 | 1.00 | 27.67 | B | C |
| ATOM | 2774 | CD | GLU | B | 871 | −14.295 | 28.709 | 15.029 | 1.00 | 30.59 | B | C |
| ATOM | 2775 | OE1 | GLU | B | 871 | −15.422 | 28.862 | 14.501 | 1.00 | 28.93 | B | O |
| ATOM | 2776 | OE2 | GLU | B | 871 | −13.542 | 29.668 | 15.326 | 1.00 | 29.15 | B | O |
| ATOM | 2777 | C | GLU | B | 871 | −10.414 | 27.353 | 13.454 | 1.00 | 30.42 | B | C |
| ATOM | 2778 | O | GLU | B | 871 | −9.746 | 28.386 | 13.315 | 1.00 | 29.98 | B | O |
| ATOM | 2779 | N | ILE | B | 872 | −9.864 | 26.147 | 13.448 | 1.00 | 30.79 | B | N |
| ATOM | 2780 | CA | ILE | B | 872 | −8.426 | 26.001 | 13.283 | 1.00 | 32.19 | B | C |
| ATOM | 2781 | CB | ILE | B | 872 | −8.012 | 24.524 | 13.279 | 1.00 | 33.29 | B | C |
| ATOM | 2782 | CG2 | ILE | B | 872 | −6.888 | 24.301 | 12.305 | 1.00 | 34.00 | B | C |
| ATOM | 2783 | CG1 | ILE | B | 872 | −7.572 | 24.114 | 14.678 | 1.00 | 33.72 | B | C |
| ATOM | 2784 | CD1 | ILE | B | 872 | −6.373 | 24.849 | 15.148 | 1.00 | 29.33 | B | C |
| ATOM | 2785 | C | ILE | B | 872 | −7.916 | 26.662 | 12.012 | 1.00 | 32.54 | B | C |
| ATOM | 2786 | O | ILE | B | 872 | −6.819 | 27.215 | 11.997 | 1.00 | 34.61 | B | O |
| ATOM | 2787 | N | GLN | B | 873 | −8.696 | 26.609 | 10.936 | 1.00 | 32.00 | B | N |
| ATOM | 2788 | CA | GLN | B | 873 | −8.253 | 27.234 | 9.697 | 1.00 | 29.37 | B | C |
| ATOM | 2789 | CB | GLN | B | 873 | −9.112 | 26.785 | 8.516 | 1.00 | 30.42 | B | C |
| ATOM | 2790 | CG | GLN | B | 873 | −9.011 | 25.305 | 8.255 | 1.00 | 33.60 | B | C |
| ATOM | 2791 | CD | GLN | B | 873 | −9.613 | 24.874 | 6.935 | 1.00 | 36.54 | B | C |
| ATOM | 2792 | OE1 | GLN | B | 873 | −9.545 | 23.695 | 6.584 | 1.00 | 40.58 | B | O |
| ATOM | 2793 | NE2 | GLN | B | 873 | −10.202 | 25.820 | 6.193 | 1.00 | 36.08 | B | N |
| ATOM | 2794 | C | GLN | B | 873 | −8.316 | 28.741 | 9.845 | 1.00 | 28.83 | B | C |
| ATOM | 2795 | O | GLN | B | 873 | −7.571 | 29.471 | 9.189 | 1.00 | 27.50 | B | O |
| ATOM | 2796 | N | ILE | B | 874 | −9.213 | 29.201 | 10.714 | 1.00 | 26.87 | B | N |
| ATOM | 2797 | CA | ILE | B | 874 | −9.365 | 30.627 | 10.971 | 1.00 | 26.03 | B | C |
| ATOM | 2798 | CB | ILE | B | 874 | −10.718 | 30.939 | 11.681 | 1.00 | 25.77 | B | C |
| ATOM | 2799 | CG2 | ILE | B | 874 | −10.687 | 32.326 | 12.277 | 1.00 | 25.42 | B | C |
| ATOM | 2800 | CG1 | ILE | B | 874 | −11.874 | 30.854 | 10.690 | 1.00 | 24.44 | B | C |
| ATOM | 2801 | CD1 | ILE | B | 874 | −13.199 | 31.183 | 11.296 | 1.00 | 25.79 | B | C |
| ATOM | 2802 | C | ILE | B | 874 | −8.216 | 31.066 | 11.875 | 1.00 | 27.22 | B | C |
| ATOM | 2803 | O | ILE | B | 874 | −7.586 | 32.106 | 11.648 | 1.00 | 26.87 | B | O |
| ATOM | 2804 | N | LEU | B | 875 | −7.947 | 30.251 | 12.898 | 1.00 | 27.62 | B | N |
| ATOM | 2805 | CA | LEU | B | 875 | −6.886 | 30.535 | 13.859 | 1.00 | 25.96 | B | C |
| ATOM | 2806 | CB | LEU | B | 875 | −7.024 | 29.638 | 15.099 | 1.00 | 24.59 | B | C |
| ATOM | 2807 | CG | LEU | B | 875 | −8.270 | 29.838 | 15.983 | 1.00 | 24.64 | B | C |
| ATOM | 2808 | CD1 | LEU | B | 875 | −8.328 | 28.786 | 17.075 | 1.00 | 22.44 | B | C |
| ATOM | 2809 | CD2 | LEU | B | 875 | −8.248 | 31.208 | 16.601 | 1.00 | 24.13 | B | C |
| ATOM | 2810 | C | LEU | B | 875 | −5.510 | 30.377 | 13.228 | 1.00 | 26.34 | B | C |
| ATOM | 2811 | O | LEU | B | 875 | −4.621 | 31.206 | 13.439 | 1.00 | 27.82 | B | O |
| ATOM | 2812 | N | LYS | B | 876 | −5.328 | 29.335 | 12.430 | 1.00 | 25.15 | B | N |
| ATOM | 2813 | CA | LYS | B | 876 | −4.034 | 29.145 | 11.796 | 1.00 | 25.86 | B | C |
| ATOM | 2814 | CB | LYS | B | 876 | −4.012 | 27.832 | 11.022 | 1.00 | 24.63 | B | C |
| ATOM | 2815 | CG | LYS | B | 876 | −2.646 | 27.477 | 10.473 | 1.00 | 24.05 | B | C |
| ATOM | 2816 | CD | LYS | B | 876 | −2.659 | 26.077 | 9.898 | 1.00 | 23.72 | B | C |
| ATOM | 2817 | CE | LYS | B | 876 | −1.280 | 25.687 | 9.445 | 1.00 | 23.59 | B | C |
| ATOM | 2818 | NZ | LYS | B | 876 | −1.240 | 24.405 | 8.706 | 1.00 | 24.88 | B | N |
| ATOM | 2819 | C | LYS | B | 876 | −3.648 | 30.307 | 10.866 | 1.00 | 26.99 | B | C |
| ATOM | 2820 | O | LYS | B | 876 | −2.461 | 30.594 | 10.689 | 1.00 | 29.84 | B | O |
| ATOM | 2821 | N | ALA | B | 877 | −4.634 | 30.973 | 10.269 | 1.00 | 26.24 | B | N |
| ATOM | 2822 | CA | ALA | B | 877 | −4.350 | 32.100 | 9.377 | 1.00 | 27.52 | B | C |
| ATOM | 2823 | CB | ALA | B | 877 | −5.592 | 32.435 | 8.548 | 1.00 | 26.74 | B | C |

-continued

| | | | | | | | | | | | |
|---|---|---|---|---|---|---|---|---|---|---|---|
| ATOM | 2824 | C | ALA | B | 877 | −3.858 | 33.352 | 10.144 | 1.00 | 28.24 | B C |
| ATOM | 2825 | O | ALA | B | 877 | −3.229 | 34.229 | 9.569 | 1.00 | 27.71 | B O |
| ATOM | 2826 | N | LEU | B | 878 | −4.140 | 33.428 | 11.442 | 1.00 | 30.40 | B N |
| ATOM | 2827 | CA | LEU | B | 878 | −3.702 | 34.561 | 12.266 | 1.00 | 29.17 | B C |
| ATOM | 2828 | CB | LEU | B | 878 | −4.304 | 34.452 | 13.656 | 1.00 | 27.14 | B C |
| ATOM | 2829 | CG | LEU | B | 878 | −5.822 | 34.321 | 13.719 | 1.00 | 27.92 | B C |
| ATOM | 2830 | CD1 | LEU | B | 878 | −6.218 | 33.768 | 15.073 | 1.00 | 27.76 | B C |
| ATOM | 2831 | CD2 | LEU | B | 878 | −6.465 | 35.663 | 13.458 | 1.00 | 26.98 | B C |
| ATOM | 2832 | C | LEU | B | 878 | −2.186 | 34.521 | 12.383 | 1.00 | 29.28 | B C |
| ATOM | 2833 | O | LEU | B | 878 | −1.619 | 33.457 | 12.610 | 1.00 | 28.90 | B O |
| ATOM | 2834 | N | HIS | B | 879 | −1.536 | 35.672 | 12.237 | 1.00 | 30.42 | B N |
| ATOM | 2835 | CA | HIS | B | 879 | −0.081 | 35.741 | 12.321 | 1.00 | 31.74 | B C |
| ATOM | 2836 | CB | HIS | B | 879 | 0.514 | 35.780 | 10.925 | 1.00 | 32.65 | B C |
| ATOM | 2837 | CG | HIS | B | 879 | 0.386 | 34.489 | 10.186 | 1.00 | 37.56 | B C |
| ATOM | 2838 | CD2 | HIS | B | 879 | 0.520 | 33.208 | 10.602 | 1.00 | 39.16 | B C |
| ATOM | 2839 | ND1 | HIS | B | 879 | 0.112 | 34.426 | 8.837 | 1.00 | 39.12 | B N |
| ATOM | 2840 | CE1 | HIS | B | 879 | 0.083 | 33.163 | 8.453 | 1.00 | 39.56 | B C |
| ATOM | 2841 | NE2 | HIS | B | 879 | 0.328 | 32.405 | 9.506 | 1.00 | 41.59 | B N |
| ATOM | 2842 | C | HIS | B | 879 | 0.459 | 36.918 | 13.125 | 1.00 | 32.27 | B C |
| ATOM | 2843 | O | HIS | B | 879 | 0.257 | 38.076 | 12.762 | 1.00 | 32.06 | B O |
| ATOM | 2844 | N | SER | B | 880 | 1.165 | 36.597 | 14.207 | 1.00 | 30.30 | B N |
| ATOM | 2845 | CA | SER | B | 880 | 1.767 | 37.590 | 15.091 | 1.00 | 30.83 | B C |
| ATOM | 2846 | CB | SER | B | 880 | 0.720 | 38.147 | 16.062 | 1.00 | 29.12 | B C |
| ATOM | 2847 | OG | SER | B | 880 | 1.336 | 38.938 | 17.063 | 1.00 | 25.06 | B O |
| ATOM | 2848 | C | SER | B | 880 | 2.923 | 36.964 | 15.882 | 1.00 | 31.96 | B C |
| ATOM | 2849 | O | SER | B | 880 | 2.840 | 35.818 | 16.334 | 1.00 | 32.79 | B O |
| ATOM | 2850 | N | ASP | B | 881 | 4.003 | 37.711 | 16.053 | 1.00 | 31.67 | B N |
| ATOM | 2851 | CA | ASP | B | 881 | 5.131 | 37.172 | 16.786 | 1.00 | 31.34 | B C |
| ATOM | 2852 | CB | ASP | B | 881 | 6.346 | 38.069 | 16.642 | 1.00 | 34.15 | B C |
| ATOM | 2853 | CG | ASP | B | 881 | 6.976 | 37.961 | 15.283 | 1.00 | 38.28 | B C |
| ATOM | 2854 | OD1 | ASP | B | 881 | 8.035 | 38.584 | 15.081 | 1.00 | 41.45 | B O |
| ATOM | 2855 | OD2 | ASP | B | 881 | 6.414 | 37.258 | 14.416 | 1.00 | 40.35 | B O |
| ATOM | 2856 | C | ASP | B | 881 | 4.806 | 37.010 | 18.249 | 1.00 | 28.71 | B C |
| ATOM | 2857 | O | ASP | B | 881 | 5.532 | 36.346 | 18.977 | 1.00 | 26.63 | B O |
| ATOM | 2858 | N | PHE | B | 882 | 3.709 | 37.618 | 18.681 | 1.00 | 26.82 | B N |
| ATOM | 2859 | CA | PHE | B | 882 | 3.319 | 37.526 | 20.081 | 1.00 | 25.00 | B C |
| ATOM | 2860 | CB | PHE | B | 882 | 3.045 | 38.923 | 20.628 | 1.00 | 25.06 | B C |
| ATOM | 2861 | CG | PHE | B | 882 | 4.170 | 39.886 | 20.397 | 1.00 | 25.00 | B C |
| ATOM | 2862 | CD1 | PHE | B | 882 | 5.431 | 39.631 | 20.899 | 1.00 | 26.44 | B C |
| ATOM | 2863 | CD2 | PHE | B | 882 | 3.979 | 41.021 | 19.631 | 1.00 | 27.51 | B C |
| ATOM | 2864 | CE1 | PHE | B | 882 | 6.491 | 40.492 | 20.636 | 1.00 | 27.79 | B C |
| ATOM | 2865 | CE2 | PHE | B | 882 | 5.030 | 41.884 | 19.365 | 1.00 | 27.41 | B C |
| ATOM | 2866 | CZ | PHE | B | 882 | 6.287 | 41.620 | 19.666 | 1.00 | 25.41 | B C |
| ATOM | 2867 | C | PHE | B | 882 | 2.093 | 36.630 | 20.254 | 1.00 | 23.95 | B C |
| ATOM | 2868 | O | PHE | B | 882 | 1.238 | 36.892 | 21.092 | 1.00 | 24.37 | B O |
| ATOM | 2869 | N | ILE | B | 883 | 2.033 | 35.561 | 19.463 | 1.00 | 23.06 | B N |
| ATOM | 2870 | CA | ILE | B | 883 | 0.921 | 34.616 | 19.492 | 1.00 | 23.35 | B C |
| ATOM | 2871 | CB | ILE | B | 883 | −0.083 | 34.904 | 18.339 | 1.00 | 25.35 | B C |
| ATOM | 2872 | CG2 | ILE | B | 883 | −0.362 | 33.652 | 17.546 | 1.00 | 25.61 | B C |
| ATOM | 2873 | CG1 | ILE | B | 883 | −1.378 | 35.470 | 18.907 | 1.00 | 24.93 | B C |
| ATOM | 2874 | CD1 | ILE | B | 883 | −1.239 | 36.865 | 19.365 | 1.00 | 23.61 | B C |
| ATOM | 2875 | C | ILE | B | 883 | 1.430 | 33.190 | 19.351 | 1.00 | 22.62 | B C |
| ATOM | 2876 | O | ILE | B | 883 | 2.351 | 32.917 | 18.587 | 1.00 | 19.13 | B O |
| ATOM | 2877 | N | VAL | B | 884 | 0.842 | 32.276 | 20.105 | 1.00 | 24.11 | B N |
| ATOM | 2878 | CA | VAL | B | 884 | 1.257 | 30.881 | 20.025 | 1.00 | 24.99 | B C |
| ATOM | 2879 | CB | VAL | B | 884 | 0.836 | 30.129 | 21.289 | 1.00 | 25.13 | B C |
| ATOM | 2880 | CG1 | VAL | B | 884 | 1.339 | 28.699 | 21.232 | 1.00 | 24.82 | B C |
| ATOM | 2881 | CG2 | VAL | B | 884 | 1.361 | 30.859 | 22.520 | 1.00 | 27.61 | B C |
| ATOM | 2882 | C | VAL | B | 884 | 0.595 | 30.252 | 18.792 | 1.00 | 24.61 | B C |
| ATOM | 2883 | O | VAL | B | 884 | −0.627 | 30.199 | 18.698 | 1.00 | 23.23 | B O |
| ATOM | 2884 | N | LYS | B | 885 | 1.415 | 29.783 | 17.857 | 1.00 | 25.26 | B N |
| ATOM | 2885 | CA | LYS | B | 885 | 0.929 | 29.198 | 16.612 | 1.00 | 25.39 | B C |
| ATOM | 2886 | CB | LYS | B | 885 | 2.100 | 28.837 | 15.702 | 1.00 | 25.63 | B C |
| ATOM | 2887 | CG | LYS | B | 885 | 3.023 | 29.989 | 15.351 | 1.00 | 28.38 | B C |
| ATOM | 2888 | CD | LYS | B | 885 | 4.276 | 29.480 | 14.643 | 1.00 | 30.17 | B C |
| ATOM | 2889 | CE | LYS | B | 885 | 5.217 | 30.615 | 14.293 | 1.00 | 32.49 | B C |
| ATOM | 2890 | NZ | LYS | B | 885 | 4.547 | 31.591 | 13.381 | 1.00 | 35.37 | B N |
| ATOM | 2891 | C | LYS | B | 885 | 0.058 | 27.968 | 16.751 | 1.00 | 25.44 | B C |
| ATOM | 2892 | O | LYS | B | 885 | 0.393 | 27.036 | 17.469 | 1.00 | 26.56 | B O |
| ATOM | 2893 | N | TYR | B | 886 | −1.073 | 27.982 | 16.063 | 1.00 | 25.34 | B N |
| ATOM | 2894 | CA | TYR | B | 886 | −1.954 | 26.833 | 16.045 | 1.00 | 25.02 | B C |
| ATOM | 2895 | CB | TYR | B | 886 | −3.417 | 27.277 | 15.944 | 1.00 | 25.04 | B C |
| ATOM | 2896 | CG | TYR | B | 886 | −4.100 | 27.564 | 17.274 | 1.00 | 21.78 | B C |
| ATOM | 2897 | CD1 | TYR | B | 886 | −4.291 | 26.560 | 18.220 | 1.00 | 20.76 | B C |
| ATOM | 2898 | CE1 | TYR | B | 886 | −4.962 | 26.809 | 19.403 | 1.00 | 18.65 | B C |
| ATOM | 2899 | CD2 | TYR | B | 886 | −4.597 | 28.820 | 17.556 | 1.00 | 20.53 | B C |
| ATOM | 2900 | CE2 | TYR | B | 886 | −5.266 | 29.075 | 18.728 | 1.00 | 20.17 | B C |
| ATOM | 2901 | CZ | TYR | B | 886 | −5.447 | 28.074 | 19.648 | 1.00 | 19.43 | B C |
| ATOM | 2902 | OH | TYR | B | 886 | −6.118 | 28.366 | 20.815 | 1.00 | 17.53 | B O |
| ATOM | 2903 | C | TYR | B | 886 | −1.508 | 26.123 | 14.768 | 1.00 | 24.51 | B C |

-continued

| | | | | | | | | | | | |
|---|---|---|---|---|---|---|---|---|---|---|---|
| ATOM | 2904 | O | TYR | B | 886 | −1.266 | 26.772 | 13.743 | 1.00 | 22.88 | B | O |
| ATOM | 2905 | N | ARG | B | 887 | −1.378 | 24.803 | 14.618 | 1.00 | 24.90 | B | N |
| ATOM | 2906 | CA | ARG | B | 887 | −0.916 | 24.070 | 13.645 | 1.00 | 24.72 | B | C |
| ATOM | 2907 | CB | ARG | B | 887 | 0.283 | 23.199 | 14.016 | 1.00 | 25.16 | B | C |
| ATOM | 2908 | CG | ARG | B | 887 | 1.551 | 23.983 | 14.248 | 1.00 | 27.60 | B | C |
| ATOM | 2909 | CD | ARG | B | 887 | 2.733 | 23.042 | 14.379 | 1.00 | 30.25 | B | C |
| ATOM | 2910 | NE | ARG | B | 887 | 2.962 | 22.287 | 13.154 | 1.00 | 31.62 | B | N |
| ATOM | 2911 | CZ | ARG | B | 887 | 3.892 | 21.349 | 13.023 | 1.00 | 32.40 | B | C |
| ATOM | 2912 | NH1 | ARG | B | 887 | 4.674 | 21.054 | 14.046 | 1.00 | 34.33 | B | N |
| ATOM | 2913 | NH2 | ARG | B | 887 | 4.049 | 20.710 | 11.669 | 1.00 | 33.94 | B | N |
| ATOM | 2914 | C | ARG | B | 887 | −1.946 | 23.220 | 12.919 | 1.00 | 23.82 | B | C |
| ATOM | 2915 | O | ARG | B | 887 | −1.855 | 23.047 | 11.706 | 1.00 | 24.22 | B | O |
| ATOM | 2916 | N | GLY | B | 888 | −2.916 | 22.681 | 13.649 | 1.00 | 23.86 | B | N |
| ATOM | 2917 | CA | GLY | B | 888 | −3.923 | 21.852 | 13.011 | 1.00 | 22.84 | B | C |
| ATOM | 2918 | C | GLY | B | 888 | −4.841 | 21.140 | 13.984 | 1.00 | 23.38 | B | C |
| ATOM | 2919 | O | GLY | B | 888 | −4.868 | 21.450 | 15.182 | 1.00 | 23.89 | B | O |
| ATOM | 2920 | N | VAL | B | 889 | −5.594 | 20.181 | 13.448 | 1.00 | 21.47 | B | N |
| ATOM | 2921 | CA | VAL | B | 889 | −6.543 | 19.373 | 14.210 | 1.00 | 21.70 | B | C |
| ATOM | 2922 | CB | VAL | B | 889 | −7.998 | 19.607 | 13.725 | 1.00 | 20.93 | B | C |
| ATOM | 2923 | CG1 | VAL | B | 889 | −8.921 | 18.534 | 14.281 | 1.00 | 19.14 | B | C |
| ATOM | 2924 | CG2 | VAL | B | 889 | −8.471 | 20.966 | 14.169 | 1.00 | 23.06 | B | C |
| ATOM | 2925 | C | VAL | B | 889 | −6.221 | 17.898 | 14.012 | 1.00 | 21.52 | B | C |
| ATOM | 2926 | O | VAL | B | 889 | −5.950 | 17.462 | 12.900 | 1.00 | 22.29 | B | O |
| ATOM | 2927 | N | SER | B | 890 | −6.276 | 17.117 | 15.080 | 1.00 | 22.47 | B | N |
| ATOM | 2928 | CA | SER | B | 890 | −5.966 | 15.705 | 14.945 | 1.00 | 24.44 | B | C |
| ATOM | 2929 | CB | SER | B | 890 | −5.233 | 15.195 | 16.183 | 1.00 | 21.47 | B | C |
| ATOM | 2930 | OG | SER | B | 890 | −6.168 | 14.893 | 17.203 | 1.00 | 23.05 | B | O |
| ATOM | 2931 | C | SER | B | 890 | −7.228 | 14.875 | 14.745 | 1.00 | 26.17 | B | C |
| ATOM | 2932 | O | SER | B | 890 | −8.289 | 15.185 | 15.291 | 1.00 | 27.00 | B | O |
| ATOM | 2933 | N | TYR | B | 891 | −7.105 | 13.820 | 13.948 | 1.00 | 27.10 | B | N |
| ATOM | 2934 | CA | TYR | B | 891 | −8.223 | 12.926 | 13.708 | 1.00 | 27.93 | B | C |
| ATOM | 2935 | CB | TYR | B | 891 | −8.644 | 12.987 | 12.243 | 1.00 | 27.86 | B | C |
| ATOM | 2936 | CG | TYR | B | 891 | −9.260 | 14.312 | 11.916 | 1.00 | 30.15 | B | C |
| ATOM | 2937 | CD1 | TYR | B | 891 | −10.480 | 14.672 | 12.447 | 1.00 | 31.47 | B | C |
| ATOM | 2938 | CE1 | TYR | B | 891 | −11.015 | 15.912 | 12.216 | 1.00 | 30.53 | B | C |
| ATOM | 2939 | CD2 | TYR | B | 891 | −8.594 | 15.231 | 11.140 | 1.00 | 27.69 | B | C |
| ATOM | 2940 | CE2 | TYR | B | 891 | −9.118 | 16.468 | 10.905 | 1.00 | 28.64 | B | C |
| ATOM | 2941 | CZ | TYR | B | 891 | −10.329 | 16.809 | 11.447 | 1.00 | 29.64 | B | C |
| ATOM | 2942 | OH | TYR | B | 891 | −10.851 | 18.069 | 11.246 | 1.00 | 30.89 | B | O |
| ATOM | 2943 | C | TYR | B | 891 | −7.863 | 11.506 | 14.116 | 1.00 | 28.23 | B | C |
| ATOM | 2944 | O | TYR | B | 891 | −6.87b | 10.943 | 13.648 | 1.00 | 25.30 | B | O |
| ATOM | 2945 | N | GLY | B | 892 | −8.698 | 10.956 | 14.992 | 1.00 | 30.66 | B | N |
| ATOM | 2946 | CA | GLY | B | 892 | −8.548 | 9.619 | 15.539 | 1.00 | 35.15 | B | C |
| ATOM | 2947 | C | GLY | B | 892 | −8.159 | 8.464 | 14.652 | 1.00 | 36.94 | B | C |
| ATOM | 2948 | O | GLY | B | 892 | −7.194 | 8.567 | 13.900 | 1.00 | 40.72 | B | O |
| ATOM | 2949 | N | PRO | B | 893 | −8.865 | 7.326 | 14.752 | 1.00 | 37.28 | B | N |
| ATOM | 2950 | CD | PRO | B | 893 | −8.482 | 6.075 | 14.068 | 1.00 | 37.20 | B | C |
| ATOM | 2951 | CA | PRO | B | 893 | −9.997 | 7.096 | 15.655 | 1.00 | 37.62 | B | C |
| ATOM | 2952 | CB | PRO | B | 893 | −10.583 | 5.791 | 15.135 | 1.00 | 37.35 | B | C |
| ATOM | 2953 | CG | PRO | B | 893 | −9.338 | 5.035 | 14.768 | 1.00 | 38.08 | B | C |
| ATOM | 2954 | C | PRO | B | 893 | −9.597 | 6.973 | 17.124 | 1.00 | 37.60 | B | C |
| ATOM | 2955 | O | PRO | B | 893 | −8.594 | 7.546 | 17.585 | 1.00 | 37.03 | B | O |
| ATOM | 2956 | N | GLY | B | 894 | −10.392 | 6.201 | 17.851 | 1.00 | 35.38 | B | N |
| ATOM | 2957 | CA | GLY | B | 894 | −10.121 | 6.004 | 19.262 | 1.00 | 33.52 | B | C |
| ATOM | 2958 | C | GLY | B | 894 | −10.552 | 7.189 | 20.100 | 1.00 | 31.99 | B | C |
| ATOM | 2959 | O | GLY | B | 894 | −11.030 | 8.188 | 19.565 | 1.00 | 29.77 | B | O |
| ATOM | 2960 | N | ARG | B | 895 | −10.383 | 7.070 | 21.417 | 1.00 | 32.32 | B | N |
| ATOM | 2961 | CA | ARG | B | 895 | −10.753 | 8.122 | 22.365 | 1.00 | 30.91 | B | C |
| ATOM | 2962 | CB | ARG | B | 895 | −10.360 | 7.722 | 23.797 | 1.00 | 32.42 | B | C |
| ATOM | 2963 | CG | ARG | B | 895 | −11.237 | 6.645 | 24.398 | 1.00 | 35.42 | B | C |
| ATOM | 2964 | CD | ARG | B | 895 | −10.720 | 6.093 | 25.744 | 1.00 | 37.59 | B | C |
| ATOM | 2965 | NE | ARG | B | 895 | −10.850 | 7.020 | 26.866 | 1.00 | 38.06 | B | N |
| ATOM | 2966 | CZ | ARG | B | 895 | −9.883 | 7.830 | 27.285 | 1.00 | 41.12 | B | C |
| ATOM | 2967 | NH1 | ARG | B | 895 | −8.699 | 7.829 | 26.676 | 1.00 | 40.31 | B | N |
| ATOM | 2968 | NH2 | ARG | B | 895 | −10.105 | 8.641 | 28.313 | 1.00 | 40.07 | B | N |
| ATOM | 2969 | C | ARG | B | 895 | −10.109 | 9.460 | 22.032 | 1.00 | 28.48 | B | C |
| ATOM | 2970 | O | ARG | B | 895 | −10.770 | 10.496 | 22.077 | 1.00 | 27.31 | B | O |
| ATOM | 2971 | N | GLN | B | 896 | −8.826 | 9.452 | 21.695 | 1.00 | 26.23 | B | N |
| ATOM | 2972 | CA | GLN | B | 896 | −8.167 | 10.711 | 21.397 | 1.00 | 27.50 | B | C |
| ATOM | 2973 | CB | GLN | B | 896 | −6.704 | 10.671 | 21.852 | 1.00 | 26.61 | B | C |
| ATOM | 2974 | CG | GLN | B | 896 | −6.539 | 10.509 | 23.361 | 1.00 | 21.98 | B | C |
| ATOM | 2975 | CD | GLN | B | 896 | −5.128 | 10.816 | 23.634 | 1.00 | 23.58 | B | C |
| ATOM | 2976 | OE1 | GLN | B | 896 | −4.150 | 10.290 | 23.298 | 1.00 | 26.22 | B | O |
| ATOM | 2977 | NE2 | GLN | B | 896 | −5.015 | 11.667 | 24.845 | 1.00 | 21.74 | B | N |
| ATOM | 2978 | C | GLN | B | 896 | −8.248 | 11.133 | 19.941 | 1.00 | 28.56 | B | C |
| ATOM | 2979 | O | GLN | B | 896 | −7.594 | 10.558 | 19.074 | 1.00 | 31.99 | B | O |
| ATOM | 2980 | N | SER | B | 897 | −9.051 | 12.158 | 19.679 | 1.00 | 28.29 | B | N |
| ATOM | 2981 | CA | SER | B | 897 | −9.218 | 12.678 | 18.327 | 1.00 | 26.97 | B | C |
| ATOM | 2982 | CB | SER | B | 897 | −10.161 | 11.770 | 17.532 | 1.00 | 26.11 | B | C |
| ATOM | 2983 | OG | SER | B | 897 | −10.161 | 12.129 | 16.162 | 1.00 | 24.03 | B | O |

-continued

| | | | | | | | | | | | |
|---|---|---|---|---|---|---|---|---|---|---|---|
| ATOM | 2984 | C | SER | B | 897 | −9.767 | 14.113 | 18.357 | 1.00 | 26.27 | B | C |
| ATOM | 2985 | O | SER | B | 897 | −10.235 | 14.587 | 19.392 | 1.00 | 24.86 | B | O |
| ATOM | 2986 | N | LEU | B | 898 | −9.722 | 14.798 | 17.219 | 1.00 | 25.36 | B | N |
| ATOM | 2987 | CA | LEU | B | 898 | −10.204 | 16.170 | 17.160 | 1.00 | 26.00 | B | C |
| ATOM | 2988 | CB | LEU | B | 896 | −11.723 | 16.216 | 17.341 | 1.00 | 26.02 | B | C |
| ATOM | 2989 | CG | LEU | B | 898 | −12.565 | 15.882 | 16.108 | 1.00 | 24.07 | B | C |
| ATOM | 2990 | CD1 | LEU | B | 898 | −14.011 | 15.662 | 16.510 | 1.00 | 23.90 | B | C |
| ATOM | 2991 | CD2 | LEU | B | 898 | −12.459 | 17.016 | 15.113 | 1.00 | 24.33 | B | C |
| ATOM | 2992 | C | LEU | B | 898 | −9.530 | 17.007 | 18.242 | 1.00 | 26.30 | B | C |
| ATOM | 2993 | O | LEU | B | 898 | −10.170 | 17.830 | 18.888 | 1.00 | 28.60 | B | O |
| ATOM | 2994 | N | ARG | B | 899 | −8.234 | 16.779 | 18.437 | 1.00 | 25.95 | B | N |
| ATOM | 2995 | CA | ARG | B | 899 | −7.457 | 17.516 | 19.425 | 1.00 | 24.40 | B | C |
| ATOM | 2996 | CB | ARG | B | 899 | −6.443 | 16.595 | 20.114 | 1.00 | 22.59 | B | C |
| ATOM | 2997 | CG | ARG | B | 899 | −7.058 | 15.350 | 20.727 | 1.00 | 22.64 | B | C |
| ATOM | 2998 | CD | ARG | B | 899 | −6.076 | 14.637 | 21.641 | 1.00 | 23.58 | B | C |
| ATOM | 2999 | NE | ARG | B | 899 | −4.855 | 14.240 | 20.951 | 1.00 | 23.78 | B | N |
| ATOM | 3000 | CZ | ARG | B | 899 | −3.763 | 13.805 | 21.570 | 1.00 | 24.40 | B | C |
| ATOM | 3001 | NH1 | ARG | B | 899 | −2.696 | 13.461 | 20.868 | 1.00 | 26.08 | B | N |
| ATOM | 3002 | NH2 | ARG | B | 899 | −3.727 | 13.730 | 22.890 | 1.00 | 23.65 | B | N |
| ATOM | 3003 | C | ARG | B | 899 | −6.731 | 18.659 | 18.711 | 1.00 | 24.37 | B | C |
| ATOM | 3004 | O | ARG | B | 899 | −6.476 | 18.601 | 17.509 | 1.00 | 25.32 | B | O |
| ATOM | 3005 | N | LEU | B | 900 | −6.394 | 19.693 | 19.461 | 1.00 | 22.83 | B | N |
| ATOM | 3006 | CA | LEU | B | 900 | −5.736 | 20.848 | 18.901 | 1.00 | 22.29 | B | C |
| ATOM | 3007 | CB | LEU | B | 900 | −6.203 | 22.095 | 19.673 | 1.00 | 23.06 | B | C |
| ATOM | 3008 | CG | LEU | B | 900 | −7.727 | 22.284 | 19.877 | 1.00 | 18.99 | B | C |
| ATOM | 3009 | CD1 | LEU | B | 900 | −8.021 | 23.367 | 20.901 | 1.00 | 20.49 | B | C |
| ATOM | 3010 | CD2 | LEU | B | 900 | −8.369 | 22.632 | 18.564 | 1.00 | 20.01 | B | C |
| ATOM | 3011 | C | LEU | B | 900 | −4.218 | 20.681 | 18.980 | 1.00 | 23.70 | B | C |
| ATOM | 3012 | O | LEU | B | 900 | −3.663 | 20.403 | 20.047 | 1.00 | 24.33 | B | O |
| ATOM | 3013 | N | VAL | B | 901 | −3.552 | 20.839 | 17.841 | 1.00 | 24.29 | B | N |
| ATOM | 3014 | CA | VAL | B | 901 | −2.102 | 20.713 | 17.765 | 1.00 | 23.11 | B | C |
| ATOM | 3015 | CB | VAL | B | 901 | −1.679 | 19.896 | 16.508 | 1.00 | 23.04 | B | C |
| ATOM | 3016 | CG1 | VAL | B | 901 | −0.170 | 19.702 | 16.485 | 1.00 | 16.20 | B | C |
| ATOM | 3017 | CG2 | VAL | B | 901 | −2.396 | 18.538 | 16.500 | 1.00 | 21.11 | B | C |
| ATOM | 3018 | C | VAL | B | 901 | −1.499 | 22.113 | 17.677 | 1.00 | 24.80 | B | C |
| ATOM | 3019 | O | VAL | B | 901 | −1.844 | 22.890 | 16.790 | 1.00 | 25.60 | B | O |
| ATOM | 3020 | N | MET | B | 902 | −0.587 | 22.433 | 18.587 | 1.00 | 26.09 | B | N |
| ATOM | 3021 | CA | MET | B | 902 | 0.026 | 23.752 | 18.591 | 1.00 | 25.58 | B | C |
| ATOM | 3022 | CB | MET | B | 902 | −0.412 | 24.530 | 19.822 | 1.00 | 26.88 | B | C |
| ATOM | 3023 | CG | MET | B | 902 | −1.678 | 24.456 | 20.127 | 1.00 | 27.85 | B | C |
| ATOM | 3024 | SD | MET | B | 902 | −2.092 | 24.944 | 21.814 | 1.00 | 28.15 | B | S |
| ATOM | 3025 | CE | MET | B | 902 | −2.056 | 23.354 | 22.644 | 1.00 | 23.45 | B | C |
| ATOM | 3026 | C | MET | B | 902 | 1.533 | 23.636 | 18.650 | 1.00 | 25.59 | B | C |
| ATOM | 3027 | O | MET | B | 902 | 2.072 | 22.556 | 18.912 | 1.00 | 24.38 | B | O |
| ATOM | 3028 | N | GLU | B | 903 | 2.205 | 24.762 | 18.420 | 1.00 | 24.65 | B | N |
| ATOM | 3029 | CA | GLU | B | 903 | 3.650 | 24.798 | 18.509 | 1.00 | 26.30 | B | C |
| ATOM | 3030 | CB | GLU | B | 903 | 4.199 | 26.136 | 17.987 | 1.00 | 25.66 | B | C |
| ATOM | 3031 | CG | GLU | B | 903 | 3.970 | 27.328 | 18.910 | 1.00 | 27.57 | B | C |
| ATOM | 3032 | CD | GLU | B | 903 | 4.572 | 28.629 | 18.381 | 1.00 | 26.55 | B | C |
| ATOM | 3033 | OE1 | GLU | B | 903 | 5.638 | 28.581 | 17.728 | 1.00 | 25.12 | B | O |
| ATOM | 3034 | OE2 | GLU | B | 903 | 3.980 | 29.699 | 18.638 | 1.00 | 25.41 | B | O |
| ATOM | 3035 | C | GLU | B | 903 | 3.910 | 24.651 | 20.010 | 1.00 | 26.13 | B | C |
| ATOM | 3036 | O | GLU | B | 903 | 3.087 | 25.068 | 20.830 | 1.00 | 28.56 | B | O |
| ATOM | 3037 | N | TYR | B | 904 | 5.039 | 24.058 | 20.369 | 1.00 | 24.40 | B | N |
| ATOM | 3038 | CA | TYR | B | 904 | 5.384 | 23.840 | 21.769 | 1.00 | 24.74 | B | C |
| ATOM | 3039 | CB | TYR | B | 904 | 5.891 | 22.409 | 21.921 | 1.00 | 23.92 | B | C |
| ATOM | 3040 | CG | TYR | B | 904 | 6.433 | 22.085 | 23.289 | 1.00 | 24.77 | B | C |
| ATOM | 3041 | CD1 | TYR | B | 904 | 5.590 | 21.959 | 24.379 | 1.00 | 24.64 | B | C |
| ATOM | 3042 | CE1 | TYR | B | 904 | 6.084 | 21.600 | 25.613 | 1.00 | 24.42 | B | C |
| ATOM | 3043 | CD2 | TYR | B | 904 | 7.791 | 21.852 | 23.480 | 1.00 | 24.71 | B | C |
| ATOM | 3044 | CE2 | TYR | B | 904 | 8.291 | 21.492 | 24.706 | 1.00 | 22.58 | B | C |
| ATOM | 3045 | CZ | TYR | B | 904 | 7.435 | 21.363 | 25.766 | 1.00 | 23.33 | B | C |
| ATOM | 3046 | OH | TYR | B | 904 | 7.932 | 20.953 | 26.978 | 1.00 | 25.34 | B | O |
| ATOM | 3047 | C | TYR | B | 904 | 6.433 | 24.809 | 22.340 | 1.00 | 24.37 | B | C |
| ATOM | 3048 | O | TYR | B | 904 | 7.525 | 24.950 | 21.780 | 1.00 | 23.11 | B | O |
| ATOM | 3049 | N | LEU | B | 905 | 6.097 | 25.470 | 23.448 | 1.00 | 23.71 | B | N |
| ATOM | 3050 | CA | LEU | B | 905 | 7.025 | 26.394 | 24.113 | 1.00 | 23.78 | B | C |
| ATOM | 3051 | CB | LEU | B | 905 | 6.398 | 27.770 | 24.306 | 1.00 | 23.71 | B | C |
| ATOM | 3052 | CG | LEU | B | 905 | 6.535 | 28.734 | 23.124 | 1.00 | 24.68 | B | C |
| ATOM | 3053 | CD1 | LEU | B | 905 | 5.750 | 28.211 | 21.936 | 1.00 | 22.49 | B | C |
| ATOM | 3054 | CD2 | LEU | B | 905 | 6.026 | 30.119 | 23.541 | 1.00 | 23.69 | B | C |
| ATOM | 3055 | C | LEU | B | 905 | 7.372 | 25.823 | 25.470 | 1.00 | 23.58 | B | C |
| ATOM | 3056 | O | LEU | B | 905 | 6.633 | 26.026 | 26.429 | 1.00 | 24.54 | B | O |
| ATOM | 3057 | N | PRO | B | 906 | 8.513 | 25.114 | 25.568 | 1.00 | 24.82 | B | N |
| ATOM | 3058 | CD | PRO | B | 906 | 9.481 | 25.084 | 24.457 | 1.00 | 26.24 | B | C |
| ATOM | 3059 | CA | PRO | B | 906 | 9.080 | 24.443 | 26.743 | 1.00 | 26.73 | B | C |
| ATOM | 3060 | CB | PRO | B | 906 | 10.366 | 23.822 | 26.191 | 1.00 | 26.64 | B | C |
| ATOM | 3061 | CG | PRO | B | 906 | 10.787 | 24.789 | 25.168 | 1.00 | 25.89 | B | C |
| ATOM | 3062 | C | PRO | B | 906 | 9.316 | 25.248 | 28.024 | 1.00 | 28.44 | B | C |
| ATOM | 3063 | O | PRO | B | 906 | 9.476 | 24.663 | 29.098 | 1.00 | 31.05 | B | O |

-continued

| | | | | | | | | | | | |
|---|---|---|---|---|---|---|---|---|---|---|---|
| ATOM | 3064 | N | SER | B | 907 | 9.338 | 26.571 | 27.938 | 1.00 | 27.81 | B | N |
| ATOM | 3065 | CA | SER | B | 907 | 9.552 | 27.360 | 29.143 | 1.00 | 25.91 | B | C |
| ATOM | 3066 | CB | SER | B | 907 | 10.091 | 28.739 | 28.793 | 1.00 | 25.32 | B | C |
| ATOM | 3067 | CG | SER | B | 907 | 11.451 | 28.635 | 28.422 | 1.00 | 25.14 | B | O |
| ATOM | 3068 | C | SER | B | 907 | 8.319 | 27.486 | 30.024 | 1.00 | 24.89 | B | C |
| ATOM | 3069 | O | SER | B | 907 | 8.420 | 27.921 | 31.164 | 1.00 | 25.08 | B | O |
| ATOM | 3070 | N | GLY | B | 908 | 7.153 | 27.115 | 29.504 | 1.00 | 24.02 | B | N |
| ATOM | 3071 | CA | GLY | B | 908 | 5.949 | 27.173 | 30.318 | 1.00 | 23.21 | B | C |
| ATOM | 3072 | C | GLY | B | 908 | 5.254 | 28.513 | 30.404 | 1.00 | 23.91 | B | C |
| ATOM | 3073 | O | GLY | B | 908 | 5.668 | 29.485 | 29.762 | 1.00 | 23.15 | B | O |
| ATOM | 3074 | N | CYS | B | 909 | 4.199 | 28.565 | 31.220 | 1.00 | 23.69 | B | N |
| ATOM | 3075 | CA | CYS | B | 909 | 3.405 | 29.783 | 31.391 | 1.00 | 24.23 | B | C |
| ATOM | 3076 | CB | CYS | B | 909 | 2.080 | 29.468 | 32.097 | 1.00 | 23.91 | B | C |
| ATOM | 3077 | SG | CYS | B | 909 | 2.192 | 28.992 | 33.844 | 1.00 | 26.62 | B | S |
| ATOM | 3078 | C | CYS | B | 909 | 4.116 | 30.922 | 32.116 | 1.00 | 25.56 | B | C |
| ATOM | 3079 | O | CYS | B | 909 | 5.124 | 30.722 | 32.781 | 1.00 | 28.14 | B | O |
| ATOM | 3080 | N | LEU | B | 910 | 3.575 | 32.126 | 31.994 | 1.00 | 25.80 | B | N |
| ATOM | 3081 | CA | LEU | B | 910 | 4.187 | 33.280 | 32.612 | 1.00 | 25.97 | B | C |
| ATOM | 3082 | CB | LEU | B | 910 | 3.703 | 34.555 | 31.928 | 1.00 | 25.51 | B | C |
| ATOM | 3083 | CG | LEU | B | 910 | 4.255 | 35.889 | 32.424 | 1.00 | 21.94 | B | C |
| ATOM | 3084 | CD1 | LEU | B | 910 | 5.764 | 35.900 | 32.325 | 1.00 | 19.02 | B | C |
| ATOM | 3085 | CD2 | LEU | B | 910 | 3.651 | 37.004 | 31.588 | 1.00 | 21.42 | B | C |
| ATOM | 3086 | C | LEU | B | 910 | 3.841 | 33.319 | 34.075 | 1.00 | 27.73 | B | C |
| ATOM | 3087 | O | LEU | B | 910 | 4.581 | 33.882 | 24.872 | 1.00 | 29.03 | B | O |
| ATOM | 3088 | N | ARG | B | 911 | 2.710 | 32.718 | 24.423 | 1.00 | 29.17 | B | N |
| ATOM | 3089 | CA | ARG | B | 911 | 2.261 | 32.677 | 25.804 | 1.00 | 30.07 | B | C |
| ATOM | 3090 | CB | ARG | B | 911 | 0.955 | 31.886 | 35.907 | 1.00 | 30.79 | B | C |
| ATOM | 3091 | CG | ARG | B | 911 | 0.360 | 31.832 | 37.299 | 1.00 | 31.95 | B | C |
| ATOM | 3092 | CD | ARG | B | 911 | 0.525 | 30.472 | 37.965 | 1.00 | 35.46 | B | C |
| ATOM | 3093 | NE | ARG | B | 911 | −0.638 | 29.607 | 37.749 | 1.00 | 37.85 | B | N |
| ATOM | 3094 | CZ | ARG | B | 911 | −0.706 | 28.645 | 36.831 | 1.00 | 37.82 | B | C |
| ATOM | 3095 | NH1 | ARG | B | 911 | 0.336 | 28.414 | 36.039 | 1.00 | 37.46 | B | N |
| ATOM | 3096 | NH2 | ARG | B | 911 | −1.819 | 27.924 | 36.696 | 1.00 | 34.64 | B | N |
| ATOM | 3097 | C | ARG | B | 911 | 3.329 | 32.051 | 36.692 | 1.00 | 31.19 | B | C |
| ATOM | 3098 | O | ARG | B | 911 | 3.693 | 32.627 | 37.711 | 1.00 | 31.62 | B | O |
| ATOM | 3099 | N | ASP | B | 912 | 3.842 | 30.886 | 36.298 | 1.00 | 31.73 | B | N |
| ATOM | 3100 | CA | ASP | B | 912 | 4.870 | 30.195 | 37.081 | 1.00 | 32.01 | B | C |
| ATOM | 3101 | CB | ASP | B | 912 | 4.969 | 28.732 | 36.654 | 1.00 | 31.15 | B | C |
| ATOM | 3102 | CG | ASP | B | 912 | 3.686 | 27.962 | 36.903 | 1.00 | 33.95 | B | C |
| ATOM | 3103 | OD1 | ASP | B | 912 | 3.597 | 26.796 | 36.461 | 1.00 | 37.34 | B | O |
| ATOM | 3104 | OD2 | ASP | B | 912 | 2.768 | 28.515 | 37.542 | 1.00 | 35.80 | B | O |
| ATOM | 3105 | C | ASP | B | 912 | 6.244 | 30.846 | 36.946 | 1.00 | 32.72 | B | C |
| ATOM | 3106 | O | ASP | B | 912 | 7.044 | 30.842 | 37.886 | 1.00 | 35.14 | B | O |
| ATOM | 3107 | N | PHE | B | 913 | 6.512 | 31.396 | 35.768 | 1.00 | 30.42 | B | N |
| ATOM | 3108 | CA | PHE | B | 913 | 7.781 | 32.047 | 35.493 | 1.00 | 27.92 | B | C |
| ATOM | 3109 | CB | PHE | B | 913 | 7.789 | 32.552 | 34.057 | 1.00 | 27.63 | B | C |
| ATOM | 3110 | CG | PHE | B | 913 | 9.131 | 32.976 | 33.575 | 1.00 | 24.31 | B | C |
| ATOM | 3111 | CD1 | PHE | B | 913 | 10.023 | 32.041 | 33.077 | 1.00 | 26.49 | B | C |
| ATOM | 3112 | CD2 | PHE | B | 913 | 9.498 | 34.313 | 33.601 | 1.00 | 25.91 | B | C |
| ATOM | 3113 | CE1 | PHE | B | 913 | 11.270 | 32.427 | 32.604 | 1.00 | 25.71 | B | C |
| ATOM | 3114 | CE2 | PHE | B | 913 | 10.741 | 34.717 | 33.133 | 1.00 | 26.67 | B | C |
| ATOM | 3115 | CZ | PHE | B | 913 | 11.632 | 33.769 | 32.630 | 1.00 | 26.64 | B | C |
| ATOM | 3116 | C | PHE | B | 913 | 7.969 | 33.228 | 36.439 | 1.00 | 28.84 | B | C |
| ATOM | 3117 | O | PHE | B | 913 | 9.021 | 33.396 | 37.061 | 1.00 | 28.01 | B | O |
| ATOM | 3118 | N | LEU | B | 914 | 6.941 | 34.059 | 36.525 | 1.00 | 28.32 | B | N |
| ATOM | 3119 | CA | LEU | B | 914 | 6.989 | 35.217 | 37.389 | 1.00 | 28.91 | B | C |
| ATOM | 3120 | CB | LEU | B | 914 | 5.641 | 35.944 | 37.369 | 1.00 | 26.17 | B | C |
| ATOM | 3121 | CG | LEU | B | 914 | 5.350 | 36.893 | 36.203 | 1.00 | 25.31 | B | C |
| ATOM | 3122 | CD1 | LEU | B | 914 | 3.852 | 37.120 | 36.120 | 1.00 | 23.40 | B | C |
| ATOM | 3123 | CD2 | LEU | B | 914 | 6.086 | 38.217 | 36.391 | 1.00 | 21.60 | B | C |
| ATOM | 3124 | C | LEU | B | 914 | 7.351 | 34.839 | 38.823 | 1.00 | 30.29 | B | C |
| ATOM | 3125 | O | LEU | B | 914 | 8.151 | 35.518 | 39.461 | 1.00 | 31.24 | B | O |
| ATOM | 3126 | N | GLN | B | 915 | 6.718 | 33.750 | 39.322 | 1.00 | 30.78 | B | N |
| ATOM | 3127 | CA | GLN | B | 915 | 7.036 | 33.326 | 40.695 | 1.00 | 31.85 | B | C |
| ATOM | 3128 | CB | GLN | B | 915 | 6.017 | 32.263 | 41.107 | 1.00 | 28.47 | B | C |
| ATOM | 3129 | CG | GLN | B | 915 | 4.599 | 32.792 | 41.121 | 1.00 | 26.27 | B | C |
| ATOM | 3130 | CD | GLN | B | 915 | 3.551 | 31.705 | 41.216 | 1.00 | 27.48 | B | C |
| ATOM | 3131 | OE1 | GLN | B | 915 | 2.756 | 31.690 | 42.143 | 1.00 | 28.95 | B | O |
| ATOM | 3132 | NE1 | GLN | B | 915 | 3.545 | 30.791 | 40.253 | 1.00 | 29.42 | B | N |
| ATOM | 3133 | C | GLN | B | 915 | 8.453 | 32.817 | 40.943 | 1.00 | 32.63 | B | C |
| ATOM | 3134 | O | GLN | B | 915 | 9.059 | 33.123 | 41.962 | 1.00 | 31.97 | B | O |
| ATOM | 3135 | N | ARG | B | 916 | 8.980 | 32.049 | 40.008 | 1.00 | 35.56 | B | N |
| ATOM | 3136 | CA | ARG | B | 916 | 10.318 | 31.510 | 40.144 | 1.00 | 39.61 | B | C |
| ATOM | 3137 | CB | ARG | B | 916 | 10.593 | 30.538 | 39.001 | 1.00 | 41.84 | B | C |
| ATOM | 3138 | CG | ARG | B | 916 | 12.058 | 30.148 | 38.868 | 1.00 | 46.16 | B | C |
| ATOM | 3139 | CD | ARG | B | 916 | 12.473 | 29.106 | 39.908 | 1.00 | 51.32 | B | C |
| ATOM | 3140 | NE | ARG | B | 916 | 12.152 | 27.738 | 39.487 | 1.00 | 55.40 | B | N |
| ATOM | 3141 | CZ | ARG | B | 916 | 12.816 | 27.058 | 38.554 | 1.00 | 55.68 | B | C |
| ATOM | 3142 | NH1 | ARG | B | 916 | 13.853 | 27.607 | 37.931 | 1.00 | 55.82 | B | N |
| ATOM | 3143 | NH2 | ARG | B | 916 | 12.441 | 25.824 | 38.243 | 1.00 | 56.52 | B | N |

| | | | | | -continued | | | | | | |
|---|---|---|---|---|---|---|---|---|---|---|---|
| ATOM | 3144 | C | ARG | B | 916 | 11.420 | 32.568 | 40.162 | 1.00 | 41.25 | B | C |
| ATOM | 3145 | O | ARG | B | 916 | 12.159 | 32.697 | 41.136 | 1.00 | 43.76 | B | O |
| ATOM | 3146 | N | HIS | B | 917 | 11.532 | 33.323 | 39.076 | 1.00 | 41.99 | B | N |
| ATOM | 3147 | CA | HIS | B | 917 | 12.578 | 34.324 | 38.954 | 1.00 | 41.77 | B | C |
| ATOM | 3148 | CB | HIS | B | 917 | 13.046 | 34.404 | 37.504 | 1.00 | 42.37 | B | C |
| ATOM | 3149 | CG | HIS | B | 917 | 13.113 | 33.077 | 36.817 | 1.00 | 43.07 | B | C |
| ATOM | 3150 | CD2 | HIS | B | 917 | 14.170 | 32.340 | 36.402 | 1.00 | 43.65 | B | C |
| ATOM | 3151 | ND1 | HIS | B | 917 | 11.987 | 32.376 | 36.443 | 1.00 | 44.34 | B | N |
| ATOM | 3152 | CE1 | HIS | B | 917 | 12.347 | 31.267 | 35.822 | 1.00 | 44.79 | B | C |
| ATOM | 3153 | NE2 | HIS | B | 917 | 13.666 | 31.222 | 35.783 | 1.00 | 44.29 | B | N |
| ATOM | 3154 | C | HIS | B | 917 | 12.179 | 35.707 | 39.419 | 1.00 | 41.88 | B | C |
| ATOM | 3155 | O | HIS | B | 917 | 12.767 | 36.696 | 38.989 | 1.00 | 41.51 | B | O |
| ATOM | 3156 | N | ARG | B | 918 | 11.184 | 35.778 | 40.294 | 1.00 | 42.86 | B | N |
| ATOM | 3157 | CA | ARG | B | 918 | 10.718 | 37.060 | 40.813 | 1.00 | 44.49 | B | C |
| ATOM | 3158 | CB | ARG | B | 918 | 9.802 | 36.849 | 42.017 | 1.00 | 45.42 | B | C |
| ATOM | 3159 | CG | ARG | B | 918 | 9.269 | 38.145 | 42.613 | 1.00 | 47.61 | B | C |
| ATOM | 3160 | CD | ARG | B | 918 | 8.412 | 37.874 | 43.839 | 1.00 | 49.68 | B | C |
| ATOM | 3161 | NE | ARG | B | 918 | 7.700 | 39.061 | 44.301 | 1.00 | 52.10 | B | N |
| ATOM | 3162 | CZ | ARG | B | 918 | 8.266 | 40.249 | 44.470 | 1.00 | 55.07 | B | C |
| ATOM | 3163 | NH1 | ARG | B | 918 | 9.557 | 40.410 | 44.208 | 1.00 | 56.53 | B | N |
| ATOM | 3164 | NH2 | ARG | B | 918 | 7.547 | 41.274 | 44.919 | 1.00 | 55.39 | B | N |
| ATOM | 3165 | C | ARG | B | 918 | 11.901 | 37.900 | 41.254 | 1.00 | 45.45 | B | C |
| ATOM | 3166 | O | ARG | B | 918 | 11.879 | 39.126 | 41.168 | 1.00 | 45.70 | B | O |
| ATOM | 3167 | N | ALA | B | 919 | 12.934 | 32.217 | 41.730 | 1.00 | 46.64 | B | N |
| ATOM | 3168 | CA | ALA | B | 919 | 14.135 | 37.868 | 42.219 | 1.00 | 46.70 | B | C |
| ATOM | 3169 | CB | ALA | B | 919 | 15.139 | 36.816 | 42.670 | 1.00 | 46.55 | B | C |
| ATOM | 3170 | C | ALA | B | 919 | 14.789 | 38.813 | 41.222 | 1.00 | 46.47 | B | C |
| ATOM | 3171 | O | ALA | B | 919 | 15.070 | 39.959 | 41.555 | 1.00 | 46.26 | B | O |
| ATOM | 3172 | N | ARG | B | 920 | 15.020 | 38.345 | 40.000 | 1.00 | 45.92 | B | N |
| ATOM | 3173 | CA | ARG | B | 920 | 15.680 | 39.180 | 39.011 | 1.00 | 46.71 | B | C |
| ATOM | 3174 | CB | ARG | B | 920 | 16.943 | 38.464 | 38.500 | 1.00 | 48.83 | B | C |
| ATOM | 3175 | CG | ARG | B | 920 | 16.764 | 36.992 | 38.107 | 1.00 | 50.57 | B | C |
| ATOM | 3176 | CD | ARG | B | 920 | 16.469 | 36.813 | 36.607 | 1.00 | 53.25 | B | C |
| ATOM | 3177 | NE | ARG | B | 920 | 16.442 | 35.401 | 36.206 | 1.00 | 54.08 | B | N |
| ATOM | 3178 | CZ | ARG | B | 920 | 16.323 | 34.966 | 34.952 | 1.00 | 52.53 | B | C |
| ATOM | 3179 | NH1 | ARG | B | 920 | 16.216 | 35.828 | 33.945 | 1.00 | 51.03 | B | N |
| ATOM | 3180 | NH2 | ARG | B | 920 | 16.317 | 33.664 | 34.707 | 1.00 | 50.11 | B | N |
| ATOM | 3181 | C | ARG | B | 920 | 14.833 | 39.657 | 37.839 | 1.00 | 45.45 | B | C |
| ATOM | 3182 | O | ARG | B | 920 | 15.245 | 39.558 | 36.688 | 1.00 | 44.69 | B | O |
| ATOM | 3183 | N | LEU | B | 921 | 13.659 | 40.204 | 38.138 | 1.00 | 45.01 | B | N |
| ATOM | 3184 | CA | LEU | B | 921 | 12.759 | 40.714 | 37.102 | 1.00 | 44.34 | B | C |
| ATOM | 3185 | CB | LEU | B | 921 | 11.623 | 39.720 | 36.840 | 1.00 | 44.36 | B | C |
| ATOM | 3186 | CG | LEU | B | 921 | 11.900 | 38.396 | 36.128 | 1.00 | 44.22 | B | C |
| ATOM | 3187 | CD1 | LEU | B | 921 | 10.599 | 37.620 | 35.958 | 1.00 | 44.74 | B | C |
| ATOM | 3188 | CD2 | LEU | B | 921 | 12.511 | 38.669 | 34.775 | 1.00 | 45.69 | B | C |
| ATOM | 3189 | C | LEU | B | 921 | 12.167 | 42.055 | 37.539 | 1.00 | 43.53 | B | C |
| ATOM | 3190 | O | LEU | B | 921 | 11.150 | 42.097 | 38.237 | 1.00 | 44.06 | B | O |
| ATOM | 3191 | N | ASP | B | 922 | 12.799 | 43.147 | 37.120 | 1.00 | 42.34 | B | N |
| ATOM | 3192 | CA | ASP | B | 922 | 12.335 | 44.477 | 37.499 | 1.00 | 41.85 | B | C |
| ATOM | 3193 | CB | ASP | B | 922 | 13.462 | 45.511 | 37.339 | 1.00 | 41.06 | B | C |
| ATOM | 3194 | CG | ASP | B | 922 | 13.976 | 45.614 | 35.909 | 1.00 | 42.29 | B | C |
| ATOM | 3195 | OD1 | ASP | B | 922 | 13.142 | 45.659 | 34.975 | 1.00 | 39.58 | B | O |
| ATOM | 3196 | OD2 | ASP | B | 922 | 15.219 | 45.666 | 35.730 | 1.00 | 43.31 | B | O |
| ATOM | 3197 | C | ASP | B | 922 | 11.106 | 44.943 | 36.731 | 1.00 | 39.87 | B | C |
| ATOM | 3198 | O | ASP | B | 922 | 10.672 | 44.306 | 35.781 | 1.00 | 41.23 | B | O |
| ATOM | 3199 | N | ALA | B | 923 | 10.552 | 46.068 | 37.158 | 1.00 | 37.59 | B | N |
| ATOM | 3200 | CA | ALA | B | 923 | 9.376 | 46.629 | 36.523 | 1.00 | 36.35 | B | C |
| ATOM | 3201 | CB | ALA | B | 923 | 9.017 | 47.950 | 37.187 | 1.00 | 35.54 | B | C |
| ATOM | 3202 | C | ALA | B | 923 | 9.553 | 46.824 | 35.017 | 1.00 | 35.68 | B | C |
| ATOM | 3203 | O | ALA | B | 923 | 8.588 | 46.730 | 34.260 | 1.00 | 35.30 | B | O |
| ATOM | 3204 | N | SER | B | 924 | 10.775 | 47.097 | 34.574 | 1.00 | 33.91 | B | N |
| ATOM | 3205 | CA | SER | B | 924 | 10.991 | 47.290 | 33.151 | 1.00 | 33.74 | B | C |
| ATOM | 3206 | CB | SER | B | 924 | 12.465 | 47.551 | 32.859 | 1.00 | 34.61 | B | C |
| ATOM | 3207 | OG | SER | B | 924 | 12.840 | 48.836 | 33.318 | 1.00 | 40.21 | B | O |
| ATOM | 3208 | C | SER | B | 924 | 10.523 | 46.061 | 32.390 | 1.00 | 33.14 | B | C |
| ATOM | 3209 | O | SER | B | 924 | 9.803 | 46.163 | 31.395 | 1.00 | 32.57 | B | O |
| ATOM | 3210 | N | ARG | B | 925 | 10.931 | 44.899 | 32.876 | 1.00 | 30.83 | B | N |
| ATOM | 3211 | CA | ARG | B | 925 | 10.552 | 43.653 | 32.259 | 1.00 | 31.63 | B | C |
| ATOM | 3212 | CB | ARG | B | 925 | 11.199 | 42.489 | 33.003 | 1.00 | 33.57 | B | C |
| ATOM | 3213 | CG | ARG | B | 925 | 10.900 | 41.147 | 32.394 | 1.00 | 35.20 | B | C |
| ATOM | 3214 | CD | ARG | B | 925 | 12.156 | 40.548 | 31.836 | 1.00 | 39.12 | B | C |
| ATOM | 3215 | NE | ARG | B | 925 | 12.823 | 41.461 | 30.920 | 1.00 | 41.44 | B | N |
| ATOM | 3216 | CZ | ARG | B | 925 | 14.029 | 41.240 | 30.416 | 1.00 | 42.69 | B | C |
| ATOM | 3217 | NH1 | ARG | B | 925 | 14.576 | 42.117 | 29.585 | 1.00 | 43.07 | B | N |
| ATOM | 3218 | NH2 | ARG | B | 925 | 14.685 | 40.138 | 30.753 | 1.00 | 41.67 | B | N |
| ATOM | 3219 | C | ARG | B | 925 | 9.035 | 43.493 | 32.286 | 1.00 | 31.85 | B | C |
| ATOM | 3220 | O | ARG | B | 925 | 8.415 | 43.165 | 31.270 | 1.00 | 30.05 | B | O |
| ATOM | 3221 | O | LEU | B | 926 | 8.442 | 43.723 | 33.457 | 1.00 | 30.42 | B | N |
| ATOM | 3222 | CA | LEU | B | 926 | 6.998 | 43.589 | 33.614 | 1.00 | 28.04 | B | C |
| ATOM | 3223 | CB | LEU | B | 926 | 6.570 | 44.056 | 35.002 | 1.00 | 27.26 | B | C |

-continued

| | | | | | | | | | | | |
|---|---|---|---|---|---|---|---|---|---|---|---|
| ATOM | 3224 | CG | LEU | B | 926 | 7.230 | 43.348 | 36.185 | 1.00 | 28.68 | B | C |
| ATOM | 3225 | CD1 | LEU | B | 926 | 6.539 | 43.811 | 37.487 | 1.00 | 26.24 | B | C |
| ATOM | 3226 | CD2 | LEU | B | 926 | 7.119 | 41.819 | 36.004 | 1.00 | 24.28 | B | C |
| ATOM | 3227 | C | LEU | B | 926 | 6.285 | 44.412 | 32.551 | 1.00 | 27.32 | B | C |
| ATOM | 3228 | O | LEU | B | 926 | 5.294 | 43.971 | 31.969 | 1.00 | 27.38 | B | O |
| ATOM | 3229 | N | LEU | B | 927 | 6.806 | 45.610 | 32.302 | 1.00 | 25.79 | B | N |
| ATOM | 3230 | CA | LEU | B | 927 | 6.239 | 46.509 | 31.305 | 1.00 | 25.06 | B | C |
| ATOM | 3231 | CB | LEU | B | 927 | 6.829 | 47.921 | 31.474 | 1.00 | 22.03 | B | C |
| ATOM | 3232 | CG | LEU | B | 927 | 6.221 | 48.706 | 32.650 | 1.00 | 20.16 | B | C |
| ATOM | 3233 | CD1 | LEU | B | 927 | 6.929 | 50.021 | 32.861 | 1.00 | 19.40 | B | C |
| ATOM | 3234 | CD2 | LEU | B | 927 | 4.742 | 48.949 | 32.363 | 1.00 | 21.09 | B | C |
| ATOM | 3235 | C | LEU | B | 927 | 6.488 | 45.959 | 29.897 | 1.00 | 25.65 | B | C |
| ATOM | 3236 | O | LEU | B | 927 | 5.660 | 46.115 | 28.996 | 1.00 | 25.31 | B | O |
| ATOM | 3237 | N | LEU | B | 928 | 7.622 | 45.298 | 29.714 | 1.00 | 26.41 | B | N |
| ATOM | 3238 | CA | LEU | B | 928 | 7.922 | 44.693 | 26.429 | 1.00 | 27.69 | B | C |
| ATOM | 3239 | CB | LEU | B | 928 | 9.310 | 44.038 | 28.452 | 1.00 | 27.36 | B | C |
| ATOM | 3240 | CG | LEU | B | 928 | 9.829 | 43.541 | 27.093 | 1.00 | 29.18 | B | C |
| ATOM | 3241 | CD1 | LEU | B | 928 | 9.870 | 44.697 | 26.100 | 1.00 | 26.86 | B | C |
| ATOM | 3242 | CD2 | LEU | B | 928 | 11.220 | 42.930 | 27.259 | 1.00 | 28.41 | B | C |
| ATOM | 3243 | C | LEU | B | 928 | 6.840 | 43.635 | 28.141 | 1.00 | 27.69 | B | C |
| ATOM | 3244 | O | LEU | B | 928 | 6.178 | 43.695 | 27.109 | 1.00 | 29.81 | B | O |
| ATOM | 3245 | N | TYR | B | 929 | 6.649 | 42.685 | 29.059 | 1.00 | 26.62 | B | N |
| ATOM | 3246 | CA | TYR | B | 929 | 5.646 | 41.634 | 28.873 | 1.00 | 25.73 | B | C |
| ATOM | 3247 | CB | TYR | B | 929 | 5.570 | 40.676 | 30.078 | 1.00 | 24.73 | B | C |
| ATOM | 3248 | CG | TYR | B | 929 | 6.863 | 39.964 | 30.423 | 1.00 | 25.65 | B | C |
| ATOM | 3249 | CD1 | TYR | B | 929 | 7.710 | 39.488 | 29.428 | 1.00 | 26.25 | B | C |
| ATOM | 3250 | CE1 | TYR | B | 929 | 8.900 | 38.847 | 29.749 | 1.00 | 26.35 | B | C |
| ATOM | 3251 | CD2 | TYR | B | 929 | 7.241 | 39.771 | 31.750 | 1.00 | 25.40 | B | C |
| ATOM | 3252 | CE2 | TYR | B | 929 | 8.421 | 39.131 | 32.077 | 1.00 | 23.77 | B | C |
| ATOM | 3253 | CZ | TYR | B | 929 | 9.245 | 38.675 | 31.077 | 1.00 | 26.10 | B | C |
| ATOM | 3254 | OH | TYR | B | 929 | 10.427 | 38.057 | 31.394 | 1.00 | 26.76 | B | O |
| ATOM | 3255 | C | TYR | B | 929 | 4.270 | 42.236 | 26.676 | 1.00 | 24.74 | B | C |
| ATOM | 3256 | O | TYR | B | 929 | 3.439 | 41.656 | 27.995 | 1.00 | 23.60 | B | O |
| ATOM | 3257 | N | SER | B | 930 | 4.029 | 43.391 | 29.289 | 1.00 | 25.64 | B | N |
| ATOM | 3258 | CA | SER | B | 930 | 2.730 | 44.052 | 29.183 | 1.00 | 26.06 | B | C |
| ATOM | 3259 | CB | SER | B | 930 | 2.622 | 45.176 | 30.213 | 1.00 | 26.82 | B | C |
| ATOM | 3260 | OG | SER | B | 930 | 2.832 | 44.674 | 31.525 | 1.00 | 28.96 | B | O |
| ATOM | 3261 | C | SER | B | 930 | 2.512 | 44.600 | 27.782 | 1.00 | 25.97 | B | C |
| ATOM | 3262 | O | SER | B | 930 | 1.434 | 44.454 | 27.210 | 1.00 | 26.37 | B | O |
| ATOM | 3263 | N | SER | B | 931 | 3.550 | 45.208 | 27.221 | 1.00 | 26.24 | B | N |
| ATOM | 3264 | CA | SER | B | 931 | 3.472 | 45.768 | 25.877 | 1.00 | 24.72 | B | C |
| ATOM | 3265 | CB | SER | B | 931 | 4.746 | 46.562 | 25.559 | 1.00 | 25.41 | B | C |
| ATOM | 3266 | OG | SER | B | 931 | 4.663 | 47.190 | 24.288 | 1.00 | 25.63 | B | O |
| ATOM | 3267 | C | SER | B | 931 | 3.272 | 44.671 | 24.829 | 1.00 | 22.71 | B | C |
| ATOM | 3268 | O | SER | B | 931 | 2.440 | 44.804 | 23.937 | 1.00 | 22.21 | B | O |
| ATOM | 3269 | N | GLN | B | 932 | 4.043 | 43.594 | 24.926 | 1.00 | 21.13 | B | N |
| ATOM | 3270 | CA | GLN | B | 932 | 3.922 | 42.501 | 23.967 | 1.00 | 20.19 | B | C |
| ATOM | 3271 | CB | GLN | B | 932 | 5.018 | 41.469 | 24.195 | 1.00 | 18.59 | B | C |
| ATOM | 3272 | CG | GLN | B | 932 | 6.417 | 42.034 | 24.201 | 1.00 | 16.41 | B | C |
| ATOM | 3273 | CD | GLN | B | 932 | 7.450 | 40.960 | 24.447 | 1.00 | 18.92 | B | C |
| ATOM | 3274 | OE1 | GLN | B | 932 | 7.173 | 39.963 | 25.111 | 1.00 | 19.34 | B | O |
| ATOM | 3275 | NE2 | GLN | B | 932 | 8.659 | 41.161 | 23.928 | 1.00 | 20.97 | B | N |
| ATOM | 3276 | C | GLN | B | 932 | 2.552 | 41.830 | 24.062 | 1.00 | 20.13 | B | C |
| ATOM | 3277 | O | GLN | B | 932 | 1.987 | 41.438 | 23.052 | 1.00 | 20.51 | B | O |
| ATOM | 3278 | N | ILE | B | 933 | 2.014 | 41.708 | 25.272 | 1.00 | 19.68 | B | N |
| ATOM | 3279 | CA | ILE | B | 933 | 0.714 | 41.087 | 25.452 | 1.00 | 20.83 | B | C |
| ATOM | 3280 | CB | ILE | B | 933 | 0.396 | 40.865 | 26.957 | 1.00 | 20.65 | B | C |
| ATOM | 3281 | CG2 | ILE | B | 933 | −1.099 | 40.537 | 27.156 | 1.00 | 18.30 | B | C |
| ATOM | 3282 | CG1 | ILE | B | 933 | 1.274 | 39.731 | 27.506 | 1.00 | 17.48 | B | C |
| ATOM | 3283 | CD1 | ILE | B | 933 | 1.297 | 39.640 | 29.005 | 1.00 | 14.75 | B | C |
| ATOM | 3284 | C | ILE | B | 933 | −0.330 | 41.997 | 24.825 | 1.00 | 23.98 | B | C |
| ATOM | 3285 | O | ILE | B | 933 | −1.262 | 41.530 | 24.165 | 1.00 | 27.92 | B | O |
| ATOM | 3286 | N | CYS | B | 934 | −0.162 | 43.302 | 25.009 | 1.00 | 24.95 | B | N |
| ATOM | 3287 | CA | CYS | B | 934 | −1.096 | 44.271 | 24.450 | 1.00 | 23.96 | B | C |
| ATOM | 3288 | CB | CYS | B | 934 | −0.771 | 45.675 | 24.962 | 1.00 | 22.48 | B | C |
| ATOM | 3289 | SG | CYS | B | 934 | −2.047 | 46.909 | 24.612 | 1.00 | 26.90 | B | S |
| ATOM | 3290 | C | CYS | B | 934 | −1.027 | 44.258 | 22.927 | 1.00 | 23.61 | B | C |
| ATOM | 3291 | O | CYS | B | 934 | −2.050 | 44.291 | 22.236 | 1.00 | 21.24 | B | O |
| ATOM | 3292 | N | LYS | B | 935 | 0.189 | 44.212 | 22.401 | 1.00 | 25.11 | B | N |
| ATOM | 3293 | CA | LYS | B | 935 | 0.378 | 44.212 | 20.957 | 1.00 | 25.85 | B | C |
| ATOM | 3294 | CB | LYS | B | 935 | 1.878 | 44.169 | 20.629 | 1.00 | 28.60 | B | C |
| ATOM | 3295 | CG | LYS | B | 935 | 2.217 | 44.378 | 19.162 | 1.00 | 31.12 | B | C |
| ATOM | 3296 | CD | LYS | B | 935 | 1.628 | 45.673 | 18.661 | 1.00 | 36.08 | B | C |
| ATOM | 3297 | CE | LYS | B | 935 | 1.778 | 45.817 | 17.159 | 1.00 | 37.38 | B | C |
| ATOM | 3298 | NZ | LYS | B | 935 | 0.958 | 46.965 | 16.669 | 1.00 | 39.57 | B | N |
| ATOM | 3299 | C | LYS | B | 935 | −0.356 | 43.008 | 20.370 | 1.00 | 25.95 | B | C |
| ATOM | 3300 | O | LYS | B | 935 | −1.099 | 43.147 | 19.403 | 1.00 | 26.64 | B | O |
| ATOM | 3301 | N | GLY | B | 936 | −0.176 | 41.840 | 20.981 | 1.00 | 24.87 | B | N |
| ATOM | 3302 | CA | GLY | B | 936 | −0.846 | 40.645 | 20.503 | 1.00 | 25.53 | B | C |
| ATOM | 3303 | C | GLY | B | 936 | −2.367 | 40.737 | 20.520 | 1.00 | 25.87 | B | C |

-continued

| | | | | | | | | | | |
|---|---|---|---|---|---|---|---|---|---|---|
| ATOM | 3304 | O | GLY | B | 936 | −3.046 | 40.382 | 19.541 | 1.00 | 22.39 | B | O |
| ATOM | 3305 | N | MET | B | 937 | −2.903 | 41.218 | 21.637 | 1.00 | 24.22 | B | N |
| ATOM | 3306 | CA | MET | B | 937 | −4.344 | 41.354 | 21.784 | 1.00 | 25.26 | B | C |
| ATOM | 3307 | CB | MET | B | 937 | −4.680 | 41.810 | 23.208 | 1.00 | 22.36 | B | C |
| ATOM | 3308 | CG | MET | B | 937 | −4.476 | 40.693 | 24.213 | 1.00 | 23.06 | B | C |
| ATOM | 3309 | SB | MET | B | 937 | −5.425 | 39.200 | 23.698 | 1.00 | 20.48 | B | S |
| ATOM | 3310 | CE | MET | B | 937 | −7.049 | 39.901 | 23.661 | 1.00 | 15.72 | B | C |
| ATOM | 3311 | C | MET | B | 937 | −4.908 | 42.319 | 20.746 | 1.00 | 25.24 | B | C |
| ATOM | 3312 | O | MET | B | 937 | −6.030 | 42.155 | 20.276 | 1.00 | 25.83 | B | O |
| ATOM | 3313 | N | GLU | B | 938 | −4.115 | 43.314 | 20.372 | 1.00 | 27.10 | B | N |
| ATOM | 3314 | CA | GLU | B | 938 | −4.553 | 44.279 | 19.373 | 1.00 | 29.62 | B | C |
| ATOM | 3315 | CB | GLU | B | 938 | −3.575 | 45.458 | 19.307 | 1.00 | 30.48 | B | C |
| ATOM | 3316 | CG | GLU | B | 938 | −3.911 | 46.454 | 18.221 | 1.00 | 35.52 | B | C |
| ATOM | 3317 | CD | GLU | B | 938 | −2.834 | 47.506 | 18.000 | 1.00 | 38.79 | B | C |
| ATOM | 3318 | OE1 | GLU | B | 938 | −1.636 | 47.140 | 17.896 | 1.00 | 40.52 | B | O |
| ATOM | 3319 | OE2 | GLU | B | 938 | −3.198 | 48.698 | 17.915 | 1.00 | 38.59 | B | O |
| ATOM | 3320 | C | GLU | B | 938 | −4.675 | 43.609 | 17.993 | 1.00 | 28.94 | B | C |
| ATOM | 3321 | O | GLU | B | 938 | −5.659 | 43.803 | 17.282 | 1.00 | 27.75 | B | O |
| ATOM | 3322 | N | TYR | B | 939 | −3.677 | 42.819 | 17.623 | 1.00 | 27.57 | B | N |
| ATOM | 3323 | CA | TYR | B | 939 | −3.720 | 42.139 | 16.345 | 1.00 | 27.18 | B | C |
| ATOM | 3324 | CB | TYR | B | 939 | −2.428 | 41.354 | 16.133 | 1.00 | 26.82 | B | C |
| ATOM | 3325 | CG | TYR | B | 939 | −2.512 | 40.410 | 14.969 | 1.00 | 28.23 | B | C |
| ATOM | 3326 | CD1 | TYR | B | 939 | −2.672 | 40.879 | 13.676 | 1.00 | 27.67 | B | C |
| ATOM | 3327 | CE1 | TYR | B | 939 | −2.818 | 39.995 | 12.613 | 1.00 | 27.50 | B | C |
| ATOM | 3328 | CD2 | TYR | B | 939 | −2.495 | 39.034 | 15.170 | 1.00 | 30.11 | B | C |
| ATOM | 3329 | CE2 | TYR | B | 939 | −2.641 | 38.143 | 14.113 | 1.00 | 27.69 | B | C |
| ATOM | 3330 | CZ | TYR | B | 939 | −2.803 | 38.630 | 12.844 | 1.00 | 25.76 | B | C |
| ATOM | 3331 | OH | TYR | B | 939 | −2.969 | 37.746 | 11.809 | 1.00 | 28.05 | B | O |
| ATOM | 3332 | C | TYR | B | 939 | −4.936 | 41.196 | 16.283 | 1.00 | 27.22 | B | C |
| ATOM | 3333 | O | TYR | B | 939 | −5.730 | 41.229 | 15.333 | 1.00 | 25.58 | B | O |
| ATOM | 3334 | N | LEU | B | 940 | −5.084 | 40.365 | 17.312 | 1.00 | 27.83 | B | N |
| ATOM | 3335 | CA | LEU | B | 940 | −6.194 | 39.422 | 17.370 | 1.00 | 27.45 | B | C |
| ATOM | 3336 | CB | LEU | B | 940 | −6.159 | 38.621 | 18.678 | 1.00 | 25.08 | B | C |
| ATOM | 3337 | CG | LEU | B | 940 | −4.922 | 37.722 | 18.864 | 1.00 | 27.64 | B | C |
| ATOM | 3338 | CD1 | LEU | B | 940 | −5.154 | 36.762 | 20.017 | 1.00 | 24.40 | B | C |
| ATOM | 3339 | CD2 | LEU | B | 940 | −4.625 | 36.931 | 17.591 | 1.00 | 27.99 | B | C |
| ATOM | 3340 | C | LEU | B | 940 | −7.533 | 40.138 | 17.216 | 1.00 | 26.86 | B | C |
| ATOM | 3341 | O | LEU | B | 940 | −8.439 | 39.627 | 16.562 | 1.00 | 28.15 | B | O |
| ATOM | 3342 | N | GLY | B | 941 | −7.643 | 41.329 | 17.796 | 1.00 | 26.05 | B | N |
| ATOM | 3343 | CA | GLY | B | 941 | −8.879 | 42.092 | 17.707 | 1.00 | 23.74 | B | C |
| ATOM | 3344 | C | GLY | B | 941 | −9.205 | 42.585 | 16.312 | 1.00 | 21.83 | B | C |
| ATOM | 3345 | O | GLY | B | 941 | −10.338 | 42.461 | 15.841 | 1.00 | 19.35 | B | O |
| ATOM | 3346 | N | SER | B | 942 | −8.206 | 43.153 | 15.651 | 1.00 | 21.40 | B | N |
| ATOM | 3347 | CA | SER | B | 942 | −8.384 | 43.660 | 14.307 | 1.00 | 23.07 | B | C |
| ATOM | 3348 | CB | SER | B | 942 | −7.086 | 44.309 | 13.815 | 1.00 | 20.62 | B | C |
| ATOM | 3349 | OG | SER | B | 942 | −6.006 | 43.388 | 13.817 | 1.00 | 16.12 | B | O |
| ATOM | 3350 | C | SER | B | 942 | −8.801 | 42.536 | 13.359 | 1.00 | 26.33 | B | C |
| ATOM | 3351 | O | SER | B | 942 | −9.307 | 42.793 | 12.260 | 1.00 | 29.50 | B | O |
| ATOM | 3352 | N | ARG | B | 943 | −8.593 | 41.293 | 13.782 | 1.00 | 24.35 | B | N |
| ATOM | 3353 | CA | ARG | B | 943 | −8.954 | 40.161 | 12.963 | 1.00 | 23.61 | B | C |
| ATOM | 3354 | CB | ARG | B | 943 | −7.827 | 39.141 | 12.956 | 1.00 | 26.33 | B | C |
| ATOM | 3355 | CG | ARG | B | 943 | −6.624 | 39.601 | 12.198 | 1.00 | 29.12 | B | C |
| ATOM | 3356 | CD | ARG | B | 943 | −6.909 | 39.625 | 10.718 | 1.00 | 34.41 | B | C |
| ATOM | 3357 | NE | ARG | B | 943 | −5.854 | 40.306 | 9.975 | 1.00 | 37.63 | B | N |
| ATOM | 3358 | CZ | ARG | B | 943 | −5.479 | 41.557 | 10.216 | 1.00 | 36.64 | B | C |
| ATOM | 3359 | NH1 | ARG | B | 943 | −4.512 | 42.127 | 9.502 | 1.00 | 38.73 | B | N |
| ATOM | 3360 | NH2 | ARG | B | 943 | −6.075 | 42.233 | 11.188 | 1.00 | 40.59 | B | N |
| ATOM | 3361 | C | ARG | B | 943 | −10.221 | 39.535 | 13.494 | 1.00 | 24.10 | B | C |
| ATOM | 3362 | O | ARG | B | 943 | −10.549 | 38.392 | 13.171 | 1.00 | 23.79 | B | O |
| ATOM | 3363 | N | ARG | B | 944 | −10.929 | 40.288 | 14.327 | 1.00 | 25.80 | B | N |
| ATOM | 3364 | CA | ARG | B | 944 | −12.190 | 39.832 | 14.902 | 1.00 | 27.06 | B | C |
| ATOM | 3365 | CB | ARG | B | 944 | −13.222 | 39.690 | 13.786 | 1.00 | 29.29 | B | C |
| ATOM | 3366 | CG | ARG | B | 944 | −13.328 | 40.944 | 12.931 | 1.00 | 33.03 | B | C |
| ATOM | 3367 | CD | ARG | B | 944 | −14.432 | 40.833 | 11.901 | 1.00 | 37.88 | B | C |
| ATOM | 3368 | NE | ARG | B | 944 | −14.475 | 42.000 | 11.018 | 1.00 | 41.34 | B | N |
| ATOM | 3369 | CZ | ARG | B | 944 | −14.967 | 43.192 | 11.345 | 1.00 | 42.38 | B | C |
| ATOM | 3370 | NH1 | ARG | B | 944 | −15.482 | 43.410 | 12.550 | 1.00 | 43.09 | B | N |
| ATOM | 3371 | NH2 | ARG | B | 944 | −14.928 | 44.179 | 10.460 | 1.00 | 43.07 | B | N |
| ATOM | 3372 | C | ARG | B | 944 | −12.137 | 38.538 | 15.722 | 1.00 | 27.11 | B | C |
| ATOM | 3373 | O | ARG | B | 944 | −13.102 | 37.777 | 15.739 | 1.00 | 27.61 | B | O |
| ATOM | 3374 | N | CYS | B | 945 | −11.020 | 38.298 | 16.404 | 1.00 | 24.94 | B | N |
| ATOM | 3375 | CA | CYS | B | 945 | −10.863 | 37.112 | 17.239 | 1.00 | 24.53 | B | C |
| ATOM | 3376 | CB | CYS | B | 945 | −9.489 | 36.485 | 17.004 | 1.00 | 25.33 | B | C |
| ATOM | 3377 | SG | CYS | B | 945 | −9.124 | 35.025 | 18.022 | 1.00 | 30.16 | B | S |
| ATOM | 3378 | C | CYS | B | 945 | −11.014 | 37.466 | 18.728 | 1.00 | 23.62 | B | C |
| ATOM | 3379 | O | CYS | B | 945 | −10.477 | 38.472 | 19.188 | 1.00 | 23.54 | B | O |
| ATOM | 3380 | N | VAL | B | 946 | −11.745 | 36.635 | 19.468 | 1.00 | 22.35 | B | N |
| ATOM | 3381 | CA | VAL | B | 946 | −11.959 | 36.844 | 20.900 | 1.00 | 21.99 | B | C |
| ATOM | 3382 | CB | VAL | B | 946 | −13.468 | 36.922 | 21.219 | 1.00 | 19.57 | B | C |
| ATOM | 3383 | CG1 | VAL | B | 946 | −13.699 | 37.058 | 22.729 | 1.00 | 17.37 | B | C |

-continued

| | | | | | | | | | | |
|---|---|---|---|---|---|---|---|---|---|---|
| ATOM | 3384 | CG2 | VAL | B | 946 | −14.064 | 38.114 | 20.500 | 1.00 | 17.89 | B | C |
| ATOM | 3385 | C | VAL | B | 946 | −11.300 | 35.725 | 21.728 | 1.00 | 23.03 | B | C |
| ATOM | 3386 | O | VAL | B | 946 | −11.554 | 34.537 | 21.510 | 1.00 | 26.36 | B | O |
| ATOM | 3387 | N | HIS | B | 947 | −10.454 | 36.120 | 22.671 | 1.00 | 20.78 | B | N |
| ATOM | 3388 | CA | HIS | B | 947 | −9.731 | 35.172 | 23.510 | 1.00 | 22.55 | B | C |
| ATOM | 3389 | CB | HIS | B | 947 | −8.707 | 35.896 | 24.395 | 1.00 | 20.18 | B | C |
| ATOM | 3390 | CG | HIS | B | 947 | −7.680 | 34.980 | 24.980 | 1.00 | 17.97 | B | C |
| ATOM | 3391 | CD2 | HIS | B | 947 | −7.802 | 33.946 | 25.842 | 1.00 | 16.23 | B | C |
| ATOM | 3392 | ND1 | HIS | B | 947 | −6.363 | 34.987 | 24.573 | 1.00 | 16.76 | B | N |
| ATOM | 3393 | CE1 | HIS | B | 947 | −5.719 | 33.990 | 25.152 | 1.00 | 14.12 | B | C |
| ATOM | 3394 | NE2 | HIS | B | 947 | −6.569 | 33.341 | 25.925 | 1.00 | 16.69 | B | N |
| ATOM | 3395 | C | HIS | B | 947 | −10.636 | 34.354 | 24.404 | 1.00 | 22.03 | B | C |
| ATOM | 3396 | O | HIS | B | 947 | −10.644 | 33.138 | 24.324 | 1.00 | 24.74 | B | O |
| ATOM | 3397 | N | ARG | B | 948 | −11.378 | 35.030 | 25.268 | 1.00 | 24.81 | B | N |
| ATOM | 3398 | CA | ARG | B | 948 | −12.302 | 34.386 | 26.204 | 1.00 | 29.26 | B | C |
| ATOM | 3399 | CB | ARG | B | 948 | −13.059 | 33.233 | 25.530 | 1.00 | 32.27 | B | C |
| ATOM | 3400 | CG | ARG | B | 948 | −14.516 | 33.556 | 25.207 | 1.00 | 37.63 | B | C |
| ATOM | 3401 | CD | ARG | B | 948 | −15.406 | 32.314 | 25.302 | 1.00 | 43.26 | B | C |
| ATOM | 3402 | NE | ARG | B | 948 | −15.330 | 31.674 | 26.617 | 1.00 | 46.10 | B | N |
| ATOM | 3403 | CZ | ARG | B | 948 | −16.182 | 30.753 | 27.057 | 1.00 | 48.54 | B | C |
| ATOM | 3404 | NH1 | ARG | B | 948 | −16.021 | 30.238 | 28.268 | 1.00 | 49.33 | B | N |
| ATOM | 3405 | NH2 | ARG | B | 948 | −17.195 | 30.352 | 26.294 | 1.00 | 49.77 | B | N |
| ATOM | 3406 | C | ARG | B | 948 | −11.697 | 33.889 | 27.522 | 1.00 | 28.75 | B | C |
| ATOM | 3407 | O | ARG | B | 948 | −12.397 | 33.831 | 28.532 | 1.00 | 30.89 | B | O |
| ATOM | 3408 | N | ASP | B | 949 | −10.415 | 33.542 | 27.536 | 1.00 | 28.05 | B | N |
| ATOM | 3409 | CA | ASP | B | 949 | −9.801 | 33.070 | 28.773 | 1.00 | 26.91 | B | C |
| ATOM | 3410 | CB | ASP | B | 949 | −9.766 | 31.535 | 28.779 | 1.00 | 28.13 | B | C |
| ATOM | 3411 | CG | ASP | B | 949 | −9.324 | 30.955 | 30.116 | 1.00 | 30.51 | B | C |
| ATOM | 3412 | OD1 | ASP | B | 949 | −9.744 | 31.469 | 31.166 | 1.00 | 32.59 | B | O |
| ATOM | 3413 | OD2 | ASP | B | 949 | −8.565 | 29.969 | 30.124 | 1.00 | 31.18 | B | O |
| ATOM | 3414 | C | ASP | B | 949 | −8.393 | 33.653 | 28.937 | 1.00 | 25.45 | B | C |
| ATOM | 3415 | O | ASP | B | 949 | −7.426 | 32.927 | 29.151 | 1.00 | 25.26 | B | O |
| ATOM | 3416 | N | LEU | B | 950 | −8.279 | 34.971 | 28.829 | 1.00 | 23.58 | B | N |
| ATOM | 3417 | CA | LEU | B | 950 | −6.976 | 35.608 | 28.958 | 1.00 | 22.80 | B | C |
| ATOM | 3418 | CB | LEU | B | 950 | −7.000 | 37.024 | 28.392 | 1.00 | 20.62 | B | C |
| ATOM | 3419 | CG | LEU | B | 950 | −5.676 | 37.798 | 28.285 | 1.00 | 18.98 | B | C |
| ATOM | 3420 | CD1 | LEU | B | 950 | −4.751 | 37.141 | 27.253 | 1.00 | 13.37 | B | C |
| ATOM | 3421 | CD2 | LEU | B | 950 | −5.970 | 39.246 | 27.867 | 1.00 | 12.59 | B | C |
| ATOM | 3422 | C | LEU | B | 950 | −6.618 | 35.644 | 30.425 | 1.00 | 22.41 | B | C |
| ATOM | 3423 | O | LEU | B | 950 | −7.473 | 35.910 | 31.264 | 1.00 | 20.85 | B | O |
| ATOM | 3424 | N | ALA | B | 951 | −5.352 | 35.362 | 30.717 | 1.00 | 20.76 | B | N |
| ATOM | 3425 | CA | ALA | B | 951 | −4.852 | 35.331 | 32.078 | 1.00 | 17.81 | B | C |
| ATOM | 3426 | CB | ALA | B | 951 | −5.594 | 34.306 | 32.859 | 1.00 | 12.31 | B | C |
| ATOM | 3427 | C | ALA | B | 951 | −3.368 | 34.997 | 32.041 | 1.00 | 19.23 | B | C |
| ATOM | 3428 | O | ALA | B | 951 | −2.879 | 34.395 | 31.084 | 1.00 | 22.05 | B | O |
| ATOM | 3429 | N | ALA | B | 952 | −2.647 | 35.393 | 33.083 | 1.00 | 19.76 | B | N |
| ATOM | 3430 | CA | ALA | B | 952 | −1.209 | 35.154 | 33.157 | 1.00 | 18.16 | B | C |
| ATOM | 3431 | CB | ALA | B | 952 | −0.671 | 35.622 | 34.518 | 1.00 | 18.36 | B | C |
| ATOM | 3432 | C | ALA | B | 952 | −0.831 | 33.696 | 32.911 | 1.00 | 17.28 | B | C |
| ATOM | 3433 | O | ALA | B | 952 | 0.298 | 33.403 | 32.503 | 1.00 | 18.38 | B | O |
| ATOM | 3434 | N | ARG | B | 953 | −1.761 | 32.783 | 33.174 | 1.00 | 17.20 | B | N |
| ATOM | 3435 | CA | ARG | B | 953 | −1.501 | 31.359 | 32.958 | 1.00 | 19.59 | B | C |
| ATOM | 3436 | CB | ARG | B | 953 | −2.502 | 30.490 | 33.734 | 1.00 | 18.77 | B | C |
| ATOM | 3437 | CG | ARG | B | 953 | −3.902 | 30.571 | 33.184 | 1.00 | 18.10 | B | C |
| ATOM | 3438 | CD | ARG | B | 953 | −4.843 | 29.692 | 33.962 | 1.00 | 19.26 | B | C |
| ATOM | 3439 | NE | ARG | B | 953 | −6.241 | 30.056 | 33.733 | 1.00 | 19.94 | B | N |
| ATOM | 3440 | CZ | ARG | B | 953 | −6.897 | 30.984 | 34.421 | 1.00 | 20.48 | B | C |
| ATOM | 3441 | NH1 | ARG | B | 953 | −6.292 | 31.652 | 35.395 | 1.00 | 22.23 | B | N |
| ATOM | 3442 | NH2 | ARG | B | 953 | −8.161 | 31.246 | 34.137 | 1.00 | 19.77 | B | N |
| ATOM | 3443 | C | ARG | B | 953 | −1.606 | 31.044 | 31.462 | 1.00 | 21.37 | B | C |
| ATOM | 3444 | O | ARG | B | 953 | −0.991 | 30.090 | 30.967 | 1.00 | 20.33 | B | O |
| ATOM | 3445 | N | ASN | B | 954 | −2.389 | 31.837 | 30.734 | 1.00 | 21.32 | B | N |
| ATOM | 3446 | CA | ASN | B | 954 | −2.507 | 31.594 | 29.301 | 1.00 | 22.57 | B | C |
| ATOM | 3447 | CB | ASN | B | 954 | −3.966 | 31.740 | 28.836 | 1.00 | 19.78 | B | C |
| ATOM | 3448 | CG | ASN | B | 954 | −4.824 | 30.542 | 29.243 | 1.00 | 18.80 | B | C |
| ATOM | 3449 | OD1 | ASN | B | 954 | −4.347 | 29.404 | 29.258 | 1.00 | 16.51 | B | O |
| ATOM | 3450 | ND2 | ASN | B | 954 | −6.088 | 30.791 | 29.568 | 1.00 | 18.61 | B | N |
| ATOM | 3451 | C | ASN | B | 954 | −1.563 | 32.460 | 28.467 | 1.00 | 23.15 | B | C |
| ATOM | 3452 | O | ASN | B | 954 | −1.837 | 32.764 | 27.305 | 1.00 | 24.11 | B | O |
| ATOM | 3453 | N | ILE | B | 955 | −0.447 | 32.840 | 29.085 | 1.00 | 22.78 | B | N |
| ATOM | 3454 | CA | ILE | B | 955 | 0.600 | 33.636 | 28.446 | 1.00 | 23.25 | B | C |
| ATOM | 3455 | CB | ILE | B | 955 | 0.911 | 34.930 | 29.252 | 1.00 | 22.42 | B | C |
| ATOM | 3456 | CG2 | ILE | B | 955 | 2.137 | 35.627 | 28.660 | 1.00 | 21.63 | B | C |
| ATOM | 3457 | CG1 | ILE | B | 955 | −0.317 | 35.851 | 29.285 | 1.00 | 20.99 | B | C |
| ATOM | 3458 | CD1 | ILE | B | 955 | −0.663 | 36.492 | 27.966 | 1.00 | 19.44 | B | C |
| ATOM | 3459 | C | ILE | B | 955 | 1.846 | 32.761 | 28.489 | 1.00 | 24.65 | B | C |
| ATOM | 3460 | O | ILE | B | 955 | 2.390 | 32.527 | 29.570 | 1.00 | 27.02 | B | O |
| ATOM | 3461 | N | LEU | B | 956 | 2.302 | 32.274 | 27.339 | 1.00 | 24.24 | B | N |
| ATOM | 3462 | CA | LEU | B | 956 | 3.480 | 31.405 | 27.315 | 1.00 | 24.52 | B | C |
| ATOM | 3463 | CB | LEU | B | 956 | 3.298 | 30.311 | 26.244 | 1.00 | 23.14 | B | C |

-continued

| | | | | | | | | | | | |
|---|---|---|---|---|---|---|---|---|---|---|---|
| ATOM | 3464 | CG | LEU | B | 956 | 2.291 | 29.206 | 26.637 | 1.00 | 21.34 | B | C |
| ATOM | 3465 | CD1 | LEU | B | 956 | 1.936 | 28.336 | 25.446 | 1.00 | 20.11 | B | C |
| ATOM | 3466 | CD2 | LEU | B | 956 | 2.875 | 28.338 | 27.737 | 1.00 | 19.45 | B | C |
| ATOM | 3467 | C | LEU | B | 956 | 4.793 | 32.169 | 27.113 | 1.00 | 26.13 | B | C |
| ATOM | 3468 | O | LEU | B | 956 | 4.827 | 33.196 | 26.437 | 1.00 | 27.09 | B | O |
| ATOM | 3469 | N | VAL | B | 957 | 5.869 | 31.664 | 27.716 | 1.00 | 26.24 | B | N |
| ATOM | 3470 | CA | VAL | B | 957 | 7.187 | 32.296 | 27.631 | 1.00 | 25.04 | B | C |
| ATOM | 3471 | CB | VAL | B | 957 | 8.000 | 32.098 | 28.950 | 1.00 | 25.69 | B | C |
| ATOM | 3472 | CG1 | VAL | B | 957 | 9.431 | 32.628 | 28.780 | 1.00 | 21.14 | B | C |
| ATOM | 3473 | CG2 | VAL | B | 957 | 7.297 | 32.805 | 30.113 | 1.00 | 24.99 | B | C |
| ATOM | 3474 | C | VAL | B | 957 | 8.045 | 31.787 | 26.477 | 1.00 | 25.81 | B | C |
| ATOM | 3475 | O | VAL | B | 957 | 8.475 | 30.630 | 26.469 | 1.00 | 27.02 | B | O |
| ATOM | 3476 | N | GLU | B | 958 | 8.288 | 32.649 | 25.498 | 1.00 | 26.44 | B | N |
| ATOM | 3477 | CA | GLU | B | 958 | 9.126 | 32.274 | 24.368 | 1.00 | 28.76 | B | C |
| ATOM | 3478 | CB | GLU | B | 958 | 8.912 | 33.237 | 23.196 | 1.00 | 28.56 | B | C |
| ATOM | 3479 | CG | GLU | B | 958 | 9.876 | 33.025 | 22.035 | 1.00 | 30.73 | B | C |
| ATOM | 3480 | CD | GLU | B | 958 | 9.599 | 31.765 | 21.224 | 1.00 | 32.95 | B | C |
| ATOM | 3481 | OE1 | GLU | B | 958 | 10.401 | 31.465 | 20.315 | 1.00 | 35.94 | B | O |
| ATOM | 3482 | OE2 | GLU | B | 958 | 8.592 | 31.075 | 21.474 | 1.00 | 33.94 | B | O |
| ATOM | 3483 | C | GLU | B | 958 | 10.567 | 32.364 | 24.868 | 1.00 | 29.72 | B | C |
| ATOM | 3484 | O | GLU | B | 958 | 11.401 | 31.514 | 24.571 | 1.00 | 30.94 | B | O |
| ATOM | 3485 | N | SER | B | 959 | 10.842 | 33.404 | 25.645 | 1.00 | 31.11 | B | N |
| ATOM | 3486 | CA | SER | B | 959 | 12.164 | 33.609 | 26.210 | 1.00 | 32.58 | B | C |
| ATOM | 3487 | CB | SER | B | 959 | 13.152 | 34.054 | 25.137 | 1.00 | 30.97 | B | C |
| ATOM | 3488 | OG | SER | B | 959 | 13.235 | 35.465 | 25.113 | 1.00 | 33.82 | B | O |
| ATOM | 3489 | C | SER | B | 959 | 12.039 | 34.688 | 27.286 | 1.00 | 34.54 | B | C |
| ATOM | 3490 | O | SER | B | 959 | 10.961 | 35.246 | 27.482 | 1.00 | 33.70 | B | O |
| ATOM | 3491 | N | GLU | B | 960 | 13.147 | 34.978 | 27.962 | 1.00 | 35.55 | B | N |
| ATOM | 3492 | CA | GLU | B | 960 | 13.189 | 35.961 | 29.038 | 1.00 | 36.85 | B | C |
| ATOM | 3493 | CB | GLU | B | 960 | 14.615 | 36.058 | 29.594 | 1.00 | 39.46 | B | C |
| ATOM | 3494 | CG | GLU | B | 960 | 15.207 | 34.704 | 29.961 | 1.00 | 46.26 | B | C |
| ATOM | 3495 | CD | GLU | B | 960 | 15.453 | 33.813 | 28.738 | 1.00 | 50.12 | B | C |
| ATOM | 3496 | OE1 | GLU | B | 960 | 15.423 | 32.565 | 28.888 | 1.00 | 51.89 | B | O |
| ATOM | 3497 | OE2 | GLU | B | 960 | 15.684 | 34.358 | 27.629 | 1.00 | 51.11 | B | O |
| ATOM | 3498 | C | GLU | B | 960 | 12.703 | 37.344 | 28.622 | 1.00 | 35.60 | B | C |
| ATOM | 3499 | O | GLU | B | 960 | 12.252 | 38.134 | 29.455 | 1.00 | 35.96 | B | O |
| ATOM | 3500 | N | ALA | B | 961 | 12.788 | 37.644 | 27.336 | 1.00 | 32.86 | B | N |
| ATOM | 3501 | CA | ALA | B | 961 | 12.347 | 38.945 | 26.869 | 1.00 | 31.54 | B | C |
| ATOM | 3502 | CB | ALA | B | 961 | 13.542 | 39.737 | 26.370 | 1.00 | 32.46 | B | C |
| ATOM | 3503 | C | ALA | B | 961 | 11.262 | 38.857 | 25.776 | 1.00 | 30.73 | B | C |
| ATOM | 3504 | O | ALA | B | 961 | 11.186 | 39.740 | 24.928 | 1.00 | 30.46 | B | O |
| ATOM | 3505 | N | HIS | B | 962 | 10.474 | 37.801 | 25.802 | 1.00 | 29.79 | B | N |
| ATOM | 3506 | CA | HIS | B | 962 | 9.433 | 37.627 | 24.791 | 1.00 | 28.25 | B | C |
| ATOM | 3507 | CB | HIS | B | 962 | 10.070 | 37.195 | 23.468 | 1.00 | 27.95 | B | C |
| ATOM | 3508 | CG | HIS | B | 962 | 9.109 | 37.137 | 22.322 | 1.00 | 28.31 | B | C |
| ATOM | 3509 | CD2 | HIS | B | 962 | 7.810 | 36.764 | 22.263 | 1.00 | 28.79 | B | C |
| ATOM | 3510 | ND1 | HIS | B | 962 | 9.461 | 37.504 | 21.041 | 1.00 | 31.00 | B | N |
| ATOM | 3511 | CE1 | HIS | B | 962 | 8.418 | 37.365 | 20.243 | 1.00 | 29.74 | B | C |
| ATOM | 3512 | NE2 | HIS | B | 962 | 7.404 | 36.918 | 20.959 | 1.00 | 30.22 | B | N |
| ATOM | 3513 | C | HIS | B | 962 | 8.354 | 36.623 | 25.191 | 1.00 | 28.20 | B | C |
| ATOM | 3514 | O | HIS | B | 962 | 8.611 | 35.419 | 25.293 | 1.00 | 28.83 | B | O |
| ATOM | 3515 | N | VAL | B | 963 | 7.139 | 37.123 | 25.393 | 1.00 | 25.95 | B | N |
| ATOM | 3516 | CA | VAL | B | 963 | 6.013 | 36.279 | 25.768 | 1.00 | 24.74 | B | C |
| ATOM | 3517 | CB | VAL | B | 963 | 5.334 | 36.815 | 27.055 | 1.00 | 23.78 | B | C |
| ATOM | 3518 | CG1 | VAL | B | 963 | 6.308 | 36.684 | 28.219 | 1.00 | 21.06 | B | C |
| ATOM | 3519 | CG2 | VAL | B | 963 | 4.897 | 38.280 | 26.876 | 1.00 | 17.99 | B | C |
| ATOM | 3520 | C | VAL | B | 963 | 4.980 | 36.159 | 24.644 | 1.00 | 25.21 | B | C |
| ATOM | 3521 | O | VAL | B | 963 | 4.918 | 37.004 | 23.754 | 1.00 | 26.73 | B | O |
| ATOM | 3522 | N | LYS | B | 964 | 4.176 | 35.102 | 24.683 | 1.00 | 24.96 | B | N |
| ATOM | 3523 | CA | LYS | B | 964 | 3.155 | 34.877 | 23.655 | 1.00 | 25.16 | B | C |
| ATOM | 3524 | CB | LYS | B | 964 | 3.553 | 33.727 | 22.729 | 1.00 | 25.01 | B | C |
| ATOM | 3525 | CG | LYS | B | 964 | 4.701 | 34.011 | 21.783 | 1.00 | 24.77 | B | C |
| ATOM | 3526 | CD | LYS | B | 964 | 5.061 | 32.737 | 21.023 | 1.00 | 26.76 | B | C |
| ATOM | 3527 | CE | LYS | B | 964 | 6.084 | 32.982 | 19.931 | 1.00 | 28.31 | B | C |
| ATOM | 3528 | NZ | LYS | B | 964 | 6.299 | 31.771 | 19.085 | 1.00 | 28.80 | B | N |
| ATOM | 3529 | C | LYS | B | 964 | 1.794 | 34.547 | 24.243 | 1.00 | 25.01 | B | C |
| ATOM | 3530 | O | LYS | B | 964 | 1.702 | 33.913 | 25.296 | 1.00 | 25.35 | B | O |
| ATOM | 3531 | N | ILE | B | 965 | 0.743 | 34.982 | 23.549 | 1.00 | 24.07 | B | N |
| ATOM | 3532 | CA | ILE | B | 965 | −0.629 | 34.721 | 23.971 | 1.00 | 23.22 | B | C |
| ATOM | 3533 | CB | ILE | B | 965 | −1.615 | 35.726 | 23.326 | 1.00 | 24.06 | B | C |
| ATOM | 3534 | CG2 | ILE | B | 965 | −3.035 | 35.382 | 23.708 | 1.00 | 22.79 | B | C |
| ATOM | 3535 | CG1 | ILE | B | 965 | −1.303 | 37.145 | 23.800 | 1.00 | 24.57 | B | C |
| ATOM | 3536 | CD1 | ILE | B | 965 | −2.055 | 38.217 | 23.050 | 1.00 | 24.62 | B | C |
| ATOM | 3537 | C | ILE | B | 965 | −1.010 | 33.305 | 23.539 | 1.00 | 23.90 | B | C |
| ATOM | 3538 | O | ILE | B | 965 | −0.729 | 32.883 | 22.406 | 1.00 | 23.98 | B | O |
| ATOM | 3539 | N | ALA | B | 966 | −1.653 | 32.577 | 24.445 | 1.00 | 23.77 | B | N |
| ATOM | 3540 | CA | ALA | B | 966 | −2.062 | 31.199 | 24.181 | 1.00 | 22.79 | B | C |
| ATOM | 3541 | CB | ALA | B | 966 | −1.185 | 30.222 | 24.992 | 1.00 | 20.10 | B | C |
| ATOM | 3542 | C | ALA | B | 966 | −3.529 | 30.935 | 24.494 | 1.00 | 21.11 | B | C |
| ATOM | 3543 | O | ALA | B | 966 | −4.151 | 31.653 | 25.272 | 1.00 | 19.04 | B | O |

-continued

| ATOM | 3544 | N   | ASP | B | 967 | −4.065  | 29.887 | 23.875 | 1.00 | 20.78 | B | N |
| ---- | ---- | --- | --- | - | --- | ------- | ------ | ------ | ---- | ----- | - | - |
| ATOM | 3545 | CA  | ASP | B | 967 | −5.440  | 29.482 | 24.089 | 1.00 | 22.00 | B | C |
| ATOM | 3546 | CB  | ASP | B | 967 | −5.625  | 29.127 | 25.555 | 1.00 | 24.96 | B | C |
| ATOM | 3547 | CG  | ASP | B | 967 | −5.199  | 27.729 | 25.851 | 1.00 | 28.88 | B | C |
| ATOM | 3548 | OD1 | ASP | B | 967 | −4.008  | 27.409 | 25.637 | 1.00 | 35.17 | B | O |
| ATOM | 3549 | OD2 | ASP | B | 967 | −6.058  | 26.943 | 26.279 | 1.00 | 30.71 | B | O |
| ATOM | 3550 | C   | ASP | B | 967 | −6.489  | 30.498 | 23.677 | 1.00 | 21.34 | B | C |
| ATOM | 3551 | O   | ASP | B | 967 | −7.487  | 30.687 | 24.374 | 1.00 | 19.28 | B | O |
| ATOM | 3552 | N   | PHE | B | 968 | −6.256  | 31.147 | 22.546 | 1.00 | 21.34 | B | N |
| ATOM | 3553 | CA  | PHE | B | 968 | −7.172  | 32.154 | 22.042 | 1.00 | 23.12 | B | C |
| ATOM | 3554 | CB  | PHE | B | 968 | −6.373  | 33.312 | 21.440 | 1.00 | 19.95 | B | C |
| ATOM | 3555 | CG  | PHE | B | 968 | −5.428  | 32.897 | 20.346 | 1.00 | 20.95 | B | C |
| ATOM | 3556 | CD1 | PHE | B | 968 | −5.844  | 32.850 | 19.021 | 1.00 | 19.89 | B | C |
| ATOM | 3557 | CD2 | PHE | B | 968 | −4.107  | 32.586 | 20.637 | 1.00 | 20.34 | B | C |
| ATOM | 3558 | CE1 | PHE | B | 968 | −4.955  | 32.507 | 18.000 | 1.00 | 19.70 | B | C |
| ATOM | 3559 | CE2 | PHE | B | 968 | −3.210  | 32.240 | 19.623 | 1.00 | 20.58 | B | C |
| ATOM | 3560 | CZ  | PHE | B | 968 | −3.633  | 32.202 | 18.304 | 1.00 | 20.85 | B | C |
| ATOM | 3561 | C   | PHE | B | 968 | −8.156  | 31.609 | 21.005 | 1.00 | 24.50 | B | C |
| ATOM | 3562 | O   | PHE | B | 968 | −7.913  | 30.571 | 20.384 | 1.00 | 24.19 | B | O |
| ATOM | 3563 | N   | GLY | B | 969 | −9.273  | 32.316 | 20.855 | 1.00 | 25.76 | B | N |
| ATOM | 3564 | CA  | GLY | B | 969 | −10.296 | 31.964 | 19.888 | 1.00 | 28.10 | B | C |
| ATOM | 3565 | C   | GLY | B | 969 | −10.837 | 30.551 | 19.900 | 1.00 | 28.39 | B | C |
| ATOM | 3566 | O   | GLY | B | 969 | −10.864 | 29.902 | 18.863 | 1.00 | 29.91 | B | O |
| ATOM | 3567 | N   | LEU | B | 970 | −11.287 | 30.083 | 21.060 | 1.00 | 29.33 | B | N |
| ATOM | 3568 | CA  | LEU | B | 970 | −11.832 | 28.733 | 21.198 | 1.00 | 27.90 | B | C |
| ATOM | 3569 | CB  | LEU | B | 970 | −11.023 | 27.938 | 22.221 | 1.00 | 25.43 | B | C |
| ATOM | 3570 | CG  | LEU | B | 970 | −10.135 | 26.800 | 21.722 | 1.00 | 27.12 | B | C |
| ATOM | 3571 | CD1 | LEU | B | 970 | −9.196  | 27.267 | 20.639 | 1.00 | 25.92 | B | C |
| ATOM | 3572 | CD2 | LEU | B | 970 | −9.351  | 26.256 | 22.897 | 1.00 | 30.60 | B | C |
| ATOM | 3573 | C   | LEU | B | 970 | −13.285 | 28.765 | 21.631 | 1.00 | 27.45 | B | C |
| ATOM | 3574 | O   | LEU | B | 970 | −13.894 | 27.714 | 21.823 | 1.00 | 28.00 | B | O |
| ATOM | 3575 | N   | ALA | B | 971 | −13.830 | 29.974 | 21.774 | 1.00 | 27.93 | B | N |
| ATOM | 3576 | CA  | ALA | B | 971 | −15.222 | 30.189 | 22.193 | 1.00 | 29.28 | B | C |
| ATOM | 3577 | CB  | ALA | B | 971 | −15.618 | 31.631 | 21.926 | 1.00 | 28.90 | B | C |
| ATOM | 3578 | C   | ALA | B | 971 | −16.220 | 29.252 | 21.519 | 1.00 | 30.92 | B | C |
| ATOM | 3579 | O   | ALA | B | 971 | −17.003 | 28.584 | 22.193 | 1.00 | 33.05 | B | O |
| ATOM | 3580 | N   | LYS | B | 972 | −16.189 | 29.209 | 20.188 | 1.00 | 30.45 | B | N |
| ATOM | 3581 | CA  | LYS | B | 972 | −17.083 | 28.348 | 19.419 | 1.00 | 30.30 | B | C |
| ATOM | 3582 | CB  | LYS | B | 972 | −16.811 | 28.512 | 17.915 | 1.00 | 32.31 | B | C |
| ATOM | 3583 | CG  | LYS | B | 972 | −17.115 | 29.900 | 17.374 | 1.00 | 33.11 | B | C |
| ATOM | 3584 | CD  | LYS | B | 972 | −18.541 | 30.263 | 17.675 | 1.00 | 35.45 | B | C |
| ATOM | 3585 | CE  | LYS | B | 972 | −18.803 | 31.733 | 17.461 | 1.00 | 38.07 | B | C |
| ATOM | 3586 | NZ  | LYS | B | 972 | −20.202 | 32.046 | 17.893 | 1.00 | 40.65 | B | N |
| ATOM | 3587 | C   | LYS | B | 972 | −16.968 | 26.868 | 19.795 | 1.00 | 29.76 | B | C |
| ATOM | 3588 | O   | LYS | B | 972 | −17.890 | 26.094 | 19.553 | 1.00 | 29.15 | B | O |
| ATOM | 3589 | N   | LEU | B | 973 | −15.837 | 26.473 | 20.375 | 1.00 | 29.72 | B | N |
| ATOM | 3590 | CA  | LEU | B | 973 | −15.630 | 25.078 | 20.766 | 1.00 | 29.44 | B | C |
| ATOM | 3591 | CB  | LEU | B | 973 | −14.195 | 24.643 | 20.436 | 1.00 | 28.00 | B | C |
| ATOM | 3592 | CG  | LEU | B | 973 | −13.825 | 24.196 | 19.010 | 1.00 | 28.81 | B | C |
| ATOM | 3593 | CD1 | LEU | B | 973 | −14.845 | 24.746 | 18.014 | 1.00 | 30.28 | B | C |
| ATOM | 3594 | CD2 | LEU | B | 973 | −12.403 | 24.649 | 18.659 | 1.00 | 24.48 | B | C |
| ATOM | 3595 | C   | LEU | B | 973 | −15.900 | 24.803 | 22.246 | 1.00 | 31.37 | B | C |
| ATOM | 3596 | O   | LEU | B | 973 | −15.989 | 23.647 | 22.649 | 1.00 | 30.12 | B | O |
| ATOM | 3597 | N   | LEU | B | 974 | −16.027 | 25.854 | 23.057 | 1.00 | 32.64 | B | N |
| ATOM | 3598 | CA  | LEU | B | 974 | −16.243 | 25.666 | 24.487 | 1.00 | 34.63 | B | C |
| ATOM | 3599 | CB  | LEU | B | 974 | −15.721 | 26.865 | 25.283 | 1.00 | 33.19 | B | C |
| ATOM | 3600 | CG  | LEU | B | 974 | −14.238 | 27.196 | 25.105 | 1.00 | 30.52 | B | C |
| ATOM | 3601 | CD1 | LEU | B | 974 | −13.887 | 28.402 | 25.940 | 1.00 | 30.49 | B | C |
| ATOM | 3602 | CD2 | LEU | B | 974 | −13.392 | 25.993 | 25.471 | 1.00 | 28.88 | B | C |
| ATOM | 3603 | C   | LEU | B | 974 | −17.681 | 25.399 | 24.870 | 1.00 | 38.43 | B | C |
| ATOM | 3604 | O   | LEU | B | 974 | −18.615 | 26.000 | 24.340 | 1.00 | 38.84 | B | O |
| ATOM | 3605 | N   | PRO | B | 975 | −17.873 | 24.500 | 25.836 | 1.00 | 42.06 | B | N |
| ATOM | 3606 | CD  | PRO | B | 975 | −16.847 | 23.998 | 26.771 | 1.00 | 40.92 | B | C |
| ATOM | 3607 | CA  | PRO | B | 975 | −19.211 | 24.148 | 26.295 | 1.00 | 42.75 | B | C |
| ATOM | 3608 | CB  | PRO | B | 975 | −18.925 | 23.212 | 27.466 | 1.00 | 43.15 | B | C |
| ATOM | 3609 | CG  | PRO | B | 975 | −17.649 | 23.768 | 28.024 | 1.00 | 41.14 | B | C |
| ATOM | 3610 | C   | PRO | B | 975 | −20.055 | 25.354 | 26.694 | 1.00 | 44.41 | B | C |
| ATOM | 3611 | O   | PRO | B | 975 | −19.644 | 26.179 | 27.501 | 1.00 | 45.61 | B | O |
| ATOM | 3612 | N   | LEU | B | 976 | −21.238 | 25.453 | 26.103 | 1.00 | 46.22 | B | N |
| ATOM | 3613 | CA  | LEU | B | 976 | −22.163 | 26.529 | 26.412 | 1.00 | 47.83 | B | C |
| ATOM | 3614 | CB  | LEU | B | 976 | −23.509 | 26.249 | 25.723 | 1.00 | 48.67 | B | C |
| ATOM | 3615 | CG  | LEU | B | 976 | −23.555 | 26.755 | 24.275 | 1.00 | 49.00 | B | C |
| ATOM | 3616 | CD1 | LEU | B | 976 | −23.755 | 28.270 | 24.297 | 1.00 | 48.21 | B | C |
| ATOM | 3617 | CD2 | LEU | B | 976 | −22.231 | 26.379 | 23.542 | 1.00 | 48.02 | B | C |
| ATOM | 3618 | C   | LEU | B | 976 | −22.340 | 26.661 | 27.929 | 1.00 | 48.28 | B | C |
| ATOM | 3619 | O   | LEU | B | 976 | −21.939 | 27.668 | 26.520 | 1.00 | 48.72 | B | O |
| ATOM | 3620 | N   | ASP | B | 977 | −22.925 | 25.646 | 28.560 | 1.00 | 48.12 | B | N |
| ATOM | 3621 | CA  | ASP | B | 977 | −23.113 | 25.678 | 30.007 | 1.00 | 48.62 | B | C |
| ATOM | 3622 | CB  | ASP | B | 977 | −24.536 | 25.268 | 30.380 | 1.00 | 50.40 | B | C |
| ATOM | 3623 | CG  | ASP | B | 977 | −24.668 | 24.898 | 31.863 | 1.00 | 53.25 | B | C |

-continued

| | | | | | | | | | | | |
|---|---|---|---|---|---|---|---|---|---|---|---|
| ATOM | 3624 | OD1 | ASP | B | 977 | −25.490 | 25.542 | 32.578 | 1.00 | 53.02 | B | O |
| ATOM | 3625 | OD2 | ASP | B | 977 | −23.943 | 23.959 | 32.302 | 1.00 | 53.55 | B | O |
| ATOM | 3626 | C | ASP | B | 977 | −22.145 | 24.730 | 30.704 | 1.00 | 48.29 | B | C |
| ATOM | 3627 | O | ASP | B | 977 | −22.227 | 23.513 | 30.525 | 1.00 | 48.69 | B | O |
| ATOM | 3628 | N | LYS | B | 978 | −21.232 | 25.273 | 31.502 | 1.00 | 47.40 | B | N |
| ATOM | 3629 | CA | LYS | B | 978 | −20.272 | 24.430 | 32.223 | 1.00 | 47.27 | B | C |
| ATOM | 3630 | CB | LYS | B | 978 | −18.848 | 24.663 | 31.710 | 1.00 | 46.05 | B | C |
| ATOM | 3631 | CG | LYS | B | 978 | −18.223 | 25.970 | 32.220 | 1.00 | 44.25 | B | C |
| ATOM | 3632 | CD | LYS | B | 978 | −16.986 | 25.663 | 33.059 | 1.00 | 42.04 | B | C |
| ATOM | 3633 | CE | LYS | B | 978 | −15.979 | 24.889 | 32.225 | 1.00 | 40.46 | B | C |
| ATOM | 3634 | NZ | LYS | B | 978 | −14.751 | 24.538 | 32.986 | 1.00 | 39.42 | B | N |
| ATOM | 3635 | C | LYS | B | 978 | −20.297 | 24.745 | 33.717 | 1.00 | 46.58 | B | C |
| ATOM | 3636 | O | LYS | B | 978 | −20.163 | 25.903 | 34.116 | 1.00 | 46.31 | B | O |
| ATOM | 3637 | N | ASP | B | 979 | −20.458 | 23.716 | 34.539 | 1.00 | 47.40 | B | N |
| ATOM | 3638 | CA | ASP | B | 979 | −20.485 | 23.904 | 35.984 | 1.00 | 47.45 | B | C |
| ATOM | 3639 | CB | ASP | B | 979 | −20.788 | 22.577 | 36.677 | 1.00 | 49.65 | B | C |
| ATOM | 3640 | CG | ASP | B | 979 | −21.116 | 22.747 | 38.138 | 1.00 | 50.70 | B | C |
| ATOM | 3641 | OD1 | ASP | B | 979 | −21.512 | 21.737 | 38.765 | 1.00 | 51.90 | B | O |
| ATOM | 3642 | OD2 | ASP | B | 979 | −20.977 | 23.883 | 38.651 | 1.00 | 50.64 | B | O |
| ATOM | 3643 | C | ASP | B | 979 | −19.140 | 24.437 | 36.453 | 1.00 | 46.35 | B | C |
| ATOM | 3644 | O | ASP | B | 979 | −18.150 | 23.702 | 36.515 | 1.00 | 44.91 | B | O |
| ATOM | 3645 | N | TYR | B | 980 | −19.115 | 25.724 | 36.781 | 1.00 | 45.52 | B | N |
| ATOM | 3646 | CA | TYR | B | 980 | −17.897 | 26.383 | 37.230 | 1.00 | 45.44 | B | C |
| ATOM | 3647 | CB | TYR | B | 980 | −18.069 | 27.899 | 37.131 | 1.00 | 43.35 | B | C |
| ATOM | 3648 | CG | TYR | B | 980 | −17.833 | 28.436 | 35.739 | 1.00 | 41.95 | B | C |
| ATOM | 3649 | CD1 | TYR | B | 980 | −16.548 | 28.502 | 35.207 | 1.00 | 39.92 | B | C |
| ATOM | 3650 | CE1 | TYR | B | 980 | −16.326 | 28.968 | 33.918 | 1.00 | 37.64 | B | C |
| ATOM | 3651 | CD2 | TYR | B | 980 | −18.893 | 28.851 | 34.944 | 1.00 | 39.33 | B | C |
| ATOM | 3652 | CE2 | TYR | B | 980 | −18.683 | 29.317 | 33.654 | 1.00 | 37.16 | B | C |
| ATOM | 3653 | CZ | TYR | B | 980 | −17.401 | 29.374 | 33.144 | 1.00 | 36.17 | B | C |
| ATOM | 3654 | OH | TYR | B | 980 | −17.205 | 29.827 | 31.859 | 1.00 | 32.46 | B | O |
| ATOM | 3655 | C | TYR | B | 980 | −17.431 | 26.006 | 38.635 | 1.00 | 46.34 | B | C |
| ATOM | 3656 | O | TYR | B | 980 | −16.342 | 26.403 | 39.061 | 1.00 | 47.06 | B | O |
| ATOM | 3657 | N | TYR | B | 981 | −18.235 | 25.229 | 39.351 | 1.00 | 46.87 | B | N |
| ATOM | 3658 | CA | TYR | B | 981 | −17.856 | 24.830 | 40.696 | 1.00 | 48.41 | B | C |
| ATOM | 3659 | CB | TYR | B | 981 | −19.096 | 24.676 | 41.570 | 1.00 | 50.55 | B | C |
| ATOM | 3660 | CG | TYR | B | 981 | −19.918 | 25.940 | 41.626 | 1.00 | 54.49 | B | C |
| ATOM | 3661 | CD1 | TYR | B | 981 | −20.882 | 26.207 | 40.655 | 1.00 | 56.05 | B | C |
| ATOM | 3662 | CE1 | TYR | B | 981 | −21.594 | 27.398 | 40.656 | 1.00 | 57.69 | B | C |
| ATOM | 3663 | CD2 | TYR | B | 981 | −19.689 | 26.902 | 42.610 | 1.00 | 55.62 | B | C |
| ATOM | 3664 | CE2 | TYR | B | 981 | −20.397 | 28.101 | 42.620 | 1.00 | 57.77 | B | C |
| ATOM | 3665 | CZ | TYR | B | 981 | −21.347 | 28.340 | 41.638 | 1.00 | 58.18 | B | C |
| ATOM | 3666 | OH | TYR | B | 981 | −22.043 | 29.525 | 41.629 | 1.00 | 59.14 | B | O |
| ATOM | 3667 | C | TYR | B | 981 | −17.037 | 23.551 | 40.688 | 1.00 | 47.81 | B | C |
| ATOM | 3668 | O | TYR | B | 981 | −16.376 | 23.211 | 41.674 | 1.00 | 47.25 | B | O |
| ATOM | 3669 | N | VAL | B | 982 | −17.076 | 22.850 | 39.563 | 1.00 | 47.13 | B | N |
| ATOM | 3670 | CA | VAL | B | 982 | −16.317 | 21.621 | 39.411 | 1.00 | 46.15 | B | C |
| ATOM | 3671 | CB | VAL | B | 982 | −17.082 | 20.599 | 38.547 | 1.00 | 45.79 | B | C |
| ATOM | 3672 | CG1 | VAL | B | 982 | −16.290 | 19.319 | 38.426 | 1.00 | 44.97 | B | C |
| ATOM | 3673 | CG2 | VAL | B | 982 | −18.435 | 20.316 | 39.161 | 1.00 | 45.38 | B | C |
| ATOM | 3674 | C | VAL | B | 982 | −14.993 | 21.971 | 38.735 | 1.00 | 46.37 | B | C |
| ATOM | 3675 | O | VAL | B | 982 | −14.864 | 21.867 | 37.515 | 1.00 | 46.84 | B | O |
| ATOM | 3676 | N | VAL | B | 983 | −14.021 | 22.401 | 39.537 | 1.00 | 46.67 | B | N |
| ATOM | 3677 | CA | VAL | B | 983 | −12.703 | 22.774 | 39.031 | 1.00 | 47.04 | B | C |
| ATOM | 3678 | CB | VAL | B | 983 | −12.512 | 24.313 | 39.075 | 1.00 | 47.43 | B | C |
| ATOM | 3679 | CG1 | VAL | B | 983 | −12.785 | 24.836 | 40.482 | 1.00 | 45.36 | B | C |
| ATOM | 3680 | CG2 | VAL | B | 983 | −11.109 | 24.681 | 38.614 | 1.00 | 44.47 | B | C |
| ATOM | 3681 | C | VAL | B | 983 | −11.594 | 22.095 | 39.837 | 1.00 | 47.73 | B | C |
| ATOM | 3682 | O | VAL | B | 983 | −11.692 | 21.968 | 41.054 | 1.00 | 48.13 | B | O |
| ATOM | 3683 | N | ARG | B | 984 | −10.545 | 21.652 | 39.148 | 1.00 | 48.65 | B | N |
| ATOM | 3684 | CA | ARG | B | 984 | −9.426 | 20.974 | 39.795 | 1.00 | 49.00 | B | C |
| ATOM | 3685 | CB | ARG | B | 984 | −8.537 | 20.268 | 38.746 | 1.00 | 51.15 | B | C |
| ATOM | 3686 | CG | ARG | B | 984 | −8.174 | 18.838 | 39.065 | 1.00 | 54.57 | B | C |
| ATOM | 3687 | CD | ARG | B | 984 | −7.740 | 18.701 | 40.513 | 1.00 | 59.55 | B | C |
| ATOM | 3688 | NE | ARG | B | 984 | −7.279 | 17.355 | 40.849 | 1.00 | 62.55 | B | N |
| ATOM | 3689 | CZ | ARG | B | 984 | −6.104 | 16.851 | 40.487 | 1.00 | 64.30 | B | C |
| ATOM | 3690 | NH1 | ARG | B | 984 | −5.780 | 15.614 | 40.843 | 1.00 | 65.05 | B | N |
| ATOM | 3691 | NH2 | ARG | B | 984 | −5.252 | 17.582 | 39.776 | 1.00 | 63.24 | B | N |
| ATOM | 3692 | C | ARG | B | 984 | −8.594 | 21.966 | 40.598 | 1.00 | 48.48 | B | C |
| ATOM | 3693 | O | ARG | B | 984 | −7.965 | 21.602 | 41.593 | 1.00 | 49.43 | B | O |
| ATOM | 3694 | N | GLU | B | 985 | −8.581 | 23.219 | 40.161 | 1.00 | 46.65 | B | N |
| ATOM | 3695 | CA | GLU | B | 985 | −7.828 | 24.248 | 40.861 | 1.00 | 43.97 | B | C |
| ATOM | 3696 | CB | GLU | B | 985 | −6.458 | 24.443 | 40.208 | 1.00 | 45.70 | B | C |
| ATOM | 3697 | CG | GLU | B | 985 | −5.408 | 25.041 | 41.147 | 1.00 | 51.85 | B | C |
| ATOM | 3698 | CD | GLU | B | 985 | −4.850 | 24.038 | 42.161 | 1.00 | 53.27 | B | C |
| ATOM | 3699 | OE1 | GLU | B | 985 | −4.300 | 24.479 | 43.195 | 1.00 | 54.45 | B | O |
| ATOM | 3700 | OE2 | GLU | B | 985 | −4.944 | 22.814 | 41.921 | 1.00 | 55.23 | B | O |
| ATOM | 3701 | C | GLU | B | 985 | −8.625 | 25.542 | 40.811 | 1.00 | 41.24 | B | C |
| ATOM | 3702 | O | GLU | B | 985 | −8.401 | 26.387 | 39.947 | 1.00 | 40.60 | B | O |
| ATOM | 3703 | N | PRO | B | 986 | −9.564 | 25.712 | 41.756 | 1.00 | 38.73 | B | N |

-continued

| ATOM | 3704 | CD  | PRO | B | 986 | −9.658  | 24.841 | 42.939 | 1.00 | 37.63 | B | C |
| ATOM | 3705 | CA  | PRO | B | 986 | −10.456 | 26.869 | 41.903 | 1.00 | 37.13 | B | C |
| ATOM | 3706 | CB  | PRO | B | 986 | −11.165 | 26.589 | 43.231 | 1.00 | 35.86 | B | C |
| ATOM | 3707 | CG  | PRO | B | 986 | −10.161 | 25.801 | 43.991 | 1.00 | 36.53 | B | C |
| ATOM | 3708 | C   | PRO | B | 986 | −9.799  | 28.258 | 41.853 | 1.00 | 36.29 | B | C |
| ATOM | 3709 | O   | PRO | B | 986 | −10.418 | 29.220 | 41.405 | 1.00 | 36.29 | B | O |
| ATOM | 3710 | N   | GLY | B | 987 | −8.557  | 28.372 | 42.310 | 1.00 | 34.80 | B | N |
| ATOM | 3711 | CA  | GLY | B | 987 | −7.900  | 29.665 | 42.266 | 1.00 | 32.48 | B | C |
| ATOM | 3712 | C   | GLY | B | 987 | −7.729  | 30.195 | 40.848 | 1.00 | 30.71 | B | C |
| ATOM | 3713 | O   | GLY | B | 987 | −7.573  | 31.397 | 40.654 | 1.00 | 28.46 | B | O |
| ATOM | 3714 | N   | GLN | B | 988 | −7.750  | 29.298 | 39.862 | 1.00 | 28.88 | B | N |
| ATOM | 3715 | CA  | GLN | B | 988 | −7.593  | 29.674 | 38.461 | 1.00 | 27.63 | B | C |
| ATOM | 3716 | CB  | GLN | B | 988 | −6.546  | 28.788 | 37.791 | 1.00 | 28.47 | B | C |
| ATOM | 3717 | CG  | GLN | B | 988 | −5.165  | 28.913 | 36.413 | 1.00 | 29.70 | B | C |
| ATOM | 3718 | CD  | GLN | B | 988 | −4.569  | 30.293 | 38.220 | 1.00 | 29.60 | B | C |
| ATOM | 3719 | OE1 | GLN | B | 988 | −4.197  | 30.621 | 37.078 | 1.00 | 25.73 | B | O |
| ATOM | 3720 | NE2 | GLN | B | 988 | −4.484  | 31.049 | 39.212 | 1.00 | 31.49 | B | O |
| ATOM | 3721 | C   | GLN | B | 988 | −8.904  | 29.588 | 37.688 | 1.00 | 28.49 | B | C |
| ATOM | 3722 | O   | GLN | B | 988 | −8.904  | 29.479 | 36.460 | 1.00 | 26.59 | B | O |
| ATOM | 3723 | N   | SER | B | 989 | −10.017 | 29.625 | 38.421 | 1.00 | 29.21 | B | N |
| ATOM | 3724 | CA  | SER | B | 989 | −11.344 | 29.581 | 37.824 | 1.00 | 29.21 | B | C |
| ATOM | 3725 | CB  | SER | B | 989 | −12.427 | 29.566 | 38.896 | 1.00 | 28.70 | B | C |
| ATOM | 3726 | OG  | SER | B | 989 | −13.694 | 29.771 | 38.300 | 1.00 | 29.29 | B | O |
| ATOM | 3727 | C   | SER | B | 989 | −11.505 | 30.833 | 36.982 | 1.00 | 29.88 | B | C |
| ATOM | 3728 | O   | SER | B | 989 | −11.334 | 31.945 | 37.474 | 1.00 | 30.64 | B | O |
| ATOM | 3729 | N   | PRO | B | 990 | −11.860 | 30.666 | 35.703 | 1.00 | 29.48 | B | N |
| ATOM | 3730 | CD  | PRO | B | 990 | −12.224 | 29.381 | 35.078 | 1.00 | 29.21 | B | C |
| ATOM | 3731 | CA  | PRO | B | 990 | −12.044 | 31.775 | 34.762 | 1.00 | 29.66 | B | C |
| ATOM | 3732 | CB  | PRO | B | 990 | −12.692 | 31.095 | 33.555 | 1.00 | 30.57 | B | C |
| ATOM | 3733 | CG  | PRO | B | 990 | −12.097 | 29.698 | 33.609 | 1.00 | 30.85 | B | C |
| ATOM | 3734 | C   | PRO | B | 990 | −12.865 | 32.951 | 35.278 | 1.00 | 27.44 | B | C |
| ATOM | 3735 | O   | PRO | B | 990 | −12.640 | 34.081 | 34.856 | 1.00 | 28.69 | B | O |
| ATOM | 3736 | N   | ILE | B | 991 | −13.807 | 32.689 | 36.180 | 1.00 | 25.37 | B | N |
| ATOM | 3737 | CA  | ILE | B | 991 | −14.656 | 33.751 | 36.717 | 1.00 | 24.21 | B | C |
| ATOM | 3738 | CB  | ILE | B | 991 | −15.636 | 33.216 | 37.789 | 1.00 | 22.18 | B | C |
| ATOM | 3739 | CG2 | ILE | B | 991 | −16.408 | 32.041 | 37.252 | 1.00 | 21.00 | B | C |
| ATOM | 3740 | CG1 | ILE | B | 991 | −14.872 | 32.797 | 39.037 | 1.00 | 22.49 | B | C |
| ATOM | 3741 | CD1 | ILE | B | 991 | −15.770 | 32.280 | 40.129 | 1.00 | 20.47 | B | C |
| ATOM | 3742 | C   | ILE | B | 991 | −13.915 | 34.956 | 37.318 | 1.00 | 22.89 | B | C |
| ATOM | 3743 | O   | ILE | B | 991 | −14.380 | 36.084 | 37.184 | 1.00 | 22.11 | B | O |
| ATOM | 3744 | N   | PHE | B | 992 | −12.771 | 34.738 | 37.961 | 1.00 | 20.98 | B | N |
| ATOM | 3745 | CA  | PHE | B | 992 | −12.052 | 35.867 | 38.555 | 1.00 | 21.73 | B | C |
| ATOM | 3746 | CB  | PHE | B | 992 | −10.972 | 35.365 | 39.528 | 1.00 | 19.62 | B | C |
| ATOM | 3747 | CG  | PHE | B | 992 | −11.520 | 34.512 | 40.634 | 1.00 | 18.15 | B | C |
| ATOM | 3748 | CD1 | PHE | B | 992 | −12.614 | 34.947 | 41.378 | 1.00 | 17.59 | B | C |
| ATOM | 3749 | CD2 | PHE | B | 992 | −10.968 | 33.272 | 40.912 | 1.00 | 16.48 | B | C |
| ATOM | 3750 | CE1 | PHE | B | 992 | −13.154 | 34.162 | 42.379 | 1.00 | 17.22 | B | C |
| ATOM | 3751 | CE2 | PHE | B | 992 | −11.495 | 32.476 | 41.909 | 1.00 | 18.83 | B | C |
| ATOM | 3752 | CZ  | PHE | B | 992 | −12.596 | 32.921 | 42.650 | 1.00 | 18.84 | B | C |
| ATOM | 3753 | C   | PHE | B | 992 | −11.439 | 36.841 | 37.544 | 1.00 | 21.99 | B | C |
| ATOM | 3754 | O   | PHE | B | 992 | −10.912 | 37.884 | 37.933 | 1.00 | 21.24 | B | O |
| ATOM | 3755 | N   | TRP | B | 993 | −11.520 | 36.494 | 36.257 | 1.00 | 21.93 | B | N |
| ATOM | 3756 | CA  | TRP | B | 993 | −11.004 | 37.325 | 35.159 | 1.00 | 23.05 | B | C |
| ATOM | 3757 | CB  | TRP | B | 993 | −10.049 | 36.515 | 34.275 | 1.00 | 19.09 | B | C |
| ATOM | 3758 | CG  | TRP | B | 993 | −8.689  | 36.325 | 34.848 | 1.00 | 20.94 | B | C |
| ATOM | 3759 | CD2 | TRP | B | 993 | −8.296  | 35.374 | 35.852 | 1.00 | 20.70 | B | C |
| ATOM | 3760 | CE2 | TRP | B | 993 | −6.932  | 35.608 | 36.129 | 1.00 | 20.32 | B | C |
| ATOM | 3761 | CE3 | TRP | B | 993 | −8.965  | 34.348 | 36.541 | 1.00 | 20.74 | B | C |
| ATOM | 3762 | CD1 | TRP | B | 993 | −7.579  | 37.065 | 34.568 | 1.00 | 21.22 | B | C |
| ATOM | 3763 | NE1 | TRP | B | 993 | −6.523  | 36.644 | 35.336 | 1.00 | 22.28 | B | N |
| ATOM | 3764 | CZ2 | TRP | B | 993 | −6.222  | 34.857 | 37.073 | 1.00 | 18.70 | B | C |
| ATOM | 3765 | CZ3 | TRP | B | 993 | −8.257  | 33.602 | 37.479 | 1.00 | 16.48 | B | C |
| ATOM | 3766 | CH2 | TRP | B | 993 | −6.897  | 33.864 | 37.734 | 1.00 | 17.27 | B | C |
| ATOM | 3767 | C   | TRP | B | 993 | −12.153 | 37.841 | 34.288 | 1.00 | 24.85 | B | C |
| ATOM | 3768 | O   | TRP | B | 993 | −11.966 | 38.714 | 33.436 | 1.00 | 26.79 | B | O |
| ATOM | 3769 | N   | TYR | B | 994 | −13.347 | 37.307 | 34.506 | 1.00 | 25.07 | B | N |
| ATOM | 3770 | CA  | TYR | B | 994 | −14.492 | 37.685 | 33.689 | 1.00 | 25.56 | B | C |
| ATOM | 3771 | CB  | TYR | B | 994 | −15.661 | 36.721 | 33.929 | 1.00 | 26.05 | B | C |
| ATOM | 3772 | CG  | TYR | B | 994 | −15.487 | 35.343 | 33.314 | 1.00 | 26.17 | B | C |
| ATOM | 3773 | CD1 | TYR | B | 994 | −14.323 | 35.005 | 32.624 | 1.00 | 25.80 | B | C |
| ATOM | 3774 | CE1 | TYR | B | 994 | −14.189 | 33.761 | 32.008 | 1.00 | 26.46 | B | C |
| ATOM | 3775 | CD2 | TYR | B | 994 | −16.510 | 34.397 | 33.376 | 1.00 | 26.01 | B | C |
| ATOM | 3776 | CE2 | TYR | B | 994 | −16.384 | 33.153 | 32.763 | 1.00 | 25.93 | B | C |
| ATOM | 3777 | CZ  | TYR | B | 994 | −15.223 | 32.840 | 32.079 | 1.00 | 26.41 | B | C |
| ATOM | 3778 | OH  | TYR | B | 994 | −15.090 | 31.616 | 31.458 | 1.00 | 27.87 | B | O |
| ATOM | 3779 | C   | TYR | B | 994 | −14.981 | 39.095 | 33.902 | 1.00 | 25.85 | B | C |
| ATOM | 3780 | O   | TYR | B | 994 | −15.005 | 39.587 | 35.020 | 1.00 | 27.26 | B | O |
| ATOM | 3781 | N   | ALA | B | 995 | −15.369 | 39.752 | 32.816 | 1.00 | 26.65 | B | N |
| ATOM | 3782 | CA  | ALA | B | 995 | −15.911 | 41.094 | 32.925 | 1.00 | 25.40 | B | C |
| ATOM | 3783 | CB  | ALA | B | 995 | −15.883 | 41.789 | 31.578 | 1.00 | 23.16 | B | C |

| | | | | | | | | | | | |
|---|---|---|---|---|---|---|---|---|---|---|---|
| ATOM | 3784 | C | ALA | B | 995 | −17.352 | 40.907 | 33.389 | 1.00 | 25.46 | B | C |
| ATOM | 3785 | O | ALA | B | 995 | −17.916 | 39.813 | 33.284 | 1.00 | 23.51 | B | O |
| ATOM | 3786 | N | PRO | B | 996 | −17.963 | 41.970 | 33.917 | 1.00 | 25.58 | B | N |
| ATOM | 3787 | CD | PRO | B | 996 | −17.400 | 43.304 | 34.173 | 1.00 | 25.53 | B | C |
| ATOM | 3788 | CA | PRO | B | 996 | −19.344 | 41.893 | 34.389 | 1.00 | 27.00 | B | C |
| ATOM | 3789 | CB | PRO | B | 996 | −19.683 | 43.349 | 34.682 | 1.00 | 24.54 | B | C |
| ATOM | 3790 | CG | PRO | B | 996 | −18.395 | 43.888 | 35.131 | 1.00 | 24.67 | B | C |
| ATOM | 3791 | C | PRO | B | 996 | −20.303 | 41.263 | 33.374 | 1.00 | 28.59 | B | C |
| ATOM | 3792 | O | PRO | B | 996 | −20.943 | 40.252 | 33.674 | 1.00 | 28.72 | B | O |
| ATOM | 3793 | N | GLU | B | 997 | −20.391 | 41.850 | 32.179 | 1.00 | 29.28 | B | N |
| ATOM | 3794 | CA | GLU | B | 997 | −21.301 | 41.342 | 31.153 | 1.00 | 30.88 | B | C |
| ATOM | 3795 | CB | GLU | B | 997 | −21.101 | 42.057 | 29.798 | 1.00 | 31.68 | B | C |
| ATOM | 3796 | CG | GLU | B | 997 | −19.734 | 41.900 | 29.169 | 1.00 | 30.63 | B | C |
| ATOM | 3797 | CD | GLU | B | 997 | −18.779 | 42.982 | 29.608 | 1.00 | 32.64 | B | C |
| ATOM | 3798 | OE1 | GLU | B | 997 | −18.945 | 43.483 | 30.745 | 1.00 | 31.73 | B | O |
| ATOM | 3799 | OE2 | GLU | B | 997 | −17.864 | 43.322 | 28.822 | 1.00 | 31.67 | B | O |
| ATOM | 3800 | C | GLU | B | 997 | −21.134 | 39.847 | 30.963 | 1.00 | 31.40 | B | C |
| ATOM | 3801 | O | GLU | B | 997 | −22.082 | 39.151 | 30.611 | 1.00 | 31.19 | B | O |
| ATOM | 3802 | N | SER | B | 998 | −19.926 | 39.348 | 31.202 | 1.00 | 31.66 | B | N |
| ATOM | 3803 | CA | SER | B | 998 | −19.676 | 37.923 | 31.053 | 1.00 | 30.81 | B | C |
| ATOM | 3804 | CB | SER | B | 998 | −18.178 | 37.633 | 31.053 | 1.00 | 29.42 | B | C |
| ATOM | 3805 | OG | SER | B | 998 | −17.611 | 37.933 | 29.793 | 1.00 | 30.14 | B | O |
| ATOM | 3806 | C | SER | B | 998 | −20.343 | 37.131 | 32.159 | 1.00 | 30.19 | B | C |
| ATOM | 3807 | O | SER | B | 998 | −20.926 | 36.081 | 31.911 | 1.00 | 32.24 | B | O |
| ATOM | 3808 | N | LEU | B | 999 | −20.261 | 37.631 | 33.381 | 1.00 | 31.65 | B | N |
| ATOM | 3809 | CA | LEU | B | 999 | −20.854 | 36.931 | 34.508 | 1.00 | 33.55 | B | C |
| ATOM | 3810 | CB | LEU | B | 999 | −20.399 | 37.560 | 35.828 | 1.00 | 30.58 | B | C |
| ATOM | 3811 | CG | LEU | B | 999 | −18.949 | 37.373 | 36.287 | 1.00 | 30.41 | B | C |
| ATOM | 3812 | CD1 | LEU | B | 999 | −18.792 | 37.992 | 37.667 | 1.00 | 29.34 | B | C |
| ATOM | 3813 | CD2 | LEU | B | 999 | −18.595 | 35.904 | 36.351 | 1.00 | 28.97 | B | C |
| ATOM | 3814 | C | LEU | B | 999 | −22.378 | 36.909 | 34.458 | 1.00 | 35.12 | B | C |
| ATOM | 3815 | O | LEU | B | 999 | −22.999 | 35.902 | 34.788 | 1.00 | 35.62 | B | O |
| ATOM | 3816 | N | SER | B | 1000 | −22.982 | 38.014 | 34.039 | 1.00 | 36.04 | B | N |
| ATOM | 3817 | CA | SER | B | 1000 | −24.433 | 38.094 | 33.986 | 1.00 | 37.54 | B | C |
| ATOM | 3818 | CB | SER | B | 1000 | −24.889 | 39.515 | 34.319 | 1.00 | 38.20 | B | C |
| ATOM | 3819 | OG | SER | B | 1000 | −24.368 | 40.453 | 33.391 | 1.00 | 39.11 | B | O |
| ATOM | 3820 | C | SER | B | 1000 | −25.076 | 37.677 | 32.671 | 1.00 | 38.49 | B | C |
| ATOM | 3821 | O | SER | B | 1000 | −26.296 | 37.563 | 32.603 | 1.00 | 38.27 | B | O |
| ATOM | 3822 | N | ASP | B | 1001 | −24.279 | 37.445 | 31.633 | 1.00 | 38.91 | B | N |
| ATOM | 3823 | CA | ASP | B | 1001 | −24.847 | 37.075 | 30.339 | 1.00 | 41.24 | B | C |
| ATOM | 3824 | CB | ASP | B | 1001 | −25.201 | 38.350 | 29.573 | 1.00 | 42.19 | B | C |
| ATOM | 3825 | CG | ASP | B | 1001 | −26.330 | 39.118 | 30.220 | 1.00 | 44.29 | B | C |
| ATOM | 3826 | OD1 | ASP | B | 1001 | −27.446 | 38.561 | 30.286 | 1.00 | 43.63 | B | O |
| ATOM | 3827 | OD2 | ASP | B | 1001 | −26.103 | 40.271 | 30.660 | 1.00 | 45.40 | B | O |
| ATOM | 3828 | C | ASP | B | 1001 | −24.001 | 36.167 | 29.434 | 1.00 | 41.18 | B | C |
| ATOM | 3829 | O | ASP | B | 1001 | −24.409 | 35.659 | 26.313 | 1.00 | 39.87 | B | O |
| ATOM | 3830 | N | ASN | B | 1002 | −22.839 | 35.735 | 29.914 | 1.00 | 40.49 | B | N |
| ATOM | 3831 | CA | ASN | B | 1002 | −21.952 | 34.892 | 29.118 | 1.00 | 41.92 | B | C |
| ATOM | 3832 | CB | ASN | B | 1002 | −22.680 | 33.636 | 26.625 | 1.00 | 43.88 | B | C |
| ATOM | 3833 | CG | ASN | B | 1002 | −23.039 | 32.696 | 29.748 | 1.00 | 47.49 | B | C |
| ATOM | 3834 | OD1 | ASN | B | 1002 | −22.165 | 32.216 | 30.465 | 1.00 | 50.58 | B | O |
| ATOM | 3835 | ND2 | ASN | B | 1002 | −24.331 | 32.425 | 29.911 | 1.00 | 48.38 | B | N |
| ATOM | 3836 | C | ASN | B | 1002 | −21.415 | 35.668 | 27.916 | 1.00 | 42.17 | B | C |
| ATOM | 3837 | O | ASN | B | 1002 | −20.720 | 35.109 | 27.072 | 1.00 | 42.74 | B | O |
| ATOM | 3838 | N | ILE | B | 1003 | −21.737 | 36.958 | 27.850 | 1.00 | 40.60 | B | N |
| ATOM | 3839 | CA | ILE | B | 1003 | −21.293 | 37.822 | 26.760 | 1.00 | 37.90 | B | C |
| ATOM | 3840 | CB | ILE | B | 1003 | −21.949 | 39.218 | 26.855 | 1.00 | 38.42 | B | C |
| ATOM | 3841 | CG2 | ILE | B | 1003 | −21.375 | 40.150 | 25.821 | 1.00 | 35.41 | B | C |
| ATOM | 3842 | CG1 | ILE | B | 1003 | −23.456 | 39.099 | 26.667 | 1.00 | 38.11 | B | C |
| ATOM | 3843 | CD1 | ILE | B | 1003 | −24.163 | 40.422 | 26.794 | 1.00 | 36.73 | B | C |
| ATOM | 3844 | C | ILE | B | 1003 | −19.781 | 38.007 | 26.777 | 1.00 | 37.25 | B | C |
| ATOM | 3845 | O | ILE | B | 1003 | −19.209 | 38.409 | 27.791 | 1.00 | 38.16 | B | O |
| ATOM | 3846 | N | PHE | B | 1004 | −19.143 | 37.710 | 25.649 | 1.00 | 34.80 | B | N |
| ATOM | 3847 | CA | PHE | B | 1004 | −17.701 | 37.846 | 25.505 | 1.00 | 33.02 | B | C |
| ATOM | 3848 | CB | PHE | B | 1004 | −17.053 | 36.468 | 25.379 | 1.00 | 31.30 | B | C |
| ATOM | 3849 | CG | PHE | B | 1004 | −17.010 | 35.695 | 26.672 | 1.00 | 33.33 | B | C |
| ATOM | 3850 | CD1 | PHE | B | 1004 | −16.122 | 36.053 | 27.681 | 1.00 | 31.07 | B | C |
| ATOM | 3851 | CD2 | PHE | B | 1004 | −17.871 | 34.619 | 26.889 | 1.00 | 33.88 | B | C |
| ATOM | 3852 | CE1 | PHE | B | 1004 | −16.088 | 35.360 | 28.882 | 1.00 | 31.19 | B | C |
| ATOM | 3853 | CE2 | PHE | B | 1004 | −17.848 | 33.913 | 28.094 | 1.00 | 33.73 | B | C |
| ATOM | 3854 | CZ | PHE | B | 1004 | −16.953 | 34.284 | 29.094 | 1.00 | 31.84 | B | C |
| ATOM | 3855 | C | PHE | B | 1004 | −17.416 | 38.672 | 24.261 | 1.00 | 33.61 | B | C |
| ATOM | 3856 | O | PHE | B | 1004 | −18.005 | 38.426 | 23.214 | 1.00 | 36.40 | B | O |
| ATOM | 3857 | N | SER | B | 1005 | −16.521 | 39.651 | 24.373 | 1.00 | 32.85 | B | N |
| ATOM | 3858 | CA | SER | B | 1005 | −16.181 | 40.507 | 23.243 | 1.00 | 31.81 | B | C |
| ATOM | 3859 | CB | SER | B | 1005 | −17.128 | 41.697 | 23.178 | 1.00 | 32.82 | B | C |
| ATOM | 3860 | OG | SER | B | 1005 | −16.862 | 42.582 | 24.254 | 1.00 | 35.29 | B | O |
| ATOM | 3861 | C | SER | B | 1005 | −14.764 | 41.038 | 23.368 | 1.00 | 31.55 | B | C |
| ATOM | 3862 | O | SER | B | 1005 | −14.071 | 40.758 | 24.346 | 1.00 | 30.74 | B | O |
| ATOM | 3863 | N | ARG | B | 1006 | −14.342 | 41.811 | 22.371 | 1.00 | 30.35 | B | N |

-continued

| | | | | | | | | | | | |
|---|---|---|---|---|---|---|---|---|---|---|---|
| ATOM | 3864 | CA | ARG | B | 1006 | −13.010 | 42.399 | 22.375 | 1.00 | 31.73 | B | C |
| ATOM | 3865 | CB | ARG | B | 1006 | −12.791 | 43.233 | 21.103 | 1.00 | 32.08 | B | C |
| ATOM | 3866 | CG | ARG | B | 1006 | −12.340 | 42.401 | 19.909 | 1.00 | 35.73 | B | C |
| ATOM | 3867 | CD | ARG | B | 1006 | −12.529 | 43.117 | 16.571 | 1.00 | 38.23 | B | C |
| ATOM | 3868 | NE | ARG | B | 1006 | −11.797 | 44.376 | 16.500 | 1.00 | 42.85 | B | N |
| ATOM | 3869 | CZ | ARG | B | 1006 | −11.646 | 45.100 | 17.393 | 1.00 | 43.99 | B | C |
| ATOM | 3870 | NH1 | ARG | B | 1006 | −10.968 | 46.238 | 17.433 | 1.00 | 42.77 | B | N |
| ATOM | 3871 | NH2 | ARG | B | 1006 | −12.159 | 44.681 | 16.244 | 1.00 | 45.31 | B | N |
| ATOM | 3872 | C | ARG | B | 1006 | −12.836 | 43.273 | 23.612 | 1.00 | 31.29 | B | C |
| ATOM | 3873 | O | ARG | B | 1006 | −11.750 | 43.352 | 24.191 | 1.00 | 30.22 | B | O |
| ATOM | 3874 | N | GLN | B | 1007 | −13.924 | 43.910 | 24.029 | 1.00 | 30.47 | B | N |
| ATOM | 3875 | CA | GLN | B | 1007 | −13.881 | 44.788 | 25.184 | 1.00 | 28.48 | B | C |
| ATOM | 3876 | CB | GLN | B | 1007 | −15.064 | 45.757 | 25.139 | 1.00 | 29.31 | B | C |
| ATOM | 3877 | CG | GLN | B | 1007 | −14.935 | 46.827 | 24.039 | 1.00 | 30.12 | B | C |
| ATOM | 3878 | CD | GLN | B | 1007 | −13.647 | 47.677 | 24.155 | 1.00 | 31.23 | B | C |
| ATOM | 3879 | OE1 | GLN | B | 1007 | −12.602 | 47.362 | 23.559 | 1.00 | 24.82 | B | O |
| ATOM | 3880 | NE2 | GLN | B | 1007 | −13.729 | 48.756 | 24.936 | 1.00 | 29.95 | B | N |
| ATOM | 3881 | C | GLN | B | 1007 | −13.838 | 44.033 | 26.509 | 1.00 | 26.99 | B | C |
| ATOM | 3882 | O | GLN | B | 1007 | −13.243 | 44.505 | 27.478 | 1.00 | 25.04 | B | O |
| ATOM | 3883 | N | SER | B | 1008 | −14.468 | 42.865 | 26.559 | 1.00 | 25.68 | B | N |
| ATOM | 3884 | CA | SER | B | 1008 | −14.434 | 42.057 | 27.772 | 1.00 | 26.10 | B | C |
| ATOM | 3885 | CB | SER | B | 1008 | −15.421 | 40.891 | 27.665 | 1.00 | 27.87 | B | C |
| ATOM | 3886 | OG | SER | B | 1008 | −15.080 | 40.026 | 26.598 | 1.00 | 31.41 | B | O |
| ATOM | 3887 | C | SER | B | 1008 | −12.995 | 41.538 | 27.944 | 1.00 | 26.67 | B | C |
| ATOM | 3888 | O | SER | B | 1008 | −12.501 | 41.384 | 29.065 | 1.00 | 26.79 | B | O |
| ATOM | 3889 | N | ASP | B | 1009 | −12.324 | 41.265 | 26.825 | 1.00 | 25.33 | B | N |
| ATOM | 3890 | CA | ASP | B | 1009 | −10.943 | 40.806 | 26.872 | 1.00 | 25.36 | B | C |
| ATOM | 3891 | CB | ASP | B | 1009 | −10.409 | 40.469 | 25.468 | 1.00 | 26.35 | B | C |
| ATOM | 3892 | CG | ASP | B | 1009 | −10.917 | 39.121 | 24.942 | 1.00 | 29.84 | B | C |
| ATOM | 3893 | OD1 | ASP | B | 1009 | −10.675 | 38.823 | 23.742 | 1.00 | 30.40 | B | O |
| ATOM | 3894 | OD2 | ASP | B | 1009 | −11.543 | 38.365 | 25.723 | 1.00 | 28.13 | B | O |
| ATOM | 3895 | C | ASP | B | 1009 | −10.105 | 41.926 | 27.472 | 1.00 | 24.93 | B | C |
| ATOM | 3896 | O | ASP | B | 1009 | −9.102 | 41.680 | 28.143 | 1.00 | 24.99 | B | O |
| ATOM | 3897 | N | VAL | B | 1010 | −10.524 | 43.162 | 27.228 | 1.00 | 22.69 | B | N |
| ATOM | 3898 | CA | VAL | B | 1010 | −9.797 | 44.307 | 27.751 | 1.00 | 23.10 | B | C |
| ATOM | 3899 | CB | VAL | B | 1010 | −10.400 | 45.641 | 27.246 | 1.00 | 21.13 | B | C |
| ATOM | 3900 | CG1 | VAL | B | 1010 | −9.916 | 46.783 | 28.110 | 1.00 | 21.03 | B | C |
| ATOM | 3901 | CG2 | VAL | B | 1010 | −9.992 | 45.886 | 25.803 | 1.00 | 18.23 | B | C |
| ATOM | 3902 | C | VAL | B | 1010 | −9.823 | 44.278 | 29.277 | 1.00 | 23.05 | B | C |
| ATOM | 3903 | O | VAL | B | 1010 | −8.823 | 44.568 | 29.927 | 1.00 | 22.50 | B | O |
| ATOM | 3904 | N | TRP | B | 1011 | −10.977 | 43.924 | 29.833 | 1.00 | 23.37 | B | N |
| ATOM | 3905 | CA | TRP | B | 1011 | −11.156 | 43.834 | 31.274 | 1.00 | 22.16 | B | C |
| ATOM | 3906 | CB | TRP | B | 1011 | −12.605 | 43.436 | 31.582 | 1.00 | 21.39 | B | C |
| ATOM | 3907 | CG | TRP | B | 1011 | −12.856 | 43.017 | 33.021 | 1.00 | 22.17 | B | C |
| ATOM | 3908 | CD2 | TRP | B | 1011 | −13.633 | 43.722 | 33.994 | 1.00 | 21.79 | B | C |
| ATOM | 3909 | CE2 | TRP | B | 1011 | −13.611 | 42.956 | 35.187 | 1.00 | 22.59 | B | C |
| ATOM | 3910 | CE3 | TRP | B | 1011 | −14.346 | 44.924 | 33.977 | 1.00 | 20.63 | B | C |
| ATOM | 3911 | CD1 | TRP | B | 1011 | −12.400 | 41.885 | 33.647 | 1.00 | 21.99 | B | C |
| ATOM | 3912 | NE1 | TRP | B | 1011 | −12.851 | 41.840 | 34.946 | 1.00 | 20.90 | B | N |
| ATOM | 3913 | CZ2 | TRP | B | 1011 | −14.276 | 43.353 | 36.350 | 1.00 | 22.92 | B | C |
| ATOM | 3914 | CZ3 | TRP | B | 1011 | −15.006 | 45.318 | 35.130 | 1.00 | 22.87 | B | C |
| ATOM | 3915 | CH2 | TRP | B | 1011 | −14.966 | 44.532 | 36.302 | 1.00 | 24.34 | B | C |
| ATOM | 3916 | C | TRP | B | 1011 | −10.199 | 42.783 | 31.832 | 1.00 | 22.62 | B | C |
| ATOM | 3917 | O | TRP | B | 1011 | −9.496 | 43.006 | 32.818 | 1.00 | 22.51 | B | O |
| ATOM | 3918 | N | SER | B | 1012 | −10.184 | 41.628 | 31.185 | 1.00 | 23.22 | B | N |
| ATOM | 3919 | CA | SER | B | 1012 | −9.329 | 40.540 | 31.614 | 1.00 | 21.86 | B | C |
| ATOM | 3920 | CB | SER | B | 1012 | −9.583 | 39.315 | 30.745 | 1.00 | 23.31 | B | C |
| ATOM | 3921 | CG | SER | B | 1012 | −10.969 | 39.024 | 30.712 | 1.00 | 26.28 | B | O |
| ATOM | 3922 | C | SER | B | 1012 | −7.869 | 40.952 | 31.547 | 1.00 | 20.42 | B | C |
| ATOM | 3923 | O | SER | B | 1012 | −7.054 | 40.446 | 32.312 | 1.00 | 19.32 | B | O |
| ATOM | 3924 | N | PHE | B | 1013 | −7.544 | 41.864 | 30.630 | 1.00 | 19.51 | B | N |
| ATOM | 3925 | CA | PHE | B | 1013 | −6.178 | 42.369 | 30.480 | 1.00 | 20.32 | B | C |
| ATOM | 3926 | CB | PHE | B | 1013 | −6.060 | 43.253 | 29.241 | 1.00 | 22.41 | B | C |
| ATOM | 3927 | CG | PHE | B | 1013 | −4.738 | 43.954 | 29.127 | 1.00 | 24.71 | B | C |
| ATOM | 3928 | CD1 | PHE | B | 1013 | −3.566 | 43.233 | 28.933 | 1.00 | 25.77 | B | C |
| ATOM | 3929 | CD2 | PHE | B | 1013 | −4.660 | 45.335 | 29.215 | 1.00 | 24.66 | B | C |
| ATOM | 3930 | CE1 | PHE | B | 1013 | −2.340 | 43.881 | 28.825 | 1.00 | 25.47 | B | C |
| ATOM | 3931 | CE2 | PHE | B | 1013 | −3.441 | 45.992 | 29.109 | 1.00 | 24.49 | B | C |
| ATOM | 3932 | CZ | PHE | B | 1013 | −2.278 | 45.263 | 28.912 | 1.00 | 24.92 | B | C |
| ATOM | 3933 | C | PHE | B | 1013 | −5.823 | 43.189 | 31.722 | 1.00 | 20.57 | B | C |
| ATOM | 3934 | O | PHE | B | 1013 | −4.671 | 43.203 | 32.178 | 1.00 | 18.68 | B | O |
| ATOM | 3935 | N | GLY | B | 1014 | −6.829 | 43.868 | 32.261 | 1.00 | 18.88 | B | N |
| ATOM | 3936 | CA | GLY | B | 1014 | −6.621 | 44.653 | 33.460 | 1.00 | 23.16 | B | C |
| ATOM | 3937 | C | GLY | B | 1014 | −6.124 | 43.788 | 34.616 | 1.00 | 25.05 | B | C |
| ATOM | 3938 | O | GLY | B | 1014 | −5.211 | 44.166 | 35.357 | 1.00 | 24.37 | B | O |
| ATOM | 3939 | N | VAL | B | 1015 | −6.729 | 42.614 | 34.762 | 1.00 | 26.14 | B | N |
| ATOM | 3940 | CA | VAL | B | 1015 | −6.365 | 41.681 | 35.819 | 1.00 | 25.90 | B | C |
| ATOM | 3941 | CB | VAL | B | 1015 | −7.414 | 40.524 | 35.941 | 1.00 | 25.19 | B | C |
| ATOM | 3942 | CG1 | VAL | B | 1015 | −7.097 | 39.649 | 37.130 | 1.00 | 26.98 | B | C |
| ATOM | 3943 | CG2 | VAL | B | 1015 | −8.611 | 41.089 | 36.094 | 1.00 | 24.45 | B | C |

-continued

| ATOM | 3944 | C | VAL | B | 1015 | −4.990 | 41.096 | 35.514 | 1.00 | 26.88 | B | C |
| --- | --- | --- | --- | --- | --- | --- | --- | --- | --- | --- | --- | --- |
| ATOM | 3945 | O | VAL | B | 1015 | −4.188 | 40.881 | 36.419 | 1.00 | 29.42 | B | O |
| ATOM | 3946 | N | VAL | B | 1016 | −4.707 | 40.835 | 34.242 | 1.00 | 26.06 | B | N |
| ATOM | 3947 | CA | VAL | B | 1016 | −3.401 | 40.296 | 33.874 | 1.00 | 25.47 | B | C |
| ATOM | 3948 | CB | VAL | B | 1016 | −3.295 | 40.064 | 32.363 | 1.00 | 26.29 | B | C |
| ATOM | 3949 | CG1 | VAL | B | 1016 | −1.629 | 40.017 | 31.953 | 1.00 | 24.37 | B | C |
| ATOM | 3950 | CG2 | VAL | B | 1016 | −4.007 | 38.774 | 31.988 | 1.00 | 25.27 | B | C |
| ATOM | 3951 | C | VAL | B | 1016 | −2.301 | 41.270 | 34.290 | 1.00 | 24.52 | B | C |
| ATOM | 3952 | O | VAL | B | 1016 | −1.230 | 40.859 | 34.711 | 1.00 | 24.76 | B | O |
| ATOM | 3953 | N | LEU | B | 1017 | −2.565 | 42.565 | 34.148 | 1.00 | 24.65 | B | N |
| ATOM | 3954 | CA | LEU | B | 1017 | −1.594 | 43.582 | 34.543 | 1.00 | 24.58 | B | C |
| ATOM | 3955 | CB | LEU | B | 1017 | −2.113 | 44.983 | 34.216 | 1.00 | 23.12 | B | C |
| ATOM | 3956 | CG | LEU | B | 1017 | −2.027 | 45.460 | 32.761 | 1.00 | 24.37 | B | C |
| ATOM | 3957 | CD1 | LEU | B | 1017 | −2.982 | 46.629 | 32.545 | 1.00 | 23.70 | B | C |
| ATOM | 3958 | CD2 | LEU | B | 1017 | −0.601 | 45.846 | 32.420 | 1.00 | 21.72 | B | C |
| ATOM | 3959 | C | LEU | B | 1017 | −1.373 | 43.457 | 36.042 | 1.00 | 25.27 | B | C |
| ATOM | 3960 | O | LEU | B | 1017 | −0.257 | 43.645 | 36.540 | 1.00 | 24.20 | B | O |
| ATOM | 3961 | N | TYR | B | 1018 | −2.452 | 43.132 | 36.752 | 1.00 | 25.30 | B | N |
| ATOM | 3962 | CA | TYR | B | 1018 | −2.402 | 42.960 | 38.195 | 1.00 | 26.88 | B | C |
| ATOM | 3963 | CB | TYR | B | 1018 | −3.794 | 42.657 | 38.729 | 1.00 | 26.68 | B | C |
| ATOM | 3964 | CG | TYR | B | 1018 | −3.862 | 42.524 | 40.231 | 1.00 | 30.83 | B | C |
| ATOM | 3965 | CD1 | TYR | B | 1018 | −3.656 | 43.624 | 41.057 | 1.00 | 32.09 | B | C |
| ATOM | 3966 | CE1 | TYR | B | 1018 | −3.736 | 43.509 | 42.430 | 1.00 | 30.76 | B | C |
| ATOM | 3967 | CD2 | TYR | B | 1018 | −4.147 | 41.301 | 40.826 | 1.00 | 31.00 | B | C |
| ATOM | 3968 | CE2 | TYR | B | 1018 | −4.228 | 41.178 | 42.198 | 1.00 | 31.86 | B | C |
| ATOM | 3969 | CZ | TYR | B | 1018 | −4.022 | 42.284 | 42.990 | 1.00 | 31.82 | B | C |
| ATOM | 3970 | OH | TYR | B | 1018 | −4.101 | 42.159 | 44.350 | 1.00 | 33.07 | B | O |
| ATOM | 3971 | C | TYR | B | 1018 | −1.449 | 41.816 | 38.549 | 1.00 | 28.71 | B | C |
| ATOM | 3972 | O | TYR | B | 1018 | −0.540 | 41.979 | 39.372 | 1.00 | 29.73 | B | O |
| ATOM | 3973 | N | GLU | B | 1019 | −1.652 | 40.669 | 37.902 | 1.00 | 29.08 | B | N |
| ATOM | 3974 | CA | GLU | B | 1019 | −0.638 | 39.475 | 38.138 | 1.00 | 28.73 | B | C |
| ATOM | 3975 | CB | GLU | B | 1019 | −1.273 | 38.322 | 37.212 | 1.00 | 28.24 | B | C |
| ATOM | 3976 | CG | GLU | B | 1019 | −2.737 | 37.877 | 37.359 | 1.00 | 28.46 | B | C |
| ATOM | 3977 | CD | GLU | B | 1019 | −3.029 | 36.554 | 36.653 | 1.00 | 29.77 | B | C |
| ATOM | 3978 | OE1 | GLU | B | 1019 | −2.463 | 35.516 | 37.057 | 1.00 | 33.63 | B | O |
| ATOM | 3979 | OE2 | GLU | B | 1019 | −3.824 | 36.536 | 35.691 | 1.00 | 30.03 | B | O |
| ATOM | 3980 | C | GLU | B | 1019 | 0.654 | 39.737 | 37.950 | 1.00 | 28.13 | B | C |
| ATOM | 3981 | O | GLU | B | 1019 | 1.475 | 39.295 | 38.759 | 1.00 | 27.79 | B | O |
| ATOM | 3982 | N | LEU | B | 1020 | 1.002 | 40.452 | 36.885 | 1.00 | 27.07 | B | N |
| ATOM | 3983 | CA | LEU | B | 1020 | 2.400 | 40.762 | 36.598 | 1.00 | 28.46 | B | C |
| ATOM | 3984 | CB | LEU | B | 1020 | 2.518 | 41.508 | 35.256 | 1.00 | 28.04 | B | C |
| ATOM | 3985 | CG | LEU | B | 1020 | 2.371 | 40.718 | 33.948 | 1.00 | 31.18 | B | C |
| ATOM | 3986 | CD1 | LEU | B | 1020 | 3.729 | 40.598 | 33.271 | 1.00 | 30.88 | B | C |
| ATOM | 3987 | CD2 | LEU | B | 1020 | 1.763 | 39.333 | 34.221 | 1.00 | 30.43 | B | C |
| ATOM | 3988 | C | LEU | B | 1020 | 3.054 | 41.592 | 37.709 | 1.00 | 27.19 | B | C |
| ATOM | 3989 | O | LEU | B | 1020 | 4.108 | 41.229 | 38.225 | 1.00 | 27.55 | B | O |
| ATOM | 3990 | N | PHE | B | 1021 | 2.428 | 42.704 | 38.070 | 1.00 | 27.54 | B | N |
| ATOM | 3991 | CA | PHE | B | 1021 | 2.962 | 43.573 | 39.108 | 1.00 | 30.47 | B | C |
| ATOM | 3992 | CB | PHE | B | 1021 | 2.370 | 44.977 | 38.954 | 1.00 | 29.66 | B | C |
| ATOM | 3993 | CG | PHE | B | 1021 | 2.887 | 45.705 | 37.750 | 1.00 | 32.67 | B | C |
| ATOM | 3994 | CD1 | PHE | B | 1021 | 4.129 | 46.331 | 37.781 | 1.00 | 32.20 | B | C |
| ATOM | 3995 | CD2 | PHE | B | 1021 | 2.190 | 45.673 | 36.556 | 1.00 | 32.11 | B | C |
| ATOM | 3996 | CE1 | PHE | B | 1021 | 4.667 | 46.902 | 36.648 | 1.00 | 32.96 | B | C |
| ATOM | 3997 | CE2 | PHE | B | 1021 | 2.726 | 46.243 | 35.416 | 1.00 | 34.86 | B | C |
| ATOM | 3998 | CZ | PHE | B | 1021 | 3.970 | 46.858 | 35.464 | 1.00 | 34.05 | B | C |
| ATOM | 3999 | C | PHE | B | 1021 | 2.687 | 43.005 | 40.498 | 1.00 | 31.35 | B | C |
| ATOM | 4000 | O | PHE | B | 1021 | 2.954 | 43.640 | 41.513 | 1.00 | 33.73 | B | O |
| ATOM | 4001 | N | THR | B | 1022 | 2.157 | 41.793 | 40.531 | 1.00 | 29.56 | B | N |
| ATOM | 4002 | CA | THR | B | 1022 | 1.855 | 41.122 | 41.782 | 1.00 | 27.88 | B | C |
| ATOM | 4003 | CB | THR | B | 1022 | 0.337 | 40.771 | 41.815 | 1.00 | 27.78 | B | C |
| ATOM | 4004 | OG1 | THR | B | 1022 | −0.276 | 41.380 | 42.959 | 1.00 | 29.16 | B | O |
| ATOM | 4005 | CG2 | THR | B | 1022 | 0.105 | 39.265 | 41.830 | 1.00 | 27.02 | B | C |
| ATOM | 4006 | C | THR | B | 1022 | 2.725 | 39.857 | 41.774 | 1.00 | 27.55 | B | C |
| ATOM | 4007 | O | THR | B | 1022 | 2.716 | 39.060 | 42.711 | 1.00 | 25.85 | B | O |
| ATOM | 4008 | N | TYR | B | 1023 | 3.482 | 39.708 | 40.686 | 1.00 | 28.38 | B | N |
| ATOM | 4009 | CA | TYR | B | 1023 | 4.349 | 38.554 | 40.446 | 1.00 | 27.73 | B | C |
| ATOM | 4010 | CB | TYR | B | 1023 | 5.563 | 38.595 | 41.375 | 1.00 | 28.82 | B | C |
| ATOM | 4011 | CG | TYR | B | 1023 | 6.554 | 39.677 | 41.004 | 1.00 | 29.97 | B | C |
| ATOM | 4012 | CD1 | TYR | B | 1023 | 6.475 | 40.948 | 41.562 | 1.00 | 30.60 | B | C |
| ATOM | 4013 | CE1 | TYR | B | 1023 | 7.373 | 41.941 | 41.213 | 1.00 | 28.91 | B | C |
| ATOM | 4014 | CD2 | TYR | B | 1023 | 7.558 | 39.432 | 40.083 | 1.00 | 29.49 | B | C |
| ATOM | 4015 | CE2 | TYR | B | 1023 | 8.455 | 40.419 | 39.732 | 1.00 | 29.77 | B | C |
| ATOM | 4016 | CZ | TYR | B | 1023 | 8.356 | 41.667 | 40.301 | 1.00 | 29.39 | B | C |
| ATOM | 4017 | OH | TYR | B | 1023 | 9.258 | 42.637 | 39.961 | 1.00 | 29.99 | B | O |
| ATOM | 4018 | C | TYR | B | 1023 | 3.600 | 37.222 | 40.610 | 1.00 | 26.68 | B | C |
| ATOM | 4019 | O | TYR | B | 1023 | 4.210 | 36.154 | 40.690 | 1.00 | 23.68 | B | O |
| ATOM | 4020 | N | CYS | B | 1024 | 2.275 | 37.305 | 40.633 | 1.00 | 25.16 | B | N |
| ATOM | 4021 | CA | CYS | B | 1024 | 1.411 | 36.141 | 40.801 | 1.00 | 30.36 | B | C |
| ATOM | 4022 | CB | CYS | B | 1024 | 1.695 | 35.062 | 39.745 | 1.00 | 29.66 | B | C |
| ATOM | 4023 | SG | CYS | B | 1024 | 0.991 | 35.464 | 38.132 | 1.00 | 31.45 | B | S |

-continued

| | | | | | | | | | | | |
|---|---|---|---|---|---|---|---|---|---|---|---|
| ATOM | 4024 | C | CYS | B | 1024 | 1.539 | 35.542 | 42.180 | 1.00 | 31.11 | B | C |
| ATOM | 4025 | O | CYS | B | 1024 | 1.458 | 34.326 | 42.353 | 1.00 | 33.32 | B | O |
| ATOM | 4026 | N | ASP | B | 1025 | 1.736 | 36.394 | 43.172 | 1.00 | 30.88 | B | N |
| ATOM | 4027 | CA | ASP | B | 1025 | 1.843 | 35.868 | 44.523 | 1.00 | 32.73 | B | C |
| ATOM | 4028 | CB | ASP | B | 1025 | 2.062 | 37.031 | 45.501 | 1.00 | 35.93 | B | C |
| ATOM | 4029 | CG | ASP | B | 1025 | 2.440 | 36.541 | 46.869 | 1.00 | 39.06 | B | C |
| ATOM | 4030 | OD1 | ASP | B | 1025 | 3.542 | 35.963 | 46.993 | 1.00 | 41.51 | B | O |
| ATOM | 4031 | OD2 | ASP | B | 1025 | 1.637 | 36.723 | 47.809 | 1.00 | 41.43 | B | O |
| ATOM | 4032 | C | ASP | B | 1025 | 0.539 | 35.165 | 44.859 | 1.00 | 31.75 | B | C |
| ATOM | 4033 | O | ASP | B | 1025 | −0.536 | 35.619 | 44.482 | 1.00 | 28.94 | B | O |
| ATOM | 4034 | N | LYS | B | 1026 | 0.637 | 34.046 | 45.567 | 1.00 | 33.64 | B | N |
| ATOM | 4035 | CA | LYS | B | 1026 | −0.545 | 33.267 | 45.934 | 1.00 | 34.91 | B | C |
| ATOM | 4036 | CB | LYS | B | 1026 | −0.140 | 31.856 | 46.378 | 1.00 | 37.07 | B | C |
| ATOM | 4037 | CG | LYS | B | 1026 | 0.308 | 30.944 | 45.244 | 1.00 | 39.64 | B | C |
| ATOM | 4038 | CD | LYS | B | 1026 | −0.822 | 30.721 | 44.235 | 1.00 | 43.37 | B | C |
| ATOM | 4039 | CE | LYS | B | 1026 | −0.378 | 29.791 | 43.097 | 1.00 | 45.58 | B | C |
| ATOM | 4040 | NZ | LYS | B | 1026 | −1.366 | 29.696 | 41.972 | 1.00 | 46.97 | B | N |
| ATOM | 4041 | C | LYS | B | 1026 | −1.358 | 33.928 | 47.035 | 1.00 | 34.73 | B | C |
| ATOM | 4042 | O | LYS | B | 1026 | −2.544 | 33.653 | 47.184 | 1.00 | 34.89 | B | O |
| ATOM | 4043 | N | SER | B | 1027 | −0.712 | 34.803 | 47.798 | 1.00 | 35.10 | B | N |
| ATOM | 4044 | CA | SER | B | 1027 | −1.366 | 35.507 | 48.891 | 1.00 | 34.69 | B | C |
| ATOM | 4045 | CB | SER | B | 1027 | −0.314 | 36.141 | 49.788 | 1.00 | 35.42 | B | C |
| ATOM | 4046 | CG | SER | B | 1027 | 0.677 | 35.191 | 50.131 | 1.00 | 39.15 | B | O |
| ATOM | 4047 | C | SER | B | 1027 | −2.329 | 36.586 | 46.410 | 1.00 | 34.71 | B | C |
| ATOM | 4048 | O | SER | B | 1027 | −3.418 | 36.741 | 48.960 | 1.00 | 35.34 | B | O |
| ATOM | 4049 | N | CYS | B | 1028 | −1.935 | 37.335 | 47.386 | 1.00 | 34.72 | B | N |
| ATOM | 4050 | CA | CYS | B | 1028 | −2.795 | 38.405 | 46.879 | 1.00 | 34.48 | B | C |
| ATOM | 4051 | CB | CYS | B | 1028 | −2.073 | 39.741 | 47.008 | 1.00 | 34.38 | B | C |
| ATOM | 4052 | SG | CYS | B | 1028 | −0.504 | 39.739 | 46.191 | 1.00 | 37.79 | B | S |
| ATOM | 4053 | C | CYS | B | 1028 | −3.262 | 38.220 | 45.434 | 1.00 | 31.11 | B | C |
| ATOM | 4054 | O | CYS | B | 1028 | −3.480 | 39.187 | 44.713 | 1.00 | 31.03 | B | O |
| ATOM | 4055 | N | SER | B | 1029 | −3.417 | 36.974 | 45.020 | 1.00 | 30.32 | B | N |
| ATOM | 4056 | CA | SER | B | 1029 | −3.867 | 36.665 | 43.670 | 1.00 | 29.14 | B | C |
| ATOM | 4057 | CB | SER | B | 1029 | −3.800 | 35.163 | 43.449 | 1.00 | 29.51 | B | C |
| ATOM | 4058 | OG | SER | B | 1029 | −4.812 | 34.543 | 44.225 | 1.00 | 32.23 | B | O |
| ATOM | 4059 | C | SER | B | 1029 | −5.317 | 37.115 | 43.517 | 1.00 | 26.52 | B | C |
| ATOM | 4060 | O | SER | B | 1029 | −5.968 | 37.498 | 44.489 | 1.00 | 27.24 | B | O |
| ATOM | 4061 | N | PRO | B | 1030 | −5.839 | 37.062 | 42.287 | 1.00 | 24.08 | B | N |
| ATOM | 4062 | CD | PRO | B | 1030 | −5.086 | 36.857 | 41.039 | 1.00 | 22.45 | B | C |
| ATOM | 4063 | CA | PRO | B | 1030 | −7.210 | 37.4*7 | 41.987 | 1.00 | 23.13 | B | C |
| ATOM | 4064 | CB | PRO | B | 1030 | −7.299 | 37.196 | 40.496 | 1.00 | 22.81 | B | C |
| ATOM | 4065 | CG | PRO | B | 1030 | −5.934 | 37.581 | 40.043 | 1.00 | 20.71 | B | C |
| ATOM | 4066 | C | PRO | B | 1030 | −8.262 | 36.702 | 42.796 | 1.00 | 24.05 | B | C |
| ATOM | 4067 | O | PRO | B | 1030 | −9.180 | 37.309 | 43.374 | 1.00 | 23.62 | B | O |
| ATOM | 4068 | N | SER | B | 1031 | −8.136 | 35.380 | 42.834 | 1.00 | 24.60 | B | N |
| ATOM | 4069 | CA | SER | B | 1031 | −9.066 | 34.567 | 43.600 | 1.00 | 25.29 | B | C |
| ATOM | 4070 | CB | SER | B | 1031 | −8.741 | 33.081 | 43.411 | 1.00 | 24.41 | B | C |
| ATOM | 4071 | OG | SER | B | 1031 | −7.367 | 32.829 | 43.619 | 1.00 | 29.84 | B | O |
| ATOM | 4072 | C | SER | B | 1031 | −9.035 | 34.936 | 45.098 | 1.00 | 26.53 | B | C |
| ATOM | 4073 | O | SER | B | 1031 | −10.082 | 35.168 | 45.707 | 1.00 | 26.40 | B | O |
| ATOM | 4074 | N | ALA | B | 1032 | −7.836 | 35.000 | 45.680 | 1.00 | 27.33 | B | N |
| ATOM | 4075 | CA | ALA | B | 1032 | −7.675 | 35.332 | 47.094 | 1.00 | 27.47 | B | C |
| ATOM | 4076 | CB | ALA | B | 1032 | −6.189 | 35.394 | 47.447 | 1.00 | 28.40 | B | C |
| ATOM | 4077 | C | ALA | B | 1032 | −8.364 | 36.646 | 47.479 | 1.00 | 28.39 | B | C |
| ATOM | 4078 | O | ALA | B | 1032 | −9.314 | 36.645 | 48.266 | 1.00 | 27.17 | B | O |
| ATOM | 4079 | N | GLU | B | 1033 | −7.887 | 37.760 | 46.925 | 1.00 | 28.39 | B | N |
| ATOM | 4080 | CA | GLU | B | 1033 | −8.474 | 39.073 | 47.208 | 1.00 | 28.46 | B | C |
| ATOM | 4081 | CB | GLU | B | 1033 | −7.907 | 40.142 | 46.270 | 1.00 | 30.40 | B | C |
| ATOM | 4082 | CG | GLU | B | 1033 | −6.432 | 40.445 | 46.464 | 1.00 | 34.55 | B | C |
| ATOM | 4083 | CD | GLU | B | 1033 | −6.063 | 40.634 | 47.920 | 1.00 | 36.21 | B | C |
| ATOM | 4084 | OE1 | GLU | B | 1033 | −6.955 | 40.978 | 46.723 | 1.00 | 35.21 | B | O |
| ATOM | 4085 | OE2 | GLU | B | 1033 | −4.874 | 40.448 | 48.257 | 1.00 | 37.70 | B | O |
| ATOM | 4086 | C | GLU | B | 1033 | −9.984 | 39.074 | 47.068 | 1.00 | 27.91 | B | C |
| ATOM | 4087 | O | GLU | B | 1033 | −10.691 | 39.580 | 47.931 | 1.00 | 28.02 | B | O |
| ATOM | 4088 | N | PHE | B | 1034 | −10.480 | 38.523 | 45.965 | 1.00 | 28.93 | B | N |
| ATOM | 4089 | CA | PHE | B | 1034 | −11.917 | 38.466 | 45.728 | 1.00 | 27.01 | B | C |
| ATOM | 4090 | CB | PHE | B | 1034 | −12.195 | 37.895 | 44.335 | 1.00 | 25.79 | B | C |
| ATOM | 4091 | CG | PHE | B | 1034 | −12.171 | 38.935 | 43.234 | 1.00 | 28.49 | B | C |
| ATOM | 4092 | CD1 | PHE | B | 1034 | −11.569 | 38.664 | 42.009 | 1.00 | 25.37 | B | C |
| ATOM | 4093 | CD2 | PHE | B | 1034 | −12.770 | 40.178 | 43.423 | 1.00 | 26.16 | B | C |
| ATOM | 4094 | CE1 | PHE | B | 1034 | −11.564 | 39.612 | 40.996 | 1.00 | 25.58 | B | C |
| ATOM | 4095 | CE2 | PHE | B | 1034 | −12.764 | 41.129 | 42.407 | 1.00 | 26.17 | B | C |
| ATOM | 4096 | CZ | PHE | B | 1034 | −12.160 | 40.842 | 41.194 | 1.00 | 25.18 | B | C |
| ATOM | 4097 | C | PHE | B | 1034 | −12.594 | 37.620 | 46.785 | 1.00 | 26.89 | B | C |
| ATOM | 4098 | O | PHE | B | 1034 | −13.633 | 37.991 | 47.324 | 1.00 | 26.48 | B | O |
| ATOM | 4099 | N | LEU | B | 1035 | −11.986 | 36.483 | 47.091 | 1.00 | 29.42 | B | N |
| ATOM | 4100 | CA | LEU | B | 1035 | −12.533 | 35.568 | 48.080 | 1.00 | 30.90 | B | C |
| ATOM | 4101 | CB | LEU | B | 1035 | −11.767 | 34.243 | 48.025 | 1.00 | 30.10 | B | C |
| ATOM | 4102 | CG | LEU | B | 1035 | −12.523 | 33.012 | 47.518 | 1.00 | 28.66 | B | C |
| ATOM | 4103 | CD1 | LEU | B | 1035 | −13.344 | 33.332 | 46.304 | 1.00 | 27.57 | B | C |

-continued

| | | | | | | | | | | |
|---|---|---|---|---|---|---|---|---|---|---|
| ATOM | 4104 | CD2 | LEU | B | 1035 | −11.527 | 31.926 | 47.229 | 1.00 | 29.37 | B | C |
| ATOM | 4105 | C | LEU | B | 1035 | −12.517 | 36.148 | 49.494 | 1.00 | 32.42 | B | C |
| ATOM | 4106 | O | LEU | B | 1035 | −13.470 | 35.959 | 50.251 | 1.00 | 33.93 | B | O |
| ATOM | 4107 | N | ARG | B | 1036 | −11.446 | 36.852 | 49.857 | 1.00 | 32.89 | B | N |
| ATOM | 4108 | CA | ARG | B | 1036 | −11.380 | 37.443 | 51.189 | 1.00 | 34.45 | B | C |
| ATOM | 4109 | CB | ARG | B | 1036 | −9.941 | 37.700 | 51.627 | 1.00 | 33.31 | B | C |
| ATOM | 4110 | CG | ARG | B | 1036 | −9.195 | 38.666 | 50.758 | 1.00 | 35.78 | B | C |
| ATOM | 4111 | CD | ARG | B | 1036 | −7.951 | 39.174 | 51.461 | 1.00 | 36.21 | B | C |
| ATOM | 4112 | NE | ARG | B | 1036 | −8.294 | 40.190 | 52.447 | 1.00 | 34.88 | B | N |
| ATOM | 4113 | CZ | ARG | B | 1036 | −8.240 | 41.498 | 52.220 | 1.00 | 33.46 | B | C |
| ATOM | 4114 | NH1 | ARG | B | 1036 | −7.850 | 41.955 | 51.040 | 1.00 | 33.99 | B | N |
| ATOM | 4115 | NH2 | ARG | B | 1036 | −8.589 | 42.352 | 53.169 | 1.00 | 34.43 | B | N |
| ATOM | 4116 | C | ARG | B | 1036 | −12.163 | 38.743 | 51.250 | 1.00 | 35.70 | B | C |
| ATOM | 4117 | O | ARG | B | 1036 | −12.517 | 39.196 | 52.333 | 1.00 | 37.83 | B | O |
| ATOM | 4118 | N | MET | B | 1037 | −12.441 | 39.342 | 50.094 | 1.00 | 37.15 | B | N |
| ATOM | 4119 | CA | MET | B | 1037 | −13.209 | 40.583 | 50.055 | 1.00 | 38.00 | B | C |
| ATOM | 4120 | CB | MET | B | 1037 | −13.090 | 41.258 | 48.678 | 1.00 | 37.73 | B | C |
| ATOM | 4121 | CG | MET | B | 1037 | −11.842 | 42.134 | 48.519 | 1.00 | 40.65 | B | C |
| ATOM | 4122 | SD | MET | B | 1037 | −11.573 | 42.840 | 46.867 | 1.00 | 38.90 | B | S |
| ATOM | 4123 | CE | MET | B | 1037 | −12.983 | 43.932 | 46.734 | 1.00 | 40.28 | B | C |
| ATOM | 4124 | C | MET | B | 1037 | −14.680 | 40.331 | 50.389 | 1.00 | 39.11 | B | C |
| ATOM | 4125 | O | MET | B | 1037 | −15.257 | 41.003 | 51.245 | 1.00 | 39.07 | B | O |
| ATOM | 4126 | N | MET | B | 1038 | −15.292 | 39.357 | 49.728 | 1.00 | 41.37 | B | N |
| ATOM | 4127 | CA | MET | B | 1038 | −16.697 | 39.072 | 49.991 | 1.00 | 43.13 | B | C |
| ATOM | 4128 | CB | MET | B | 1038 | −17.395 | 38.660 | 48.692 | 1.00 | 43.22 | B | C |
| ATOM | 4129 | CG | MET | B | 1038 | −16.556 | 37.788 | 47.794 | 1.00 | 43.58 | B | C |
| ATOM | 4130 | SD | MET | B | 1038 | −17.231 | 37.655 | 46.142 | 1.00 | 41.45 | B | S |
| ATOM | 4131 | CE | MET | B | 1038 | −18.295 | 36.342 | 46.357 | 1.00 | 41.55 | B | C |
| ATOM | 4132 | C | MET | B | 1038 | −16.910 | 38.037 | 51.097 | 1.00 | 44.01 | B | C |
| ATOM | 4133 | O | MET | B | 1038 | −18.017 | 37.543 | 51.301 | 1.00 | 44.45 | B | O |
| ATOM | 4134 | N | GLY | B | 1039 | −15.834 | 37.739 | 51.820 | 1.00 | 46.15 | B | N |
| ATOM | 4135 | CA | GLY | B | 1039 | −15.889 | 36.795 | 52.923 | 1.00 | 47.55 | B | C |
| ATOM | 4136 | C | GLY | B | 1039 | −16.353 | 35.393 | 52.593 | 1.00 | 49.20 | B | C |
| ATOM | 4137 | O | GLY | B | 1039 | −17.181 | 34.831 | 53.309 | 1.00 | 50.66 | B | O |
| ATOM | 4138 | N | CYS | B | 1040 | −15.810 | 34.814 | 51.526 | 1.00 | 48.90 | B | N |
| ATOM | 4139 | CA | CYS | B | 1040 | −16.198 | 33.471 | 51.119 | 1.00 | 47.27 | B | C |
| ATOM | 4140 | CB | CYS | B | 1040 | −16.251 | 33.391 | 49.597 | 1.00 | 46.11 | B | C |
| ATOM | 4141 | SG | CYS | B | 1040 | −16.885 | 31.828 | 48.977 | 1.00 | 45.49 | B | S |
| ATOM | 4142 | C | CYS | B | 1040 | −15.242 | 32.411 | 51.655 | 1.00 | 47.59 | B | C |
| ATOM | 4143 | O | CYS | B | 1040 | −14.040 | 32.468 | 51.405 | 1.00 | 46.95 | B | O |
| ATOM | 4144 | N | GLU | B | 1041 | −15.780 | 31.445 | 52.395 | 1.00 | 48.51 | B | N |
| ATOM | 4145 | CA | GLU | B | 1041 | −14.968 | 30.369 | 52.951 | 1.00 | 49.20 | B | C |
| ATOM | 4146 | CB | GLU | B | 1041 | −15.517 | 29.926 | 54.317 | 1.00 | 48.69 | B | C |
| ATOM | 4147 | CG | GLU | B | 1041 | −17.032 | 29.972 | 54.468 | 1.00 | 48.21 | B | C |
| ATOM | 4148 | CD | GLU | B | 1041 | −17.513 | 29.317 | 55.764 | 1.00 | 48.81 | B | C |
| ATOM | 4149 | OE1 | GLU | B | 1041 | −18.715 | 29.444 | 56.080 | 1.00 | 47.24 | B | O |
| ATOM | 4150 | OE2 | GLU | B | 1041 | −16.691 | 28.670 | 56.461 | 1.00 | 48.13 | B | O |
| ATOM | 4151 | C | GLU | B | 1041 | −14.894 | 29.186 | 51.986 | 1.00 | 49.69 | B | C |
| ATOM | 4152 | O | GLU | B | 1041 | −14.219 | 28.186 | 52.243 | 1.00 | 49.89 | B | O |
| ATOM | 4153 | N | ARG | B | 1042 | −15.598 | 29.315 | 50.868 | 1.00 | 50.29 | B | N |
| ATOM | 4154 | CA | ARG | B | 1042 | −15.597 | 28.293 | 49.830 | 1.00 | 50.96 | B | C |
| ATOM | 4155 | CB | ARG | B | 1042 | −16.953 | 28.251 | 49.123 | 1.00 | 52.40 | B | C |
| ATOM | 4156 | CG | ARG | B | 1042 | −18.076 | 27.691 | 49.965 | 1.00 | 54.46 | B | C |
| ATOM | 4157 | CD | ARG | B | 1042 | −19.371 | 27.654 | 49.179 | 1.00 | 56.84 | B | C |
| ATOM | 4158 | NE | ARG | B | 1042 | −20.129 | 26.438 | 49.455 | 1.00 | 59.33 | B | N |
| ATOM | 4159 | CZ | ARG | B | 1042 | −19.777 | 25.222 | 49.041 | 1.00 | 60.78 | B | C |
| ATOM | 4160 | NH1 | ARG | B | 1042 | −18.675 | 25.047 | 48.321 | 1.00 | 60.88 | B | N |
| ATOM | 4161 | NH2 | ARG | B | 1042 | −20.529 | 24.177 | 49.355 | 1.00 | 61.43 | B | N |
| ATOM | 4162 | C | ARG | B | 1042 | −14.506 | 28.647 | 48.818 | 1.00 | 50.04 | B | C |
| ATOM | 4163 | O | ARG | B | 1042 | −14.296 | 29.822 | 48.511 | 1.00 | 49.09 | B | O |
| ATOM | 4164 | N | ASP | B | 1043 | −13.808 | 27.633 | 46.313 | 1.00 | 49.24 | B | N |
| ATOM | 4165 | CA | ASP | B | 1043 | −12.747 | 27.846 | 47.336 | 1.00 | 46.56 | B | C |
| ATOM | 4166 | CB | ASP | B | 1043 | −12.223 | 26.510 | 46.820 | 1.00 | 49.16 | B | C |
| ATOM | 4167 | CG | ASP | B | 1043 | −11.444 | 25.747 | 47.864 | 1.00 | 52.26 | B | C |
| ATOM | 4168 | OD1 | ASP | B | 1043 | −10.478 | 26.327 | 46.401 | 1.00 | 52.24 | B | O |
| ATOM | 4169 | OD2 | ASP | B | 1043 | −11.793 | 24.571 | 46.135 | 1.00 | 53.66 | B | O |
| ATOM | 4170 | C | ASP | B | 1043 | −13.247 | 28.673 | 46.160 | 1.00 | 43.96 | B | C |
| ATOM | 4171 | O | ASP | B | 1043 | −12.509 | 29.483 | 45.609 | 1.00 | 43.39 | B | O |
| ATOM | 4172 | N | VAL | B | 1044 | −14.496 | 28.448 | 45.768 | 1.00 | 42.85 | B | N |
| ATOM | 4173 | CA | VAL | B | 1044 | −15.104 | 29.173 | 44.653 | 1.00 | 41.15 | B | C |
| ATOM | 4174 | CB | VAL | B | 1044 | −15.403 | 28.255 | 43.436 | 1.00 | 38.53 | B | C |
| ATOM | 4175 | CG1 | VAL | B | 1044 | −16.208 | 29.008 | 42.390 | 1.00 | 37.89 | B | C |
| ATOM | 4176 | CG2 | VAL | B | 1044 | −14.120 | 27.781 | 42.821 | 1.00 | 38.24 | B | C |
| ATOM | 4177 | C | VAL | B | 1044 | −16.416 | 29.743 | 45.143 | 1.00 | 40.47 | B | C |
| ATOM | 4178 | O | VAL | B | 1044 | −17.240 | 29.034 | 45.701 | 1.00 | 40.60 | B | O |
| ATOM | 4179 | N | PRO | B | 1045 | −16.621 | 31.042 | 44.938 | 1.00 | 40.56 | B | N |
| ATOM | 4180 | CD | PRO | B | 1045 | −15.641 | 32.000 | 44.385 | 1.00 | 40.52 | B | C |
| ATOM | 4181 | CA | PRO | B | 1045 | −17.843 | 31.719 | 45.362 | 1.00 | 40.24 | B | C |
| ATOM | 4182 | CB | PRO | B | 1045 | −17.381 | 33.160 | 45.519 | 1.00 | 41.27 | B | C |
| ATOM | 4183 | CG | PRO | B | 1045 | −16.426 | 33.307 | 44.352 | 1.00 | 40.98 | B | C |

-continued

| ATOM | 4184 | C | PRO | B | 1045 | −18.935 | 31.597 | 44.318 | 1.00 | 39.56 | B | C |
| --- | --- | --- | --- | --- | --- | --- | --- | --- | --- | --- | --- | --- |
| ATOM | 4185 | O | PRO | B | 1045 | −18.665 | 31.260 | 43.173 | 1.00 | 39.45 | B | O |
| ATOM | 4186 | N | ALA | B | 1046 | −20.170 | 31.868 | 44.725 | 1.00 | 40.46 | B | N |
| ATOM | 4187 | CA | ALA | B | 1046 | −21.300 | 31.839 | 43.809 | 1.00 | 40.51 | B | C |
| ATOM | 4188 | CB | ALA | B | 1046 | −22.600 | 32.073 | 44.568 | 1.00 | 40.27 | B | C |
| ATOM | 4189 | C | ALA | B | 1046 | −21.038 | 32.989 | 42.838 | 1.00 | 40.45 | B | C |
| ATOM | 4190 | O | ALA | B | 1046 | −20.504 | 34.029 | 43.235 | 1.00 | 39.83 | B | O |
| ATOM | 4191 | N | LEU | B | 1047 | −21.403 | 32.807 | 41.574 | 1.00 | 39.65 | B | N |
| ATOM | 4192 | CA | LEU | B | 1047 | −21.169 | 33.846 | 40.583 | 1.00 | 40.13 | B | C |
| ATOM | 4193 | CB | LEU | B | 1047 | −21.357 | 33.289 | 39.162 | 1.00 | 40.46 | B | C |
| ATOM | 4194 | CG | LEU | B | 1047 | −20.193 | 32.428 | 38.639 | 1.00 | 41.20 | B | C |
| ATOM | 4195 | CD1 | LEU | B | 1047 | −20.117 | 31.114 | 39.423 | 1.00 | 41.20 | B | C |
| ATOM | 4196 | CD2 | LEU | B | 1047 | −20.380 | 32.145 | 37.162 | 1.00 | 40.74 | B | C |
| ATOM | 4197 | C | LEU | B | 1047 | −22.024 | 35.095 | 40.781 | 1.00 | 39.34 | B | C |
| ATOM | 4198 | O | LEU | B | 1047 | −21.537 | 36.212 | 40.610 | 1.00 | 38.91 | B | O |
| ATOM | 4199 | N | CYS | B | 1048 | −23.287 | 34.920 | 41.151 | 1.00 | 39.20 | B | N |
| ATOM | 4200 | CA | CYS | B | 1048 | −24.162 | 36.068 | 41.363 | 1.00 | 39.30 | B | C |
| ATOM | 4201 | CB | CYS | B | 1048 | −25.573 | 35.603 | 41.723 | 1.00 | 39.50 | B | C |
| ATOM | 4202 | SG | CYS | B | 1048 | −25.664 | 34.837 | 43.349 | 1.00 | 42.73 | B | S |
| ATOM | 4203 | C | CYS | B | 1048 | −23.600 | 36.928 | 42.495 | 1.00 | 39.35 | B | C |
| ATOM | 4204 | O | CYS | B | 1048 | −23.779 | 36.145 | 42.519 | 1.00 | 39.73 | B | O |
| ATOM | 4205 | N | ARG | B | 1049 | −22.916 | 36.282 | 43.432 | 1.00 | 38.09 | B | N |
| ATOM | 4206 | CA | ARG | B | 1049 | −22.316 | 36.974 | 44.568 | 1.00 | 38.17 | B | C |
| ATOM | 4207 | CB | ARG | B | 1049 | −21.897 | 35.931 | 45.600 | 1.00 | 40.51 | B | C |
| ATOM | 4208 | CG | ARG | B | 1049 | −21.512 | 36.458 | 46.959 | 1.00 | 44.21 | B | C |
| ATOM | 4209 | CD | ARG | B | 1049 | −21.091 | 35.286 | 47.845 | 1.00 | 48.40 | B | C |
| ATOM | 4210 | NE | ARG | B | 1049 | −20.499 | 35.709 | 49.111 | 1.00 | 51.54 | B | N |
| ATOM | 4211 | CZ | ARG | B | 1049 | −19.797 | 34.906 | 49.903 | 1.00 | 52.10 | B | C |
| ATOM | 4212 | NH1 | ARG | B | 1049 | −19.293 | 35.360 | 51.039 | 1.00 | 52.46 | B | N |
| ATOM | 4213 | NH2 | ARG | B | 1049 | −19.592 | 33.644 | 49.551 | 1.00 | 53.64 | B | N |
| ATOM | 4214 | C | ARG | B | 1049 | −21.098 | 37.790 | 44.092 | 1.00 | 36.74 | B | C |
| ATOM | 4215 | O | ARG | B | 1049 | −20.865 | 38.922 | 44.526 | 1.00 | 34.35 | B | O |
| ATOM | 4216 | N | LEU | B | 1050 | −20.335 | 37.198 | 43.183 | 1.00 | 34.32 | B | N |
| ATOM | 4217 | CA | LEU | B | 1050 | −19.152 | 37.840 | 42.630 | 1.00 | 33.57 | B | C |
| ATOM | 4218 | CB | LEU | B | 1050 | −18.341 | 36.816 | 41.815 | 1.00 | 30.44 | B | C |
| ATOM | 4219 | CG | LEU | B | 1050 | −17.161 | 37.394 | 41.031 | 1.00 | 29.65 | B | C |
| ATOM | 4220 | CD1 | LEU | B | 1050 | −16.365 | 38.366 | 41.921 | 1.00 | 26.93 | B | C |
| ATOM | 4221 | CD2 | LEU | B | 1050 | −16.306 | 36.283 | 40.494 | 1.00 | 22.80 | B | C |
| ATOM | 4222 | C | LEU | B | 1050 | −19.563 | 39.028 | 41.753 | 1.00 | 33.51 | B | C |
| ATOM | 4223 | O | LEU | B | 1050 | −18.971 | 40.105 | 41.835 | 1.00 | 32.04 | B | O |
| ATOM | 4224 | N | LEU | B | 1051 | −20.581 | 38.817 | 40.920 | 1.00 | 34.24 | B | N |
| ATOM | 4225 | CA | LEU | B | 1051 | −21.113 | 39.857 | 40.041 | 1.00 | 34.48 | B | C |
| ATOM | 4226 | CB | LEU | B | 1051 | −22.277 | 39.287 | 39.216 | 1.00 | 34.57 | B | C |
| ATOM | 4227 | CG | LEU | B | 1051 | −23.108 | 40.276 | 38.394 | 1.00 | 33.44 | B | C |
| ATOM | 4228 | CD1 | LEU | B | 1051 | −22.273 | 40.636 | 37.250 | 1.00 | 31.21 | B | C |
| ATOM | 4229 | CD2 | LEU | B | 1051 | −24.341 | 39.583 | 37.871 | 1.00 | 30.70 | B | C |
| ATOM | 4230 | C | LEU | B | 1051 | −21.604 | 41.043 | 40.887 | 1.00 | 35.06 | B | C |
| ATOM | 4231 | O | LEU | B | 1051 | −21.340 | 42.104 | 40.571 | 1.00 | 35.49 | B | O |
| ATOM | 4232 | N | GLU | B | 1052 | −22.329 | 40.746 | 41.957 | 1.00 | 35.65 | B | N |
| ATOM | 4233 | CA | GLU | B | 1052 | −22.837 | 41.781 | 42.848 | 1.00 | 37.17 | B | C |
| ATOM | 4234 | CB | GLU | B | 1052 | −23.554 | 41.124 | 44.025 | 1.00 | 39.94 | B | C |
| ATOM | 4235 | CG | GLU | B | 1052 | −24.094 | 42.072 | 45.076 | 1.00 | 42.75 | B | C |
| ATOM | 4236 | CD | GLU | B | 1052 | −24.868 | 41.331 | 46.152 | 1.00 | 46.05 | B | C |
| ATOM | 4237 | OE1 | GLU | B | 1052 | −24.237 | 40.571 | 46.921 | 1.00 | 49.05 | B | O |
| ATOM | 4238 | OE2 | GLU | B | 1052 | −26.106 | 41.495 | 46.225 | 1.00 | 46.95 | B | O |
| ATOM | 4239 | C | GLU | B | 1052 | −21.701 | 42.667 | 43.369 | 1.00 | 37.09 | B | C |
| ATOM | 4240 | O | GLU | B | 1052 | −21.793 | 43.892 | 43.353 | 1.00 | 35.90 | B | O |
| ATOM | 4241 | N | LEU | B | 1053 | −20.633 | 42.028 | 43.839 | 1.00 | 37.03 | B | N |
| ATOM | 4242 | CA | LEU | B | 1053 | −19.476 | 42.735 | 44.371 | 1.00 | 34.66 | B | C |
| ATOM | 4243 | CB | LEU | B | 1053 | −18.366 | 41.736 | 44.720 | 1.00 | 33.52 | B | C |
| ATOM | 4244 | CG | LEU | B | 1053 | −17.020 | 42.336 | 45.133 | 1.00 | 33.63 | B | C |
| ATOM | 4245 | CD1 | LEU | B | 1053 | −17.136 | 42.940 | 46.515 | 1.00 | 32.45 | B | C |
| ATOM | 4246 | CD2 | LEU | B | 1053 | −15.945 | 41.268 | 45.100 | 1.00 | 34.11 | B | C |
| ATOM | 4247 | C | LEU | B | 1053 | −18.970 | 43.734 | 43.340 | 1.00 | 34.06 | B | C |
| ATOM | 4248 | O | LEU | B | 1053 | −18.637 | 44.868 | 43.678 | 1.00 | 33.84 | B | O |
| ATOM | 4249 | N | LEU | B | 1054 | −24.341 | 43.303 | 42.083 | 1.00 | 33.58 | B | N |
| ATOM | 4250 | CA | LEU | B | 1054 | −18.460 | 44.166 | 40.988 | 1.00 | 34.37 | B | C |
| ATOM | 4251 | CB | LEU | B | 1054 | −18.126 | 43.323 | 39.747 | 1.00 | 33.25 | B | C |
| ATOM | 4252 | CG | LEU | B | 1054 | −16.669 | 42.443 | 39.809 | 1.00 | 32.78 | B | C |
| ATOM | 4253 | CD1 | LEU | B | 1054 | −16.779 | 41.554 | 38.584 | 1.00 | 32.14 | B | C |
| ATOM | 4254 | CD2 | LEU | B | 1054 | −15.649 | 43.321 | 39.897 | 1.00 | 31.57 | B | C |
| ATOM | 4255 | C | LEU | B | 1054 | −19.522 | 45.217 | 40.635 | 1.00 | 34.18 | B | C |
| ATOM | 4256 | O | LEU | B | 1054 | −19.198 | 46.362 | 40.311 | 1.00 | 32.80 | B | O |
| ATOM | 4257 | N | GLU | B | 1055 | −20.790 | 44.626 | 40.704 | 1.00 | 36.25 | B | N |
| ATOM | 4258 | CA | GLU | B | 1055 | −21.877 | 45.748 | 40.396 | 1.00 | 38.15 | B | C |
| ATOM | 4259 | CB | GLU | B | 1055 | −23.212 | 44.996 | 40.321 | 1.00 | 37.35 | B | C |
| ATOM | 4260 | CG | GLU | B | 1055 | −23.379 | 44.222 | 39.022 | 1.00 | 40.80 | B | C |
| ATOM | 4261 | CD | GLU | B | 1055 | −24.735 | 43.542 | 38.884 | 1.00 | 41.88 | B | C |
| ATOM | 4262 | OE1 | GLU | B | 1055 | −25.159 | 43.295 | 37.735 | 1.00 | 41.74 | B | O |
| ATOM | 4263 | OE2 | GLU | B | 1055 | −25.372 | 43.240 | 39.914 | 1.00 | 44.00 | B | O |

-continued

| ATOM | 4264 | C | GLU | B | 1055 | −21.957 | 46.873 | 41.421 | 1.00 | 38.20 | B | C |
| --- | --- | --- | --- | --- | --- | --- | --- | --- | --- | --- | --- | --- |
| ATOM | 4265 | O | GLU | B | 1055 | −22.727 | 47.816 | 41.261 | 1.00 | 38.44 | B | O |
| ATOM | 4266 | N | GLU | B | 1056 | −21.155 | 46.777 | 42.473 | 1.00 | 38.46 | B | N |
| ATOM | 4267 | CA | GLU | B | 1056 | −21.156 | 47.811 | 43.490 | 1.00 | 39.89 | B | C |
| ATOM | 4268 | CB | GLU | B | 1056 | −21.195 | 47.207 | 44.890 | 1.00 | 42.00 | B | C |
| ATOM | 4269 | CG | GLU | B | 1056 | −22.401 | 46.326 | 45.151 | 1.00 | 47.57 | B | C |
| ATOM | 4270 | CD | GLU | B | 1056 | −22.500 | 45.872 | 46.602 | 1.00 | 49.21 | B | C |
| ATOM | 4271 | OE1 | GLU | B | 1056 | −21.445 | 45.560 | 47.205 | 1.00 | 48.52 | B | O |
| ATOM | 4272 | OE2 | GLU | B | 1056 | −23.639 | 45.820 | 47.127 | 1.00 | 50.36 | B | O |
| ATOM | 4273 | C | GLU | B | 1056 | −19.935 | 48.701 | 43.368 | 1.00 | 40.12 | B | C |
| ATOM | 4274 | O | GLU | B | 1056 | −19.733 | 49.575 | 44.203 | 1.00 | 42.38 | B | O |
| ATOM | 4275 | N | GLY | B | 1057 | −19.114 | 48.474 | 42.347 | 1.00 | 38.76 | B | N |
| ATOM | 4276 | CA | GLY | B | 1057 | −17.934 | 49.302 | 42.155 | 1.00 | 36.47 | B | C |
| ATOM | 4277 | C | GLY | B | 1057 | −16.638 | 48.773 | 42.739 | 1.00 | 36.71 | B | C |
| ATOM | 4278 | O | GLY | B | 1057 | −15.565 | 49.343 | 42.521 | 1.00 | 37.03 | B | O |
| ATOM | 4279 | N | GLN | B | 1058 | −16.728 | 47.677 | 43.481 | 1.00 | 35.24 | B | N |
| ATOM | 4280 | CA | GLN | B | 1058 | −15.560 | 47.069 | 44.099 | 1.00 | 32.79 | B | C |
| ATOM | 4281 | CB | GLN | B | 1058 | −16.011 | 45.969 | 45.057 | 1.00 | 32.99 | B | C |
| ATOM | 4282 | CG | GLN | B | 1058 | −16.917 | 46.467 | 46.169 | 1.00 | 34.23 | B | C |
| ATOM | 4283 | CD | GLN | B | 1058 | −16.242 | 46.452 | 47.527 | 1.00 | 34.06 | B | C |
| ATOM | 4284 | OE1 | GLN | B | 1058 | −15.024 | 46.622 | 47.630 | 1.00 | 34.44 | B | O |
| ATOM | 4285 | NE2 | GLN | B | 1058 | −17.035 | 46.262 | 48.581 | 1.00 | 31.51 | B | N |
| ATOM | 4286 | C | GLN | B | 1058 | −14.588 | 46.487 | 43.072 | 1.00 | 33.29 | B | C |
| ATOM | 4287 | O | GLN | B | 1058 | −14.984 | 45.704 | 42.209 | 1.00 | 34.91 | B | O |
| ATOM | 4288 | N | ARG | B | 1059 | −13.317 | 46.872 | 43.174 | 1.00 | 32.14 | B | N |
| ATOM | 4289 | CA | ARG | B | 1059 | −12.267 | 46.385 | 42.283 | 1.00 | 31.05 | B | C |
| ATOM | 4290 | CB | ARG | B | 1059 | −11.729 | 47.519 | 41.417 | 1.00 | 31.00 | B | C |
| ATOM | 4291 | CG | ARG | B | 1059 | −12.191 | 47.492 | 39.963 | 1.00 | 33.01 | B | C |
| ATOM | 4292 | CD | ARG | B | 1059 | −13.652 | 47.142 | 39.862 | 1.00 | 32.34 | B | C |
| ATOM | 4293 | NE | ARG | B | 1059 | −14.329 | 47.791 | 38.746 | 1.00 | 30.92 | B | N |
| ATOM | 4294 | CZ | ARG | B | 1059 | −15.643 | 47.738 | 38.558 | 1.00 | 32.32 | B | C |
| ATOM | 4295 | NH1 | ARG | B | 1059 | −16.399 | 47.054 | 39.409 | 1.00 | 29.29 | B | N |
| ATOM | 4296 | NH2 | ARG | B | 1059 | −16.203 | 48.402 | 37.554 | 1.00 | 32.00 | B | N |
| ATOM | 4297 | C | ARG | B | 1059 | −11.122 | 45.814 | 43.112 | 1.00 | 30.78 | B | C |
| ATOM | 4298 | O | ARG | B | 1059 | −11.116 | 45.937 | 44.328 | 1.00 | 31.26 | B | O |
| ATOM | 4299 | N | LEU | B | 1060 | −10.155 | 45.188 | 42.449 | 1.00 | 31.98 | B | N |
| ATOM | 4300 | CA | LEU | B | 1060 | −8.999 | 44.620 | 43.131 | 1.00 | 32.82 | B | C |
| ATOM | 4301 | CB | LEU | B | 1060 | −8.147 | 43.810 | 42.156 | 1.00 | 30.99 | B | C |
| ATOM | 4302 | CG | LEU | B | 1060 | −8.791 | 42.576 | 41.510 | 1.00 | 33.63 | B | C |
| ATOM | 4303 | CD1 | LEU | B | 1060 | −7.897 | 42.047 | 40.385 | 1.00 | 32.89 | B | C |
| ATOM | 4304 | CD2 | LEU | B | 1060 | −9.035 | 41.513 | 42.570 | 1.00 | 30.44 | B | C |
| ATOM | 4305 | C | LEU | B | 1060 | −8.137 | 45.719 | 43.731 | 1.00 | 35.16 | B | C |
| ATOM | 4306 | O | LEU | B | 1060 | −8.011 | 46.808 | 43.165 | 1.00 | 35.31 | B | O |
| ATOM | 4307 | N | PRO | B | 1061 | −7.526 | 45.448 | 44.891 | 1.00 | 37.66 | B | N |
| ATOM | 4308 | CD | PRO | B | 1061 | −7.628 | 44.209 | 45.686 | 1.00 | 38.68 | B | C |
| ATOM | 4309 | CA | PRO | B | 1061 | −6.666 | 46.429 | 45.557 | 1.00 | 38.74 | B | C |
| ATOM | 4310 | CB | PRO | B | 1061 | −6.472 | 45.829 | 46.945 | 1.00 | 37.50 | B | C |
| ATOM | 4311 | CG | PRO | B | 1061 | −6.461 | 44.351 | 46.661 | 1.00 | 39.71 | B | C |
| ATOM | 4312 | C | PRO | B | 1061 | −5.355 | 46.560 | 44.798 | 1.00 | 40.11 | B | C |
| ATOM | 4313 | O | PRO | B | 1061 | −4.671 | 45.566 | 44.570 | 1.00 | 42.72 | B | O |
| ATOM | 4314 | N | ALA | B | 1062 | −5.023 | 47.787 | 44.406 | 1.00 | 40.89 | B | N |
| ATOM | 4315 | CA | ALA | B | 1062 | −3.795 | 48.078 | 43.669 | 1.00 | 41.43 | B | C |
| ATOM | 4316 | CB | ALA | B | 1062 | −3.455 | 49.565 | 43.791 | 1.00 | 42.02 | B | C |
| ATOM | 4317 | C | ALA | B | 1062 | −2.620 | 47.242 | 44.162 | 1.00 | 40.81 | B | C |
| ATOM | 4318 | O | ALA | B | 1062 | −2.380 | 47.136 | 45.365 | 1.00 | 40.36 | B | O |
| ATOM | 4319 | N | PRO | B | 1063 | −1.874 | 46.629 | 43.230 | 1.00 | 40.11 | B | N |
| ATOM | 4320 | CD | PRO | B | 1063 | −2.038 | 46.655 | 41.768 | 1.00 | 38.16 | B | C |
| ATOM | 4321 | CA | PRO | B | 1063 | −0.727 | 45.810 | 43.619 | 1.00 | 40.35 | B | C |
| ATOM | 4322 | CB | PRO | B | 1063 | −0.190 | 45.305 | 42.279 | 1.00 | 38.03 | B | C |
| ATOM | 4323 | CG | PRO | B | 1063 | −0.667 | 46.318 | 41.298 | 1.00 | 36.80 | B | C |
| ATOM | 4324 | C | PRO | B | 1063 | 0.292 | 46.630 | 44.415 | 1.00 | 41.69 | B | C |
| ATOM | 4325 | O | PRO | B | 1063 | 0.612 | 47.763 | 44.052 | 1.00 | 40.07 | B | O |
| ATOM | 4326 | N | PRO | B | 1064 | 0.787 | 46.064 | 45.532 | 1.00 | 42.80 | B | N |
| ATOM | 4327 | CD | PRO | B | 1064 | 0.311 | 44.773 | 46.054 | 1.00 | 42.45 | B | C |
| ATOM | 4328 | CA | PRO | B | 1064 | 1.766 | 46.652 | 46.455 | 1.00 | 43.51 | B | C |
| ATOM | 4329 | CB | PRO | B | 1064 | 2.019 | 45.522 | 47.442 | 1.00 | 43.04 | B | C |
| ATOM | 4330 | CG | PRO | B | 1064 | 0.685 | 44.873 | 47.521 | 1.00 | 43.10 | B | C |
| ATOM | 4331 | C | PRO | B | 1064 | 3.051 | 47.123 | 45.798 | 1.00 | 43.88 | B | C |
| ATOM | 4332 | O | PRO | B | 1064 | 3.897 | 46.309 | 45.439 | 1.00 | 44.89 | B | O |
| ATOM | 4333 | N | ALA | B | 1065 | 3.182 | 48.437 | 45.639 | 1.00 | 43.57 | B | N |
| ATOM | 4334 | CA | ALA | B | 1065 | 4.363 | 49.047 | 45.033 | 1.00 | 44.73 | B | C |
| ATOM | 4335 | CB | ALA | B | 1065 | 5.617 | 48.244 | 45.384 | 1.00 | 44.54 | B | C |
| ATOM | 4336 | C | ALA | B | 1065 | 4.254 | 49.204 | 43.518 | 1.00 | 44.87 | B | C |
| ATOM | 4337 | O | ALA | B | 1065 | 5.240 | 49.491 | 42.840 | 1.00 | 45.51 | B | O |
| ATOM | 4338 | N | CYS | B | 1066 | 3.051 | 49.017 | 42.991 | 1.00 | 44.57 | B | N |
| ATOM | 4339 | CA | CYS | B | 1066 | 2.813 | 49.148 | 41.560 | 1.00 | 42.80 | B | C |
| ATOM | 4340 | CB | CYS | B | 1066 | 1.385 | 48.702 | 41.220 | 1.00 | 41.77 | B | C |
| ATOM | 4341 | SG | CYS | B | 1066 | 0.764 | 49.168 | 39.564 | 1.00 | 42.74 | B | S |
| ATOM | 4342 | C | CYS | B | 1066 | 2.999 | 50.582 | 41.111 | 1.00 | 41.34 | B | C |
| ATOM | 4343 | O | CYS | B | 1066 | 2.634 | 51.516 | 41.809 | 1.00 | 41.68 | B | O |

| | | | | | -continued | | | | | | |
|---|---|---|---|---|---|---|---|---|---|---|---|
| ATOM | 4344 | N | PRO | B | 1067 | 3.599 | 50.774 | 39.941 | 1.00 | 40.50 | B | N |
| ATOM | 4345 | CD | PRO | B | 1067 | 4.318 | 49.776 | 39.135 | 1.00 | 40.21 | B | C |
| ATOM | 4346 | CA | PRO | B | 1067 | 3.803 | 52.123 | 39.423 | 1.00 | 40.36 | B | C |
| ATOM | 4347 | CB | PRO | B | 1067 | 4.405 | 51.863 | 38.054 | 1.00 | 39.69 | B | C |
| ATOM | 4348 | CG | PRO | B | 1067 | 5.223 | 50.636 | 38.290 | 1.00 | 38.76 | B | C |
| ATOM | 4349 | C | PRO | B | 1067 | 2.434 | 52.803 | 39.326 | 1.00 | 41.40 | B | C |
| ATOM | 4350 | O | PRO | B | 1067 | 1.429 | 52.153 | 39.022 | 1.00 | 42.80 | B | O |
| ATOM | 4351 | N | ALA | B | 1068 | 2.402 | 54.105 | 39.576 | 1.00 | 41.17 | B | N |
| ATOM | 4352 | CA | ALA | B | 1068 | 1.163 | 54.887 | 39.535 | 1.00 | 41.52 | B | C |
| ATOM | 4353 | CB | ALA | B | 1068 | 1.473 | 56.353 | 39.907 | 1.00 | 41.43 | B | C |
| ATOM | 4354 | C | ALA | B | 1068 | 0.383 | 54.829 | 38.203 | 1.00 | 40.64 | B | C |
| ATOM | 4355 | O | ALA | B | 1068 | −0.825 | 54.584 | 38.192 | 1.00 | 39.24 | B | O |
| ATOM | 4356 | N | GLU | B | 1069 | 1.065 | 55.072 | 37.089 | 1.00 | 40.27 | B | N |
| ATOM | 4357 | CA | GLU | B | 1069 | 0.414 | 55.043 | 35.784 | 1.00 | 41.72 | B | C |
| ATOM | 4358 | CB | GLU | B | 1069 | 1.305 | 55.718 | 34.738 | 1.00 | 44.54 | B | C |
| ATOM | 4359 | CG | GLU | B | 1069 | 2.792 | 55.431 | 34.901 | 1.00 | 47.65 | B | C |
| ATOM | 4360 | CD | GLU | B | 1069 | 3.412 | 56.113 | 36.114 | 1.00 | 47.70 | B | C |
| ATOM | 4361 | OE1 | GLU | B | 1069 | 3.262 | 57.343 | 36.252 | 1.00 | 47.97 | B | O |
| ATOM | 4362 | OE2 | GLU | B | 1069 | 4.060 | 55.419 | 36.925 | 1.00 | 48.18 | B | O |
| ATOM | 4363 | C | GLU | B | 1069 | 0.040 | 53.627 | 35.332 | 1.00 | 41.70 | B | C |
| ATOM | 4364 | O | GLU | B | 1069 | −0.907 | 53.441 | 34.562 | 1.00 | 41.28 | B | O |
| ATOM | 4365 | N | VAL | B | 1070 | 0.780 | 52.631 | 35.810 | 1.00 | 40.03 | B | N |
| ATOM | 4366 | CA | VAL | B | 1070 | 0.485 | 51.249 | 35.462 | 1.00 | 39.46 | B | C |
| ATOM | 4367 | CB | VAL | B | 1070 | 1.559 | 50.276 | 36.014 | 1.00 | 41.14 | B | C |
| ATOM | 4368 | CG1 | VAL | B | 1070 | 0.924 | 48.927 | 36.330 | 1.00 | 41.59 | B | C |
| ATOM | 4369 | CG2 | VAL | B | 1070 | 2.681 | 50.091 | 34.987 | 1.00 | 40.03 | B | C |
| ATOM | 4370 | C | VAL | B | 1070 | −0.872 | 50.875 | 36.053 | 1.00 | 39.70 | B | C |
| ATOM | 4371 | O | VAL | B | 1070 | −1.700 | 50.261 | 35.381 | 1.00 | 39.20 | B | O |
| ATOM | 4372 | N | HIS | B | 1071 | −1.088 | 51.264 | 37.312 | 1.00 | 40.03 | B | N |
| ATOM | 4373 | CA | HIS | B | 1071 | −2.331 | 50.994 | 38.041 | 1.00 | 40.05 | B | C |
| ATOM | 4374 | CB | HIS | B | 1071 | −2.165 | 51.344 | 39.528 | 1.00 | 40.50 | B | C |
| ATOM | 4375 | CG | HIS | B | 1071 | −3.399 | 51.124 | 40.349 | 1.00 | 41.67 | B | C |
| ATOM | 4376 | CD2 | HIS | B | 1071 | −4.059 | 51.943 | 41.203 | 1.00 | 40.99 | B | C |
| ATOM | 4377 | ND1 | HIS | B | 1071 | −4.090 | 49.932 | 40.358 | 1.00 | 42.50 | B | N |
| ATOM | 4378 | CE1 | HIS | B | 1071 | −5.123 | 50.025 | 41.177 | 1.00 | 38.81 | B | C |
| ATOM | 4379 | NE2 | HIS | B | 1071 | −5.125 | 51.235 | 41.701 | 1.00 | 39.78 | B | N |
| ATOM | 4380 | C | HIS | B | 1071 | −3.488 | 51.794 | 37.462 | 1.00 | 40.65 | B | C |
| ATOM | 4381 | O | HIS | B | 1071 | −4.645 | 51.403 | 37.587 | 1.00 | 40.56 | B | O |
| ATOM | 4382 | N | GLU | B | 1072 | −3.178 | 52.919 | 36.829 | 1.00 | 40.18 | B | N |
| ATOM | 4383 | CA | GLU | B | 1072 | −4.221 | 53.743 | 36.240 | 1.00 | 40.50 | B | C |
| ATOM | 4384 | CB | GLU | B | 1072 | −3.693 | 55.157 | 35.975 | 1.00 | 44.39 | B | C |
| ATOM | 4385 | CG | GLU | B | 1072 | −4.766 | 56.138 | 35.550 | 1.00 | 50.86 | B | C |
| ATOM | 4386 | CD | GLU | B | 1072 | −4.385 | 57.579 | 35.834 | 1.00 | 55.90 | B | C |
| ATOM | 4387 | OE1 | GLU | B | 1072 | −3.348 | 58.034 | 35.303 | 1.00 | 57.49 | B | O |
| ATOM | 4388 | OE2 | GLU | B | 1072 | −5.122 | 58.253 | 36.593 | 1.00 | 58.81 | B | O |
| ATOM | 4389 | C | GLU | B | 1072 | −4.735 | 53.102 | 34.947 | 1.00 | 36.98 | B | C |
| ATOM | 4390 | O | GLU | B | 1072 | −5.900 | 53.263 | 34.588 | 1.00 | 37.76 | B | O |
| ATOM | 4391 | N | LEU | B | 1073 | −3.870 | 52.367 | 34.249 | 1.00 | 37.52 | B | N |
| ATOM | 4392 | CA | LEU | B | 1073 | −4.287 | 51.697 | 33.023 | 1.00 | 35.30 | B | C |
| ATOM | 4393 | CB | LEU | B | 1073 | −3.090 | 51.114 | 32.267 | 1.00 | 34.93 | B | C |
| ATOM | 4394 | CG | LEU | B | 1073 | −2.101 | 52.111 | 31.674 | 1.00 | 34.74 | B | C |
| ATOM | 4395 | CD1 | LEU | B | 1073 | −1.079 | 51.384 | 30.837 | 1.00 | 33.55 | B | C |
| ATOM | 4396 | CD2 | LEU | B | 1073 | −2.857 | 53.111 | 30.823 | 1.00 | 36.36 | B | C |
| ATOM | 4397 | C | LEU | B | 1073 | −5.252 | 50.568 | 33.359 | 1.00 | 34.77 | B | C |
| ATOM | 4398 | O | LEU | B | 1073 | −6.318 | 50.467 | 32.765 | 1.00 | 34.13 | B | O |
| ATOM | 4399 | N | MET | B | 1074 | −4.878 | 49.719 | 34.313 | 1.00 | 35.06 | B | N |
| ATOM | 4400 | CA | MET | B | 1074 | −5.742 | 48.608 | 34.690 | 1.00 | 33.81 | B | C |
| ATOM | 4401 | CB | MET | B | 1074 | −5.022 | 47.632 | 35.632 | 1.00 | 32.66 | B | C |
| ATOM | 4402 | CG | MET | B | 1074 | −4.646 | 48.183 | 36.999 | 1.00 | 30.09 | B | C |
| ATOM | 4403 | SD | MET | B | 1074 | −3.884 | 46.950 | 38.130 | 1.00 | 23.51 | B | S |
| ATOM | 4404 | CE | MET | B | 1074 | −2.271 | 46.878 | 37.495 | 1.00 | 21.36 | B | C |
| ATOM | 4405 | C | MET | B | 1074 | −6.983 | 49.137 | 35.361 | 1.00 | 33.43 | B | C |
| ATOM | 4406 | O | MET | B | 1074 | −7.960 | 48.422 | 35.516 | 1.00 | 35.76 | B | O |
| ATOM | 4407 | N | LYS | B | 1075 | −6.956 | 50.401 | 35.748 | 1.00 | 32.86 | B | N |
| ATOM | 4408 | CA | LYS | B | 1075 | −8.105 | 50.984 | 36.412 | 1.00 | 34.05 | B | C |
| ATOM | 4409 | CB | LYS | B | 1075 | −7.717 | 52.305 | 37.081 | 1.00 | 36.76 | B | C |
| ATOM | 4410 | CG | LYS | B | 1075 | −8.596 | 52.684 | 38.266 | 1.00 | 36.63 | B | C |
| ATOM | 4411 | CD | LYS | B | 1075 | −8.189 | 51.893 | 39.498 | 1.00 | 36.73 | B | C |
| ATOM | 4412 | CE | LYS | B | 1075 | −9.300 | 51.859 | 40.545 | 1.00 | 38.31 | B | C |
| ATOM | 4413 | NZ | LYS | B | 1075 | −10.509 | 51.069 | 40.106 | 1.00 | 33.91 | B | N |
| ATOM | 4414 | C | LYS | B | 1075 | −9.193 | 51.241 | 35.380 | 1.00 | 32.72 | B | C |
| ATOM | 4415 | O | LYS | B | 1075 | −10.364 | 50.956 | 35.614 | 1.00 | 33.59 | B | O |
| ATOM | 4416 | N | LEU | B | 1076 | −8.784 | 51.790 | 34.240 | 1.00 | 30.33 | B | N |
| ATOM | 4417 | CA | LEU | B | 1076 | −9.687 | 52.113 | 33.143 | 1.00 | 27.87 | B | C |
| ATOM | 4418 | CB | LEU | B | 1076 | −8.935 | 52.919 | 32.080 | 1.00 | 27.60 | B | C |
| ATOM | 4419 | CG | LEU | B | 1076 | −8.395 | 54.307 | 32.467 | 1.00 | 25.81 | B | C |
| ATOM | 4420 | CD1 | LEU | B | 1076 | −7.729 | 54.956 | 31.266 | 1.00 | 23.58 | B | C |
| ATOM | 4421 | CD2 | LEU | B | 1076 | −9.539 | 55.179 | 32.947 | 1.00 | 23.87 | B | C |
| ATOM | 4422 | C | LEU | B | 1076 | −10.263 | 50.853 | 32.511 | 1.00 | 27.92 | B | C |
| ATOM | 4423 | O | LEU | B | 1076 | −11.416 | 50.818 | 32.067 | 1.00 | 27.92 | B | O |

-continued

| | | | | | | | | | | | |
|---|---|---|---|---|---|---|---|---|---|---|---|
| ATOM | 4424 | N | CYS | B | 1077 | −9.437 | 49.818 | 32.466 | 1.00 | 25.91 | B | N |
| ATOM | 4425 | CA | CYS | B | 1077 | −9.838 | 48.550 | 31.899 | 1.00 | 23.62 | B | C |
| ATOM | 4426 | CB | CYS | B | 1077 | −8.695 | 47.538 | 32.002 | 1.00 | 21.19 | B | C |
| ATOM | 4427 | SG | CYS | B | 1077 | −7.269 | 47.783 | 30.894 | 1.00 | 21.49 | B | S |
| ATOM | 4428 | C | CYS | B | 1077 | −11.065 | 47.966 | 32.610 | 1.00 | 22.56 | B | C |
| ATOM | 4429 | O | CYS | B | 1077 | −11.830 | 47.257 | 31.997 | 1.00 | 23.55 | B | O |
| ATOM | 4430 | N | TRP | B | 1078 | −11.251 | 48.323 | 33.892 | 1.00 | 23.18 | B | N |
| ATOM | 4431 | CA | TRP | B | 1078 | −12.374 | 47.797 | 34.684 | 1.00 | 21.44 | B | C |
| ATOM | 4432 | CB | TRP | B | 1078 | −11.905 | 47.359 | 36.077 | 1.00 | 21.43 | B | C |
| ATOM | 4433 | CG | TRP | B | 1078 | −10.755 | 46.398 | 36.077 | 1.00 | 23.00 | B | C |
| ATOM | 4434 | CD2 | TRP | B | 1078 | −9.714 | 46.318 | 37.054 | 1.00 | 23.77 | B | C |
| ATOM | 4435 | CE2 | TRP | B | 1078 | −8.834 | 45.293 | 36.647 | 1.00 | 24.28 | B | C |
| ATOM | 4436 | CE3 | TRP | B | 1078 | −9.438 | 47.017 | 38.233 | 1.00 | 22.51 | B | C |
| ATOM | 4437 | CD1 | TRP | B | 1078 | −10.478 | 45.437 | 35.145 | 1.00 | 26.11 | B | C |
| ATOM | 4438 | NE1 | TRP | B | 1078 | −9.322 | 44.772 | 35.478 | 1.00 | 25.75 | B | N |
| ATOM | 4439 | CZ2 | TRP | B | 1078 | −7.697 | 44.954 | 37.376 | 1.00 | 23.37 | B | C |
| ATOM | 4440 | CZ3 | TRP | B | 1078 | −8.314 | 46.679 | 38.950 | 1.00 | 22.43 | B | C |
| ATOM | 4441 | CH2 | TRP | B | 1078 | −7.455 | 45.656 | 38.520 | 1.00 | 22.90 | B | C |
| ATOM | 4442 | C | TRP | B | 1078 | −13.592 | 48.712 | 34.831 | 1.00 | 20.28 | B | C |
| ATOM | 4443 | O | TRP | B | 1078 | −14.348 | 48.621 | 35.798 | 1.00 | 15.97 | B | O |
| ATOM | 4444 | N | ALA | B | 1079 | −13.772 | 49.593 | 33.860 | 1.00 | 21.94 | B | N |
| ATOM | 4445 | CA | ALA | B | 1079 | −14.918 | 50.480 | 33.844 | 1.00 | 23.82 | B | C |
| ATOM | 4446 | CB | ALA | B | 1079 | −14.838 | 51.408 | 32.645 | 1.00 | 21.74 | B | C |
| ATOM | 4447 | C | ALA | B | 1079 | −16.138 | 49.569 | 33.726 | 1.00 | 26.53 | B | C |
| ATOM | 4448 | O | ALA | B | 1079 | −16.111 | 48.555 | 33.027 | 1.00 | 26.44 | B | O |
| ATOM | 4449 | N | PRO | B | 1080 | −17.221 | 49.918 | 34.417 | 1.00 | 28.40 | B | N |
| ATOM | 4450 | CD | PRO | B | 1080 | −17.374 | 51.083 | 35.305 | 1.00 | 28.57 | B | C |
| ATOM | 4451 | CA | PRO | B | 1080 | −18.441 | 49.113 | 34.374 | 1.00 | 29.60 | B | C |
| ATOM | 4452 | CB | PRO | B | 1080 | −19.463 | 49.997 | 35.088 | 1.00 | 27.68 | B | C |
| ATOM | 4453 | CG | PRO | B | 1080 | −18.624 | 50.737 | 36.086 | 1.00 | 27.42 | B | C |
| ATOM | 4454 | C | PRO | B | 1080 | −18.876 | 48.741 | 32.954 | 1.00 | 30.91 | B | C |
| ATOM | 4455 | O | PRO | B | 1080 | −18.977 | 47.556 | 32.625 | 1.00 | 33.35 | B | O |
| ATOM | 4456 | N | SER | B | 1081 | −19.119 | 49.745 | 32.116 | 1.00 | 30.36 | B | N |
| ATOM | 4457 | CA | SER | B | 1081 | −19.568 | 49.498 | 30.749 | 1.00 | 30.13 | B | C |
| ATOM | 4458 | CB | SER | B | 1081 | −20.373 | 50.684 | 30.214 | 1.00 | 32.93 | B | C |
| ATOM | 4459 | OG | SER | B | 1081 | −19.514 | 51.762 | 29.886 | 1.00 | 37.08 | B | O |
| ATOM | 4460 | C | SER | B | 1081 | −18.422 | 49.223 | 29.799 | 1.00 | 28.16 | B | C |
| ATOM | 4461 | O | SER | B | 1081 | −17.355 | 49.822 | 29.894 | 1.00 | 28.59 | B | O |
| ATOM | 4462 | N | PRO | B | 1082 | −18.643 | 48.313 | 28.849 | 1.00 | 26.55 | B | N |
| ATOM | 4463 | CD | PRO | B | 1082 | −19.807 | 47.418 | 28.779 | 1.00 | 23.40 | B | C |
| ATOM | 4464 | CA | PRO | B | 1082 | −17.633 | 47.938 | 27.861 | 1.00 | 26.35 | B | C |
| ATOM | 4465 | CB | PRO | B | 1082 | −18.315 | 46.807 | 27.103 | 1.00 | 23.94 | B | C |
| ATOM | 4466 | CG | PRO | B | 1082 | −19.214 | 46.207 | 28.152 | 1.00 | 22.82 | B | C |
| ATOM | 4467 | C | PRO | B | 1082 | −17.209 | 49.097 | 26.954 | 1.00 | 28.24 | B | C |
| ATOM | 4468 | O | PRO | B | 1082 | −16.021 | 49.294 | 26.681 | 1.00 | 27.35 | B | O |
| ATOM | 4469 | N | GLN | B | 1083 | −18.184 | 49.866 | 26.493 | 1.00 | 26.90 | B | N |
| ATOM | 4470 | CA | GLN | B | 1083 | −17.897 | 50.992 | 25.629 | 1.00 | 32.63 | B | C |
| ATOM | 4471 | CB | GLN | B | 1083 | −19.208 | 51.615 | 25.163 | 1.00 | 36.33 | B | C |
| ATOM | 4472 | CG | GLN | B | 1083 | −20.063 | 52.140 | 26.290 | 1.00 | 44.10 | B | C |
| ATOM | 4473 | CD | GLN | B | 1083 | −21.349 | 52.781 | 25.796 | 1.00 | 47.98 | B | C |
| ATOM | 4474 | OE1 | GLN | B | 1083 | −22.121 | 52.160 | 25.059 | 1.00 | 50.30 | B | O |
| ATOM | 4475 | NE2 | GLN | B | 1083 | −21.592 | 54.029 | 26.208 | 1.00 | 50.00 | B | N |
| ATOM | 4476 | C | GLN | B | 1083 | −17.012 | 52.050 | 26.318 | 1.00 | 33.60 | B | C |
| ATOM | 4477 | O | GLN | B | 1083 | −16.493 | 52.961 | 25.669 | 1.00 | 33.23 | B | O |
| ATOM | 4478 | N | ASP | B | 1084 | −16.821 | 51.926 | 27.626 | 1.00 | 34.03 | B | N |
| ATOM | 4479 | CA | ASP | B | 1084 | −15.999 | 52.895 | 28.341 | 1.00 | 35.82 | B | C |
| ATOM | 4480 | CB | ASP | B | 1084 | −16.627 | 53.227 | 29.704 | 1.00 | 38.13 | B | C |
| ATOM | 4481 | CG | ASP | B | 1084 | −17.865 | 54.113 | 29.579 | 1.00 | 38.77 | B | C |
| ATOM | 4482 | OD1 | ASP | B | 1084 | −18.596 | 54.275 | 30.580 | 1.00 | 40.28 | B | O |
| ATOM | 4483 | OD2 | ASP | B | 1084 | −18.102 | 54.655 | 28.479 | 1.00 | 40.01 | B | O |
| ATOM | 4484 | C | ASP | B | 1084 | −14.549 | 52.438 | 26.521 | 1.00 | 35.43 | B | C |
| ATOM | 4485 | O | ASP | B | 1084 | −13.646 | 53.262 | 28.708 | 1.00 | 34.85 | B | O |
| ATOM | 4486 | N | ARG | B | 1085 | −14.325 | 51.129 | 28.460 | 1.00 | 33.57 | B | N |
| ATOM | 4487 | CA | ARG | B | 1085 | −12.980 | 50.589 | 28.603 | 1.00 | 31.02 | B | C |
| ATOM | 4488 | CB | ARG | B | 1085 | −13.025 | 49.064 | 28.690 | 1.00 | 27.37 | B | C |
| ATOM | 4489 | CG | ARG | B | 1085 | −13.849 | 48.558 | 29.856 | 1.00 | 25.02 | B | C |
| ATOM | 4490 | CD | ARG | B | 1085 | −14.021 | 47.069 | 29.800 | 1.00 | 22.29 | B | C |
| ATOM | 4491 | NE | ARG | B | 1085 | −15.125 | 46.671 | 30.665 | 1.00 | 21.69 | B | N |
| ATOM | 4492 | CZ | ARG | B | 1085 | −15.985 | 45.702 | 30.374 | 1.00 | 20.52 | B | C |
| ATOM | 4493 | NH1 | ARG | B | 1085 | −15.873 | 45.015 | 29.246 | 1.00 | 17.94 | B | N |
| ATOM | 4494 | NH2 | ARG | B | 1085 | −16.975 | 45.438 | 31.210 | 1.00 | 20.52 | B | N |
| ATOM | 4495 | C | ARG | B | 1085 | −12.194 | 51.012 | 27.375 | 1.00 | 30.75 | B | C |
| ATOM | 4496 | O | ARG | B | 1085 | −12.742 | 51.116 | 26.289 | 1.00 | 32.84 | B | O |
| ATOM | 4497 | N | PRO | B | 1086 | −10.897 | 51.280 | 27.532 | 1.00 | 30.76 | B | N |
| ATOM | 4498 | CD | PRO | B | 1086 | −10.048 | 51.250 | 28.734 | 1.00 | 29.24 | B | C |
| ATOM | 4499 | CA | PRO | B | 1086 | −10.132 | 51.688 | 26.355 | 1.00 | 30.29 | B | C |
| ATOM | 4500 | CB | PRO | B | 1086 | −8.802 | 52.147 | 26.950 | 1.00 | 29.66 | B | C |
| ATOM | 4501 | CG | PRO | B | 1086 | −8.654 | 51.273 | 26.137 | 1.00 | 29.74 | B | C |
| ATOM | 4502 | C | PRO | B | 1086 | −9.971 | 50.509 | 25.421 | 1.00 | 29.51 | B | C |
| ATOM | 4503 | O | PRO | B | 1086 | −10.398 | 49.407 | 25.732 | 1.00 | 32.54 | B | O |

-continued

| ATOM | 4504 | N | SER | B | 1087 | −9.364 | 50.742 | 24.270 | 1.00 | 29.78 | B | N |
| --- | --- | --- | --- | --- | --- | --- | --- | --- | --- | --- | --- | --- |
| ATOM | 4505 | CA | SER | B | 1087 | −9.141 | 49.668 | 23.325 | 1.00 | 29.49 | B | C |
| ATOM | 4506 | CB | SER | B | 1087 | −9.447 | 50.139 | 21.906 | 1.00 | 26.96 | B | C |
| ATOM | 4507 | OG | SER | B | 1087 | −8.416 | 50.983 | 21.422 | 1.00 | 30.79 | B | O |
| ATOM | 4508 | C | SER | B | 1087 | −7.664 | 49.300 | 23.439 | 1.00 | 29.09 | B | C |
| ATOM | 4509 | O | SER | B | 1087 | −6.864 | 50.087 | 23.936 | 1.00 | 30.95 | B | O |
| ATOM | 4510 | N | PHE | B | 1088 | −7.303 | 48.108 | 22.987 | 1.00 | 28.19 | B | N |
| ATOM | 4511 | CA | PHE | B | 1088 | −5.919 | 47.679 | 23.038 | 1.00 | 27.93 | B | C |
| ATOM | 4512 | CB | PHE | B | 1088 | −5.809 | 46.252 | 22.509 | 1.00 | 26.98 | B | C |
| ATOM | 4513 | CG | PHE | B | 1088 | −6.217 | 45.204 | 23.510 | 1.00 | 26.32 | B | C |
| ATOM | 4514 | CD1 | PHE | B | 1088 | −5.428 | 44.957 | 24.627 | 1.00 | 23.88 | B | C |
| ATOM | 4515 | CD2 | PHE | B | 1088 | −7.384 | 44.466 | 23.336 | 1.00 | 23.74 | B | C |
| ATOM | 4516 | CE1 | PHE | B | 1088 | −5.793 | 43.997 | 25.545 | 1.00 | 23.97 | B | C |
| ATOM | 4517 | CE2 | PHE | B | 1088 | −7.757 | 43.500 | 24.257 | 1.00 | 23.15 | B | C |
| ATOM | 4518 | CZ | PHE | B | 1088 | −6.961 | 43.264 | 25.362 | 1.00 | 24.05 | B | C |
| ATOM | 4519 | C | PHE | B | 1088 | −5.037 | 48.622 | 22.226 | 1.00 | 29.08 | B | C |
| ATOM | 4520 | O | PHE | B | 1088 | −3.855 | 48.786 | 22.517 | 1.00 | 30.69 | B | O |
| ATOM | 4521 | N | SER | B | 1089 | −5.619 | 49.253 | 21.213 | 1.00 | 29.50 | B | N |
| ATOM | 4522 | CA | SER | B | 1089 | −4.867 | 50.177 | 20.381 | 1.00 | 31.30 | B | C |
| ATOM | 4523 | CB | SER | B | 1089 | −5.679 | 50.555 | 19.143 | 1.00 | 31.23 | B | C |
| ATOM | 4524 | OG | SER | B | 1089 | −6.889 | 51.188 | 19.509 | 1.00 | 34.90 | B | O |
| ATOM | 4525 | C | SER | B | 1089 | −4.530 | 51.427 | 21.190 | 1.00 | 32.13 | B | C |
| ATOM | 4526 | O | SER | B | 1089 | −3.568 | 52.140 | 20.880 | 1.00 | 30.23 | B | O |
| ATOM | 4527 | N | ALA | B | 1090 | −5.337 | 51.678 | 22.221 | 1.00 | 31.60 | B | N |
| ATOM | 4528 | CA | ALA | B | 1090 | −5.138 | 52.816 | 23.107 | 1.00 | 33.02 | B | C |
| ATOM | 4529 | CB | ALA | B | 1090 | −6.446 | 53.174 | 23.792 | 1.00 | 32.78 | B | C |
| ATOM | 4530 | C | ALA | B | 1090 | −4.064 | 52.521 | 24.157 | 1.00 | 33.92 | B | C |
| ATOM | 4531 | O | ALA | B | 1090 | −3.083 | 53.262 | 24.286 | 1.00 | 34.82 | B | O |
| ATOM | 4532 | N | LEU | B | 1091 | −4.241 | 51.430 | 24.895 | 1.00 | 33.05 | B | N |
| ATOM | 4533 | CA | LEU | B | 1091 | −3.284 | 51.053 | 25.929 | 1.00 | 32.35 | B | C |
| ATOM | 4534 | CB | LEU | B | 1091 | −3.745 | 49.772 | 26.618 | 1.00 | 30.82 | B | C |
| ATOM | 4535 | CG | LEU | B | 1091 | −5.128 | 49.884 | 27.254 | 1.00 | 29.77 | B | C |
| ATOM | 4536 | CD1 | LEU | B | 1091 | −5.770 | 48.510 | 27.366 | 1.00 | 27.39 | B | C |
| ATOM | 4537 | CD2 | LEU | B | 1091 | −4.999 | 50.558 | 28.605 | 1.00 | 31.11 | B | C |
| ATOM | 4538 | C | LEU | B | 1091 | −1.879 | 50.858 | 25.366 | 1.00 | 32.88 | B | C |
| ATOM | 4539 | O | LEU | B | 1091 | −0.893 | 51.290 | 25.974 | 1.00 | 32.53 | B | O |
| ATOM | 4540 | N | GLY | B | 1092 | −1.807 | 50.208 | 24.204 | 1.00 | 32.64 | B | N |
| ATOM | 4541 | CA | GLY | B | 1092 | −0.540 | 49.928 | 23.538 | 1.00 | 32.84 | B | C |
| ATOM | 4542 | C | GLY | B | 1092 | 0.515 | 51.017 | 23.583 | 1.00 | 32.38 | B | C |
| ATOM | 4543 | O | GLY | B | 1092 | 1.548 | 50.839 | 24.215 | 1.00 | 30.96 | B | O |
| ATOM | 4544 | N | PRO | B | 1093 | 0.293 | 52.152 | 22.904 | 1.00 | 34.39 | B | N |
| ATOM | 4545 | CD | PRO | B | 1093 | −0.890 | 52.468 | 22.089 | 1.00 | 35.39 | B | C |
| ATOM | 4546 | CA | PRO | B | 1093 | 1.239 | 53.269 | 22.881 | 1.00 | 36.18 | B | C |
| ATOM | 4547 | CB | PRO | B | 1093 | 0.530 | 54.305 | 22.000 | 1.00 | 36.68 | B | C |
| ATOM | 4548 | CG | PRO | B | 1093 | −0.915 | 53.969 | 22.159 | 1.00 | 35.69 | B | C |
| ATOM | 4549 | C | PRO | B | 1093 | 1.557 | 53.779 | 24.284 | 1.00 | 35.73 | B | C |
| ATOM | 4550 | O | PRO | B | 1093 | 2.705 | 54.093 | 24.583 | 1.00 | 34.76 | B | O |
| ATOM | 4551 | N | GLN | B | 1094 | 0.547 | 53.852 | 25.146 | 1.00 | 37.32 | B | N |
| ATOM | 4552 | CA | GLN | B | 1094 | 0.783 | 54.301 | 26.516 | 1.00 | 39.11 | B | C |
| ATOM | 4553 | CB | GLN | B | 1094 | −0.526 | 54.389 | 27.309 | 1.00 | 39.49 | B | C |
| ATOM | 4554 | CG | GLN | B | 1094 | −1.545 | 55.394 | 26.781 | 1.00 | 43.75 | B | C |
| ATOM | 4555 | CD | GLN | B | 1094 | −2.660 | 55.693 | 27.789 | 1.00 | 47.08 | B | C |
| ATOM | 4556 | OE1 | GLN | B | 1094 | −2.397 | 56.218 | 28.874 | 1.00 | 49.17 | B | O |
| ATOM | 4557 | NE2 | GLN | B | 1094 | −3.903 | 55.362 | 27.434 | 1.00 | 46.08 | B | N |
| ATOM | 4558 | C | GLN | B | 1094 | 1.740 | 53.335 | 27.222 | 1.00 | 39.18 | B | C |
| ATOM | 4559 | O | GLN | B | 1094 | 2.728 | 53.758 | 27.817 | 1.00 | 40.18 | B | O |
| ATOM | 4560 | N | LEU | B | 1095 | 1.452 | 52.038 | 27.154 | 1.00 | 39.55 | B | N |
| ATOM | 4561 | CA | LEU | B | 1095 | 2.312 | 51.045 | 27.793 | 1.00 | 40.38 | B | C |
| ATOM | 4562 | CB | LEU | B | 1095 | 1.740 | 49.637 | 27.607 | 1.00 | 38.68 | B | C |
| ATOM | 4563 | CG | LEU | B | 1095 | 0.575 | 49.259 | 28.533 | 1.00 | 39.13 | B | C |
| ATOM | 4564 | CD1 | LEU | B | 1095 | −0.133 | 48.024 | 28.010 | 1.00 | 37.02 | B | C |
| ATOM | 4565 | CD2 | LEU | B | 1095 | 1.104 | 49.031 | 29.943 | 1.00 | 37.97 | B | C |
| ATOM | 4566 | C | LEU | B | 1095 | 3.741 | 51.087 | 27.257 | 1.00 | 41.75 | B | C |
| ATOM | 4567 | O | LEU | B | 1095 | 4.704 | 51.027 | 28.023 | 1.00 | 40.09 | B | O |
| ATOM | 4568 | N | ASP | B | 1096 | 3.879 | 51.192 | 25.941 | 1.00 | 43.20 | B | N |
| ATOM | 4569 | CA | ASP | B | 1096 | 5.199 | 51.229 | 25.336 | 1.00 | 45.21 | B | C |
| ATOM | 4570 | CB | ASP | B | 1096 | 5.086 | 51.289 | 23.814 | 1.00 | 47.28 | B | C |
| ATOM | 4571 | CG | ASP | B | 1096 | 6.277 | 50.658 | 23.127 | 1.00 | 50.41 | B | C |
| ATOM | 4572 | OD1 | ASP | B | 1096 | 7.018 | 51.376 | 22.411 | 1.00 | 51.05 | B | O |
| ATOM | 4573 | OD2 | ASP | B | 1096 | 6.471 | 49.434 | 23.317 | 1.00 | 51.68 | B | O |
| ATOM | 4574 | C | ASP | B | 1096 | 5.969 | 52.432 | 25.857 | 1.00 | 44.84 | B | C |
| ATOM | 4575 | O | ASP | B | 1096 | 7.188 | 52.389 | 26.014 | 1.00 | 43.07 | B | O |
| ATOM | 4576 | N | MET | B | 1097 | 5.240 | 53.506 | 26.132 | 1.00 | 46.20 | B | N |
| ATOM | 4577 | CA | MET | B | 1097 | 5.839 | 54.722 | 26.655 | 1.00 | 47.53 | B | C |
| ATOM | 4578 | CB | MET | B | 1097 | 4.805 | 55.845 | 26.679 | 1.00 | 50.08 | B | C |
| ATOM | 4579 | CG | MET | B | 1097 | 5.362 | 57.174 | 27.161 | 1.00 | 53.76 | B | C |
| ATOM | 4580 | SD | MET | B | 1097 | 4.083 | 58.421 | 27.455 | 1.00 | 59.09 | B | S |
| ATOM | 4581 | CE | MET | B | 1097 | 3.697 | 58.094 | 29.210 | 1.00 | 56.01 | B | C |
| ATOM | 4582 | C | MET | B | 1097 | 6.378 | 54.482 | 28.069 | 1.00 | 47.41 | B | C |
| ATOM | 4583 | O | MET | B | 1097 | 7.551 | 54.746 | 28.346 | 1.00 | 47.55 | B | O |

-continued

| | | | | | | | | | | | |
|---|---|---|---|---|---|---|---|---|---|---|---|
| ATOM | 4584 | N | LEU | B | 1098 | 5.524 | 53.979 | 28.960 | 1.00 | 45.95 | B | N |
| ATOM | 4585 | CA | LEU | B | 1098 | 5.934 | 53.703 | 30.340 | 1.00 | 46.87 | B | C |
| ATOM | 4586 | CB | LEU | B | 1098 | 4.808 | 53.000 | 31.109 | 1.00 | 45.75 | B | C |
| ATOM | 4587 | CG | LEU | B | 1098 | 3.507 | 53.792 | 31.244 | 1.00 | 45.44 | B | C |
| ATOM | 4588 | CD1 | LEU | B | 1098 | 2.490 | 53.006 | 32.075 | 1.00 | 45.54 | B | C |
| ATOM | 4589 | CD2 | LEU | B | 1098 | 3.809 | 55.143 | 31.891 | 1.00 | 45.95 | B | C |
| ATOM | 4590 | C | LEU | B | 1098 | 7.195 | 52.841 | 30.395 | 1.00 | 47.11 | B | C |
| ATOM | 4591 | O | LEU | B | 1098 | 8.103 | 53.096 | 31.188 | 1.00 | 48.02 | B | O |
| ATOM | 4592 | N | TRP | B | 1099 | 7.240 | 51.821 | 29.547 | 1.00 | 47.69 | B | N |
| ATOM | 4593 | CA | TRP | B | 1099 | 8.380 | 50.920 | 29.480 | 1.00 | 48.25 | B | C |
| ATOM | 4594 | CB | TRP | B | 1099 | 8.231 | 49.990 | 28.279 | 1.00 | 47.18 | B | C |
| ATOM | 4595 | CG | TRP | B | 1099 | 9.403 | 49.114 | 28.085 | 1.00 | 45.90 | B | C |
| ATOM | 4596 | CD2 | TRP | B | 1099 | 10.442 | 49.287 | 27.124 | 1.00 | 46.24 | B | C |
| ATOM | 4597 | CE2 | TRP | B | 1099 | 11.365 | 48.244 | 27.319 | 1.00 | 46.53 | B | C |
| ATOM | 4598 | CE3 | TRP | B | 1099 | 10.689 | 50.229 | 26.126 | 1.00 | 46.72 | B | C |
| ATOM | 4599 | CD1 | TRP | B | 1099 | 9.720 | 48.004 | 28.800 | 1.00 | 46.60 | B | C |
| ATOM | 4600 | NE1 | TRP | B | 1099 | 10.899 | 47.469 | 28.346 | 1.00 | 45.86 | B | N |
| ATOM | 4601 | CZ2 | TRP | B | 1099 | 12.508 | 48.110 | 26.541 | 1.00 | 47.39 | B | C |
| ATOM | 4602 | CZ3 | TRP | B | 1099 | 11.825 | 50.095 | 25.356 | 1.00 | 46.84 | B | C |
| ATOM | 4603 | CH2 | TRP | B | 1099 | 12.723 | 49.047 | 25.570 | 1.00 | 47.41 | B | C |
| ATOM | 4604 | C | TRP | B | 1099 | 9.682 | 51.707 | 29.361 | 1.00 | 49.00 | B | C |
| ATOM | 4605 | O | TRP | B | 1099 | 10.600 | 51.531 | 30.160 | 1.00 | 48.96 | B | O |
| ATOM | 4606 | N | SER | B | 1100 | 9.757 | 52.575 | 28.358 | 1.00 | 49.38 | B | N |
| ATOM | 4607 | CA | SER | B | 1100 | 10.943 | 53.395 | 28.149 | 1.00 | 50.99 | B | C |
| ATOM | 4608 | CB | SER | B | 1100 | 10.966 | 53.916 | 26.714 | 1.00 | 50.66 | B | C |
| ATOM | 4609 | OG | SER | B | 1100 | 9.892 | 54.814 | 26.492 | 1.00 | 50.60 | B | O |
| ATOM | 4610 | C | SER | B | 1100 | 10.975 | 54.579 | 29.128 | 1.00 | 51.72 | B | C |
| ATOM | 4611 | O | SER | B | 1100 | 11.903 | 54.640 | 29.961 | 1.00 | 52.69 | B | O |
| ATOM | 4612 | OXT | SER | B | 1100 | 10.071 | 55.437 | 29.060 | 1.00 | 52.10 | B | O |
| TER | 1 | | SER | B | 1100 | | | | | | B | O |
| HETATM | 4625 | P1 | AMP | Y | 1 | 26.248 | 46.926 | 4.305 | 1.00 | 28.91 | Y | P |
| HETATM | 4626 | O1 | AMP | Y | 1 | 24.959 | 46.349 | 4.017 | 1.00 | 29.03 | Y | O |
| HETATM | 4627 | O2 | AMP | Y | 1 | 26.471 | 48.087 | 3.460 | 1.00 | 23.13 | Y | O |
| HETATM | 4628 | O3 | AMP | Y | 1 | 27.346 | 45.981 | 4.135 | 1.00 | 27.39 | Y | O |
| HETATM | 4629 | P2 | AMP | Y | 1 | 25.260 | 48.053 | 6.796 | 1.00 | 28.00 | Y | P |
| HETATM | 4630 | O4 | AMP | Y | 1 | 24.100 | 47.197 | 6.818 | 1.00 | 27.56 | Y | O |
| HETATM | 4631 | O5 | AMP | Y | 1 | 25.860 | 48.106 | 8.087 | 1.00 | 27.82 | Y | O |
| HETATM | 4632 | N2 | AMP | Y | 1 | 26.211 | 47.226 | 5.864 | 1.00 | 28.12 | Y | N |
| HETATM | 4633 | P3 | AMP | Y | 1 | 23.678 | 50.169 | 5.602 | 1.00 | 24.33 | Y | P |
| HETATM | 4634 | O6 | AMP | Y | 1 | 24.107 | 51.460 | 4.951 | 1.00 | 28.59 | Y | O |
| HETATM | 4635 | O7 | AMP | Y | 1 | 23.048 | 49.307 | 4.652 | 1.00 | 25.29 | Y | O |
| HETATM | 4636 | O8 | AMP | Y | 1 | 25.027 | 49.513 | 6.240 | 1.00 | 26.20 | Y | O |
| HETATM | 4637 | O9 | AMP | Y | 1 | 22.642 | 50.469 | 6.693 | 1.00 | 23.79 | Y | O |
| HETATM | 4638 | C1 | AMP | Y | 1 | 22.965 | 51.477 | 7.584 | 1.00 | 22.50 | Y | C |
| HETATM | 4639 | C3 | AMP | Y | 1 | 22.381 | 51.189 | 8.968 | 1.00 | 23.70 | Y | C |
| HETATM | 4640 | O10 | AMP | Y | 1 | 20.972 | 51.326 | 8.978 | 1.00 | 22.51 | Y | O |
| HETATM | 4641 | C7 | AMP | Y | 1 | 22.646 | 49.806 | 9.574 | 1.00 | 23.88 | Y | C |
| HETATM | 4642 | O11 | AMP | Y | 1 | 22.712 | 49.938 | 10.970 | 1.00 | 27.97 | Y | O |
| HETATM | 4643 | C9 | AMP | Y | 1 | 21.390 | 49.035 | 9.243 | 1.00 | 23.07 | Y | C |
| HETATM | 4644 | O12 | AMP | Y | 1 | 21.146 | 48.025 | 10.175 | 1.00 | 20.17 | Y | O |
| HETATM | 4645 | C10 | AMP | Y | 1 | 20.313 | 50.104 | 9.309 | 1.00 | 22.71 | Y | C |
| HETATM | 4646 | N4 | AMP | Y | 1 | 19.162 | 49.846 | 8.397 | 1.00 | 23.97 | Y | N |
| HETATM | 4647 | C8 | AMP | Y | 1 | 19.211 | 49.660 | 7.018 | 1.00 | 23.33 | Y | C |
| HETATM | 4648 | N5 | AMP | Y | 1 | 17.986 | 49.386 | 6.524 | 1.00 | 23.11 | Y | N |
| HETATM | 4649 | C5 | AMP | Y | 1 | 17.127 | 49.389 | 7.573 | 1.00 | 23.16 | Y | C |
| HETATM | 4650 | C6 | AMP | Y | 1 | 15.741 | 49.186 | 7.842 | 1.00 | 23.60 | Y | C |
| HETATM | 4651 | N6 | AMP | Y | 1 | 14.807 | 48.895 | 6.873 | 1.00 | 22.95 | Y | N |
| HETATM | 4652 | N1 | AMP | Y | 1 | 15.244 | 49.269 | 9.124 | 1.00 | 26.75 | Y | N |
| HETATM | 4653 | C2 | AMP | Y | 1 | 15.984 | 49.546 | 10.260 | 1.00 | 22.61 | Y | C |
| HETATM | 4654 | N3 | AMP | Y | 1 | 17.313 | 49.758 | 10.097 | 1.00 | 23.12 | Y | N |
| HETATM | 4655 | C4 | AMP | Y | 1 | 17.889 | 49.687 | 8.808 | 1.00 | 23.32 | Y | C |
| HETATM | 4656 | MG | MG | Y | 2 | 22.965 | 47.144 | 4.708 | 1.00 | 27.65 | Y | MG |
| HETATM | 4657 | P1 | AMP | Z | 1 | −6.811 | 27.348 | 31.249 | 1.00 | 29.75 | Z | P |
| HETATM | 4658 | O1 | AMP | Z | 1 | −6.300 | 27.933 | 30.032 | 1.00 | 25.93 | Z | O |
| HETATM | 4659 | O2 | AMP | Z | 1 | −7.551 | 26.124 | 30.969 | 1.00 | 24.41 | Z | O |
| HETATM | 4660 | O3 | AMP | Z | 1 | −7.613 | 28.224 | 32.090 | 1.00 | 26.59 | Z | O |
| HETATM | 4661 | P2 | AMP | Z | 1 | −4.222 | 26.039 | 31.829 | 1.00 | 26.40 | Z | P |
| HETATM | 4662 | O4 | AMP | Z | 1 | −3.371 | 26.742 | 30.880 | 1.00 | 26.33 | Z | O |
| HETATM | 4663 | O5 | AMP | Z | 1 | −3.594 | 25.914 | 33.084 | 1.00 | 27.90 | Z | O |
| HETATM | 4664 | N2 | AMP | Z | 1 | −5.480 | 27.010 | 32.143 | 1.00 | 28.13 | Z | N |
| HETATM | 4665 | P3 | AMP | Z | 1 | −4.457 | 23.966 | 29.840 | 1.00 | 26.27 | Z | P |
| HETATM | 4666 | O6 | AMP | Z | 1 | −5.338 | 22.775 | 29.725 | 1.00 | 28.28 | Z | O |
| HETATM | 4667 | O7 | AMP | Z | 1 | −4.637 | 24.880 | 28.724 | 1.00 | 27.16 | Z | O |
| HETATM | 4668 | O8 | AMP | Z | 1 | −4.755 | 24.626 | 31.283 | 1.00 | 25.90 | Z | O |
| HETATM | 4669 | O9 | AMP | Z | 1 | −2.951 | 23.529 | 29.790 | 1.00 | 25.56 | Z | O |
| HETATM | 4670 | C1 | AMP | Z | 1 | −2.309 | 22.819 | 30.848 | 1.00 | 22.33 | Z | C |
| HETATM | 4671 | C3 | AMP | Z | 1 | −0.795 | 23.071 | 30.857 | 1.00 | 23.34 | Z | C |
| HETATM | 4672 | O10 | AMP | Z | 1 | −0.234 | 22.965 | 29.547 | 1.00 | 22.37 | Z | O |
| HETATM | 4673 | C7 | AMP | Z | 1 | −0.408 | 24.496 | 31.335 | 1.00 | 23.19 | Z | C |
| HETATM | 4674 | O11 | AMP | Z | 1 | 0.745 | 24.342 | 32.105 | 1.00 | 25.77 | Z | O |

-continued

| | | | | | | | | | | | |
|---|---|---|---|---|---|---|---|---|---|---|---|
| HETATM | 4675 | C9 | AMP | Z | 1 | −0.090 | 25.231 | 30.042 | 1.00 | 22.68 | Z | C |
| HETATM | 4676 | O12 | AMP | Z | 1 | 0.844 | 26.255 | 30.179 | 1.00 | 22.55 | Z | O |
| HETATM | 4677 | C10 | AMP | Z | 1 | 0.452 | 24.151 | 29.138 | 1.00 | 22.80 | Z | C |
| HETATM | 4678 | N4 | AMP | Z | 1 | 0.396 | 24.436 | 27.666 | 1.00 | 24.01 | Z | N |
| HETATM | 4679 | C8 | AMP | Z | 1 | −0.742 | 24.730 | 26.933 | 1.00 | 24.62 | Z | C |
| HETATM | 4680 | N5 | AMP | Z | 1 | −0.447 | 24.966 | 25.604 | 1.00 | 25.25 | Z | N |
| HETATM | 4681 | C5 | AMP | Z | 1 | 0.891 | 24.823 | 25.461 | 1.00 | 24.14 | Z | C |
| HETATM | 4682 | C6 | AMP | Z | 1 | 1.915 | 24.885 | 24.448 | 1.00 | 24.17 | Z | C |
| HETATM | 4683 | N6 | AMP | Z | 1 | 1.681 | 25.214 | 23.143 | 1.00 | 20.34 | Z | N |
| HETATM | 4684 | N1 | AMP | Z | 1 | 3.266 | 24.622 | 24.771 | 1.00 | 25.74 | Z | N |
| HETATM | 4685 | C2 | AMP | Z | 1 | 3.694 | 24.311 | 26.030 | 1.00 | 22.91 | Z | C |
| HETATM | 4686 | N3 | AMP | Z | 1 | 2.771 | 24.244 | 27.043 | 1.00 | 21.55 | Z | N |
| HETATM | 4687 | C4 | AMP | Z | 1 | 1.437 | 24.478 | 26.810 | 1.00 | 22.73 | Z | C |
| HETATM | 4688 | MG | MG | Z | 2 | −4.549 | 27.191 | 28.573 | 1.00 | 31.30 | Z | MG |
| HETATM | 4689 | O | HOH | W | 1 | −2.475 | 30.329 | 15.504 | 1.00 | 11.40 | W | O |
| HETATM | 4690 | O | HOH | W | 2 | 12.414 | 45.490 | 15.244 | 1.00 | 13.21 | W | O |
| HETATM | 4691 | O | HOH | W | 3 | 29.299 | 47.960 | 7.015 | 1.00 | 20.72 | W | O |
| HETATM | 4692 | O | HOH | W | 4 | −8.081 | 23.906 | 29.636 | 1.00 | 24.82 | W | O |
| HETATM | 4693 | O | HOH | W | 5 | 19.546 | 44.643 | 17.339 | 1.00 | 5.81 | W | O |
| HETATM | 4694 | O | HOH | W | 6 | −5.932 | 29.329 | 7.200 | 1.00 | 26.30 | W | O |
| HETATM | 4695 | O | HOH | W | 7 | 13.335 | 45.024 | 29.684 | 1.00 | 26.89 | W | O |
| HETATM | 4696 | O | HOH | W | 8 | −2.722 | 34.331 | 39.767 | 1.00 | 28.35 | W | O |
| HETATM | 4697 | O | HOH | W | 9 | 35.150 | 40.728 | −7.044 | 1.00 | 32.32 | W | O |
| HETATM | 4698 | O | HOH | W | 10 | −21.199 | 33.084 | 32.518 | 1.00 | 29.13 | W | O |
| HETATM | 4699 | O | HOH | W | 11 | 1.946 | 41.700 | 15.699 | 1.00 | 17.00 | W | O |
| HETATM | 4700 | O | HOH | W | 12 | −4.135 | 15.706 | 24.394 | 1.00 | 26.37 | W | O |
| HETATM | 4701 | O | HOH | W | 13 | 18.978 | 58.280 | 2.913 | 1.00 | 29.75 | W | O |
| HETATM | 4702 | O | HOH | W | 14 | 24.050 | 58.118 | 8.115 | 1.00 | 33.81 | W | O |
| HETATM | 4703 | O | HOH | W | 15 | 8.875 | 64.811 | 12.194 | 1.00 | 32.66 | W | O |
| HETATM | 4704 | O | HOH | W | 16 | 48.673 | 31.147 | 15.865 | 1.00 | 19.28 | W | O |
| HETATM | 4705 | O | HOH | W | 17 | 51.031 | 42.556 | 6.078 | 1.00 | 39.02 | W | O |
| HETATM | 4706 | O | HOH | W | 18 | 25.398 | 50.597 | 2.357 | 1.00 | 20.20 | W | O |
| HETATM | 4707 | O | HOH | W | 19 | 40.324 | 26.361 | 16.008 | 1.00 | 27.85 | W | O |
| HETATM | 4708 | O | HOH | W | 20 | 33.653 | 51.255 | 1.318 | 1.00 | 24.99 | W | O |
| HETATM | 4709 | O | HOH | W | 21 | 28.596 | 48.674 | 9.568 | 1.00 | 27.69 | W | O |
| HETATM | 4710 | O | HOH | W | 22 | 3.864 | 6.537 | 26.814 | 1.00 | 30.27 | W | O |
| HETATM | 4711 | O | HOH | W | 23 | 34.593 | 52.731 | −2.102 | 1.00 | 21.01 | W | O |
| HETATM | 4712 | O | HOH | W | 24 | 3.459 | 12.452 | 32.479 | 1.00 | 16.68 | W | O |
| HETATM | 4713 | O | HOH | W | 25 | 21.173 | 61.854 | 13.602 | 1.00 | 18.35 | W | O |
| HETATM | 4714 | O | HOH | W | 26 | −9.899 | 40.661 | 21.126 | 1.00 | 14.79 | W | O |
| HETATM | 4715 | O | HOH | W | 27 | −6.606 | 26.300 | 34.986 | 1.00 | 26.71 | W | O |
| HETATM | 4716 | O | HOH | W | 28 | 31.882 | 37.812 | 13.934 | 1.00 | 24.97 | W | O |
| HETATM | 4717 | O | HOH | W | 29 | 5.767 | 35.379 | −5.080 | 1.00 | 26.68 | W | O |
| HETATM | 4718 | O | HOH | W | 30 | −0.387 | 12.747 | 10.060 | 1.00 | 30.83 | W | O |
| HETATM | 4719 | O | HOH | W | 31 | −2.871 | 16.142 | 31.823 | 1.00 | 27.26 | W | O |
| HETATM | 4720 | O | HOH | W | 32 | −11.338 | 17.892 | 21.567 | 1.00 | 24.99 | W | O |
| HETATM | 4721 | O | HOH | W | 33 | 27.741 | 41.030 | 9.385 | 1.00 | 35.57 | W | O |
| HETATM | 4722 | O | HOH | W | 34 | 4.219 | 40.947 | 15.023 | 1.00 | 26.11 | W | O |
| HETATM | 4723 | O | HOH | W | 35 | 13.358 | 40.025 | 45.175 | 1.00 | 33.41 | W | O |
| HETATM | 4724 | O | HOH | W | 36 | 10.178 | 43.642 | −0.473 | 1.00 | 21.44 | W | O |
| HETATM | 4725 | O | HOH | W | 37 | −5.670 | 25.835 | 23.600 | 1.00 | 26.16 | W | O |
| HETATM | 4726 | O | HOH | W | 38 | 22.553 | 65.325 | 10.636 | 1.00 | 35.15 | W | O |
| HETATM | 4727 | O | HOH | W | 39 | −19.914 | 17.680 | 11.168 | 1.00 | 22.16 | W | O |
| HETATM | 4728 | O | HOH | W | 40 | 14.142 | 46.495 | 2.450 | 1.00 | 24.14 | W | O |
| HETATM | 4729 | O | HOH | W | 41 | 30.519 | 39.861 | 12.539 | 1.00 | 36.50 | W | O |
| HETATM | 4730 | O | HOH | W | 42 | 19.597 | 33.906 | −3.688 | 1.00 | 17.47 | W | O |
| HETATM | 4731 | O | HOH | W | 43 | 16.289 | 45.356 | 3.477 | 1.00 | 17.51 | W | O |
| HETATM | 4732 | O | HOH | W | 44 | 21.782 | 43.355 | −2.963 | 1.00 | 20.88 | W | O |
| HETATM | 4733 | O | HOH | W | 45 | −8.473 | 49.357 | 41.780 | 1.00 | 25.18 | W | O |
| HETATM | 4734 | O | HOH | W | 46 | −14.467 | 25.593 | 49.502 | 1.00 | 36.38 | W | O |
| HETATM | 4735 | O | HOH | W | 47 | 2.639 | 57.400 | 5.791 | 1.00 | 28.77 | W | O |
| HETATM | 4736 | O | HOH | W | 48 | 9.875 | 15.041 | 10.250 | 1.00 | 39.43 | W | O |
| HETATM | 4737 | O | HOH | W | 49 | 12.865 | 4.298 | 11.454 | 1.00 | 42.78 | W | O |
| HETATM | 4738 | O | HOH | W | 50 | −18.417 | 36.077 | 56.375 | 1.00 | 34.15 | W | O |
| HETATM | 4739 | O | HOH | W | 51 | −1.916 | 27.652 | 19.935 | 1.00 | 22.92 | W | O |
| HETATM | 4740 | O | HOH | W | 52 | 7.220 | 17.804 | 12.275 | 1.00 | 44.35 | W | O |
| HETATM | 4741 | O | HOH | W | 53 | 48.699 | 45.704 | 12.632 | 1.00 | 30.47 | W | O |
| HETATM | 4742 | O | HOH | W | 54 | −2.981 | 8.858 | 20.070 | 1.00 | 23.68 | W | O |
| HETATM | 4743 | O | HOH | W | 55 | −4.013 | 26.398 | 36.017 | 1.00 | 22.25 | W | O |
| HETATM | 4744 | O | HOH | W | 56 | 40.677 | 24.839 | −3.765 | 1.00 | 25.15 | W | O |
| HETATM | 4745 | O | HOH | W | 57 | −20.509 | 33.232 | 20.262 | 1.00 | 42.21 | W | O |
| HETATM | 4746 | O | HOH | W | 58 | 18.916 | 63.958 | 14.464 | 1.00 | 33.09 | W | O |
| HETATM | 4747 | O | HOH | W | 59 | 6.936 | 41.796 | 15.875 | 1.00 | 31.02 | W | O |
| HETATM | 4748 | O | HOH | W | 60 | 12.623 | 66.714 | 5.890 | 1.00 | 23.87 | W | O |
| HETATM | 4749 | O | HOH | W | 61 | 11.893 | 47.134 | 39.605 | 1.00 | 23.05 | W | O |
| HETATM | 4750 | O | HOH | W | 62 | 7.474 | 40.610 | 3.914 | 1.00 | 31.03 | W | O |
| HETATM | 4751 | O | HOH | W | 63 | 22.606 | 52.920 | −12.732 | 1.00 | 42.64 | W | O |
| HETATM | 4752 | O | HOH | W | 64 | 2.426 | 54.692 | 4.984 | 1.00 | 26.28 | W | O |
| HETATM | 4753 | O | HOH | W | 65 | 48.775 | 30.973 | 5.752 | 1.00 | 25.77 | W | O |
| HETATM | 4754 | O | HOH | W | 66 | −11.173 | 53.513 | 23.526 | 1.00 | 41.70 | W | O |

-continued

| | | | | | | | | | | | |
|---|---|---|---|---|---|---|---|---|---|---|---|
| HETATM | 4755 | O | HOH | W | 67 | 23.529 | 26.529 | 24.314 | 1.00 | 38.02 | W | O |
| HETATM | 4756 | O | HOH | W | 68 | 9.992 | 28.475 | 25.594 | 1.00 | 34.12 | W | O |
| HETATM | 4757 | O | HOH | W | 69 | 3.366 | 44.401 | −5.013 | 1.00 | 50.58 | W | O |
| HETATM | 4758 | O | HOH | W | 70 | 34.274 | 34.206 | 2.671 | 1.00 | 24.77 | W | O |
| HETATM | 4759 | O | HOH | W | 71 | 20.152 | 56.215 | −4.144 | 1.00 | 22.22 | W | O |
| HETATM | 4760 | O | HOH | W | 72 | −8.710 | 24.835 | 37.208 | 1.00 | 27.50 | W | O |
| HETATM | 4761 | O | HOH | W | 73 | 32.146 | 41.427 | 14.964 | 1.00 | 28.71 | W | O |
| HETATM | 4762 | O | HOH | W | 74 | −19.018 | 31.978 | 53.014 | 1.00 | 38.25 | W | O |
| HETATM | 4763 | O | HOH | W | 75 | 0.080 | 8.693 | 33.017 | 1.00 | 42.67 | W | O |
| HETATM | 4764 | O | HOH | W | 76 | −7.947 | 47.660 | 19.560 | 1.00 | 23.76 | W | O |
| HETATM | 4765 | O | HOH | W | 77 | 36.529 | 54.767 | 10.120 | 1.00 | 28.79 | W | O |
| HETATM | 4766 | O | HOH | W | 78 | −12.852 | 35.028 | 17.783 | 1.00 | 25.41 | W | O |
| HETATM | 4767 | O | HOH | W | 79 | −0.559 | 47.749 | 21.052 | 1.00 | 24.10 | W | O |
| HETATM | 4768 | O | HOH | W | 80 | −17.156 | 21.792 | 34.959 | 1.00 | 42.68 | W | O |
| HETATM | 4769 | O | HOH | W | 81 | −13.699 | 23.195 | 35.641 | 1.00 | 33.42 | W | O |
| HETATM | 4770 | O | HOH | W | 82 | −9.587 | 42.543 | 56.480 | 1.00 | 34.56 | W | O |
| HETATM | 4771 | O | HOH | W | 83 | 43.873 | 33.067 | −8.277 | 1.00 | 39.60 | W | O |
| HETATM | 4772 | O | HOH | W | 84 | 5.761 | 57.407 | 37.269 | 1.00 | 45.64 | W | O |
| HETATM | 4773 | O | HOH | W | 85 | 16.884 | 21.454 | 20.877 | 1.00 | 52.96 | W | O |
| HETATM | 4774 | O | HOH | W | 86 | 47.763 | 34.049 | 1.316 | 1.00 | 36.54 | W | O |
| HETATM | 4775 | O | HOH | W | 87 | −6.209 | 31.119 | 46.066 | 1.00 | 44.92 | W | O |
| HETATM | 4776 | O | HOH | W | 88 | 40.750 | 51.712 | 5.730 | 1.00 | 33.72 | W | O |
| HETATM | 4777 | O | HOH | W | 89 | −21.569 | 39.844 | 47.646 | 1.00 | 29.53 | W | O |
| HETATM | 4778 | O | HOH | W | 90 | 26.302 | 31.299 | 25.877 | 1.00 | 24.97 | W | O |
| HETATM | 4779 | O | HOH | W | 91 | −7.619 | 56.473 | 35.928 | 1.00 | 33.44 | W | O |
| HETATM | 4780 | O | HOH | W | 92 | 19.370 | 29.016 | −3.829 | 1.00 | 36.95 | W | O |
| HETATM | 4781 | O | HOH | W | 93 | 22.912 | 21.947 | 20.348 | 1.00 | 34.74 | W | O |
| HETATM | 4782 | O | HOH | W | 94 | 6.640 | 33.210 | 4.482 | 1.00 | 25.32 | W | O |
| HETATM | 4783 | O | HOH | W | 95 | 19.761 | 65.159 | 5.818 | 1.00 | 28.63 | W | O |
| HETATM | 4784 | O | HOH | W | 96 | −2.429 | 28.740 | 22.618 | 1.00 | 17.06 | W | O |
| HETATM | 4785 | O | HOH | W | 97 | −3.064 | 31.778 | 42.427 | 1.00 | 42.96 | W | O |
| HETATM | 4786 | O | HOH | W | 98 | −5.388 | 7.268 | 11.141 | 1.00 | 30.44 | W | O |
| HETATM | 4787 | O | HOH | W | 99 | −22.456 | 19.371 | 11.638 | 1.00 | 31.53 | W | O |
| HETATM | 4788 | O | HOH | W | 100 | 4.576 | 39.683 | 11.824 | 1.00 | 34.42 | W | O |
| HETATM | 4789 | O | HOH | W | 101 | −11.699 | 42.668 | 37.871 | 1.00 | 20.12 | W | O |
| HETATM | 4790 | O | HOH | W | 102 | −20.248 | 30.467 | 21.517 | 1.00 | 43.20 | W | O |
| HETATM | 4791 | O | HOH | W | 103 | −2.130 | 27.300 | 28.199 | 1.00 | 34.69 | W | O |
| HETATM | 4792 | O | HOH | W | 104 | −28.854 | 35.295 | 32.405 | 1.00 | 26.50 | W | O |
| HETATM | 4793 | O | HOH | W | 105 | 47.956 | 33.744 | 15.640 | 1.00 | 34.20 | W | O |
| HETATM | 4794 | O | HOH | W | 106 | 9.854 | 66.277 | −3.306 | 1.00 | 36.84 | W | O |
| HETATM | 4795 | O | HOH | W | 107 | 24.030 | 38.651 | −11.161 | 1.00 | 50.50 | W | O |
| HETATM | 4796 | O | HOH | W | 108 | 48.420 | 31.498 | 3.256 | 1.00 | 39.12 | W | O |
| HETATM | 4797 | O | HOH | W | 109 | −1.253 | 45.553 | 15.262 | 1.00 | 38.50 | W | O |
| HETATM | 4798 | O | HOH | W | 110 | 33.843 | 42.792 | 13.225 | 1.00 | 30.63 | W | O |
| HETATM | 4799 | O | HOH | W | 111 | 28.703 | 42.535 | −2.829 | 1.00 | 30.19 | W | O |
| HETATM | 4800 | O | HOH | W | 112 | 8.622 | 12.687 | 11.102 | 1.00 | 29.60 | W | O |
| HETATM | 4801 | O | HOH | W | 113 | 20.128 | 67.529 | 1.352 | 1.00 | 33.55 | W | O |
| HETATM | 4802 | O | HOH | W | 114 | −0.770 | 14.323 | 8.166 | 1.00 | 52.45 | W | O |
| HETATM | 4803 | O | HOH | W | 115 | −3.656 | 9.896 | 7.101 | 1.00 | 32.62 | W | O |
| HETATM | 4804 | O | HOH | W | 116 | −13.602 | 22.480 | 44.154 | 1.00 | 35.16 | W | O |
| HETATM | 4805 | O | HOH | W | 117 | 22.128 | 20.904 | −3.627 | 1.00 | 30.87 | W | O |
| HETATM | 4806 | O | HOH | W | 118 | −5.070 | 15.045 | 27.353 | 1.00 | 23.93 | W | O |
| HETATM | 4807 | O | HOH | W | 119 | 36.061 | 37.125 | 23.788 | 1.00 | 24.47 | W | O |
| HETATM | 4808 | O | HOH | W | 120 | −25.322 | 30.252 | 30.726 | 1.00 | 41.44 | W | O |
| HETATM | 4809 | O | HOH | W | 121 | 35.690 | 29.845 | 5.576 | 1.00 | 16.76 | W | O |
| HETATM | 4810 | O | HOH | W | 122 | −24.680 | 19.112 | 17.711 | 1.00 | 37.84 | W | O |
| HETATM | 4811 | O | HOH | W | 123 | 13.080 | 52.502 | 31.871 | 1.00 | 41.89 | W | O |
| HETATM | 4812 | O | HOH | W | 124 | 2.957 | 25.901 | 31.930 | 1.00 | 19.65 | W | O |
| HETATM | 4813 | O | HOH | W | 125 | 39.312 | 38.534 | −13.393 | 1.00 | 31.38 | W | O |
| HETATM | 4814 | O | HOH | W | 126 | 38.067 | 33.591 | −15.755 | 1.00 | 35.74 | W | O |
| HETATM | 4815 | O | HOH | W | 127 | 29.602 | 55.694 | 2.224 | 1.00 | 36.44 | W | O |
| HETATM | 4816 | O | HOH | W | 128 | 34.510 | 31.619 | 3.906 | 1.00 | 29.94 | W | O |
| HETATM | 4817 | O | HOH | W | 129 | 9.989 | 23.860 | 20.084 | 1.00 | 32.28 | W | O |
| HETATM | 4818 | O | HOH | W | 130 | −17.671 | 35.139 | 20.740 | 1.00 | 51.29 | W | O |
| HETATM | 4819 | O | HOH | W | 131 | 36.267 | 31.168 | −11.638 | 1.00 | 51.65 | W | O |
| HETATM | 4820 | O | HOH | W | 132 | −14.553 | 50.627 | 22.253 | 1.00 | 36.45 | W | O |
| HETATM | 4821 | O | HOH | W | 133 | −16.661 | 11.632 | 17.334 | 1.00 | 19.62 | W | O |
| HETATM | 4822 | O | HOH | W | 134 | 23.273 | 35.371 | −10.468 | 1.00 | 27.93 | W | O |
| HETATM | 4823 | O | HOH | W | 135 | −23.607 | 44.003 | 35.480 | 1.00 | 29.99 | W | O |
| HETATM | 4824 | O | HOH | W | 136 | −11.964 | 57.410 | 34.233 | 1.00 | 59.88 | W | O |
| HETATM | 4825 | O | HOH | W | 137 | −19.087 | 51.552 | 39.458 | 1.00 | 34.48 | W | O |
| HETATM | 4826 | O | HOH | W | 138 | 6.012 | 22.773 | 15.789 | 1.00 | 32.08 | W | O |
| HETATM | 4827 | O | HOH | W | 139 | 19.642 | 44.693 | −8.548 | 1.00 | 30.54 | W | O |
| HETATM | 4828 | O | HOH | W | 140 | 3.705 | 36.386 | 50.313 | 1.00 | 38.47 | W | O |
| HETATM | 4829 | O | HOH | W | 141 | 1.298 | 37.283 | 7.120 | 1.00 | 51.13 | W | O |
| HETATM | 4830 | O | HOH | W | 142 | −23.191 | 29.343 | 32.125 | 1.00 | 50.13 | W | O |
| HETATM | 4831 | O | HOH | W | 143 | 46.067 | 49.093 | 7.670 | 1.00 | 42.60 | W | O |
| HETATM | 4832 | O | HOH | W | 144 | 31.146 | 48.281 | 12.422 | 1.00 | 40.48 | W | O |
| HETATM | 4833 | O | HOH | W | 145 | 31.480 | 33.377 | 27.417 | 1.00 | 40.50 | W | O |
| HETATM | 4834 | O | HOH | W | 146 | −0.521 | 7.311 | 18.965 | 1.00 | 40.93 | W | O |

-continued

| | | | | | | | | | | | |
|---|---|---|---|---|---|---|---|---|---|---|---|
| HETATM | 4835 | O | HOH | W | 147 | 4.938 | 47.003 | 20.293 | 1.00 | 35.68 | W O |
| HETATM | 4836 | O | HOH | W | 148 | 2.572 | 56.018 | 12.990 | 1.00 | 38.20 | W O |
| HETATM | 4837 | O | HOH | W | 149 | 4.166 | 41.330 | 46.439 | 1.00 | 51.22 | W O |
| HETATM | 4838 | O | HOH | W | 150 | −27.096 | 42.038 | 36.548 | 1.00 | 54.71 | W O |
| HETATM | 4839 | O | HOH | W | 151 | −9.606 | 44.717 | 20.161 | 1.00 | 26.34 | W O |
| HETATM | 4840 | O | HOH | W | 152 | −12.543 | 24.530 | 50.664 | 1.00 | 31.97 | W O |
| HETATM | 4841 | O | HOH | W | 153 | 23.986 | 57.755 | 13.449 | 1.00 | 41.58 | W O |
| HETATM | 4842 | O | HOH | W | 154 | 4.142 | 48.610 | −7.954 | 1.00 | 41.73 | W O |
| HETATM | 4843 | O | HOH | W | 155 | −8.571 | 34.493 | 10.496 | 1.00 | 35.68 | W O |
| HETATM | 4844 | O | HOH | W | 156 | 6.535 | 43.683 | −0.301 | 1.00 | 28.35 | W O |
| HETATM | 4845 | O | HOH | W | 157 | 5.098 | 9.837 | 31.389 | 1.00 | 32.69 | W O |
| HETATM | 4846 | O | HOH | W | 158 | 4.605 | 38.451 | 46.567 | 1.00 | 44.80 | W O |
| HETATM | 4847 | O | HOH | W | 159 | −12.373 | 9.262 | 29.626 | 1.00 | 43.00 | W O |
| HETATM | 4848 | O | HOH | W | 160 | 21.944 | 64.392 | 14.788 | 1.00 | 43.27 | W O |
| HETATM | 4849 | O | HOH | W | 161 | 8.410 | 42.221 | 0.553 | 1.00 | 38.42 | W O |
| HETATM | 4850 | O | HOH | W | 162 | −15.092 | 24.451 | 51.951 | 1.00 | 33.87 | W O |
| HETATM | 4851 | O | HOH | W | 163 | −28.497 | 40.660 | 38.549 | 1.00 | 42.45 | W O |
| HETATM | 4852 | O | HOH | W | 164 | 4.677 | 56.197 | 15.176 | 1.00 | 39.88 | W O |
| HETATM | 4853 | O | HOH | W | 165 | 9.008 | 31.037 | 17.696 | 1.00 | 37.12 | W O |
| HETATM | 4854 | O | HOH | W | 166 | −13.943 | 48.188 | 19.442 | 1.00 | 51.59 | W O |
| HETATM | 4855 | O | HOH | W | 167 | −16.372 | 52.024 | 18.619 | 1.00 | 30.94 | W O |
| HETATM | 4856 | O | HOH | W | 168 | 36.587 | 31.130 | −14.714 | 1.00 | 37.59 | W O |
| HETATM | 4857 | O | HOH | W | 169 | 40.198 | 33.790 | −13.561 | 1.00 | 51.85 | W O |
| HETATM | 4858 | O | HOH | W | 170 | 11.326 | 50.791 | 32.880 | 1.00 | 41.20 | W O |
| HETATM | 4859 | O | HOH | W | 171 | 24.824 | 41.289 | −12.891 | 1.00 | 48.97 | W O |
| HETATM | 4860 | O | HOH | W | 172 | −19.243 | 31.094 | 23.985 | 1.00 | 65.07 | W O |
| HETATM | 4861 | O | HOH | W | 173 | 22.235 | 20.511 | 18.399 | 1.00 | 35.72 | W O |
| HETATM | 4862 | O | HOH | W | 174 | 25.487 | 19.422 | 20.119 | 1.00 | 42.44 | W O |
| HETATM | 4863 | O | HOH | W | 175 | −0.531 | 31.883 | 14.385 | 1.00 | 36.04 | W O |
| HETATM | 4864 | O | HOH | W | 176 | 21.134 | 46.888 | 6.137 | 1.00 | 20.06 | W O |
| END | | | | | | | | | | | |

We claim:

1. A crystal comprising:

a human Janus Kinase 3 kinase domain consisting of amino acid residues 810-1115 of SEQ ID NO: 1, wherein said human Janus Kinase 3 kinase domain is in complex with a chemical entity selected from the group consisting of adenosine, ATP, an ATP analogue, AMP-PNP, a nucleotide triphosphate, a nucleotide diphosphate, and phosphate, and wherein said crystal is characterized by either:

(i) space group $P2_1$ and has unit cell parameters of a=59.98±4 Å, b=90.19 ±4 Å, c=69.00±4 Å, α=90°, β=111.5°±8°, and γ=90°, or (ii) space group $P2_12_12_1$ and has unit cell parameters of a=72.36±4 Å, b=90.04±4 Å, c=105.60±4 Å, α=90°, β=90°, and γ=90°.

2. The crystal according to claim 1, wherein said chemical entity is AMP-PNP.

3. A crystallizable composition comprising:

(a) a human Janus Kinase 3 kinase domain, wherein said human Janus Kinase 3 kinase domain consists of amino acid residues 810-1115 of SEQ ID NO: 1;

(b) a chemical entity selected from the group consisting of adenosine, ATP, an ATP analogue, AMP-PNP, a nucleotide triphosphate, a nucleotide diphosphate, and phosphate;

(c) 20-26% PEG 3350;

(d) 200-260 mM KCl;

(e) 20 mM spermine;

(f) 10 mM DTT; and (g) 100 mM bis-tris pH 6.0.

4. The crystallizable composition according to claim 3, wherein said chemical entity is AMP-PNP.

5. A method of obtaining a crystal of claim 1, comprising the steps of:

(a) producing and purifying a mixture comprising a human Janus Kinase 3 kinase domain consisting of amino acid residues 810-1115 of SEQ ID NO: 1, and a chemical entity selected from the group consisting of adenosine, ATP, an ATP analogue, AMP-PNP, a nucleotide triphosphate, a nucleotide diphosphate, and phosphate; and (b) subjecting the mixture of step (a) to conditions which promote crystallization, thereby obtaining said crystal.

6. The method according to claim 5, wherein said chemical entity is AMP-PNP.

7. A method of obtaining a crystal, comprising the steps of;

(a) obtaining the crystallizable composition of claim 3 or 4; and (b) subjecting the crystallizable composition of step (a) to conditions which promote crystallization, thereby obtaining said crystal.

* * * * *

SEQUENCE LISTING

<160> NUMBER OF SEQ ID NOS: 8

<210> SEQ ID NO 1
<211> LENGTH: 1124
<212> TYPE: PRT
<213> ORGANISM: Homo sapiens

<400> SEQUENCE: 1

```
Met Ala Pro Pro Ser Glu Glu Thr Pro Leu Ile Pro Gln Arg Ser Cys
 1               5                  10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
```

```
                    165                 170                 175
Gln Ala Gln Arg Pro Gly Glu Leu Leu Lys Thr Val Ser Tyr Lys Ala
                180                 185                 190

Cys Leu Pro Pro Ser Leu Arg Asp Leu Ile Gln Gly Leu Ser Phe Val
            195                 200                 205

Thr Arg Arg Arg Ile Arg Arg Thr Val Arg Arg Ala Leu Arg Arg Val
        210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
    370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525

His Gly Ser Phe Thr Lys Ile Tyr Arg Gly Cys Arg His Glu Val Val
    530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590
```

-continued

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
    610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
    690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
        755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
        835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
    930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
        995                 1000                1005

Asp Val Trp Ser Phe Gly Val Val Leu Tyr Glu Leu Phe Thr Tyr Cys
    1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
            1045                1050                1055

Gly Gln Arg Leu Pro Ala Pro Pro Ala Cys Pro Ala Glu Val His Glu
        1060                1065                1070

Leu Met Lys Leu Cys Trp Ala Pro Ser Pro Gln Asp Arg Pro Ser Phe
    1075                1080                1085

Ser Ala Leu Gly Pro Gln Leu Asp Met Leu Trp Ser Gly Ser Arg Gly
1090                1095                1100

Cys Glu Thr His Ala Phe Thr Ala His Pro Glu Gly Lys His His Ser
1105                1110                1115                1120

Leu Ser Phe Ser

<210> SEQ ID NO 2
<211> LENGTH: 72
<212> TYPE: PRT
<213> ORGANISM: Homo sapiens

<400> SEQUENCE: 2

Asp Phe Gly Leu Met Arg Ala Leu Pro Gln Asn Asp Asp His Tyr Val
1               5                   10                  15

Met Gln Glu His Arg Lys Val Pro Phe Ala Trp Cys Ala Pro Glu Ser
            20                  25                  30

Leu Lys Thr Arg Thr Phe Ser His Ala Ser Asp Thr Trp Met Phe Gly
        35                  40                  45

Val Thr Leu Trp Glu Met Phe Thr Tyr Gly Gln Glu Pro Trp Ile Gly
    50                  55                  60

Leu Asn Gly Ser Gln Ile Leu His
65                  70

<210> SEQ ID NO 3
<211> LENGTH: 67
<212> TYPE: PRT
<213> ORGANISM: Homo sapiens

<400> SEQUENCE: 3

Asp Phe Gly Leu Ser Arg Asn Ile Tyr Ser Ala Asp Tyr Tyr Lys Asp
1               5                   10                  15

Ala Ile Pro Ile Arg Trp Met Pro Pro Glu Ser Ile Phe Tyr Asn Arg
            20                  25                  30

Tyr Thr Thr Glu Ser Asp Val Trp Ala Tyr Gly Val Val Leu Trp Glu
        35                  40                  45

Ile Phe Ser Tyr Gly Leu Gln Pro Tyr Tyr Gly Met Ala His Glu Glu
    50                  55                  60

Val Ile Tyr
65

<210> SEQ ID NO 4
<211> LENGTH: 71
<212> TYPE: PRT
<213> ORGANISM: Homo sapiens

<400> SEQUENCE: 4

Asp Phe Gly Met Thr Arg Asp Ile Tyr Glu Thr Asp Tyr Tyr Arg Lys
1               5                   10                  15

Gly Gly Lys Gly Leu Leu Pro Val Arg Trp Met Ala Pro Glu Ser Leu
            20                  25                  30

```
Lys Asp Gly Val Phe Thr Thr Ser Ser Asp Met Trp Ser Phe Gly Val
        35                  40                  45

Val Leu Trp Glu Ile Thr Ser Leu Ala Glu Gln Pro Tyr Gln Gly Leu
    50                  55                  60

Ser Asn Glu Gln Val Leu Lys
65                  70

<210> SEQ ID NO 5
<211> LENGTH: 71
<212> TYPE: PRT
<213> ORGANISM: Homo sapiens

<400> SEQUENCE: 5

Asp Phe Gly Leu Ala Arg Asp Ile His His Ile Asp Tyr Tyr Lys Lys
1               5                   10                  15

Thr Thr Asn Gly Arg Leu Pro Val Lys Trp Met Ala Pro Glu Ala Leu
            20                  25                  30

Phe Asp Arg Ile Tyr Thr His Gln Ser Asp Val Trp Ser Phe Gly Val
        35                  40                  45

Leu Leu Trp Glu Ile Phe Thr Leu Gly Gly Ser Pro Tyr Pro Gly Val
    50                  55                  60

Pro Val Glu Glu Leu Phe Lys
65                  70

<210> SEQ ID NO 6
<211> LENGTH: 70
<212> TYPE: PRT
<213> ORGANISM: Homo sapiens

<400> SEQUENCE: 6

Asp Phe Gly Leu Ala Arg Leu Ile Glu Asp Asn Glu Tyr Thr Ala Arg
1               5                   10                  15

Gln Gly Ala Lys Phe Pro Ile Lys Trp Thr Ala Pro Glu Ala Ala Leu
            20                  25                  30

Tyr Gly Arg Phe Thr Ile Lys Ser Asp Val Trp Ser Phe Gly Ile Leu
        35                  40                  45

Leu Thr Glu Leu Thr Thr Lys Gly Arg Val Pro Tyr Pro Gly Met Val
    50                  55                  60

Asn Arg Glu Val Leu Asp
65                  70

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 7

Gly Xaa Gly Xaa Xaa Gly
1               5

<210> SEQ ID NO 8
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Glu Glu Glu Tyr
 1               5
```